(12) United States Patent
Andrews et al.

(10) Patent No.: US 11,414,450 B1
(45) Date of Patent: Aug. 16, 2022

(54) AMINOGLYCOSIDES AND USES THEREOF

(71) Applicant: REVAGENIX, INC., San Mateo, CA (US)

(72) Inventors: Logan Andrews, San Mateo, CA (US); Andrew Calabrese, San Mateo, CA (US); Timothy Robert Kane, San Mateo, CA (US); Ryan Cirz, San Mateo, CA (US); Frederick Cohen, San Mateo, CA (US); Michael Lopez, San Mateo, CA (US); John Knox, San Mateo, CA (US); Nikolai Evdokimov, San Mateo, CA (US)

(73) Assignee: REVAGENIX, INC., San Mateo, CA (US)

( * ) Notice: Subject to any disclaimer, the term of this patent is extended or adjusted under 35 U.S.C. 154(b) by 19 days.

(21) Appl. No.: 16/642,879

(22) PCT Filed: Aug. 24, 2018

(86) PCT No.: PCT/US2018/047969
§ 371 (c)(1),
(2) Date: Feb. 27, 2020

(87) PCT Pub. No.: WO2019/046126
PCT Pub. Date: Mar. 7, 2019

Related U.S. Application Data

(60) Provisional application No. 62/652,161, filed on Apr. 3, 2018, provisional application No. 62/563,025, filed on Sep. 25, 2017, provisional application No. 62/551,107, filed on Aug. 28, 2017.

(51) Int. Cl.
*C07H 15/232* (2006.01)
*C07H 15/26* (2006.01)
*C07H 15/22* (2006.01)
*A61P 31/04* (2006.01)

(52) U.S. Cl.
CPC ............ *C07H 15/232* (2013.01); *A61P 31/04* (2018.01); *C07H 15/26* (2013.01)

(58) Field of Classification Search
None
See application file for complete search history.

(56) References Cited

U.S. PATENT DOCUMENTS

| | | | |
|---|---|---|---|
| 4,424,345 A | 1/1984 | Kirst et al. | |
| 4,439,196 A | 3/1984 | Higuchi | |
| 4,447,224 A | 5/1984 | DeCant, Jr. et al. | |
| 4,447,233 A | 5/1984 | Mayfield | |
| 4,475,196 A | 10/1984 | La Zor | |
| 4,486,194 A | 12/1984 | Ferrara | |
| 4,487,603 A | 12/1984 | Harris | |
| 4,596,556 A | 6/1986 | Morrow et al. | |
| 4,790,824 A | 12/1988 | Morrow et al. | |
| 4,941,880 A | 7/1990 | Burns | |
| 5,064,413 A | 11/1991 | McKinnon et al. | |
| 5,152,923 A | 10/1992 | Weder et al. | |
| 5,312,335 A | 5/1994 | McKinnon et al. | |
| 5,383,851 A | 1/1995 | McKinnon, Jr. et al. | |
| 5,399,163 A | 3/1995 | Peterson et al. | |
| 5,698,219 A | 12/1997 | Valdivia et al. | |
| 5,753,241 A | 5/1998 | Ribier et al. | |
| 5,925,341 A | 7/1999 | Cervantes et al. | |
| 6,039,936 A | 3/2000 | Restle et al. | |
| 6,120,778 A | 9/2000 | Simonnet | |
| 6,274,150 B1 | 8/2001 | Simonnet et al. | |
| 6,335,022 B1 | 1/2002 | Simonnet et al. | |
| 6,375,960 B1 | 4/2002 | Simonnet et al. | |
| 6,413,527 B1 | 7/2002 | Simonnet et al. | |
| 6,419,946 B1 | 7/2002 | Sonneville et al. | |
| 6,461,625 B1 | 10/2002 | Simonnet et al. | |
| 6,464,990 B2 | 10/2002 | Simonnet et al. | |
| 6,541,018 B1 | 4/2003 | Simonnet et al. | |
| 6,689,371 B1 | 2/2004 | Simonnet et al. | |
| 6,902,737 B2 | 6/2005 | Quemin | |
| 6,998,426 B2 | 2/2006 | L'Alloret et al. | |
| 7,314,624 B2 | 1/2008 | Baker et al. | |
| 7,468,402 B2 | 12/2008 | Yang et al. | |
| 7,476,393 B2 | 1/2009 | Dubief et al. | |
| 8,318,685 B2 | 11/2012 | Goldblum et al. | |

(Continued)

FOREIGN PATENT DOCUMENTS

| | | | |
|---|---|---|---|
| DE | 2350169 A1 | 4/1974 | |
| EP | 0048614 A1 | 3/1982 | |

(Continued)

OTHER PUBLICATIONS

Allen et al. Comparison of aminoglycoside antibiotics with respect to uptake and lethal activity in *Escherichia coli*. J Med Chem. Feb. 1987;30(2):333-40.

Alper et al. Probing the Specificity of Aminoglycoside—Ribosomal RNA Interactions with Designed Synthetic Analogs. J Am Chem Soc 120(9):1965-1978 (Feb. 24, 1998). DOI: https://doi.org/10.1021/ja972599h.

Anish et al. Chemical biology approaches to designing defined carbohydrate vaccines. Chem Biol. Jan. 16, 2014;21(1):38-50.doi: 10.1016/j.chembiol.2014.01.002.

Chandrika et al. Comprehensive review of chemical strategies for the preparation of new aminoglycosides and their biological activities. Chem Soc Rev. Feb. 19, 2018;47(4):1189-1249.doi: 10.1039/c7cs00407a.

(Continued)

*Primary Examiner* — Traviss C McIntosh, III
(74) *Attorney, Agent, or Firm* — Womble Bond Dickinson (US) LLP

(57) ABSTRACT

Provided herein are aminoglycoside compounds, such as compounds of formula (I), (II), (III), (IV), (IVa), (V), (VI), (VIIa), or (VIIb) or pharmaceutically acceptable salts, solvates, stereoisomers, or tautomers of any of the foregoing, useful as therapeutic or prophylactic agents. Also provided herein are methods for their preparation. The compounds may be useful in treating a bacterial infection in a subject, for example a Gram-negative bacterial infection.

14 Claims, 1 Drawing Sheet

(56) References Cited

U.S. PATENT DOCUMENTS

| | | |
|---|---|---|
| 8,481,502 B2 | 7/2013 | Aggen et al. |
| 2004/0054164 A1 | 3/2004 | Buchanan et al. |
| 2004/0058880 A1 | 3/2004 | Liang et al. |
| 2004/0170661 A1 | 9/2004 | Brode, III et al. |
| 2006/0269485 A1 | 11/2006 | Friedman et al. |
| 2011/0218173 A1 | 9/2011 | Wu et al. |
| 2012/0208781 A1 | 8/2012 | Bruss et al. |
| 2014/0323422 A1 | 10/2014 | Kett et al. |

FOREIGN PATENT DOCUMENTS

| | | | |
|---|---|---|---|
| WO | WO-0187263 A2 | 11/2001 | |
| WO | WO-2018187738 A1 * | 10/2018 | ........... C07H 15/222 |
| WO | WO-2019046126 A1 | 3/2019 | |
| WO | WO-2019194858 A1 | 10/2019 | |

OTHER PUBLICATIONS

Hamouda et al. A novel surfactant nanoemulsion with broad-spectrum sporicidal activity against Bacillus species. J Infect Dis. Dec. 1999;180(6):1939-49.doi: 10.1086/315124.

Kim et al. Reaction Catalyzed by GenK, a Cobalamin-Dependent Radical S-Adenosyl-l-methionine Methyltransferase in the Biosynthetic Pathway of Gentamicin, Proceeds with Retention of Configuration. J Am Chem Soc. Nov. 15, 2017;139(45):16084-16087 and Supplementary Material, pp. S1-S52.doi: 10.1021/jacs.7b09890. Epub Nov. 7, 2017.

Maianti et al. Toxicity modulation, resistance enzyme evasion, and A-site X-ray structure of broad-spectrum antibacterial neomycin analogs. ACS Chem Biol. Sep. 19, 2014;9(9):2067-73.doi: 10.1021/cb5003416. Epub Jul. 14, 2014.

Moazed et al. Interaction of antibiotics with functional sites in 16S ribosomal RNA. Nature. Jun. 4-10, 1987;327(6121):389-94.doi: 10.1038/327389a0.

PCT/US2018/047969 International Search Report and Written Opinion dated Dec. 4, 2018.

PCT/US2018/047993 International Search Report and Written Opinion dated Dec. 6, 2018.

Qin et al. Total Synthesis of a Densely Functionalized Plesiomonas shigelloides Serotype 51 Aminoglycoside Trisaccharide Antigen. J. Am. Chem. Soc. 140(8):3120-3127 (Jan. 29, 2018). DOI: https://doi.org/10.1021/jacs.8b00148.

Sati et al. N6', N6'', and O4' Modifications to Neomycin Affect Ribosomal Selectivity without Compromising Antibacterial Activity. ACS Infect. Dis. 2017, 3, 5, 368-377 with Supporting Information, pp. S1-S71 (Mar. 27, 2017). DOI: https://doi.org/10.1021/acsinfecdis.6b00214.

Silva et al. New insights into aminoglycoside antibiotics and derivatives. Curr Med Chem. 2007;14(10) :1101-19.doi: 10.2174/092986707780362817.

* cited by examiner

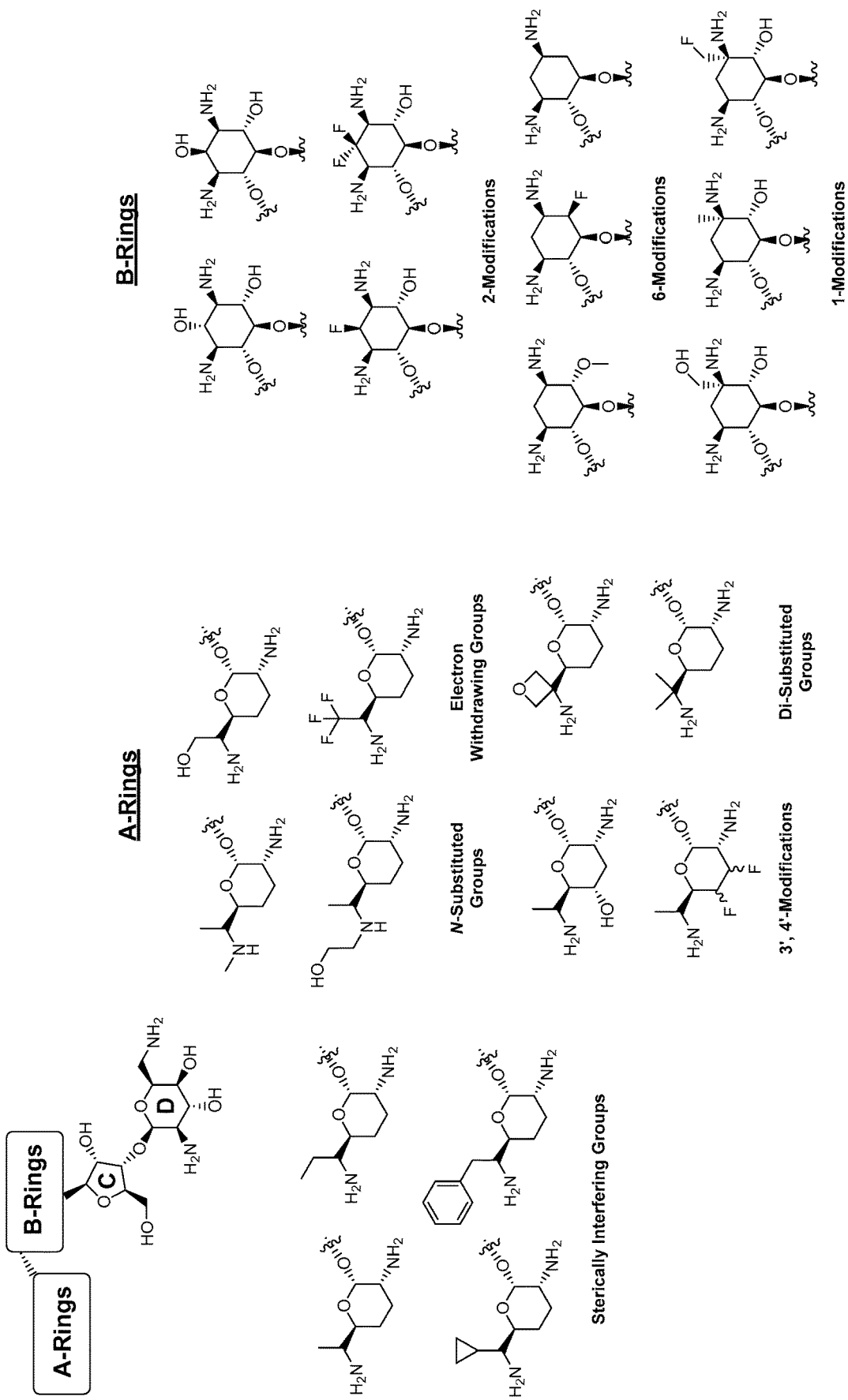

AMINOGLYCOSIDES AND USES THEREOF

CROSS-REFERENCE TO RELATED APPLICATIONS

This application claims the benefit of U.S. Provisional Application No. 62/551,107, filed Aug. 28, 2017; U.S. Provisional Application No. 62/563,025, filed Sep. 25, 2017; and U.S. Provisional Application No. 62/652,161, filed Apr. 3, 2018, the entireties of which are incorporated herein by reference.

FIELD

The present disclosure is directed to novel aminoglycoside compounds useful as therapeutic or prophylactic agents and methods for their preparation.

BACKGROUND

The rapid spread of antibiotic resistance in pathogenic bacteria has prompted a continuing search for new agents capable of antibacterial activity. Aminoglycosides (AGs) are highly potent, broad-spectrum antibiotics with many desirable properties for the treatment of life threatening infections. Examples of aminoglycosides include tobramycin, gentamicin, and amikacin. Aminoglycoside antibiotics have long been known to bind RNA in a fashion that leads to misreading of the genetic code. They exert their antibacterial effects by binding to specific target sites in the bacterial ribosome. For the structurally related antibiotics neamine, ribostamycin, neomycin B, and paromomycin, the binding site has been localized to the A-site of the prokaryotic 16S ribosomal decoding region RNA (see Moazed, D.; Noller, H. F., Nature, 1987, 327, 389). Binding of aminoglycosides to this RNA target interferes with the fidelity of mRNA translation and results in miscoding and truncation, leading ultimately to bacterial cell death (see Alper, P. B.; Hendrix, M.; Sears, P.; Wong, C., J. Am. Chem. Soc., 1998, 120, 1965). For example, misreading of the code during translation of integral membrane proteins is thought to produce abnormal proteins that compromise the barrier properties of the bacterial membrane.

Over time, resistance to AGs has emerged clinically. AG resistance (AG-R) can be categorized mechanistically into three types: (1) AG-modifying enzymes (AMEs); (2) target modifying enzymes called ribosomal methyltransferases (RMTs); and (3) reduction of intracellular AG concentrations, primarily mediated by the overexpression of efflux pumps. At present, the most significant contribution to AG-R amongst clinical isolates is conferred by AMEs, which are diverse and widely distributed in both developed and developing nations. RMTs, while less common than AMEs in Enterobacteriaceae and P. aeruginosa, are a serious threat because they modify the 16S rRNA AG binding site and prevent AG target engagement, conferring high-level resistance to all clinically available AGs. Alarmingly, approximately 30% of isolates from a contemporary Acinetobacter spp. panel (n=80) contain RMTs. As an additional concern, AME and RMT genes are typically located on plasmids or transposons together with genes encoding resistance to other classes of antibacterials, which leads to multidrug resistant isolates.

In addition, prolonged clinical use of aminoglycosides can lead to adverse events in the kidney (nephrotoxicity) and ear (ototoxicity). These are cumulative processes, with the likelihood of observing toxicity increasing with treatment duration. The nephrotoxicity potential of AGs limits the dose and the length of treatment, making it challenging to achieve the systemic exposures required for efficacy against P. aeruginosa and A. baumannii infections. The origin of this toxicity is assumed to result from a combination of different factors and mechanisms such as interactions with phospholipids, inhibition of phospholipases and the formation of free radicals.

For the foregoing reasons, while progress has been made in this field there is a need for new chemical entities that possess antibacterial activity and reduced toxicity with a sufficient therapeutic window (TW) to enable high-dose, long duration treatment for the most difficult to treat Gram-negative infections, such as P. aeruginosa and A. baumannii, and/or which are refractory to the common RMTs. Further, in order to accelerate the drug discovery process, new methods for synthesizing aminoglycoside antibiotics are needed to provide an array of compounds that are potentially new drugs for the treatment of bacterial infections. New methods for synthesizing aminoglycoside antibiotics are also needed to facilitate their production and reduce associated costs. The present disclosure fulfills these needs and provides further related advantages.

BRIEF SUMMARY

The present disclosure relates to aminoglycoside compounds, having antibacterial activity, including stereoisomers, tautomers, solvates, and pharmaceutically acceptable salts thereof, and to uses thereof in, for example, treatment of medical conditions associated with a pathogenic microorganism, which are also referred to herein as "bacterial infections."

One aspect of the disclosure relates to a compound of formula (IV):

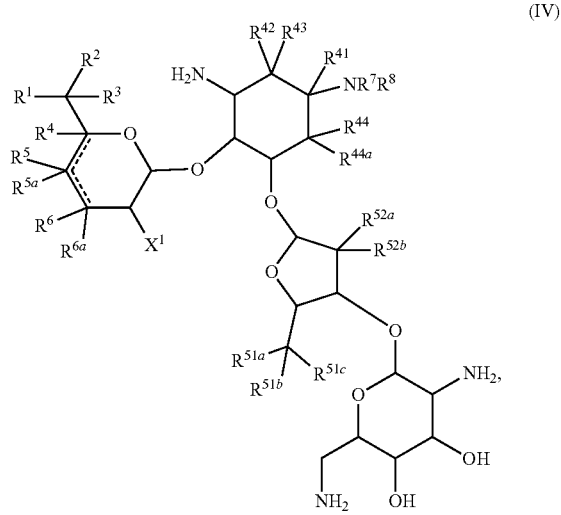

or a pharmaceutically acceptable salt, solvate, tautomer, or stereoisomer thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl, wherein the alkyl, cycloalkyl, or aryl is unsubstituted or substituted with one or more substituents independently selected from the group consisting of halogen, cyano, aryl, —$SR^{12}$, —$SO_{2R}{}^{13}$, —$OSF_2NR^{14}R^{15}$, —$NR^{14}R^{15}$, and —$OR^{16}$, and
wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O,
  wherein the heterocycloalkyl group is unsubstituted or substituted with one or more substituents independently selected from the group consisting of halogen, cyano, —$SR^{17}$, —$SO_{2R}{}^{18}$, —$NR^{19}R^{20}$, and —$OR^{21}$, and
  wherein each $R^{17}$, $R^{18}$, $R^{19}$, $R^{20}$, and $R^{21}$ is independently H or alkyl, or $R^2$ and $R^3$, together with the atom to which they are attached, form a cycloalkyl group or a heterocycloalkyl group,
  wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and
  wherein each $R^{22}$, $R^{23}$, $R^{24}$, $R^{25}$, and $R^{26}$ is independently H or alkyl; $R^4$ is H or absent;

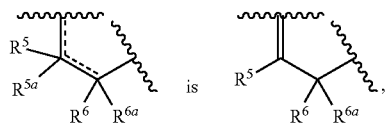

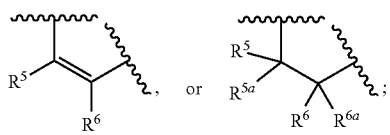

$R^5$ and $R^6$ are independently H, —$OR^{27}$, —$NR^{28}R^{29}$, halogen, or alkyl, wherein each $R^{27}$, $R^{28}$, and $R^{29}$ is independently H or $C_1$-$C_6$alkyl,
  wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_{2R}{}^{34}$, and
  wherein each $R^{30}$, $R^{31}$, $R^{32}$, $R^{33}$, and $R^{34}$ is independently H or alkyl, $R^{5a}$ and $R^{6a}$ are, independently, absent or independently H, —$OR^{53}$, —$NR^{54}R^{55}$, halogen, or alkyl, wherein each $R^{53}$, $R^{54}$, and $R^{55}$ is independently H or $C_1$-$C_6$alkyl,
  wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_{2R}{}^{60}$, and
  wherein each $R^{56}$, $R^{57}$, $R^{58}$, $R^{59}$, and $R^{60}$ is independently H or alkyl, or $R^5$ and $R^{5a}$ form an oxo group, or $R^6$ and $R^{6a}$ form an oxo group;

$R^7$ is H or $C_1$-$C_3$alkyl;

$R^8$ is H, $C_1$-$C_6$alkyl, an amino protecting group, or

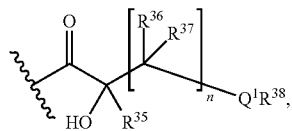

wherein $Q^1$ is NH, O, or S, n is an integer from 0 to 4, $R^{35}$ is H or $C_1$-$C_3$alkyl, each $R^{36}$ and $R^{37}$ is independently H, alkyl, halogen, or —OH, and $R^{38}$ is H, alkyl, or —C(=NH)$NR^{39}R^{40}$, wherein $R^{39}$ and $R^{40}$ are independently H or $C_1$-$C_3$alkyl, or $R^{35}$ and $R^{38}$, together with the atoms to which they are attached, form a heterocycloalkyl group comprising at least one N;

$R^{41}$ is H, —CN, —$CONH_2$ or $C_1$-$C_3$alkyl, wherein the $C_1$-$C_3$alkyl is unsubstituted or substituted with one or more substituents selected from the group consisting of —OH, —$OC(O)CH_3$, —$NH_2$, —CN, —$CONH_2$, and halogen;

$R^{42}$ $R^{43}$ are, independently H, —OH, —$OR^{45}$, —$NR^{46}R^{47}$, or halogen,
  wherein each $R^{45}$, $R^{46}$, and $R^{47}$ is independently H, alkyl, —$CONH_2$, or —$COCH_3$,
  wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{44}$ and $R^{44a}$ are, independently, H, halogen, —OH, $C_1$-$C_3$alkoxy, or —$OC(O)CH_3$;

$X^1$ is H, $NH_2$, OH, or halogen:

$R^{51a}$, $R^{51b}$, and $R^{51c}$ are, independently, H, OH, or —$OR^{51d}$,
  wherein each $R^{51d}$ is, independently. alkyl or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{52a}$ and $R^{52b}$ are independently H, OH, or —$OR^{52c}$,
  wherein each $R^{52c}$ is, independently, alkyl or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

wherein if $R^2$ and $R^3$ are both H and $R^5$ is —$OR^{27}$ or $R^{5a}$ is —$OR^{53}$, then $R^6$ is not —$OR^{27}$, wherein if $R^2$ and $R^3$ are both H and $R^5$ is —$OR^{27}$ or $R^{5a}$ is —$OR^{53}$, then $R^{6a}$ is not —$OR^{53}$, wherein if $R^2$ and $R^3$ are both H, then at least one of $R^{41}$, $R^{42}$, $R^{43}$, $R^{44}$, or $R^{44a}$ is not H, and wherein if $R^2$ and $R^3$ are both H and one of $R^{44}$ and $R^{44a}$ is —OH, then at least one of $R^{41}$, $R^{42}$, or $R^{43}$ is not H.

In some embodiments, the compound of formula (IV) is of formula (IV-X):

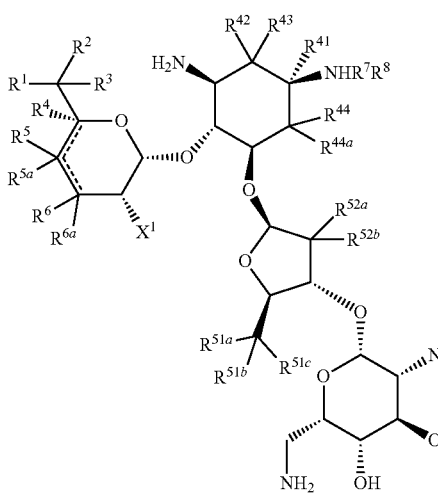

(IV-X)

or a pharmaceutically acceptable salt, solvate, or tautomer thereof.

In some embodiments, the compound of formula (IV) is of formula (IVa):

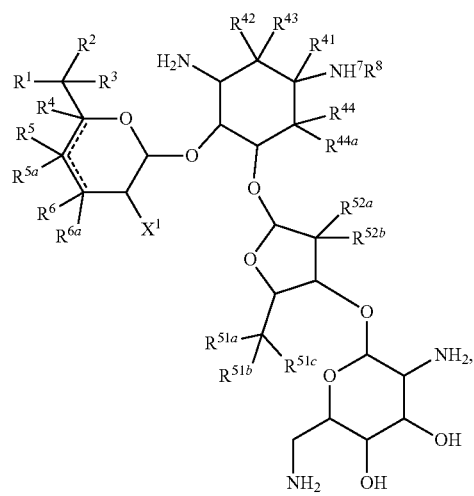

(IVa)

or a pharmaceutically acceptable salt, solvate, tautomer, or stereoisomer thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl, wherein the alkyl, cycloalkyl, or aryl is unsubstituted or substituted with one or more substituents independently selected from the group consisting of halogen, cyano, aryl, —$SR^{12}$, —$SO_{2R}^{13}$, —$OSF_2NR^{14}R^{15}$, —$NR^{14}R^{15}$, and —$OR^{16}$, and wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and wherein each $R^{17}$, $R^{18}$, $R^{19}$, $R^{20}$, and $R^{21}$ is independently H or alkyl, or $R^2$ and $R^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, wherein each $R^{22}$, $R^{23}$, $R^{24}$, $R^{25}$, and $R^{26}$ is independently H or alkyl, and wherein at least one of $R^2$ and $R^3$ is other than H;

$R^4$ is H or absent;

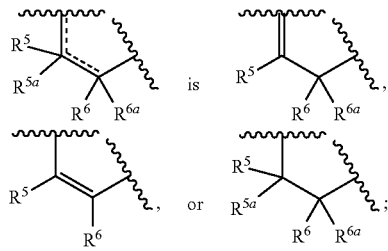

$R^5$ and $R^6$ are independently H, —$OR^{27}$, —$NR^{28}R^{29}$, halogen, or alkyl, wherein each $R^{27}$, $R^{28}$, and $R^{29}$ is independently H or $C_1$-$C_6$alkyl, wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and wherein each $R^{30}$, $R^{31}$, $R^{32}$, $R^{33}$, and $R^{34}$ is independently H or alkyl, $R^{5a}$ and $R^{6a}$ are, independently, absent or independently H, —$OR^{53}$, —$NR^{54}R^{55}$, halogen, or alkyl, wherein each $R^{53}$, $R^{54}$, and $R^{55}$ is independently H or $C_1$-$C_6$alkyl, wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and wherein each $R^{56}$, $R^{57}$, $R^{58}$, $R^{59}$, and $R^{60}$ is independently H or alkyl, or $R^5$ and $R^{5a}$ form an oxo group, or $R^6$ and $R^{6a}$ form an oxo group;

$R^7$ is H or $C_1$-$C_3$alkyl;

$R^8$ is H, $C_1$-$C_6$alkyl, an amino protecting group, or

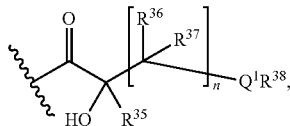

wherein $Q^1$ is NH, O, or S, n is an integer from 0 to 4, $R^{35}$ is H or $C_1$-$C_3$alkyl, each $R^{36}$ and $R^{37}$ is independently H, alkyl, halogen, or —OH, and $R^{38}$ is H, alkyl, or —C(=NH)NR$^{39}$R$^{40}$, wherein R$^{39}$ and R$^{40}$ are independently H or C$_1$-C$_3$alkyl, or $R^{35}$ and $R^{38}$, together with the atoms to which they are attached, form a heterocycloalkyl group comprising at least one N;

$R^{41}$ is H, —CN, —CONH$_2$ or C$_1$-C$_3$alkyl, wherein the C$_1$-C$_3$alkyl is unsubstituted or substituted with one or more substituents selected from the group consisting of —OH, —OC(O)CH$_3$, —NH$_2$, —CN, —CONH$_2$, and halogen;

$R^{42}$ and $R^{43}$ are, independently, H, —OH, —OR$^{45}$, —NR$^{46}$R$^{47}$, or halogen, wherein each R$^{45}$, R$^{46}$, and R$^{47}$ is independently H, alkyl, —CONH$_2$, or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

$R^{44}$ and $R^{44a}$ are, independently, H, halogen, —OH, C$_1$-C$_3$alkoxy, or —OC(O)CH$_3$;

$X^1$ is H, NH$_2$, OH, or halogen;

$R^{51a}$, $R^{51b}$, and $R^{51c}$ are, independently, H, OH, or —OR$^{51d}$, wherein each $R^{51d}$ is, independently, alkyl or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

$R^{52a}$ and $R^{52b}$ are independently H, OH, or —OR$^{52c}$, wherein each $R^{52c}$ is, independently, alkyl or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl.

In some embodiments, the compound of formula (IVa) is of formula (IVa-X):

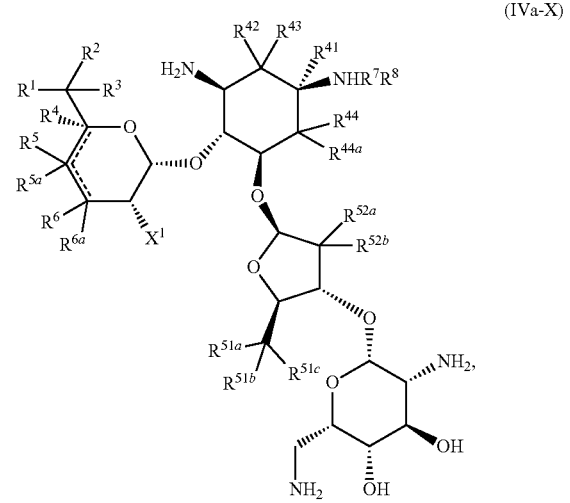

(IVa-X)

or a pharmaceutically acceptable salt, tautomer, or solvate thereof.

In some embodiments, the compound of formula (IV) is of formula (V):

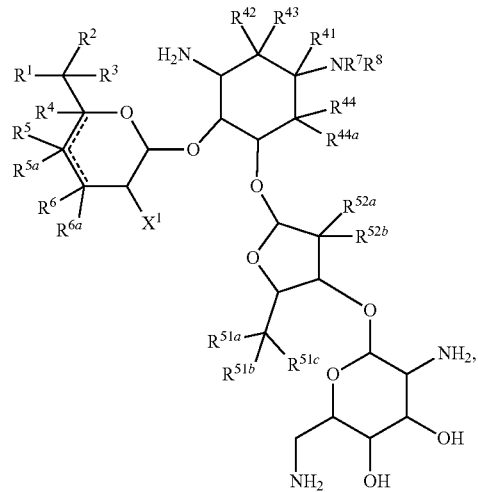

(V)

or a pharmaceutically acceptable salt, solvate, tautomer, or stereoisomer thereof, wherein as valence and stability permit, $R^1$ is —OR$^9$ or —NR$^{10}$R$^{11}$, wherein R$^9$, R$^{10}$, and R$^{11}$ are independently H or C$_1$-C$_6$alkyl, wherein the C$_1$-C$_6$alkyl is unsubstituted or substituted with one or more —OH;

$R^2$ and $R^3$ are independently H, alkyl, cycloalkyl, or aryl, wherein the alkyl, cycloalkyl, or aryl is unsubstituted or substituted with one or more substituents independently selected from the group consisting of halogen, cyano, aryl, —SR$^{12}$, —SO$_2$R$^{13}$, —OSF$_2$NR$^{14}$R$^{15}$, —NR$^{14}$R$^{15}$, and —OR$^{16}$, and wherein each R$^{12}$, R$^{13}$, R$^{11}$, R$^{15}$, and R$^{16}$ is independently H or alkyl, or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —SR$^{17}$, —SO$_2$R$^{18}$, —NR$^{19}$R$^{20}$, and —OR$^{21}$, and wherein each R$^{17}$, R$^{18}$, R$^{19}$, R$^{20}$, and R$^{21}$ is independently H or alkyl, or R$^2$ and R$^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, —SR$^{22}$, —SO$_2$R$^{23}$, —NR$^{24}$R$^{25}$, and —OR$^{26}$, and wherein each R$^{22}$, R$^{23}$, R$^{24}$, R$^{25}$, and R$^{26}$ is independently H or alkyl; R$^4$ is H or absent;

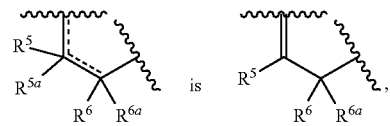

-continued

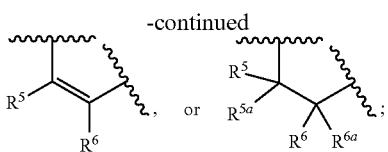

$R^5$ and $R^6$ are independently H, —$OR^{27}$, —$NR^{28}R^{29}$, halogen, or alkyl, wherein each $R^{27}$, $R^{28}$, and $R^{29}$ is independently H or $C_1$-$C_6$alkyl,
  wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and
  wherein each $R^{30}$, $R^{31}$, $R^{32}$, $R^{33}$, and $R^{34}$ is independently H or alkyl, $R^{5a}$ and $R^{6a}$ are, independently, absent or independently H, —$OR^{53}$, —$NR^{54}R^{55}$, halogen, or alkyl, wherein each $R^{53}$, $R^{54}$, and $R^{55}$ is independently H or $C_1$-$C_6$alkyl,
  wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and
  wherein each $R^{56}$, $R^{57}$, $R^{58}$, $R^{59}$, and $R^{60}$ is independently H or alkyl, or $R^5$ and $R^{5a}$ form an oxo group, or
$R^6$ and $R^{6a}$ form an oxo group,
  wherein if $R^5$ is —$OR^{27}$ or $R^{5a}$ is —$OR^{53}$, then $R^6$ is not —$OR^{27}$, and
  wherein if $R^5$ is —$OR^{27}$ or $R^{5a}$ is —$OR^{53}$, then $R^{6a}$ is not —$OR^{53}$;

$R^7$ is H or $C_1$-$C_3$alkyl;
$R^8$ is H, $C_1$-$C_6$alkyl, an amino protecting group, or

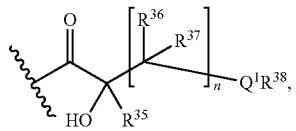

wherein $Q^1$ is NH, O, or S,
n is an integer from 0 to 4,
$R^{35}$ is H or $C_1$-$C_3$alkyl,
each $R^{36}$ and $R^{37}$ is independently H, alkyl, halogen, or —OH, and
$R^{38}$ is H, alkyl, or —C(=NH)$NR^{39}R^{40}$, wherein $R^{39}$ and $R^{40}$ are independently H or $C_1$-$C_3$alkyl, or
$R^{35}$ and $R^{38}$, together with the atoms to which they are attached, form a heterocycloalkyl group comprising at least one N;
$R^{41}$ is H, —CN, —$CONH_2$ or $C_1$-$C_3$alkyl, wherein the $C_1$-$C_3$alkyl is unsubstituted or substituted with one or more substituents selected from the group consisting of —OH, —OC(O)$CH_3$, —$NH_2$, —CN, —$CONH_2$, and halogen;
$R^{42}$ and $R^{43}$ are, independently, H, —OH, —$OR^{45}$, —$NR^{46}R^{47}$, or halogen,
  wherein each $R^{45}$, $R^{46}$, and $R^{47}$ is independently H, alkyl, —$CONH_2$, or —$COCH_3$,
  wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;
$R^{44}$ and $R^{44a}$ are, independently H, OH, halogen, $C_1$-$C_3$alkoxy, or —OC(O)$CH_3$, wherein when $R^{44}$ or $R^{44a}$ is OH, then $R^{41}$ is not H;

$X^1$ is H, $NH_2$, OH, or halogen;
$R^{51a}$, $R^{51b}$, and $R^{51c}$ are, independently, H, OH, or —$OR^{51d}$,
  wherein each $R^{51d}$ is, independently, alkyl or —$COCH_3$,
    wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;
$R^{52a}$ and $R^{52b}$ are independently H, OH, or —$OR^{52c}$,
  wherein each $R^{52c}$ is, independently, alkyl or —$COCH_3$,
    wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl.

In some embodiments, the compound of formula (V) is of formula (V-X):

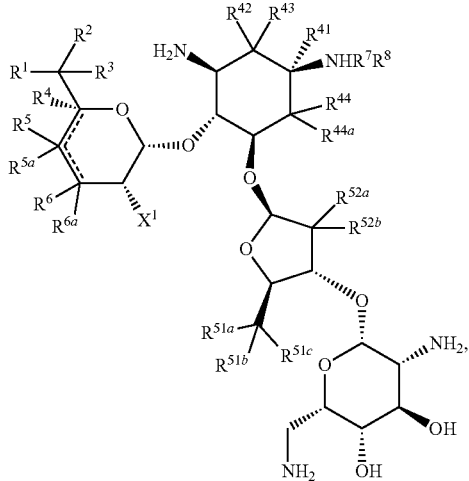

(V-X)

or a pharmaceutically acceptable salt, tautomer, or solvate thereof.

In some embodiments, the compound of formula (IV) is of formula (VI):

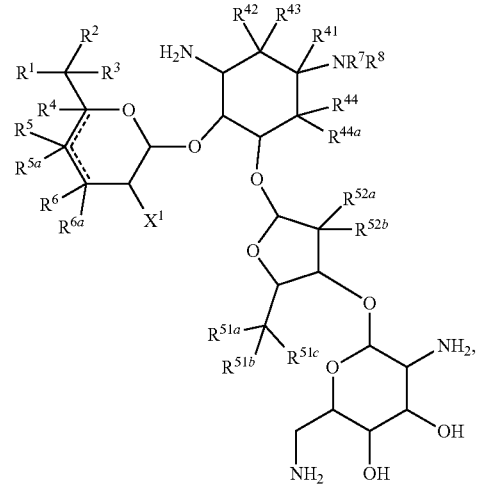

(VI)

or a pharmaceutically acceptable salt, solvate, tautomer, or stereoisomer thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl,
wherein the alkyl, cycloalkyl, or aryl is unsubstituted or substituted with one or more substituents independently selected from the group consisting of halogen, cyano, aryl, —$SR^{12}$, —$SO_2R^{13}$, —$OSF_2NR^{14}R^{15}$, —$NR^{14}R^{15}$, and —$OR^{16}$, and
wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O,
wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and
wherein each $R^{17}$, $R^{18}$, $R^{19}$, $R^{20}$, and $R^{21}$ is independently H or alkyl, or $R^2$ and $R^3$, together with the atom to which they are attached, form a cycloalkyl group or a heterocycloalkyl group,
wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and
wherein each $R^{22}$, $R^{23}$, $R^{24}$, $R^{25}$, and $R^{26}$ is independently H or alkyl, and $R^4$ is H or absent;

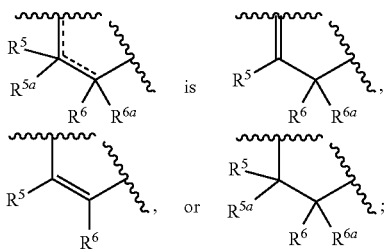

$R^5$ and $R^6$ are independently H, —$OR^{27}$, —$NR^{28}R^{29}$, halogen, or alkyl, wherein each $R^{27}$, $R^{28}$, and $R^{29}$ is independently H or $C_1$-$C_6$alkyl,
wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and
wherein each $R^{30}$, $R^{31}$, $R^{32}$, $R^{33}$, and $R^{34}$ is independently H or alkyl, $R^{5a}$ and $R^{6a}$ are, independently, absent or independently H, —$OR^{53}$, —$NR^{54}R^{55}$, halogen, or alkyl, wherein each $R^{53}$, $R^{54}$, and $R^{55}$ is independently H or $C_1$-$C_6$alkyl,
wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and
wherein each $R^{56}$, $R^{57}$, $R^{58}$, $R^{59}$, and $R^{60}$ is independently H or alkyl, or $R^5$ and $R^{5a}$ form an oxo group, or
$R^6$ and $R^{6a}$ form an oxo group,
wherein if $R^5$ is —$OR^{27}$ or $R^{5a}$ is —$OR^{53}$, then $R^6$ is not —$OR^{27}$, and
wherein if $R^5$ is —$OR^{27}$ or $R^{5a}$ is —$OR^{53}$, then $R^{6a}$ is not —$OR^{53}$;

$R^7$ is H or $C_1$-$C_3$alkyl;
$R^8$ is H, $C_1$-$C_6$alkyl, an amino protecting group, or

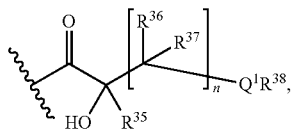

wherein $Q_1$ is NH, O, or S,
n is an integer from 0 to 4,
$R^{35}$ is H or $C_1$-$C_3$alkyl,
each $R^{36}$ and $R^{37}$ is independently H, alkyl, halogen, or —OH, and
$R^{38}$ is H, alkyl, or —$C(=NH)NR^{39}R^{40}$, wherein $R^{39}$ and $R^{40}$ are independently H or $C_1$-$C_3$alkyl, or
$R^{35}$ and $R^{38}$, together with the atoms to which they are attached, form a heterocycloalkyl group comprising at least one N;

$R^{41}$ is H, —CN, —$CONH_2$ or $C_1$-$C_3$alkyl, wherein the $C_1$-$C_3$alkyl is unsubstituted or substituted with one or more substituents selected from the group consisting of —OH, —$OC(O)CH_3$, —$NH_2$, —CN, —$CONH_2$, and halogen;

$R^{42}$ and $R^{43}$ are, is independently H, —OH, —$OR^{45}$, —$NR^{46}R^{47}$, or halogen,
wherein each $R^{45}$, $R^{46}$, and $R^{47}$ is independently H, alkyl, —$CONH_2$, or —$COCH_3$,
wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl, and
wherein at least one of $R^{42}$ and $R^{43}$ is other than H;

$R^{44}$ and $R^{44a}$ are, independently H, halogen, —OH, $C_1$-$C_3$alkoxy, or —$OC(O)CH_3$;
$X^1$ is H, $NH_2$, OH, or halogen;
$R^{51a}$, $R^{51b}$, and $R^{51c}$ are, independently, H, OH, or —$OR^{51d}$,
wherein each $R^{51d}$ is, independently, alkyl or —$COCH_3$,
wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{52a}$ and $R^{52b}$ are independently H, OH, or —$OR^{52c}$,
wherein each $R^{52c}$ is, independently, alkyl or —$COCH_3$,
wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl.

In some embodiments, the compound of formula (VI) is of formula (VI-X):

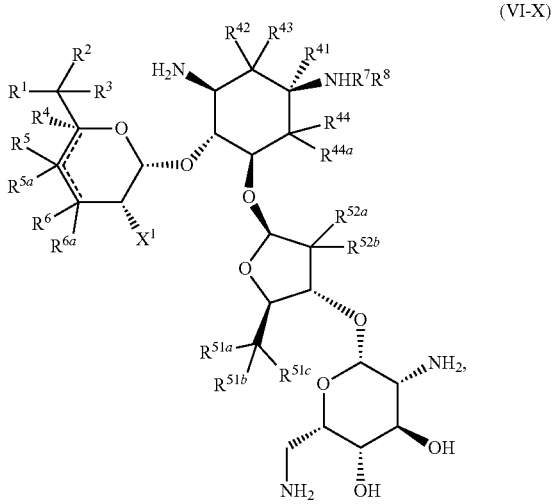

(VI-X)

or a pharmaceutically acceptable salt, tautomer, or solvate thereof.

Another aspect of the disclosure relates to a compound of formula (VIIa):

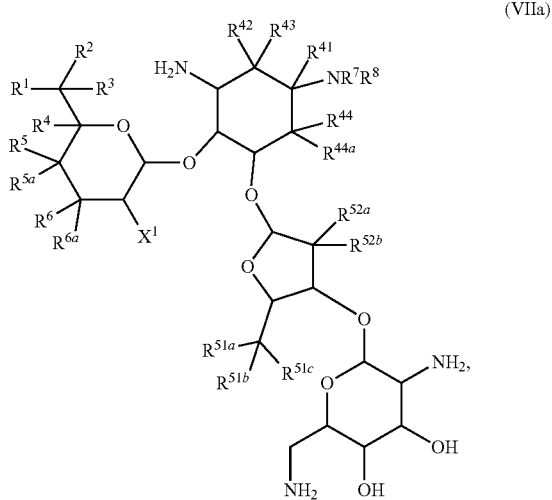

(VIIa)

or a pharmaceutically acceptable salt, solvate, tautomer, or stereoisomer thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl, wherein the alkyl, cycloalkyl, or aryl is unsubstituted or substituted with one or more substituents independently selected from the group consisting of halogen, cyano, aryl, —$SR^{12}$, —$SO_2R^{13}$, —$OSF_2NR^{14}R^{15}$, —$NR^{14}R^{15}$, and —$OR^{16}$, and wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and 1wherein each $R^{17}$, $R^{18}$, $R^{19}$, $R^{20}$, and $R^{21}$ is independently H or alkyl, or $R^2$ and $R^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl; $R^4$ is H;

$R^5$ is H, —$OR^{27}$, —$NR^{28}R^{29}$, halogen, or alkyl, wherein each $R^{27}$, $R^{28}$, and $R^{29}$ is independently H or $C_1$-$C_6$alkyl, wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and wherein each $R^{30}$, $R^{31}$, $R^{32}$, $R^{33}$, and $R^{34}$ is independently H or alkyl, $R^6$ is H, $NR^{28}R^{29}$, F, Br, I, or alkyl, wherein each $R^{28}$ and $R^{29}$ is independently H or $C_1$-$C_6$alkyl, wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and wherein each $R^{30}$, $R^{31}$, $R^{32}$, $R^{33}$, and $R^{34}$ is independently H or alkyl, $R^{5a}$ is H, —$OR^{53}$, —$NR^{54}R^{55}$, halogen, or alkyl, wherein each $R^{53}$, $R^{54}$, and $R^{55}$ is independently H or $C_1$-$C_6$alkyl, wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and wherein each $R^{56}$, $R^{57}$, $R^{58}$, $R^{59}$, and $R^{60}$ is independently H or alkyl, $R^{6a}$ is H, $NR^{54}R^{55}$, F, Br, I, or alkyl, wherein each $R^{54}$ and $R^{55}$ is independently H or $C_1$-$C_6$alkyl, wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and wherein each $R^{56}$, $R^{57}$, $R^{58}$, $R^{59}$, and $R^{60}$ is independently H or alkyl;

$R^7$ is H or $C_1$-$C_3$alkyl;

$R^8$ is H, $C_1$-$C_6$alkyl, an amino protecting group, or

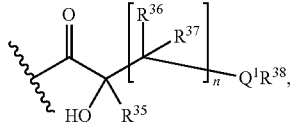

wherein $Q^1$ is NH, O, or S, n is an integer from 0 to 4, $R^{35}$ is H or $C_1$-$C_3$alkyl, each $R^{36}$ and $R^{37}$ is independently H, alkyl, halogen, or —OH, and $R^{38}$ is H, alkyl, or —C(=NH)$NR^{39}R^{40}$, wherein $R^{39}$ and $R^{40}$ are independently H or $C_1$-$C_3$alkyl, or $R^{35}$ and $R^{38}$, together with the atoms to which they are attached, form a heterocycloalkyl group comprising at least one N;

$R^{41}$ is H, —CN, —CONH$_2$ or C$_1$-C$_3$alkyl, wherein the C$_1$-C$_3$alkyl is unsubstituted or substituted with one or more substituents selected from the group consisting of —OH, —OC(O)CH$_3$, —NH$_2$, —CN, —CONH$_2$, and halogen;

$R^{42}$ and $R^{43}$ are, independently H, —OH, —OR$^{45}$, —NR$^{46}$R$^{47}$, or halogen,
 wherein each $R^{45}$, $R^{46}$ and $R^{47}$ is independently H, alkyl, —CONH$_2$, or —COCH$_3$,
 wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

$R^{44}$ and $R^{44a}$ are, independently H, halogen, —OH, C$_1$-C$_3$alkoxy, or —OC(O)CH$_3$;

X$^1$ is H, NH$_2$, OH, or halogen;

$R^{51a}$, $R^{51b}$, and $R^{51c}$ are, independently, H, OH, or —OR$^{51d}$,
 wherein each $R^{51d}$ is, independently, alkyl or —COCH$_3$,
 wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

$R^{52a}$ and $R^{52b}$ are independently H, OH, or —OR$^{52c}$,
 wherein each $R^{52c}$ is, independently, alkyl or —COCH$_3$,
 wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;
 wherein if R$^5$ is —OR$^{27}$ or R$^{5a}$ is —OR$^{53}$, then at least one of R$^6$ and R$^{6a}$ are other than H,
 wherein if each of R$^5$, R$^{5a}$, R$^6$, and R$^{6a}$ are H, then R$^1$ is not —OR$^9$, wherein R$^9$ is H, and
 wherein if each of R$^5$, R$^{5a}$, R$^6$, and R$^{6a}$ are H and R$^1$ is —NR$^{10}$R$^{11}$, then R$^8$ is not In some embodiments, the compound of formula (VIIa) is of formula (VIIa-X):

or a pharmaceutically acceptable salt, tautomer, or solvate thereof.

One aspect of the disclosure relates to a compound of formula (VIIb):

or a pharmaceutically acceptable salt, solvate, tautomer, or stereoisomer thereof, wherein as valence and stability permit, R$^1$ is —OR$^9$ or —NR$^{10}$R$^{11}$, wherein R$^9$, R$^{10}$, and R$^{11}$ are independently H or C$_1$-C$_6$alkyl, wherein the C$_1$-C$_6$alkyl is unsubstituted or substituted with one or more —OH;

R$^2$ and R$^3$ are independently H, alkyl, cycloalkyl, or aryl,
 wherein the alkyl, cycloalkyl, or aryl is unsubstituted or substituted with one or more substituents independently selected from the group consisting of halogen, cyano, aryl, —SR$^{12}$, —SO$_2$R$^{13}$, —OSF$_2$NR$^{14}$R$^{15}$, —NR$^{14}$R$^{15}$, and —OR$^{16}$, and
 wherein each R$^{12}$, R$^{13}$, R$^{14}$, R$^{15}$, and R$^{16}$ is independently H or alkyl, or R$^1$ and R$^2$, together with the atom to which they are attached, form a heterocycloalkyl group comprising at least one heteroatom selected from the group consisting of N and O,
 wherein the heterocycloalkyl group is unsubstituted or substituted with one or more substituents independently selected from the group consisting of halogen, cyano, —SR$^{17}$, —SO$_2$R$^{18}$, —NR$^{19}$R$^{20}$, and —OR$^{21}$, and
 wherein each R$^{17}$, R$^{18}$, R$^{19}$, R$^{20}$, and R$^{21}$ is independently H or alkyl, or R$^2$ and R$^3$, together with the atom to which they are attached, form a cycloalkyl group or a heterocycloalkyl group,
 wherein the cycloalkyl group or heterocycloalkyl group is unsubstituted or substituted with one or more substituents independently selected from the group consisting of halogen, cyano, —SR$^{22}$, —SO$_2$R$^{23}$, —NR$^{24}$R$^{25}$, and —OR$^{26}$, and
 wherein each R$^{22}$, R$^{23}$, R$^{24}$, R$^{25}$, and R$^{26}$ is independently H or alkyl; R$^4$ is H;

R$^5$ is H, NR$^{28}$R$^{29}$, F, Br, I, or alkyl, wherein each R$^{28}$ and R$^{29}$ is independently H or C$_1$-C$_6$alkyl,
 wherein the alkyl or C$_1$-C$_6$alkyl is unsubstituted or substituted with one or more substituents selected from the group consisting of halogen, —OR$^{30}$, —NR$^{31}$R$^{32}$, —SR$^{33}$, and —SO$_2$R$^{34}$, and wherein each R$^{30}$, R$^{31}$, R$^{32}$, R$^{33}$, and R$^{34}$ is independently H or alkyl, R$^6$ is H, —OR$^{27}$, —NR$^{28}$R$^{29}$, halogen, or alkyl, wherein each R$^{27}$, R$^{28}$, and R$^{29}$ is independently H or C$_1$-C$_6$alkyl,
wherein the alkyl or C$_1$-C$_6$alkyl is unsubstituted or substituted with one or more substituents selected from the group consisting of halogen, —OR$^{30}$, —NR$^{31}$R$^{32}$, —SR$^{33}$, and —SO$_2$R$^{34}$, and wherein each R$^{30}$, R$^{31}$, R$^{32}$, R$^{33}$, and R$^{34}$ is independently H or alkyl, R$^{5a}$ is H, NR$^{54}$R$^{55}$, F, Br, I, or alkyl, wherein each R$^{54}$ and R$^{55}$ is independently H or C$_1$-C$_6$alkyl,
wherein the alkyl or C$_1$-C$_6$alkyl is unsubstituted or substituted with one or more substituents selected from the group consisting of halogen, —OR$^{56}$, —NR$^{57}$R$^{58}$, —SR$^{59}$, and —SO$_2$R$^{60}$, and wherein each R$^{56}$, R$^{57}$, R$^{58}$, R$^{59}$, and R$^{69}$ is independently H or alkyl, R$^{6a}$ is H, —OR$^{53}$, —NR$^{54}$R$^{55}$, halogen, or alkyl, wherein each R$^{53}$, R$^{54}$, and R$^{55}$ is independently H or C$_1$-C$_6$alkyl,
wherein the alkyl or C$_1$-C$_6$alkyl is unsubstituted or substituted with one or more substituents selected from the group consisting of halogen, —OR$^{56}$, —NR$^{57}$R$^{58}$, —SR$^{59}$, and —SO$_2$R$^{60}$, and wherein each R$^{56}$, R$^{57}$, R$^{58}$, R$^{59}$, and R$^{60}$ is independently H or alkyl; R$^7$ is H or C$_1$-C$_3$alkyl;

R$^8$ is H, C$_1$-C$_6$alkyl, an amino protecting group, or

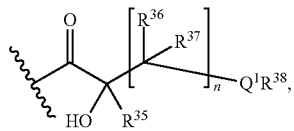

wherein Q$^1$ is NH, O, or S,
n is an integer from 0 to 4,
R$^{35}$ is H or C$_1$-C$_3$alkyl,
each R$^{36}$ and R$^{37}$ is independently H, alkyl, halogen, or —OH, and
R$^{38}$ is H, alkyl, or —C(=NH)NR$^{39}$R$^{49}$, wherein R$^{39}$ and R$^{40}$ are independently H or C$_1$-C$_3$alkyl, or
R$^{35}$ and R$^{38}$, together with the atoms to which they are attached, form a heterocycloalkyl group comprising at least one N;
R$^{41}$ is H, —CN, —CONH$_2$ or C$_1$-C$_3$alkyl, wherein the C$_1$-C$_3$alkyl is unsubstituted or substituted with one or more substituents selected from the group consisting of —OH, —OC(O)CH$_3$, —NH$_2$, —CN, —CONH$_2$, and halogen;
R$^{42}$ and R$^{43}$ are, independently H, —OH, —OR$^{45}$, —NR$^{46}$R$^{47}$, or halogen,
wherein each R$^{45}$, R$^{46}$ and R$^{47}$ is independently H, alkyl, —CONH$_2$, or —COCH$_3$,
wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;
R$^{44}$ and R$^{44a}$ are, independently H, halogen, —OH, C$_1$-C$_3$alkoxy, or —OC(O)CH$_3$;
X$^1$ is H, NH$_2$, OH, or halogen;
R$^{51a}$, R$^{51b}$, and R$^{51c}$ are, independently, H, OH, or —OR$^{51d}$,
wherein each R$^{51d}$ is, independently, alkyl or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

R$^{52a}$ and R$^{52b}$ are independently H, OH, or —OR$^{52c}$,
wherein each R$^{52c}$ is, independently, alkyl or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

wherein if R$^6$ is —OR$^{27}$ or R$^{11a}$ is —OR$^{53}$, then at least one of R$^5$ and R$^{5a}$ are other than H, wherein if R$^5$ is NR$^{28}$R$^{29}$ or R$^{5a}$ is NR$^{54}$R$^{55}$, then R$^1$ is not —OR$^9$, wherein R$^9$ is H, wherein if each of R$^5$, R$^{5a}$, R$^6$, and R$^{6a}$ are H, then R$^1$ is not —OR$^9$, wherein R$^9$ is H, and wherein if each of R$^5$, R$^{5a}$, R$^6$, and R$^{6a}$ are H and R$^1$ is —NR$^{10}$R$^{11}$, then R$^8$ is not

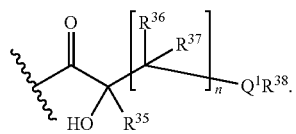

In some embodiments, the compound of formula (VIIb) is of formula (VIIb-X):

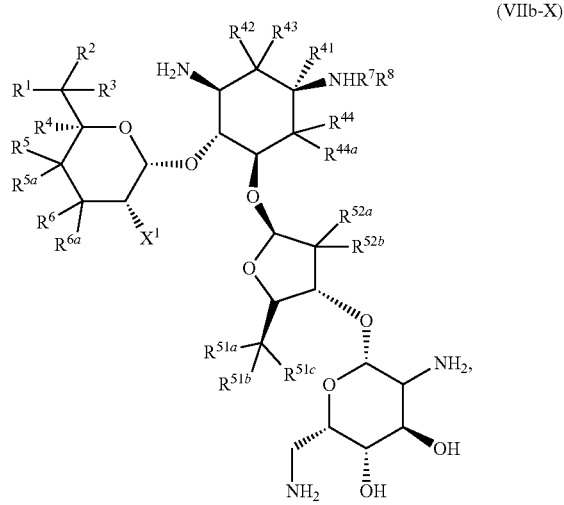

(VIIb-X)

or a pharmaceutically acceptable salt, tautomer, or solvate thereof.

In some embodiments, the compound of formula (IV) is of formula (II):

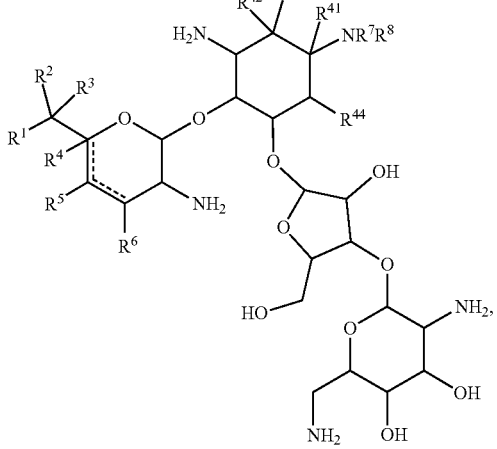

(II)

or a pharmaceutically acceptable salt, solvate, tautomer, or stereoisomer thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the alkyl is unsubstituted or substituted with one or more —OH;

$R^2$ and $R^3$ are independently selected from the group consisting of H, alkyl, cycloalkyl, and aryl,
  wherein the alkyl, cycloalkyl, or aryl is unsubstituted or substituted with one or more substituents independently selected from the group consisting of halogen, cyano, aryl, —$SR^{12}$, —$SO_2R^{13}$, —$NR^{14}R^{15}$, and —$OR^{16}$, and
  wherein each $R^{12}$, $R^{13}$, $R^{14}$, $R^{15}$, and $R^{16}$ is independently H or alkyl; or $R^1$ and $R^2$, together with the atom to which they are attached, form a heterocycloalkyl group comprising at least one heteroatom selected from the group consisting of N and O,
  wherein the heterocycloalkyl group is unsubstituted or substituted with one or more substituents independently selected from the group consisting of halogen, cyano, —$SO_2R^{18}$, —$NR^{19}R^{20}$, and —$OR^{21}$, and
  wherein each $R^{17}$, $R^{18}$, $R^{19}$, $R^{20}$, and $R^{21}$ is independently H or alkyl; or $R^2$ and $R^3$, together with the atom to which they are attached, form a cycloalkyl group or a heterocycloalkyl group,
  wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and
  wherein each $R^{22}$, $R^{23}$, $R^{24}$, $R^{25}$, and $R^{26}$ is independently H or alkyl; and wherein at least one of $R^2$ and $R^3$ is other than H;

$R^4$ is H or absent;

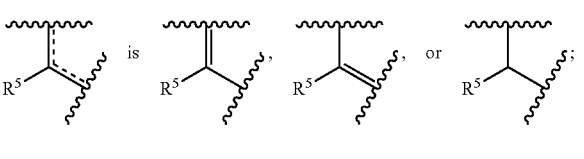

$R^5$ and $R^6$ are independently selected from the group consisting of H, —$OR^{27}$, —$NR^{28}R^{29}$, halogen, and alkyl, wherein each $R^{27}$, $R^{28}$, and $R^{29}$ is independently H or $C_1$-$C_6$alkyl,
  wherein the alkyl is unsubstituted or substituted with one or more substituents selected from the group consisting of halogen, —$OR^{30}$, —$NR^{31}R^{32}$, —$SR^{33}$, and —$SO_2R^{34}$; and
  wherein each $R^{30}$, $R^{31}$, $R^{32}$, $R^{33}$, and $R^{34}$ is independently H or alkyl;

$R^7$ is H or $C_1$-$C_3$alkyl;

$R^8$ is H or

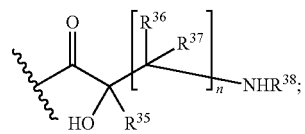

wherein n is an integer from 0 to 4, $R^{35}$ is H or $C_1$-$C_3$alkyl;

each $R^{36}$ and $R^{37}$ is independently selected from the group consisting of H, alkyl, halogen, and —OH, and $R^{38}$ is H, alkyl, or —C(═NH)$NR^{39}R^{49}$, wherein $R^{39}$ and $R^{40}$ are independently H or $C_1$-$C_3$alkyl; or $R^{35}$ and $R^{38}$, together with the atoms to which they are attached, form a heterocycloalkyl group comprising at least one N;

$R^{41}$ is H, $C_1$-$C_3$alkyl, wherein the alkyl is unsubstituted or substituted by —OH or halogen;

$R^{42}$ and $R^{43}$ are, independently H, —OH, or halogen; and $R^{44}$ is H, halogen, —OH, or $C_1$-$C_3$alkoxy.

In some embodiments, the compound of formula (II) is of formula (II-A):

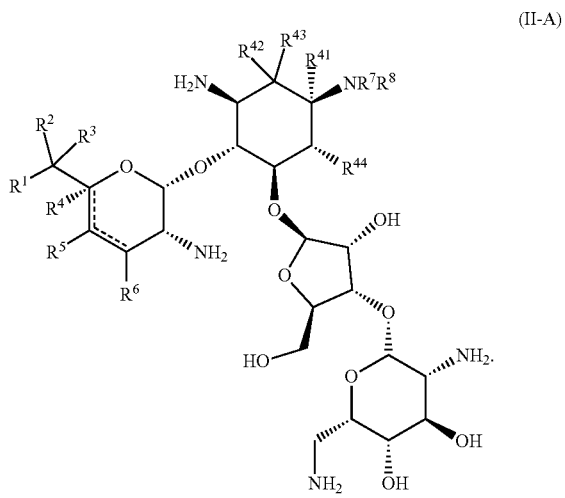

(II-A)

In some embodiments, the compound of formula (IV) is of formula (I):

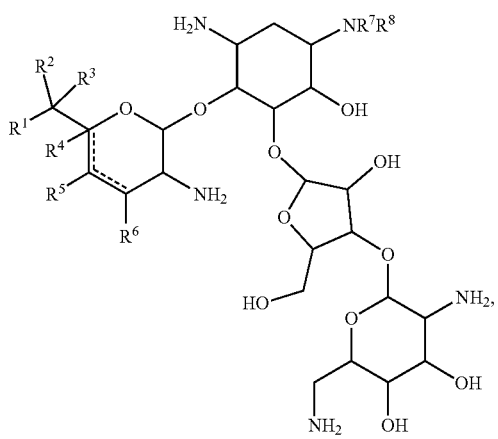

(I)

or a pharmaceutically acceptable salt, solvate, tautomer, or stereoisomer thereof, wherein as valence and stability permit, $R^1$ is $-OR^9$ or $-NR^{10}R^{11}$, wherein $R^9$, $R^{10}$, and $R^{11}$ are independently H or $C_1$-$C_6$alkyl, wherein the alkyl is unsubstituted or substituted with one or more $-OH$;

$R^2$ and $R^3$ are independently selected from the group consisting of H, alkyl, cycloalkyl, and aryl,
wherein the alkyl, cycloalkyl, or aryl is unsubstituted or substituted with one or more substituents independently selected from the group consisting of halogen, cyano, aryl, $-SR^{12}$, $-SO_2R^{13}$, $-NR^{14}R^{15}$, and $-OR^{16}$, and
wherein each $R^{12}$, $R^{13}$, $R^{14}$, $R^{15}$, and $R^{16}$ is independently H or alkyl; or $R^1$ and $R^2$, together with the atom to which they are attached, form a heterocycloalkyl group comprising at least one heteroatom selected from the group consisting of N and O,
wherein the heterocycloalkyl group is unsubstituted or substituted with one or more substituents independently selected from the group consisting of halogen, cyano, $-SR^{17}$, $-SO_2R^{18}$, $-NR^{19}R^{20}$, and $-OR^{21}$, and
wherein each $R^{17}$, $R^{18}$, $R^{19}$, $R^{20}$, and $R^{21}$ is independently H or alkyl; or $R^2$ and $R^3$, together with the atom to which they are attached, form a cycloalkyl group or a heterocycloalkyl group,
wherein the cycloalkyl group or heterocycloalkyl group is unsubstituted or substituted with one or more substituents independently selected from the group consisting of halogen, cyano, $-SR^{22}$, $-SO_2R^{23}$, $-NR^{24}R^{25}$, and $-OR^{26}$, and
wherein each $R^{22}$, $R^{23}$, $R^{24}$, $R^{25}$, and $R^{26}$ is independently H or alkyl; and wherein at least one of $R^2$ and $R^3$ is other than H;

$R^4$ is H or absent;

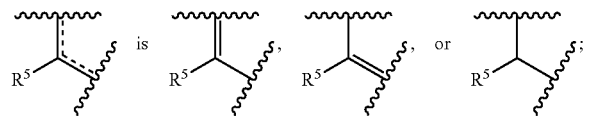

$R^5$ and $R^6$ are independently selected from the group consisting of H, $-OR^{27}$, $-NR^{28}R^{29}$, halogen, and alkyl, wherein each $R^{27}$, $R^{28}$, and $R^{29}$ is independently H or $C_1$-$C_6$alkyl,
wherein the alkyl is unsubstituted or substituted with one or more substituents selected from the group consisting of halogen, $-OR^{30}$, $-NR^{31}R^{32}$, $-SR^{33}$, and $-SO_2R^{34}$; and
wherein each $R^{30}$, $R^{31}$, $R^{32}$, $R^{33}$, and $R^{34}$ is independently H or alkyl;

$R^7$ is H or $C_1$-$C_3$alkyl;

$R^8$ is H or

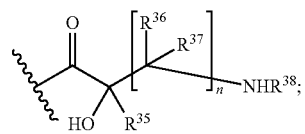

wherein n is an integer from 0 to 4, $R^{35}$ is H or $C_1$-$C_3$alkyl;

each $R^{36}$ and $R^{37}$ is independently selected from the group consisting of H, alkyl, halogen, and $-OH$, and $R^{38}$ is H, alkyl, or $-C(=NH)NR^{39}R^{40}$, wherein $R^{39}$ and $R^{40}$ are independently H or $C_1$-$C_3$ alkyl; or $R^{35}$ and $R^{38}$, together with the atoms to which they are attached, form a heterocycloalkyl group comprising at least one N.

In some embodiments, the compound of formula (I) is of formula (I-A):

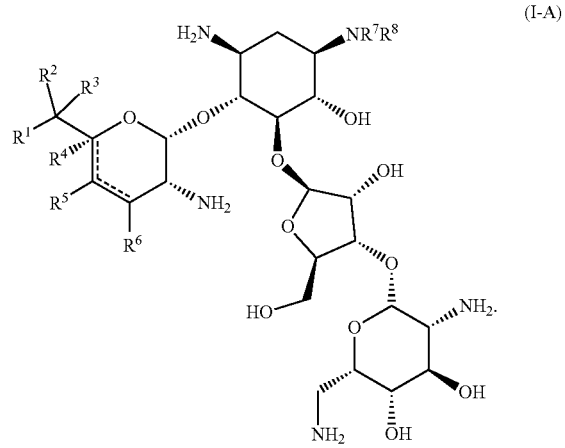

(I-A)

One aspect of the disclosure relates to a pharmaceutical composition comprising a compound disclosed herein, or a pharmaceutically acceptable salt, solvate, tautomer, or stereoisomer thereof, and a pharmaceutically acceptable carrier.

Another aspect of the disclosure relates to a method for treating a bacterial infection in a subject, comprising administering to a subject in need thereof a therapeutically effective amount of a compound disclosed herein, or a pharmaceutically acceptable salt, solvate, tautomer, or stereoisomer thereof.

One aspect of the disclosure relates to a method for treating a bacterial infection in a subject, comprising administering to a subject in need thereof a therapeutically effective amount of a pharmaceutical composition disclosed herein.

Another aspect of the disclosure relates to use of a compound disclosed herein, or a pharmaceutically acceptable salt, solvate, tautomer, or stereoisomer thereof, in the manufacture of a medicament for treating a bacterial infection in a subject in need thereof.

One aspect of the disclosure relates to use of a pharmaceutical composition disclosed herein in the manufacture of a medicament for treating a bacterial infection in a subject in need thereof.

Another aspect of the disclosure relates to a compound disclosed herein, or a pharmaceutically acceptable salt, solvate, tautomer, or stereoisomer thereof, for use in a method of treating a bacterial infection in a subject in need thereof.

One aspect of the disclosure relates to a pharmaceutical composition disclosed herein for use in a method of treating a bacterial infection in a subject in need thereof.

In some embodiments of any of the foregoing or following, the bacterial infection is a Gram-negative bacterial infection.

In some embodiments of any of the foregoing or following, the bacterial infection is infection of a *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella, Francisella, Yersinia, Corynebacterium, Moraxella* , or *Enterococcus* species.

DESCRIPTION OF THE FIGURES

FIG. 1 shows various possible, but not limiting, substituents on the compounds of the present disclosure.

DETAILED DESCRIPTION

The present disclosure provides antibacterial aminoglycoside compounds, including stereoisomers, tautomers, solvates, and pharmaceutically acceptable salts thereof, and pharmaceutical compositions comprising said compounds, or stereoisomers, tautomers, solvates, and pharmaceutically acceptable salts thereof. The compounds and pharmaceutical compositions of the disclosure may be useful for treating bacterial infections as well as medical conditions associated therewith. The compounds and pharmaceutical compositions of the disclosure may also be useful for treating difficult-to-treat resistance mechanisms as well as multidrug resistant (MDR) bacterial infections.

This disclosure also features methods of and uses for treating a bacterial infection comprising administering to a subject in need thereof a therapeutically effective amount of a compound of the disclosure, or a pharmaceutically acceptable salt, solvate, stereoisomer, or tautomer thereof, or a therapeutically effective amount of a pharmaceutical composition comprising a compound of the disclosure, or a pharmaceutically acceptable salt, solvate, stereoisomer, or tautomer thereof The compounds and pharmaceutical compositions of the present disclosure may be useful for treating a variety of bacterial infections including, but not limited to, bacterial infections caused by *Staphylococcus* sp., *Lactobacillus* sp., *Streptococcus* sp., *Sarcina* sp., *Escherichia* sp., *Enterobacter* sp., *Klebsiella* sp., *Pseudomonas* sp., *Acinetobacter* sp., *Mycobacterium* sp., *Proteus* sp., *Campylobacter* sp., *Citrobacter* sp., *Nisseria* sp., *Baccillus* sp., *Bacteroides* sp., *Peptococcus* sp., *Clostridium* sp., *Salmonella* sp., *Shigella* sp., *Serratia* sp., *Haemophilus* sp., *Brucella* sp., *Francisella* sp., *Yersinia* sp., *Corynebacterium* sp., *Moraxella* sp., or *Enterococcus* sp.

The compounds and pharmaceutical compositions of the present disclosure may be useful for treating a variety of bacterial infections including, but not limited to, bacterial infections caused by *Escherichia coli, Klebsiella* sp., *Klebsiella pneumoniae, Klebsiella oxytoca, Enterobacter* sp., *Enterobacter cloacae, Enterobacter aerogenes, Citrobacter* sp., *Citrobacter freundii, Citrobacter koseri, Proteus mirabilis, Bacillus anthraces, P. aeruginosa, A. baumannii, Proteus vulgaris,* or *Yersinia pestis.*

In some embodiments, the compounds and pharmaceutical compositions of the present disclosure may be useful for treating a bacterial infection caused by Gram-negative bacteria. In certain such embodiments, the Gram-negative bacteria may include, but are not limited to, *Escherichia* sp., *Enterobacter* sp., *Klebsiella* sp., *Pseudomonas* sp., *Acinetobacter* sp., *Proteus* sp., *Campylobacter* sp., *Citrobacter* sp., *Nisseria* sp., *Bacteroides* sp., *Salmonella* sp., *Shigella* sp., *Serratia* sp., *Haemophilus* sp., *Brucella* sp., *Francisella* sp., *Yersinia* sp., or *Moraxella* sp.

In some embodiments, the compounds and pharmaceutical compositions of the present disclosure may be useful for treating a bacterial infection caused by Gram-positive bacteria. In certain such embodiments, the Gram-positive bacteria may include, but are not limited to, *Staphylococcus* sp., *Lactobacillus* sp., *Streptococcus* sp., *Sarcina* sp., *Baccillus* sp., *Peptococcus* sp., *Clostridium* sp., *Corynebacterium* sp., or *Enterococcus* sp.

In some embodiments, the compounds and pharmaceutical compositions of the present disclosure may be useful for treating a bacterial infection caused by Methicillin-resistant *Staphylococcus aureus* (MRSA).

In some embodiments, the compounds or pharmaceutical compositions disclosed herein are also useful for treating bacterial infections caused by *Enterobacteriaceae.*

In some embodiments, the compounds or pharmaceutical compositions disclosed herein are also useful for treating bacterial infections caused by KPC-producing carbapenem-resistant *Enterobacteriaceae* (CRE).

In some embodiments, the compounds or pharmaceutical compositions of the disclosure may be useful for treating bacterial infections caused by multidrug resistant (MDR) bacteria.

The following description sets forth numerous exemplary configurations, methods, parameters, and the like. It should be recognized, however, that such description is not intended as a limitation on the scope of the present disclosure, but is instead provided as a description of exemplary embodiments.

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, as used herein, the terms "including," "containing," and "comprising" are used in their open, non-limiting sense.

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The articles "a" and "an" as used in this disclosure may refer to one or more than one (i.e., to at least one) of the grammatical object of the article. By way of example, "an element" may mean one element or more than one element.

The term "and/or" as used in this disclosure may mean either "and" or "or" unless indicated otherwise.

"Amino" refers to —$NH_2$.

"Hydroxy" or "hydroxyl" refers to —OH.

The term "oxo" as used herein refers to an "=O" group. It can also be abbreviated herein as C(O) or as C=O.

"Alkyl" refers to a saturated straight or branched hydrocarbon chain radical consisting solely of carbon and hydrogen atoms, having from one to twelve carbon atoms ($C_1$-$C_{12}$alkyl); one to eight carbon atoms ($C_1$-$C_8$alkyl); one to six carbon atoms ($C_1$-$C_6$alkyl), e.g., methyl, ethyl, n-propyl, 1-methylethyl (iso-propyl), n-butyl, n-pentyl, 1,1-dimethylethyl (t-butyl), 3-methylhexyl, or 2-methylhexyl; or one to three carbon atoms ($C_1$-$C_3$alkyl). An alkyl group can be unsubstituted or substituted.

"Cycloalkyl" refers to a single saturated all carbon ring having 3 to 20 carbon atoms (i.e., $C_3$-$C_{20}$ cycloalkyl), for example from 3 to 15 carbon atoms, for example, from 3 to 12 carbon atoms. In certain embodiments, the cycloalkyl group is either monocyclic ("monocyclic cycloalkyl") or contains a fused, bridged or spiro ring system such as a bicyclic system ("bicyclic cycloalkyl") and can be saturated. "Cycloalkyl" includes ring systems where the cycloalkyl ring, as defined herein, is fused with one or more cycloalkyl, cycloalkenyl, heterocyclyl, aryl or heteroaryl groups, wherein the point of attachment is on a cycloalkyl ring, and, in such instances, the number of carbon atoms recited continues to designate the number of carbons in the cycloalkyl ring containing the point of attachment. Examples of cycloalkyl groups include cyclohexyl, and cycloheptyl.

"Heteroaryl," as used herein, refers to a monocyclic or polycyclic group comprising at least one aromatic ring, wherein the aromatic ring comprises at least one ring heteroatom independently selected from the group consisting of N, O, and S. The heteroaryl group may comprise 5, 6, 7, 8, 9, 10, 11, 12, or more ring atoms, where ring atoms refer to the sum of carbon and heteroatoms in the one or more rings (e.g., be a 5-membered, 6-membered, 7-membered, 8-membered, 9-membered, 10-membered, 11-membered, or 12-membered heteroaryl). In some embodiments, heteroaryl includes groups with an aromatic ring that comprises at least one ring heteroatom independently selected from the group consisting of N, O, and S, (e.g., pyridinyl, pyrazinyl, furanyl, thiophenyl). In certain embodiments, heteroaryl includes polycyclic groups with an aromatic ring comprising at least one ring heteroatom, fused to a non-aromatic hydrocarbon ring (e.g., 5,6,7,8-tetrahydroquinolinyl; 4,5,6,7-tetrahydroisobenzofuranyl). In some embodiments, heteroaryl includes polycyclic groups with an aromatic ring comprising at least one ring heteroatom fused to an aromatic hydrocarbon ring (e.g., quinolinyl, quinoxalinyl, benzothiazolyl). In still further embodiments, heteroaryl includes polycyclic groups with two fused aromatic rings, wherein each ring comprises at least one ring heteroatom (e.g., naphthyridinyl). Heteroaryl may include groups comprising 1 to 5 ring heteroatoms, 1 to 4 ring heteroatoms, 1 to 3 ring heteroatoms, 1 or 2 ring heteroatoms, or 1 ring heteroatom, wherein each ring heteroatom is independently selected from the group consisting of N, O, and S. In one example, a heteroaryl has 3 to 8 ring carbon atoms, with 1 to 3 ring heteroatoms independently selected from N, O, and S. Examples of heteroaryl groups include pyridyl, pyridazinyl, pyrimidinyl, benzothiazolyl, and pyrazolyl.

"Aryl" refers to cyclic, aromatic hydrocarbon group that has 1 to 3 aromatic rings, including monocyclic or bicyclic groups. Where the aryl group has two aromatic rings (bicyclic, etc.), the aromatic rings of the aryl group may be joined at a single point. An aryl group with two fused rings may include an unsaturated or partially saturated ring fused with a fully saturated ring. Examples of aryl groups include, but are not limited to, phenyl, naphthyl, phenalenyl, indanyl, indenyl, and tetrahydronaphthalenyl. Unless stated otherwise specifically in the specification, an aryl group may be substituted or unsubstituted.

"Heterocycloalkyl" refers to non-aromatic, monocyclic or polycyclic ring containing carbon and at least one heteroatom selected from the group consisting of oxygen, nitrogen, and sulfur. The heterocycloakyl group may be saturated or unsaturated, and may comprise 3, 4, 5, 6, 7, or more ring atoms. Examples of heterocyclyl rings include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxinyl, piperidinyl, morpholinyl, thiomorpholinyl, thiomorpholinyl S-oxide, thiomorpholinyl S-dioxide, piperazinyl, azepinyl, oxepinyl, diazepinyl, and tropanyl. Unless stated otherwise specifically in the specification, a heterocycloalkyl group may be substituted or unsubstituted.

"Halo" or "halogen" refers to bromo, chloro, fluoro, or iodo.

The term "substituted" used herein means a group wherein at least one hydrogen atom is replaced by a bond to a non-hydrogen atom such as, but not limited to: a halogen atom such as F, Cl, Br, and I; an oxygen atom in a hydroxyl group; and a nitrogen atom in an amino group. Combinations of substituents envisioned by the present disclosure are typically those that result in the formation of stable or chemically feasible compounds.

As used herein, the term "unsubstituted" may mean that the specified group bears no substituents beyond the moiety recited (e.g., where valency satisfied by hydrogen).

"Stable compound" and "stable structure" may indicate a compound that is sufficiently robust to survive isolation to a useful degree of purity from a reaction mixture, and formulation into an efficacious therapeutic agent.

Compounds of Disclosed Formulae: Compounds of Formula (I), Formula (II), Formula (III), Formula (IV), Formula (IVa), Formula (V), Formula (VI), Formula (VIIa), and Formula (VIIb)

Provided herein are compounds of Formula (I), Formula (II), Formula (III), Formula (IV), Formula (IVa), Formula (V), Formula (VI), Formula (VIIa), and Formula (VIIb).

Provided herein are compounds of formula (IV):

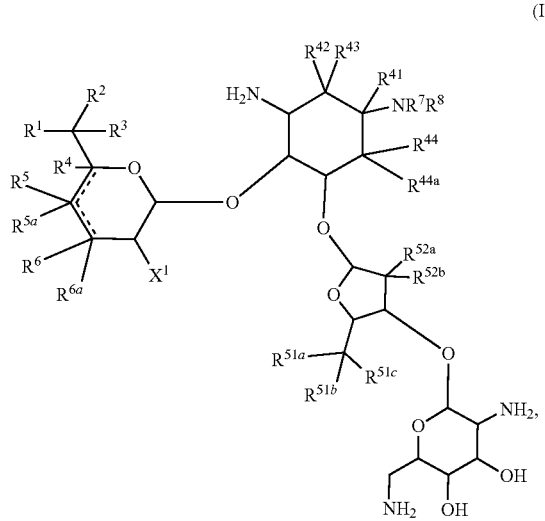

(IV)

and pharmaceutically acceptable salts, solvates, tautomers, or stereoisomers thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl, wherein the alkyl, cycloalkyl, or aryl is unsubstituted or substituted with one or more substituents independently selected from the group consisting of halogen, cyano, aryl, —$SR^{12}$, —$SO_2R^{13}$, —$OSF_2NR^{14}R^{15}$, —$NR^{14}R^{15}$, and —$OR^{16}$, and
wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O,
wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and
wherein each $R^{17}$, $R^{18}$, $R^{19}$, $R^{20}$, and $R^{21}$ is independently H or alkyl, or
$R^2$ and $R^3$, together with the atom to which they are attached, form a cycloalkyl group or a heterocycloalkyl group,
wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and
wherein each $R^{22}$, $R^{23}$, $R^{24}$, $R^{25}$, and $R^{26}$ is independently H or alkyl;

$R^4$ is H or absent;

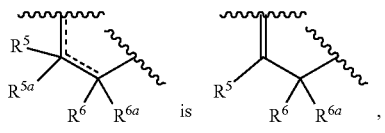

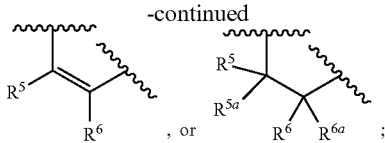

$R^5$ and $R^6$ are independently H, —$OR^{27}$, —$NR^{28}R^{29}$, halogen, or alkyl, wherein each $R^{27}$, $R^{28}$, and $R^{29}$ is independently H or $C_1$-$C_6$alkyl,
wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and
wherein each $R^{30}$, $R^{31}$, $R^{32}$, $R^{33}$, and $R^{34}$ is independently H or alkyl, $R^{5a}$ and $R^{6a}$ are, independently, absent or independently H, —$OR^{53}$, —$NR^{54}R^{55}$, halogen, or alkyl, wherein each $R^{53}$, $R^{54}$, and $R^{55}$ is independently H or $C_1$-$C_6$alkyl,
wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and
wherein each $R^{56}$, $R^{57}$, $R^{58}$, $R^{59}$, and $R^{60}$ is independently H or alkyl, or $R^5$ and $R^{5a}$ form an oxo group, or
$R^6$ and $R^{6a}$ form an oxo group;

$R^7$ is H or $C_1$-$C_3$alkyl;

$R^8$ is H, $C_1$-$C_6$alkyl, an amino protecting group, or

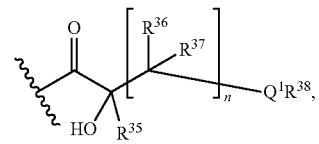

wherein $Q^1$ is NH, O, or S,
n is an integer from 0 to 4,
$R^{35}$ is H or $C_1$-$C_3$alkyl,
each $R^{36}$ and $R^{37}$ is independently H, alkyl, halogen, or —OH, and
$R^{38}$ is H, alkyl, or —C(=NH)$NR^{39}R^{40}$, wherein $R^{39}$ and $R^{40}$ are independently H or $C_1$-$C_3$alkyl, or
$R^{35}$ and $R^{38}$, together with the atoms to which they are attached, form a heterocycloalkyl group comprising at least one N;

$R^{41}$ is H, —CN, —$CONH_2$ or $C_1$-$C_3$alkyl, wherein the $C_1$-$C_3$alkyl is unsubstituted or substituted with one or more substituents selected from the group consisting of —OH, —OC(O)$CH_3$, —$NH_2$, —CN, —$CONH_2$, and halogen;

$R^{42}$ and $R^{43}$ are, independently H, —OH, —$OR^{45}$, —$NR^{46}R^{47}$, or halogen,
wherein each $R^{45}$, $R^{46}$, and $R^{47}$ is independently H, alkyl, —$CONH_2$, or —$COCH_3$,
wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{44}$ and $R^{44a}$ are, independently H, halogen, —OH, $C_1$-$C_3$alkoxy, or —OC(O)$CH_3$;

$X^1$ is H, $NH_2$, OH, or halogen:

$R^{51a}$, $R^{51b}$, and $R^{51c}$ are, independently, H, OH, or —$OR^{51d}$, wherein each $R^{51d}$ is, independently. alkyl or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl; $R^{52a}$ and $R^{52b}$ are independently H, OH, or —OR$^{52c}$, wherein each $R^{52c}$ is, independently, alkyl or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

wherein if $R^2$ and $R^3$ are both H and $R^5$ is —OR$^{27}$ or $R^{5a}$ is —OR$^{53}$, then $R^6$ is not —OR$^{27}$, wherein if $R^2$ and $R^3$ are both H and $R^5$ is —OR$^{27}$ or $R^{5a}$ is —OR$^{53}$, then $R^{6a}$ is not —OR$^{53}$, wherein if $R^2$ and $R^3$ are both H, then at least one of $R^{41}$, $R^{42}$, $R^{43}$, $R^{44}$, or $R^{44a}$ is not H, and wherein if $R^2$ and $R^3$ are both H and one of $R^{44}$ and $R^{44a}$ is —OH, then at least one of $R^{41}$, $R^{42}$, or $R^{43}$ is not H.

In some embodiments, the compound of formula (IV) is of formula (IV-X):

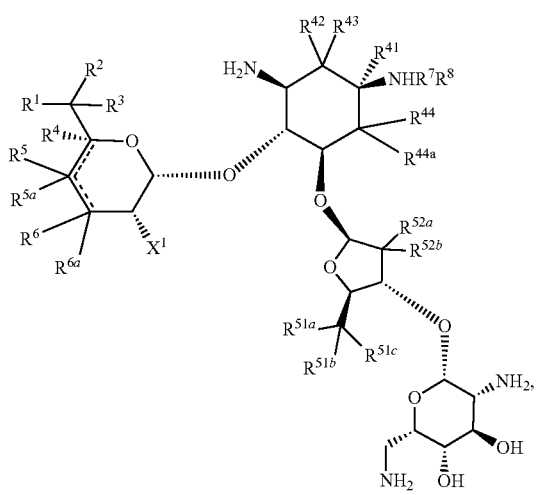

(IV-X)

or a pharmaceutically acceptable salt, solvate, or tautomer thereof, wherein R$^1$, R$^2$, R$^3$, R$^4$,

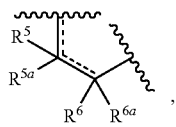

R$^7$, R$^8$, R$^{41}$, R$^{42}$, R$^{43}$, R$^{44}$, R$^{44a}$, X$^1$, R$^{51a}$, R$^{51b}$, R$^{51c}$, R$^{52a}$, and R$^{52b}$ are as defined for formula (IV) herein.

In one aspect, the compound of formula (IV) is a compound of formula (I), including formula (I-A), formula (I-Ai), formula (I-Aii), formula (I-B), formula (I-Bi), and formula (I-Bii), and formula (II), or formula (II-A), or a pharmaceutically acceptable salt, solvate, stereoisomer, or tautomer of any of the foregoing, as disclosed herein.

In one aspect, the compound of formula (IV) is a compound of formula (IV-X); formula (IVa), including formula (IVa-X); formula (V), including formula (V-X); or formula (VI), including formula (VI-X), or a pharmaceutically acceptable salt, solvate, stereoisomer, or tautomer of any of the foregoing, as disclosed herein.

In some embodiments of formula (IV), including formula (IV-X), R$^1$ is —NR$^{10}$R$^{11}$, wherein R$^{10}$ and R$^{11}$ are independently H or C$_1$-C$_6$alkyl, wherein the alkyl is unsubstituted or substituted with one or more —OH. In certain embodiments, R$^{10}$ and R$^{11}$ are independently H, methyl, or hydroxyethyl. In certain embodiments, R$^{10}$ and R$^{11}$ are both H.

In some embodiments of formula (IV), including formula (IV-X), R$^1$ is OR$^9$, wherein R$^9$ is H or C$_1$-C$_6$alkyl, wherein the alkyl is unsubstituted or substituted with one or more —OH. In certain embodiments, R$^9$ is H, methyl, or hydroxyethyl. In certain embodiments, R$^9$ is H.

In some embodiments of formula (IV), including formula (IV-X), R$^2$ and R$^3$ are independently selected from the group consisting of H, alkyl, cycloalkyl, and aryl. In some embodiments, at least one of R$^2$ and R$^3$ is other than H. In certain embodiments, one of R$^2$ and R$^3$ is H.

In some embodiments of formula (IV), including formula (IV-X), R$^2$ is alkyl, cyclopropyl, or phenyl; wherein the alkyl is unsubstituted or substituted with one, two, or three substituents selected from the group consisting of —NH$_2$, —OH, F, —CN, and —S(O)$_2$CH$_3$. In some embodiments, R$^2$ is methyl, ethyl, propyl, butyl, pentyl, hexyl, cyclopropyl, cyclobutyl, cyclopentyl, cyclohexyl, or phenyl. In other embodiments, R$^2$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —SR$^{12}$, —SO$_2$R$^{13}$, —NR$^{14}$R$^{15}$, and —OR$^{16}$. In some embodiments, the one or more substituents are independently selected from the group consisting of halogen, cyano, aryl, —SO$_2$R$^{13}$, —NR$^{14}$R$^{15}$, and —OR$^{16}$. For example, in certain embodiments, the one or more substituents are independently selected from the group consisting of F, Cl, B, I, cyano, —SO$_2$CH$_3$, —NH$_2$, and —OH. In still other embodiments, R$^2$ is methyl; methyl substituted with one or two F; methyl substituted with —SO$_2$CH$_3$; methyl substituted with —NH$_2$; methyl substituted with —OH; ethyl; cyclopropyl; or phenyl. In some embodiments, R$^2$ is H or unsubstituted methyl.

In some embodiments of formula (IV), including formula (IV-X), R$^3$ is methyl, ethyl, propyl, butyl, pentyl, hexyl, cyclopropyl, cyclobutyl, cyclopentyl, cyclohexyl, or phenyl. In other embodiments, R$^3$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —SR$^{12}$, —SO$_2$R$^{13}$, —NR$^{14}$R$^{15}$, and —OR$^{16}$. In some embodiments, the one or more substituents are independently selected from the group consisting of halogen, cyano, aryl, —SO$_2$R$^{13}$, —NR$^{14}$R$^{15}$, and —OR$^{16}$. For example, in certain embodiments, the one or more substituents are independently selected from the group consisting of F, Cl, B, I, cyano, —SO$_2$CH$_3$, —NH$_2$, and —OH. In still other embodiments, R$^3$ is methyl; methyl substituted with one or two F; methyl substituted with —SO$_2$CH$_3$; methyl substituted with —NH$_2$; methyl substituted with —OH; ethyl; cyclopropyl; or phenyl. In certain embodiments, R$^3$ is H or unsubstituted methyl.

In some embodiments of formula (IV), including formula (IV-X), R$^2$ and R$^3$, together with the atom to which they are attached, form a cycloalkyl group or a heterocycloalkyl group. In some embodiments, the cycloalkyl group or heterocycloalkyl group may be unsubstituted or substituted with one or more substituents independently selected from the group consisting of halogen, cyano, —$SR^{22}$, —$SO_2R^{23}$, —$NR^{24}R^{25}$, and —$OR^{26}$, wherein each $R^{22}R^{23}$, $R^{24}$, $R^{25}$, and $R^{26}$ may be independently H or alkyl. In certain embodiments, $R^2$ and $R^3$ together with the atom to which they are attached form a cyclopropyl or oxetanyl. In certain embodiments, $R^2$ and $R^3$ together with the atom to which they are attached form a cyclopropyl.

In some embodiments of formula (IV), including formula (IV-X), $R^4$ is H or absent.

In some embodiments of formula (IV), including formula (IV-X), $R^5$ and $R^6$ are H and $R^{5a}$ and $R^{6a}$ are independently absent or H.

In some embodiments of formula (IV), including formula (IV-X), both $R^5$ and $R^6$ are H.

In some embodiments of formula (IV), including formula (IV-X), both $R^{5a}$ and $R^{6a}$ are H.

In some embodiments of formula (IV), including formula (IV-X), $R^5$ is H or —OH. In some embodiments of formula (IV), including formula (IV-X), $R^5$ is —OH. In some embodiments of formula (IV), including formula (IV-X), $R^5$ is H.

In some embodiments of formula (IV), including formula (IV-X), $R^{5a}$ is H or —OH. In some embodiments of formula (IV), including formula (IV-X), $R^{5a}$ is —OH. In some embodiments of formula (IV), including formula (IV-X), $R^{5a}$ is H.

In some embodiments of formula (IV), including formula (IV-X), $R^6$ is H or —OH. In some embodiments of formula (IV), including formula (IV-X), $R^6$ is —OH. In some embodiments of formula (IV), including formula (IV-X), $R^6$ is H.

In some embodiments of formula (IV), including formula (IV-X), $R^{6a}$ is H or —OH. In some embodiments of formula (IV), including formula (IV-X), $R^{6a}$ is —OH. In some embodiments of formula (IV), including formula (IV-X), $R^{6a}$ is H.

In some embodiments of formula (IV), including formula (IV-X), $R^5$ is H, halogen, or —OH. In certain such embodiments, $R^5$ is halogen. In certain such embodiments, $R^5$ is F.

In some embodiments of formula (IV), including formula (IV-X), $R^{5a}$ is H, halogen, or —OH. In certain such embodiments, $R^{5a}$ is halogen. In certain such embodiments, $R^{5a}$ is F.

In some embodiments of formula (IV), including formula (IV-X), $R^6$ is H, halogen, or —OH. In certain such embodiments, $R^6$ is halogen. In certain such embodiments, $R^6$ is F.

In some embodiments of formula (IV), including formula (IV-X), $R^{6a}$ is H, halogen, or —OH. In certain such embodiments, $R^{6a}$ is halogen. In certain such embodiments, $R^{6a}$ is F.

In some embodiments of formula (IV), including formula (IV-X), $R^5$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (IV), including formula (IV-X), $R^{5a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (IV), including formula (IV-X), $R^6$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (IV), including formula (IV-X), $R^{6a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (IV), including formula (IV-X), $R^4$ is H.

In some embodiments of formula (IV), including formula (IV-X), $X^1$ is $NH_2$. In some embodiments of formula (IV), including formula (IV-X), $X^1$ is OH. In some embodiments of formula (IV), including formula (IV-X), $X^1$ is halogen. In some embodiments of formula (IV), including formula (IV-X), $X^1$ is F. In some embodiments of formula (IV), including formula (IV-X), $X^1$ is Cl. In some embodiments of formula (IV), including formula (IV-X), $X^1$ is Br. In some embodiments of formula (IV), including formula (IV-X), $X^1$ is I.

In some embodiments of formula (IV), including formula (IV-X), $R^{41}$ is H.

In some embodiments of formula (IV), including formula (IV-X), one of $R^{42}$ and $R^{43}$ is —OH. In some embodiments of formula (IV), including formula (IV-X), one of $R^{42}$ and $R^{43}$ is halogen. In some embodiments of formula (IV), including formula (IV-X), one of $R^{42}$ and $R^{43}$ is H. In some embodiments of formula (IV), including formula (IV-X), one of $R^{42}$ and $R^{43}$ is —$NR^{46}R^{47}$. In some embodiments of formula (IV), including formula (IV-X), one of $R^{42}$ and $R^{43}$ is —F. In some embodiments of formula (IV), including formula (IV-X), $R^{42}$ is —F and $R^{43}$ is —F. In some embodiments of formula (IV), including formula (IV-X), one of $R^{42}$ and $R^{43}$ is —OH. In some embodiments of formula (IV), including formula (IV-X), one of $R^{42}$ and $R^{43}$ is —$OR^{45}$.

In some embodiments of formula (IV), including formula (IV-X), $R^{42}$ and $R^{43}$ are H.

In some embodiments of formula (IV), including formula (IV-X), one of $R^{44}$ and $R^{44a}$ is —OH. In some embodiments of formula (IV), including formula (IV-X), one of $R^{44}$ and $R^{44a}$ is —$OCH_3$. In some embodiments of formula (IV), including formula (IV-X), one of $R^{44}$ and $R^{44a}$ is —F. In some embodiments of formula (IV), including formula (IV-X), $R^{44}$ and $R^{44a}$ are —F. In some embodiments of formula (IV), including formula (IV-X), $R^{44}$ and $R^{44a}$ are H. In some embodiments of formula (IV), including formula (IV-X), one of $R^{44}$ and $R^{44a}$ is H. In some embodiments of formula (IV), including formula (IV-X), $R^{44}$ and $R^{44a}$ are, independently H, halogen, $C_1$-$C_3$alkoxy, or —$OC(O)CH_3$.

In some embodiments of formula (IV), including formula (IV-X), $R^{51a}$, $R^{51b}$, and $R^{51c}$ are, independently, H, OH, or —$OR^{51d}$. In some embodiments of formula (IV), including formula (IV-X), one of $R^{51a}$, $R^{51b}$, and $R^{51c}$ is —OH. In some embodiments of formula (IV), including formula (IV-X), one of $R^{51a}$, $R^{51b}$, and $R^{51c}$ is —$OR^{51d}$. In some embodiments of formula (IV), including formula (IV-X), $R^{51a}$ is —OH and $R^{51b}$ and $R^{51c}$ are H. In some embodiments of formula (IV), including formula (IV-X), $R^{51a}$ is —$OR^{51d}$ and $R^{51b}$ and $R^{51c}$ are H.

In some embodiments of formula (IV), including formula (IV-X), $R^{52a}$ and $R^{52b}$ are independently H, OH, or —$OR^{52c}$. In some embodiments of formula (IV), including formula (IV-X), $R^{52a}$ and $R^{52b}$ are —OH. In some embodiments of formula (IV), including formula (IV-X), one of $R^{52a}$ and $R^{52b}$ is —$OR^{52c}$. In some embodiments of formula (IV), including formula (IV-X), one of $R^{52a}$ and $R^{52b}$ is —OH. In some embodiments of formula (IV), including formula (IV-X), $R^{52a}$ is H and $R^{52b}$ is —$OR^{52c}$. In some embodiments of formula (IV), including formula (IV-X), $R^{52a}$ is H and $R^{52b}$ is —OH.

In some embodiments of formula (IV), including formula (IV-X), $R^7$ is H. In other embodiments, $R^7$ is $C_1$-$C_3$alkyl, for example $C_1$-alkyl, $C_2$-alkyl, or $C_3$-alkyl. In some embodiments, $R^8$ is H. In some embodiments of formula (IV), including formula (IV-X), $R^7$ is H and $R^8$ is H.

In some embodiments of formula (IV), including formula (IV-X), $R^8$ is $C_1$-$C_6$alkyl, for example $C_1$-alkyl, $C_2$-alkyl, $C_3$-alkyl, $C_4$-alkyl, $C_5$-alkyl, or $C_6$-alkyl.

In some embodiments of formula (IV), including formula (IV-X), $R^8$ is

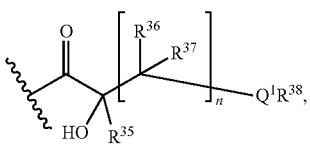

wherein $Q^1$ is NH, O, or S. In certain embodiments, $Q^1$ is NH. In certain embodiments, $Q^1$ is O. In certain embodiments, $Q^1$ is S. In certain embodiments, wherein when n is one, then $R^{36}$ and $R^{37}$ are not halo.

In some embodiments of formula (IV), including formula (IV-X), n is an integer from 0 to 4, from 0 to 3, from 0 to 2, from 1 to 4, from 2 to 4, or from 1 to 3. In certain embodiments, n is 0, or n is 1, or n is 2, or n is 3, or n is 4.

In Formula (IV), the ring substituted by $R^1$, $R^2$, $R^3$, $R^4$, $R^5$, $R^{5a}$, $R^6$, $R^{6a}$, and $X^1$ may also be referred to as Ring A, as shown below. The ring substituted $R^7$, $R^8$, $R^{41}$, $R^{42}$, $R^{43}$, $R^{44}$, and $R^{44a}$ may also referred to as Ring B, as shown below. Ring C is also used to refer to the moiety connected to Ring B through —O— moiety, as shown below. Ring D is also used to refer to the moiety connected to Ring C through —O— moiety, as shown below.

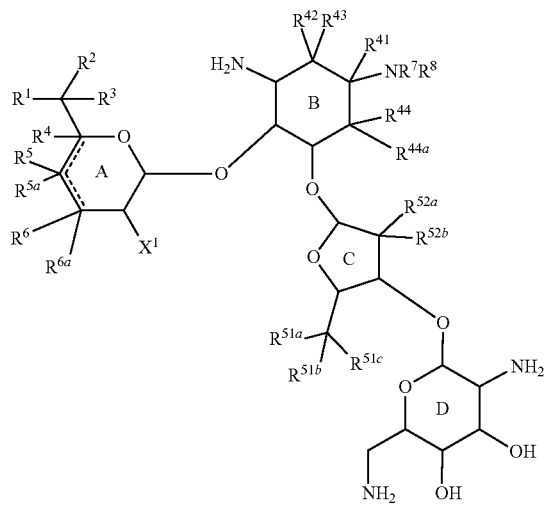

In some embodiments of the compound of Formula (IV), Ring A is selected from

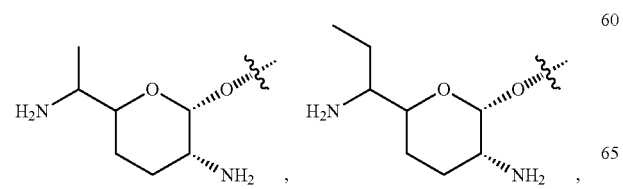

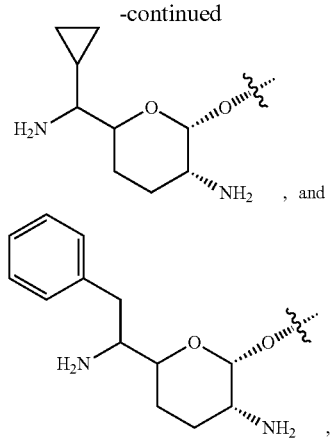

In some embodiments of the compound of Formula (IV), Ring A is selected from

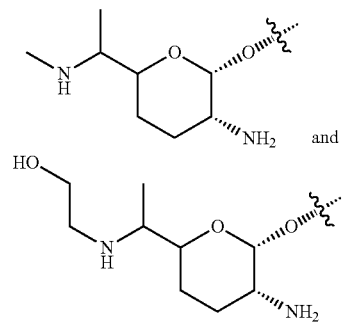

In some embodiments of the compound of Formula (IV), Ring A is selected from

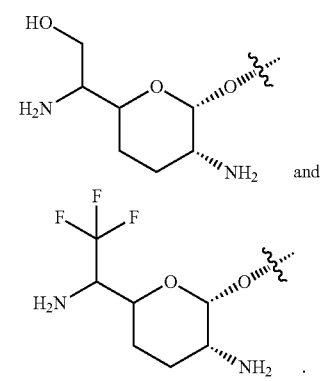

In some embodiments of the compound of Formula (IV), Ring A is selected from

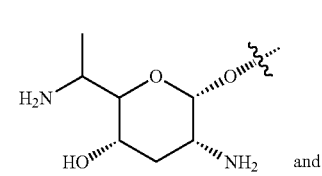

-continued
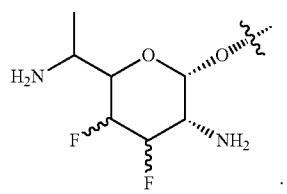
In some embodiments of the compound of Formula (IV), Ring A is selected from
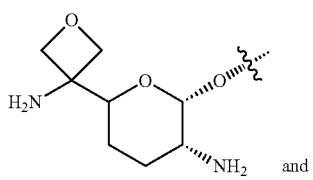
and
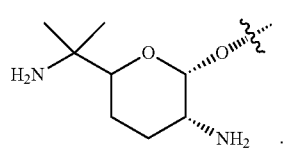
In some embodiments of the compound of Formula (IV), Ring A is selected from
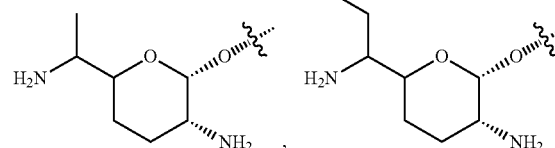
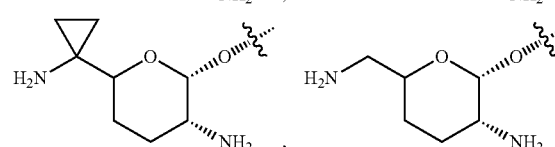
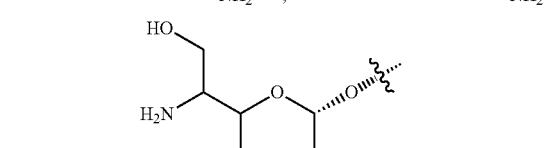
, and
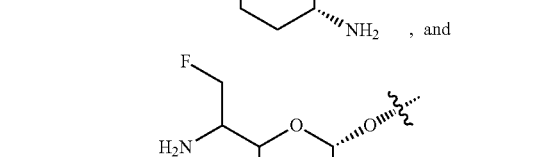
In some embodiments of the compound of Formula (IV), Ring A is selected from
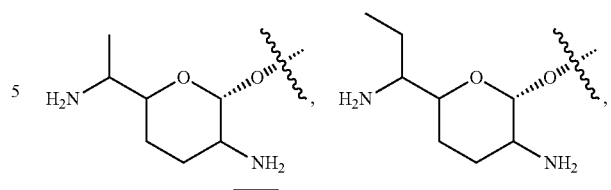
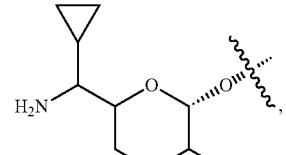
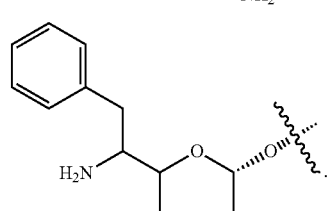
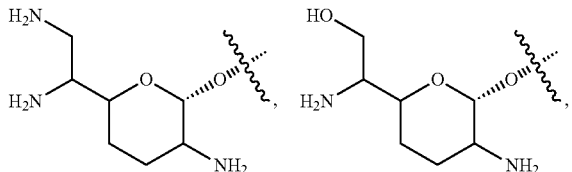
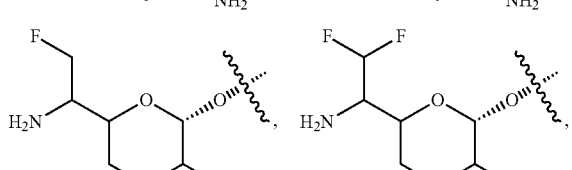
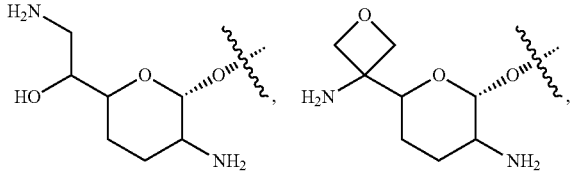
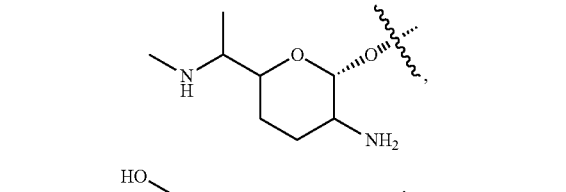
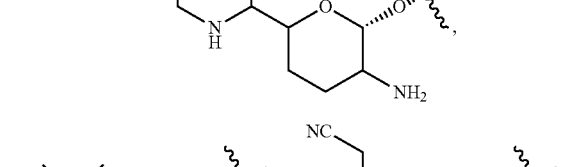

-continued
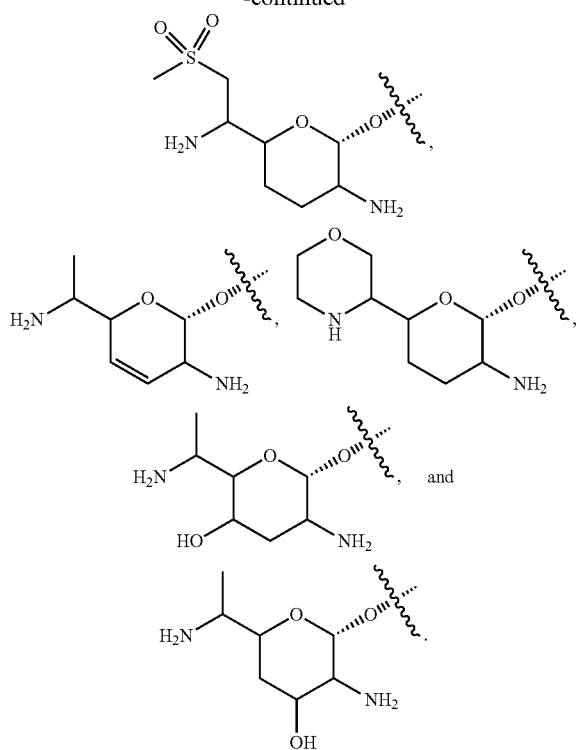
In some embodiments of the compound of Formula (IV), Ring A is selected from
In some embodiments of the compound of Formula (IV), Ring B is selected from
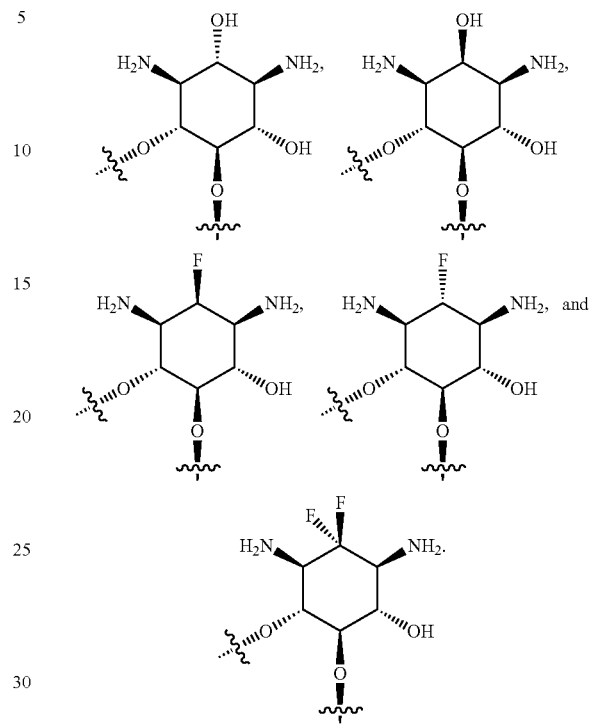
In some embodiments of the compound of Formula (IV), Ring B is selected from
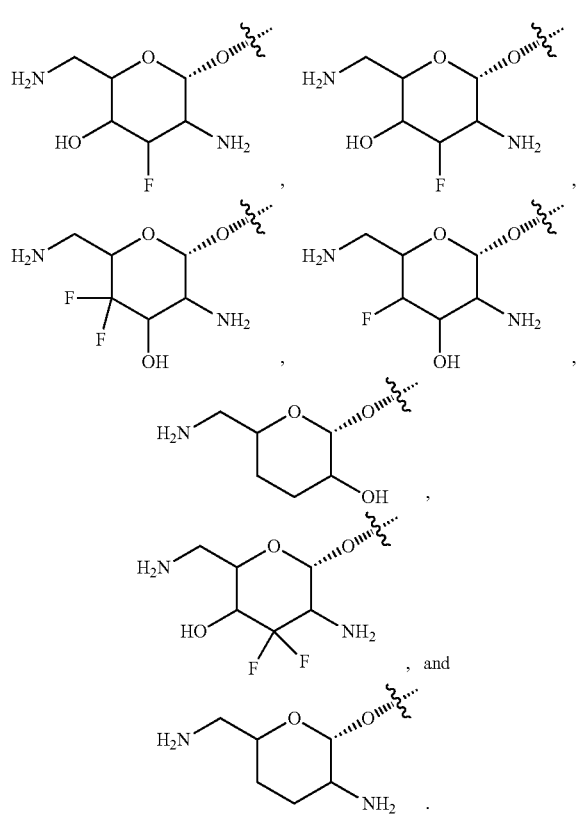
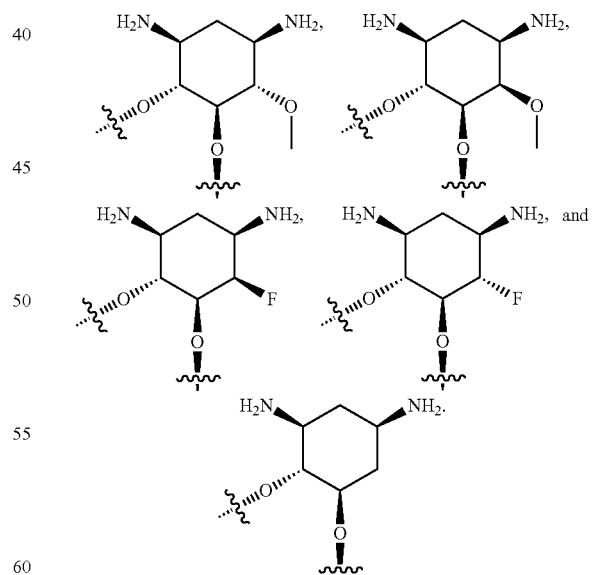
In some embodiments of the compound of Formula (IV), Ring B is

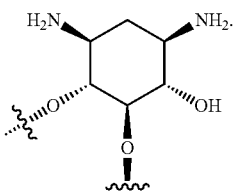

In some embodiments of the compound of Formula (IV), Ring B is selected from

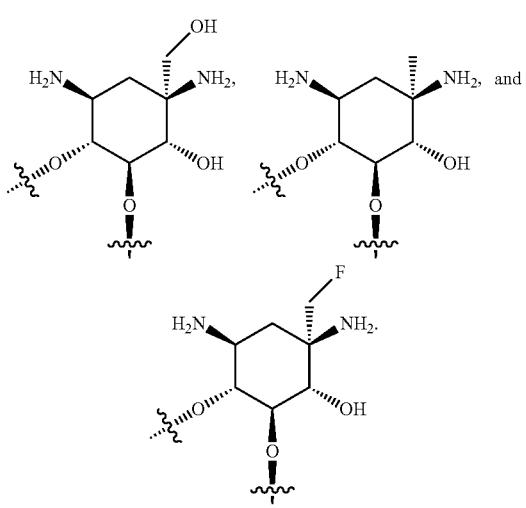

In some embodiments of the compound of Formula (IV), Ring B is

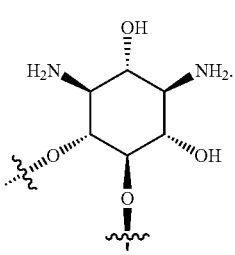

In some embodiments of the compound of Formula (IV), Ring B is

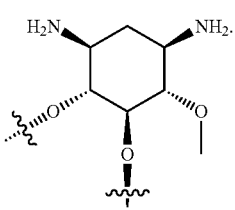

In some embodiments of the compound of Formula (IV), Ring B is selected from

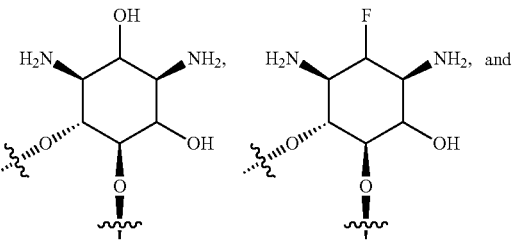

In some embodiments of the compound of Formula (IV), Ring B is

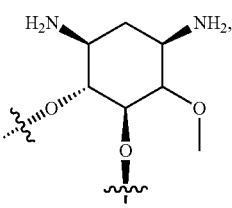

In some embodiments of the compound of Formula (IV), Ring B is

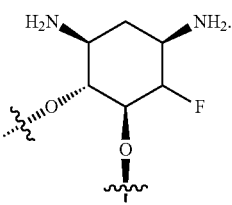

In some embodiments of the compound of Formula (IV), Ring B is

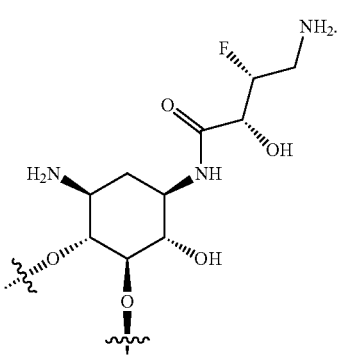

In some embodiments of the compound of Formula (IV), Ring B is

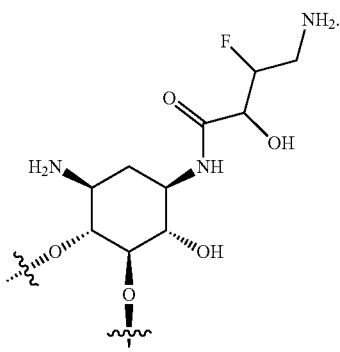

In some embodiments of the compound of Formula (IV), Ring B is

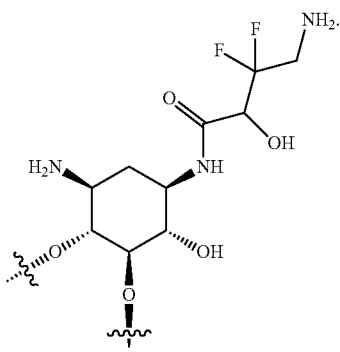

In some embodiments of the compound of Formula (IV), Ring B is

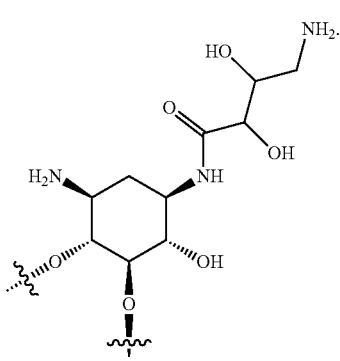

In some embodiments of the compound of Formula (IV), Ring B is

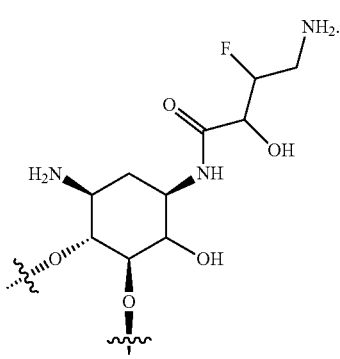

In some embodiments of the compound of Formula (IV), Ring B is

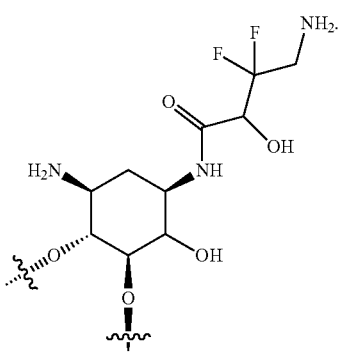

In some embodiments of the compound of Formula (IV), Ring B is

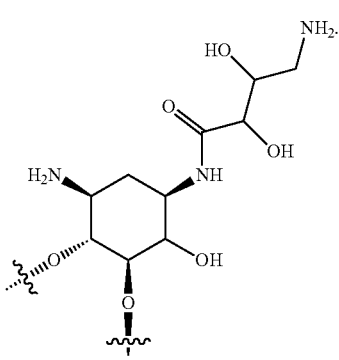

In some embodiments of the compound of Formula (IV), Ring B is

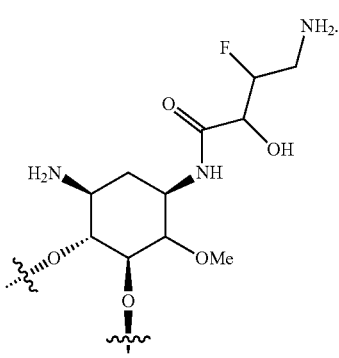

In some embodiments of the compound of Formula (IV), Ring B is

In some embodiments of the compound of Formula (IV), Ring B is

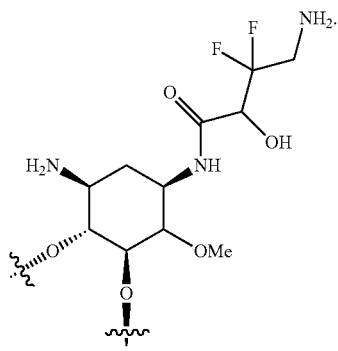

In some embodiments of the compound of Formula (IV), Ring B is

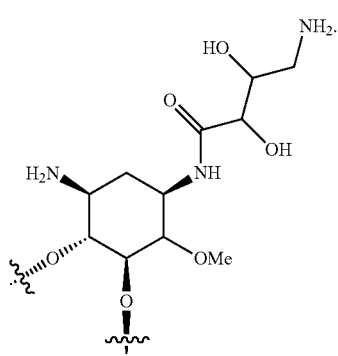

In some embodiments of the compound of Formula (IV), Ring B is

In some embodiments of the compound of Formula (IV), Ring B is

In some embodiments of the compound of Formula (IV), Ring B is

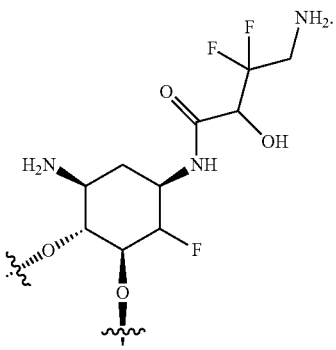

In some embodiments of the compound of Formula (IV), Ring B is

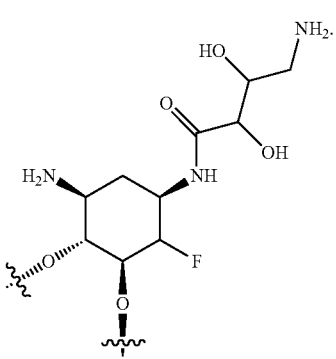

In some embodiments, the compound of formula (IV) is of formula (IVa):

(IVa)

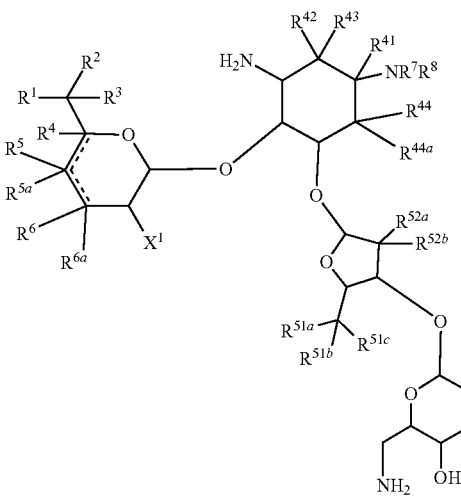

or a pharmaceutically acceptable salt, solvate, tautomer, or stereoisomer thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl, wherein the alkyl, cycloalkyl, or aryl is unsubstituted or substituted with one or more substituents independently selected from the group consisting of halogen, cyano, aryl, —$SR^{12}$, —$SO_2R^{13}$, —$OSF_2NR^{14}R^{15}$, —$NR^{14}R^{15}$, and —$OR^{16}$, and wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and wherein each $R^{17}$, $R^{18}$, $R^{19}$, $R^{20}$, and $R^{21}$ is independently H or alkyl, or $R^2$ and $R^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, wherein each $R^{22}$, $R^{23}$, $R^{24}$, $R^{25}$, and $R^{26}$ is independently H or alkyl, and wherein at least one of $R^2$ and $R^3$ is other than H; $R^4$ is H or absent;

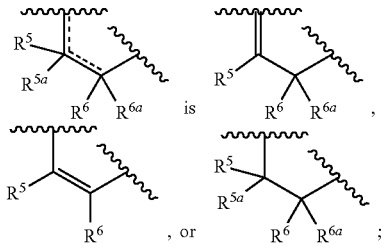

$R^5$ and $R^6$ are independently H, —$OR^{27}$, —$NR^{28}R^{29}$, halogen, or alkyl, wherein each $R^{27}$, $R^{28}$, and $R^{29}$ is independently H or $C_1$-$C_6$alkyl, wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and wherein each $R^{30}$, $R^{31}$, $R^{32}$, $R^{33}$, and $R^{34}$ is independently H or alkyl, $R^{5a}$ and $R^{6a}$ are, independently, absent or independently H, —$OR^{53}$, —$NR^{54}R^{55}$, halogen, or alkyl, wherein each $R^{53}$, $R^{54}$, and $R^{55}$ is independently H or $C_1$-$C_6$alkyl, wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and wherein each $R^{56}$, $R^{57}$, $R^{58}$, $R^{59}$, and $R^{60}$ is independently H or alkyl, or $R^5$ and $R^{5a}$ form an oxo group, or $R^6$ and $R^{6a}$ form an oxo group;

$R^7$ is H or $C_1$-$C_3$alkyl;

$R^8$ is H, $C_1$-$C_6$alkyl, an amino protecting group, or

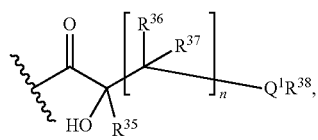

wherein $Q^1$ is NH, O, or S, n is an integer from 0 to 4, $R^{35}$ is H or $C_1$-$C_3$alkyl, each $R^{36}$ and $R^{37}$ is independently H, alkyl, halogen, or —OH, and $R^{38}$ is H, alkyl, or —C(=NH)$NR^{39}R^{40}$, wherein $R^{39}$ and $R^{40}$ are independently H or $C_1$-$C_3$alkyl, or $R^{35}$ and $R^{38}$, together with the atoms to which they are attached, form a heterocycloalkyl group comprising at least one N;

$R^{41}$ is H, —CN, —$CONH_2$ or $C_1$-$C_3$alkyl, wherein the $C_1$-$C_3$alkyl is unsubstituted or substituted with one or more substituents selected from the group consisting of —OH, —OC(O)$CH_3$, —$NH_2$, —CN, —$CONH_2$, and halogen;

$R^{42}$ and $R^{43}$ are, independently, H, —OH, —$OR^{45}$, —$NR^{46}R^{47}$, or halogen, wherein each $R^{45}$, $R^{46}$, and $R^{47}$ is independently H, alkyl, —$CONH_2$, or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{44}$ and $R^{44a}$ are, independently, H, halogen, —OH, $C_1$-$C_3$alkoxy, or —OC(O)$CH_3$:

$X^1$ is H, $NH_2$, OH, or halogen:

$R^{51a}$, $R^{51b}$, and $R^{51c}$ are, independently, H, OH, or —$OR^{51d}$, wherein each $R^{51d}$ is, independently, alkyl or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{52a}$ and $R^{52b}$ are independently H, OH, or —$OR^{52c}$, wherein each $R^{52c}$ is, independently, alkyl or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl:

In some embodiments, the compound of formula (IVa) is of formula (IVa-X):

(IVa-X)

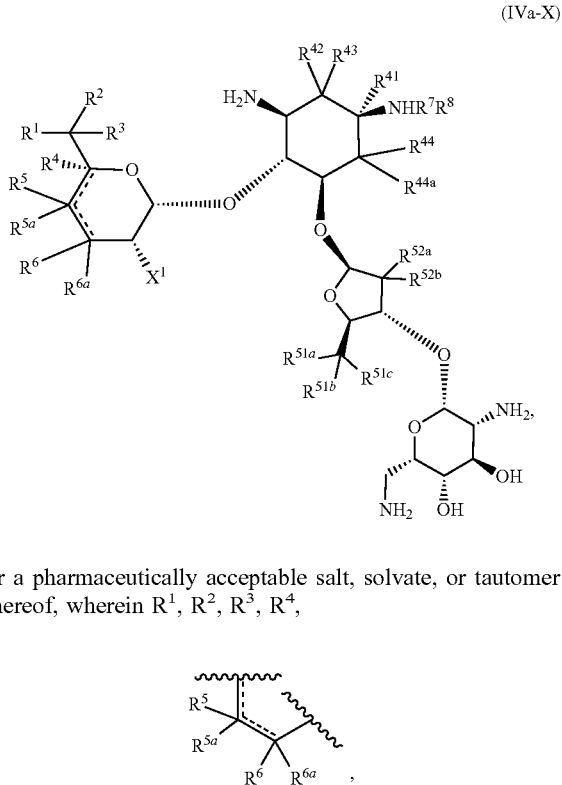

or a pharmaceutically acceptable salt, solvate, or tautomer thereof, wherein $R^1$, $R^2$, $R^3$, $R^4$, $R^7$, $R^8$, $R^{41}$, $R^{42}$, $R^{43}$, $R^{44}$, $R^{44a}$, $X^1$, $R^{51a}$, $R^{51b}$, $R^{51c}$, $R^{52a}$, and $R^{52b}$ are as defined for formula (IVa) herein.

In some embodiments of formula (IVa), including formula (IVa-X), $R^1$ is —$NR^{10}R^{11}$, wherein $R^{10}$ and $R^{11}$ are independently H or $C_1$-$C_6$alkyl, wherein the alkyl is unsubstituted or substituted with one or more —OH. In certain embodiments, $R^{10}$ and $R^{11}$ are independently H, methyl, or hydroxyethyl. In certain embodiments, $R^{10}$ and $R^{11}$ are both H.

In some embodiments of formula (IVa), including formula (IVa-X), $R^1$ is $OR^9$, wherein $R^9$ is H or $C_1$-$C_6$alkyl, wherein the alkyl is unsubstituted or substituted with one or more —OH. In certain embodiments, $R^9$ is H, methyl, or hydroxyethyl. In certain embodiments, $R^9$ is H.

In some embodiments of formula (IVa), including formula (IVa-X), $R^2$ and $R^3$ are independently selected from the group consisting of H, alkyl, cycloalkyl, and aryl, wherein at least one of $R^2$ and $R^3$ is other than H.

In some embodiments of formula (IVa), including formula (IVa-X), $R^2$ is alkyl, cyclopropyl, or phenyl; wherein the alkyl is unsubstituted or substituted with one, two, or three substituents selected from the group consisting of —$NH_2$, —OH, F, —CN, and —$S(O)_2CH_3$. In some embodiments, $R^2$ is methyl, ethyl, propyl, butyl, pentyl, hexyl, cyclopropyl, cyclobutyl, cyclopentyl, cyclohexyl, or phenyl. In other embodiments, $R^2$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —$SR^{12}$, —$SO_2R^{13}$, —$NR^{14}R^{15}$, and —$OR^{16}$. In some embodiments, the one or more substituents are independently selected from the group consisting of halogen, cyano, aryl, —$SO_2R^{13}$, —$NR^{14}R^{15}$, and —$OR^{16}$. For example, in certain embodiments, the one or more substituents are independently selected from the group consisting of F, Cl, B, I, cyano, —$SO_2CH_3$, —$NH_2$, and —OH. In still other embodiments, $R^2$ is methyl; methyl substituted with one or two F; methyl substituted with —$SO_2CH_3$; methyl substituted with —$NH_2$; methyl substituted with —OH; ethyl; cyclopropyl; or phenyl. In some embodiments, $R^2$ is H or unsubstituted methyl.

In some embodiments of formula (IVa), including formula (IVa-X), $R^3$ is methyl, ethyl, propyl, butyl, pentyl, hexyl, cyclopropyl, cyclobutyl, cyclopentyl, cyclohexyl, or phenyl. In other embodiments, $R^3$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —$SR^{12}$, —$SO_2R^{13}$, —$NR^{14}R^{15}$, and —$OR^{16}$. In some embodiments, the one or more substituents are independently selected from the group consisting of halogen, cyano, aryl, —$SO_2R^{13}$, —$NR^{14}R^{15}$, and —$OR^{16}$. For example, in certain embodiments, the one or more substituents are independently selected from the group consisting of F, Cl, B, I, cyano, —$SO_2CH_3$, —$NH_2$, and —OH. In still other embodiments, $R^3$ is methyl; methyl substituted with one or two F; methyl substituted with —$SO_2CH_3$; methyl substituted with —$NH_2$; methyl substituted with —OH; ethyl; cyclopropyl; or phenyl. In certain embodiments, $R^3$ is H or unsubstituted methyl.

In some embodiments of formula (IVa), including formula (IVa-X), $R^2$ and $R^3$, together with the atom to which they are attached, form a cycloalkyl group or a heterocycloalkyl group. In some embodiments, the cycloalkyl group or heterocycloalkyl group may be unsubstituted or substituted with one or more substituents independently selected from the group consisting of halogen, cyano, —$SR^{22}$, —$SO_2R^{23}$, —$NR^{24}R^{25}$, and —$OR^{26}$, wherein each $R^{22}$, $R^{23}$, $R^{24}$, $R^{25}$, and $R^{26}$ may be independently H or alkyl. In certain embodiments, $R^2$ and $R^3$ together with the atom to which they are attached form a cyclopropyl or oxetanyl. In certain embodiments, $R^2$ and $R^3$ together with the atom to which they are attached form a cyclopropyl.

In some embodiments of formula (IVa), including formula (IVa-X), $R^4$ is H or absent.

In some embodiments of formula (IVa), including formula (IVa-X), $R^5$ and $R^6$ are H and $R^{5a}$ and $R^{6a}$ are independently absent or H.

In some embodiments of formula (IVa), including formula (IVa-X), both $R^5$ and $R^6$ are H.

In some embodiments of formula (IVa), including formula (IVa-X), both $R^{5a}$ and $R^{6a}$ are H.

In some embodiments of formula (IVa), including formula (IVa-X), $R^5$ is H or —OH. In some embodiments of formula (IVa), including formula (IVa-X), $R^5$ is —OH. In some embodiments of formula (IVa), including formula (IVa-X), $R^5$ is H.

In some embodiments of formula (IVa), including formula (IVa-X), $R^{5a}$ is H or —OH. In some embodiments of formula (IVa), including formula (IVa-X), $R^{5a}$ is —OH. In some embodiments of formula (IVa), including formula (IVa-X), $R^{5a}$ is H.

In some embodiments of formula (IVa), including formula (IVa-X), $R^6$ is H or —OH. In some embodiments of formula (IVa), including formula (IVa-X), $R^6$ is —OH. In some embodiments of formula (IVa), including formula (IVa-X), $R^6$ is H.

In some embodiments of formula (IVa), including formula (IVa-X), $R^{6a}$ is H or —OH. In some embodiments of formula (IVa), including formula (IVa-X), $R^{6a}$ is —OH. In some embodiments of formula (IVa), including formula (IVa-X), $R^{6a}$ is H.

In some embodiments of formula (IVa), including formula (IVa-X), $R^5$ is H, halogen, or —OH. In certain such embodiments, $R^5$ is halogen. In certain such embodiments, $R^5$ is F.

In some embodiments of formula (IVa), including formula (IVa-X), $R^{5a}$ is H, halogen, or —OH. In certain such embodiments, $R^{5a}$ is halogen. In certain such embodiments, $R^{5a}$ is F.

In some embodiments of formula (IVa), including formula (IVa-X), $R^6$ is H, halogen, or —OH. In certain such embodiments, $R^6$ is halogen. In certain such embodiments, $R^6$ is F.

In some embodiments of formula (IVa), including formula (IVa-X), $R^{6a}$ is H, halogen, or —OH. In certain such embodiments, $R^{6a}$ is halogen. In certain such embodiments, $R^{6a}$ is F.

In some embodiments of formula (IVa), including formula (IVa-X), $R^5$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (IVa), including formula (IVa-X), $R^{5a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (IVa), including formula (IVa-X), $R^6$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (IVa), including formula (IVa-X), $R^{6a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (IVa), including formula (IVa-X), $R^4$ is H.

In some embodiments of formula (IVa), including formula (IVa-X), $X^1$ is $NH_2$. In some embodiments of formula (IVa), including formula (IVa-X), $X^1$ is OH. In some embodiments of formula (IVa), including formula (IVa-X), $X^1$ is halogen. In some embodiments of formula (IVa), including formula (IVa-X), $X^1$ is F. In some embodiments of formula (IVa), including formula (IVa-X), $X^1$ is Cl. In some embodiments of formula (IVa), including formula (IVa-X), $X^1$ is Br. In some embodiments of formula (IVa), including formula (IVa-X), $X^1$ is I.

In some embodiments of formula (IVa), including formula (IVa-X), $R^{41}$ is H.

In some embodiments of formula (IVa), including formula (IVa-X), one of $R^{42}$ and $R^{43}$ is —OH. In some embodiments of formula (IVa), including formula (IVa-X), one of $R^{42}$ and $R^{43}$ is halogen. In some embodiments of formula (IVa), including formula (IVa-X), one of $R^{42}$ and $R^{43}$ is H. In some embodiments of formula (IVa), including formula (IVa-X), one of $R^{42}$ and $R^{43}$ is —$NR^{46}R^{47}$. In some embodiments of formula (IVa), including formula (IVa-X), one of $R^{42}$ and $R^{43}$ is —F. In some embodiments of formula (IVa), including formula (IVa-X), $R^{42}$ is —F and $R^{43}$ is —F. In some embodiments of formula (IVa), including formula (IVa-X), one of $R^{42}$ and $R^{43}$ is —OH. In some embodiments of formula (IVa), including formula (IVa-X), one of $R^{42}$ and $R^{43}$ is —$OR^{45}$.

In some embodiments of formula (IVa), including formula (IVa-X), $R^{42}$ and $R^{43}$ are H.

In some embodiments of formula (IVa), including formula (IVa-X), one of $R^{44}$ and $R^{44a}$ is —OH. In some embodiments of formula (IVa), including formula (IVa-X), one of $R^{44}$ and $R^{44a}$ is —$OCH_3$. In some embodiments of formula (IVa), including formula (IVa-X), one of $R^{44}$ and $R^{44a}$ is —F. In some embodiments of formula (IVa), including formula (IVa-X), $R^{44}$ and $R^{44a}$ are —F. In some embodiments of formula (IVa), including formula (IVa-X), $R^{44}$ and $R^{44a}$ are H. In some embodiments of formula (IVa), including formula (IVa-X), one of $R^{44}$ and $R^{44a}$ is H. In some embodiments of formula (IVa), including formula (IVa-X), $R^{44}$ and $R^{44a}$ are, independently H, halogen, $C_1$-$C_3$alkoxy, or —$OC(O)CH_3$.

In some embodiments of formula (IVa), including formula (IVa-X), $R^{51a}$, $R^{51b}$ and $R^{51c}$ are, independently, H, OH, or —$OR^{51d}$. In some embodiments of formula (IVa), including formula (IVa-X), one of $R^{51a}$, $R^{51b}$, and $R^{51c}$ is —OH. In some embodiments of formula (IVa), including formula (IVa-X), one of $R^{51a}$, $R^{51b}$, and $R^{51c}$ is —$OR^{51d}$. In some embodiments of formula (IVa), including formula (IVa-X), $R^{51a}$ is —OH and $R^{51b}$ and $R^{51c}$ are H. In some embodiments of formula (IVa), including formula (IVa-X), $R^{51a}$ is —$OR^{51d}$ and $R^{51b}$ and $R^{51c}$ are H.

In some embodiments of formula (IVa), including formula (IVa-X), $R^{52a}$ and $R^{52b}$ are independently H, OH, or —$OR^{52c}$. In some embodiments of formula (IVa), including formula (IVa-X), $R^{52a}$ and $R^{52b}$ are —OH. In some embodiments of formula (IVa), including formula (IVa-X), one of $R^{52a}$ and $R^{52b}$ is —$OR^{52c}$. In some embodiments of formula (IVa), including formula (IVa-X), one of $R^{52a}$ and $R^{52b}$ is —OH. In some embodiments of formula (IVa), including formula (IVa-X), $R^{52a}$ is H and $R^{52b}$ is —$OR^{52c}$. In some embodiments of formula (IVa), including formula (IVa-X), $R^{52a}$ is H and $R^{52b}$ is —OH.

In some embodiments of formula (IVa), including formula (IVa-X), $R^7$ is H. In other embodiments, $R^7$ is $C_1$-$C_3$alkyl, for example $C_1$-alkyl, $C_2$-alkyl, or $C_3$-alkyl. In some embodiments, $R^8$ is H. In some embodiments of formula (IVa), including formula (IVa-X), $R^7$ is H and $R^8$ is H.

In some embodiments of formula (IVa), including formula (IVa-X), $R^8$ is $C_1$-$C_6$alkyl, for example $C_1$-alkyl, $C_2$-alkyl, $C_3$-alkyl, $C_4$-alkyl, $C_5$-alkyl, or $C_6$-alkyl.

In some embodiments of formula (IVa), including formula (IVa-X), $R^8$ is

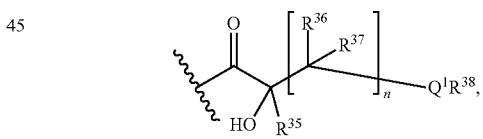

wherein $Q^1$ is NH, O, or S. In certain embodiments, $Q^1$ is NH. In certain embodiments, $Q^1$ is O. In certain embodiments, $Q^1$ is S. In certain embodiments, wherein when n is one, then $R^{36}$ and $R^{37}$ are not halo.

In some embodiments of formula (IVa), including formula (IVa-X), n is an integer from 0 to 4, from 0 to 3, from 0 to 2, from 1 to 4, from 2 to 4, or from 1 to 3. In certain embodiments, n is 0, or n is 1, or n is 2, or n is 3, or n is 4.

In Formula (IVa), the ring substituted by $R^1$, $R^2$, $R^3$, $R^4$, $R^5$, $R^{5a}$, $R^6$, $R^{6a}$, and $X^1$ may also be referred to as Ring A, as shown below. The ring substituted $R^7$, $R^8$, $R^{41}$, $R^{42}$, $R^{43}$, $R^{44}$, $R^{44a}$ may also referred to as Ring B, as shown below. Ring C is also used to refer to the moiety connected to Ring B through —O— moiety, as shown below. Ring D is also used to refer to the moiety connected to Ring C through —O— moiety, as shown below.

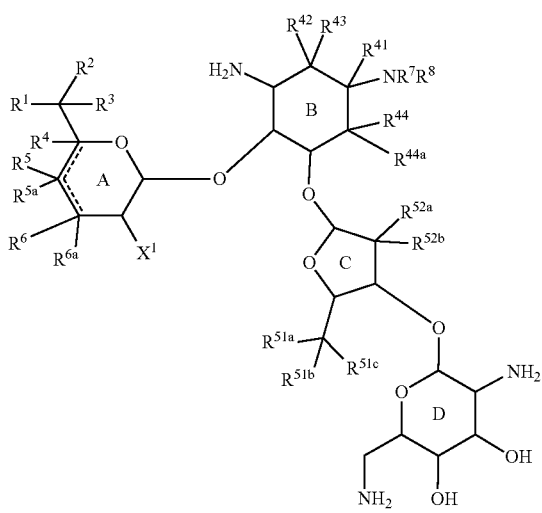

In some embodiments of the compound of Formula (IVa), Ring A is selected from

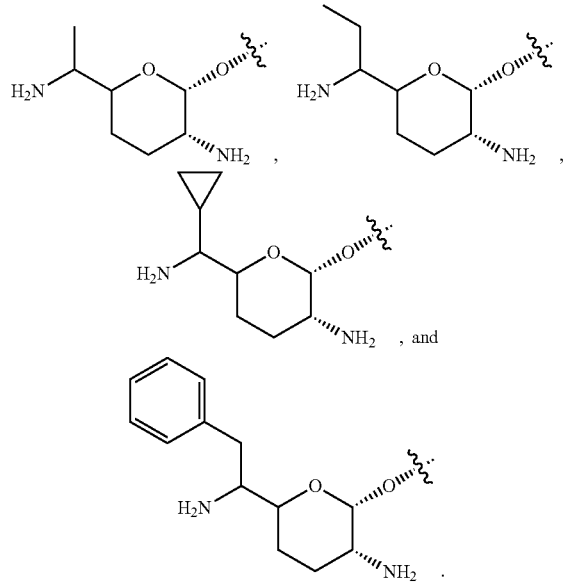

In some embodiments of the compound of Formula (IVa), Ring A is selected from

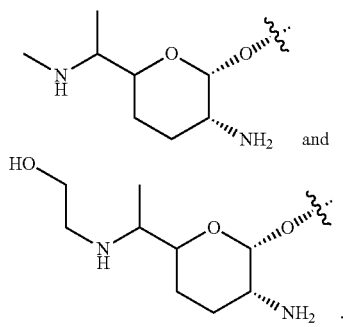

In some embodiments of the compound of Formula (IVa), Ring A is selected from

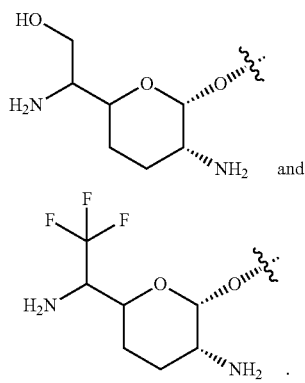

In some embodiments of the compound of Formula (IVa), Ring A is selected from

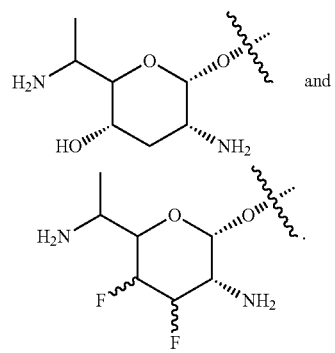

In some embodiments of the compound of Formula (IVa), Ring A is selected from

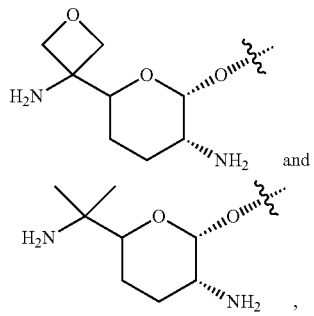

In some embodiments of the compound of Formula (IVa), Ring A is selected from

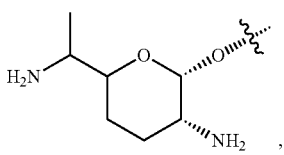

-continued
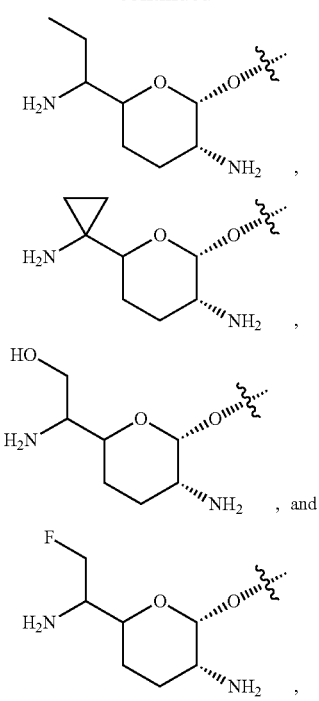
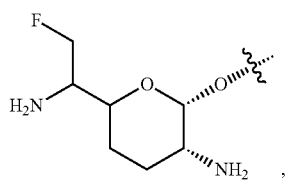
In some embodiments of the compound of Formula (IVa), Ring A is selected from
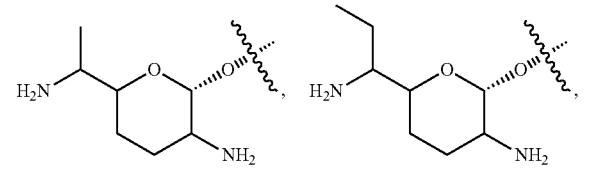
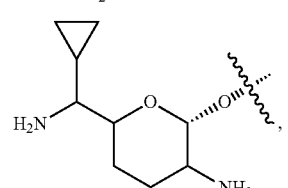
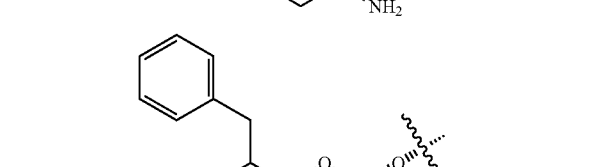
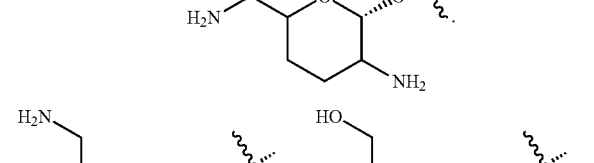
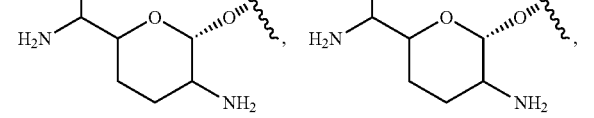
-continued
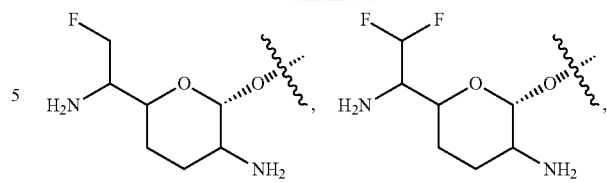
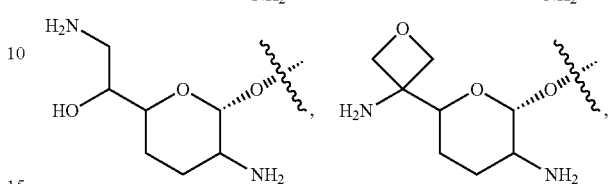
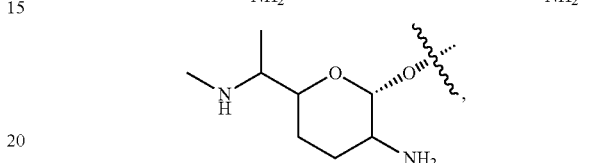
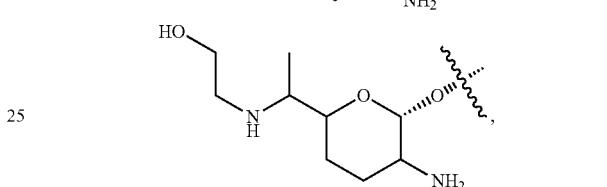
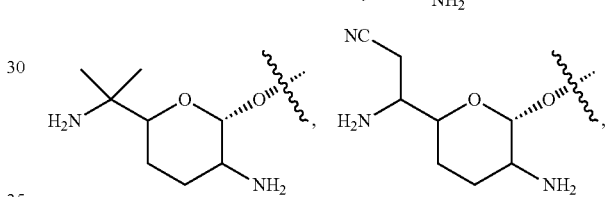
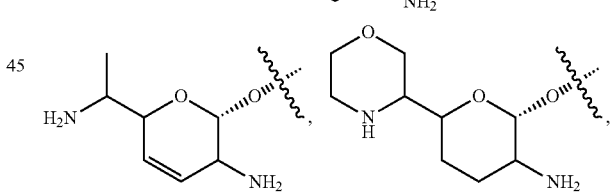
In some embodiments of the compound of Formula (IVa), Ring B is selected from

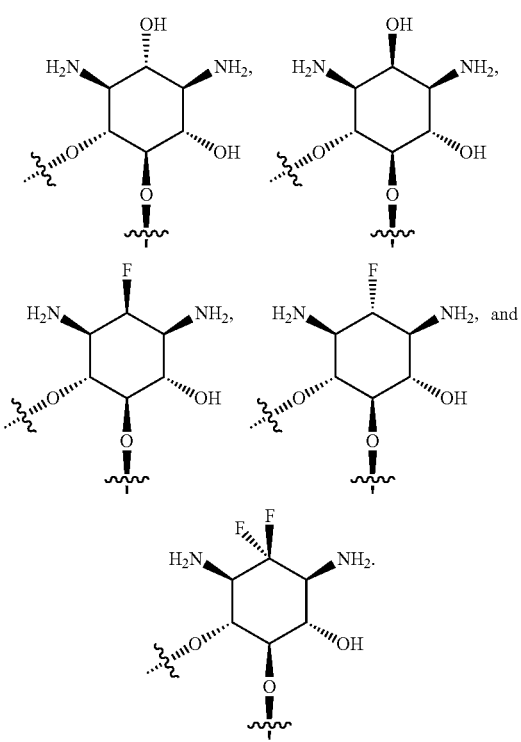

In some embodiments of the compound of Formula (IVa), Ring B is selected from

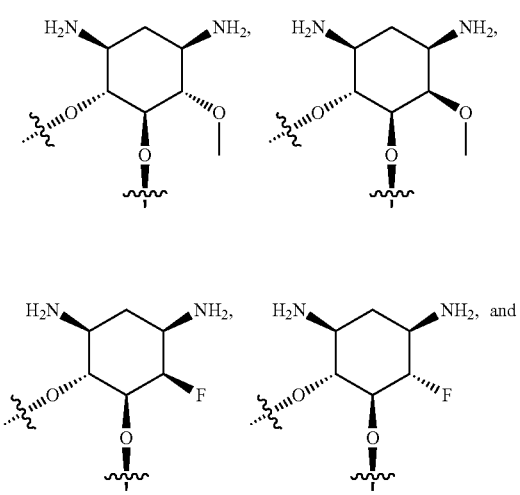

In some embodiments of the compound of Formula (IVa), Ring B is

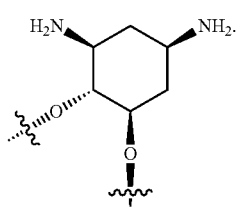

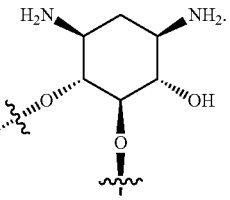

In some embodiments of the compound of Formula (IVa), Ring B is selected from

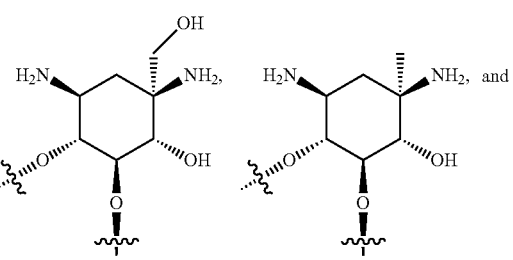

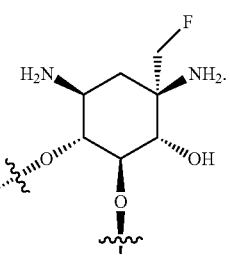

In some embodiments of the compound of Formula (IVa), Ring B is

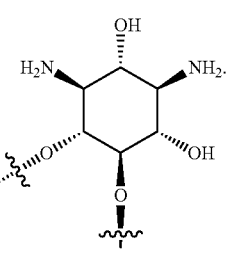

In some embodiments of the compound of Formula (IVa), Ring B is

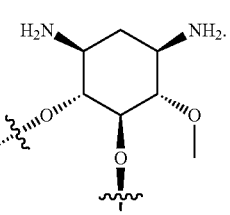

In some embodiments of the compound of Formula (IVa), Ring B is selected from

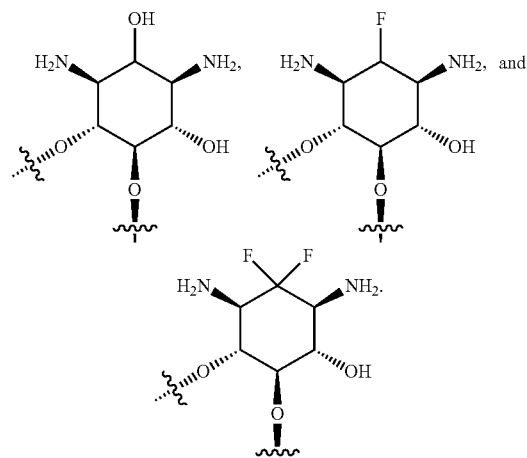

In some embodiments of the compound of Formula (IVa), Ring B is

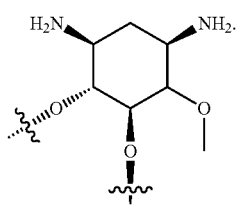

In some embodiments of the compound of Formula (IVa), Ring B is

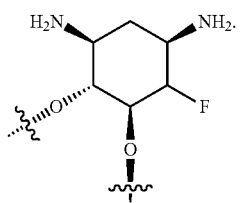

In some embodiments of the compound of Formula (IVa), Ring B is

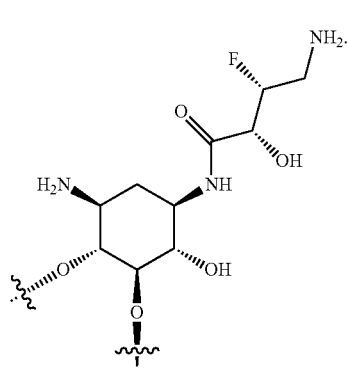

In some embodiments of the compound of Formula (IVa), Ring B is

In some embodiments of the compound of Formula (IVa), Ring B is

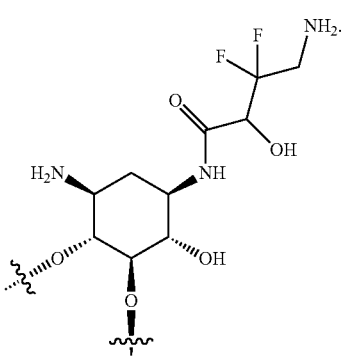

In some embodiments of the compound of Formula (IVa), Ring B is

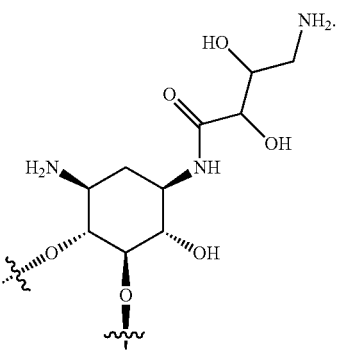

In some embodiments of the compound of Formula (IVa), Ring B is

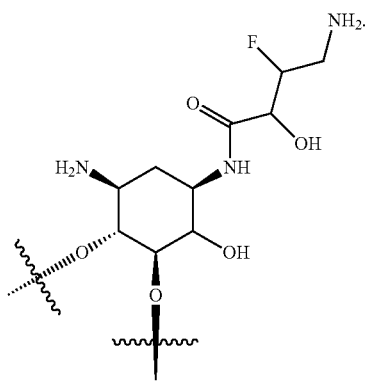
In some embodiments of the compound of Formula (IV), Ring B is
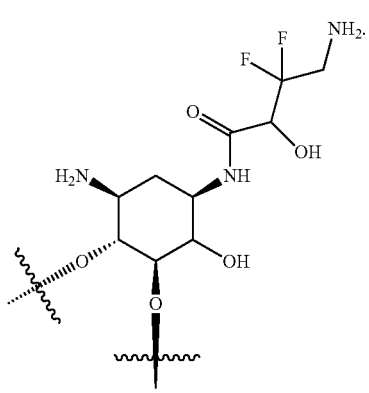
In some embodiments of the compound of Formula (IVa), Ring B is
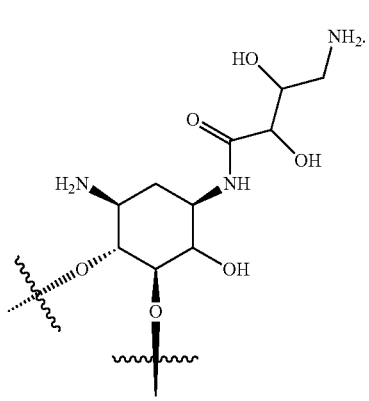
In some embodiments of the compound of Formula (IVa), Ring B is
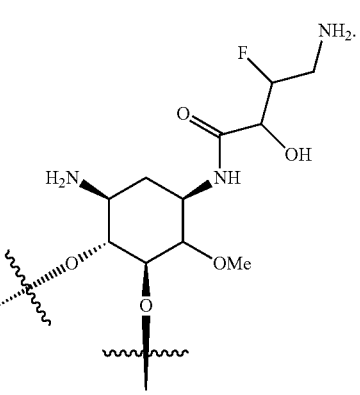
In some embodiments of the compound of Formula (IVa), Ring B is
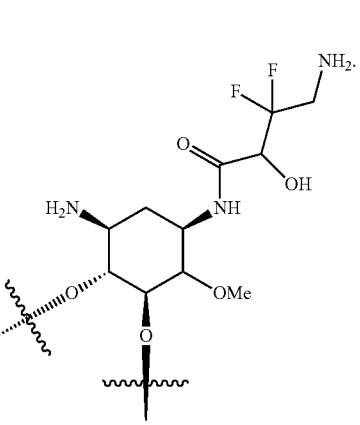
In some embodiments of the compound of Formula (IVa), Ring B is
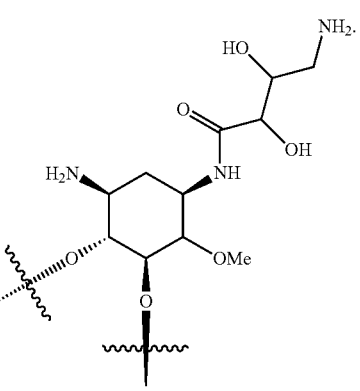
In some embodiments of the compound of Formula (IVa), Ring B is

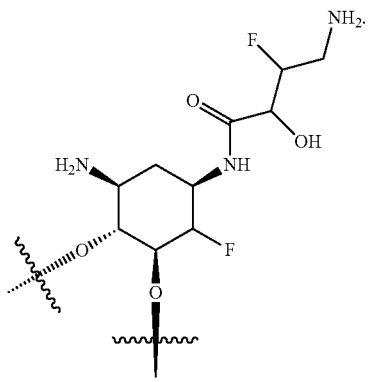

In some embodiments of the compound of Formula (IVa), Ring B is

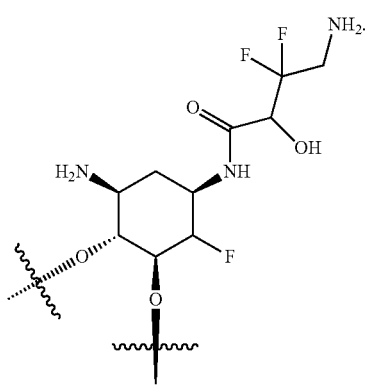

In some embodiments of the compound of Formula (IVa), Ring B is

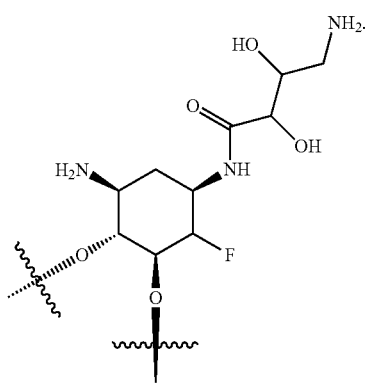

In some embodiments, the compound of formula (IV) is of formula (V):

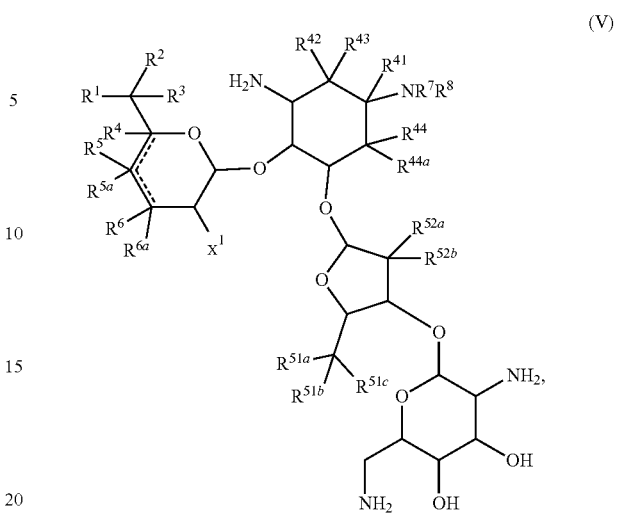

or a pharmaceutically acceptable salt, solvate, tautomer, or stereoisomer thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl,
wherein the alkyl, cycloalkyl, or aryl is unsubstituted or substituted with one or more substituents independently selected from the group consisting of halogen, cyano, aryl, —$SR^{12}$, —$SO_2R^{13}$, —$OSF_2NR^{14}R^{15}$, —$NR^{14}R^{15}$, and —$OR^{16}$, and wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and wherein each $R^{17}$, $R^{18}$, $R^{19}$, $R^{20}$, and $R^{21}$ is independently H or alkyl, or $R^2$ and $R^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl; $R^4$ is H or absent;

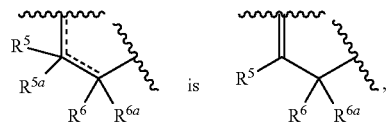

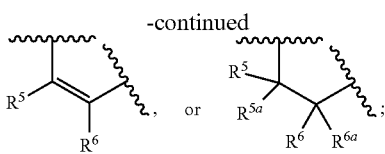

$R^5$ and $R^6$ are independently H, —$OR^{27}$, —$NR^{28}R^{29}$, halogen, or alkyl, wherein each $R^{27}$, $R^{28}$, and $R^{29}$ is independently H or $C_1$-$C_6$alkyl,
  wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and
  wherein each $R^{30}$, $R^{31}$, $R^{32}$, $R^{33}$, and $R^{34}$ is independently H or alkyl, $R^{5a}$ and $R^{6a}$ are, independently, absent or independently H, —$OR^{53}$, —$NR^{54}R^{55}$, halogen, or alkyl, wherein each $R^{53}$, $R^{54}$, and $R^{55}$ is independently H or $C_1$-$C_6$alkyl,
  wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and
  wherein each $R^{56}$, $R^{57}$, $R^{58}$, $R^{59}$, and $R^{60}$ is independently H or alkyl, or $R^5$ and $R^{5a}$ form an oxo group, or
$R^6$ and $R^{6a}$ form an oxo group;
  wherein if $R^5$ is —$OR^{27}$ or $R^{5a}$ is —$OR^{53}$, then $R^6$ is not —$OR^{27}$, and
  wherein if $R^5$ is —$OR^{27}$ or $R^{5a}$ is —$OR^{53}$, then $R^{6a}$ is not —$OR^{53}$,
$R^7$ is H or $C_1$-$C_3$alkyl;
$R^8$ is H, $C_1$-$C_6$alkyl, an amino protecting group, or

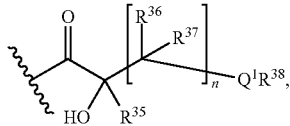

wherein $Q^1$ is NH, O, or S,
n is an integer from 0 to 4,
$R^{35}$ is H or $C_1$-$C_3$alkyl,
each $R^{36}$ and $R^{37}$ is independently H, alkyl, halogen, or —OH, and
$R^{38}$ is H, alkyl, or —C(=NH)$NR^{39}R^{40}$, wherein $R^{39}$ and $R^{40}$ are independently H or $C_1$-$C_3$alkyl, or
$R^{35}$ and $R^{38}$, together with the atoms to which they are attached, form a heterocycloalkyl group comprising at least one N;
$R^{41}$ is H, —CN, —$CONH_2$ or $C_1$-$C_3$alkyl, wherein the $C_1$-$C_3$alkyl is unsubstituted or substituted with one or more substituents selected from the group consisting of —OH, —OC(O)$CH_3$, —$NH_2$, —CN, —$CONH_2$, and halogen;
$R^{42}$ and $R^{43}$ are, independently, H, —OH, —$OR^{45}$, —$NR^{46}R^{47}$, or halogen,
  wherein each $R^{45}$, $R^{46}$, and $R^{47}$ is independently H, alkyl, —$CONH_2$, or —$COCH_3$,
    wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;
$R^{44}$ and $R^{44a}$ are, independently H, OH, halogen, $C_1$-$C_3$alkoxy, or —OC(O)$CH_3$, wherein when $R^{44}$ or $R^{44a}$ is OH, then $R^{41}$ is not H;

$X^1$ is H, $NH_2$, OH, or halogen;
$R^{51a}$, $R^{51b}$, and $R^{51c}$ are, independently, H, OH, or —$OR^{51d}$,
  wherein each $R^{51d}$ is, independently, alkyl or —$COCH_3$,
    wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;
$R^{52a}$ and $R^{52b}$ are independently H, OH, or —$OR^{52c}$,
  wherein each $R^{52c}$ is, independently, alkyl or —$COCH_3$,
    wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl.

In some embodiments, the compound of formula (V) is of formula (V-X)

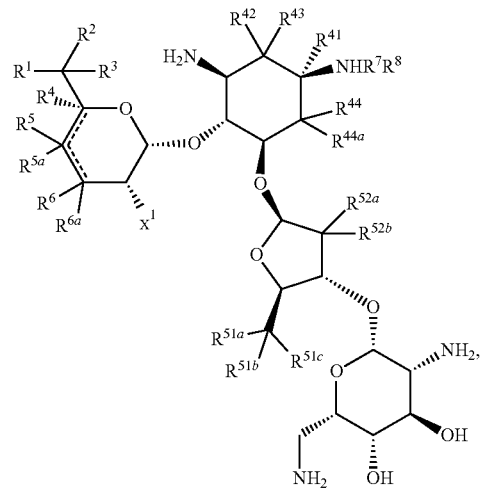

(V-X)

or a pharmaceutically acceptable salt, solvate, or tautomer thereof, wherein $R^1$, $R^2$, $R^3$, $R^4$,

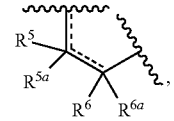

$R^7$, $R^8$, $R^{41}$, $R^{42}$, $R^{43}$, $R^{44}$, $R^{44a}$, $R^{51a}$, $R^{51b}$, $R^{51c}$, $R^{52a}$, and $R^{52b}$ are as defined for formula (V) herein.

In some embodiments of formula (V), including formula (V-X), $R^1$ is —$NR^{10}R^{11}$, wherein $R^{10}$ and $R^{11}$ are independently H or $C_1$-$C_6$alkyl, wherein the alkyl is unsubstituted or substituted with one or more —OH. In certain embodiments, $R^{10}$ and $R^{11}$ are independently H, methyl, or hydroxyethyl. In certain embodiments, $R^{10}$ and $R^{11}$ are both H.

In some embodiments of formula (V), including formula (V-X), $R^1$ is $OR^9$, wherein $R^9$ is H or $C_1$-$C_6$alkyl, wherein the alkyl is unsubstituted or substituted with one or more —OH. In certain embodiments, $R^9$ is H, methyl, or hydroxyethyl. In certain embodiments, $R^9$ is H.

In some embodiments of formula (V), including formula (V-X), $R^2$ and $R^3$ are independently selected from the group consisting of H, alkyl, cycloalkyl, and aryl. In some embodiments, at least one of $R^2$ and $R^3$ is other than H. In certain embodiments, one of $R^2$ and $R^3$ is H.

In some embodiments of formula (V), including formula (V-X), $R^2$ is alkyl, cyclopropyl, or phenyl; wherein the alkyl is unsubstituted or substituted with one, two, or three substituents selected from the group consisting of —$NH_2$, —OH, F, —CN, and —$S(O)_2CH_3$. In some embodiments, $R^2$ is methyl, ethyl, propyl, butyl, pentyl, hexyl, cyclopropyl, cyclobutyl, cyclopentyl, cyclohexyl, or phenyl. In other embodiments, $R^2$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —$SR^{12}$, —$SO_2R^{13}$, —$NR^{14}R^{15}$, and —$OR^{16}$. In some embodiments, the one or more substituents are independently selected from the group consisting of halogen, cyano, aryl, —$SO_2R^{13}$, —$NR^{14}R^{15}$, and —$OR^{16}$. For example, in certain embodiments, the one or more substituents are independently selected from the group consisting of F, Cl, B, I, cyano, —$SO_2CH_3$, —$NH_2$, and —OH. In still other embodiments, $R^2$ is methyl; methyl substituted with one or two F; methyl substituted with —$SO_2CH_3$; methyl substituted with —$NH_2$; methyl substituted with —OH; ethyl; cyclopropyl; or phenyl. In some embodiments, $R^2$ is H or unsubstituted methyl.

In some embodiments of formula (V), including formula (V-X), $R^3$ is methyl, ethyl, propyl, butyl, pentyl, hexyl, cyclopropyl, cyclobutyl, cyclopentyl, cyclohexyl, or phenyl. In other embodiments, $R^3$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —$SR^{12}$, —$SO_2R^{13}$, —$NR^{14}R^{15}$, and —$OR^{16}$. In some embodiments, the one or more substituents are independently selected from the group consisting of halogen, cyano, aryl, —$SO_2R^{13}$, —$NR^{14}R^{15}$, and —$OR^{16}$. For example, in certain embodiments, the one or more substituents are independently selected from the group consisting of F, Cl, B, I, cyano, —$SO_2CH_3$, —$NH_2$, and —OH. In still other embodiments, $R^3$ is methyl; methyl substituted with one or two F; methyl substituted with —$SO_2CH_3$; methyl substituted with —$NH_2$; methyl substituted with —OH; ethyl; cyclopropyl; or phenyl. In certain embodiments, $R^3$ is H or unsubstituted methyl.

In some embodiments of formula (V), including formula (V-X), $R^2$ and $R^3$, together with the atom to which they are attached, form a cycloalkyl group or a heterocycloalkyl group. In some embodiments, the cycloalkyl group or heterocycloalkyl group may be unsubstituted or substituted with one or more substituents independently selected from the group consisting of halogen, cyano, —$SR^{22}$, —$SO_2R^{23}$, —$NR^{24}R^{25}$, and —$OR^{26}$, wherein each $R^{22}$, $R^{23}$, $R^{24}$, $R^{25}$, and $R^{26}$ may be independently H or alkyl. In certain embodiments, $R^2$ and $R^3$ together with the atom to which they are attached form a cyclopropyl or oxetanyl. In certain embodiments, $R^2$ and $R^3$ together with the atom to which they are attached form a cyclopropyl.

In some embodiments of formula (V), including formula (V-X), $R^4$ is H or absent.

In some embodiments of formula (V), including formula (V-X), $R^5$ and $R^6$ are H and $R^{5a}$ and $R^{6a}$ are independently absent or H.

In some embodiments of formula (V), including formula (V-X), both $R^5$ and $R^6$ are H.

In some embodiments of formula (V), including formula (V-X), both $R^{5a}$ and $R^{6a}$ are H.

In some embodiments of formula (V), including formula (V-X), $R^5$ is H or —OH. In some embodiments of formula (V), including formula (V-X), $R^5$ is —OH. In some embodiments of formula (V), including formula (V-X), $R^5$ is H.

In some embodiments of formula (V), including formula (V-X), $R^{5a}$ is H or —OH. In some embodiments of formula (V), including formula (V-X), $R^{5a}$ is —OH. In some embodiments of formula (V), including formula (V-X), $R^{5a}$ is H.

In some embodiments of formula (V), including formula (V-X), $R^6$ is H or —OH. In some embodiments of formula (V), including formula (V-X), $R^6$ is —OH. In some embodiments of formula (V), including formula (V-X), $R^6$ is H.

In some embodiments of formula (V), including formula (V-X), $R^{6a}$ is H or —OH. In some embodiments of formula (V), including formula (V-X), $R^{6a}$ is —OH. In some embodiments of formula (V), including formula (V-X), $R^{6a}$ is H.

In some embodiments of formula (V), including formula (V-X), $R^5$ is H, halogen, or —OH. In certain such embodiments, $R^5$ is halogen. In certain such embodiments, $R^5$ is F.

In some embodiments of formula (V), including formula (V-X), $R^{5a}$ is H, halogen, or —OH. In certain such embodiments, $R^{5a}$ is halogen. In certain such embodiments, $R^{5a}$ is F.

In some embodiments of formula (V), including formula (V-X), $R^6$ is H, halogen, or —OH. In certain such embodiments, $R^6$ is halogen. In certain such embodiments, $R^6$ is F.

In some embodiments of formula (V), including formula (V-X), $R^{6a}$ is H, halogen, or —OH. In certain such embodiments, $R^{6a}$ is halogen. In certain such embodiments, $R^{6a}$ is F.

In some embodiments of formula (V), including formula (V-X), $R^5$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (V), including formula (V-X), $R^{5a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (V), including formula (V-X), $R^6$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (V), including formula (V-X), $R^{6a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (V), including formula (V-X), $R^4$ is H.

In some embodiments of formula (V), including formula (V-X), $X^1$ is $NH_2$. In some embodiments of formula (V), including formula (V-X), $X^1$ is OH. In some embodiments of formula (V), including formula (V-X), $X^1$ is halogen. In some embodiments of formula (V), including formula (V-X), $X^1$ is F. In some embodiments of formula (V), including formula (V-X), $X^1$ is Cl. In some embodiments of formula (V), including formula (V-X), $X^1$ is Br. In some embodiments of formula (V), including formula (V-X), $X^1$ is I.

In some embodiments of formula (V), including formula (V-X), $R^{41}$ is H.

In some embodiments of formula (V), including formula (V-X), one of $R^{42}$ and $R^{43}$ is —OH. In some embodiments of formula (V), including formula (V-X), one of $R^{42}$ and $R^{43}$ is halogen. In some embodiments of formula (V), including formula (V-X), one of $R^{42}$ and $R^{43}$ is H. In some embodiments of formula (V), including formula (V-X), one of $R^{42}$ and $R^{43}$ is —$NR^{46}R^{47}$. In some embodiments of formula (V), including formula (V-X), one of $R^{42}$ and $R^{43}$ is —F. In some embodiments of formula (V), including formula (V-X), $R^{42}$ is —F and $R^{43}$ is —F. In some embodiments of formula (V), including formula (V-X), one of $R^{42}$ and $R^{43}$ is —OH. In some embodiments of formula (V), including formula (V-X), one of $R^{42}$ and $R^{43}$ is —$OR^{45}$.

In some embodiments of formula (V), including formula (V-X), $R^{42}$ and $R^{43}$ are H.

In some embodiments of formula (V), including formula (V-X), one of $R^{44}$ and $R^{44a}$ is —$OCH_3$. In some embodiments of formula (V), including formula (V-X), one of $R^{44}$ and $R^{44a}$ is —F. In some embodiments of formula (V), including formula (V-X), $R^{44}$ and $R^{44a}$ are —F. In some embodiments of formula (V), including formula (V-X), $R^{44}$ and $R^{44a}$ are H. In some embodiments of formula (V), including formula (V-X), one of $R^{44}$ and $R^{44a}$ is H. In some embodiments of formula (V), including formula (V-X), $R^{44}$ and $R^{44a}$ are, independently, H, halogen, $C_1$-$C_3$alkoxy, or —$OC(O)CH_3$.

In some embodiments of formula (V), including formula (V-X), $R^{51a}$, $R^{51b}$, and $R^{51c}$ are, independently, H, OH, or —$OR^{51d}$. In some embodiments of formula (V), including formula (V-X), one of $R^{51a}$, $R^{51b}$, and $R^{51c}$ is —OH. In some embodiments of formula (V), including formula (V-X), one of $R^{51a}$, $R^{51b}$, and $R^{51c}$ is —$OR^{51d}$. In some embodiments of formula (V), including formula (V-X), $R^{51a}$ is —OH and $R^{51b}$ and $R^{51c}$ are H. In some embodiments of formula (V), including formula (V-X), $R^{51a}$ is —$OR^{51d}$ and $R^{51b}$ and $R^{51c}$ are H.

In some embodiments of formula (V), including formula (V-X), $R^{52a}$ and $R^{52b}$ are independently H, OH, or —$OR^{52c}$. In some embodiments of formula (V), including formula (V-X), $R^{52a}$ and $R^{52b}$ are —OH. In some embodiments of formula (V), including formula (V-X), one of $R^{52a}$ and $R^{52b}$ is —$OR^{52c}$. In some embodiments of formula (V), including formula (V-X), one of $R^{52a}$ and $R^{52b}$ is —OH. In some embodiments of formula (V), including formula (V-X), $R^{52a}$ is H and $R^{52b}$ is —$OR^{52c}$. In some embodiments of formula (V), including formula (V-X), $R^{52a}$ is H and $R^{52b}$ is —OH.

In some embodiments of formula (V), including formula (V-X), $R^7$ is H. In other embodiments, $R^7$ is $C_1$-$C_3$alkyl, for example $C_1$-alkyl, $C_2$-alkyl, or $C_3$-alkyl. In some embodiments, $R^8$ is H. In some embodiments of formula (V), including formula (V-X), $R^7$ is H and $R^8$ is H.

In some embodiments of formula (V), including formula (V-X), $R^8$ is $C_1$-$C_6$alkyl, for example $C_1$-alkyl, $C_2$-alkyl, $C_3$-alkyl, $C_4$-alkyl, $C_5$-alkyl, or $C_6$-alkyl.

In some embodiments of formula (V), including formula (V-X), $R^8$ is

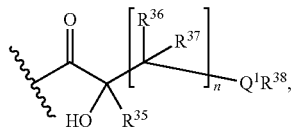

wherein $Q^1$ is NH, O, or S. In certain embodiments, $Q^1$ is NH. In certain embodiments, $Q^1$ is O. In certain embodiments, $Q^1$ is S. In certain embodiments, wherein when n is one, then $R^{36}$ and $R^{37}$ are not halo.

In some embodiments of formula (V), including formula (V-X), n is an integer from 0 to 4, from 0 to 3, from 0 to 2, from 1 to 4, from 2 to 4, or from 1 to 3. In certain embodiments, n is 0, or n is 1, or n is 2, or n is 3, or n is 4.

In Formula (V), the ring substituted by $R^1$, $R^2$, $R^3$, $R^4$, $R^5$, $R^{5a}$, $R^6$, $R^{6a}$, and $X^1$ may also be referred to as Ring A, as shown below. The ring substituted $R^7$, $R^8$, $R^{41}$, $R^{42}$, $R^{43}$, $R^{44}$, and $R^{44a}$ may also referred to as Ring B, as shown below. Ring C is also used to refer to the moiety connected to Ring B through —O— moiety, as shown below. Ring D is also used to refer to the moiety connected to Ring C through —O— moiety, as shown below.

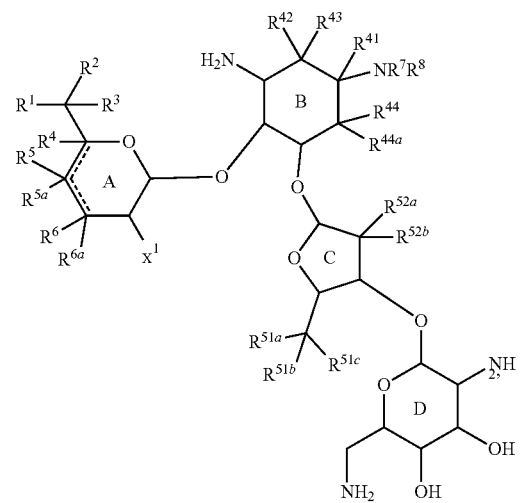

In some embodiments of the compound of Formula (V), Ring A is selected from

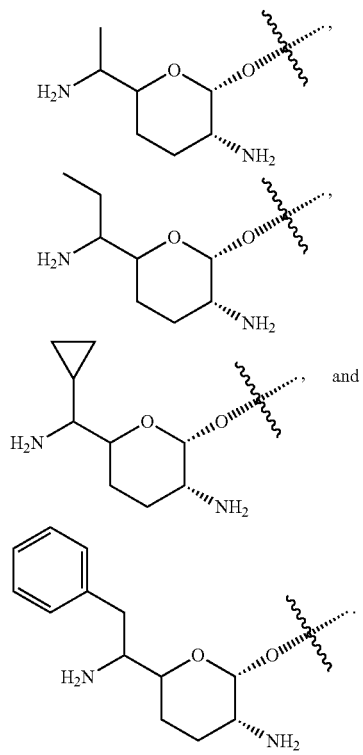

In some embodiments of the compound of Formula (V), Ring A is selected from

In some embodiments of the compound of Formula (V), Ring A is selected from
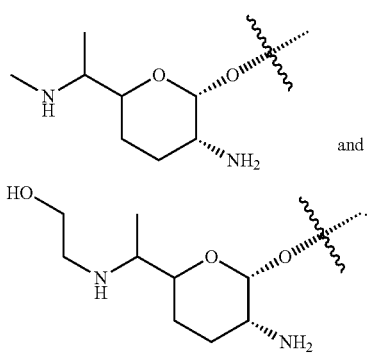
and
In some embodiments of the compound of Formula (V), Ring A is selected from
In some embodiments of the compound of Formula (V), Ring A is selected from
In some embodiments of the compound of Formula (V), Ring A is selected from
In some embodiments of the compound of Formula (V), Ring A is selected from

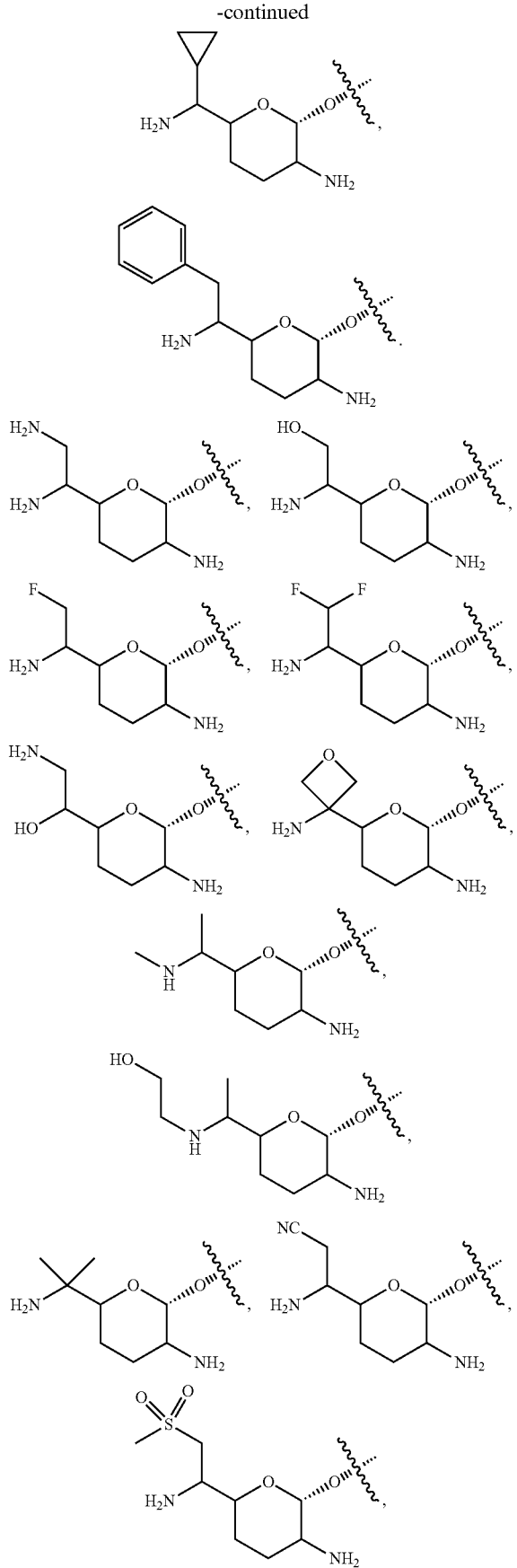
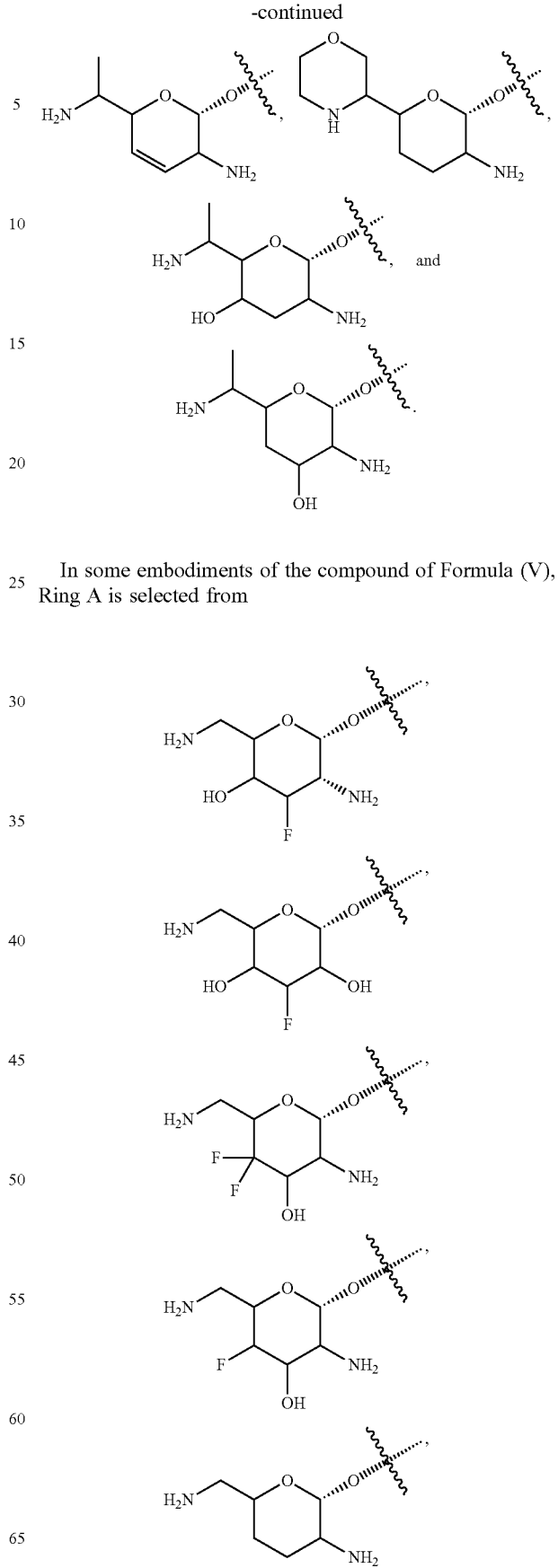
In some embodiments of the compound of Formula (V), Ring A is selected from

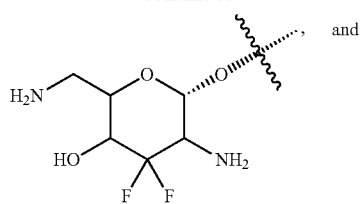
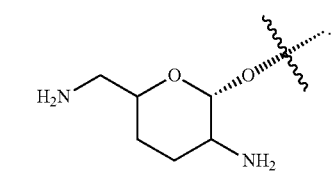
In some embodiments of the compound of Formula (V), Ring B is selected from
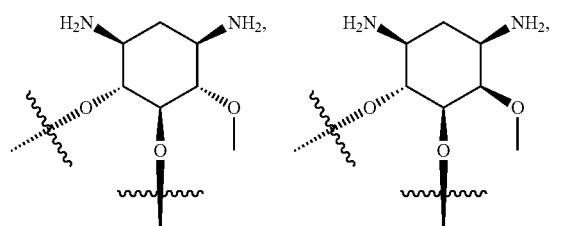
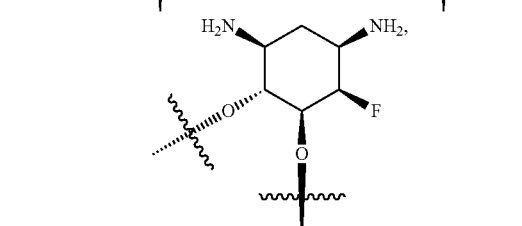
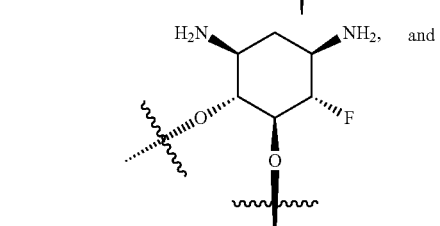
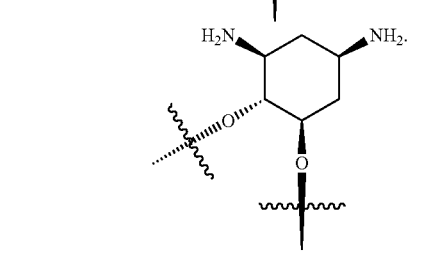
In some embodiments of the compound of Formula (V), Ring B is selected from
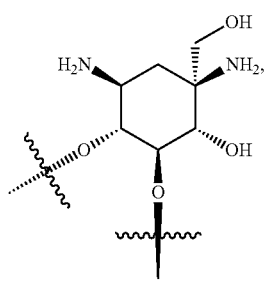
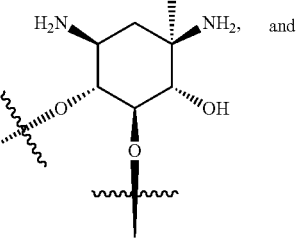
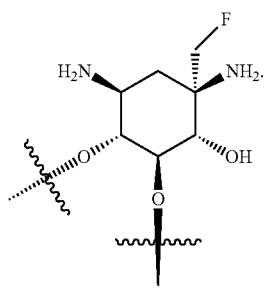
In some embodiments of the compound of Formula (V), Ring B is
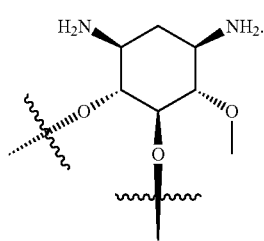
In some embodiments of the compound of Formula (V), Ring B is
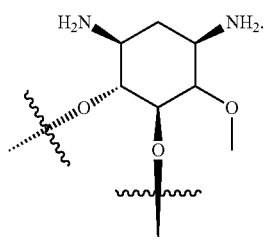
In some embodiments of the compound of Formula (V), Ring B is

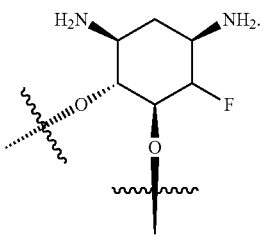

In some embodiments of the compound of Formula (V), Ring B is

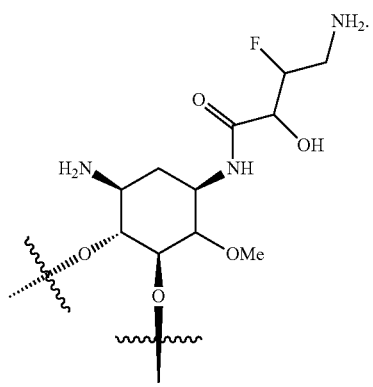

In some embodiments of the compound of Formula (V), Ring B is

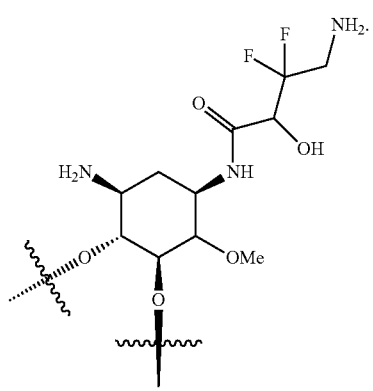

In some embodiments of the compound of Formula (V), Ring B is

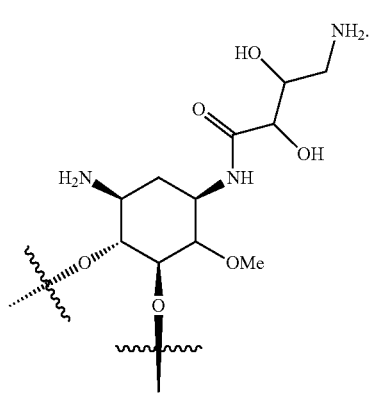

In some embodiments of the compound of Formula (V), Ring B is

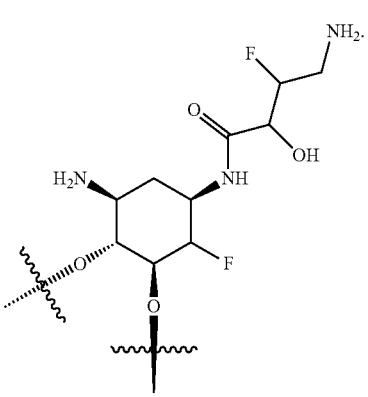

In some embodiments of the compound of Formula (V), Ring B is

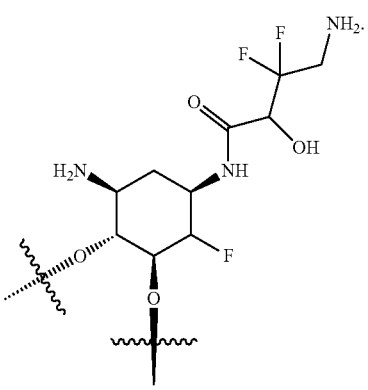

In some embodiments of the compound of Formula (V), Ring B is

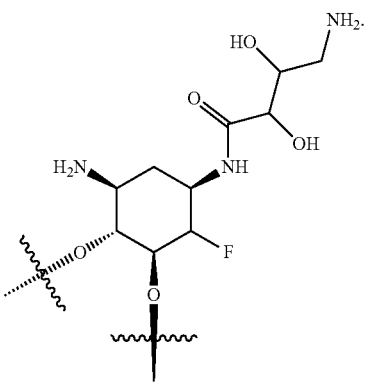

In some embodiments, the compound of formula (IV) is of formula (VI):

(VI)

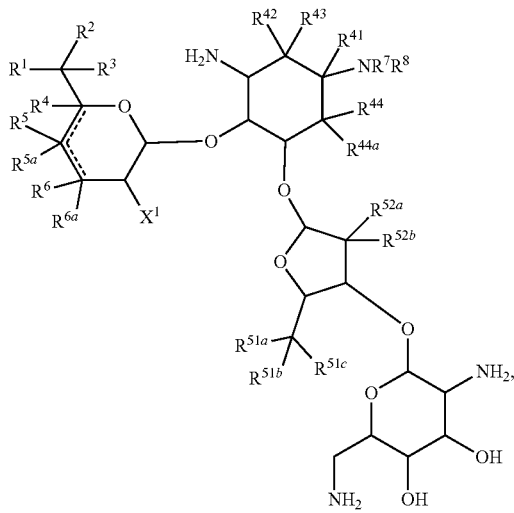

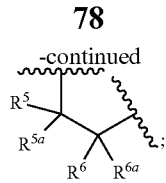

-continued

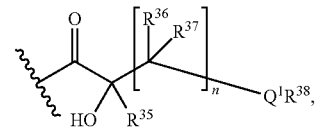

or a pharmaceutically acceptable salt, solvate, tautomer, or stereoisomer thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl,
  wherein the alkyl, cycloalkyl, or aryl is unsubstituted or substituted with one or more substituents independently selected from the group consisting of halogen, cyano, aryl, —$SR^{12}$, —$SO_{2R}^{13}$, —$OSF_2NR^{14}R^{15}$, —$NR^{14}R^{15}$, and —$OR^{16}$, and
  wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O,
  wherein the heterocycloalkyl group is unsubstituted or substituted with one or more substituents independently selected from the group consisting of halogen, cyano, —$SR^{17}$, —$SO_{2R}^{18}$, —$NR^{19}R^{20}$, and —$OR^{21}$, and
  wherein each $R^{17}$, $R^{18}$, $R^{19}$, $R^{20}$, and $R^{21}$ is independently H or alkyl, or $R^2$ and $R^3$, together with the atom to which they are attached, form a cycloalkyl group or a heterocycloalkyl group,
  wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and
  wherein each $R^{22}$, $R^{23}$, $R^{24}$, $R^{25}$, and $R^{26}$ is independently H or alkyl; $R^4$ is H or absent;

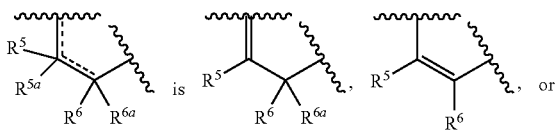

$R^5$ and $R^6$ are independently H, —$OR^{27}$, —$NR^{28}R^{29}$, halogen, or alkyl, wherein each $R^{27}$, $R^{28}$, and $R^{29}$ is independently H or $C_1$-$C_6$alkyl,
  wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_{2R}^{34}$, and
  wherein each $R^{30}$, $R^{31}$, $R^{32}$, $R^{33}$, and $R^{34}$ is independently H or alkyl, $R^{5a}$ and $R^{6a}$ are, independently, absent or independently H, —$OR^{53}$, —$NR^{54}R^{55}$, halogen, or alkyl, wherein each $R^{53}$, $R^{54}$, and $R^{55}$ is independently H or $C_1$-$C_6$alkyl,
  wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_{2R}^{60}$, and
  wherein each $R^{56}$, $R^{57}$, $R^{58}$, $R^{59}$, and $R^{60}$ is independently H or alkyl, or $R^5$ and $R^{5a}$ form an oxo group, or
$R^6$ and $R^{6a}$ form an oxo group;
$R^7$ is H or $C_1$-$C_3$alkyl;
$R^8$ is H, $C_1$-$C_6$alkyl, an amino protecting group, or wherein $Q^1$ is NH, O, or S,
n is an integer from 0 to 4,
$R^{35}$ is H or $C_1$-$C_3$alkyl,
each $R^{36}$ and $R^{37}$ is independently H, alkyl, halogen, or —OH, and
$R^{38}$ is H, alkyl, or —C(=NH)$NR^{39}R^{40}$, wherein $R^{39}$ and $R^{40}$ are independently H or
$C_1$-$C_3$alkyl, or
$R^{35}$ and $R^{38}$, together with the atoms to which they are attached, form a heterocycloalkyl group comprising at least one N;

$R^{41}$ is H, —CN, —$CONH_2$ or $C_1$-$C_3$alkyl, wherein the $C_1$-$C_3$alkyl is unsubstituted or substituted with one or more substituents selected from the group consisting of —OH, —$OC(O)CH_3$, —$NH_2$, —CN, —$CONH_2$, and halogen;

$R^{42}$ $R^{43}$ are, independently H, —OH, —$OR^{45}$, —$NR^{46}R^{47}$, or halogen,
  wherein each $R^{45}$, $R^{46}$, and $R^{47}$ is independently H, alkyl, —$CONH_2$, or —$COCH_3$,
  wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{44}$ and $R^{44a}$ are, independently H, halogen, —OH, $C_1$-$C_3$alkoxy, or —$OC(O)CH_3$;

$X^1$ is H, $NH_2$, OH, or halogen:

$R^{51a}$, $R^{51b}$, and $R^{51c}$ are, independently, H, OH, or —$OR^{51d}$, wherein each $R^{51d}$ is, independently. alkyl or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl; $R^{52a}$ and $R^{52b}$ are independently H, OH, or —OR$^{52c}$, wherein each $R^{52c}$ is, independently. alkyl or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

In some embodiments, the compound of formula (VI) is of formula (VI-X)

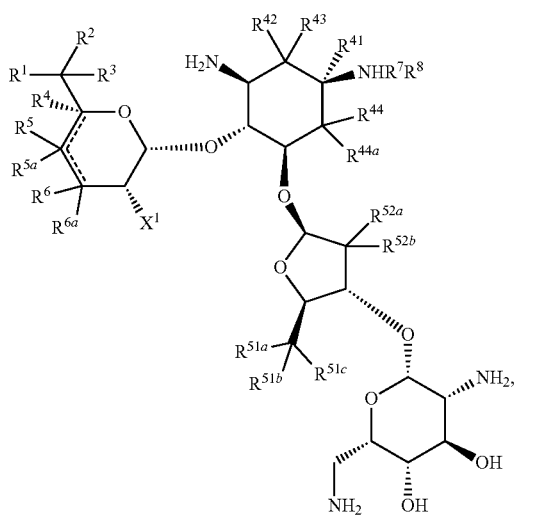

(VI-X)

or a pharmaceutically acceptable salt, solvate, or tautomer thereof, wherein $R^1$, $R^2$, $R^3$, $R^4$,

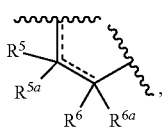

$R^7$, $R^8$, $R^{41}$, $R^{42}$, $R^{43}$, $R^{44}$, $R^{44a}$, $R^{51a}$, $R^{51b}$, $R^{51c}$, $R^{52a}$, and $R^{52b}$ are as defined for formula (VI) herein.

In some embodiments of formula (VI), including formula (VI-X), $R^1$ is —NR$^{10}$R$^{11}$, wherein $R^{10}$ and $R^{11}$ are independently H or C$_1$-C$_6$alkyl, wherein the alkyl is unsubstituted or substituted with one or more —OH. In certain embodiments, $R^{10}$ and $R^{11}$ are independently H, methyl, or hydroxyethyl. In certain embodiments, $R^{10}$ and $R^{11}$ are both H.

In some embodiments of formula (VI), including formula (VI-X), $R^1$ is OR$^9$, wherein $R^9$ is H or C$_1$-C$_6$alkyl, wherein the alkyl is unsubstituted or substituted with one or more —OH. In certain embodiments, $R^9$ is H, methyl, or hydroxyethyl. In certain embodiments, $R^9$ is H.

In some embodiments of formula (VI), including formula (VI-X), $R^2$ and $R^3$ are independently selected from the group consisting of H, alkyl, cycloalkyl, and aryl. In some embodiments, at least one of $R^2$ and $R^3$ is other than H. In certain embodiments, one of $R^2$ and $R^3$ is H.

In some embodiments of formula (VI), including formula (VI-X), $R^2$ and $R^3$ are independently selected from the group consisting of H, alkyl, cycloalkyl, and aryl. In some embodiments, at least one of $R^2$ and $R^3$ is other than H. In certain embodiments, one of $R^2$ and $R^3$ is H.

In some embodiments of formula (VI), including formula (V-X), $R^2$ is alkyl, cyclopropyl, or phenyl; wherein the alkyl is unsubstituted or substituted with one, two, or three substituents selected from the group consisting of —NH$_2$, —OH, F, —CN, and —S(O)$_2$CH$_3$. In some embodiments, $R^2$ is methyl, ethyl, propyl, butyl, pentyl, hexyl, cyclopropyl, cyclobutyl, cyclopentyl, cyclohexyl, or phenyl. In other embodiments, $R^2$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —SR$^{12}$, —SO$_2$R$^{13}$, —NR$^{14}$R$^{15}$, and —OR$^{16}$. In some embodiments, the one or more substituents are independently selected from the group consisting of halogen, cyano, aryl, —SO$_2$R$^{13}$, —NR$^{14}$R$^{15}$, and —OR$^{16}$. For example, in certain embodiments, the one or more substituents are independently selected from the group consisting of F, Cl, B, I, cyano, —SO$_2$CH$_3$, —NH$_2$, and —OH. In still other embodiments, $R^2$ is methyl; methyl substituted with one or two F; methyl substituted with —SO$_2$CH$_3$; methyl substituted with —NH$_2$; methyl substituted with —OH; ethyl; cyclopropyl; or phenyl. In some embodiments, $R^2$ is H or unsubstituted methyl.

In some embodiments of formula (VI), including formula (VI-X), $R^3$ is methyl, ethyl, propyl, butyl, pentyl, hexyl, cyclopropyl, cyclobutyl, cyclopentyl, cyclohexyl, or phenyl. In other embodiments, $R^3$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —SR$^{12}$, —SO$_2$R$^{13}$, —NR$^{14}$R$^{15}$, and —OR$^{16}$. In some embodiments, the one or more substituents are independently selected from the group consisting of halogen, cyano, aryl, —SO$_2$R$^{13}$, —NR$^{14}$R$^{15}$, and —OR$^{16}$. For example, in certain embodiments, the one or more substituents are independently selected from the group consisting of F, Cl, B, I, cyano, —SO$_2$CH$_3$, —NH$_2$, and —OH. In still other embodiments, $R^3$ is methyl; methyl substituted with one or two F; methyl substituted with —SO$_2$CH$_3$; methyl substituted with —NH$_2$; methyl substituted with —OH; ethyl; cyclopropyl; or phenyl. In certain embodiments, $R^3$ is H or unsubstituted methyl.

In some embodiments of formula (VI), including formula (VI-X), $R^2$ and $R^3$, together with the atom to which they are attached, form a cycloalkyl group or a heterocycloalkyl group. In some embodiments, the cycloalkyl group or heterocycloalkyl group may be unsubstituted or substituted with one or more substituents independently selected from the group consisting of halogen, cyano, —SR$^{22}$, —SO$_2$R$^{23}$, —NR$^{24}$R$^{25}$, and —OR$^{26}$, wherein each $R^{22}$, $R^{23}$, $R^{24}$, $R^{25}$, and $R^{26}$ may be independently H or alkyl. In certain embodiments, $R^2$ and $R^3$ together with the atom to which they are attached form a cyclopropyl or oxetanyl. In certain embodiments, $R^2$ and $R^3$ together with the atom to which they are attached form a cyclopropyl.

In some embodiments of formula (VI), including formula (VI-X), $R^4$ is H or absent.

In some embodiments of formula (VI), including formula (VI-X), $R^5$ and $R^6$ are H and $R^{5a}$ and $R^{6a}$ are independently absent or H.

In some embodiments of formula (VI), including formula (VI-X), both $R^5$ and $R^6$ are H.

In some embodiments of formula (VI), including formula (VI-X), both $R^{5a}$ and $R^{6a}$ are H.

In some embodiments of formula (VI), including formula (VI-X), $R^5$ is H or —OH. In some embodiments of formula (VI), including formula (VI-X), $R^5$ is —OH. In some embodiments of formula (VI), including formula (VI-X), $R^5$ is H.

In some embodiments of formula (VI), including formula (VI-X), $R^{5a}$ is H or —OH. In some embodiments of formula (VI), including formula (VI-X), $R^{5a}$ is —OH. In some embodiments of formula (VI), including formula (VI-X), $R^{5a}$ is H.

In some embodiments of formula (VI), including formula (VI-X), $R^6$ is H or —OH. In some embodiments of formula (VI), including formula (VI-X), $R^6$ is —OH. In some embodiments of formula (VI), including formula (VI-X), $R^6$ is H.

In some embodiments of formula (VI), including formula (VI-X), $R^{6a}$ is H or —OH. In some embodiments of formula (VI), including formula (VI-X), $R^{6a}$ is —OH. In some embodiments of formula (VI), including formula (VI-X), $R^{6a}$ is H.

In some embodiments of formula (VI), including formula (VI-X), $R^5$ is H, halogen, or —OH. In certain such embodiments, $R^5$ is halogen. In certain such embodiments, $R^5$ is F.

In some embodiments of formula (VI), including formula (VI-X), $R^{5a}$ is H, halogen, or —OH. In certain such embodiments, $R^{5a}$ is halogen. In certain such embodiments, $R^{5a}$ is F.

In some embodiments of formula (VI), including formula (VI-X), $R^6$ is H, halogen, or —OH. In certain such embodiments, $R^6$ is halogen. In certain such embodiments, $R^6$ is F.

In some embodiments of formula (VI), including formula (VI-X), $R^{6a}$ is H, halogen, or —OH. In certain such embodiments, $R^{6a}$ is halogen. In certain such embodiments, $R^{6a}$ is F.

In some embodiments of formula (VI), including formula (VI-X), $R^5$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (VI), including formula (VI-X), $R^{5a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (VI), including formula (VI-X), $R^6$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (VI), including formula (VI-X), $R^{6a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (VI), including formula (VI-X), $R^4$ is H.

In some embodiments of formula (VI), including formula (VI-X), $X^1$ is $NH_2$. In some embodiments of formula (VI), including formula (VI-X), $X^1$ is OH. In some embodiments of formula (VI), including formula (VI-X), $X^1$ is halogen. In some embodiments of formula (VI), including formula (VI-X), $X^1$ is F. In some embodiments of formula (VI), including formula (VI-X), $X^1$ is Cl. In some embodiments of formula (VI), including formula (VI-X), $X^1$ is Br. In some embodiments of formula (VI), including formula (VI-X), $X^1$ is I.

In some embodiments of formula (VI), including formula (VI-X), $R^{41}$ is H.

In some embodiments of formula (VI), including formula (VI-X), one of $R^{42}$ and $R^{43}$ is —OH. In some embodiments of formula (VI), including formula (VI-X), one of $R^{42}$ and $R^{43}$ is halogen. In some embodiments of formula (VI), including formula (VI-X), one of $R^{42}$ and $R^{43}$ is H. In some embodiments of formula (VI), including formula (VI-X), one of $R^{42}$ and $R^{43}$ is —$NR^{46}R^{47}$. In some embodiments of formula (VI), including formula (VI-X), one of $R^{42}$ and $R^{43}$ is —F. In some embodiments of formula (VI), including formula (VI-X), $R^{42}$ is —F and $R^{43}$ is —F. In some embodiments of formula (VI), including formula (VI-X), one of $R^{42}$ and $R^{43}$ is —OH. In some embodiments of formula (VI), including formula (VI-X), one of $R^{42}$ and $R^{43}$ is —$OR^{45}$.

In some embodiments of formula (VI), including formula (VI-X), one of $R^{44}$ and $R^{44a}$ is —OH. In some embodiments of formula (VI), including formula (VI-X), one of $R^{44}$ and $R^{44a}$ is —$OCH_3$. In some embodiments of formula (VI), including formula (VI-X), one of $R^{44}$ and $R^{44a}$ is —F. In some embodiments of formula (VI), including formula (VI-X), $R^{44}$ and $R^{44a}$ are —F. In some embodiments of formula (VI), including formula (VI-X), $R^{44}$ and $R^{44a}$ are H. In some embodiments of formula (VI), including formula (VI-X), one of $R^{44}$ and $R^{44a}$ is H. In some embodiments of formula (VI), including formula (VI-X), $R^{44}$ and $R^{44a}$ are, independently H, halogen, $C_1$-$C_3$alkoxy, or —$OC(O)CH_3$.

In some embodiments of formula (VI), including formula (VI-X), $R^{51a}$, $5^{51b}$, and $R^{51c}$ are, independently, H, OH, or —$OR^{51d}$. In some embodiments of formula (VI), including formula (VI-X), one of $R^{51a}$, $R^{51b}$, and $R^{51c}$ is —OH. In some embodiments of formula (VI), including formula (VI-X), one of $R^{51a}$, $R^{51b}$, and $R^{51c}$ is —$OR^{51d}$. In some embodiments of formula (VI), including formula (VI-X), $R^{51a}$ is —OH and $R^{51b}$ and $R^{51c}$ are H. In some embodiments of formula (VI), including formula (VI-X), $R^{51a}$ is —$OR^{51d}$ and $R^{51b}$ and $R^{51c}$ are H.

In some embodiments of formula (VI), including formula (VI-X), $R^{52a}$ and $R^{52b}$ are independently H, OH, or —$OR^{52c}$. In some embodiments of formula (VI), including formula (VI-X), $R^{52a}$ and $R^{52b}$ are —OH. In some embodiments of formula (VI), including formula (VI-X), one of $R^{52a}$ and $R^{52b}$ is —$OR^{52c}$. In some embodiments of formula (VI), including formula (VI-X), one of $R^{52a}$ and $R^{52b}$ is —OH. In some embodiments of formula (VI), including formula (VI-X), $R^{52a}$ is H and $R^{52b}$ is —$OR^{52c}$. In some embodiments of formula (VI), including formula (VI-X), $R^{52a}$ is H and $R^{52b}$ is —OH.

In some embodiments of formula (VI), including formula (VI-X), $R^7$ is H. In other embodiments, $R^7$ is $C_1$-$C_3$alkyl, for example $C_1$-alkyl, $C_2$-alkyl, or $C_3$-alkyl. In some embodiments, $R^8$ is H. In some embodiments of formula (VI), including formula (VI-X), $R^7$ is H and $R^8$ is H.

In some embodiments of formula (VI), including formula (VI-X), $R^8$ is $C_1$-$C_6$alkyl, for example $C_1$-alkyl, $C_2$-alkyl, $C_3$-alkyl, $C_4$-alkyl, $C_5$-alkyl, or $C_6$-alkyl.

In some embodiments of formula (VI), including formula (VI-X), $R^8$ is

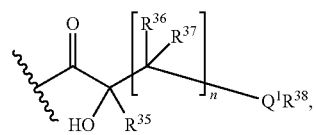

wherein $Q^1$ is NH, O, or S. In certain embodiments, $Q^1$ is NH. In certain embodiments, $Q^1$ is O. In certain embodiments, $Q^1$ is S. In certain embodiments, wherein when n is one, then $R^{36}$ and $R^{37}$ are not halo.

In some embodiments of formula (VI), including formula (VI-X), n is an integer from 0 to 4, from 0 to 3, from 0 to 2, from 1 to 4, from 2 to 4, or from 1 to 3. In certain embodiments, n is 0, or n is 1, or n is 2, or n is 3, or n is 4.

In Formula (VI), the ring substituted by $R^1$, $R^2$, $R^3$, $R^4$, $R^5$, $R^{5a}$, $R^6$, $R^{6a}$, and $X^1$ may also be referred to as Ring A, as shown below. The ring substituted $R^7$, $R^8$, $R^{41}$, $R^{42}$, $R^{43}$, $R^{44}$, and $R^{44a}$ may also referred to as Ring B, as shown below. Ring C is also used to refer to the moiety connected to Ring B through —O— moiety, as shown below. Ring D is also used to refer to the moiety connected to Ring C through —O— moiety, as shown below.

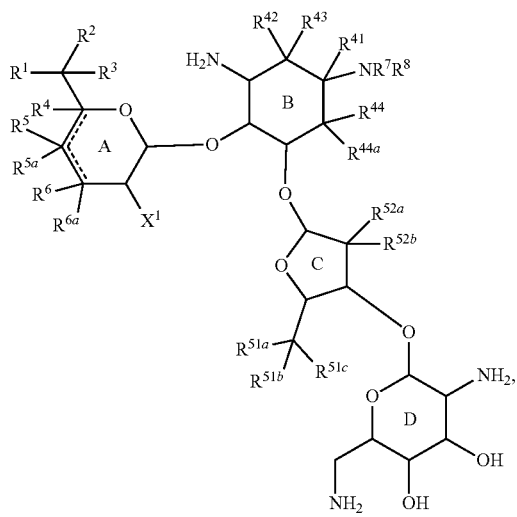

In some embodiments of the compound of Formula (VI), Ring A is selected from

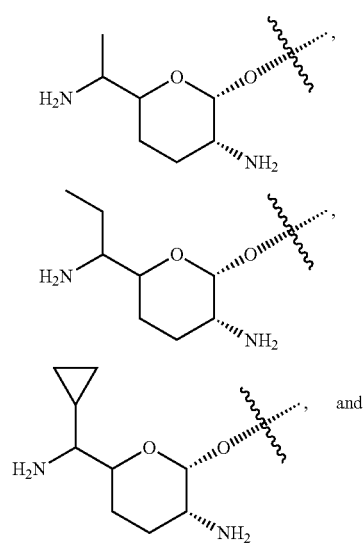

In some embodiments of the compound of Formula (VI), Ring A is selected from

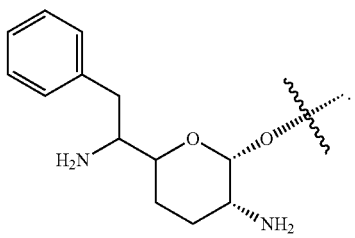

In some embodiments of the compound of Formula (VI), Ring A is selected from

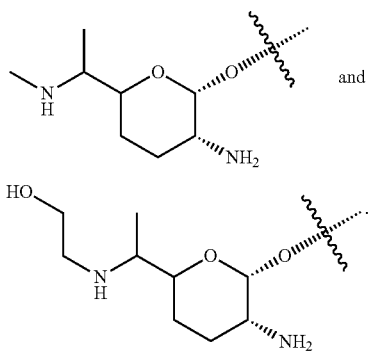

In some embodiments of the compound of Formula (VI), Ring A is selected from

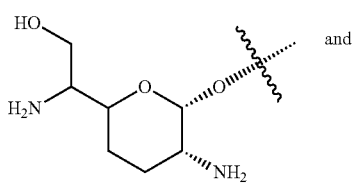

In some embodiments of the compound of Formula (VI), Ring A is selected from

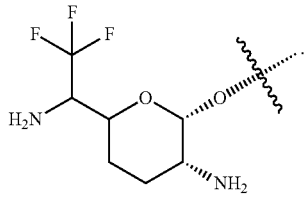

In some embodiments of the compound of Formula (VI), Ring A is selected from

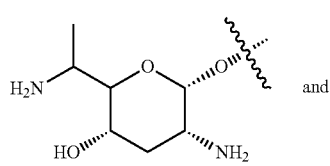

-continued
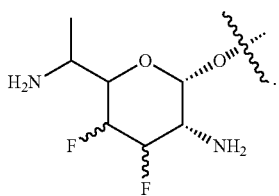
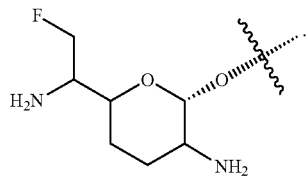
In some embodiments of the compound of Formula (VI), Ring A is selected from
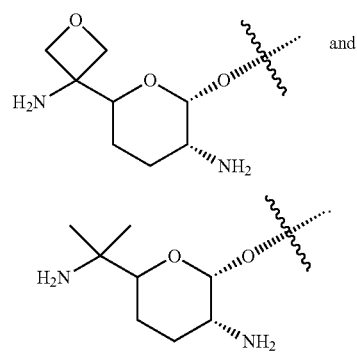
In some embodiments of the compound of Formula (VI), Ring A is selected from
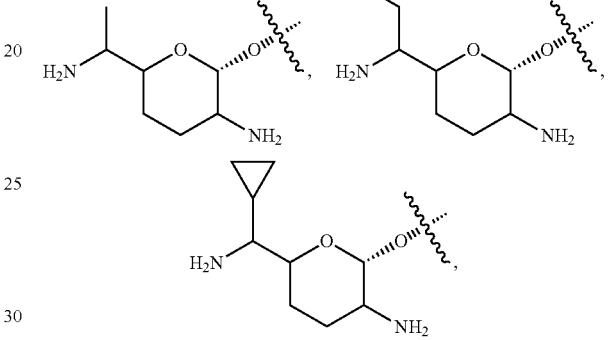
In some embodiments of the compound of Formula (VI), Ring A is selected from
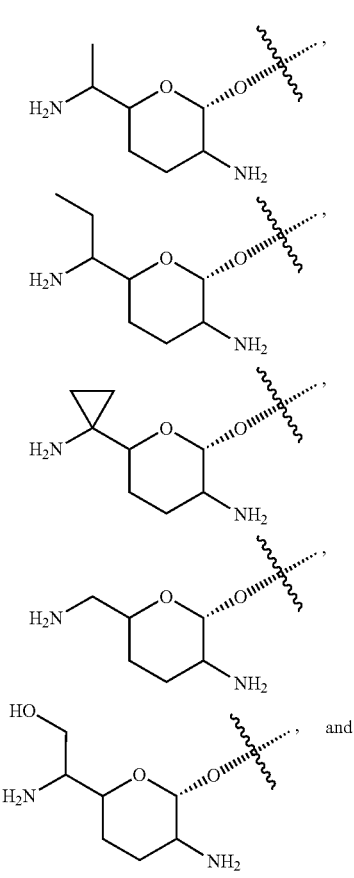
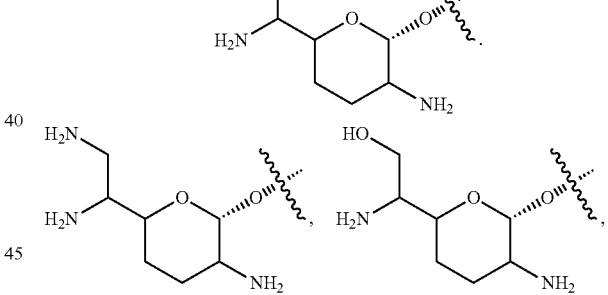
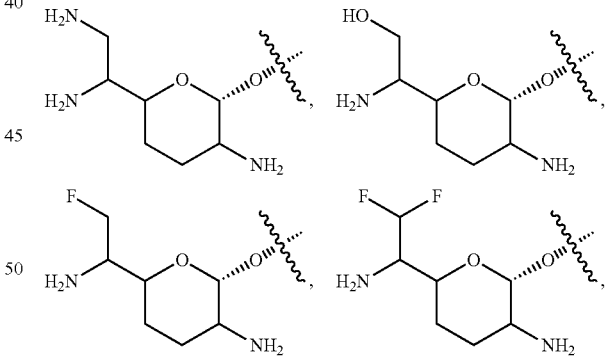
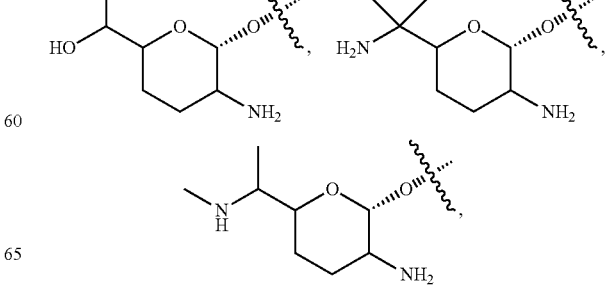

-continued
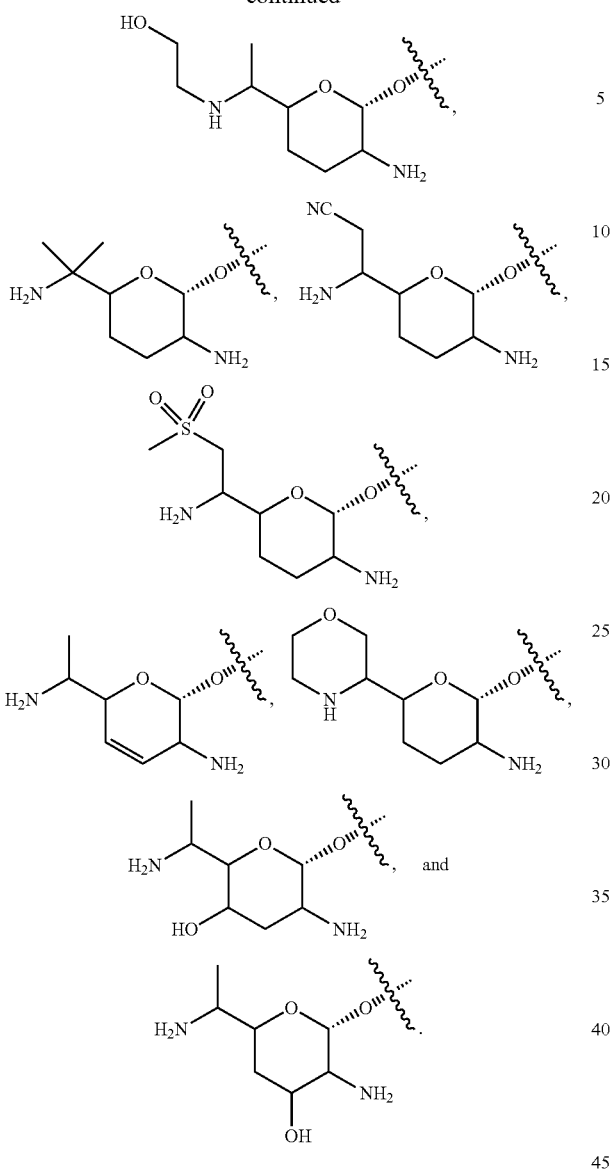
In some embodiments of the compound of Formula (VI), Ring A is selected from
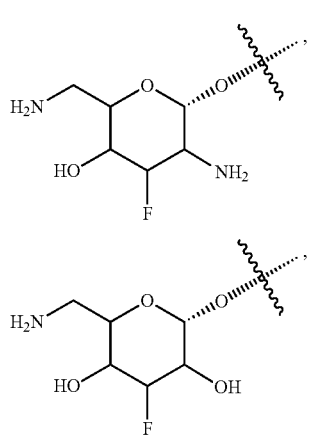
-continued
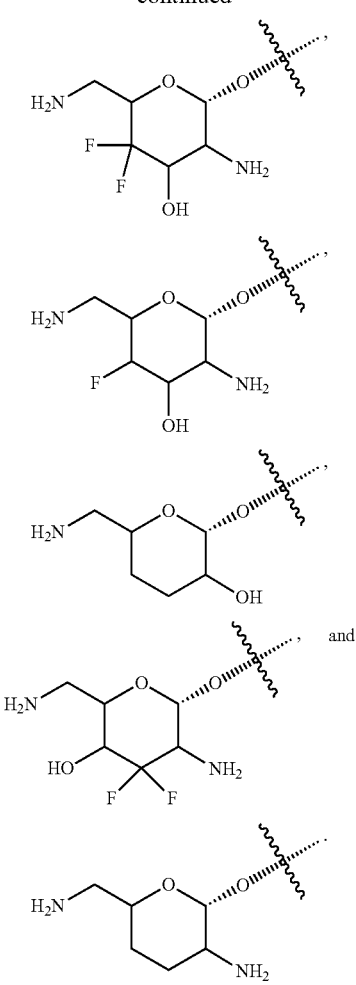
In some embodiments of the compound of Formula (VI), Ring B is selected from
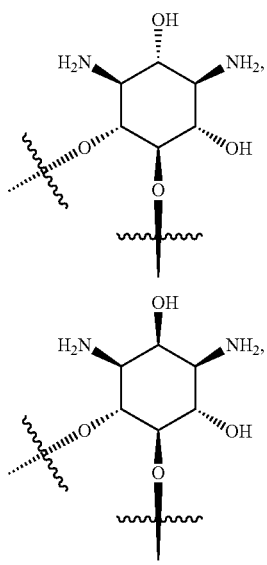

-continued

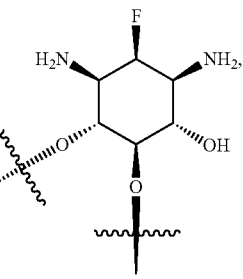

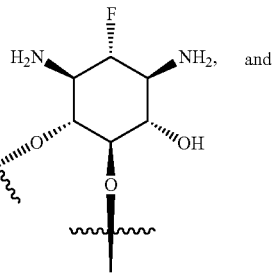 and

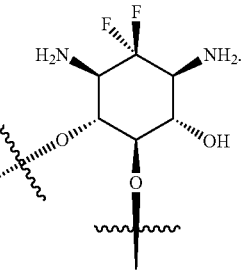

In some embodiments of the compound of Formula (VI), Ring B is

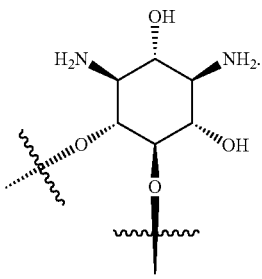

In some embodiments of the compound of Formula (VI), Ring B is selected from

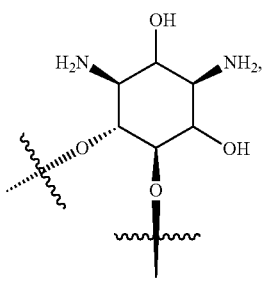

-continued

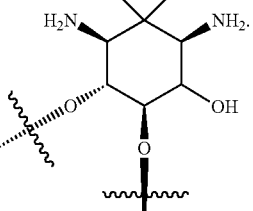

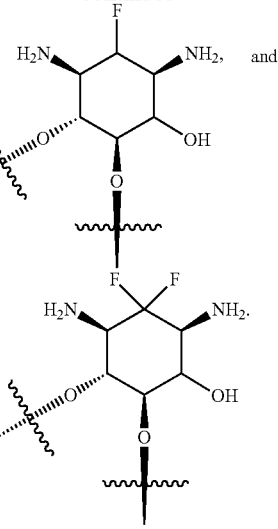

Provided herein are compounds of formula (VIIa):

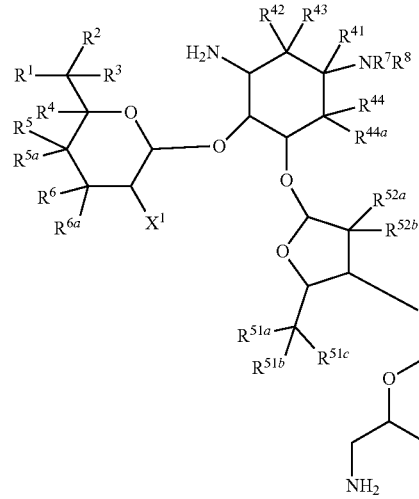

(VIIa)

and pharmaceutically acceptable salts, solvates, tautomers, or stereoisomers thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl, wherein the alkyl, cycloalkyl, or aryl is unsubstituted or substituted with one or more substituents independently selected from the group consisting of halogen, cyano, aryl, —$SR^{12}$, —$SO_2R^{13}$, —$OSF_2NR^{14}R^{15}$, —$NR^{14}R^{15}$, and —$OR^{16}$, and wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —$SO_2R^{18}$, —$NR^{19}R^{20}$, and —$OR^{21}$, and
wherein each $R^{17}$, $R^{18}$, $R^{19}$, $R^{20}$, and $R^{21}$ is independently H or alkyl, or $R^2$ and $R^3$, together with the atom to which they are attached, form a cycloalkyl group or a heterocycloalkyl group,
wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and
wherein each $R^{22}$, $R^{23}$, $R^{24}$, $R^{25}$, and $R^{26}$ is independently H or alkyl;

$R^4$ is H;
$R^5$ is H, —$OR^{27}$, —$NR^{28}R^{29}$, halogen, or alkyl, wherein each $R^{27}$, $R^{28}$, and $R^{29}$ is independently H or $C_1$-$C_6$alkyl,
wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and
wherein each $R^{30}$, $R^{31}$, $R^{32}$, $R^{33}$, and $R^{34}$ is independently H or alkyl, $R^6$ is H, $NR^{28}R^{29}$, F, Br, I, or alkyl, wherein each $R^{28}$ and $R^{29}$ is independently H or $C_1$-$C_6$alkyl,
wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and
wherein each $R^{30}$, $R^{31}$, $R^{32}$, $R^{33}$, and $R^{34}$ is independently H or alkyl, $R^{5a}$ is H, —$OR^{53}$, —$NR^{54}R^{55}$, halogen, or alkyl, wherein each $R^{53}$, $R^{54}$, and $R^{55}$ is independently H or $C_1$-$C_6$alkyl,
wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and
wherein each $R^{56}$, $R^{57}$, $R^{58}$, $R^{59}$, and $R^{60}$ is independently H or alkyl, $R^{6a}$ is H, $NR^{54}R^{55}$, F, Br, I, or alkyl, wherein each $R^{54}$ and $R^{55}$ is independently H or $C_1$-$C_6$alkyl,
wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and
wherein each $R^{56}$, $R^{57}$, $R^{58}$, $R^{59}$, and $R^{60}$ is independently H or alkyl;

$R^7$ is H or $C_1$-$C_3$alkyl;
$R^8$ is H, $C_1$-$C_6$alkyl, an amino protecting group, or

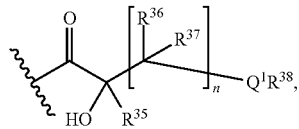

wherein $Q^1$ is NH, O, or S,
n is an integer from 0 to 4,
$R^{35}$ is H or $C_1$-$C_3$alkyl,
each $R^{36}$ and $R^{37}$ is independently H, alkyl, halogen, or —OH, and
$R^{38}$ is H, alkyl, or —C(=NH)$NR^{39}R^{40}$, wherein $R^{39}$ and $R^{40}$ are independently H or $C_1$-$C_3$alkyl, or $R^{35}$ and $R^{38}$, together with the atoms to which they are attached, form a heterocycloalkyl group comprising at least one N;

$R^{41}$ is H, —CN, —$CONH_2$ or $C_1$-$C_3$alkyl, wherein the $C_1$-$C_3$alkyl is unsubstituted or substituted with one or more substituents selected from the group consisting of —OH, —OC(O)$CH_3$, —$NH_2$, —CN, —$CONH_2$, and halogen;

$R^{42}$ and $R^{43}$ are, independently H, —OH, —$OR^{45}$, —$NR^{46}R^{47}$, or halogen,
wherein each $R^{45}$, $R^{46}$ and $R^{47}$ is independently H, alkyl, —$CONH_2$, or —$COCH_3$,
wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{44}$ and $R^{44a}$ are, independently H, halogen, —OH, $C_1$-$C_3$alkoxy, or —OC(O)$CH_3$;

$X^1$ is H, $NH_2$, OH, or halogen;

$R^{51a}$, $R^{51b}$, and $R^{51c}$ are, independently, H, OH, or —$OR^{51d}$,
wherein each $R^{51d}$ is, independently, alkyl or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{52a}$ and $R^{52b}$ are independently H, OH, or —$OR^{52c}$,
wherein each $R^{52c}$ is, independently, alkyl or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

wherein if $R^5$ is —$OR^{27}$ or $R^{5a}$ is —$OR^{53}$, then at least one of $R^6$ and $R^{6a}$ are other than H, wherein if each of $R^5$, $R^{5a}$, $R^6$, and $R^{6a}$ are H, then $R^1$ is not —$OR^9$, wherein $R^9$ is H, and wherein if $R^5$ is —$OR^{27}$ or $R^{5a}$ is —$OR^{53}$, then at least one of $R^6$ and $R^{6a}$ are other than H, wherein if each of $R^5$, $R^{5a}$, $R^6$, and $R^{6a}$ are H, then $R^1$ is not —$OR^9$, wherein $R^9$ is H, and wherein if each of $R^5$, $R^{5a}$, $R^6$, and $R^{6a}$ are H and $R^1$ is —$NR^{10}R^{11}$, then $R^8$ is not

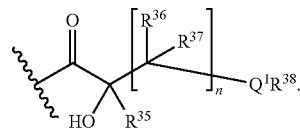

In some embodiments, the compound of formula (VIIa) is of formula (VIIa-X):

(VIIa-X)

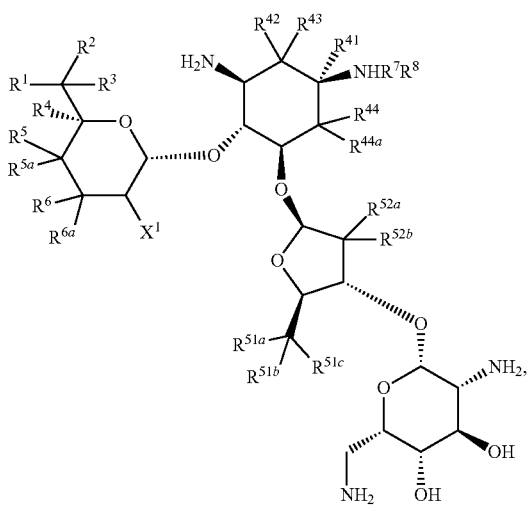

or a pharmaceutically acceptable salt, solvate, or tautomer thereof, wherein $R^1$, $R^2$, $R^3$, $R^4$, $R^5$, $R^{5a}$, $R^6$, $R^{6a}$, $R^7$, $R^8$, $R^{41}$, $R^{42}$, $R^{43}$, $R^{44}$, $R^{44a}$, $R^{51a}$, $R^{51b}$, $R^{51c}$, $R^{52a}$, and $R^{52b}$ are as defined for formula (VIIa) herein.

In some embodiments of formula (VIIa), including formula (VIIa-X), $R^1$ is $-NR^{10}R^{11}$, wherein $R^{10}$ and $R^{11}$ are independently H or $C_1$-$C_6$alkyl, wherein the alkyl is unsubstituted or substituted with one or more $-OH$. In certain embodiments, Rth and $R^{11}$ are independently H, methyl, or hydroxyethyl. In certain embodiments, $R^{10}$ and $R^{11}$ are both H.

In some embodiments of formula (VIIa), including formula (VIIa-X), $R^1$ is $OR^9$, wherein $R^9$ is H or $C_1$-$C_6$alkyl, wherein the alkyl is unsubstituted or substituted with one or more $-OH$. In certain embodiments, $R^9$ is H, methyl, or hydroxyethyl. In certain embodiments, $R^9$ is H.

In some embodiments of formula (VIIa), including formula (VIIa-X), $R^2$ and $R^3$ are independently selected from the group consisting of H, alkyl, cycloalkyl, and aryl. In some embodiments, at least one of $R^2$ and $R^3$ is other than H. In certain embodiments, one of $R^2$ and $R^3$ is H.

In some embodiments of formula (VIIa), including formula (VIIa-X), $R^2$ is alkyl, cyclopropyl, or phenyl; wherein the alkyl is unsubstituted or substituted with one, two, or three substituents selected from the group consisting of $-NH_2$, $-OH$, F, $-CN$, and $-S(O)_2CH_3$. In some embodiments, $R^2$ is methyl, ethyl, propyl, butyl, pentyl, hexyl, cyclopropyl, cyclobutyl, cyclopentyl, cyclohexyl, or phenyl. In other embodiments, $R^2$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, $-SR^{12}$, $-SO_2R^{13}$, $-NR^{14}R^{15}$, and $-OR^{16}$. In some embodiments, the one or more substituents are independently selected from the group consisting of halogen, cyano, aryl, $-SO_2R^{13}$, $-NR^{14}R^{15}$, and $-OR^{16}$. For example, in certain embodiments, the one or more substituents are independently selected from the group consisting of F, Cl, B, I, cyano, $-SO_2CH_3$, $-NH_2$, and $-OH$. In still other embodiments, $R^2$ is methyl; methyl substituted with one or two F; methyl substituted with $-SO_2CH_3$; methyl substituted with $-NH_2$; methyl substituted with $-OH$; ethyl; cyclopropyl; or phenyl. In some embodiments, $R^2$ is H or unsubstituted methyl.

In some embodiments of formula (VIIa), including formula (VIIa-X), $R^3$ is methyl, ethyl, propyl, butyl, pentyl, hexyl, cyclopropyl, cyclobutyl, cyclopentyl, cyclohexyl, or phenyl. In other embodiments, $R^3$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, $-SR^{12}$, $-SO_2R^{13}$, $-NR^{14}R^{15}$, and $-OR^{16}$. In some embodiments, the one or more substituents are independently selected from the group consisting of halogen, cyano, aryl, $-SO_2R^{13}$, $-NR^{14}R^{15}$, and $-OR^{16}$. For example, in certain embodiments, the one or more substituents are independently selected from the group consisting of F, Cl, B, I, cyano, $-SO_2CH_3$, $-NH_2$, and $-OH$. In still other embodiments, $R^3$ is methyl; methyl substituted with one or two F; methyl substituted with $-SO_2CH_3$; methyl substituted with $-NH_2$; methyl substituted with $-OH$; ethyl; cyclopropyl; or phenyl. In certain embodiments, $R^3$ is H or unsubstituted methyl.

In some embodiments of formula (VIIa), including formula (VIIa-X), $R^2$ and $R^3$, together with the atom to which they are attached, form a cycloalkyl group or a heterocycloalkyl group. In some embodiments, the cycloalkyl group or heterocycloalkyl group may be unsubstituted or substituted with one or more substituents independently selected from the group consisting of halogen, cyano, $-SR^{22}$, $-SO_2R^{23}$, $-NR^{24}R^{25}$, and $-OR^{26}$, wherein each $R^{22}$, $R^{23}$, $R^{24}$, $R^{25}$, and $R^{26}$ may be independently H or alkyl. In certain embodiments, $R^2$ and $R^3$ together with the atom to which they are attached form a cyclopropyl or oxetanyl. In certain embodiments, $R^2$ and $R^3$ together with the atom to which they are attached form a cyclopropyl.

In some embodiments of formula (VIIa), including formula (VIIa-X), both $R^5$ and $R^6$ are H.

In some embodiments of formula (VIIa), including formula (VIIa-X), both $R^{5a}$ and $R^{6a}$ are H.

In some embodiments of formula (VIIa), including formula (VIIa-X), $R^5$, $R^{5a}$, $R^6$, and $R^{6a}$ are H.

In some embodiments of formula (VIIa), including formula (VIIa-X), $R^5$ is H.

In some embodiments of formula (VIIa), including formula (VIIa-X), $R^{5a}$ is H.

In some embodiments of formula (VIIa), including formula (VIIa-X), $R^6$ is H.

In some embodiments of formula (VIIa), including formula (VIIa-X), $R^{6a}$ is H.

In some embodiments of formula (VIIa), including formula (VIIa-X), $R^5$ is $-OH$. In some embodiments of formula (VIIa), including formula (VIIa-X), $R^5$ is H.

In some embodiments of formula (VIIa), including formula (VIIa-X), $R^{5a}$ is H or $-OH$. In some embodiments of formula (VIIa), including formula (VIIa-X), $R^{5a}$ is $-OH$. In some embodiments of formula (VIIa), including formula (VIIa-X), $R^{5a}$ is H.

In some embodiments of formula (VIIa), including formula (VIIa-X), $R^5$ is H, halogen, or $-OH$. In certain such embodiments, $R^5$ is halogen. In certain such embodiments, $R^5$ is F.

In some embodiments of formula (VIIa), including formula (VIIa-X), $R^5$ is halogen and $R^{5a}$ is H. In certain such embodiments, $R^5$ is F and $R^{5a}$ is H. In some embodiments of formula (VIIa), including formula (VIIa-X), $R^5$ is halogen and $R^{5a}$ is halogen. In some embodiments of formula (VIIa), including formula (VIIa-X), $R^5$ is halogen and $R^{5a}$ is F. In some embodiments of formula (VIIa), including formula (VIIa-X), $R^5$ is F and $R^{5a}$ is F. In some embodiments of formula (VIIa), including formula (VIIa-X), $R^5$ is F and $R^{5a}$ is halogen.

In some embodiments of formula (VIIa), including formula (VIIa-X), $R^5$ is —OH and $R^{5a}$ is H. In some embodiments of formula (VIIa), including formula (VIIa-X), $R^5$ is —OH and $R^{5a}$ is halogen. In some embodiments of formula (VIIa), including formula (VIIa-X), $R^5$ is —OH and $R^{5a}$ is F. In some embodiments of formula (VIIa), including formula (VIIa-X), $R^5$ is —OH and $R^{5a}$ is —OH. In some embodiments of formula (VIIa), including formula (VIIa-X), $R^{5a}$ is —OH and $R^5$ is H. In some embodiments of formula (VIIa), including formula (VIIa-X), $R^{5a}$ is —OH and $R^5$ is halogen. In some embodiments of formula (VIIa), including formula (VIIa-X), $R^{5a}$ is —OH and $R^5$ is F.

In some embodiments of formula (VIIa), including formula (VIIa-X), $R^{5a}$ is H, halogen, or —OH. In certain such embodiments, $R^{5a}$ is halogen. In certain such embodiments, $R^{5a}$ is F.

In some embodiments of formula (VIIa), including formula (VIIa-X), $R^5$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (VIIa), including formula (VIIa-X), $R^{5a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (VIIa), including formula (VIIa-X), $R^6$ and $R^{6a}$ are independently H, F, Br, or I. In certain such embodiments, $R^6$ and $R^{6a}$ are independently H or F. In some embodiments of formula (VIIa), including formula (VIIa-X), $R^6$ is F. In some embodiments of formula (VIIa), including formula (VIIa-X), $R^6$ is F and $R^{6a}$ is H. In some embodiments of formula (VIIa), including formula (VIIa-X), $R^{6a}$ is F. In some embodiments of formula (VIIa), including formula (VIIa-X), $R^6$ is F and $R^{6a}$ is F. In some embodiments of formula (VIIa), including formula (VIIa-X), $R^{6a}$ is F and $R^6$ is H.

In some embodiments of formula (VIIa), including formula (VIIa-X), $X^1$ is $NH_2$. In some embodiments of formula (VIIa), including formula (VIIa-X), $X^1$ is OH. In some embodiments of formula (VIIa), including formula (VIIa-X), $X^1$ is halogen. In some embodiments of formula (VIIa), including formula (VIIa-X), $X^1$ is F. In some embodiments of formula (VIIa), including formula (VIIa-X), $X^1$ is Cl. In some embodiments of formula (VIIa), including formula (VIIa-X), $X^1$ is Br. In some embodiments of formula (VIIa), including formula (VIIa-X), $X^1$ is I.

In some embodiments of formula (VIIa), including formula (VIIa-X), $R^{41}$ is H.

In some embodiments of formula (VIIa), including formula (VIIa-X), one of $R^{42}$ and $R^{43}$ is —OH. In some embodiments of formula (VIIa), including formula (VIIa-X), one of $R^{42}$ and $R^{43}$ is halogen. In some embodiments of formula (VIIa), including formula (VIIa-X), one of $R^{42}$ and $R^{43}$ is H. In some embodiments of formula (VIIa), including formula (VIIa-X), one of $R^{42}$ and $R^{43}$ is —$NR^{46}R^{47}$. In some embodiments of formula (VIIa), including formula (VIIa-X), one of $R^{42}$ and $R^{43}$ is —F. In some embodiments of formula (VIIa), including formula (VIIa-X), $R^{42}$ is —F and $R^{43}$ is —F. In some embodiments of formula (VIIa), including formula (VIIa-X), one of $R^{42}$ and $R^{43}$ is —OH. In some embodiments of formula (VIIa), including formula (VIIa-X), one of $R^{42}$ and $R^{43}$ is —$OR^{45}$.

In some embodiments of formula (VIIa), including formula (VIIa-X), $R^{42}$ and $R^{43}$ are H.

In some embodiments of formula (VIIa), including formula (VIIa-X), one of $R^{44}$ and $R^{44a}$ is —OH. In some embodiments of formula (VIIa), including formula (VIIa-X), one of $R^{44}$ and $R^{44a}$ is —$OCH_3$. In some embodiments of formula (VIIa), including formula (VIIa-X), one of $R^{44}$ and $R^{44a}$ is —F. In some embodiments of formula (VIIa), including formula (VIIa-X), $R^{44}$ and $R^{44a}$ are —F. In some embodiments of formula (VIIa), including formula (VIIa-X), $R^{44}$ and $R^{44a}$ are H. In some embodiments of formula (VIIa), including formula (VIIa-X), one of $R^{44}$ and $R^{44a}$ is H. In some embodiments of formula (VIIa), including formula (VIIa-X), $R^{44}$ and $R^{44a}$ are, independently H, halogen, $C_1$-$C_3$alkoxy, or —$OC(O)CH_3$.

In some embodiments of formula (VIIa), including formula (VIIa-X), $R^{51a}$, $R^{51b}$, and $R^{51c}$ are, independently, H, OH, or —$OR^{51d}$. In some embodiments of formula (VIIa), including formula (VIIa-X), one of $R^{51a}$, $R^{51b}$, and $R^{51}$c is —OH. In some embodiments of formula (VIIa), including formula (VIIa-X), one of $R^{51a}$, $R^{51b}$, and $R^{51c}$ is —$OR^{51d}$. In some embodiments of formula (VIIa), including formula (VIIa-X), $R^{51a}$ is —OH and $R^{51b}$ and $R^{51c}$ are H. In some embodiments of formula (VIIa), including formula (VIIa-X), $R^{51a}$ is —$OR^{51d}$ and $R^{51b}$ and $R^{51c}$ are H.

In some embodiments of formula (VIIa), including formula (VIIa-X), $R^{52a}$ and $R^{52b}$ are independently H, OH, or —$OR^{52c}$. In some embodiments of formula (VIIa), including formula (VIIa-X), $R^{52a}$ and $R^{52b}$ are —OH. In some embodiments of formula (VIIa), including formula (VIIa-X), one of $R^{52a}$ and $R^{52b}$ is —$OR^{52c}$. In some embodiments of formula (VIIa), including formula (VIIa-X), one of $R^{52a}$ and $R^{52b}$ is —OH. In some embodiments of formula (VIIa), including formula (VIIa-X), $R^{52a}$ is H and $R^{52b}$ is —$OR^{52c}$. In some embodiments of formula (VIIa), including formula (VIIa-X), $R^{52a}$ is H and $R^{52b}$ is —OH.

In some embodiments of formula (VIIa), including formula (VIIa-X), $R^7$ is H. In other embodiments, $R^7$ is $C_1$-$C_3$alkyl, for example $C_1$-alkyl, $C_2$-alkyl, or $C_3$-alkyl. In some embodiments, $R^8$ is H. In some embodiments of formula (VIIa), including formula (VIIa-X), $R^7$ is H and $R^8$ is H.

In some embodiments of formula (VIIa), including formula (VIIa-X), $R^8$ is $C_1$-$C_6$alkyl, for example $C_1$-alkyl, $C_2$-alkyl, $C_3$-alkyl, $C_4$-alkyl, $C_5$-alkyl, or $C_6$-alkyl.

In some embodiments of formula (VIIa), including formula (VIIa-X), $R^8$ is

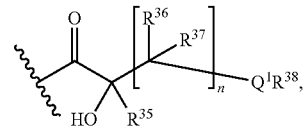

wherein $Q^1$ is NH, O, or S. In certain embodiments, $Q^1$ is NH. In certain embodiments, $Q^1$ is O. In certain embodiments, $Q^1$ is S. In certain embodiments, wherein when n is one, then $R^{36}$ and $R^{37}$ are not halo.

In some embodiments of formula (VIIa), including formula (VIIa-X), n is an integer from 0 to 4, from 0 to 3, from 0 to 2, from 1 to 4, from 2 to 4, or from 1 to 3. In certain embodiments, n is 0, or n is 1, or n is 2, or n is 3, or n is 4.

In Formula (VIIa), the ring substituted by $R^1$, $R^2$, $R^3$, $R^4$, $R^5$, $R^{5a}$, $R^6$, $R^{6a}$, and $X^1$ may also be referred to as Ring A, as shown below. The ring substituted $R^7$, $R^8$, $R^{41}$, $R^{42}$, $R^{43}$, $R^{44}$, and $R^{44a}$ may also referred to as Ring B, as shown below. Ring C is also used to refer to the moiety connected to Ring B through —O— moiety, as shown below. Ring D is also used to refer to the moiety connected to Ring C through —O— moiety, as shown below.

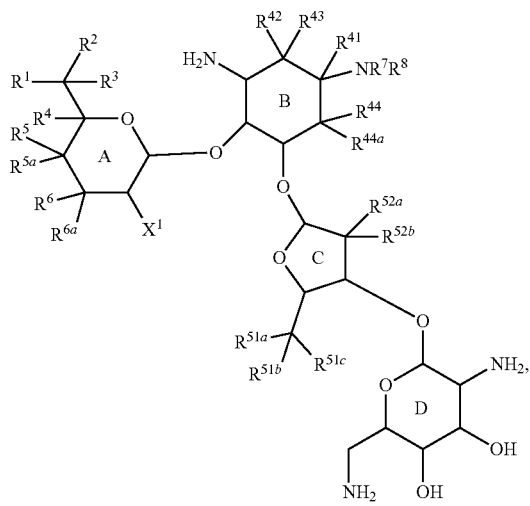

In some embodiments of the compound of Formula (VIIa), Ring A is

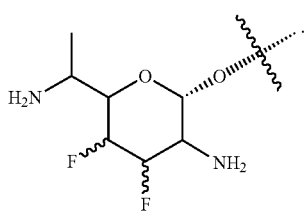

In some embodiments of the compound of Formula (VIIa), Ring A is selected from

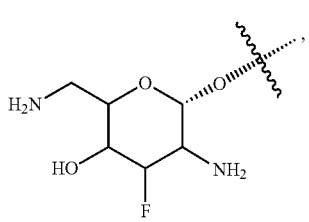

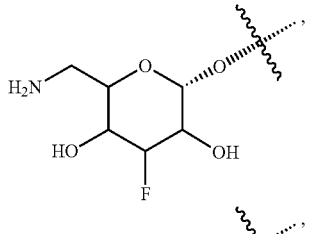

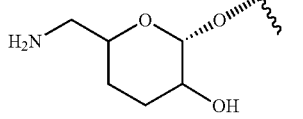

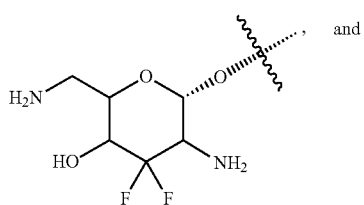

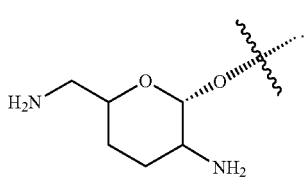

In some embodiments of the compound of Formula (VIIa), Ring B is selected from

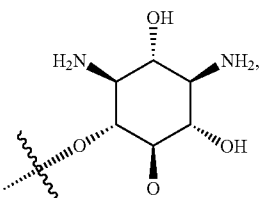

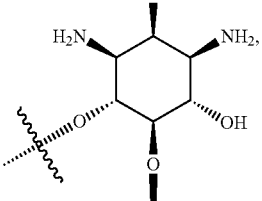

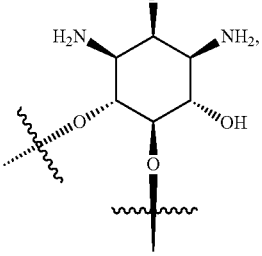

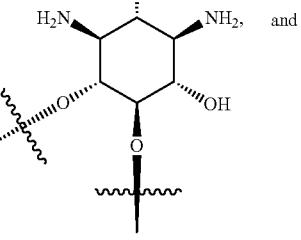

-continued
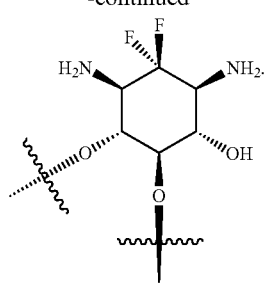
In some embodiments of the compound of Formula (VIIa), Ring B is selected from
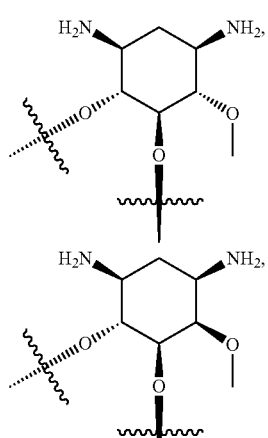
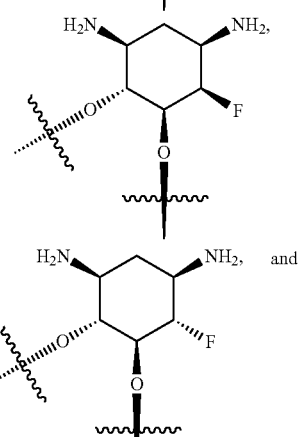
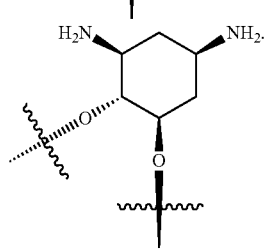
In some embodiments of the compound of Formula (VIIa), Ring B is
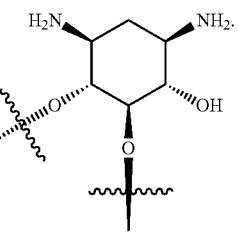
In some embodiments of the compound of Formula (VIIa), Ring B is selected from
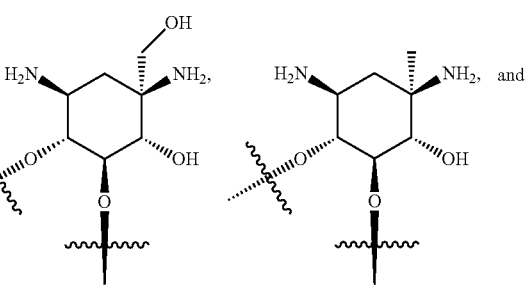
In some embodiments of the compound of Formula (VIIa), Ring B is
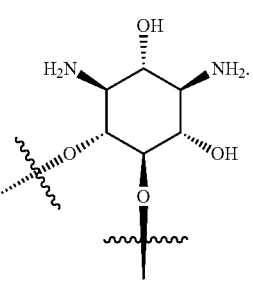
In some embodiments of the compound of Formula (VIIa), Ring B is
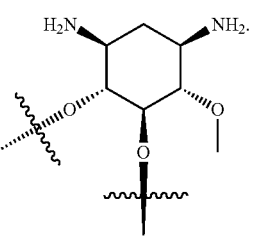

In some embodiments of the compound of Formula (VIIa), Ring B is selected from

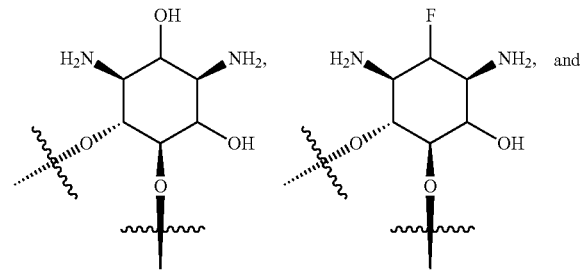

In some embodiments of the compound of Formula (VIIa), Ring B is

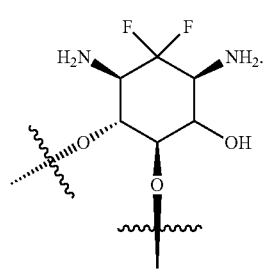

In some embodiments of the compound of Formula (VIIa), Ring B is

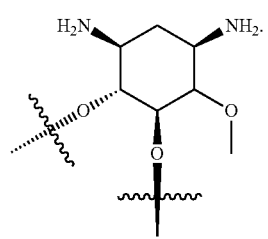

In some embodiments of the compound of Formula (VIIa), Ring B is

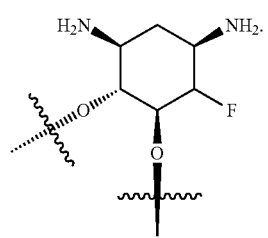

In some embodiments of the compound of Formula (VIIa), Ring B is

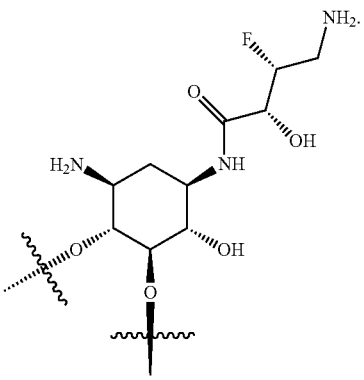

In some embodiments of the compound of Formula (VIIa), Ring B is

In some embodiments of the compound of Formula (VIIa), Ring B is

In some embodiments of the compound of Formula (VIIa), Ring B is

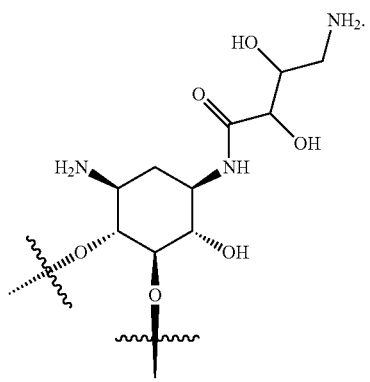

In some embodiments of the compound of Formula (VIIa), Ring B is

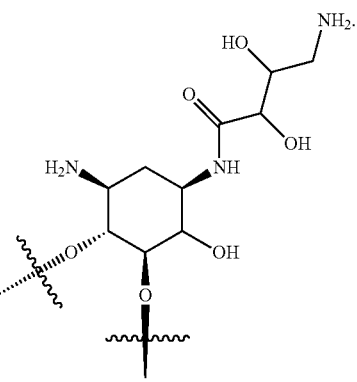

In some embodiments of the compound of Formula (VIIa), Ring B is

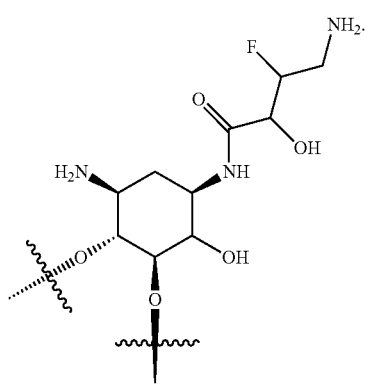

In some embodiments of the compound of Formula (VIIa), Ring B is

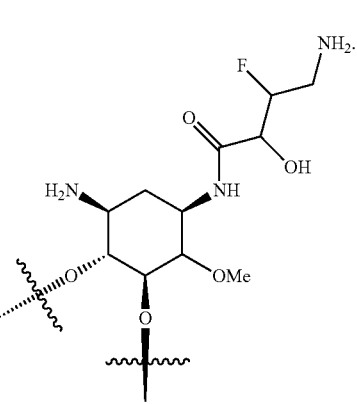

In some embodiments of the compound of Formula (VIIa), Ring B is

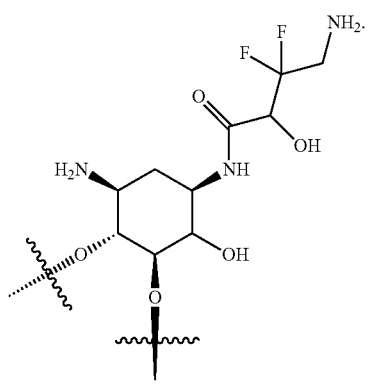

In some embodiments of the compound of Formula (VIIa), Ring B is

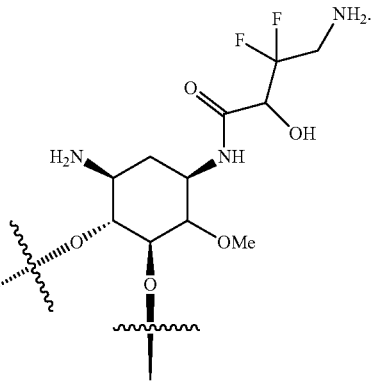

In some embodiments of the compound of Formula (VIIa), Ring B is

In some embodiments of the compound of Formula (VIIa), Ring B is

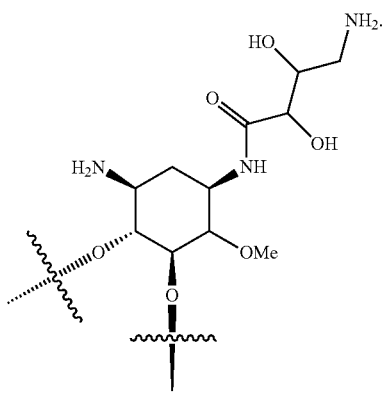

In some embodiments of the compound of Formula (VIIa), Ring B is

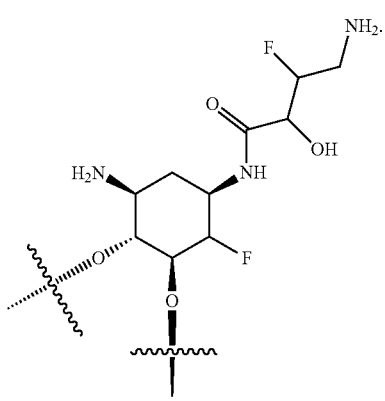

In some embodiments of the compound of Formula (VIIa), Ring B is

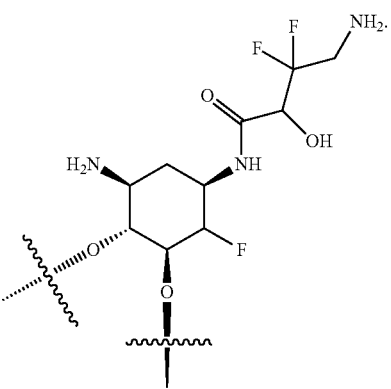

Provided herein are compounds of formula (VIIb):

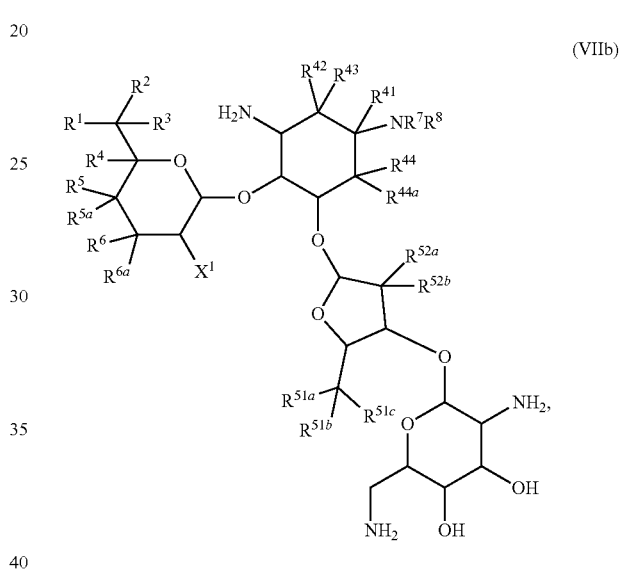

(VIIb)

and pharmaceutically acceptable salts, solvates, tautomers, or stereoisomers thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl, wherein the alkyl, cycloalkyl, or aryl is unsubstituted or substituted with one or more substituents independently selected from the group consisting of halogen, cyano, aryl, —$SR^{12}$, —$SO_2R^{13}$, —$OSF_2NR^{14}R^{15}$, —$NR^{14}R^{15}$, and —$OR^{16}$, and wherein each $R^{12}$, $R^{13}$, $R^{11}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and wherein each $R^{17}$, $R^{18}$, $R^{19}$, $R^{20}$, and $R^{21}$ is independently H or alkyl, or $R^2$ and $R^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl;

$R^4$ is H;

$R^5$ is H, $NR^{28}R^{29}$, F, Br, I, or alkyl, wherein each $R^{28}$ and $R^{29}$ is independently H or $C_1$-$C_6$alkyl, wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and wherein each $R^{30}$, $R^{31}$, $R^{32}$, $R^{33}$, and $R^{34}$ is independently H or alkyl, $R^6$ is H, —$OR^{27}$, —$NR^{28}R^{29}$, halogen, or alkyl, wherein each $R^{27}$, $R^{28}$, and $R^{29}$ is independently H or $C_1$-$C_6$alkyl, wherein the alkyl or $C_1$-$C_6$alkyl is unsubstituted or substituted with one or more substituents selected from the group consisting of halogen, —$OR^{30}$, —$NR^{31}R^{32}$, —$SR^{33}$, and —$SO_2R^{34}$, and wherein each $R^{30}$, $R^{31}$, $R^{32}$, $R^{33}$, and $R^{34}$ is independently H or alkyl, $R^{5a}$ is H, $NR^{54}R^{55}$, F, Br, I, or alkyl, wherein each $R^{54}$ and $R^{55}$ is independently H or $C_1$-$C_6$alkyl, wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and wherein each $R^{56}$, $R^{57}$, $R^{58}$, $R^{59}$, and $R^{69}$ is independently H or alkyl, $R^{6a}$ is H, —$OR^{53}$, —$NR^{54}R^{55}$, halogen, or alkyl, wherein each $R^{53}$, $R^{54}$, and $R^{55}$ is independently H or $C_1$-$C_6$alkyl, wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and wherein each $R^{56}$, $R^{57}$, $R^{58}$, $R^{59}$, and $R^{60}$ is independently H or alkyl; $R^7$ is H or $C_1$-$C_3$alkyl;

$R^8$ is H, $C_1$-$C_6$alkyl, an amino protecting group, or

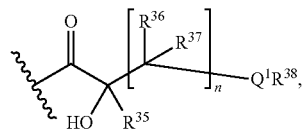

wherein $Q^1$ is NH, O, or S, n is an integer from 0 to 4, $R^{35}$ is H or $C_1$-$C_3$alkyl, each $R^{36}$ and $R^{37}$ is independently H, alkyl, halogen, or —OH, and $R^{38}$ is H, alkyl, or —C(=NH)$NR^{39}R^{49}$, wherein $R^{39}$ and $R^{40}$ are independently H or $C_1$-$C_3$alkyl, or $R^{35}$ and $R^{38}$, together with the atoms to which they are attached, form a heterocycloalkyl group comprising at least one N;

$R^{41}$ is H, —CN, —$CONH_2$ or $C_1$-$C_3$alkyl, wherein the $C_1$-$C_3$alkyl is unsubstituted or substituted with one or more substituents selected from the group consisting of —OH, —OC(O)$CH_3$, —$NH_2$, —CN, —$CONH_2$, and halogen;

$R^{42}$ and $R^{43}$ are, independently H, —OH, —$OR^{45}$, —$NR^{46}R^{47}$, or halogen, wherein each $R^{45}$, $R^{46}$ and $R^{47}$ is independently H, alkyl, —$CONH_2$, or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{44}$ and $R^{44a}$ are, independently H, halogen, —OH, $C_1$-$C_3$alkoxy, or —OC(O)$CH_3$;

$X^1$ is H, $NH_2$, OH, or halogen;

$R^{51a}$, $R^{51b}$, and $R^{51c}$ are, independently, H, OH, or —$OR^{51d}$, wherein each $R^{51d}$ is, independently, alkyl or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{52a}$ and $R^{52b}$ are independently H, OH, or —$OR^{52c}$, wherein each $R^{52c}$ is, independently, alkyl or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

wherein if $R^6$ is —$OR^{27}$ or $R^{11a}$ is —$OR^{53}$, then at least one of $R^5$ and $R^{5a}$ are other than H, wherein if $R^5$ is $NR^{28}R^{29}$ or $R^{5a}$ is $NR^{54}R^{55}$, then $R^1$ is not —$OR^9$, wherein $R^9$ is H, wherein if each of $R^5$, $R^{5a}$, $R^6$, and $R^{6a}$ are H, then $R^1$ is not —$OR^9$, wherein $R^9$ is H, and wherein if each of $R^5$, $R^{5a}$, $R^6$, and $R^{6a}$ are H and $R^1$ is —$NR^{10}R^{11}$, then $R^8$ is not

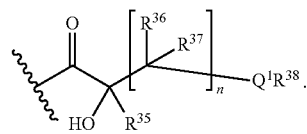

In some embodiments, the compound of formula (VIIb) is of formula (VIIb-X):

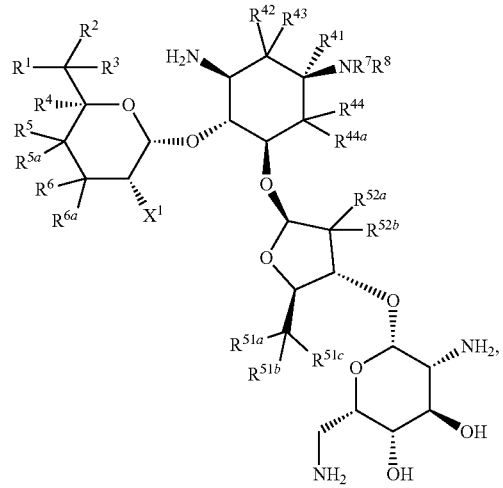

(VIIb-X)

or a pharmaceutically acceptable salt, solvate, or tautomer thereof, wherein $R^1$, $R^2$, $R^3$, $R^4$, $R^5$, $R^{5a}$, $R^6$, $R^{6a}$, $R^7$, $R^8$, $R^{41}$, $R^{42}$, $R^{43}$, $R^{44}$, $R^{44a}$, $X^1$, $R^{51a}$, $R^{51b}$, $R^{51c}$, $R^{52a}$, and $R^{52b}$ are as defined for formula (VIIb) herein.

In some embodiments of formula (VIIb), including formula (VIIb-X), $R^1$ is —$NR^{10}R^{11}$, wherein $R^{10}$ and $R^{11}$ are independently H or $C_1$-$C_6$alkyl, wherein the alkyl is unsubstituted or substituted with one or more —OH. In certain embodiments, $R^{10}$ and $R^{11}$ are independently H, methyl, or hydroxyethyl. In certain embodiments, $R^{10}$ and $R^{11}$ are both H.

In some embodiments of formula (VIIb), including formula (VIIb-X), $R^1$ is $OR^9$, wherein $R^9$ is H or $C_1$-$C_6$alkyl, wherein the alkyl is unsubstituted or substituted with one or more —OH. In certain embodiments, $R^9$ is H, methyl, or hydroxyethyl. In certain embodiments, $R^9$ is H.

In some embodiments of formula (VIIb), including formula (VIIb-X), $R^2$ and $R^3$ are independently selected from the group consisting of H, alkyl, cycloalkyl, and aryl, In some embodiments, at least one of $R^2$ and $R^3$ is other than H. In certain embodiments, one of $R^2$ and $R^3$ is H.

In some embodiments of formula (VIIb), including formula (VIIb-X), $R^2$ is alkyl, cyclopropyl, or phenyl; wherein the alkyl is unsubstituted or substituted with one, two, or three substituents selected from the group consisting of —$NH_2$, —OH, F, —CN, and —$S(O)_2CH_3$. In some embodiments, $R^2$ is methyl, ethyl, propyl, butyl, pentyl, hexyl, cyclopropyl, cyclobutyl, cyclopentyl, cyclohexyl, or phenyl. In other embodiments, $R^2$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —$SR^{12}$, —$SO_2R^{13}$, —$NR^{14}R^{15}$, and —$OR^{16}$. In some embodiments, the one or more substituents are independently selected from the group consisting of halogen, cyano, aryl, —$SO_2R^{13}$, —$NR^{14}R^{15}$, and —$OR^{16}$. For example, in certain embodiments, the one or more substituents are independently selected from the group consisting of F, Cl, B, I, cyano, —$SO_2CH_3$, —$NH_2$, and —OH. In still other embodiments, $R^2$ is methyl; methyl substituted with one or two F; methyl substituted with —$SO_2CH_3$; methyl substituted with —$NH_2$; methyl substituted with —OH; ethyl; cyclopropyl; or phenyl. In some embodiments, $R^2$ is H or unsubstituted methyl.

In some embodiments of formula (VIIb), including formula (VIIb-X), $R^3$ is methyl, ethyl, propyl, butyl, pentyl, hexyl, cyclopropyl, cyclobutyl, cyclopentyl, cyclohexyl, or phenyl. In other embodiments, $R^3$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —$SR^{12}$, —$SO_2R^{13}$, —$NR^{14}R^{15}$, and —$OR^{16}$. In some embodiments, the one or more substituents are independently selected from the group consisting of halogen, cyano, aryl, —$SO_2R^{13}$, —$NR^{14}R^{15}$, and —$OR^{16}$. For example, in certain embodiments, the one or more substituents are independently selected from the group consisting of F, Cl, B, I, cyano, —$SO_2CH_3$, —$NH_2$, and —OH. In still other embodiments, $R^3$ is methyl; methyl substituted with one or two F; methyl substituted with —$SO_2CH_3$; methyl substituted with —$NH_2$; methyl substituted with —OH; ethyl; cyclopropyl; or phenyl. In certain embodiments, $R^3$ is H or unsubstituted methyl.

In some embodiments of formula (VIIb), including formula (VIIb-X), $R^2$ and $R^3$, together with the atom to which they are attached, form a cycloalkyl group or a heterocycloalkyl group. In some embodiments, the cycloalkyl group or heterocycloalkyl group may be unsubstituted or substituted with one or more substituents independently selected from the group consisting of halogen, cyano, —$SR^{22}$, —$SO_2R^{23}$, —$NR^{24}R^{25}$, and —$OR^{26}$, wherein each $R^{22}$, $R^{23}$, $R^{24}$, $R^{25}$, and $R^{26}$ may be independently H or alkyl. In certain embodiments, $R^2$ and $R^3$ together with the atom to which they are attached form a cyclopropyl or oxetanyl. In certain embodiments, $R^2$ and $R^3$ together with the atom to which they are attached form a cyclopropyl.

In some embodiments of formula (VIIb), including formula (VIIb-X), both $R^5$ and $R^6$ are H.

In some embodiments of formula (VIIb), including formula (VIIb-X), both $R^{5a}$ and $R^{6a}$ are H.

In some embodiments of formula (VIIb), including formula (VIIb-X), $R^5$, $R^{5a}$, $R^6$, and $R^{6a}$ are H.

In some embodiments of formula (VIIb), including formula (VIIb-X), $R^5$ is H.

In some embodiments of formula (VIIb), including formula (VIIb-X), $R^{5a}$ is H.

In some embodiments of formula (VIIb), including formula (VIIb-X), $R^6$ is H.

In some embodiments of or formula (VIIb), including formula (VIIb-X), $R^{6a}$ is H.

In some embodiments of formula (VIIb), including formula (VIIb-X), $R^6$ is H or —OH. In some embodiments of formula (VIIb), including formula (VIIb-X), $R^6$ is —OH. In some embodiments of formula (VIIb), including formula (VIIb-X), $R^6$ is H.

In some embodiments of formula (VIIb), including formula (VIIb-X), $R^{6a}$ is H or —OH. In some embodiments of formula (VIIb), including formula (VIIb-X), $R^{6a}$ is —OH. In some embodiments of formula (VIIb), including formula (VIIb-X), $R^{6a}$ is H.

In some embodiments of formula (VIIb), including formula (VIIb-X), $R^6$ is H, halogen, or —OH. In certain such embodiments, $R^6$ is halogen. In certain such embodiments, $R^6$ is F.

In some embodiments of formula (VIIb), including formula (VIIb-X), $R^6$ is halogen and $R^{6a}$ is H. In certain such embodiments, $R^6$ is F and $R^{6a}$ is H. In some embodiments of formula (VIIb), including formula (VIIb-X), $R^6$ is halogen and $R^{6a}$ is halogen. In some embodiments of formula (VIIb), including formula (VIIb-X), $R^6$ is halogen and $R^{6a}$ is F. In some embodiments of formula (VIIb), including formula (VIIb-X), $R^6$ is F and $R^{6a}$ is F. In some embodiments of formula (VIIb), including formula (VIIb-X), $R^6$ is F and $R^{6a}$ is halogen.

In some embodiments of formula (VIIb), including formula (VIIb-X), $R^6$ is —OH and $R^{6a}$ is H. In some embodiments of formula (VIIb), including formula (VIIb-X), $R^6$ is —OH and $R^{6a}$ is halogen. In some embodiments of formula (VIIb), including formula (VIIb-X), $R^6$ is —OH and $R^{6a}$ is F. In some embodiments of formula (VIIb), including formula (VIIb-X), $R^6$ is —OH and $R^{6a}$ is —OH. In some embodiments of formula (VIIb), including formula (VIIb-X), $R^{6a}$ is —OH and $R^6$ is H. In some embodiments of formula (VIIb), including formula (VIIb-X), $R^{6a}$ is —OH and $R^6$ is halogen. In some embodiments of formula (VIIb), including formula (VIIb-X), $R^{6a}$ is —OH and $R^6$ is F.

In some embodiments of formula (VIIb), including formula (VIIb-X), $R^{6a}$ is H, halogen, or —OH. In certain such embodiments, $R^{6a}$ is halogen. In certain such embodiments, $R^{6a}$ is F.

In some embodiments of formula (VIIb), including formula (VIIb-X), $R^6$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (VIIb), including formula (VIIb-X), $R^{6a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (VIIb), including formula (VIIb-X), $R^5$ and $R^{5a}$ are independently H, F, Br, or I. In certain such embodiments, $R^5$ and $R^{5a}$ are independently H or F. In some embodiments of formula (VIIb), including formula (VIIb-X), $R^5$ is F. In some embodiments of formula (VIIb), including formula (VIIb-X), $R^5$ is F and $R^{5a}$ is H. In some embodiments of formula (VIIb), including formula (VIIb-X), $R^{5a}$ is F. In some embodiments of formula (VIIb), including formula (VIIb-X), $R^5$ is F and $R^{5a}$ is F.

In some embodiments of formula (VIIb), including formula (VIIb-X), $X^1$ is $NH_2$. In some embodiments of formula (VIIb), including formula (VIIb-X), $X^1$ is OH. In some embodiments of formula (VIIb), including formula (VIIb-X), $X^1$ is halogen. In some embodiments of formula (VIIb), including formula (VIIb-X), $X^1$ is F. In some embodiments of formula (VIIb), including formula (VIIb-X), $X^1$ is Cl. In some embodiments of formula (VIIb), including formula (VIIb-X), $X^1$ is Br. In some embodiments of formula (VIIb), including formula (VIIb-X), $X^1$ is I.

In some embodiments of formula (VIIb), including formula (VIIb-X), $R^{41}$ is H.

In some embodiments of formula (VIIb), including formula (VIIb-X), one of $R^{42}$ and $R^{43}$ is —OH. In some embodiments of formula (VIIb), including formula (VIIb-X), one of $R^{42}$ and $R^{43}$ is halogen. In some embodiments of formula (VIIb), including formula (VIIb-X), one of $R^{42}$ and $R^{43}$ is H. In some embodiments of formula (VIIb), including formula (VIIb-X), one of $R^{42}$ and $R^{43}$ is —$NR^{46}R^{47}$. In some embodiments of formula (VIIb), including formula (VIIb-X), one of $R^{42}$ and $R^{43}$ is —F. In some embodiments of formula (VIIb), including formula (VIIb-X), $R^{42}$ is —F and $R^{43}$ is —F. In some embodiments of formula (VIIb), including formula (VIIb-X), one of $R^{42}$ and $R^{43}$ is —OH. In some embodiments of formula (VIIb), including formula (VIIb-X), one of $R^{42}$ and $R^{43}$ is —$OR^{45}$.

In some embodiments of formula (VIIb), including formula (VIIb-X), $R^{42}$ and $R^{43}$ are H.

In some embodiments of formula (VIIb), including formula (VIIb-X), one of $R^{44}$ and $R^{44a}$ is —OH. In some embodiments of formula (VIIb), including formula (VIIb-X), one of $R^{44}$ and $R^{44a}$ is —$OCH_3$. In some embodiments of formula (VIIb), including formula (VIIb-X), $_{and\ R}R^{44a\ is}$ one of $R^{44}$ —F. In some embodiments of formula (VIIb), including formula (VIIb-X), $R^{44}$ and $R^{44a}$ are —F. In some embodiments of formula (VIIb), including formula (VIIb-X), $R^{44}$ and $R^{44a}$ are H. In some embodiments of formula (VIIb), including formula (VIIb-X), one of $R^{44}$ and $R^{44a}$ is H. In some embodiments of formula (VIIb), including formula (VIIb-X), $R^{44}$ and $R^{44a}$ are, independently H, halogen, $C_1$-$C_3$alkoxy, or —OC(O)$CH_3$.

In some embodiments of formula (VIIb), including formula (VIIb-X), $R^{51a}$, $R^{51b}$, and $R^{51c}$ are, independently, H, OH, or —$OR^{51d}$. In some embodiments of formula (VIIb), including formula (VIIb-X), one of $R^{51a}$, $R^{51b}$, and $R^{51c}$ is —OH. In some embodiments of formula (VIIb), including formula (VIIb-X), one of $R^{51a}$, $R^{51b}$, and $R^{51c}$ is —$OR^{51d}$. In some embodiments of formula (VIIb), including formula (VIIb-X), $R^{51a}$ —OH and $R^{51b}$ and $R^{51c}$ are H. In some embodiments of formula (VIIb), including formula (VIIb-X), $R^{51a}$ is —$OR^{51d}$ and $R^{51b}$ and $R^{51c}$ are H.

In some embodiments of formula (VIIb), including formula (VIIb-X), $R^{52a}$ and $R^{52b}$ are independently H, OH, or —$OR^{52c}$. In some embodiments of formula (VIIb), including formula (VIIb-X), $R^{52a}$ and $R^{52b}$ are —OH. In some embodiments of formula (VIIb), including formula (VIIb-X), one of $R^{52a}$ and $R^{52b}$ is —$OR^{52c}$. In some embodiments of formula (VIIb), including formula (VIIb-X), one of $R^{52a}$ and $R^{52b}$ is —OH. In some embodiments of formula (VIIb), including formula (VIIb-X), $R^{52a}$ is H and $R^{52b}$ is —$OR^{52c}$. In some embodiments of formula (VIIb), including formula (VIIb-X), $R^{52a}$ is H and $R^{52b}$ is —OH.

In some embodiments of formula (VIIb), including formula (VIIb-X), $R^7$ is H. In other embodiments, $R^7$ is $C_1$-$C_3$alkyl, for example $C_1$-alkyl, $C_2$-alkyl, or $C_3$-alkyl. In some embodiments, $R^8$ is H. In some embodiments of formula (VIIb), including formula (VIIb-X), $R^7$ is H and $R^8$ is H.

In some embodiments of formula (VIIb), including formula (VIIb-X), $R^8$ is $C_1$-$C_6$alkyl, for example $C_1$-alkyl, $C_2$-alkyl, $C_3$-alkyl, $C_4$-alkyl, $C_5$-alkyl, or $C_6$-alkyl.

In some embodiments of formula (VIIb), including formula (VIIb-X), $R^8$ is

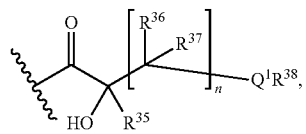

wherein $Q^1$ is NH, O, or S. In certain embodiments, $Q^1$ is NH. In certain embodiments, $Q^1$ is O. In certain embodiments, $Q^1$ is S. In certain embodiments, wherein when n is one, then $R^{36}$ and $R^{37}$ are not halo.

In some embodiments of formula (VIIb), including formula (VIIb-X), n is an integer from 0 to 4, from 0 to 3, from 0 to 2, from 1 to 4, from 2 to 4, or from 1 to 3. In certain embodiments, n is 0, or n is 1, or n is 2, or n is 3, or n is 4.

In Formula (VIIb), the ring substituted by $R^1$, $R^2$, $R^3$, $R^4$, $R^5$, $R^{5a}$, $R^6$, $R^{6a}$, and $X^1$ may also be referred to as Ring A, as shown below. The ring substituted $R^7$, $R^8$, $R^{41}$, $R^{42}$, $R^{43}$, $R^{44}$, and $R^{44a}$ may also referred to as Ring B, as shown below. Ring C is also used to refer to the moiety connected to Ring B through —O— moiety, as shown below. Ring D is also used to refer to the moiety connected to Ring C through —O— moiety, as shown below.

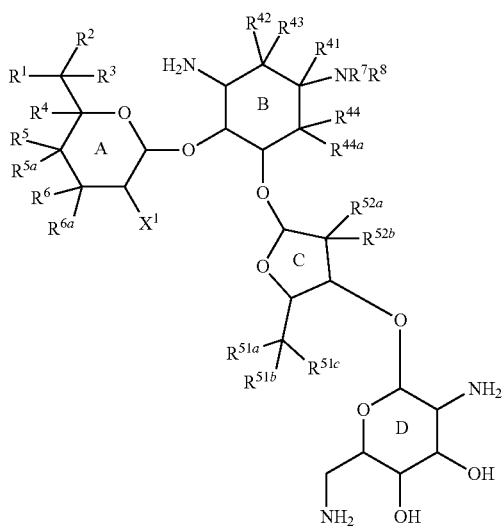
In some embodiments of the compound of Formula (VIIb), Ring A is
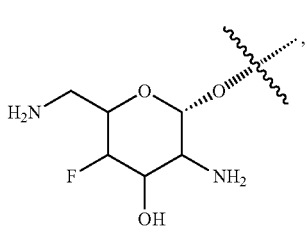
In some embodiments of the compound of Formula (VIIb), Ring A is selected from
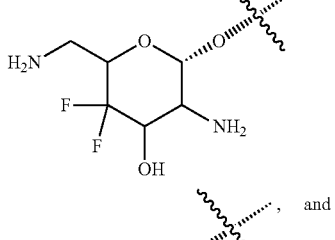
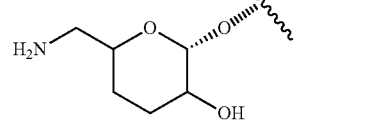
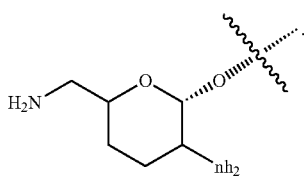
In some embodiments of the compound of Formula (VIIb), Ring B is selected from
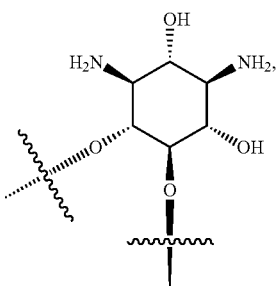
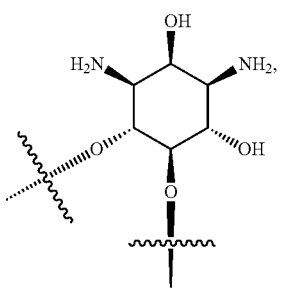
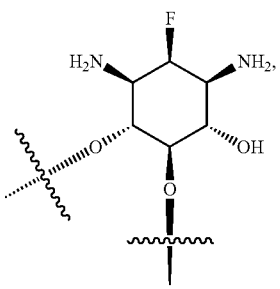
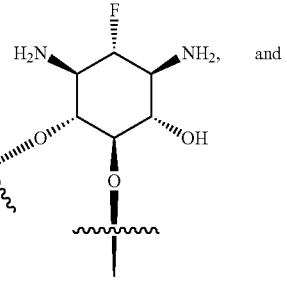

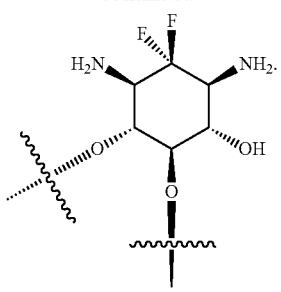
In some embodiments of the compound of Formula (VIIb), Ring B is selected from
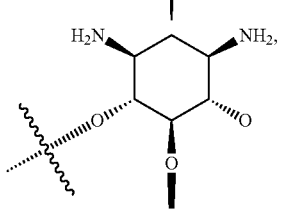
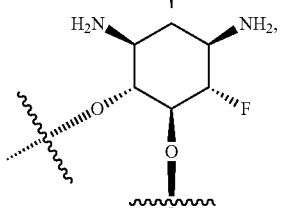
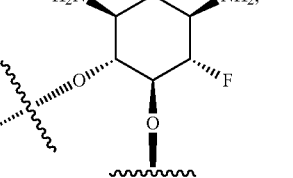
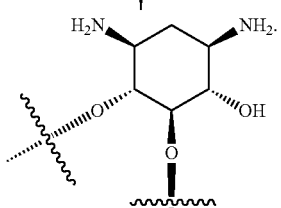
and
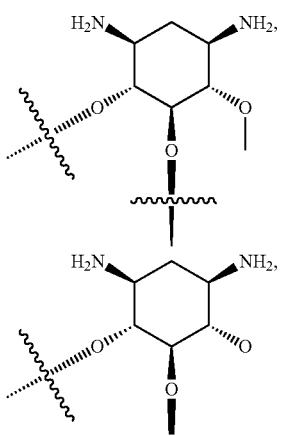
In some embodiments of the compound of Formula (VIIb), Ring B is
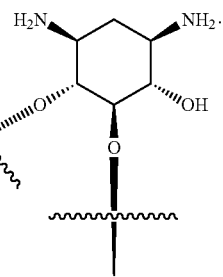
In some embodiments of the compound of Formula (VIIb), Ring B is selected from
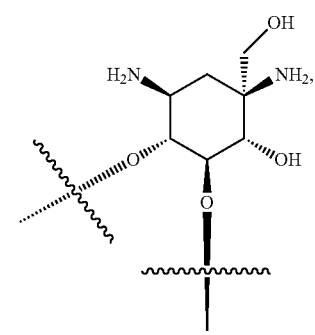
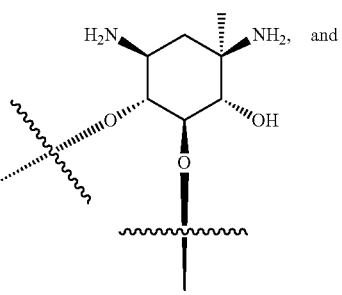
and
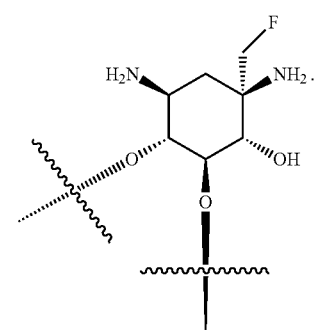
In some embodiments of the compound of Formula (VIIb), Ring B is

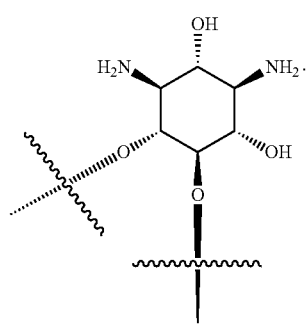
In some embodiments of the compound of Formula (VIIb), Ring B is
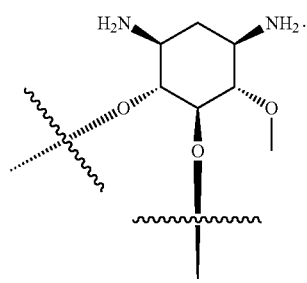
In some embodiments of the compound of Formula (VIIb), Ring B is selected from
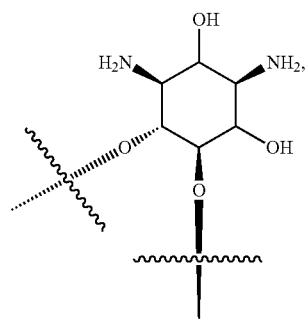
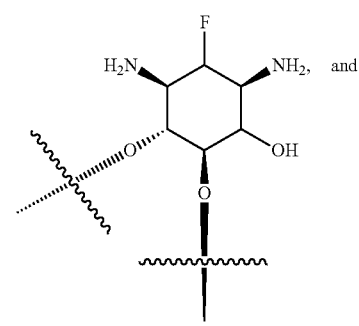
-continued
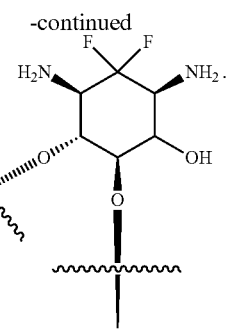
In some embodiments of the compound of Formula (VIIb), Ring B is
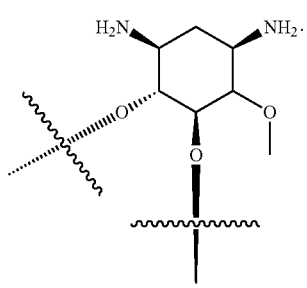
In some embodiments of the compound of Formula (VIIb), Ring B is
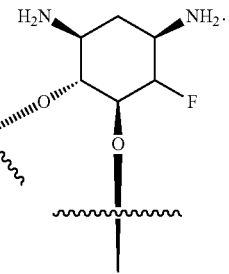
In some embodiments of the compound of Formula (VIIb), Ring B is
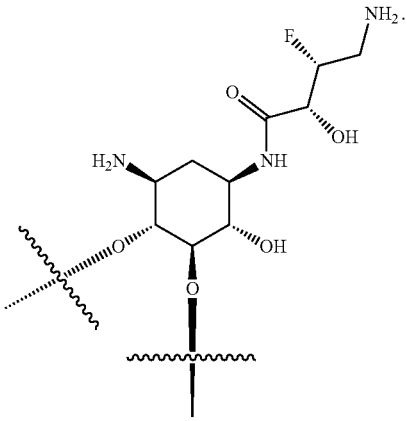

In some embodiments of the compound of Formula (VIIb), Ring B is

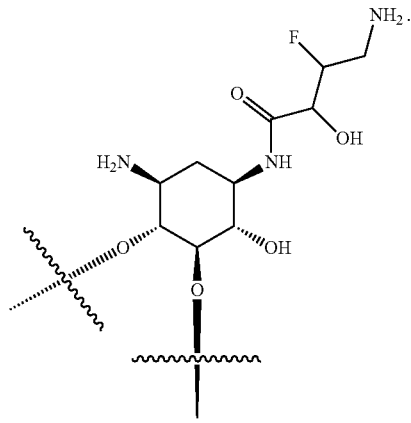

In some embodiments of the compound of Formula (VIIb), Ring B is

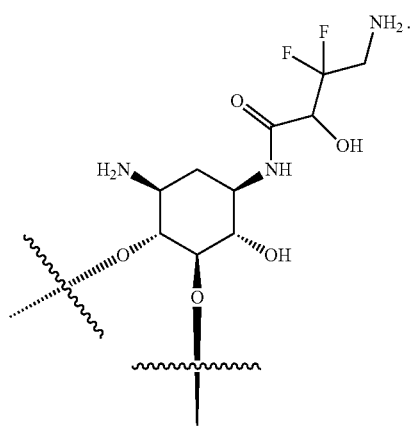

In some embodiments of the compound of Formula (VIIb), Ring B is

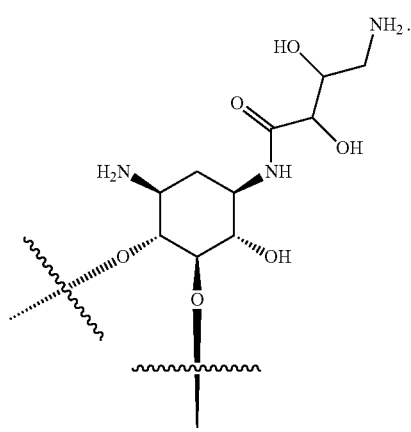

In some embodiments of the compound of Formula (VIIb), Ring B is

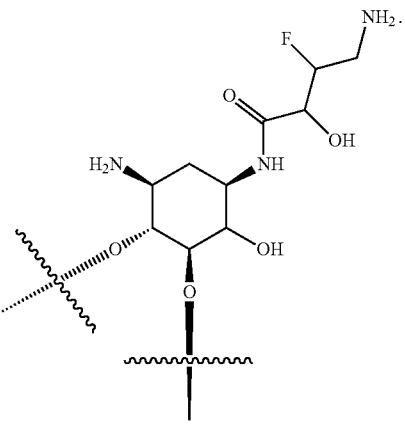

In some embodiments of the compound of Formula (VIIb), Ring B is

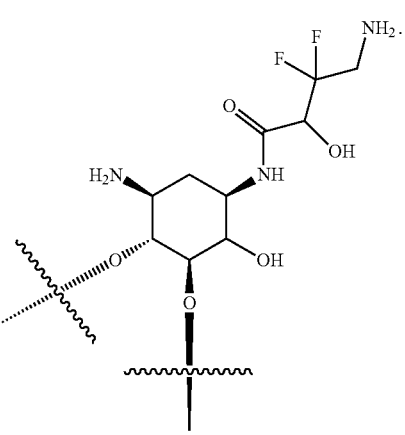

In some embodiments of the compound of Formula (VIIb), Ring B is

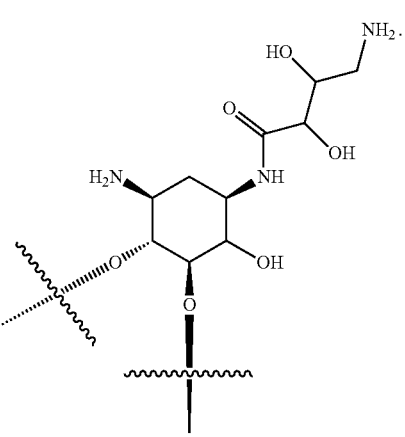

In some embodiments of the compound of Formula (VIIb), Ring B is

In some embodiments of the compound of Formula (VIIb), Ring B is

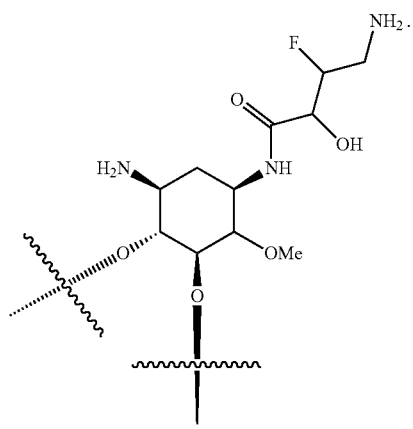

In some embodiments of the compound of Formula (VIIb), Ring B is

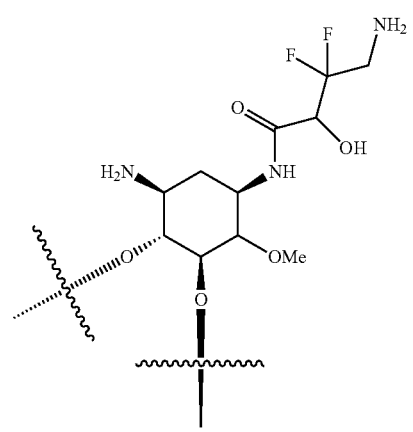

In some embodiments of the compound of Formula (VIIb), Ring B is

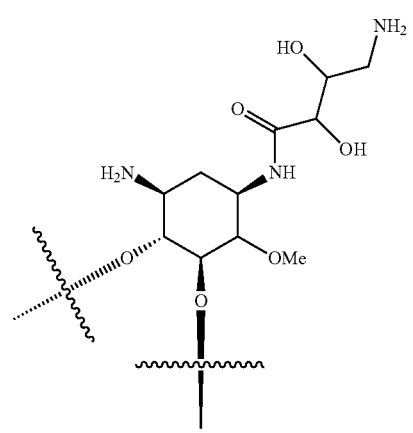

In some embodiments of the compound of Formula (VIIb), Ring B is

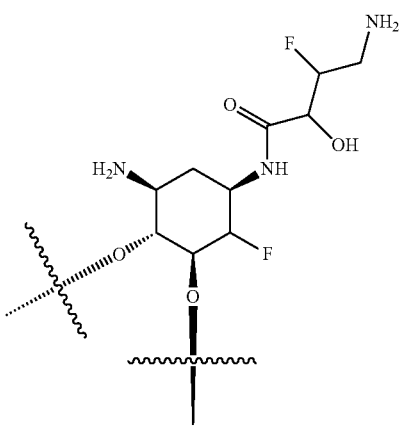

In some embodiments of the compound of Formula (VIIb), Ring B is

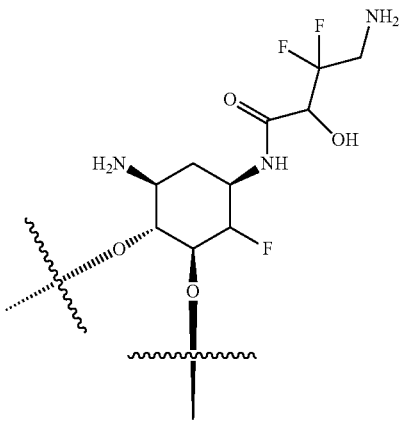

In some embodiments of the compound of Formula (VIIb), Ring B is

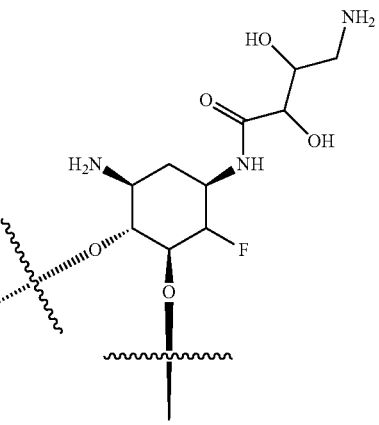

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^1$ is —$NR^{10}R^{11}$, wherein $R^{10}$ and $R^{11}$ are independently H or $C_1$-$C_6$alkyl, wherein the alkyl is unsubstituted or substituted with one or more —OH. In certain embodiments, $R^{10}$ and $R^{11}$ are independently H, methyl, or hydroxyethyl. In certain embodiments, $R^{10}$ and $R^{11}$ are both H. In other embodiments, $R^{10}$ is H and is unsubstituted $C_1$-$C_6$alkyl or $C_1$-$C_6$alkyl substituted with one or more —OH. For example, in some embodiments, may be methyl, ethyl, propyl, butyl, pentyl, or hexyl. In other embodiments, $R^{11}$ is methyl substituted with one or more —OH, ethyl substituted with one or more —OH, propyl substituted with one or more —OH, butyl substituted with one or more —OH, pentyl substituted with one or more —OH, or hexyl substituted with one or more —OH. In some embodiments, $R^{11}$ is methyl. In other embodiments, $R^{11}$ is hydroxyethyl. In some embodiments, $R^1$ is —NHCH$_3$. In other embodiments, $R^1$ is —NHCH$_2$CH$_2$OH.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^1$ is $OR^9$, wherein $R^9$ is H or $C_1$-$C_6$alkyl, wherein the alkyl is unsubstituted or substituted with one or more —OH. In certain embodiments, $R^9$ is H, methyl, or hydroxyethyl. In certain embodiments, $R^9$ is H. In other embodiments, $R^9$ is unsubstituted $C_1$-$C_6$alkyl or $C_1$-$C_6$alkyl substituted with one or more —OH. For example, in some embodiments, $R^9$ may be methyl, ethyl, propyl, butyl, pentyl, or hexyl. In other embodiments, $R^9$ is methyl substituted with one or more —OH, ethyl substituted with one or more —OH, propyl substituted with one or more —OH, butyl substituted with one or more —OH, pentyl substituted with one or more —OH, or hexyl substituted with one or more —OH. In some embodiments, $R^9$ is methyl. In other embodiments, $R^9$ is hydroxyethyl. In certain embodiments, $R^1$ is —OH.

In some embodiments of formula (IV), including formula (IV-X); formula (V), including formula (V-X); formula (VI), including formula (VI-X); formula (VIIa), including formula (VIIa-X); or formula (VIIb), including formula (VIIb-X), $R^2$ and $R^3$ are independently selected from the group consisting of H, alkyl, cycloalkyl, and aryl. In some embodiments, at least one of $R^2$ and $R^3$ is other than H. In some embodiments of formula (IVa), including formula (IVa-X), $R^2$ and $R^3$ are independently selected from the group consisting of H, alkyl, cycloalkyl, and aryl, wherein at least one of $R^2$ and $R^3$ is other than H. In some embodiments, the alkyl, cycloalkyl, or aryl may be unsubstituted or substituted with one or more substituents independently selected from the group consisting of halogen, cyano, aryl, —$SR^{12}$, —$SO_2R^{13}$, —$OSF_2NR^{14}R^{15}$, —$NR^{14}R^{15}$, and —$OR^{16}$, wherein each $R^{12}$, $R^{13}$, $R^{14}$, $R^{15}$, and $R^{16}$ may independently be H or alkyl. In some embodiments, the one or more substituents are independently selected from the group consisting of halogen, cyano, —$SO_2R^{13}$, —$NR^{14}R^{15}$, and —$OR^{16}$, wherein each $R^{13}$, $R^{14}$, $R^{15}$, and $R^{16}$ may independently be H or alkyl. In certain embodiments, one of $R^2$ and $R^3$ is H.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^2$ is alkyl, cyclopropyl, or phenyl; wherein the alkyl is unsubstituted or substituted with one, two, or three substituents selected from the group consisting of —NH$_2$, —OH, F, —CN, and —S(O)$_2$CH$_3$. In some embodiments, $R^2$ is methyl, ethyl, propyl, butyl, pentyl, hexyl, cyclopropyl, cyclobutyl, cyclopentyl, cyclohexyl, or phenyl. In other embodiments, $R^2$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —$SR^{12}$, —$SO_2R^{13}$, —$NR^{14}R^{15}$, and —$OR^{16}$. In some embodiments, the one or more substituents are independently selected from the group consisting of halogen, cyano, aryl, —$SO_2R^{13}$, —$NR^{14}R^{15}$, and —$OR^{16}$. For example, in certain embodiments, the one or more substituents are independently selected from the group consisting of F, Cl, B, I, cyano, —$SO_2CH_3$, —NH$_2$, and —OH. In still other embodiments, $R^2$ is methyl; methyl substituted with one or two F; methyl substituted with —$SO_2CH_3$; methyl substituted with —NH$_2$; methyl substituted with —OH; ethyl; cyclopropyl; or phenyl. In some embodiments, $R^2$ is H or unsubstituted methyl.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^3$ is methyl, ethyl, propyl, butyl, pentyl, hexyl, cyclopropyl, cyclobutyl, cyclopentyl, cyclohexyl, or phenyl. In other embodiments, $R^3$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —$SR^{12}$, $SO_2R^{13}$, —$NR^{14}R^{15}$, and —$OR^{16}$. In some embodiments, the one or more substituents are independently selected from the group consisting of halogen, cyano, aryl, —$SO_2R^{13}$, —$NR^{14}R^{15}$, and —$OR^{16}$. For example, in certain embodiments, the one or more substituents are independently selected from the group consisting of F, Cl, B, I, cyano, —$SO_2CH_3$, —NH$_2$, and —OH. In still other embodiments, $R^3$ is methyl; methyl substituted with one or two F; methyl substituted with —$SO_2CH_3$; methyl substituted with —NH$_2$; methyl substituted with —OH; ethyl; cyclopropyl; or phenyl. In certain embodiments, $R^3$ is H or unsubstituted methyl.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^1$ and $R^2$, together with the atom to which they are attached, form a heterocycloalkyl group comprising at least one heteroatom selected from the group consisting of N and O. In some embodiments, the heterocycloalkyl group may be unsubstituted or substituted with one or more substituents independently selected from the group consisting of halogen, cyano, —$SR^{17}$, —$SO_2R^{18}$, —$NR^{19}R^{20}$, and —$OR^{21}$, wherein each $R^{17}$, $R^{18}$, $R^{19}$, $R^{20}$, and $R^{21}$ may be independently H or alkyl. In certain embodiments, the heterocycloalkyl group is 5-membered, in other embodiments it is 6-membered. In some embodiments, the heterocycloalkyl group comprises one N and one O. In certain embodiments, $R^1$ and $R^2$, together with the atom to which they are attached, form an unsubstituted 6-membered group comprising one N and one 0. In some embodiments, $R^1$ and $R^2$, together with the atom to which they are attached, form:

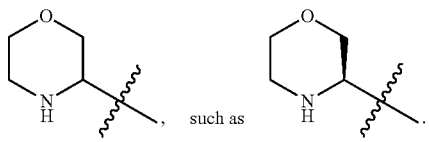 [SMILES: *C1COCCN1 ; *[C@@H]1COCCN1], such as

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^2$ and $R^3$, together with the atom to which they are attached, form a cycloalkyl group or a heterocycloalkyl group. In some embodiments, the cycloalkyl group or heterocycloalkyl group may be unsubstituted or substituted with one or more substituents independently selected from the group consisting of halogen, cyano —$SR^{22}$, —$SO_2R^{23}$, —$NR^{24}R^{25}$, and —$OR^{26}$, wherein each $R^{22}$, $R^{23}$, $R^{24}$, $R^{25}$, and $R^{26}$ may be independently H or alkyl. In certain embodiments, $R^2$ and $R^3$ together with the atom to which they are attached form a cyclopropyl or oxetanyl. In certain embodiments, $R^2$ and $R^3$ together with the atom to which they are attached form a cyclopropyl.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^2$ and $R^3$, together with the atom to which they are attached, form a substituted or unsubstituted cycloalkyl group. For example, in some embodiments, $R^2$ and $R^3$, together with the atom to which they are attached, may form cyclopropyl, cyclobutyl, cyclopentyl, or cyclohexyl. In some embodiments, $R^2$ and $R^3$, together with the atom to which they are attached, may form substituted cyclopropyl, substituted cyclobutyl, substituted cyclopentyl, or substituted cyclohexyl, wherein the one or more substituents are independently selected from the group consisting of halogen, cyano, —$SR^{22}$, —$SO_2R^{23}$, —$NR^{24}R^{25}$, and —$OR^{26}$, wherein each $R^{22}$, $R^{23}$, $R^{24}$, $R^{25}$, and $R^{26}$ may be independently H or alkyl. In some embodiments, $R^2$ and $R^3$, together with the atom to which they are attached, form cyclopropyl.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^2$ and $R^3$, together with the atom to which they are attached, form an unsubstituted or substituted heterocycloalkyl. For example, in some embodiments, $R^2$ and $R^3$, together with the atom to which they are attached, may form a 4-membered heterocycloalkyl, a 5-membered heterocycloalkyl, or a 6-membered heterocycloalkyl, wherein the heterocycloalkyl is unsubstituted or substituted with one or more substituents independently selected from the group consisting of halogen, cyano, —$SR^{22}$, —$SO_2R^{23}$, —$NR^{24}R^{25}$, and —$OR^{26}$. In some embodiments, the heterocycloalkyl comprises one or more heteroatoms selected from the group consisting of O and N. In certain embodiments, $R^2$ and $R^3$, together with the atom to which they are attached, form 4-membered heterocycloalkyl comprising one O. In some embodiments, $R^2$ and $R^3$, together with the atom to which they are attached, form:

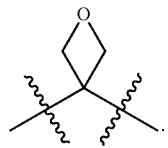 [SMILES: *C1(*)COC1]

In some embodiments of formula (IV), including formula (IV-X); formula (IVa), including formula (IVa-X); formula (V), including formula (V-X); or formula (VI), including formula (VI-X),

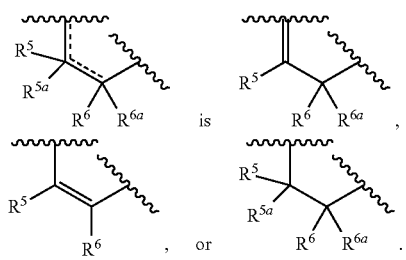

In some embodiments of formula (IV), including formula (IV-X); formula (IVa), including formula (IVa -X); formula (V), including formula (V-X); or formula (VI), including formula (VI-X),

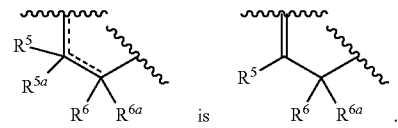

In some embodiments of formula (IV), including formula (IV-X); formula (IVa), including formula (IVa-X); formula (V), including formula (V-X); or formula (VI), including formula (VI-X),

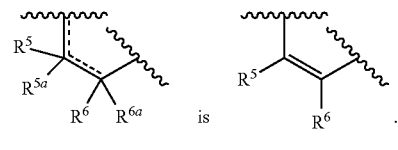

In some embodiments of formula (IV), including formula (IV-X); formula (IVa), including formula (IVa-X); formula (V), including formula (V-X); or formula (VI), including formula (VI-X),

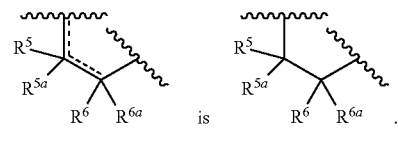

In some embodiments of formula (IV), including formula (IV-X); formula (IVa), including formula (IVa-X); formula (V), including formula (V-X); or formula (VI), including formula (VI-X), $R^4$ is H or absent.

In some embodiments of formula (IV), including formula (IV-X); formula (IVa), including formula (IVa-X); formula (V), including formula (V-X); or formula (VI), including formula (VI-X), $R^4$ is H and

[structure]  is  [structure] .

In some embodiments of formula (IV), including formula (IV-X); formula (IVa), including formula (IVa-X); formula (V), including formula (V-X); or formula (VI), including formula (VI-X), $R^5$ and $R^{5a}$ are independently H, halogen, or —OH. In certain such embodiments, $R^5$ and $R^{5a}$ are independently H, F, or —OH. In some embodiments of formula (IV), including formula (IV-X); formula (IVa), including formula (IVa-X); formula (V), including formula (V-X); or formula (VI), including formula (VI-X), $R^6$ and $R^{6a}$ are independently H, halogen, or —OH. In certain such embodiments, $R^6$ and $R^{6a}$ are independently H, F, or —OH.

In some embodiments of formula (IV), including formula (IV-X); formula (IVa), including formula (IVa-X); formula (V), including formula (V-X); or formula (VI), including formula (VI-X), $R^4$ is absent and

[structure]  is  [structure] .

In some embodiments of formula (IV), including formula (IV-X); formula (IVa), including formula (IVa-X); formula (V), including formula (V-X); or formula (VI), including formula (VI-X), $R^5$ is H, halogen, or —OH. In certain such embodiments, $R^5$ and $R^{5a}$ are independently H, F, or —OH. In some embodiments of formula (IV), including formula (IV-X); formula (IVa), including formula (IVa-X); formula (V), including formula (V-X); or formula (VI), including formula (VI-X), $R^6$ and $R^{6a}$ are independently H, halogen, or —OH. In certain such embodiments, $R^6$ and $R^{6a}$ are independently H, F, or —OH.

In some embodiments of formula (IV), including formula (IV-X); formula (IVa), including formula (IVa-X); formula (V), including formula (V-X); or formula (VI), including formula (VI-X), $R^4$ is H and

[structure]  is  [structure] .

In some embodiments of formula (IV), including formula (IV-X); formula (IVa), including formula (IVa-X); formula (V), including formula (V-X); or formula (VI), including formula (VI-X), $R^5$ is H, halogen, or —OH. In certain such embodiments, $R^5$ and $R^{5a}$ are independently H, F, or —OH. In some embodiments of formula (IV), including formula (IV-X); formula (IVa), including formula (IVa-X); formula (V), including formula (V-X); or formula (VI), including formula (VI-X), $R^6$ is H, halogen, or —OH. In certain such embodiments, $R^6$ and $R^{6a}$ are independently H, F, or —OH.

In some embodiments of formula (IV), including formula (IV-X); formula (IVa), including formula (IVa-X); formula (V), including formula (V-X); or formula (VI), including formula (VI-X), $R^5$ and $R^6$ are H and $R^{5a}$ and $R^{6a}$ are independently absent or H.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), both $R^5$ and $R^6$ are H.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), both $R^{5a}$ and $R^{6a}$ are H.

In some embodiments of formula (VIIa), including formula (VIIa-X), or formula (VIIb), including formula (VIIb-X), $R^5$, $R^{5a}$, $R^6$, and $R^{6a}$ are H.

In some embodiments of formula (VIIa), including formula (VIIa-X), or formula (VIIb), including formula (VIIb-X), $R^5$ is H.

In some embodiments of formula (VIIa), including formula (VIIa-X), or formula (VIIb), including formula (VIIb-X), $R^{5a}$ is H.

In some embodiments of formula (VIIa), including formula (VIIa-X), or formula (VIIb), including formula (VIIb-X), $R^6$ is H.

In some embodiments of formula (VIIa), including formula (VIIa-X), or formula (VIIb), including formula (VIIb-X), $R^{6a}$ is H.

In some embodiments of formula (IV), including formula (IV-X); formula (IVa), including formula (IVa-X); formula (V), including formula (V-X); formula (VI), including formula (VI-X); or formula (VIIa), including formula (VIIa-X), $R^5$ is H or —OH. In some embodiments of formula (IV), including formula (IV-X); formula (IVa), including formula (IVa -X); formula (V), including formula (V-X); formula (VI), including formula (VI-X); or formula (VIIa), including formula (VIIa-X), $R^5$ is —OH. In some embodiments of formula (IV), including formula (IV-X); formula (IVa), including formula (IVa-X); formula (V), including formula (V -X); formula (VI), including formula (VI-X); or formula (VIIa), including formula (VIIa-X), $R^5$ is H.

In some embodiments of formula (IV), including formula (IV-X); formula (IVa), including formula (IVa-X); formula (V), including formula (V-X); formula (VI), including formula (VI-X); or formula (VIIa), including formula (VIIa-X), $R^{5a}$ is H or —OH. In some embodiments of formula (IV), including formula (IV-X); formula (IVa), including formula (IVa -X); formula (V), including formula (V-X); formula (VI), including formula (VI-X); or formula (VIIa), including formula (VIIa-X), $R^{5a}$ is —OH. In some embodiments of formula (IV), including formula (IV-X); formula (IVa), including formula (IVa-X); formula (V), including formula (V -X); formula (VI), including formula (VI-X); or formula (VIIa), including formula (VIIa-X), $R^{5a}$ is H.

In some embodiments of formula (IV), including formula (IV-X); formula (IVa), including formula (IVa-X); formula (V), including formula (V-X); formula (VI), including for- mula (VI-X); or formula (VIIb), including formula (VIIb-X), $R^6$ is H or —OH. In some embodiments of formula (IV), including formula (IV-X); formula (IVa), including formula (IVa -X); formula (V), including formula (V-X); formula (VI), including formula (VI-X); or formula (VIIb), including formula (VIIb-X), $R^6$ is —OH. In some embodiments of formula (IV), including formula (IV-X); formula (IVa), including formula (IVa-X); formula (V), including formula (V-X); formula (VI), including formula (VI-X); or formula (VIIb), including formula (VIIb-X), $R^6$ is H.

In some embodiments of formula (IV), including formula (IV-X); formula (IVa), including formula (IVa-X); formula (V), including formula (V-X); formula (VI), including formula (VI-X); or formula (VIIb), including formula (VIIb-X), $R^{6a}$ is H or —OH. In some embodiments of formula (IV), including formula (IV-X); formula (IVa), including formula (IVa -X); formula (V), including formula (V-X); formula (VI), including formula (VI-X); or formula (VIIb), including formula (VIIb-X), $R^{6a}$ is —OH. In some embodiments of formula (IV), including formula (IV-X); formula (IVa), including formula (IVa-X); formula (V), including formula (V-X); formula (VI), including formula (VI-X); or formula (VIIb), including formula (VIIb-X), $R^{6a}$ is H.

In some embodiments of formula (IV), including formula (IV-X); formula (IVa), including formula (IVa-X); formula (V), including formula (V-X); formula (VI), including formula (VI-X); or formula (VIIa), including formula (VIIa-X), $R^5$ is H, halogen, or —OH. In certain such embodiments, $R^5$ is halogen. In certain such embodiments, $R^5$ is F.

In some embodiments of formula (VIIa), including formula (VIIa-X), $R^5$ is halogen and $R^{5a}$ is H. In certain such embodiments, $R^5$ is F and $R^{5a}$ is H. In some embodiments of formula (VIIa), including formula (VIIa-X), $R^5$ is halogen and $R^{5a}$ is halogen. In some embodiments of formula (VIIa), including formula (VIIa-X), $R^5$ is halogen and $R^{5a}$ is F. In some embodiments of formula (VIIa), including formula (VIIa-X), $R^5$ is F and $R^{5a}$ is F. In some embodiments of formula (VIIa), including formula (VIIa-X), $R^5$ is F and $R^{5a}$ is halogen.

In some embodiments of formula (VIIa), including formula (VIIa-X), $R^5$ is —OH and $R^{5a}$ is H. In some embodiments of formula (VIIa), including formula (VIIa-X), $R^5$ is —OH and $R^{5a}$ is halogen. In some embodiments of formula (VIIa), including formula (VIIa-X), $R^5$ is —OH and $R^{5a}$ is F. In some embodiments of formula (VIIa), including formula (VIIa-X), $R^5$ is —OH and $R^{5a}$ is —OH. In some embodiments of formula (VIIa), including formula (VIIa-X), $R^{5a}$ is —OH and $R^5$ is H. In some embodiments of formula (VIIa), including formula (VIIa-X), $R^{5a}$ is —OH and $R^5$ is halogen. In some embodiments of formula (VIIa), including formula (VIIa-X), $R^{5a}$ is —OH and $R^5$ is F.

In some embodiments of formula (IV), including formula (IV-X); formula (IVa), including formula (IVa-X); formula (V), including formula (V-X); formula (VI), including formula (VI-X); or formula (VIIa), including formula (VIIa-X), $R^{5a}$ is H, halogen, or —OH. In certain such embodiments, $R^{5a}$ is halogen. In certain such embodiments, $R^{5a}$ is F.

In some embodiments of formula (IV), including formula (IV-X); formula (IVa), including formula (IVa-X); formula (V), including formula (V-X); formula (VI), including formula (VI-X); or formula (VIIb), including formula (VIIb-X), $R^6$ is H, halogen, or —OH. In certain such embodiments, $R^6$ is halogen. In certain such embodiments, $R^6$ is F.

In some embodiments of formula (VIIb), including formula (VIIb-X), $R^6$ is halogen and $R^{6a}$ is H. In certain such embodiments, $R^6$ is F and $R^{6a}$ is H. In some embodiments of formula (VIIb), including formula (VIIb-X), $R^6$ is halogen and $R^{6a}$ is halogen. In some embodiments of formula (VIIb), including formula (VIIb-X), $R^6$ is halogen and $R^{6a}$ is F. In some embodiments of formula (VIIb), including formula (VIIb-X), $R^6$ is F and $R^{6a}$ is F. In some embodiments of formula (VIIb), including formula (VIIb-X), $R^6$ is F and $R^{6a}$ is halogen.

In some embodiments of formula (VIIb), including formula (VIIb-X), $R^6$ is —OH and $R^{6a}$ is H. In some embodiments of formula (VIIb), including formula (VIIb-X), $R^6$ is —OH and $R^{6a}$ is halogen. In some embodiments of formula (VIIb), including formula (VIIb-X), $R^6$ is —OH and $R^{6a}$ is F. In some embodiments of formula (VIIb), including formula (VIIb-X), $R^6$ is —OH and $R^{6a}$ is —OH. In some embodiments of formula (VIIb), including formula (VIIb-X), $R^{6a}$ is —OH and $R^6$ is H. In some embodiments of formula (VIIb), including formula (VIIb-X), $R^{6a}$ is —OH and $R^6$ is halogen. In some embodiments of formula (VIIb), including formula (VIIb-X), $R^{6a}$ is —OH and $R^6$ is F.

In some embodiments of formula (IV), including formula (IV-X); formula (IVa), including formula (IVa-X); formula (V), including formula (V-X); formula (VI), including formula (VI-X); or formula (VIIb), including formula (VIIb-X), $R^{6a}$ is H, halogen, or —OH. In certain such embodiments, $R^{6a}$ is halogen. In certain such embodiments, $R^{6a}$ is F.

In some embodiments of formula (IV), including formula (IV-X); formula (IVa), including formula (IVa-X); formula (V), including formula (V-X); formula (VI), including formula (VI-X); or formula (VIIa), including formula (VIIa-X), $R^5$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (IV), including formula (IV-X); formula (IVa), including formula (IVa-X); formula (V), including formula (V-X); formula (VI), including formula (VI-X); or formula (VIIa), including formula (VIIa-X), $R^{5a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (IV), including formula (IV-X); formula (IVa), including formula (IVa-X); formula (V), including formula (V-X); formula (VI), including formula (VI-X); or formula (VIIb), including formula (VIIb-X), $R^6$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (IV), including formula (IV-X); formula (IVa), including formula (IVa-X); formula (V), including formula (V-X); formula (VI), including formula (VI-X); or formula (VIIb), including formula (VIIb-X), $R^{6a}$ is —$OR^{27}$ or —$NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (VIIa), including formula (VIIa-X), $R^6$ and $R^{6a}$ are independently H, F, Br, or I. In certain such embodiments, $R^6$ and $R^{6a}$ are independently H or F. In some embodiments of formula (VIIa), including formula (VIIa-X), $R^6$ is F. In some embodiments of formula (VIIa), including formula (VIIa-X), $R^6$ is F and $R^{6a}$ is H. In some embodiments of formula (VIIa), including formula (VIIa-X), $R^{6a}$ is F. In some embodiments of formula (VIIa), including formula (VIIa-X), $R^6$ is F and $R^{6a}$ is F. In some embodiments of formula (VIIa), including formula (VIIa-X), $R^{6a}$ is F and $R^6$ is H.

In some embodiments of formula (VIIb), including formula (VIIb-X), $R^5$ and $R^{5a}$ are independently H, F, Br, or I. In certain such embodiments, $R^5$ and $R^{5a}$ are independently H or F. In some embodiments of formula (VIIb), including formula (VIIb-X), $R^5$ is F. In some embodiments of formula (VIIb), including formula (VIIb-X), $R^5$ is F and $R^{5a}$ is H. In some embodiments of formula (VIIb), including formula (VIIb-X), $R^{5a}$ is F. In some embodiments of formula (VIIb), including formula (VIIb-X), $R^5$ is F and $R^{5a}$ is F.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^4$ is H.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $X^1$ is selected from the group consisting of H, $NH_2$, OH, and halogen. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $X^1$ is $NH_2$ or OH. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $X^1$ is $NH_2$. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $X^1$ is OH. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $X^1$ is halogen. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $X^1$ is F. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $X^1$ is Cl. In some embodiments of formula (IV), including formula (IV-X); formula (IVa), including formula (IVa -X); formula (V), including formula (V-X); formula (VI), including formula (VI-X); formula (VIIa), including formula (VIIa-X); or formula (VIIb), including formula (VIIb-X), $X^1$ is Br. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $X^1$ is I.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{41}$ is H, —CN, —$CONH_2$ or $C_1$-$C_3$alkyl, wherein the alkyl is unsubstituted or substituted with one or more substituents selected from the group consisting of —OH, —$OC(O)CH_3$, —$NH_2$, —CN, —$CONH_2$, and halogen. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{41}$ is H. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{41}$ is unsubstituted $C_1$-$C_3$alkyl. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{41}$ is $C_1$-$C_3$alkyl substituted by —OH. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{41}$ is $C_1$-$C_3$alkyl substituted by —$NH_2$. In some embodiments of formula (IV), including formula (IV-X); formula (IVa), including formula (IVa-X); formula (V), including formula (V-X); formula (VI), including formula (VI -X); formula (VIIa), including formula (VIIa-X); or formula (VIIb), including formula (VIIb-X), $R^{41}$ is —CN. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{41}$ is —$CONH_2$. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{41}$ is $C_1$-$C_3$alkyl substituted by one or more halogen. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{41}$ is $C_1$-$C_3$alkyl substituted by one or more —F. In some embodiments of formula (IV), including formula (IV-X); formula (IVa), including formula (IVa-X); formula (V), including formula (V -X); formula (VI), including formula (VI-X); formula (VIIa), including formula (VIIa-X); or formula (VIIb), including formula (VIIb-X), $R^{41}$ is $C_1$-$C_3$alkyl substituted by —CN.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{42}$ and $R^{43}$ are, independently H, —OH, —$OR^{45}$, —$NR^{46}R^{47}$, or halogen. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{42}$ and $R^{43}$ is —OH. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{42}$ and $R^{43}$ is halogen. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{42}$ and $R^{43}$ is H. In some embodiments of formula (IV), including formula (IV-X); formula (IVa), including formula (IVa-X);

formula (V), including formula (V-X); formula (VI), including formula (VI-X); formula (VIIa), including formula (VIIa-X); or formula (VIIb), including formula (VIIb-X), $R^{42}$ and $R^{43}$ are —$OR^{45}$. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{42}$ and $R^{43}$ is —$NR^{46}R^{47}$. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{42}$ and $R^{43}$ is —F. In some embodiments of formula (IV), including formula (IV-X); formula (IVa), including formula (IVa -X); formula (V), including formula (V-X); formula (VI), including formula (VI-X); formula (VIIa), including formula (VIIa-X); or formula (VIIb), including formula (VIIb-X), $R^{42}$ is —F and $R^{43}$ is —F. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{42}$ and $R^{43}$ is —OH. In some embodiments of formula (IV), including formula (IV-X); formula (IVa), including formula (IVa-X); formula (V), including formula (V -X); formula (VI), including formula (VI-X); formula (VIIa), including formula (VIIa-X); or formula (VIIb), including formula (VIIb-X), one of $R^{42}$ and $R^{43}$ is —OR'.

In some embodiments of formula (IV), including formula (IV-X); formula (IVa), including formula (IVa-X); formula (V), including formula (V-X); formula (VIIa), including formula (VIIa-X); or formula (VIIb), including formula (VIIb-X), $R^{42}$ and $R^{43}$ are H.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{44}$ and $R^{44a}$ are, independently H, halogen, —OH, $C_1$-$C_3$alkoxy, or —OC(O)$CH_3$. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{44}$ and $R^{44a}$ are, independently H, halogen, $C_1$-$C_3$alkoxy, or —OC(O)$CH_3$. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{44}$ and $R^{44a}$ is —OH. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{44}$ and $R^{44a}$ is —$OCH_3$. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{44}$ and $R^{44a}$ is —F. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{44}$ and $R^{44a}$ are —F. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{44}$ and $R^{44a}$ are H. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{44}$ and $R^{44a}$ is H.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{51a}$, $R^{51b}$, and $R^{51c}$ are, independently, H, OH, or —$OR^{51d}$. In some embodiments of formula (IV), including formula (IV-X); formula (IVa), including formula (IVa -X); formula (V), including formula (V-X); formula (VI), including formula (VI-X); formula (VIIa), including formula (VIIa-X); or formula (VIIb), including formula (VIIb-X), one of $R^{51}$a, $R^{51}$b, and $R^{51}$c is —OH. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{51a}$, $R^{51b}$, and $R^{51c}$ is —$OR^{51d}$. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{51a}$ is —OH and $R^{51b}$ and $R^{51c}$ are H. In some embodiments of formula (IV), including formula (IV-X); formula (IVa), including formula (IVa-X); formula (V), including formula (V-X); formula (VI), including formula (VI -X); formula (VIIa), including formula (VIIa-X); or formula (VIIb), including formula (VIIb-X), $R^{51a}$ is —$OR^{51d}$ and $R^{51b}$ and $R^{51c}$ are H.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{52a}$ and $R^{52b}$ are independently H, OH, or —$OR^{52c}$. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{52a}$ and $R^{52b}$ are —OH. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), one of $R^{52a}$ and $R^{52b}$ is —$OR^{52c}$. In some embodiments of formula (IV), including formula (IVa-X); formula (V), including formula (V-X); formula (VI), including formula (VI-X); formula (VIIa), including formula (VIIa-X); or formula (VIIb), including formula (VIIb-X), one of $R^{52a}$ and $R^{52b}$ is —OH. In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{52a}$ is H and $R^{52b}$ is —$OR^{52c}$. In some embodiments of formula (IV), including formula (IV-X); formula (IVa), including formula (IVa -X); formula (V), including formula (V-X); formula (VI), including formula (VI-X); formula (VIIa), including formula (VIIa-X); or formula (VIIb), including formula (VIIb-X), $R^{52a}$ is H and $R^{52b}$ is —OH.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^7$ is H. In other embodiments, $R^7$ is $C_1$-$C_3$alkyl, for example $C_1$-alkyl, $C_2$-alkyl, or $C_3$-alkyl. In some embodiments, $R^8$ is H. In some embodiments, $R^7$ is H and $R^8$ is H.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^8$ is $C_1$-$C_6$alkyl, for example $C_1$-alkyl, $C_2$-alkyl, $C_3$-alkyl, $C_4$-alkyl, $C_5$-alkyl, or $C_6$-alkyl.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^8$ is

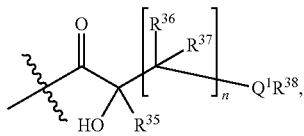

wherein $Q^1$ is NH, O, or S. In certain embodiments, $Q^1$ is NH. In certain embodiments, $Q^1$ is O. In certain embodiments, $Q^1$ is S. In certain embodiments, wherein when n is one, then $R^{36}$ and $R^{37}$ are not halo.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including
formula (VIIb-X), $R^8$ is

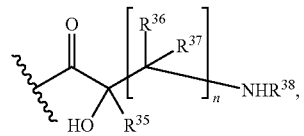

for example

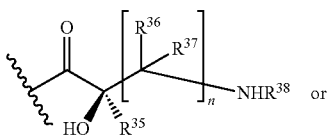

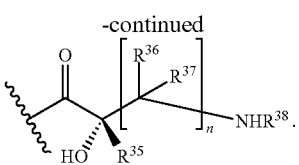

In some embodiments, $R^{35}$ is H. In certain embodiments, each $R^{36}$ and $R^{37}$ are H. In certain embodiments, $R^{38}$ is H. In other embodiments, $R^{38}$ is alkyl, for example $C_1$alkyl, $C_2$alkyl, or $C_3$alkyl. In other embodiments, $R^{38}$ is —C(=NH)$NR^{39}R^{40}$, for example —C(=NH)$NH_2$. In certain embodiments, $R^{35}$ and $R^{38}$, together with the atoms to which they are attached, form a heterocycloalkyl group comprising at least one N.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), n is an integer from 0 to 4, from 0 to 3, from 0 to 2, from 1 to 4, from 2 to 4, or from 1 to 3. In certain embodiments, n is 0, or n is 1, or n is 2, or n is 3, or n is 4.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^8$ is:

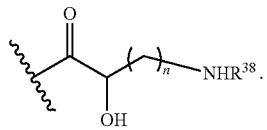

In some embodiments, $R^8$ may be:

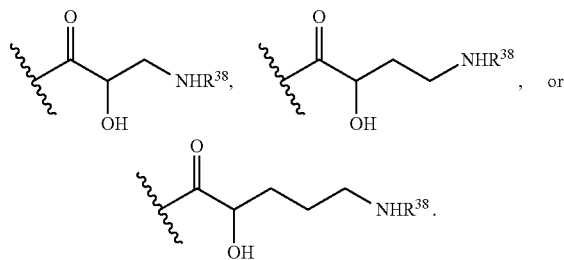

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{38}$ is H. In some embodiments, $R^8$ may be:

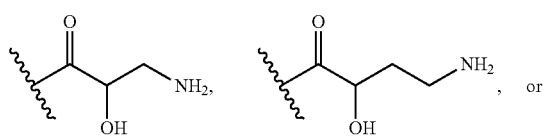

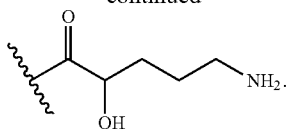

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^8$ may be:

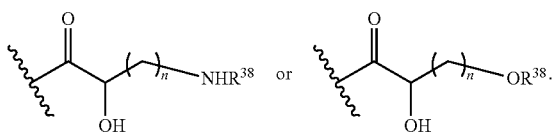

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^8$ may be:

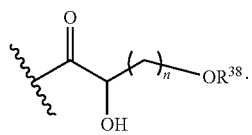

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^8$ is:

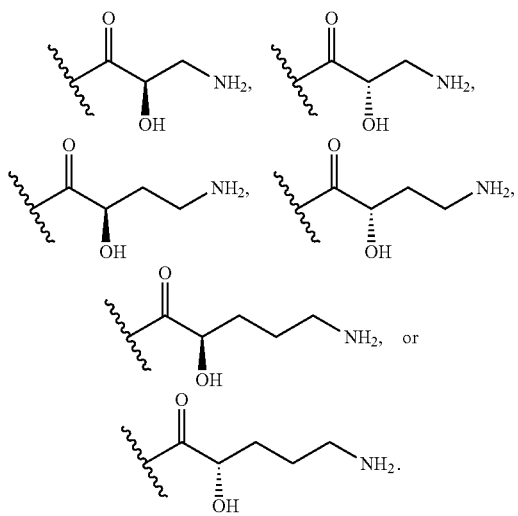

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^8$ is:

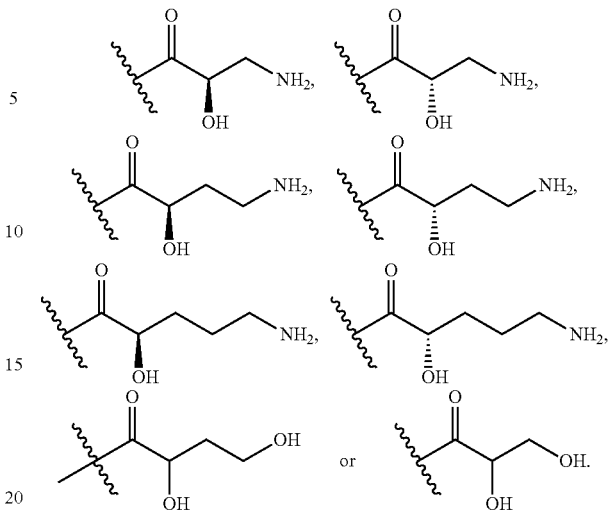

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^8$ is:

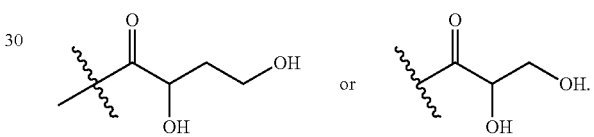

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), at least one $R^{36}$ or $R^{37}$ is halogen. For example, in certain embodiments, $R^8$ is:

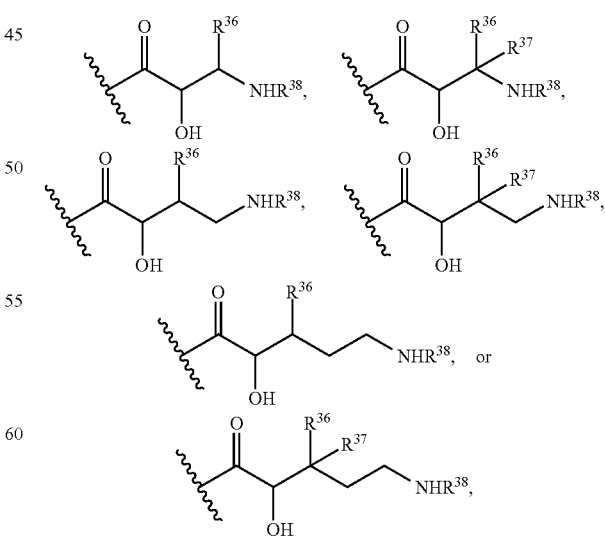

wherein each $R^{36}$ and $R^{37}$ is independently halogen, for example fluoro.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), at least one $R^{36}$ or $R^{37}$ is halogen, and $R^{38}$ is H. For example, in some embodiments, $R^8$ may be:

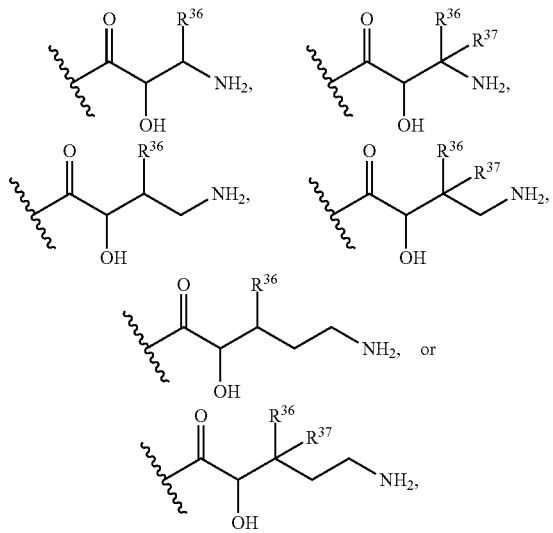

wherein each $R^{36}$ and $R^{37}$ are independently halogen, for example fluoro.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), at least one $R^{36}$ or $R^{37}$ is halogen. For example, in certain embodiments, $R^8$ is:

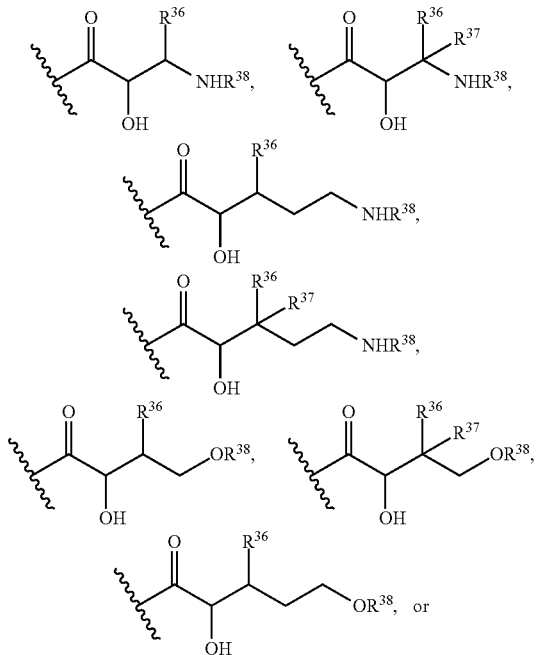

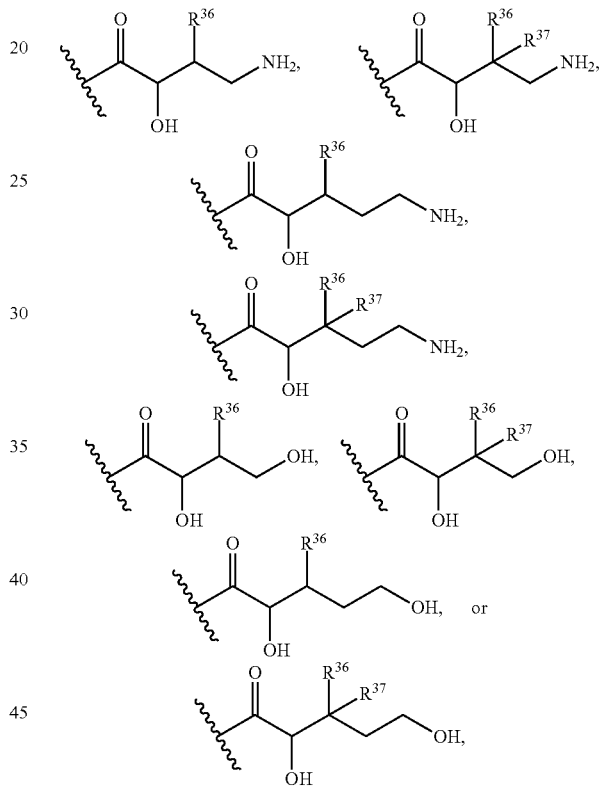

wherein each $R^{36}$ and $R^{37}$ is independently halogen, for example fluoro.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), at least one $R^{36}$ or $R^{37}$ is halogen, and $R^{38}$ is H. For example, in some embodiments, $R^8$ may be:

wherein each $R^{36}$ and $R^{37}$ are independently halogen, for example fluoro.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^8$ is

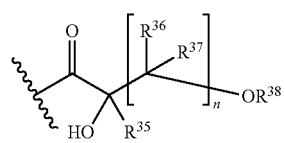

wherein at least one $R^{36}$ or $R^{37}$ is hydroxyl.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^8$ is

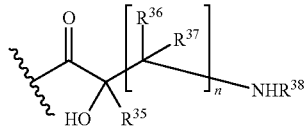

wherein at least one $R^{36}$ or $R^{37}$ is hydroxyl.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), and $R^8$ is:

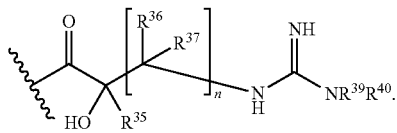

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{39}$ and $R^{40}$ are both H. In other embodiments, $R^{39}$ and $R^{40}$ are both $C_1$-$C_3$alkyl. In still other embodiments, one of $R^{39}$ and $R^{40}$ is H and the other is $C_1$-$C_3$alkyl.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{38}$ may be —C(=NH)NH$_2$. Thus, in certain embodiments, $R^8$ is:

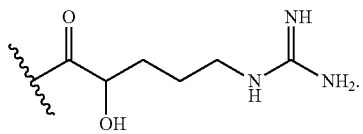 [SMILES: *C(=O)C(O)CCCNC(=N)N]

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^7$ and $R^8$ are H.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^7$ is H and $R^8$ is ethyl.

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^7$ is H and $R^8$ is

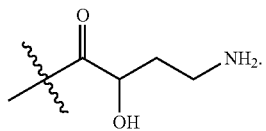

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^7$ is H and $R^8$ is

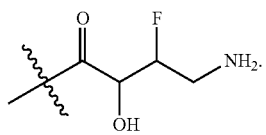 [SMILES: *C(=O)C(O)C(F)CN]

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^7$ is H and $R^8$ is

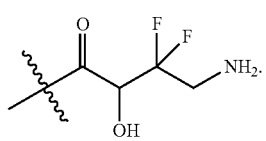 [SMILES: *C(=O)C(O)C(F)(F)CN]

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^7$ is H and $R^8$ is

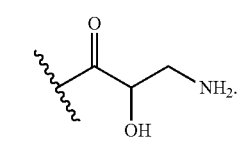 [SMILES: *C(=O)C(O)CN]

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^7$ is H and $R^8$ is

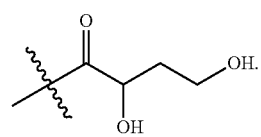 [SMILES: *C(=O)C(O)CCO]

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^7$ is H and $R^8$ is

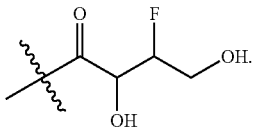 [SMILES: *C(=O)C(O)C(F)CO]

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^7$ is H and $R^8$ is

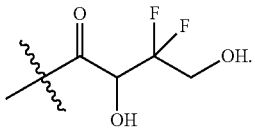 [SMILES: *C(=O)C(O)C(F)(F)CO]

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^7$ is H and $R^8$ is

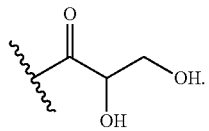 [SMILES: *C(=O)C(O)CO]

In some embodiments of formula (IV), including formula (IV-X); formula (IVa), including formula (IVa-X); formula (V), including formula (V-X); formula (VI), including formula (VI-X); formula (VIIa), including formula (VIIa-X); or formula (VIIb), including formula (VIIb-X), $R^{35}$ and $R^{38}$, together with the atoms to which they are attached, form a heterocycloalkyl group comprising at least one N. In some embodiments, the heterocycloalkyl group may comprise, for example, 4, 5, 6, or more ring members. In some embodiments, the heterocycloalkyl group comprises a 4-membered ring. In certain embodiments, the heterocycloalkyl group comprises a 4-membered ring comprising one N atom. It should be understood that when $R^{35}$ and $R^{38}$, together with the atoms to which they are attached, form a heterocycloalkyl group. In some embodiments, $R^8$ is:

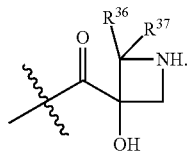

In some embodiments, $R^8$ is:

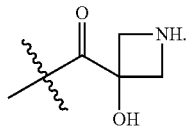 [SMILES: *C(=O)C1(O)CNC1]

Provided herein are compounds of formula (III):

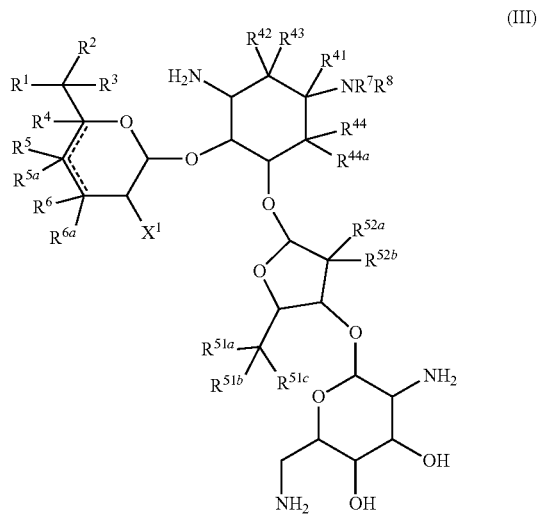

(III)

and pharmaceutically acceptable salts, solvates, stereoisomers, and tautomers thereof, wherein $R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl, wherein the alkyl, cycloalkyl, or aryl is unsubstituted or substituted with one or more substituents independently selected from the group consisting of halogen, cyano, aryl, —$SR^{12}$, —$SO_2R^{13}$, —$OSF_2NR^{14}R^{15}$, —$NR^{14}R^{15}$, and —$OR^{16}$, and wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and wherein each $R^{17}$, $R^{18}$, $R^{19}$, $R^{20}$, and $R^{21}$ is independently H or alkyl, or $R^2$ and $R^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl;

$R^4$ is H or absent;

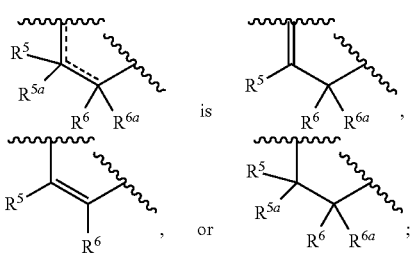

R$^5$ and R$^6$ are independently H, —OR$^{27}$, —NR$^{28}$R$^{29}$, halogen, or alkyl, wherein each R$^{27}$, R$^{28}$, and R$^{29}$ is independently H or C$_1$-C$_6$alkyl, wherein the alkyl or C$_1$-C$_6$alkyl is unsubstituted or substituted with one or more substituents selected from the group consisting of halogen, —OR$^{30}$, —NR$^{31}$R$^{32}$, —SR$^{33}$, and —SO$_2$R$^{34}$, and wherein each R$^{30}$, R$^{31}$, R$^{32}$, R$^{33}$, and R$^{34}$ is independently H or alkyl, R$^{5a}$ and R$^{6a}$ are, independently, absent or independently H, —OR$^{53}$, —NR$^{54}$R$^{55}$, halogen, or alkyl, wherein each R$^{53}$, R$^{54}$, and R$^{55}$ is independently H or C$_1$-C$_6$alkyl, wherein the alkyl or C$_1$-C$_6$alkyl is unsubstituted or substituted with one or more substituents selected from the group consisting of halogen, —OR$^{56}$, —NR$^{57}$R$^{58}$, —SR$^{59}$, and —SO$_2$R$^{60}$, and wherein each R$^{56}$, R$^{57}$, R$^{58}$, R$^{59}$, and R$^{60}$ is independently H or alkyl, or R$^5$ and R$^{5a}$ form an oxo group, or R$^6$ and R$^{6a}$ form an oxo group;

wherein if R$^5$ is —OR$^{27}$ or R$^{5a}$ is —OR$^{53}$, then R$^6$ is not —OR$^{27}$, and wherein if R$^5$ is —OR$^{27}$ or R$^{5a}$ is —OR$^{53}$, then R$^{6a}$ is not —OR$^{53}$, R$^7$ is H or C$_1$-C$_3$alkyl;

R$^8$ is H, C$_1$-C$_6$alkyl, an amino protecting group, or

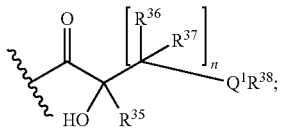

wherein Q$^1$ is NH, O, or S, n is an integer from 0 to 4,

R$^{35}$ is H or C$_1$-C$_3$alkyl, each R$^{36}$ and R$^{37}$ is independently H, alkyl, halogen, or —OH, and R$^{38}$ is H, alkyl, or —C(=NH)NR$^{39}$R$^{40}$, wherein R$^{39}$ and R$^{40}$ are independently H or C$_1$-C$_3$alkyl, or R$^{35}$ and R$^{38}$, together with the atoms to which they are attached, form a heterocycloalkyl group comprising at least one N;

R$^{41}$ is H, —CN, —CONH$_2$ or C$_1$-C$_3$alkyl, wherein the alkyl is unsubstituted or substituted with one or more substituents selected from the group consisting of —OH, —OC(O)CH$_3$, —NH$_2$, —CN, —CONH$_2$, and halogen;

R$^{42}$ and R$^{43}$ are, independently, H, —OH, —OR$^{45}$, —NR$^{46}$R$^{47}$, or halogen, wherein each R$^{45}$, R$^{46}$, and R$^{47}$ is independently H, alkyl, —CONH$_2$, or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

R$^{44}$ and R$^{44a}$ are, independently H, halogen, C$_1$-C$_3$alkoxy, or —OC(O)CH$_3$;

X$^1$ is selected from the group consisting of H, NH$_2$, OH, and halogen;

R$^{51a}$, R$^{51b}$, and R$^{51c}$ are, independently, H, OH, or —OR$^{51d}$;

wherein each R$^{51d}$ is, independently, alkyl or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

R$^{52a}$ and R$^{52b}$ are independently H, OH, or —OR$^{52c}$, wherein each R$^{52c}$ is, independently, alkyl or —COCH$_3$, wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl.

In one aspect, the compound of formula (III) is a compound of formula (I), including formula (I-A), formula (I-Ai), formula (I-Aii), formula (I-B), formula (I-Bi), and formula (I-Bii), and formula (II), formula (II-A), or formula (III-A), or a pharmaceutically acceptable salt, solvate, stereoisomer, or tautomer of any of the foregoing, as disclosed herein.

In one aspect, the compound of formula (III) is a compound of formula (III-A):

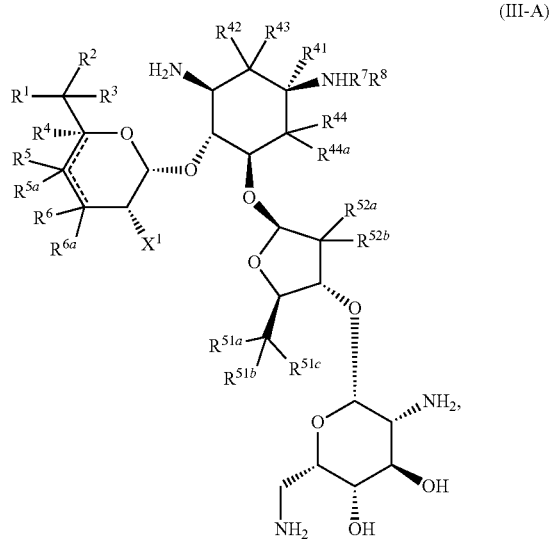

(III-A)

or a pharmaceutically acceptable salt, solvate, or tautomer thereof, wherein R$^1$, R$^2$, R$^3$, R$^4$,

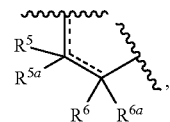

R$^7$, R$^8$, R$^{41}$, R$^{42}$, R$^{43}$, R$^{44}$, R$^{44a}$, R$^{51a}$, R$^{51b}$, R$^{51c}$, R$^{52a}$, and R$^{52b}$ are as defined for formula (III) herein.

In some embodiments of the compound of Formula (III),

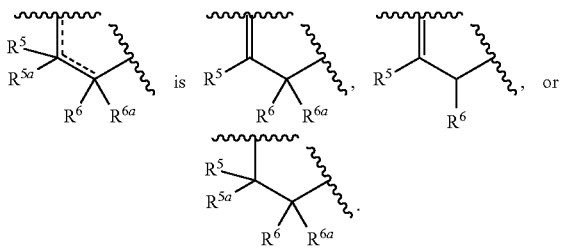

In some embodiments of the compound of Formula (III),

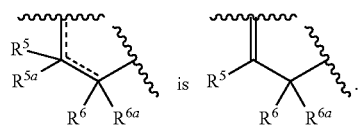

In some embodiments of the compound of Formula (III),

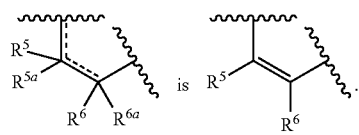

In some embodiments of the compound of Formula (III),

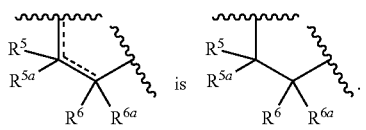

In some embodiments of the compound of Formula (III), $R^4$ is H or absent.

In some embodiments of the compound of Formula (III), $R^4$ is H and

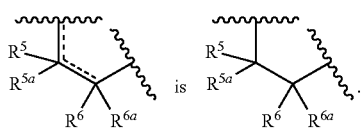

In some embodiments of the compound of Formula (III), $R^5$ and $R^{5a}$ are independently H, halogen, or —OH. In some embodiments of the compound of Formula (III), $R^6$ and $R^{6a}$ are independently H, halogen, or —OH.

In some embodiments of the compound of Formula (III), $R^4$ is absent and

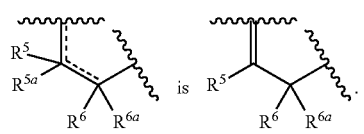

In some embodiments of the compound of Formula (III), $R^5$ is H, halogen, or —OH. In some embodiments of the compound of Formula (III), $R^6$ and $R^{6a}$ are independently H, halogen, or —OH.

In some embodiments of the compound of Formula (III), $R^4$ is H and

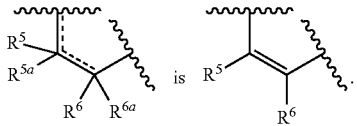

In some embodiments of the compound of Formula (III), $R^5$ is H, halogen, or —OH. In some embodiments of the compound of Formula (III), $R^6$ is H, halogen, or —OH.

In some embodiments of the compound of Formula (III), $X^1$ is selected from the group consisting of H, $NH_2$, OH, and halogen. In some embodiments of the compound of Formula (III), $X^1$ is $NH_2$ or OH. In some embodiments of the compound of Formula (III), $X^1$ is $NH_2$. In some embodiments of the compound of Formula (III), $X^1$ is OH.

In some embodiments of the compound of Formula (III), $R^{41}$ is H, —CN, —$CONH_2$ or $C_1$-$C_3$alkyl, wherein the alkyl is unsubstituted or substituted with one or more substituents selected from the group consisting of —OH, —OC(O)$CH_3$, —$NH_2$, —CN, —$CONH_2$, and halogen. In some embodiments of the compound of Formula (III), $R^{41}$ is H. In some embodiments of the compound of Formula (III), $R^{41}$ is unsubstituted $C_1$-$C_3$alkyl. In some embodiments of the compound of Formula (III), $R^{41}$ is $C_1$-$C_3$alkyl substituted by —OH. In some embodiments of the compound of Formula (III), $R^{41}$ is $C_1$-$C_3$alkyl substituted by —$NH_2$. In some embodiments of the compound of Formula (III), $R^{41}$ is —CN. In some embodiments of the compound of Formula (III), $R^{41}$ is —$CONH_2$. In some embodiments of the compound of Formula (III), $R^{41}$ is $C_1$-$C_3$alkyl substituted by one or more halogen. In some embodiments of the compound of Formula (III), $R^{41}$ is $C_1$-$C_3$alkyl substituted by one or more —F. In some embodiments of the compound of Formula (III), $R^{41}$ is $C_1$-$C_3$alkyl substituted by —CN.

In some embodiments of the compound of Formula (III), $R^{42}$ and $R^{43}$ are, independently H, —OH, —$NR^{46}R^{47}$, or halogen. In some embodiments of the compound of Formula (III), one of $R^{42}$ and $R^{43}$ is —OH. In some embodiments of the compound of Formula (III), one of $R^{42}$ and $R^{43}$ is halogen. In some embodiments of the compound of Formula (III), $R^{42}$ and $R^{43}$ are —$OR^{45}$. In some embodiments of the compound of Formula (III), one of $R^{42}$ and $R^{43}$ is —$NR^{46}R^{47}$. In some embodiments of the compound of Formula (III), one of $R^{42}$ and $R^{43}$ is —F. In some embodiments of the compound of Formula (III), $R^{42}$ is —F and $R^{43}$ is —F. In some embodiments of the compound of Formula (III), $R^{42}$ and $R^{43}$ are H. In some embodiments of the compound of Formula (III), one of $R^{42}$ and $R^{43}$ is —$OR^{45}$.

In some embodiments of the compound of Formula (III), $R^{44}$ and $R^{44a}$ are, independently H, halogen, —OH, $C_1$-$C_3$alkoxy, or —OC(O)$CH_3$. In some embodiments of the compound of Formula (III), one of $R^{44}$ and $R^{44a}$ mis —OH. In some embodiments of the compound of Formula (III), one of $R^{44}$ and $R^{44a}$ is —$OCH_3$. In some embodiments of the compound of Formula (III), one of $R^{44}$ and $R^{44a}$ is —F. In some embodiments of the compound of Formula (III), $R^{44}$ and $R^{44a}$ are —F. In some embodiments of the compound of Formula (III), $R^{44}$ and $R^{44a}$ are H.

In some embodiments of the compound of Formula (III), $R^{51a}$, $R^{51b}$, and $R^{51c}$ are, independently, H, OH, or —$OR^{51d}$. In some embodiments of the compound of Formula (III), one of $R^{51a}$, $R^{51b}$, and $R^{51c}$ is —OH. In some embodiments of the compound of Formula (III), one of $R^{51a}$, $R^{51b}$, and $R^{51c}$ is —$OR^{51d}$.

In some embodiments of the compound of Formula (III), $R^{52a}$ and $R^{52b}$ are independently H, OH, or —$OR^{52c}$. In some embodiments of the compound of Formula (III), $R^{52a}$ and $R^{52b}$ are —OH. In some embodiments of the compound of Formula (III), one of $R^{52a}$ and $R^{52b}$ is —$OR^{52c}$. In some embodiments of the compound of Formula (III), one of $R^{52a}$ and $R^{52b}$ is —OH.

In some embodiments of the compound of Formula (III), if $R^2$ and $R^3$ are both H and $R^5$ is —$OR^{27}$ or $R^{5a}$ is —$OR^{53}$, then $R^6$ is not —$OR^{27}$.

In some embodiments of the compound of Formula (III), if $R^2$ and $R^3$ are both H and $R^5$ is —$OR^{27}$ or $R^{5a}$ is —$OR^{53}$, then $R^{6a}$ is not —$OR^{53}$.

In some embodiments of the compound of Formula (III), if $R^2$ and $R^3$ are both H and $R^5$ is —$OR^{27}$ or $R^{5a}$ is —$OR^{53}$, then $R^6$ is not —$OR^{27}$ and $R^{6a}$ is not —$OR^{53}$.

In some embodiments of the compound of Formula (III), if $R^2$ and $R^3$ are both H, then at least one of $R^{41}$, $R^{42}$, $R^{43}$, $R^{44}$, or $R^{44a}$ is not H.

In some embodiments of the compound of Formula (III), if $R^2$ and $R^3$ are both H and one of $R^{44}$ and $R^{44a}$ is —OH, then at least one of $R^{41}$, $R^{42}$, or $R^{43}$ is not H.

In Formula (III), the ring substituted by $R^1$, $R^2$, $R^3$, $R^4$, $R^5$, $R^{5a}$, $R^6$, $R^{6a}$, and $X^1$ may also be referred to as Ring A, as shown below. The ring substituted $R^7$, $R^8$, $R^{41}$, $R^{42}$, $R^{43}$, $R^{44}$, and $R^{44a}$ may also referred to as Ring B, as shown below. Ring C is also used to refer to the moiety connected to Ring B through —O— moiety, as shown below. Ring D is also used to refer to the moiety connected to Ring C through —O— moiety, as shown below.

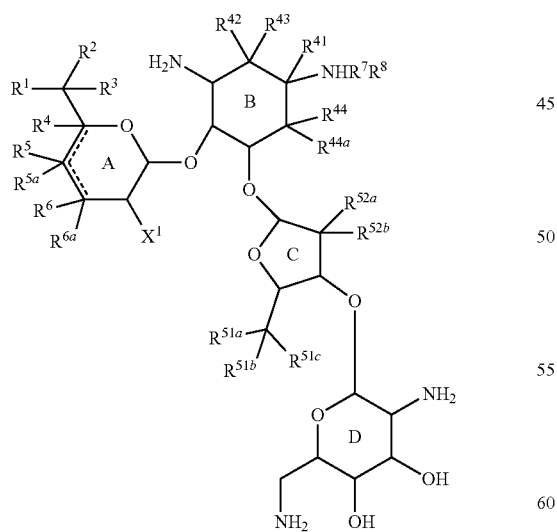

In some embodiments of the compound of Formula (III), Ring A is selected from

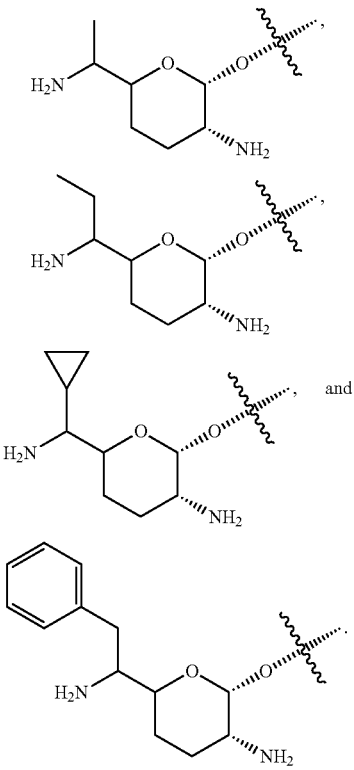

In some embodiments of the compound of Formula (III), Ring A is selected from

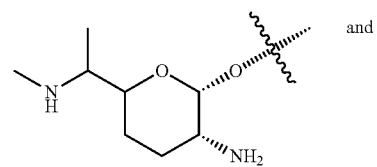

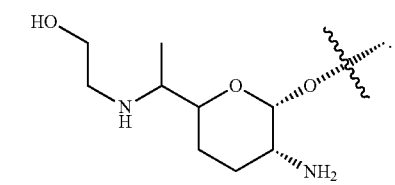

In some embodiments of the compound of Formula (III), Ring A is selected from

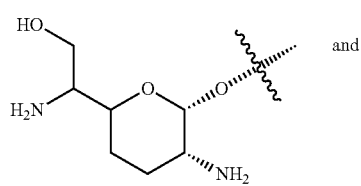

-continued

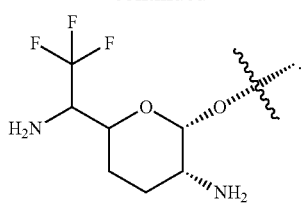

In some embodiments of the compound of Formula (III), Ring A is selected from

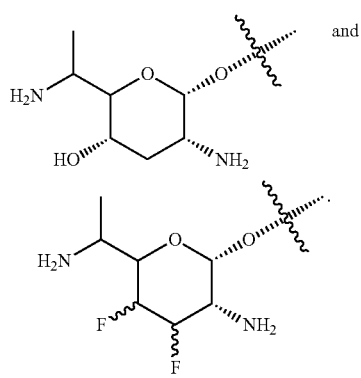

In some embodiments of the compound of Formula (III), Ring A is selected from

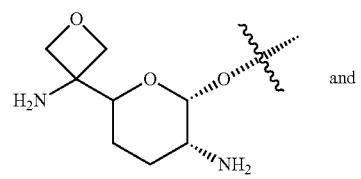

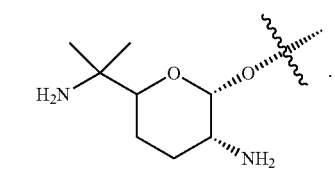

In some embodiments of the compound of Formula (III), Ring B is selected from

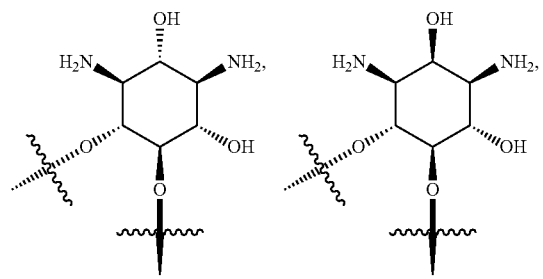

-continued

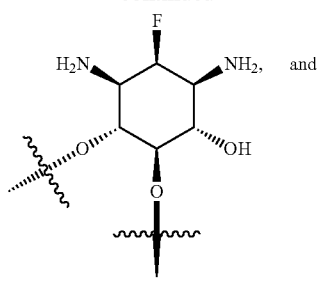

In some embodiments of the compound of Formula (III), Ring B is selected from

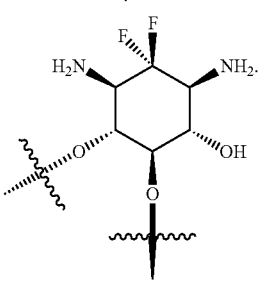

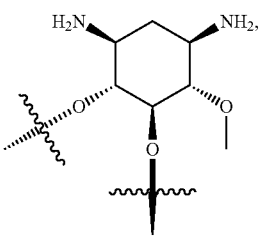

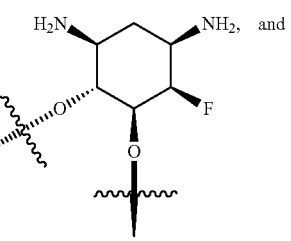

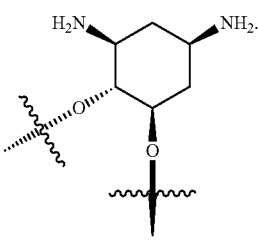

In some embodiments of the compound of Formula (III), Ring B is selected from

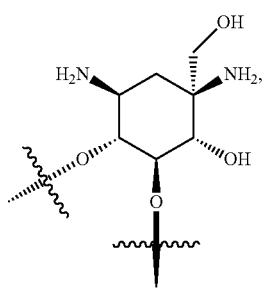

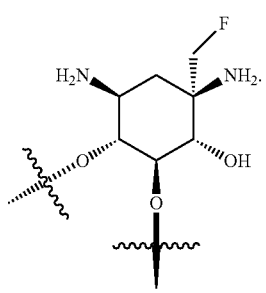

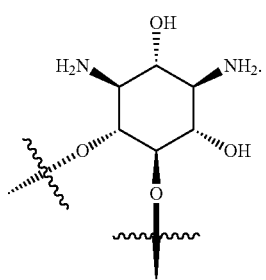

In some embodiments of the compound of Formula (III), Ring B is

Provided herein are compounds of formula (II):

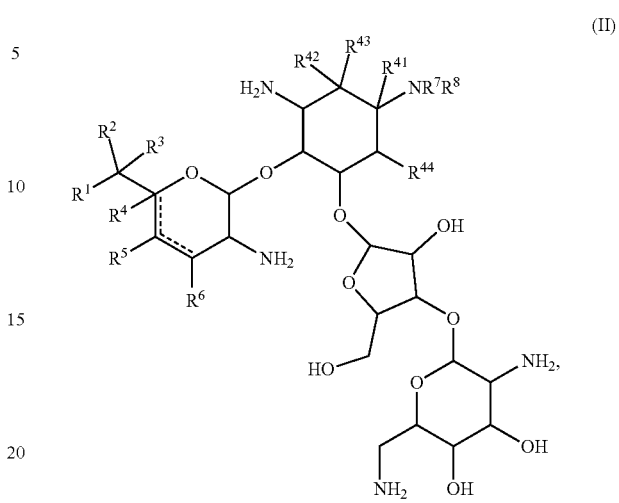

(II)

and pharmaceutically acceptable salts, solvates, stereoisomers, and tautomers thereof, wherein:

$R^1$ is $-OR^9$ or $-NR^{10}R^{11}$, wherein $R^9$, $R^{10}$, and $R^{11}$ are independently H or $C_1$-$C_6$alkyl, wherein the alkyl is unsubstituted or substituted with one or more —OH;

$R^2$ and $R^3$ are independently selected from the group consisting of H, alkyl, cycloalkyl, and aryl, wherein the alkyl, cycloalkyl, or aryl is unsubstituted or substituted with one or more substituents independently selected from the group consisting of halogen, cyano, aryl, $-SR^{12}$, $-SO_{2R}{}^{13}$, $-OSF_2NR^{14}R^{15}$, $-NR^{14}R^{15}$, and $-OR^{16}$, and wherein each $R^{12}$, $R^{13}$, $R^{14}$, $R^{15}$, and $R^{16}$ is independently H or alkyl; or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, $-SR^{17}$, $-SO_2R^{18}$, $-NR^{19R20}$, and $-OR^{21}$, and wherein each $R^{17}$, $R^{18}$, $R^{19}$, $R^{20}$, and $R^{21}$ is independently H or alkyl; or $R^2$ and $R^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, $-SR^{22}$, $-SO_2R^{23}$, $-NR^{24}R^{25}$, and $-OR^{26}$, and wherein each $R^{22}$, $R^{23}$, $R^{24}$, $R^{25}$, and $R^{26}$ is independently H or alkyl; and wherein at least one of $R^2$ and $R^3$ is other than H;

$R^4$ is H or absent;

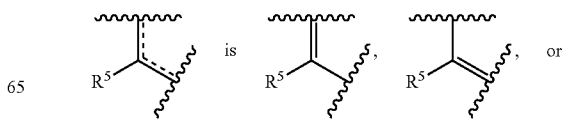

-continued

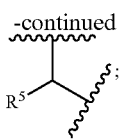

$R^5$ and $R^6$ are independently selected from the group consisting of H, —$OR^{27}$, —$NR^{28}R^{29}$, halogen, and alkyl, wherein $R^{27}$, $R^{28}$, and $R^{29}$ are independently H or $C_1$-$C_6$alkyl, wherein the alkyl is unsubstituted or substituted with one or more substituents selected from the group consisting of halogen, —$OR^{30}$, —$NR^{31}R^{32}$, —$SR^{33}$, and —$SO_2R^{34}$, and wherein each $R^{30}$, $R^{31}$, $R^{32}$, $R^{33}$, and $R^{34}$ is independently H or alkyl;

$R^7$ is H or $C_1$-$C_3$alkyl;

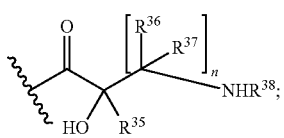

$R^8$ is H or wherein n is an integer from 0 to 4, $R^{35}$ is H or $C_1$-$C_3$alkyl;

each $R^{36}$ and $R^{37}$ is independently selected from the group consisting of H, alkyl, halogen, and —OH, and $R^{38}$ is H, alkyl, or —C(=NH)$NR^{39}R^{40}$, wherein $R^{39}$ and $R^{40}$ are independently H or $C_1$-$C_3$ alkyl; or $R^{35}$ and $R^{38}$, together with the atoms to which they are attached, form a heterocycloalkyl group comprising at least one N;

$R^{41}$ is H or $C_1$-$C_3$alkyl, wherein the alkyl is unsubstituted or substituted by —OH or halogen;

$R^{42}$ and $R^{43}$ are, independently H, —OH, or halogen; and $R^{44}$ is H, halogen, —OH, or $C_1$-$C_3$alkoxy.

In one aspect, the compound of formula (II) is a compound of formula (II-A):

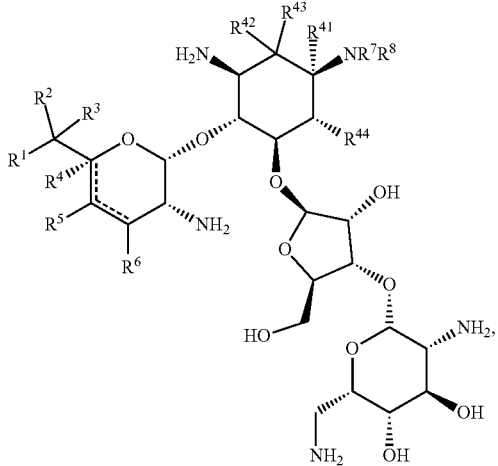

or a pharmaceutically acceptable salt, solvate, or tautomer thereof, wherein $R^1$, $R^2$, $R^3$,

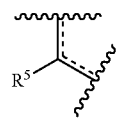

$R^4$, $R^5$, $R^6$, $R^7$, $R^8$, $R^{41}$, $R^{42}$, $R^{43}$, $R^{44}$, and are as defined for formula (II) herein.

In some embodiments of the compound of Formula (II), $R^{41}$ is H or $C_1$-$C_3$alkyl, wherein the alkyl is unsubstituted or substituted by —OH or halogen. In some embodiments of the compound of Formula (II), $R^{41}$ is $C_1$-$C_3$alkyl substituted by —OH. In some embodiments of the compound of Formula (II), $R^{41}$ is $C_1$-$C_3$alkyl substituted by halogen. In some embodiments of the compound of Formula (II), $R^{41}$ is unsubstituted $C_1$-$C_3$alkyl. In some embodiments of the compound of Formula (II), $R^{41}$ is $C_1$-$C_3$alkyl substituted by —F. In some embodiments of the compound of Formula (II), $R^{41}$ is $CH_2OH$, $CH_2F$, or $CH_3$. In some embodiments of the compound of Formula (II), $R^{41}$ is H. In some embodiments of the compound of Formula (II), $R^{41}$ is $CH_2OH$. In some embodiments of the compound of Formula (II), $R^{41}$ is $CH_2F$. In some embodiments of the compound of Formula (II), $R^{41}$ is $CH_3$.

In some embodiments of the compound of Formula (II), $R^{42}$ and $R^{43}$ are, independently H, —OH, or halogen. In some embodiments of the compound of Formula (II), one of $R^{42}$ and $R^{43}$ is —OH. In some embodiments of the compound of Formula (II), one of $R^{42}$ and $R^{43}$ is halogen. In some embodiments of the compound of Formula (II), both of $R^{42}$ and $R^{43}$ are halogen. In some embodiments of the compound of Formula (II), $R^{42}$ is H and $R^{43}$ is —OH. In some embodiments of the compound of Formula (II), $R^{42}$ is H and $R^{43}$ is —F. In some embodiments of the compound of Formula (II), $R^{42}$ is —F and $R^{43}$ is —F. In some embodiments of the compound of Formula (II), $R^{42}$ and $R^{43}$ are H.

In some embodiments of the compound of Formula (II), $R^{44}$ is H, halogen, —OH, or $C_1$-$C_3$alkoxy. In some embodiments of the compound of Formula (II), $R^{44}$ is $C_1$-$C_3$alkoxy. In some embodiments of the compound of Formula (II), $R^{44}$ is halogen. In some embodiments of the compound of Formula (II), $R^{44}$ is —OH. In some embodiments of the compound of Formula (II), $R^{44}$ is —$OCH_3$. In some embodiments of the compound of Formula (II), $R^{44}$ is —F. In some embodiments of the compound of Formula (II), $R^{44}$ is —H.

In Formula (II), the ring substituted by $R^1$, $R^2$, $R^3$, $R^4$, $R^5$, and $R^6$ may also be referred to as Ring A, as shown below. The ring substituted $R^7$, R8, $R^{41}$, $R^{42}$, $R^{43}$, and $R^{44}$ may also referred to as Ring B, as shown below. Ring C is also used to refer to the moiety connected to Ring B through —O— moiety, as shown below. Ring D is also used to refer to the moiety connected to Ring C through —O— moiety, as shown below.

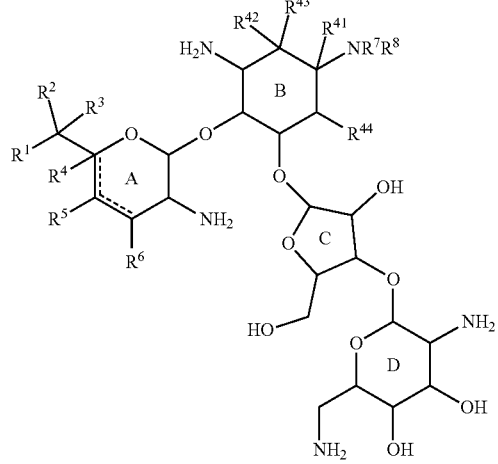

In some embodiments of the compound of Formula (II), Ring A is selected from

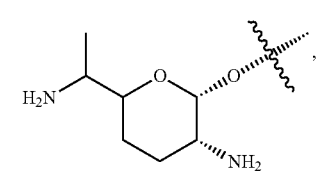

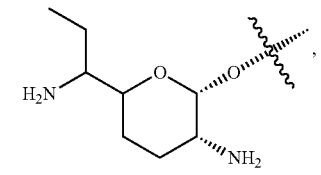

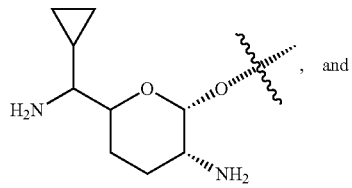, and

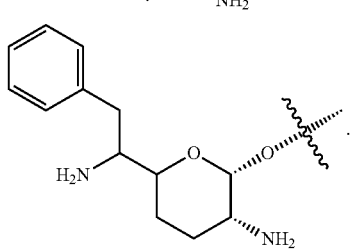

In some embodiments of the compound of Formula (II), Ring A is selected from

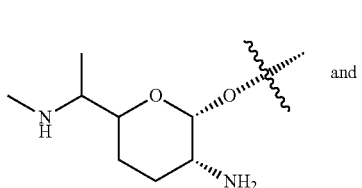 and

-continued

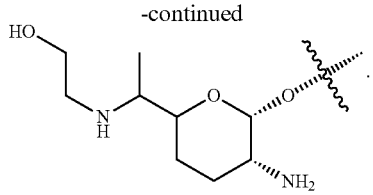

In some embodiments of the compound of Formula (II), Ring A is selected from

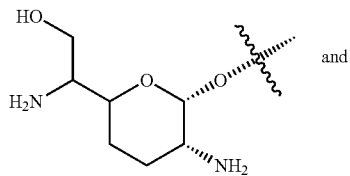 and

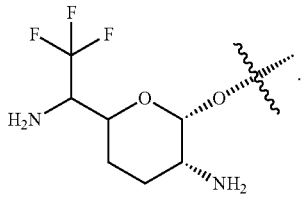

In some embodiments of the compound of Formula (II), Ring A is selected from

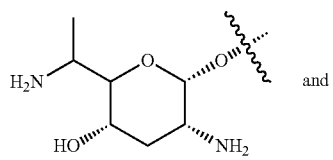 and

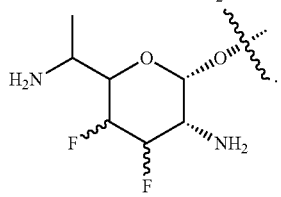.

In some embodiments of the compound of Formula (II), Ring A is selected from

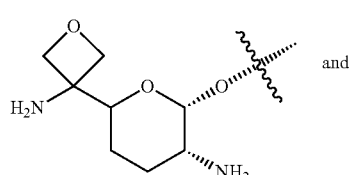 and

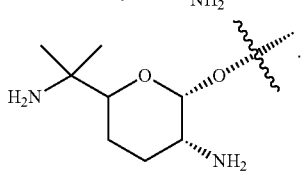.

In some embodiments of the compound of Formula (II), Ring B is selected from

In some embodiments of the compound of Formula (II), Ring B is selected from

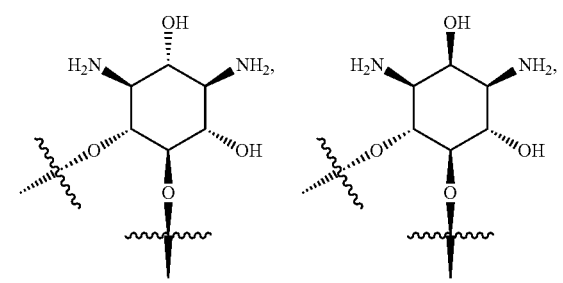

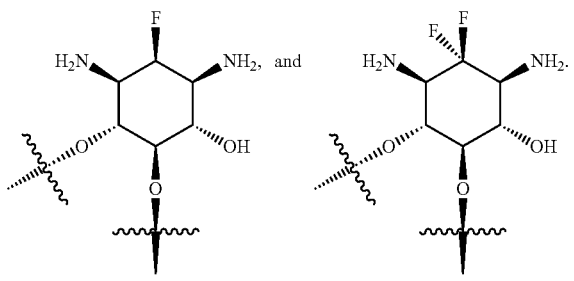

In some embodiments of the compound of Formula (II), Ring B is selected from

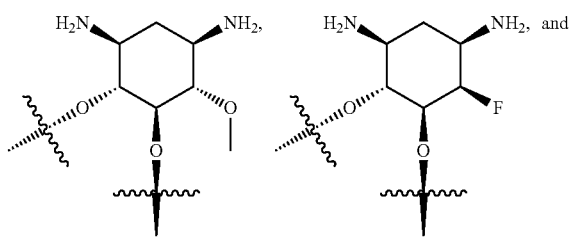

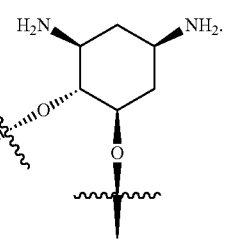

In some embodiments of the compound of Formula (II), Ring B is selected from

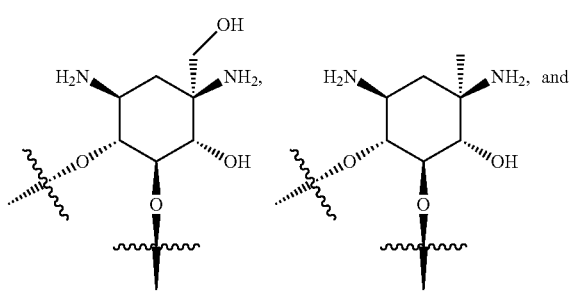

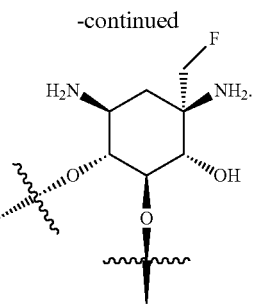

In some embodiments of the compound of Formula (II), Ring B is

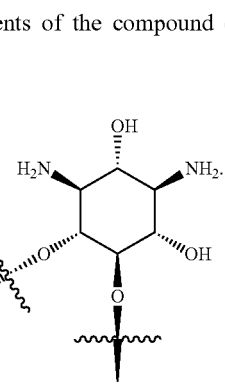

Provided herein are compounds of formula (I):

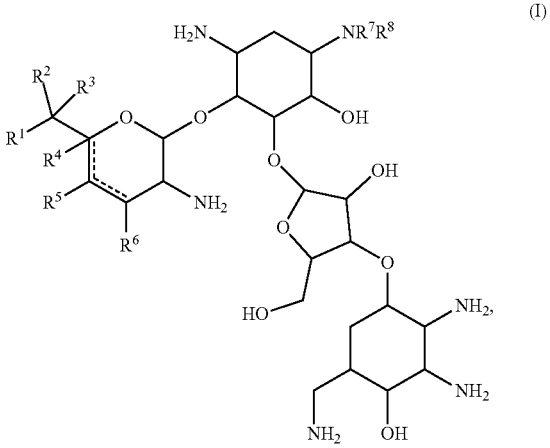

and pharmaceutically acceptable salts, solvates, stereoisomers, and tautomers thereof, wherein:

$R^1$ is —$OR^9$ or —$NR^{10}R^{11}$, wherein $R^9$, $R^{10}$, and $R^{11}$ are independently H or $C_1$-$C_6$alkyl, wherein the alkyl is unsubstituted or substituted with one or more —OH;

$R^2$ and $R^3$ are independently selected from the group consisting of H, alkyl, cycloalkyl, and aryl,
  wherein the alkyl, cycloalkyl, or aryl is unsubstituted or substituted with one or more substituents independently selected from the group consisting of halogen, cyano, aryl, —$SR^{12}$, —$SR^{13}$, —$NR^{14}R^{15}$, and —$OR^{16}$, and
  wherein each $R^{12}$, $R^{13}$, $R^{14}$, $R^{15}$, and $R^{16}$ is independently H or alkyl; or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —$SO_2R^{18}$, —$NR^{19}R^{20}$, and —$OR^{21}$, and wherein each $R^{17}$, $R^{18}$, $R^{19}$, $R^{20}$, and $R^{21}$ is independently H or alkyl; or $R^2$ and $R^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl;

and wherein at least one of $R^2$ and $R^3$ is other than H;

$R^4$ is H or absent;

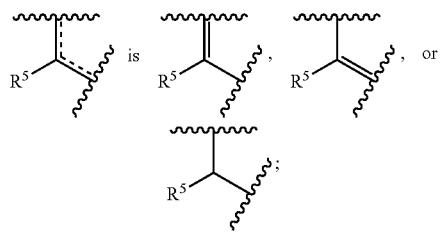

is $R^5$ and $R^6$ are independently selected from the group consisting of H, —$OR^{27}$, —$NR^{28}R^{29}$, halogen, and alkyl, wherein $R^{27}$, $R^{28}$, and $R^{29}$ are independently H or $C_1$-$C_6$alkyl, wherein the alkyl is unsubstituted or substituted with one or more substituents selected from the group consisting of halogen, —$OR^{30}$, —$NR^{31}R^{32}$, —$SR^{33}$, and —$SO_2R^{34}$; and wherein each $R^{30}$, $R^{31}$, $R^{32}$, $R^{33}$, and $R^{34}$ is independently H or alkyl;

$R^7$ is H or $C_1$-$C_3$alkyl;

$R^8$ is H or

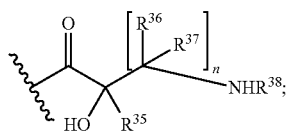

wherein n is an integer from 0 to 4, $R^{35}$ is H or $C_1$-$C_3$alkyl;

each $R^{36}$ and $R^{37}$ is independently selected from the group consisting of H, alkyl, halogen, and —OH, and $R^{38}$ is H, alkyl, or —C(=NH)$NR^{39}R^{40}$, wherein $R^{39}$ and $R^{40}$ are independently H or $C_1$-$C_3$alkyl; or $R^{35}$ and $R^{38}$, together with the atoms to which they are attached, form a heterocycloalkyl group comprising at least one N.

In some embodiments, the compound of formula (I) is a compound of formula (I-A):

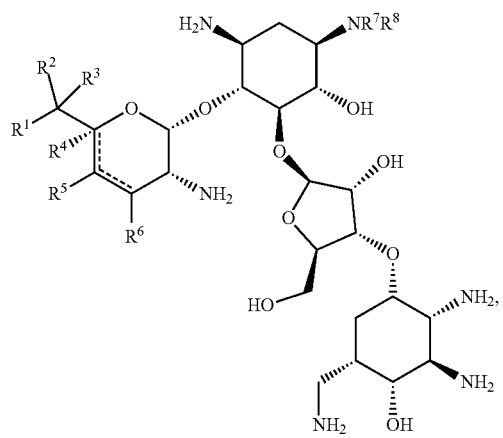

(I-A)

or a pharmaceutically acceptable salt, solvate, or tautomer thereof, wherein $R^1$, $R^2$, $R^3$, $R^4$, $R^5$, $R^6$, $R^7$, $R^8$ and

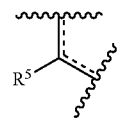

are as defined for formula (I) herein.

In certain embodiments, the compound of formula (I-A) is a compound of formula (I-Ai):

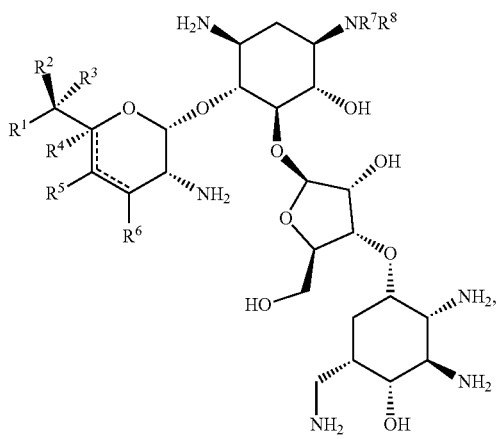

(I-Ai)

or a pharmaceutically acceptable salt, solvate, or tautomer thereof, wherein $R^1$, $R^2$, $R^3$, $R^4$, $R^5$, $R^6$, $R^7$, $R^8$, and

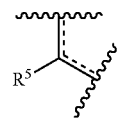

are as defined for formula (I) herein.

In some embodiments, the compound of formula (I) is a compound of formula (I -Ai), or a pharmaceutically acceptable salt, solvate, stereoisomer, or tautomer thereof, wherein the compound has one, two, three, four, five, or more of the following features:

$R^1$ is —$OR^9$ or —$NR^{10}R^{11}$, wherein $R^9$, $R^{10}$, and $R^{11}$ are independently H, $C_1$-alkyl, or $C_2$-alkyl, wherein the $C_1$-alkyl or $C_2$-alkyl is unsubstituted or substituted with one —OH;

$R^2$ is $C_1$-alkyl, $C_2$-alkyl, cyclopropyl, or phenyl, wherein the $C_1$-alkyl, $C_2$-alkyl, cyclopropyl or phenyl is unsubstituted or substituted with one or more substituents selected from the group consisting of halogen, —$SO_2R^{13}$, —$NR^{14}R^{15}$, and —$OR^{16}$;

or $R^1$ and $R^2$, together with the atom to which they are attached, form a 6-membered heterocycloalkyl comprising one O and one N;

$R^3$ is H or unsubstituted alkyl;

or $R^2$ and $R^3$, together with the atom to which they are attached, form a cycloalkyl or heterocycloalkyl group;

$R^4$ is H;

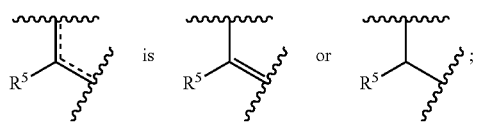

$R^5$ and $R^6$ are independently H or —$OR^{27}$ wherein $R^{27}$ is H or $C_1$-$C_6$alkyl;

$R^7$ is H;

and $R^8$ is H,

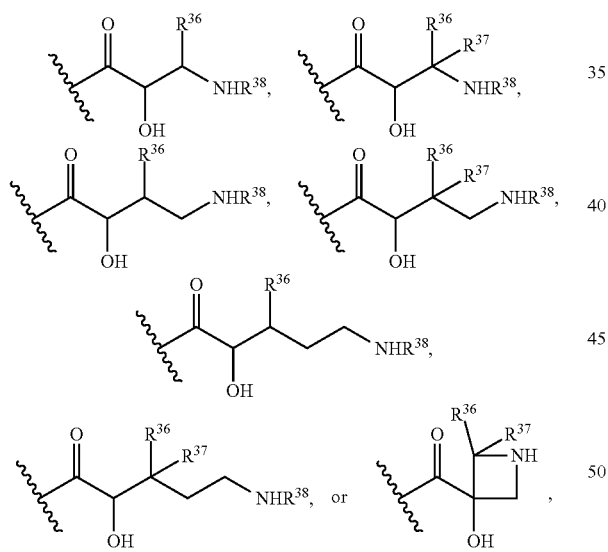

wherein each $R^{36}$ and $R^{37}$ is independently H, —OH, or halogen.

In some embodiments, the compound of formula (I) is a compound of formula (I-Ai), or a pharmaceutically acceptable salt, solvate, or tautomer thereof, wherein the compound has one, two, three, four, five, or more of the following features:

$R^1$ is —$NH_2$, —$NHCH_3$, —$NHCH_2CH_2OH$, or —OH;

$R^2$ is methyl, ethyl, cyclopropyl, phenyl, —$CH_2NH_2$, —$CH_2OH$, —$CH_2F$, —$CHF_2$, —$CH_2CN$, —$CH_2S(O)_2CH_3$;

or $R^1$ and $R^2$, together with the atom to which they are attached, form a 6-membered heterocycloalkyl comprising one O and one N;

$R^3$ is H or methyl; or $R^2$ and $R^3$, together with the atom to which they are attached, form cyclopropyl or a 4-membered heterocylcoalkyl comprising one O;

$R^4$ is H;

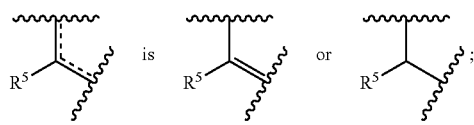

$R^5$ and $R^6$ are independently H or —OH;

$R^7$ is H;

and $R^8$ is H, —C(O)CH(OH)CH$_2$NH$_2$, —C(O)CH(OH)CH$_2$CH$_2$NH$_2$,

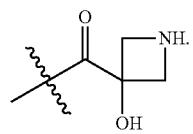 [SMILES: *C(=O)C1(O)CNC1]

—C(O)CH(OH)CH$_2$CH$_2$CH$_2$NH$_2$, or

In other embodiments, the compound of formula (I-A) is a compound of formula
(I-Aii):

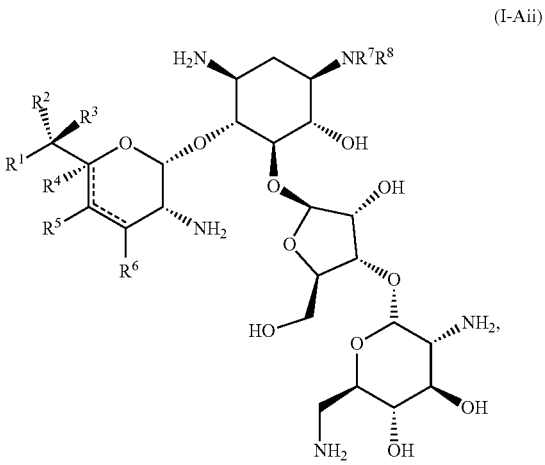

or a pharmaceutically acceptable salt, solvate, or tautomer thereof, wherein $R^1$, $R^2$, $R^3$, $R^4$, $R^5$, $R^6$, $R^7$, $R^8$, and

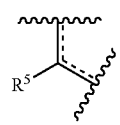

are as defined for formula (I) herein.

In some embodiments, the compound of formula (I) is a compound of formula (I-B):

(I-B)

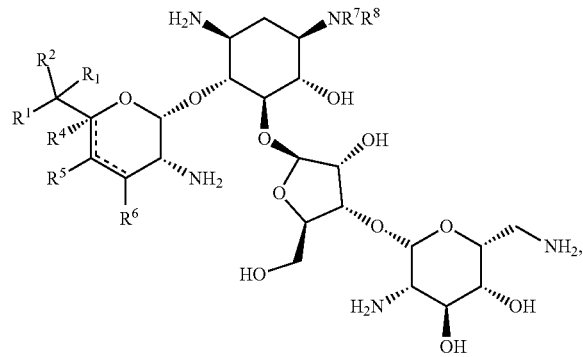

or a pharmaceutically acceptable salt, solvate, or tautomer thereof, wherein $R^1$, $R^2$, $R^3$, $R^4$, $R^5$, $R^6$, $R^7$, $R^8$, and

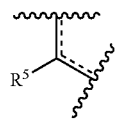

are as defined for formula (I) herein.

In certain embodiments, the compound of formula (I-B) is a compound of formula (I-Bi):

(I-Bi)

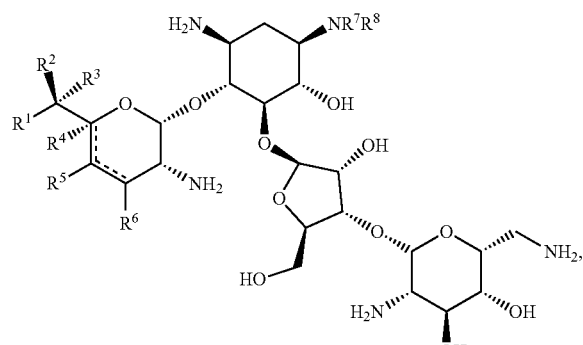

or a pharmaceutically acceptable salt, solvate, or tautomer thereof, wherein $R^1$, $R^2$, $R^3$, $R^4$, $R^5$, $R^6$, $R^7$, $R^8$, and

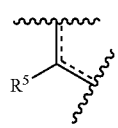

are as defined for formula (I) herein.

In other embodiments, the compound of formula (I-B) is a compound of formula (I-Bii):

(I-Bii)

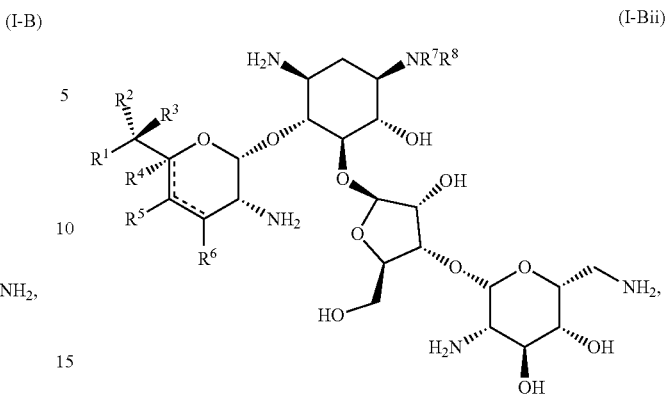

or a pharmaceutically acceptable salt, solvate, or tautomer thereof, wherein $R^1$, $R^2$, $R^3$, $R^4$, $R^5$, $R^6$, $R^7$, $R^8$, and

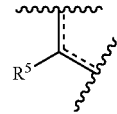

are as defined for formula (I) herein.

In some embodiments of the compound of Formula (I), IV is —$OR^9$ or —$NR^{10}R^{11}$. In some embodiments of the compound of Formula (I), $R^1$ is —$OR^9$, wherein $R^9$ is H or alkyl, wherein the alkyl is unsubstituted or substituted with one or more —OH. For example, in some embodiments, $R^9$ may be methyl, ethyl, propyl, butyl, pentyl, or hexyl.

In Formula (I), the ring substituted by $R^1$, $R^2$, $R^3$, $R^4$, $R^5$, and $R^6$ may also be referred to as Ring A, as shown below. The ring substituted $R^7$ and $R^8$ may also referred to as Ring B, as shown below. Ring C is also used to refer to the moiety connected to Ring B through —O— moiety, as shown below. Ring D is also used to refer to the moiety connected to Ring C through —O— moiety, as shown below.

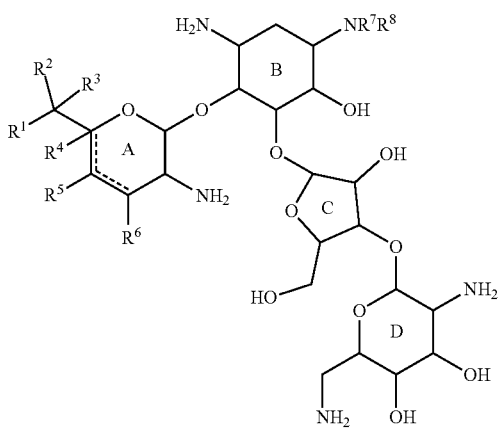

In some embodiments of the compound of Formula (I), Ring A is selected from

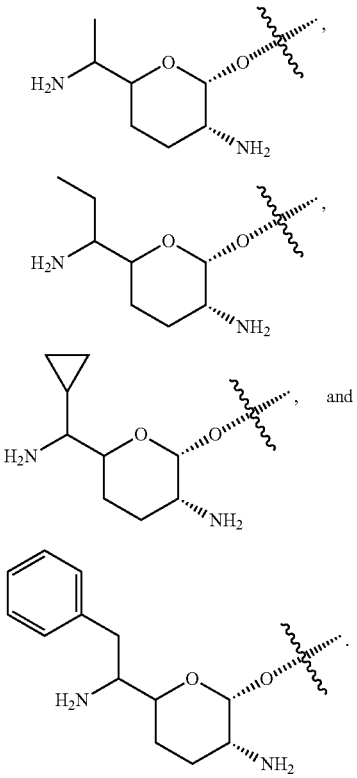

In some embodiments of the compound of Formula (I), Ring A is selected from

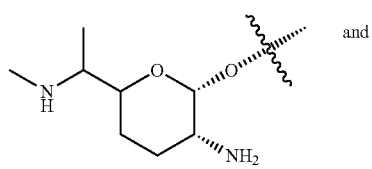

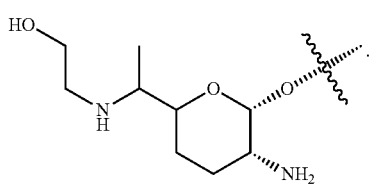

In some embodiments of the compound of Formula (I), Ring A is selected from

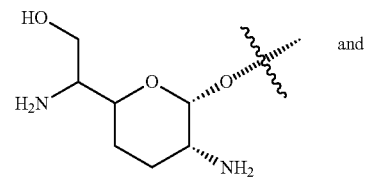

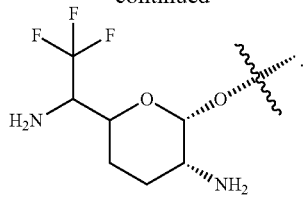

In some embodiments of the compound of Formula (I), Ring A is selected from

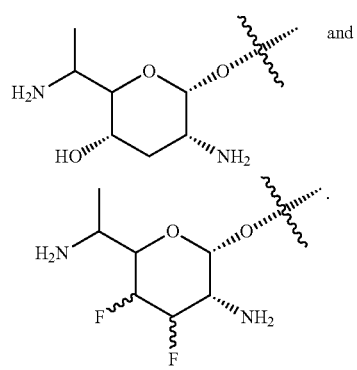

In some embodiments of the compound of Formula (I), Ring A is selected from

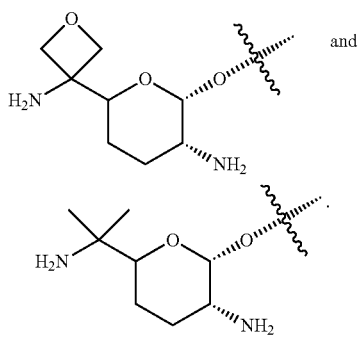

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^1$ is —$NR^{10}R^{11}$, wherein $R^{10}$ and $R^{11}$ are independently H or $C_1$-$C_6$alkyl, wherein the alkyl is unsubstituted or substituted with one or more —OH. In certain embodiments, Rth and $R^{11}$ are independently H, methyl, or hydroxyethyl. In certain embodiments, $R^{10}$ and $R^{11}$ are both H. In other embodiments, $R^{10}$ is H and $R^{11}$ is unsubstituted $C_1$-$C_6$alkyl or $C_1$-$C_6$alkyl substituted with one or more —OH. For example, in some embodiments, $R^{11}$ may be methyl, ethyl, propyl, butyl, pentyl, or hexyl. In other embodiments, $R^{11}$ is methyl substituted with one or more —OH, ethyl substituted with one or more —OH, propyl substituted with one or more —OH, butyl substituted with one or more —OH, pentyl substituted with one or more —OH, or hexyl substituted with one or more —OH. In some embodiments, $R^{11}$ is methyl. In other embodiments, $R^{11}$ is hydroxyethyl. In some embodiments, $R^1$ is —$NHCH_3$. In other embodiments, $R^1$ is —$NHCH_2CH_2OH$.

In some embodiments of formula (I), including formula (I-A), formula (I-Ai), formula formula (I-B), formula (I-Bi), and formula (I-Bii); formula (II), including formula (II-A); or formula (III), including formula (III-A), $R^1$ is $OR^9$, wherein $R^9$ is H or $C_1$-$C_6$alkyl, wherein the alkyl is unsubstituted or substituted with one or more —OH. In certain embodiments, $R^9$ is H, methyl, or hydroxyethyl. In certain embodiments, $R^9$ is H. In other embodiments, $R^9$ is unsubstituted $C_1$-$C_6$alkyl or $C_1$-$C_6$alkyl substituted with one or more —OH. For example, in some embodiments, $R^9$ may be methyl, ethyl, propyl, butyl, pentyl, or hexyl. In other embodiments, $R^9$ is methyl substituted with one or more —OH, ethyl substituted with one or more —OH, propyl substituted with one or more —OH, butyl substituted with one or more —OH, pentyl substituted with one or more —OH, or hexyl substituted with one or more —OH. In some embodiments, $R^9$ is methyl. In other embodiments, $R^9$ is hydroxyethyl. In certain embodiments, $R^1$ is —OH.

In some embodiments of formula (I), including formula (I-A), formula (I-Ai), formula formula (I-B), formula (I-Bi), and formula (I-Bii); formula (II), including formula (II-A); formula (III), including formula (III-A), $R^2$ and $R^3$ are independently selected from the group consisting of H, alkyl, cycloalkyl, and aryl. In some embodiments, at least one of $R^2$ and $R^3$ is other than H. In some embodiments, the alkyl, cycloalkyl, or aryl may be unsubstituted or substituted with one or more substituents independently selected from the group consisting of halogen, cyano, aryl, —$SR^{12}$, —$SO_{2R}^{13}$, —$OSF_2NR^{14}R^{15}$, —$NR^{14}R^{15}$, and —$OR^{16}$, wherein each $R^{12}$, $R^{13}$, $R^{14}$, $R^{15}$, and $R^{16\ may}$ independently be H or alkyl. In some embodiments, the one or more substituents are independently selected from the group consisting of halogen, cyano, —$SO_2R^{13}$, —$NR^{14}R^{15}$, and —$OR^{16}$, wherein each $R^{13}$, $R^{14}$, $R^{15}$, and $R^{16}$ may independently be H or alkyl. In certain embodiments, one of $R^2$ and $R^3$ is H.

In some embodiments of formula (I), including formula (I-A), formula (I-Ai), formula formula (I-B), formula (I-Bi), and formula (I-Bii); formula (II), including formula (II-A); or formula (III), including formula (III-A), $R^2$ is alkyl, cyclopropyl, or phenyl; wherein the alkyl is unsubstituted or substituted with one, two, or three substituents selected from the group consisting of —$NH_2$, —OH, F, —CN, and —$S(O)_2CH_3$. In some embodiments, $R^2$ is methyl, ethyl, propyl, butyl, pentyl, hexyl, cyclopropyl, cyclobutyl, cyclopentyl, cyclohexyl, or phenyl. In other embodiments, $R^2$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —$SR^{12}$, —$SO_2R^{13}$ —$NR^{14}R^{15}$, and —$OR^{16}$. In some embodiments, the one or more substituents are independently selected from the group consisting of halogen, cyano, aryl, —$SO_2R^{13}$, —$NR^{14}R^{15}$, and —$OR^{16}$. For example, in certain embodiments, the one or more substituents are independently selected from the group consisting of F, Cl, B, I, cyano, —$SO_2CH_3$, —$NH_2$, and —OH. In still other embodiments, $R^2$ is methyl; methyl substituted with one or two F; methyl substituted with —$SO_2CH_3$; methyl substituted with —$NH_2$; methyl substituted with —OH; ethyl; cyclopropyl; or phenyl.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^3$ is methyl, ethyl, propyl, butyl, pentyl, hexyl, cyclopropyl, cyclobutyl, cyclopentyl, cyclohexyl, or phenyl. In other embodiments, $R^3$ is substituted methyl, substituted ethyl, substituted propyl, substituted butyl, substituted pentyl, substituted hexyl, substituted cyclopropyl, substituted cyclobutyl, substituted cyclopentyl, substituted cyclohexyl, or substituted phenyl, wherein the one or more substituents are independently selected from the group consisting of halogen, cyano, aryl, —$SR^{12}$, —$SO_2R^{13}$, —$NR^{14}R^{15}$, and —$OR^{16}$. In some embodiments, the one or more substituents are independently selected from the group consisting of halogen, cyano, aryl, —$SO_2R^{13}$, —$NR^{14}R^{15}$, and —$OR^{16}$. For example, in certain embodiments, the one or more substituents are independently selected from the group consisting of F, Cl, B, I, cyano, —$SO_2CH_3$, —$NH_2$, and —OH. In still other embodiments, $R^3$ is methyl; methyl substituted with one or two F; methyl substituted with —$SO_2CH_3$; methyl substituted with —$NH_2$; methyl substituted with —OH; ethyl; cyclopropyl; or phenyl. In certain embodiments, $R^3$ is H or unsubstituted methyl.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^1$ and $R^2$, together with the atom to which they are attached, form a heterocycloalkyl group comprising at least one heteroatom selected from the group consisting of N and O. In some embodiments, the heterocycloalkyl group may be unsubstituted or substituted with one or more substituents independently selected from the group consisting of halogen, cyano, —$SR^{17}$, —$SO_2R^{18}$, —$NR^{19}R^{20}$, and —$OR^{21}$, wherein $_{each\ R}{}^{17}$, $R^{18}$, $R^{19}$, $R^{20}$, and $R^{21}$ may be independently H or alkyl. In certain embodiments, the heterocycloalkyl group is 5-membered, in other embodiments it is 6-membered. In some embodiments, the heterocycloalkyl group comprises one N and one O. In certain embodiments, $R^1$ and $R^2$, together with the atom to which they are attached, form an unsubstituted 6-membered group comprising one N and one O. In some embodiments, $R^1$ and $R^2$, together with the atom to which they are attached, form:

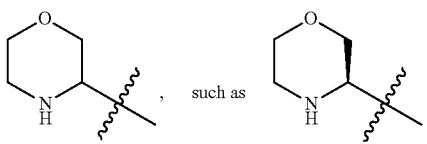

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^2$ and $R^3$, together with the atom to which they are attached, form a cycloalkyl group or a heterocycloalkyl group. In some embodiments, the cycloalkyl group or heterocycloalkyl group may be unsubstituted or substituted with one or more substituents independently selected from the group consisting of halogen, cyano, —$SR^{22}$, —$SO_2R^{23}$, —$NR^{24}R^{25}$, and —$OR^{26}$, wherein each $R^{22}$, $R^{23}$, $R^{24}$, $R^{25}$, and $R^{26}$ may be independently H or alkyl. In certain embodiments, $R^2$ and $R^3$ together with the atom to which they are attached form a cyclopropyl or oxetanyl.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^2$ and $R^3$, together with the atom to which they are attached, form a substituted or unsubstituted cycloalkyl group. For example, in some embodiments, $R^2$ and $R^3$, together with the atom to which they are attached, may form cyclopropyl, cyclobutyl, cyclopentyl, or cyclohexyl. In some embodiments, $R^2$ and $R^3$, together with the atom to which they are attached, may form substituted cyclopropyl, substituted cyclobutyl, substituted cyclopentyl, or substituted cyclohexyl, wherein the one or more substituents are independently selected from the group consisting of halogen, cyano, $-SR^{22}$, $-SO_2R^{23}$, $-NR^{24}R^{25}$, and $-OR^{26}$, wherein each $R^{22}$, $R^{23}$, $R^{24}$, $R^{25}$, and $R^{26}$ may be independently H or alkyl. In some embodiments, $R^2$ and $R^3$, together with the atom to which they are attached, form cyclopropyl.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^2$ and $R^3$, together with the atom to which they are attached, form an unsubstituted or substituted heterocycloalkyl. For example, in some embodiments, $R^2$ and $R^3$, together with the atom to which they are attached, may form a 4-membered heterocycloalkyl, a 5-membered heterocycloalkyl, or a 6-membered heterocycloalkyl, wherein the heterocycloalkyl is unsubstituted or substituted with one or more substituents independently selected from the group consisting of halogen, cyano, $-SR^{22}$, $-SO_2R^{23}$, $-NR^{24}R^{25}$, and $-OR^{26}$. In some embodiments, the heterocycloalkyl comprises one or more heteroatoms selected from the group consisting of O and N. In certain embodiments, $R^2$ and $R^3$, together with the atom to which they are attached, form an unsubstituted 4-membered heterocycloalkyl comprising one O. In some embodiments, $R^2$ and $R^3$, together with the atom to which they are attached, form:

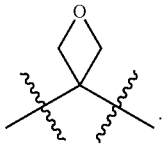 [SMILES: *C1(*)COC1]

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), both $R^5$ and $R^6$ are H.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^5$ is H or $-OH$.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^6$ is H or $-OH$.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^5$ is H, halogen, or $-OH$.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^6$ is H, halogen, or $-OH$.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^5$ is $-OR^{27}$ or $-NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^6$ is $-OR^{27}$ or $-NR^{28}R^{29}$, wherein $R^{27}$, $R^{28}$, and $R^{29}$ are independently H or $C_1$-$C_6$alkyl, such as $C_1$-$C_4$alkyl.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^7$ is H. In other embodiments, $R^7$ is $C_1$-$C_3$alkyl, for example $C_1$-alkyl, $C_2$-alkyl, or $C_3$-alkyl. In some embodiments, $R^8$ is H.

In some embodiments of formula (III), including formula (III-A), $R^8$ is $C_1$-$C_6$alkyl, for example $C_1$-alkyl, $C_2$-alkyl, $C_3$-alkyl, $C_4$-alkyl, $C_5$-alkyl, or $C_6$-alkyl.

In some embodiments of formula (III), including formula (III-A), $R^8$ is

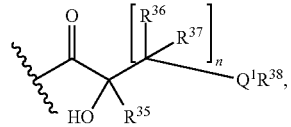

wherein $Q^1$ is NH, O, or S. In certain embodiments, $Q^1$ is NH. In certain embodiments, $Q^1$ is O. In certain embodiments, $Q^1$ is S. In certain embodiments, wherein when n is one, then $R^{36}$ and $R^{37}$ are not halo.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^8$ is

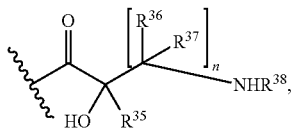

for example

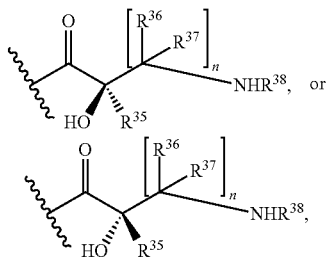

In some embodiments, $R^{35}$ is H. In certain embodiments, each $R^{36}$ and $R^{37}$ are H. In certain embodiments, $R^{38}$ is H. In other embodiments, $R^{38}$ is alkyl, for example $C_1$alkyl, $C_2$alkyl, or $C_3$alkyl. In other embodiments, $R^{38}$ is —C(=NH)NR$^{39}$R$^{40}$, for example —C(=NH)NH$_2$. In certain embodiments, $R^{35}$ and $R^{38}$, together with the atoms to which they are attached, form a heterocycloalkyl group comprising at least one N.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), n is an integer from 0 to 4, from 0 to 3, from 0 to 2, from 1 to 4, from 2 to 4, or from 1 to 3. In certain embodiments, n is 0, or n is 1, or n is 2, or n is 3, or n is 4.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^8$ is:

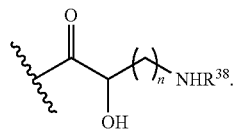

In some embodiments, $R^8$ may be:

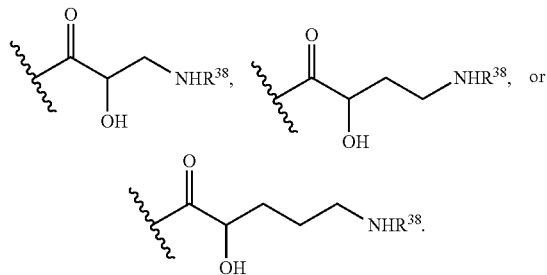

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^{38}$ is H. In some embodiments, $R^8$ may be:

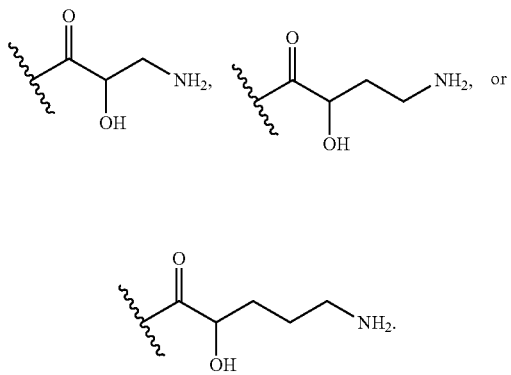

In some embodiments of formula (III), including formula (III-A), $R^8$ may be:

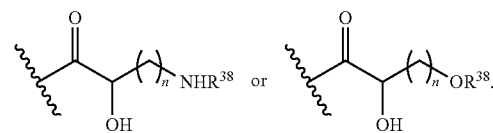

In some embodiments of formula (III), including formula (III-A), $R^8$ may be:

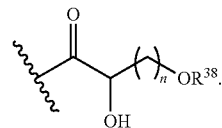

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^8$ is:

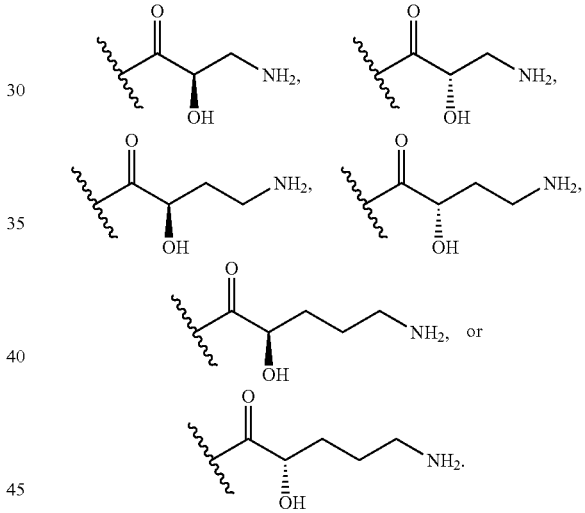

In some embodiments of formula (III), including formula (III-A), $R^8$ is:

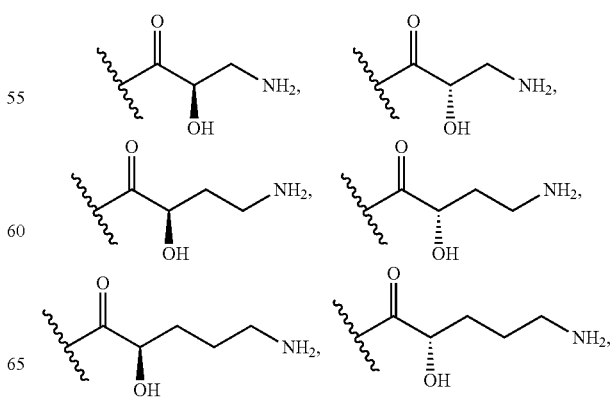

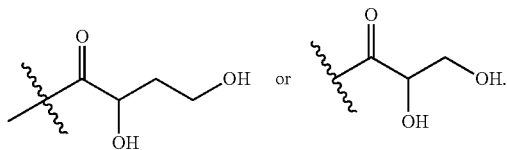 [SMILES: *C(=O)C(O)CCO ; "or" ; *C(=O)C(O)CO]

In some embodiments of formula (III), including formula (III-A), $R^8$ is:

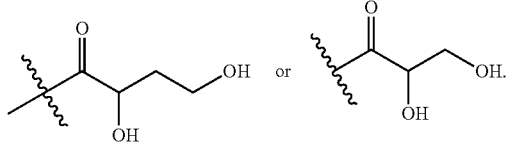

In some embodiments of formula (I), including formula (I-A), formula (I-Ai), formula formula (I-B), formula (I-Bi), and formula (I-Bii); formula (II), including formula (II-A); or formula (III), including formula (III-A), at least one $R^{36}$ or $R^{37}$ is halogen. For example, in certain embodiments, $R^8$ is:

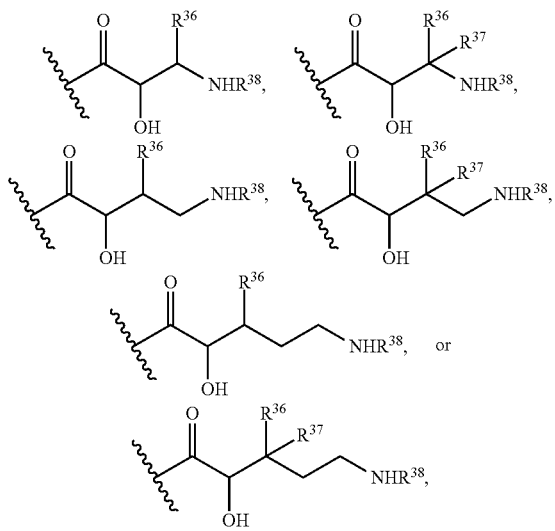

wherein each $R^{36}$ and $R^{37}$ is independently halogen, for example fluoro.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), at least one $R^{36}$ or $R^{37}$ is halogen, and $R^{38}$ is H. For example, in some embodiments, $R^8$ may be:

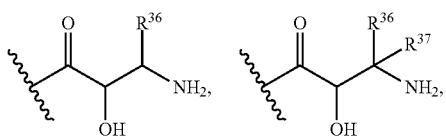

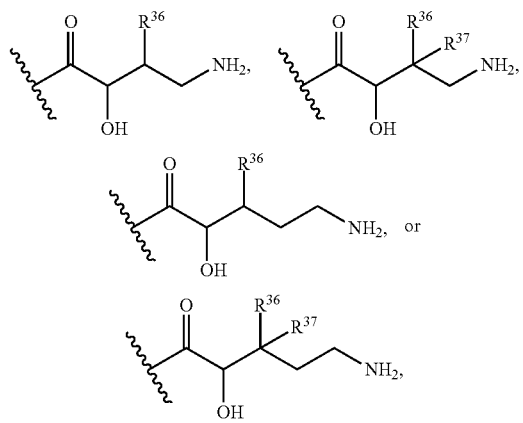

wherein each $R^{36}$ and $R^{37}$ are independently halogen, for example fluoro.

In some embodiments of formula (III), including formula (III-A), at least one $R^{36}$ or $R^{37}$ is halogen. For example, in certain embodiments, $R^8$ is:

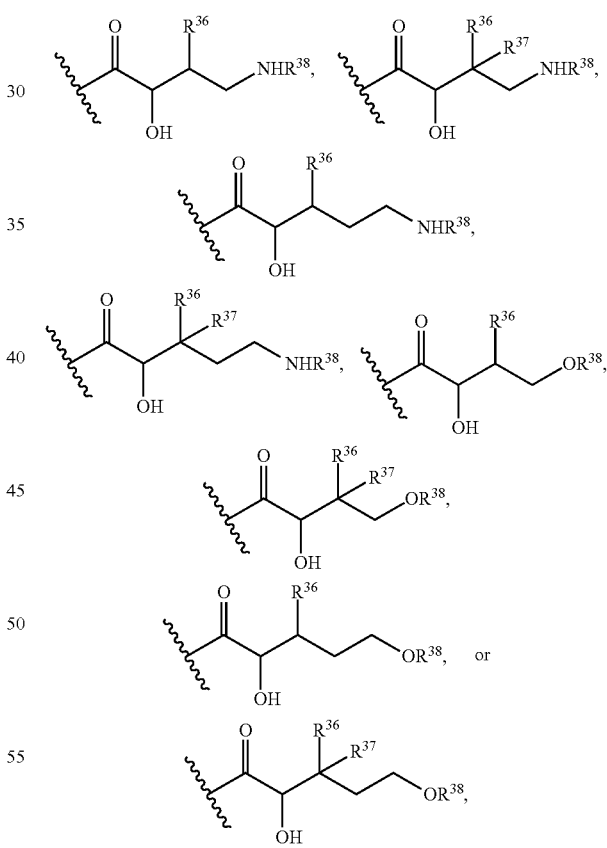

wherein each $R^{36}$ and $R^{37}$ is independently halogen, for example fluoro.

In some embodiments of formula (III), including formula (III-A), at least one $R^{36}$ or $R^{37}$ is halogen, and $R^{38}$ is H. For example, in some embodiments, $R^8$ may be:

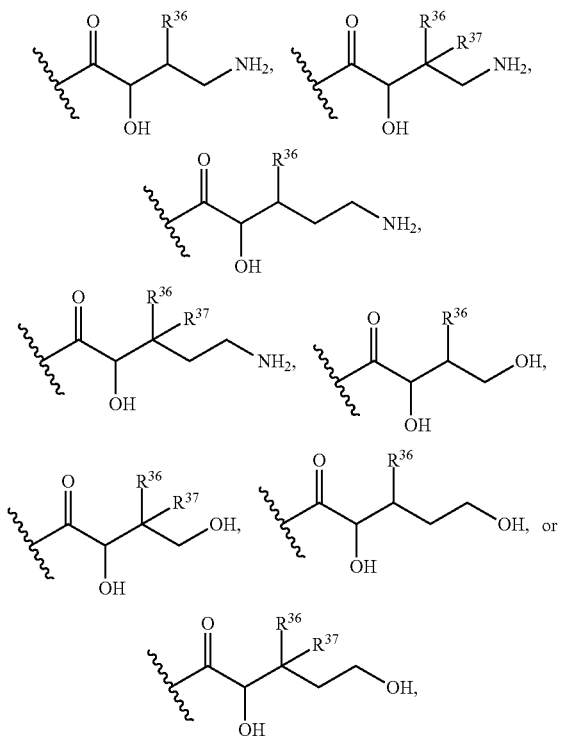

wherein each $R^{36}$ and $R^{37}$ are independently halogen, for example fluoro.

In some embodiments of formula (III), including formula (III-A), $R^8$ is

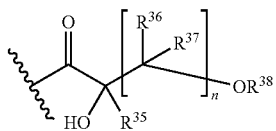

wherein at least one $R^{36}$ or $R^{37}$ is hydroxyl.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^8$ is

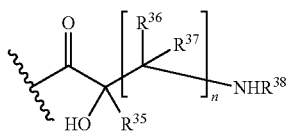

wherein at least one $R^{36}$ or $R^{37}$ is hydroxyl.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), and $R^8$ is:

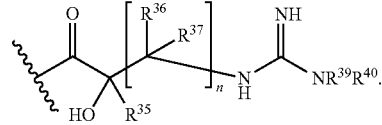

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^{39}$ and $R^{40}$ are both H. In other embodiments, $R^{39}$ and $R^{40}$ are both $C_1$-$C_3$alkyl. In still other embodiments, one of $R^{39}$ and $R^{40}$ is H and the other is $C_1$-$C_3$alkyl.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^{38}$ may be —C(=NH)NH$_2$. Thus, in certain embodiments, $R^8$ is:

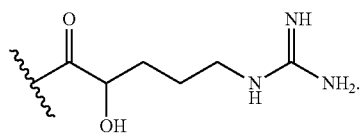 [SMILES: *C(=O)C(O)CCCNC(=N)N]

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^7$ and $R^8$ are H.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^7$ is H and $R^8$ is ethyl.

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^7$ is H and $R^8$ is

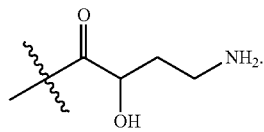 [SMILES: *C(=O)C(O)CCN]

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^7$ is H and $R^8$ is

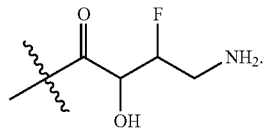 [SMILES: *C(=O)C(O)C(F)CN]

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^7$ is H and $R^8$ is

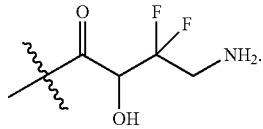 [SMILES: *C(=O)C(O)C(F)(F)CN]

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^7$ is H and $R^8$ is

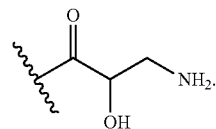 [SMILES: *C(=O)C(O)CN]

In some embodiments of formula (III), including formula (III-A), $R^7$ is H and $R^8$ is

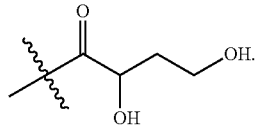 [SMILES: *C(=O)C(O)CCO]

In some embodiments of formula (III), including formula (III-A), $R^7$ is H and $R^8$ is

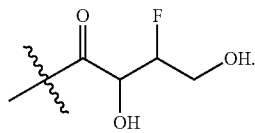 [SMILES: *C(=O)C(O)C(F)CO]

In some embodiments of formula (III), including formula (III-A), $R^7$ is H and $R^8$ is

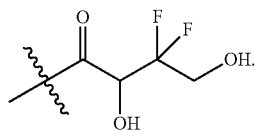 [SMILES: *C(=O)C(O)C(F)(F)CO]

In some embodiments of formula (III), including formula (III-A), $R^7$ is H and $R^8$ is

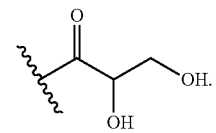

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), which may be combined with any of the preceding embodiments,

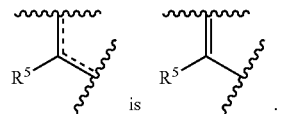

In other embodiments,

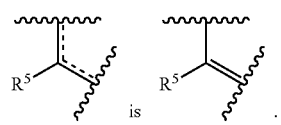

In yet other embodiments,

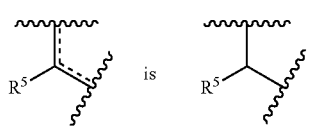

In some embodiments of formula (I), including formula (I-A), formula (I-Ai), formula (I-Aii), formula (I-B), formula (I-Bi), and formula (I-Bii); formula (II), including formula (II-A); or formula (III), including formula (III-A), $R^{35}$ and $R^{38}$, together with the atoms to which they are attached, form a heterocycloalkyl group comprising at least one N. In some embodiments, the heterocycloalkyl group may comprise, for example, 4, 5, 6, or more ring members. In some embodiments, the heterocycloalkyl group comprises a 4-membered ring. In certain embodiments, the heterocycloalkyl group comprises a 4-membered ring comprising one N atom. It should be understood that when $R^{35}$ and $R^{38}$, together with the atoms to which they are attached, form a heterocycloalkyl group. In some embodiments, $R^8$ is:

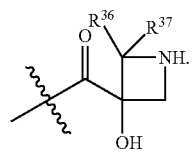

In some embodiments, $R^8$ is:

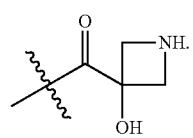 [SMILES: *C(=O)C1(O)CNC1]

The present disclosure further provides a compound of formula (I), formula (I-A), formula (II), formula (II-A), formula (III), or formula (III-A), wherein the compound is selected from the group consisting of:

181
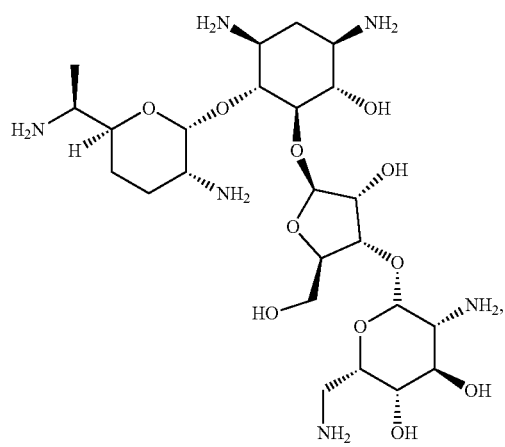
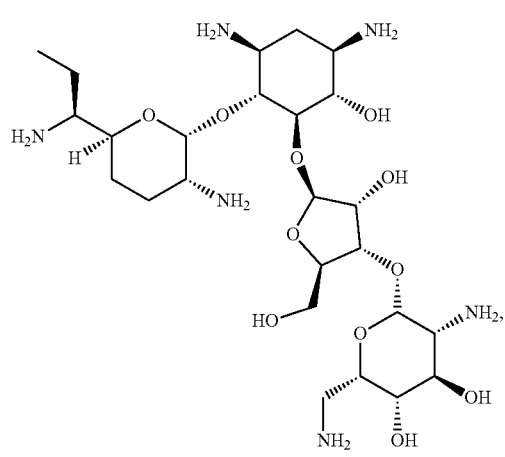
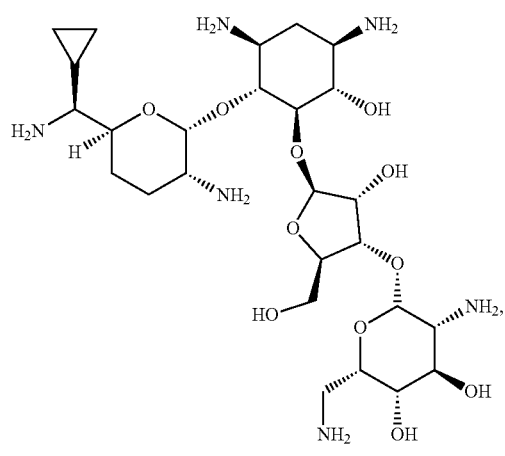
182
-continued
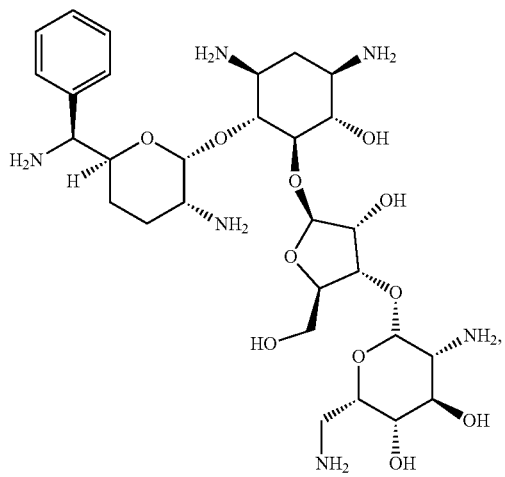
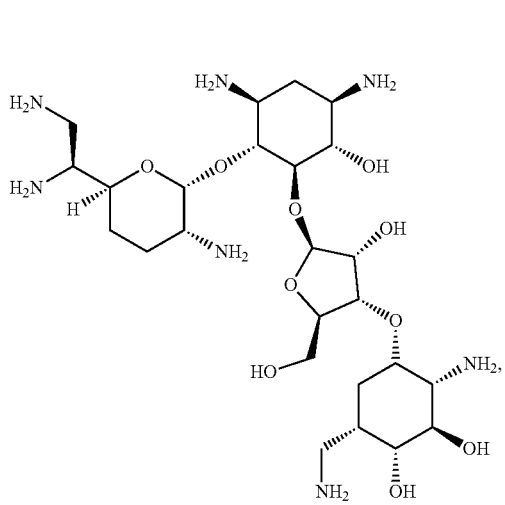
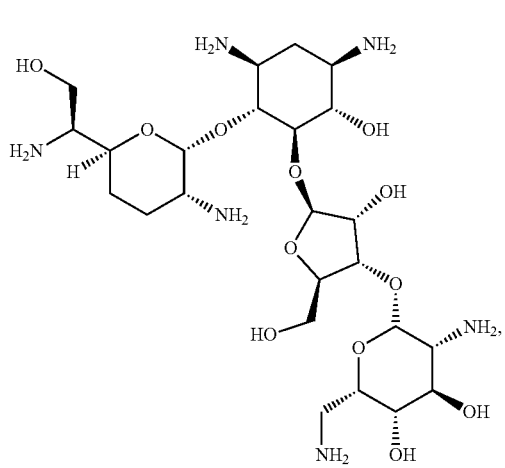

183
-continued
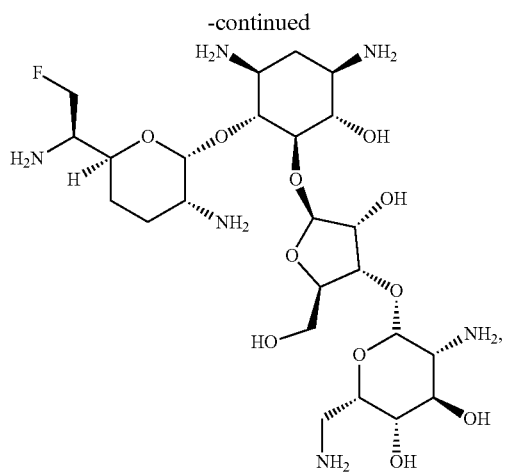
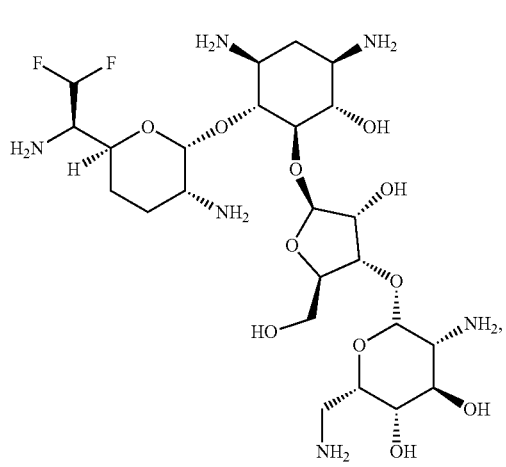
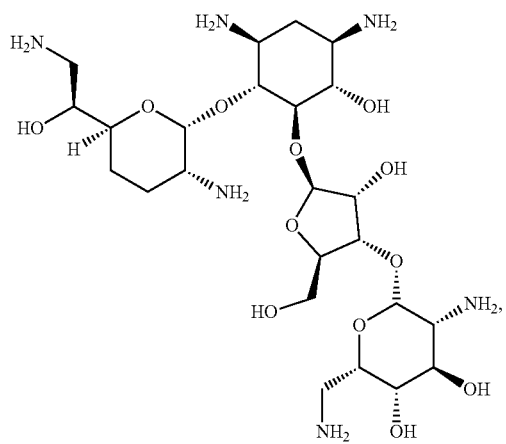
184
-continued
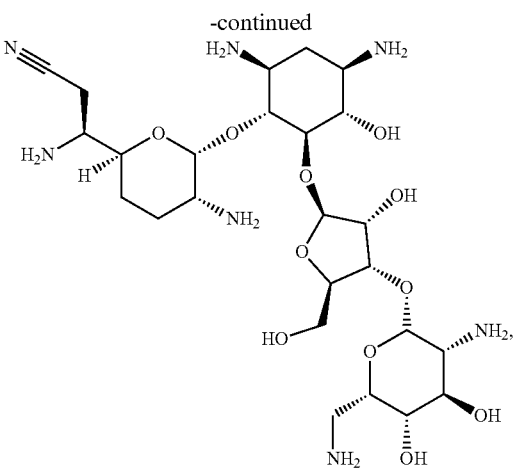
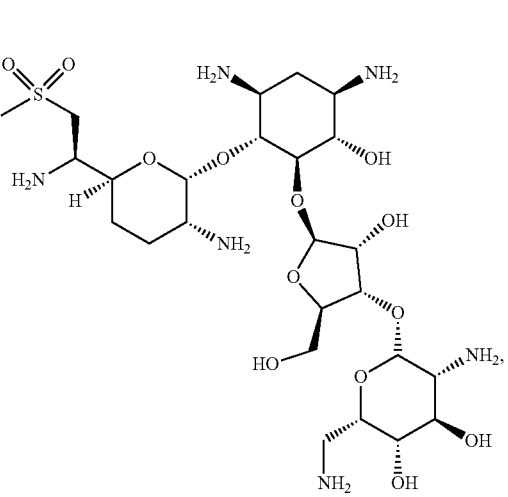
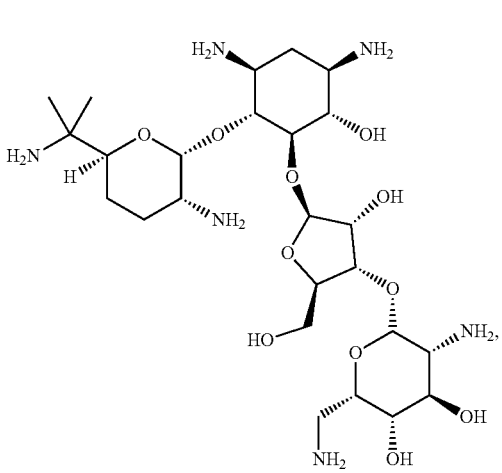

185
-continued
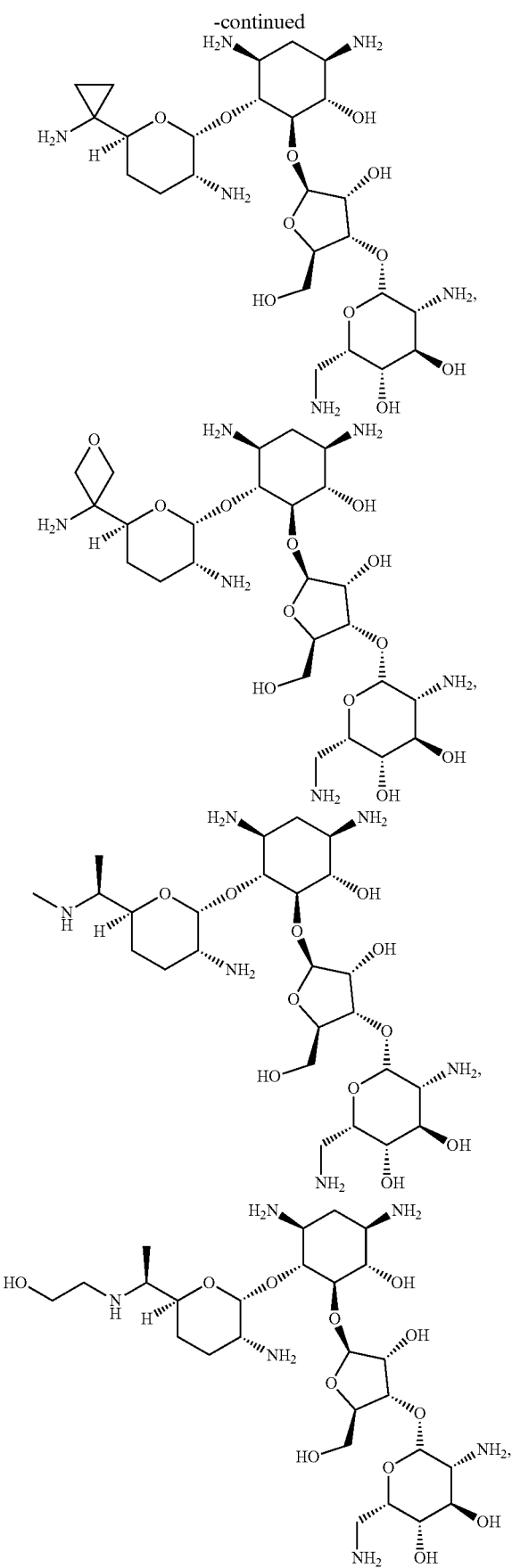
186
-continued
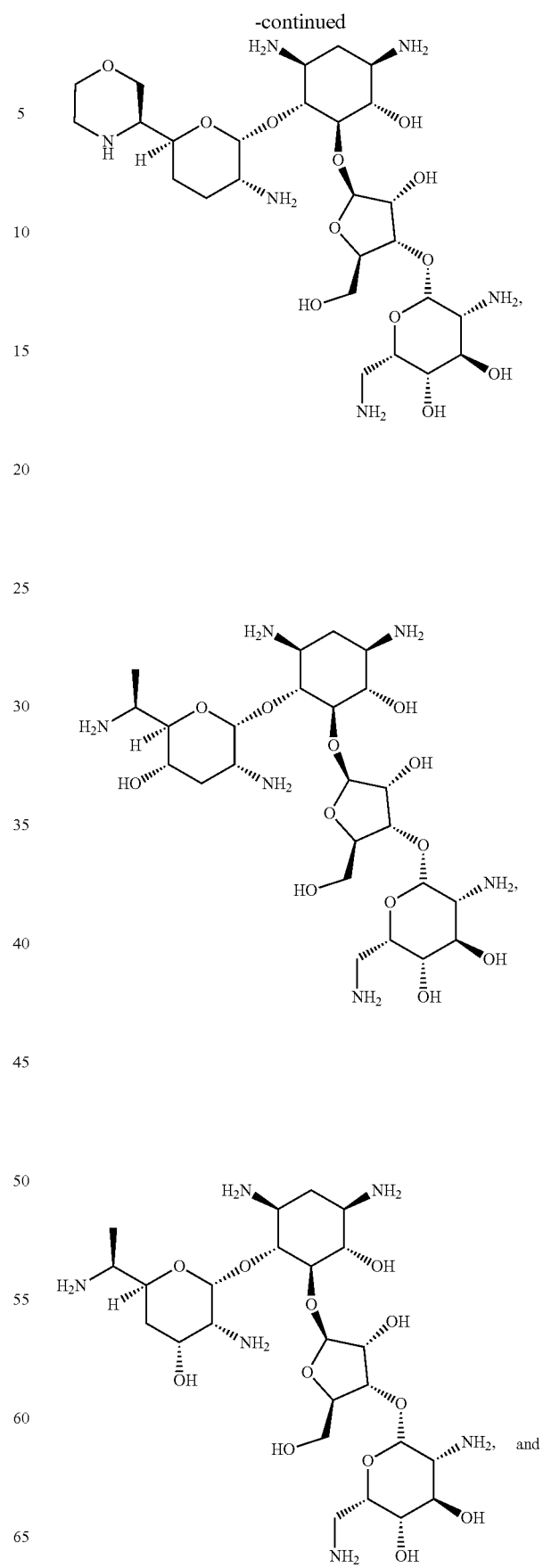

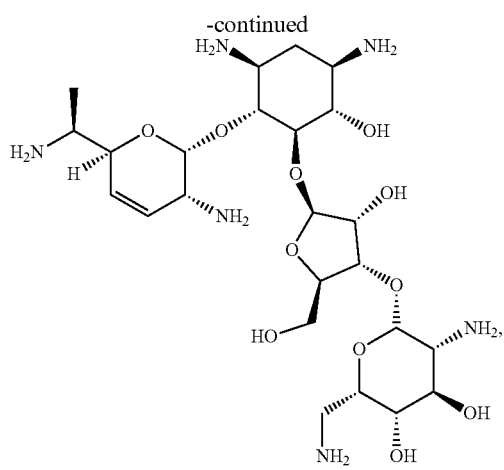
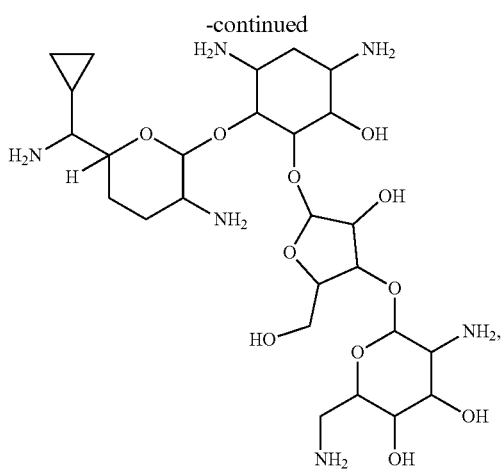
or a pharmaceutically acceptable salt, solvate, or tautomer of any of the foregoing.
The present disclosure further provides a compound of formula (I), formula (I-A), formula (II), formula (II-A), formula (III), or formula (III-A), wherein the compound is selected from the group consisting of:
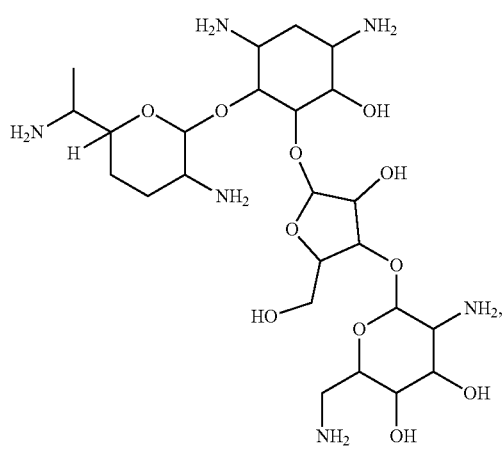
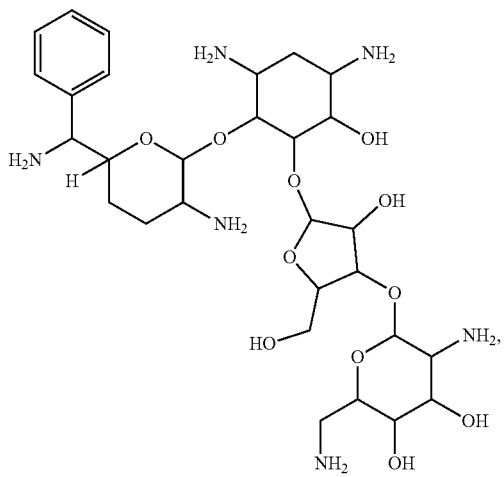
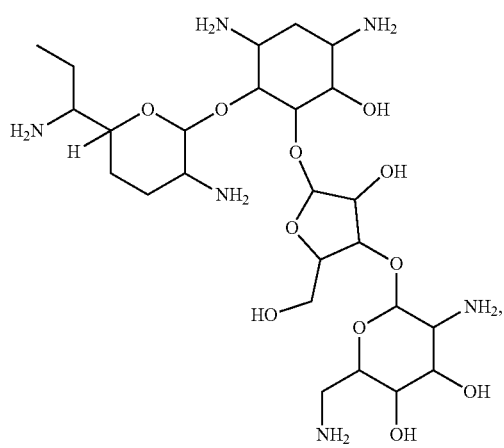
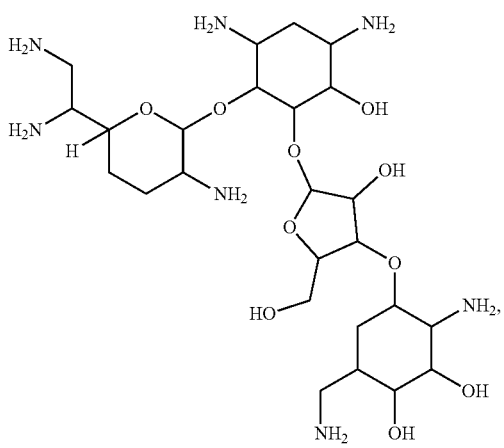

-continued
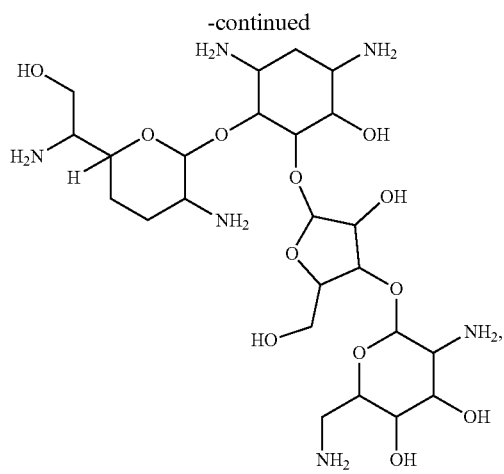
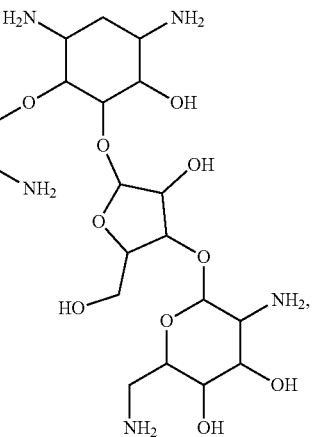
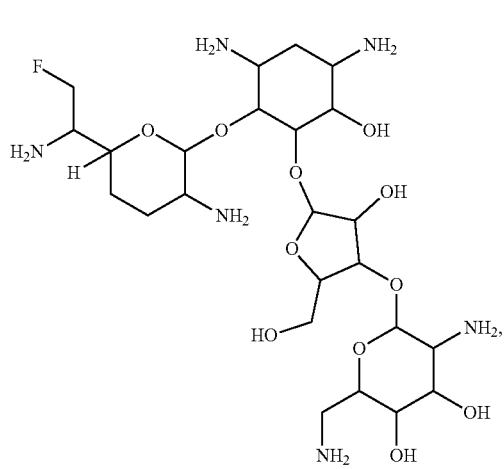
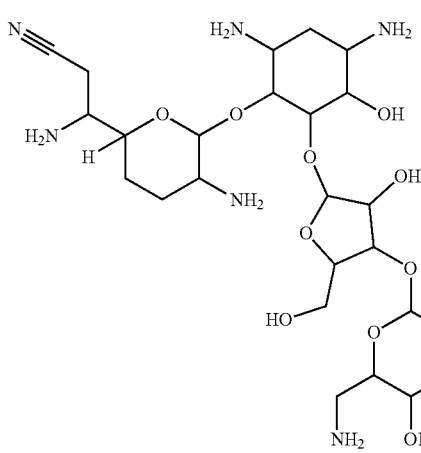
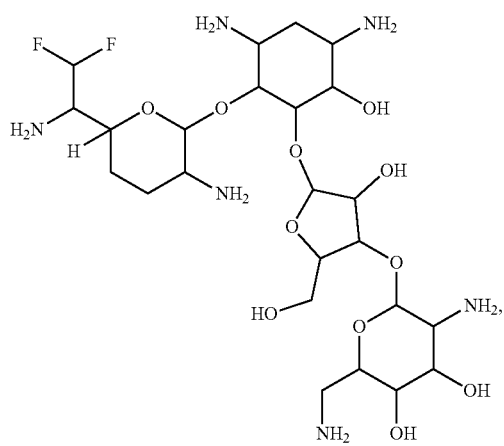
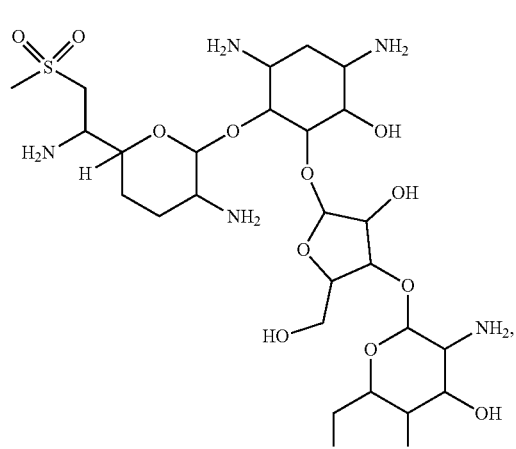

191
-continued
192
-continued
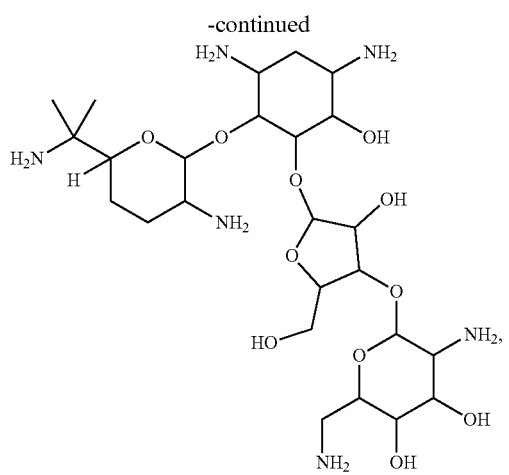
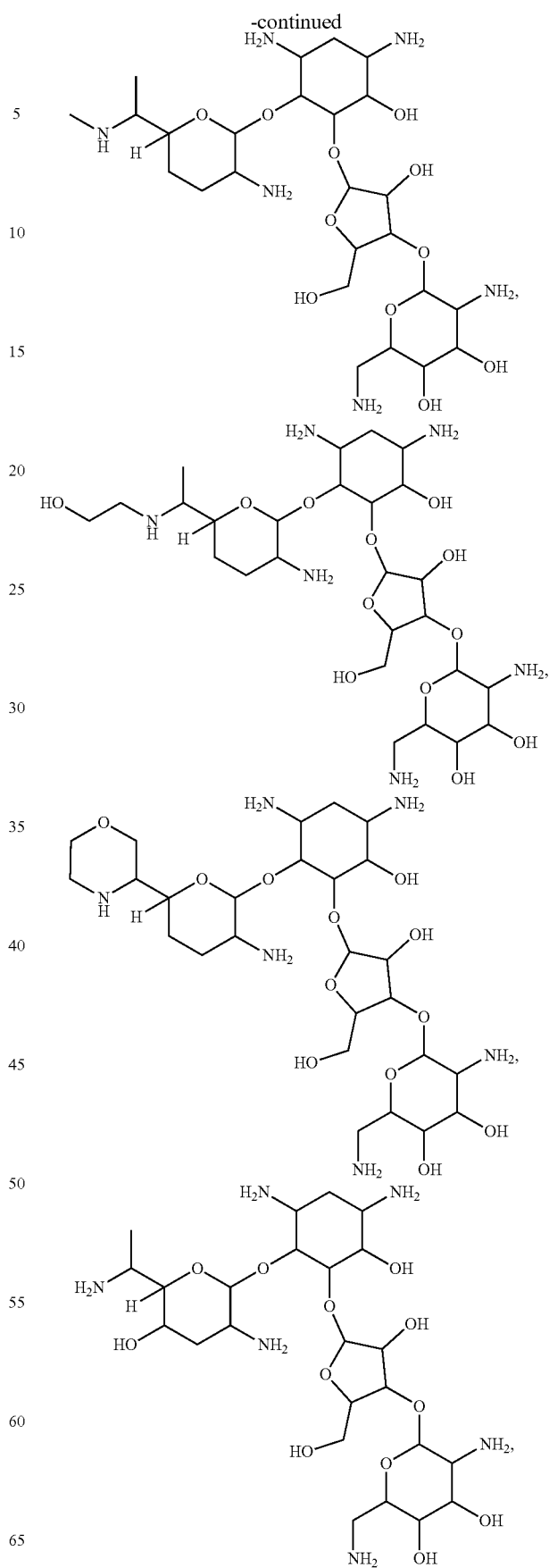

193

-continued

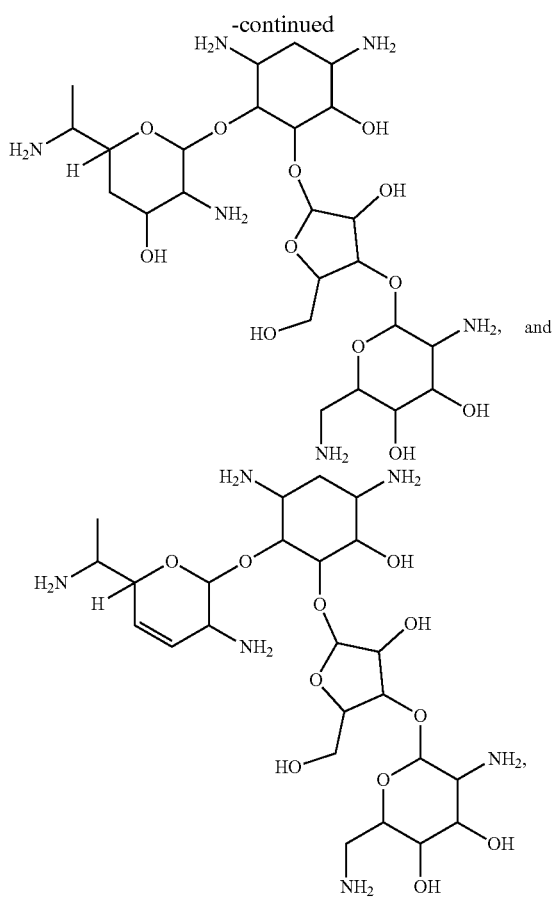

or a pharmaceutically acceptable salt, solvate, stereoisomer, or tautomer of any of the foregoing.

The present disclosure further provides a compound of formula (I), formula (I-A), formula (II), formula (II-A), formula (III), or formula (III-A), wherein the compound is selected from the group consisting of:

(2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-(aminomethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol

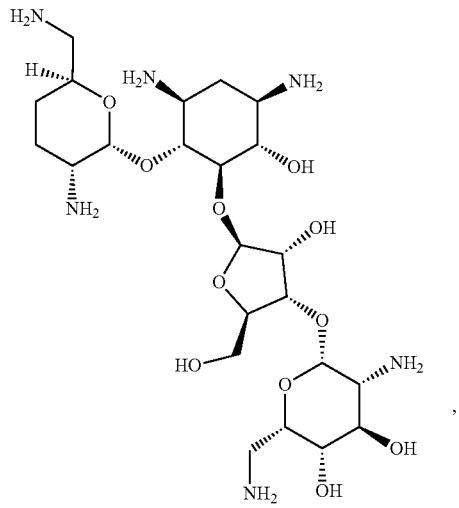 [SMILES: NC[C@@H]1CC[C@@H](N)[C@@H](O[C@H]2[C@H](O[C@@H]3O[C@H](CO)[C@@H](O[C@H]4O[C@@H](CN)[C@@H](O)[C@H](O)[C@H]4N)[C@H]3O)[C@@H](O)[C@H](N)C[C@@H]2N)O1]

(2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((R)-1-aminoethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol

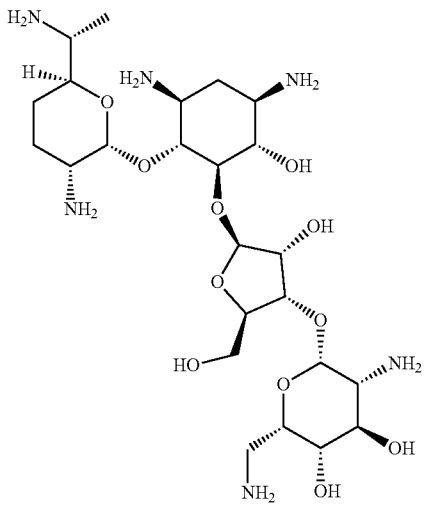

(2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S)-1-aminoethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol

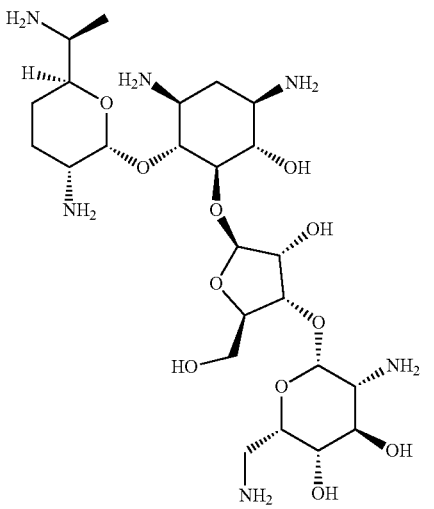

(2S,3S,4R,5R,6R)-5-amino-2-(aminomethyl)-6-(((2R,3S,4R,5S)-5-(((1R,2R,3S,5R,6S)-3,5-diamino-2-(((2R,3S,4R,5R,6R)-3-amino-6-(aminomethyl)-4-fluoro-5-hydroxytetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol

195

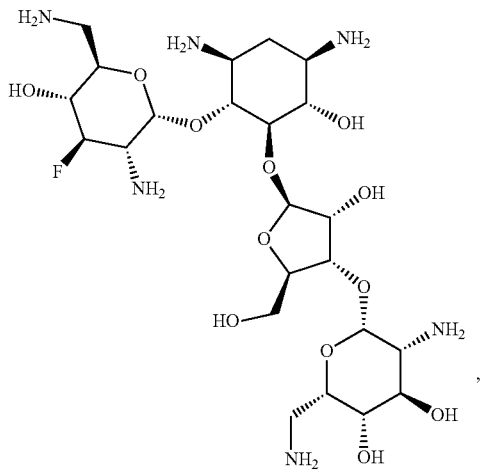 [SMILES: NC[C@@H]1O[C@H](O[C@H]2[C@@H](O)[C@H](O[C@@H]3[C@@H](O)[C@H](N)C[C@H](N)[C@H]3O[C@H]3O[C@H](CN)[C@@H](O)[C@H](F)[C@H]3N)O[C@@H]2CO)[C@H](N)[C@@H](O)[C@@H]1O]

(2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((R)-1-aminopropyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol

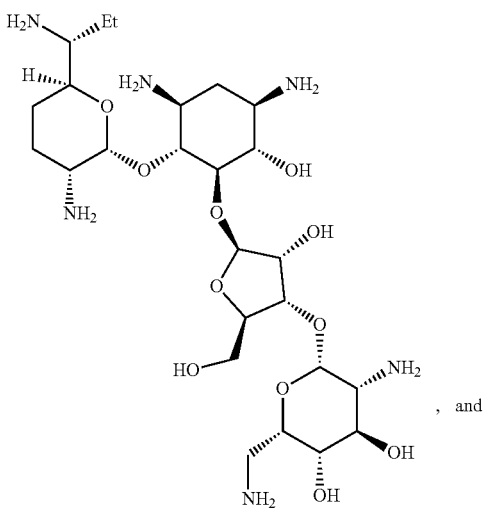 [SMILES: CC[C@@H](N)[C@@H]1CC[C@@H](N)[C@@H](O[C@H]2[C@H](O[C@@H]3O[C@H](CO)[C@@H](O[C@H]4O[C@@H](CN)[C@@H](O)[C@H](O)[C@H]4N)[C@H]3O)[C@@H](O)[C@H](N)C[C@@H]2N)O1]

(2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S)-1-aminopropyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol

196

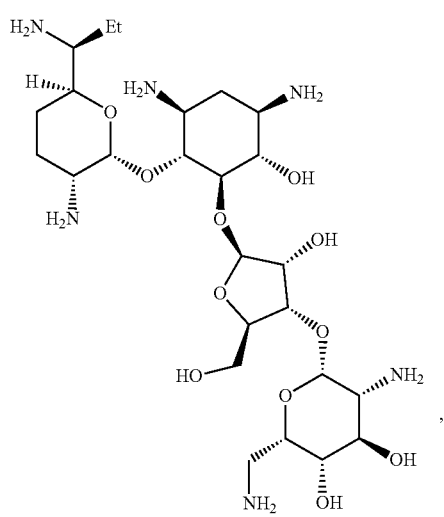 [SMILES: CC[C@H](N)[C@@H]1CC[C@@H](N)[C@@H](O[C@H]2[C@H](O[C@@H]3O[C@H](CO)[C@@H](O[C@H]4O[C@@H](CN)[C@@H](O)[C@H](O)[C@H]4N)[C@H]3O)[C@@H](O)[C@H](N)C[C@@H]2N)O1]

or a pharmaceutically acceptable salt, solvate, or tautomer of any of the foregoing.

The present disclosure further provides a compound of formula (I), formula (I-A), formula (II), formula (II-A), formula (III), or formula (III-A), wherein the compound is selected from the group consisting of:

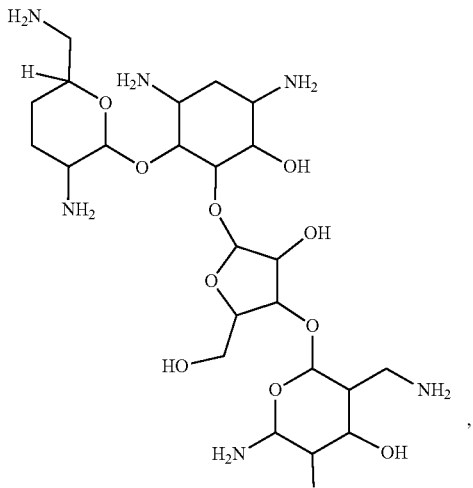

197
-continued
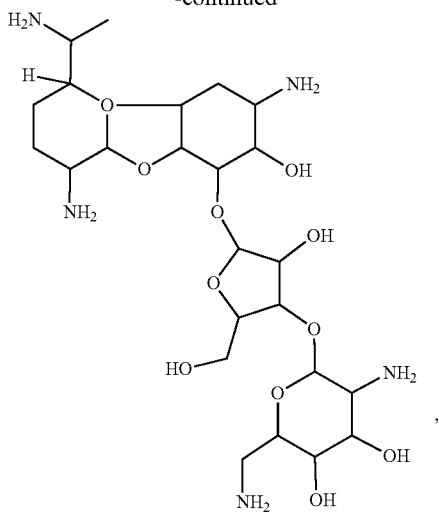
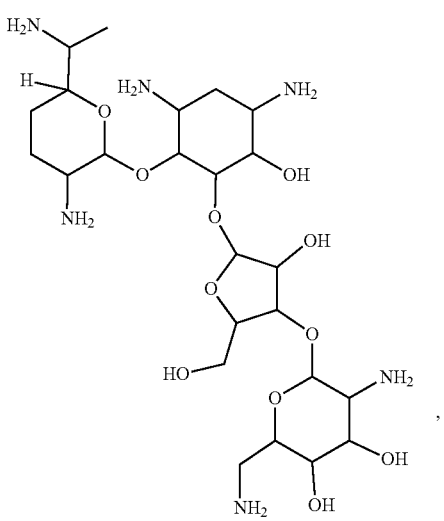
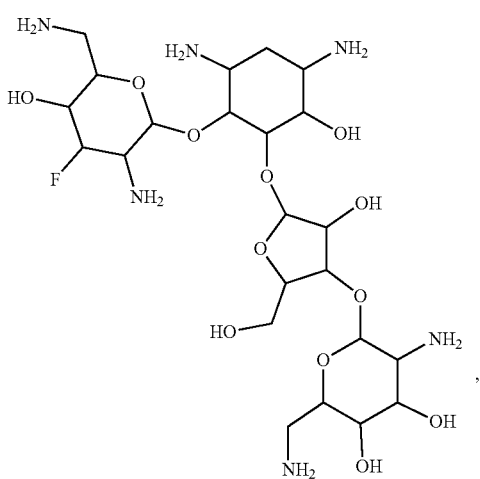
198
-continued
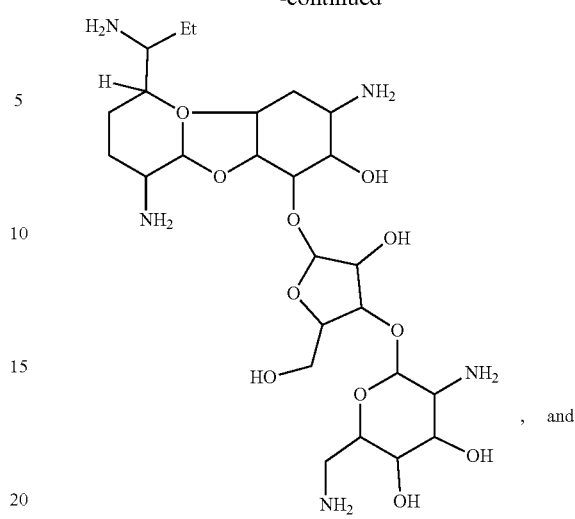
, and
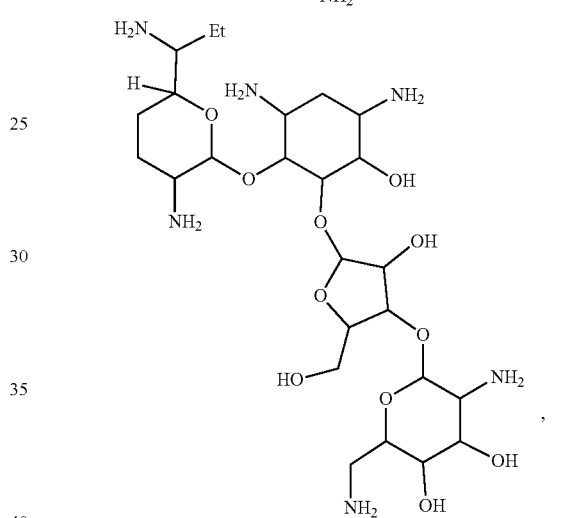
,
or a pharmaceutically acceptable salt, solvate, stereoisomer, or tautomer of any of the foregoing.
The present disclosure further provides a compound of formula (I), formula (I-A), formula (II), formula (II-A), formula (III), or formula (III-A), wherein the compound is selected from the group consisting of:
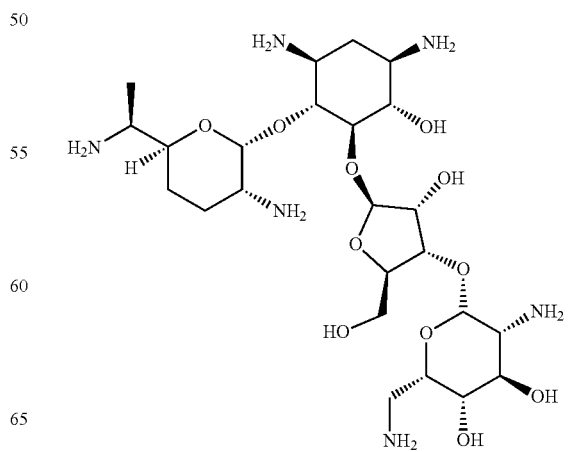
, 199
-continued
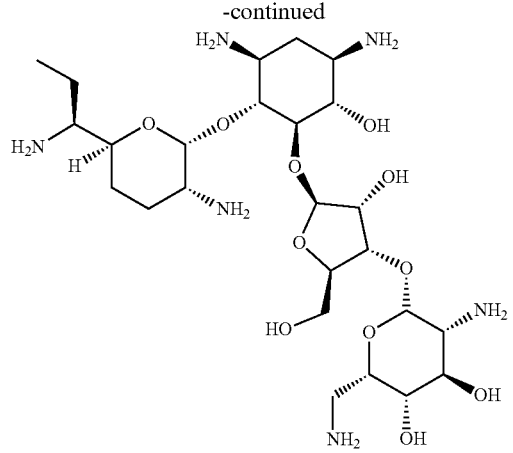
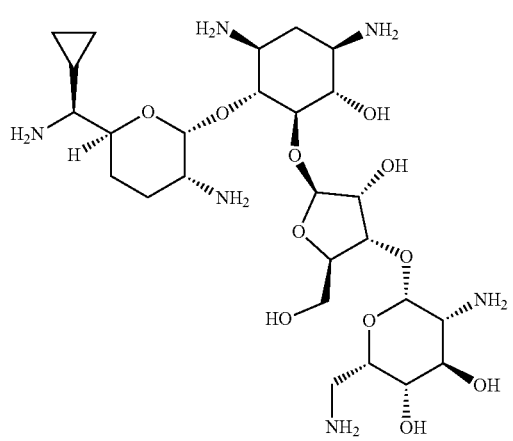
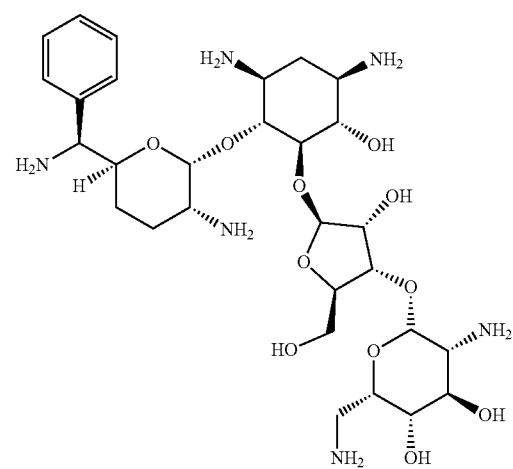
200
-continued
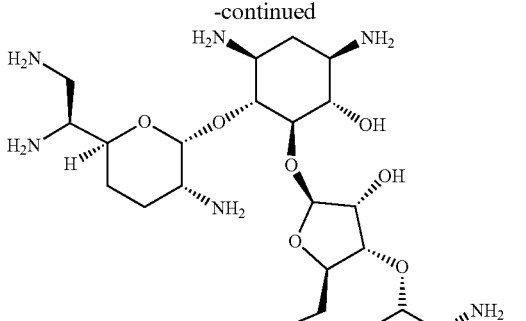
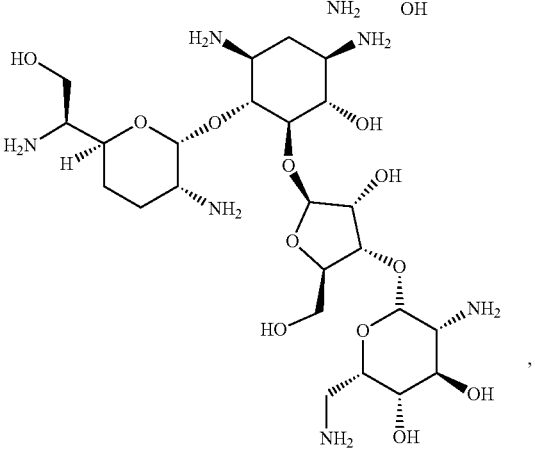

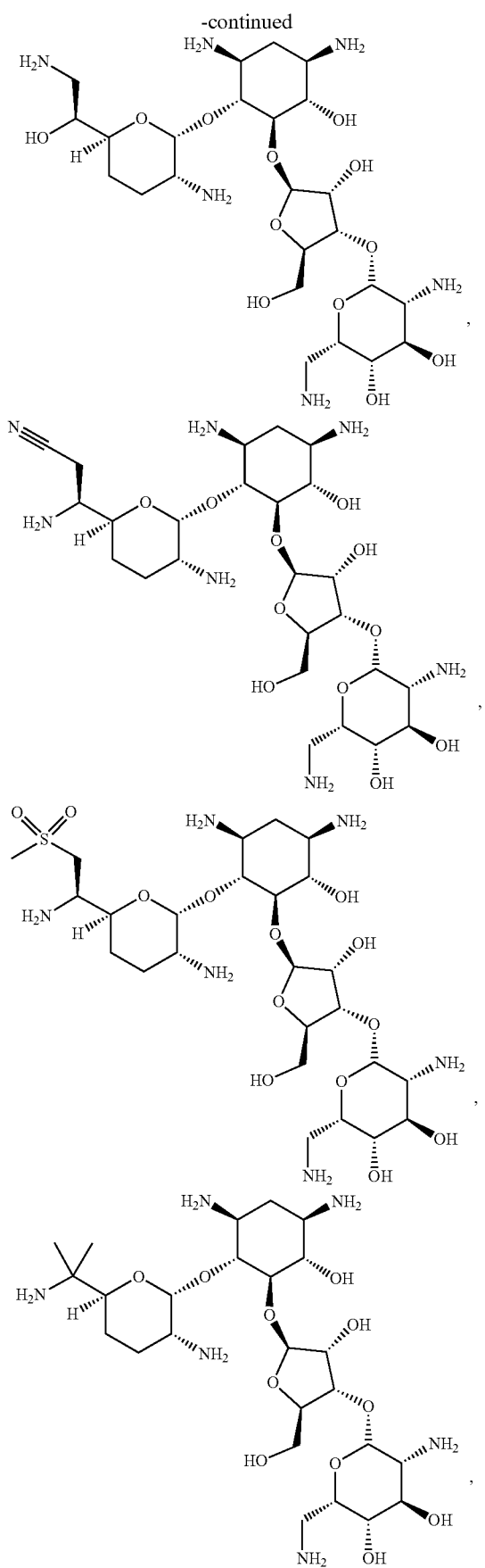

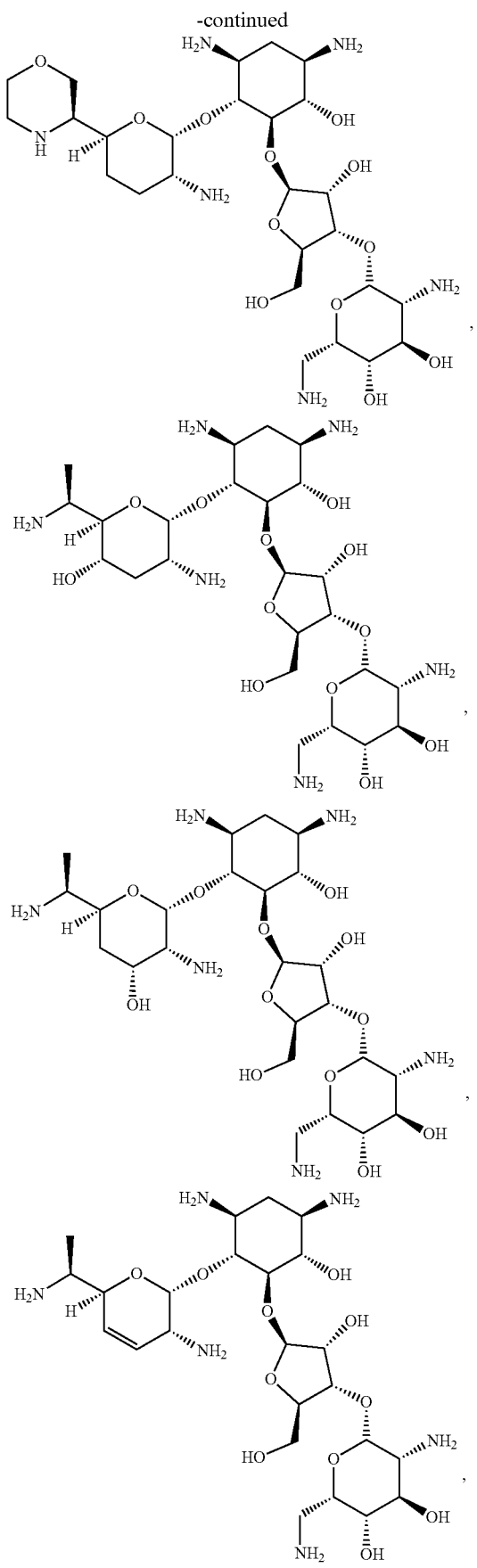
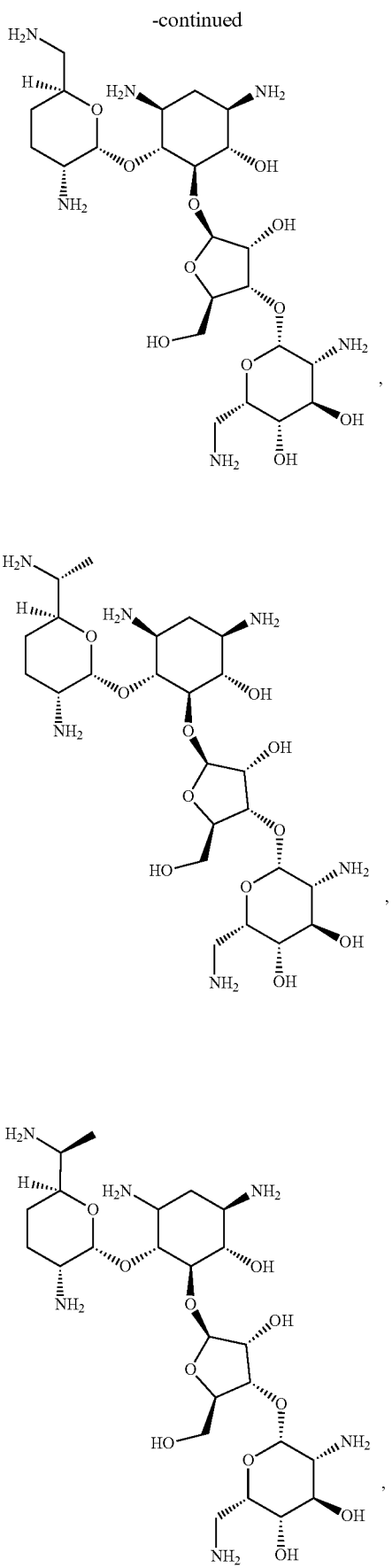

205
-continued
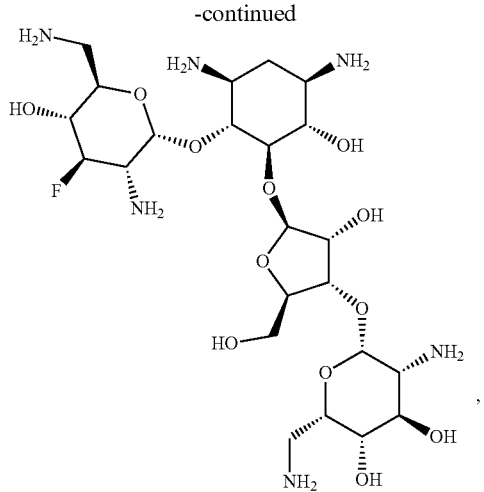

and

or a pharmaceutically acceptable salt, solvate, or tautomer of any of the foregoing.
The present disclosure further provides a compound of formula (I), formula (I-A), formula (II), formula (II-A), formula (III), or formula (III-A), wherein the compound is selected from the group consisting of:
206
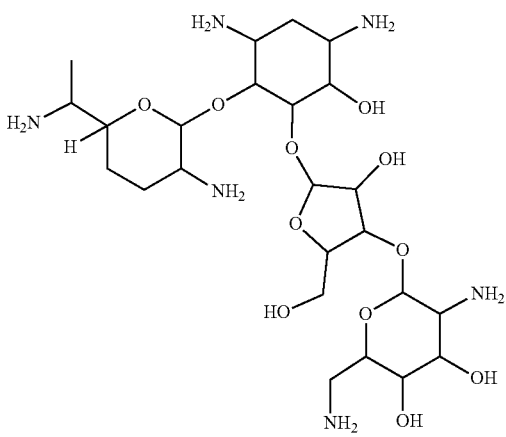
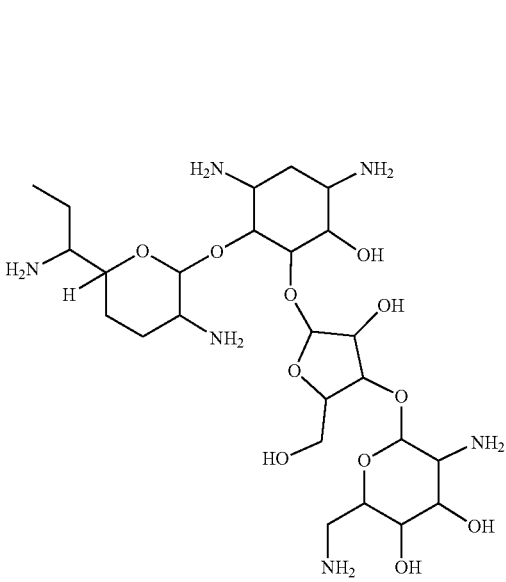
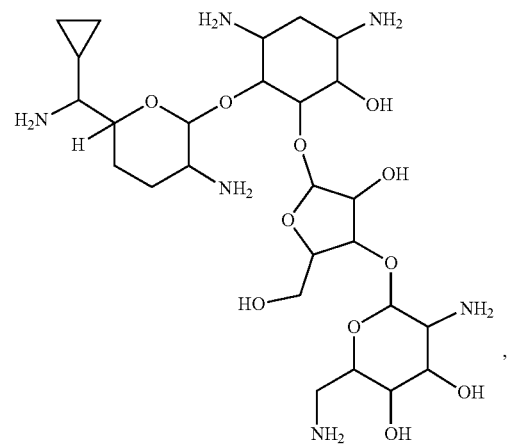

207
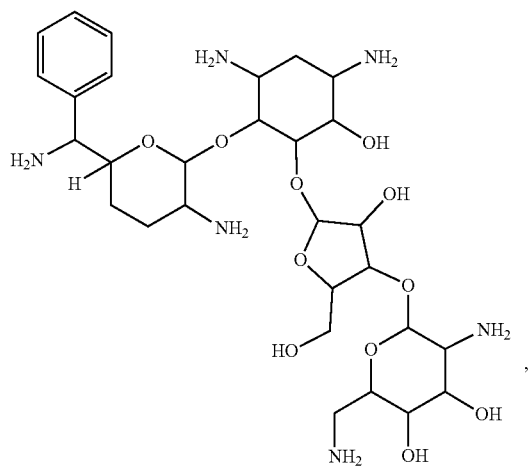
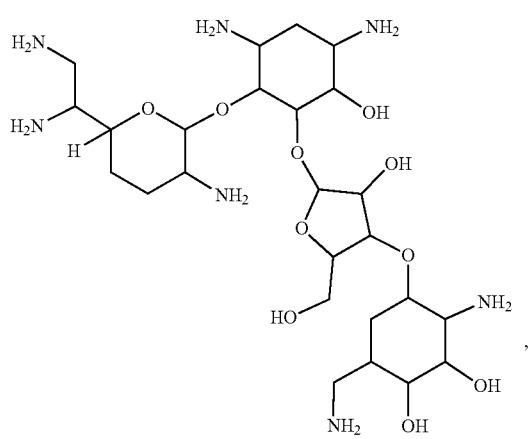
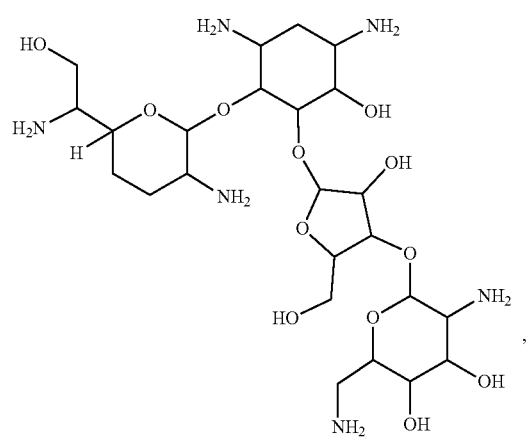
208
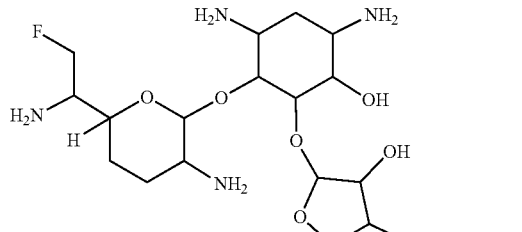
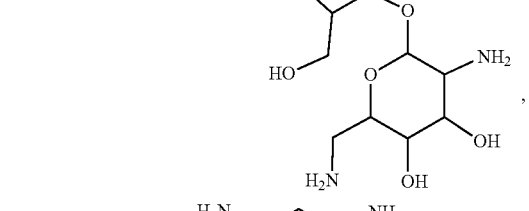
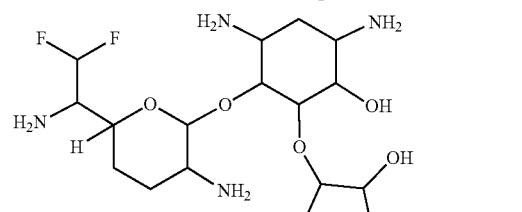
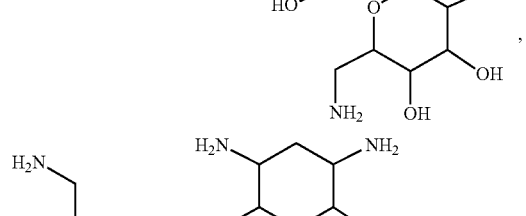
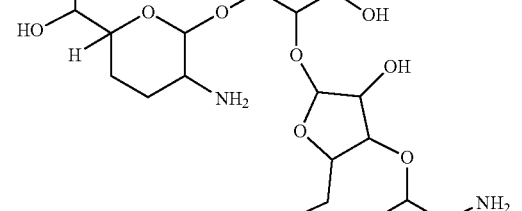
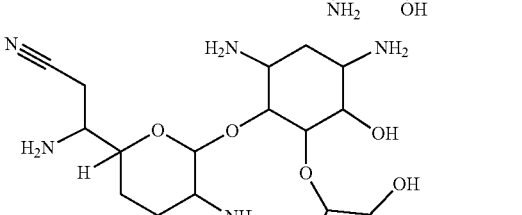
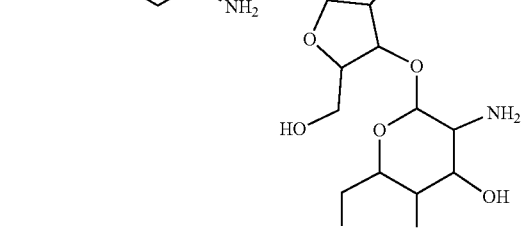

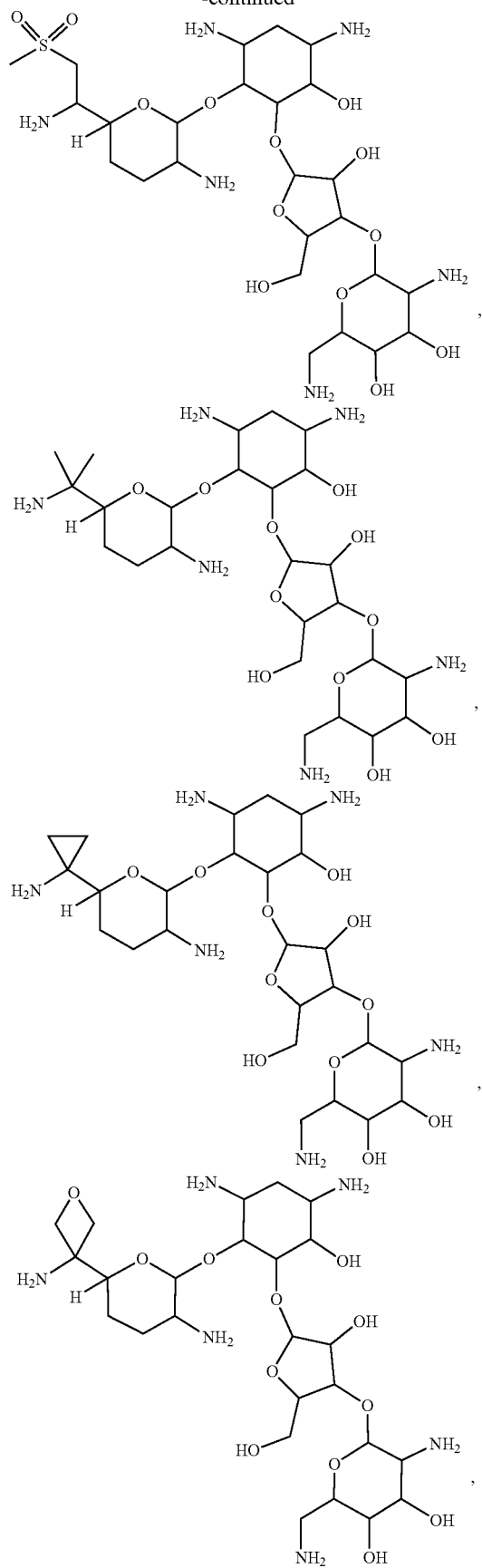
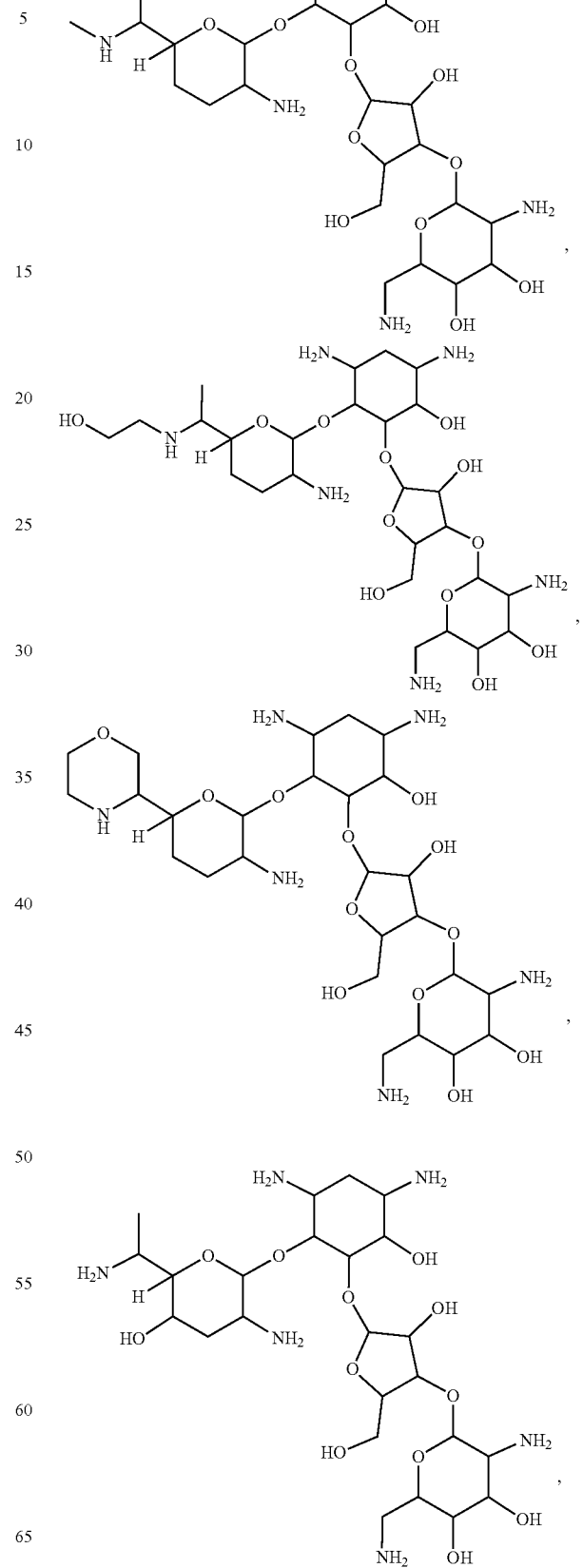

211
-continued
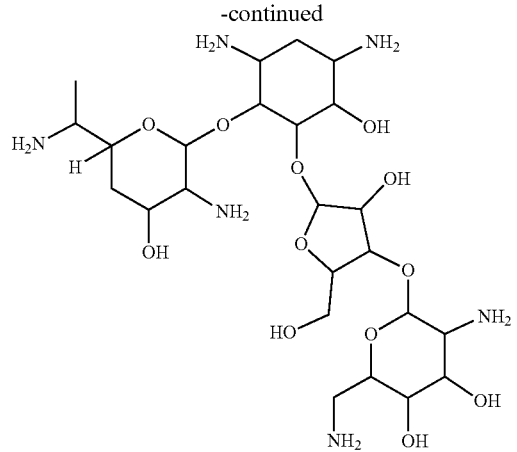
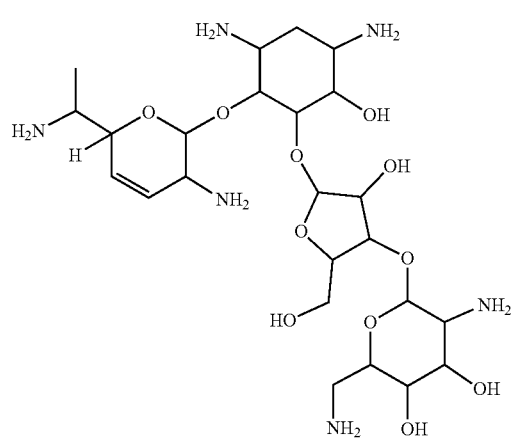
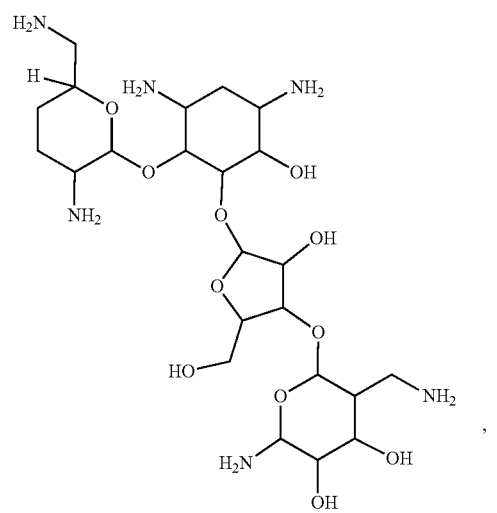
212
-continued
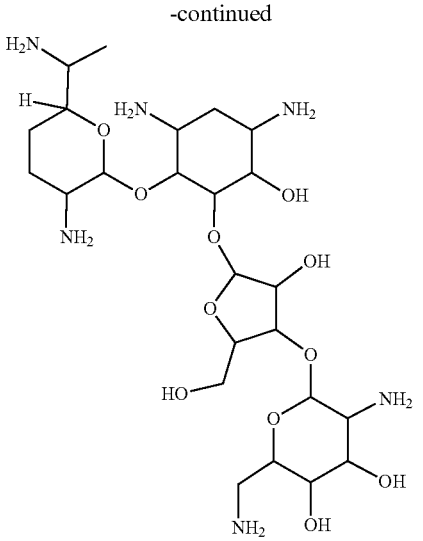
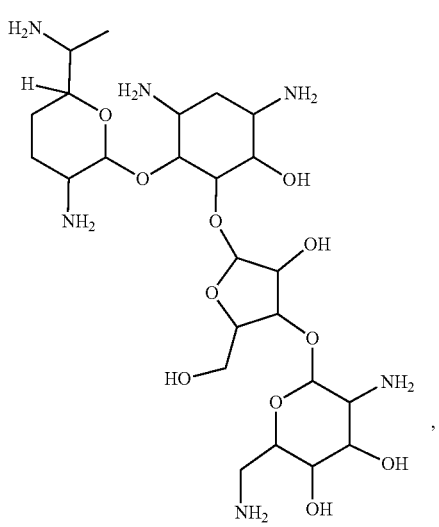
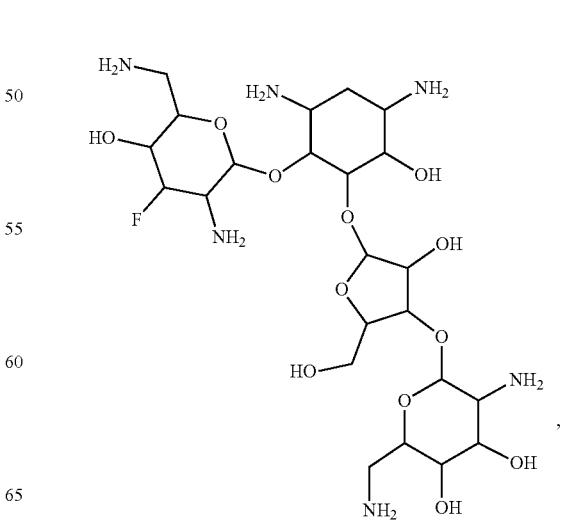

213
-continued
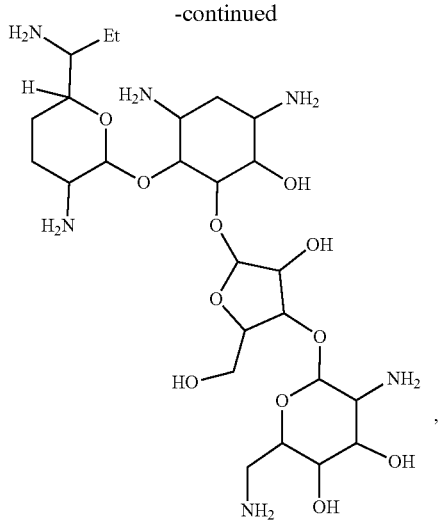
and
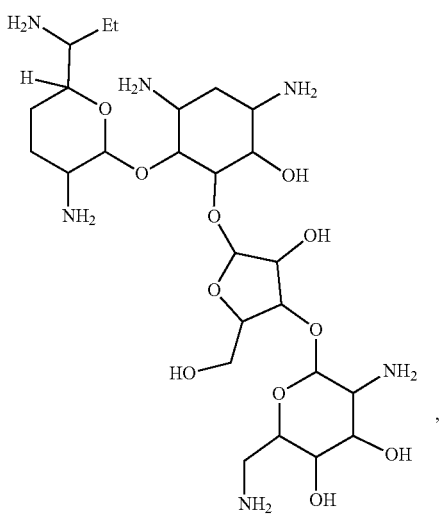
or a pharmaceutically acceptable salt, solvate, stereoisomer, or tautomer of any of the foregoing.
The present disclosure further provides a compound of formula (IV) (e.g., formula (IVa), formula (V), or formula (VI)), wherein the compound is selected from the group consisting of:
214
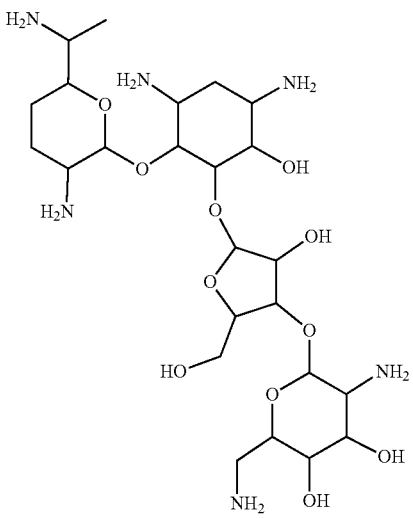
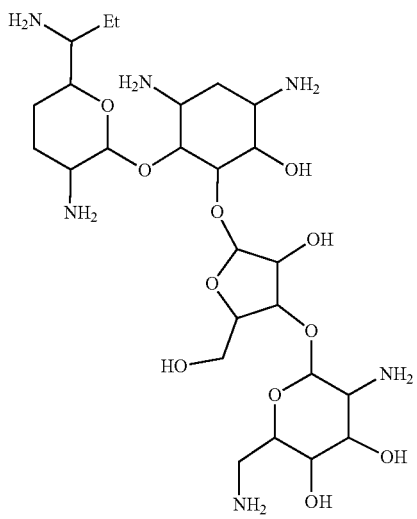
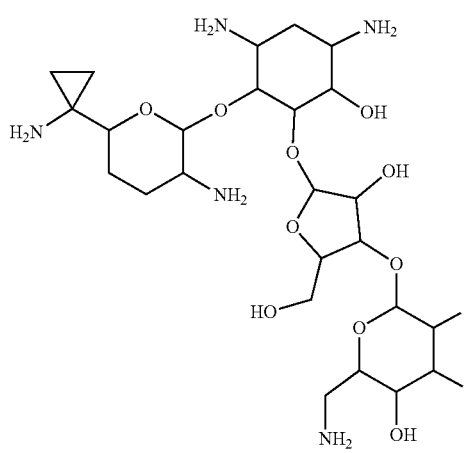

215
-continued
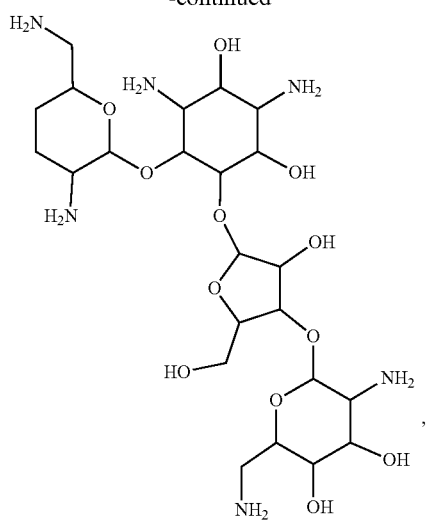
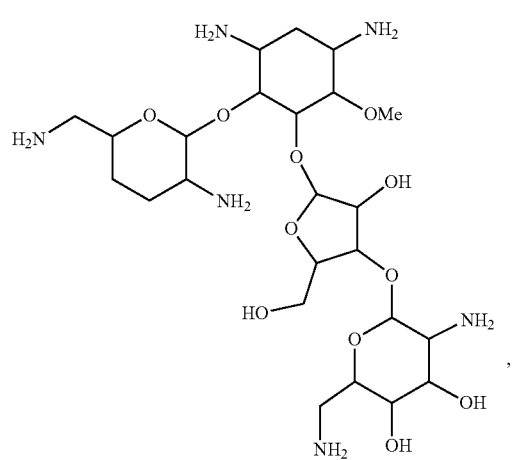
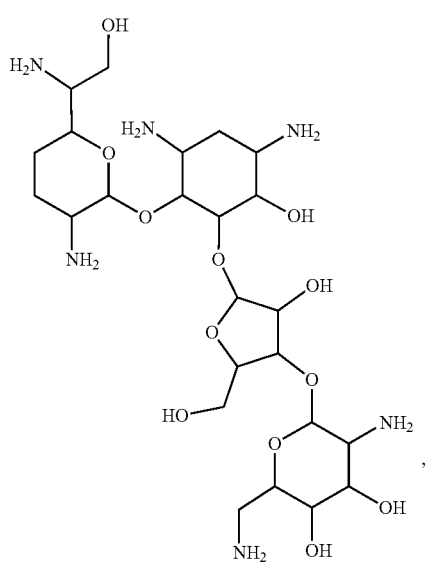
216
-continued
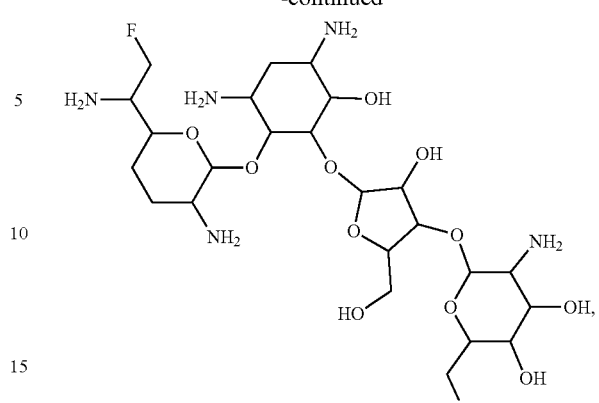
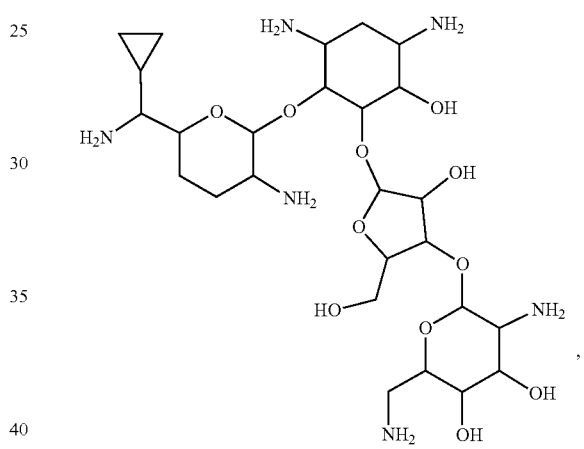
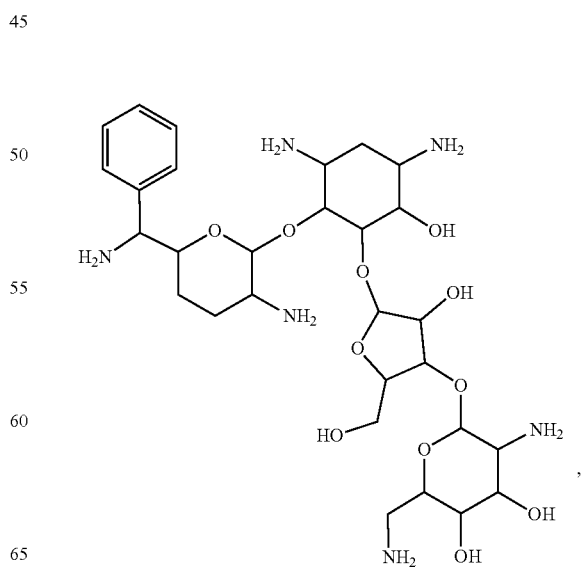

217
-continued
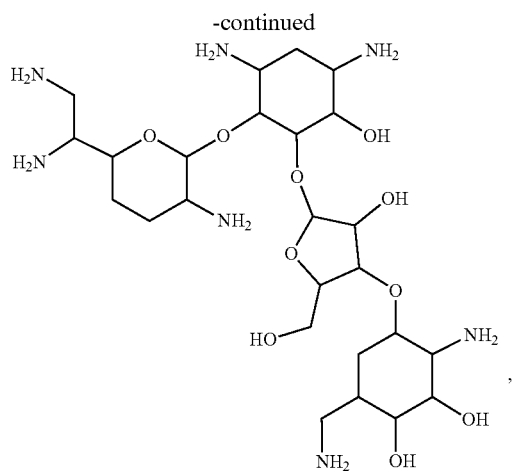
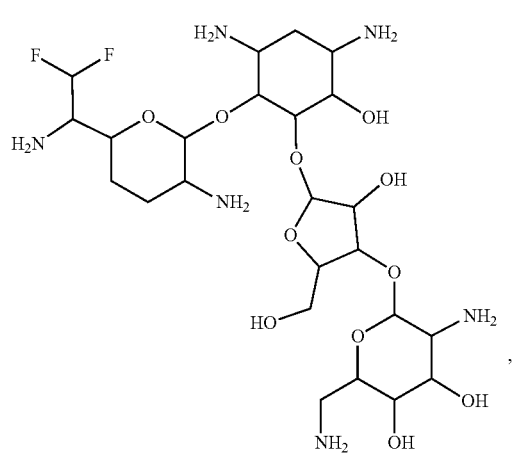
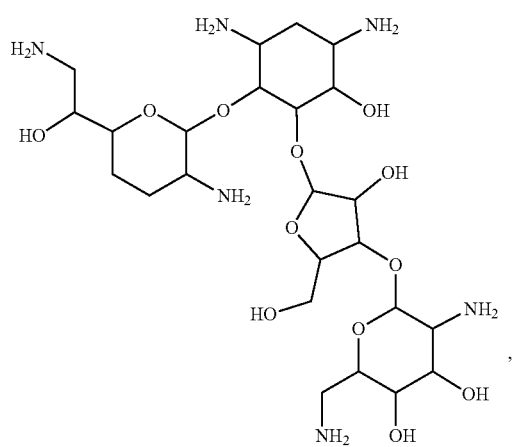
218
-continued
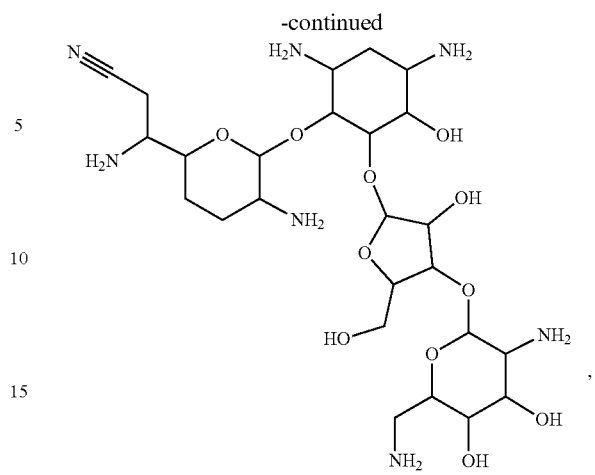
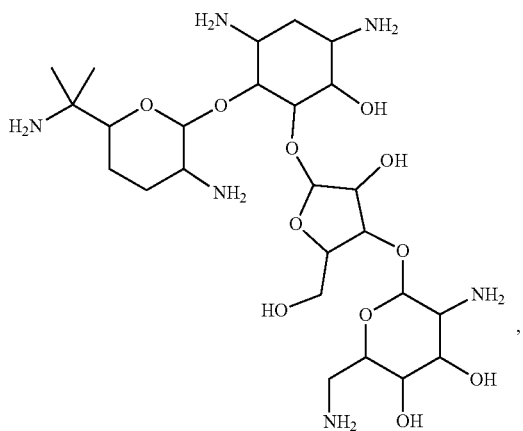

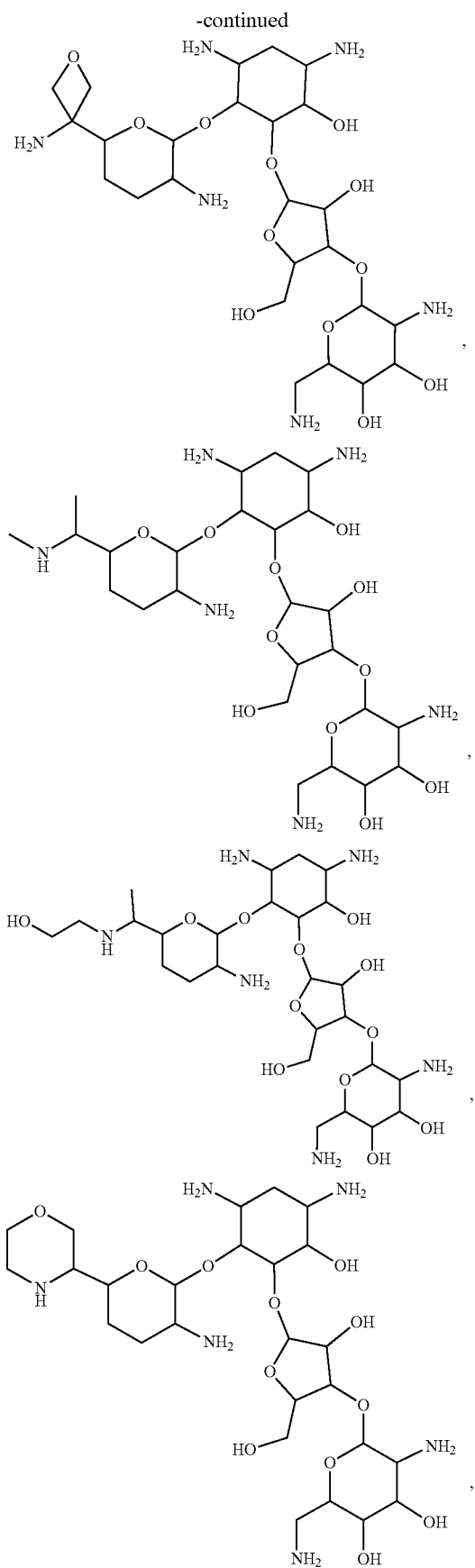
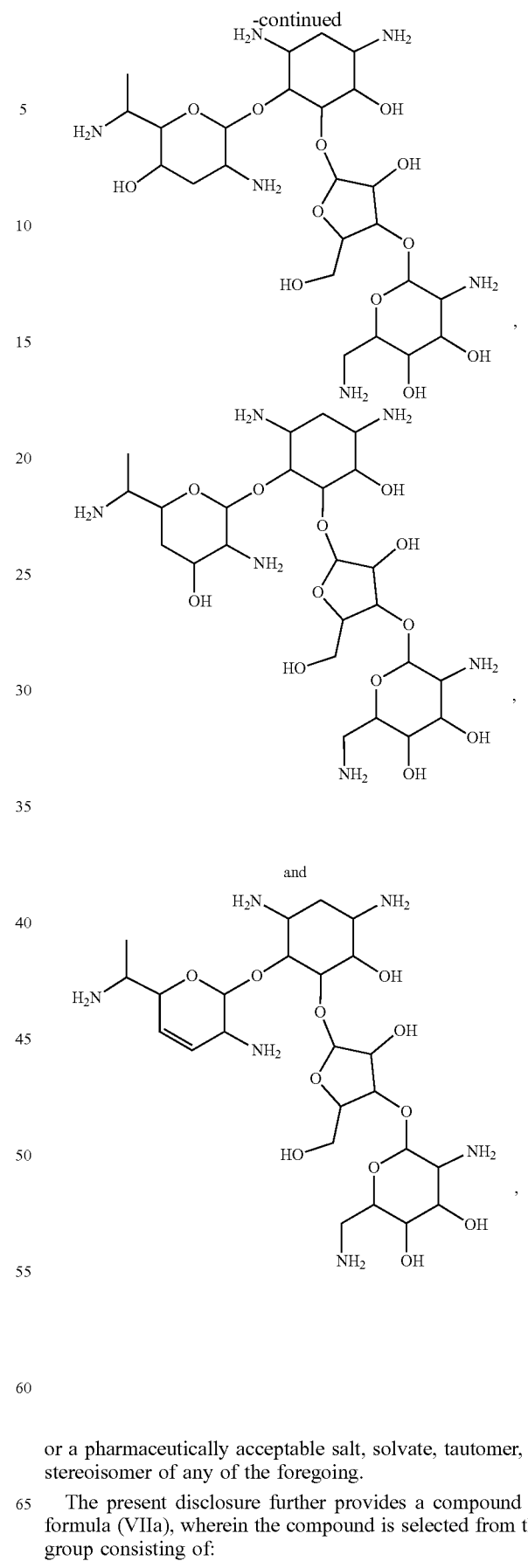
or a pharmaceutically acceptable salt, solvate, tautomer, or stereoisomer of any of the foregoing.
The present disclosure further provides a compound of formula (VIIa), wherein the compound is selected from the group consisting of:

221
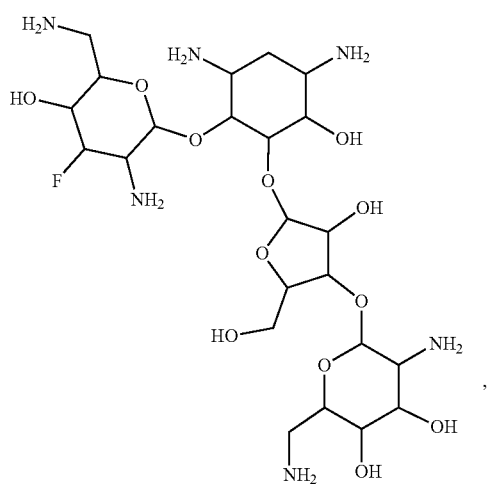
222
-continued
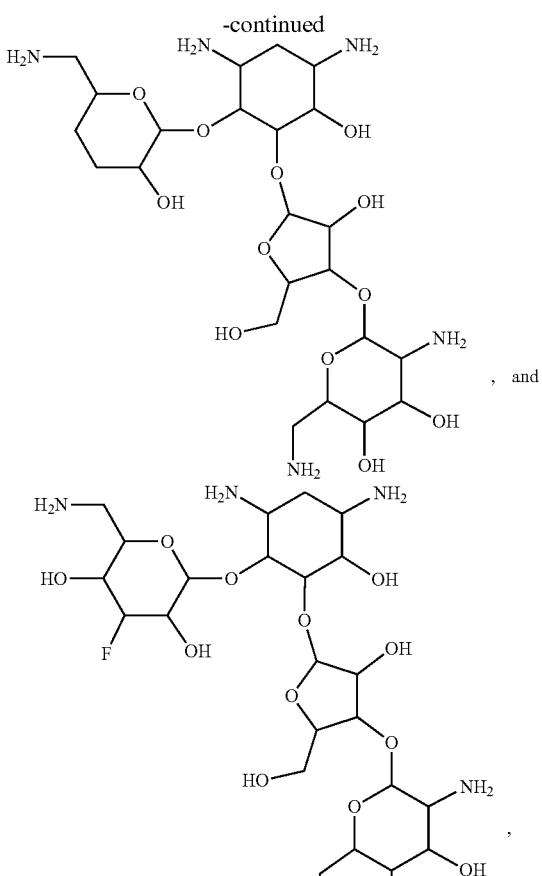
or a pharmaceutically acceptable salt, solvate, tautomer, or stereoisomer of any of the foregoing.
The present disclosure further provides a compound of formula (VIIb), wherein the compound is selected from the group consisting of:
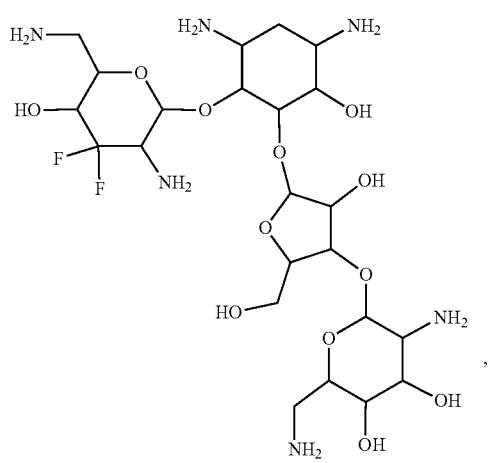
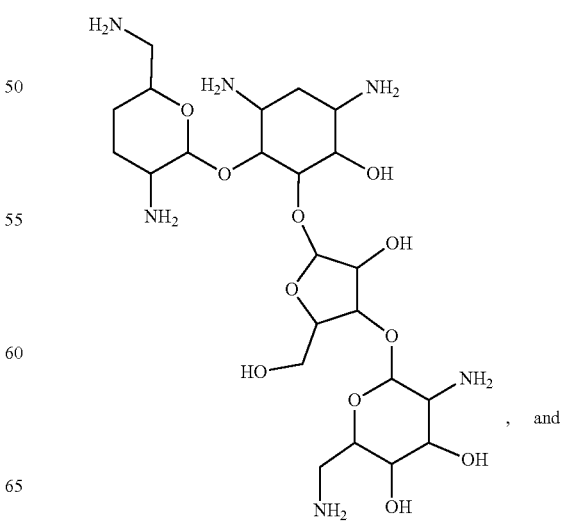

223
-continued
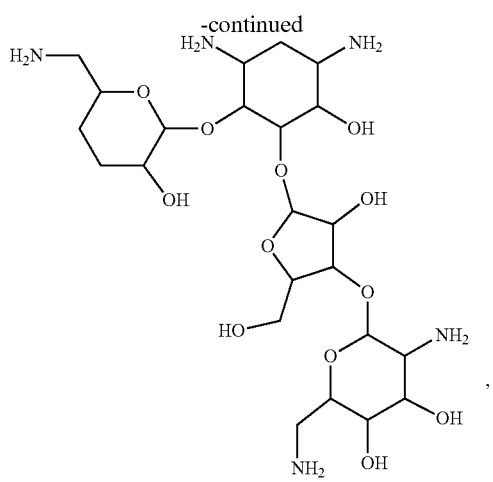
or a pharmaceutically acceptable salt, solvate, tautomer, or stereoisomer of any of the foregoing.
The present disclosure further provides a compound of formula (IV) (e.g., formula (IVa), formula (V), or formula (VI)), wherein the compound is selected from the group consisting of:
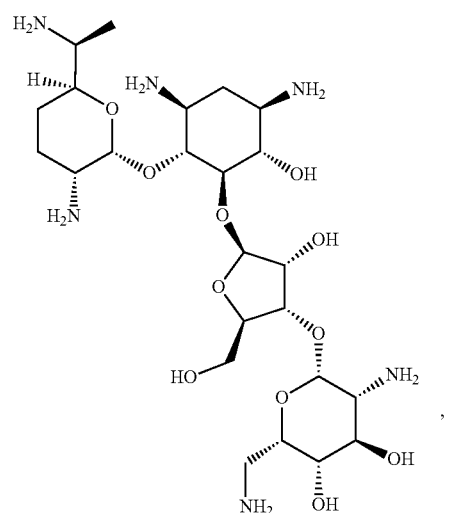
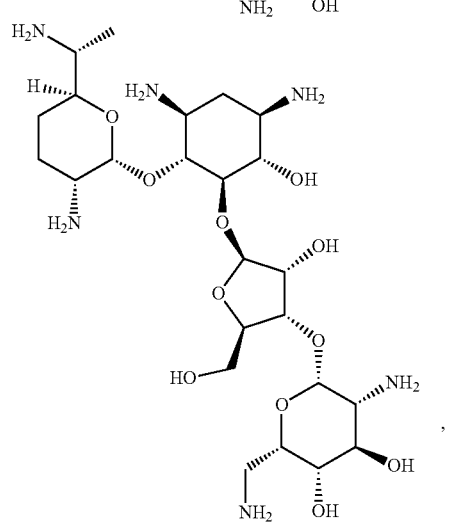
224
-continued
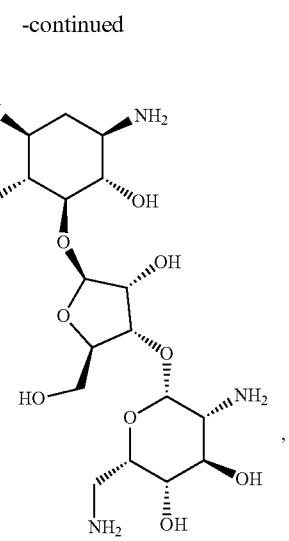
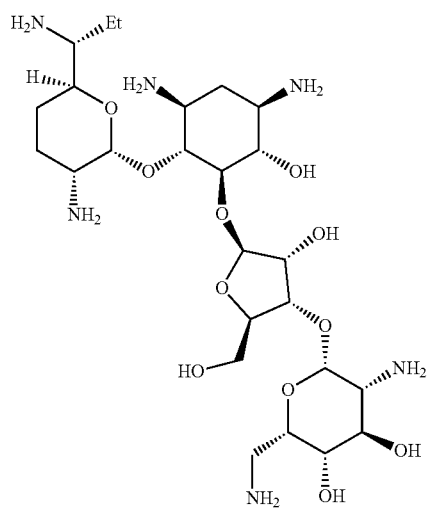
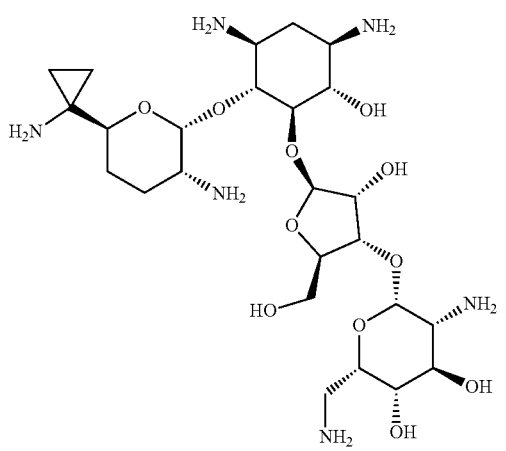

225
-continued
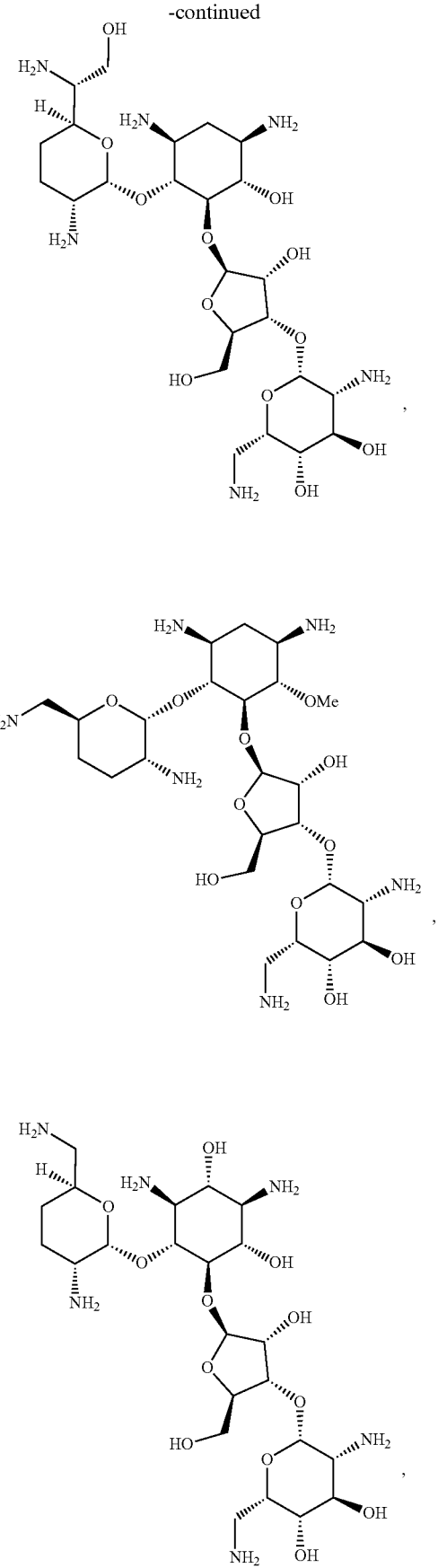
226
-continued
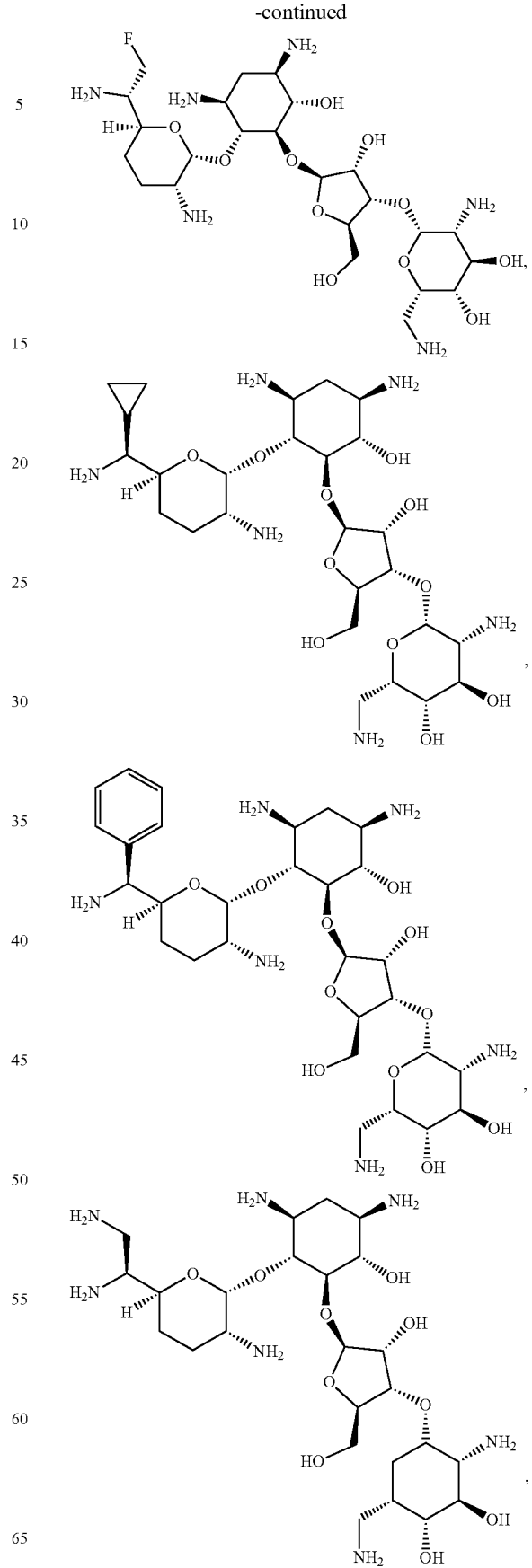

227
-continued
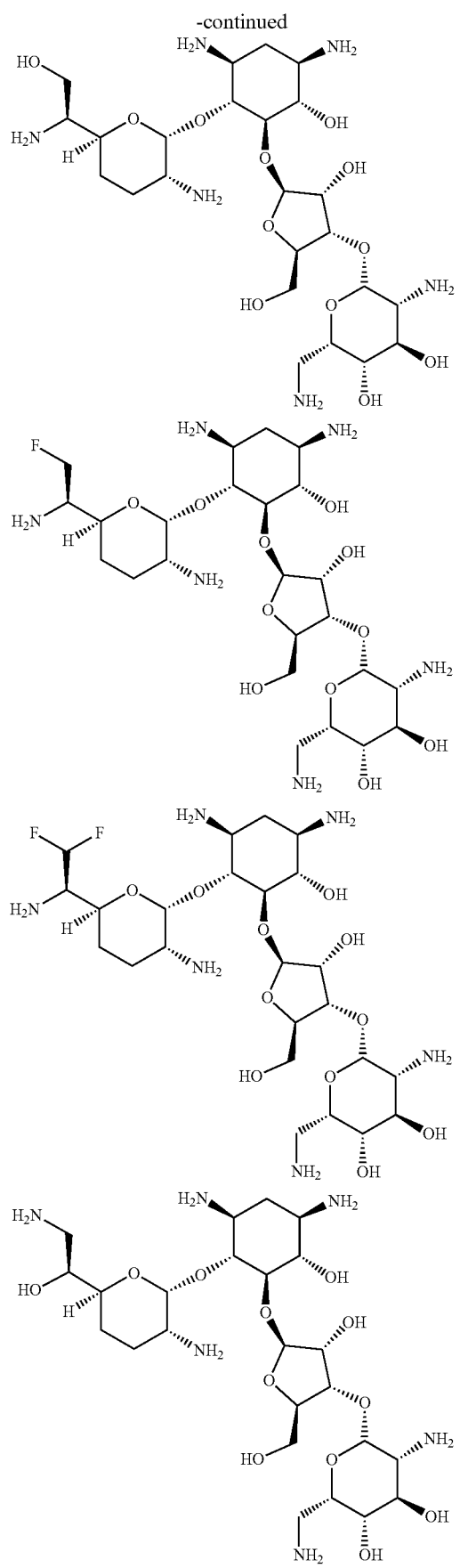
228
-continued
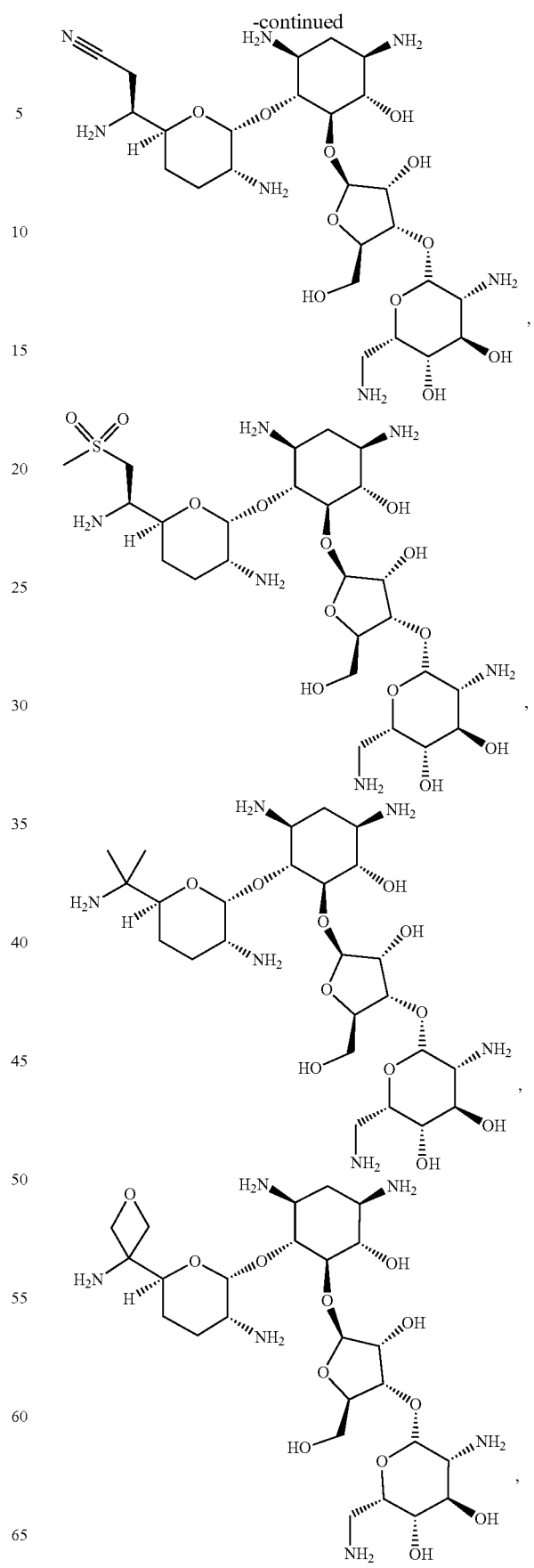

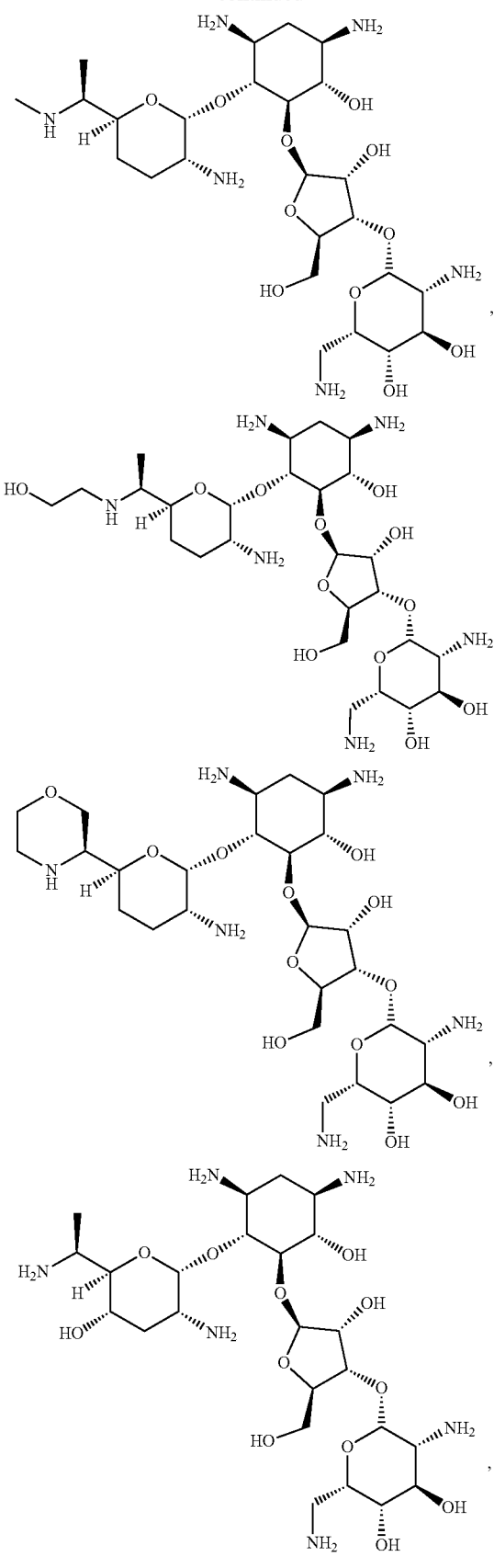
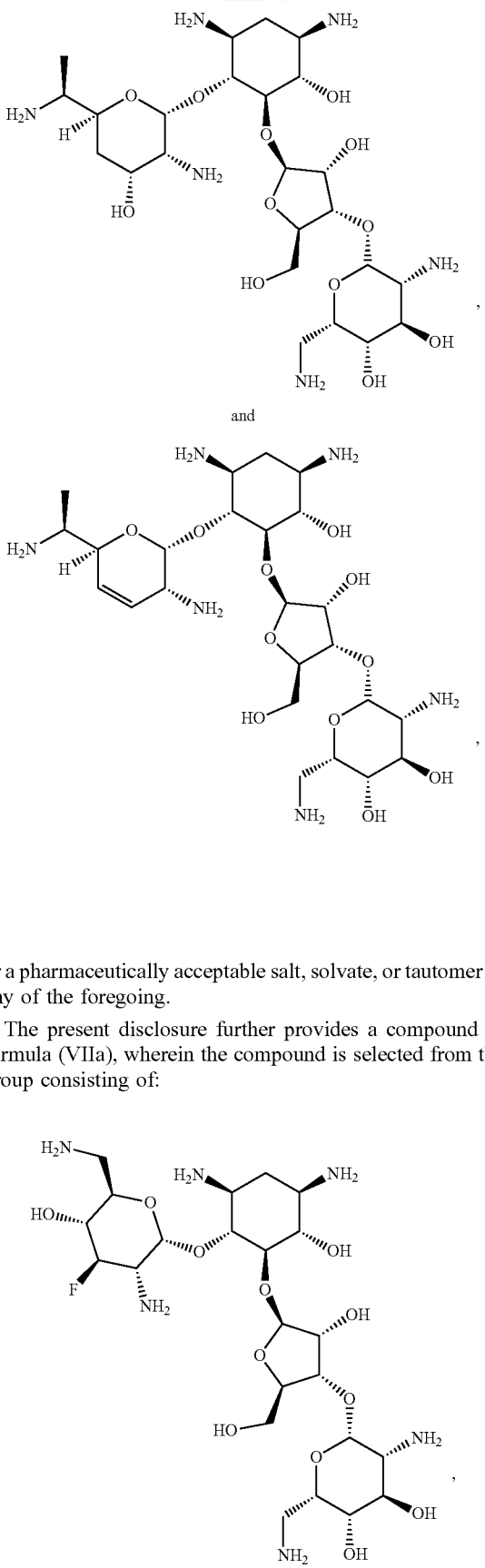
or a pharmaceutically acceptable salt, solvate, or tautomer of any of the foregoing.
The present disclosure further provides a compound of formula (VIIa), wherein the compound is selected from the group consisting of:

231
-continued
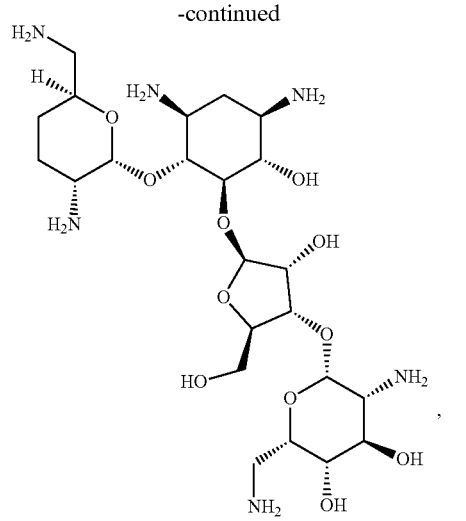
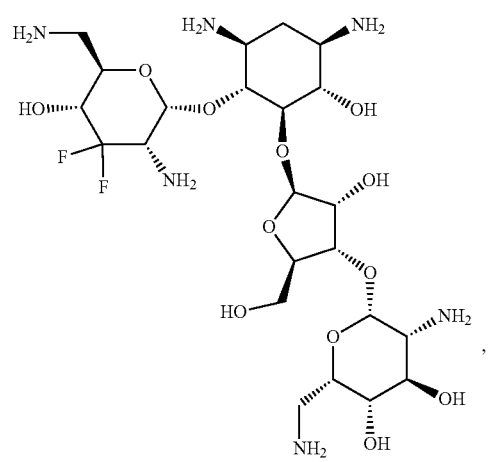
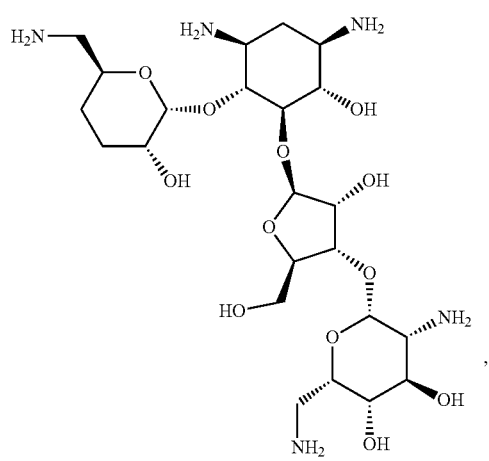
232
-continued
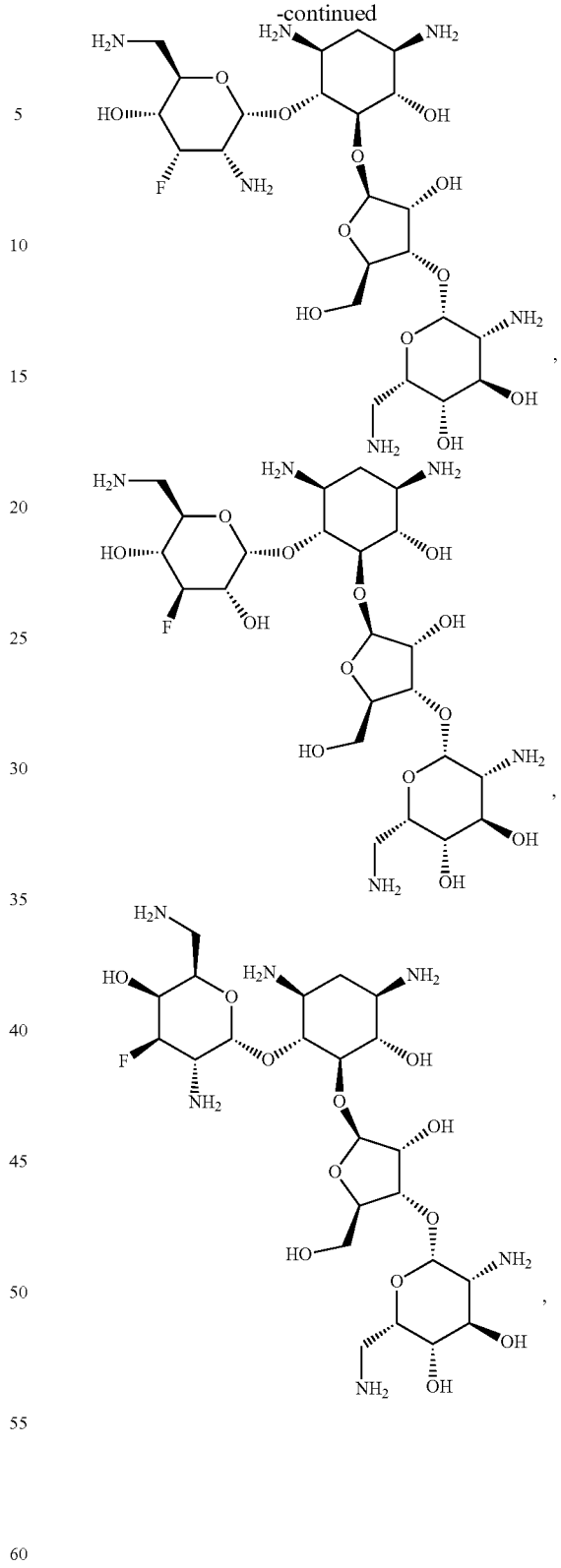
or a pharmaceutically acceptable salt, solvate, or tautomer of any of the foregoing.
The present disclosure further provides a compound of formula (VIIb), wherein the compound is selected from the group consisting of:

233
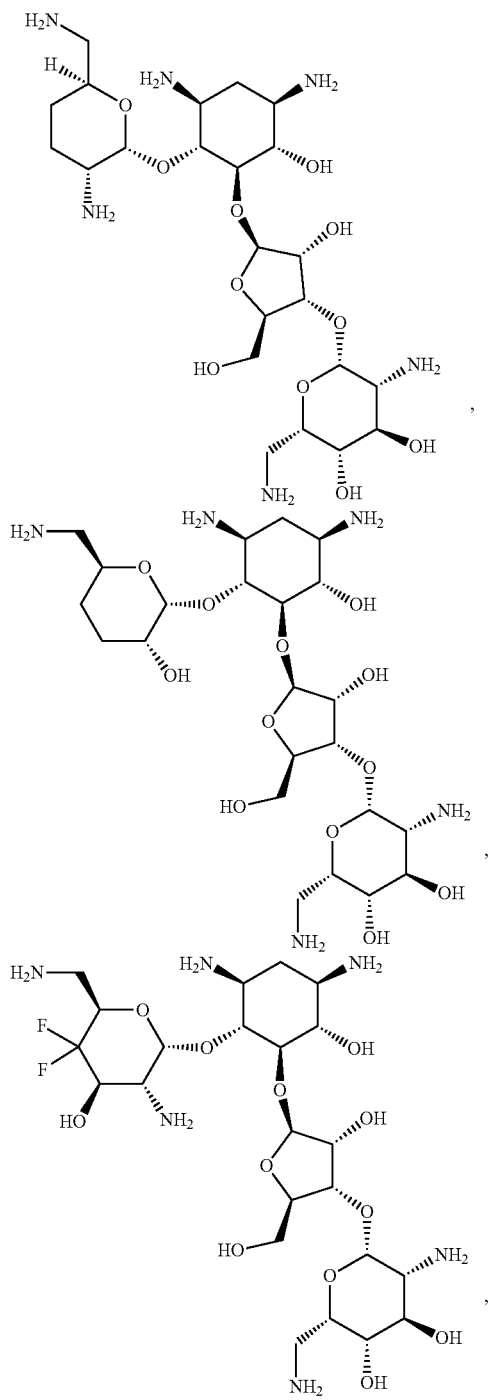
234
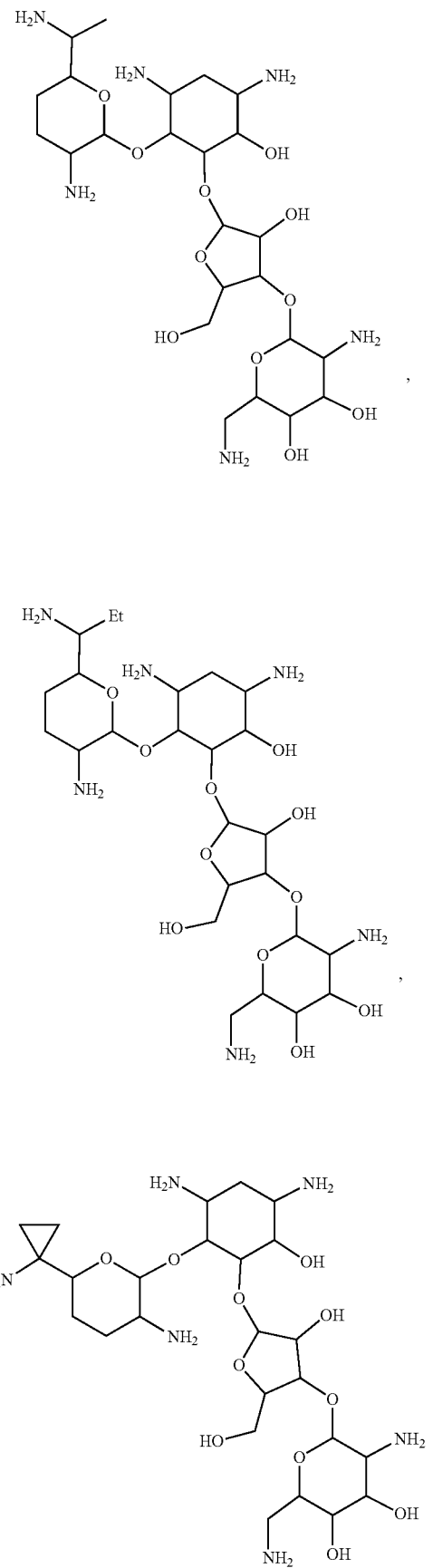
or a pharmaceutically acceptable salt, solvate, or tautomer of any of the foregoing.
The present disclosure further provides a compound of formula (IV) (e.g., formula (IVa), formula (V), or formula (VI)), wherein the compound is selected from the group consisting of:

-continued
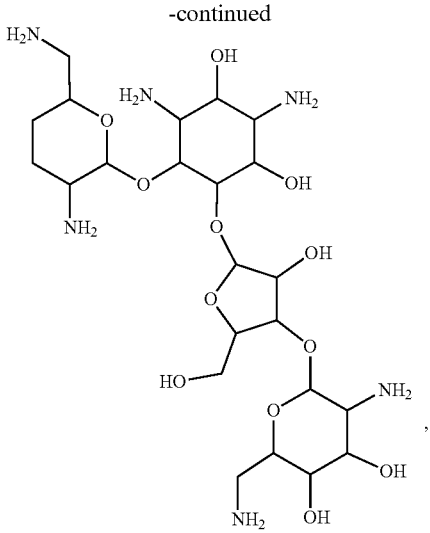
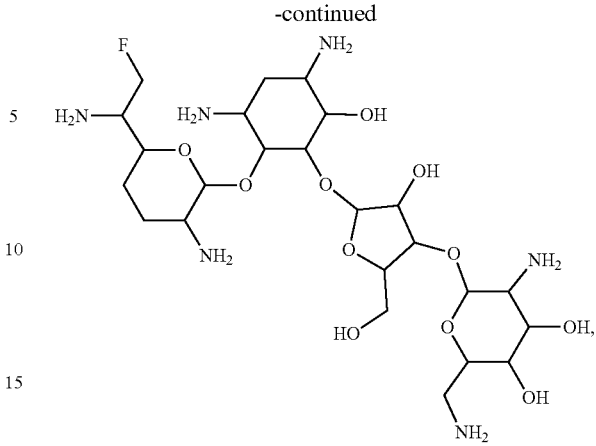
or a pharmaceutically acceptable salt, solvate, tautomer, or stereoisomer of any of the foregoing.
The present disclosure further provides a compound of formula (IV) (e.g., formula (IVa), formula (V), or formula (VI)), wherein the compound is selected from the group consisting of:
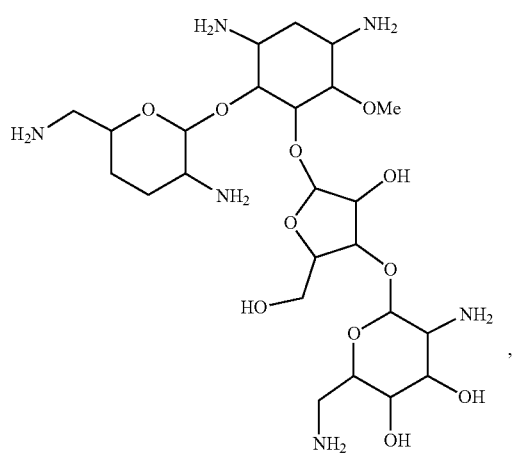
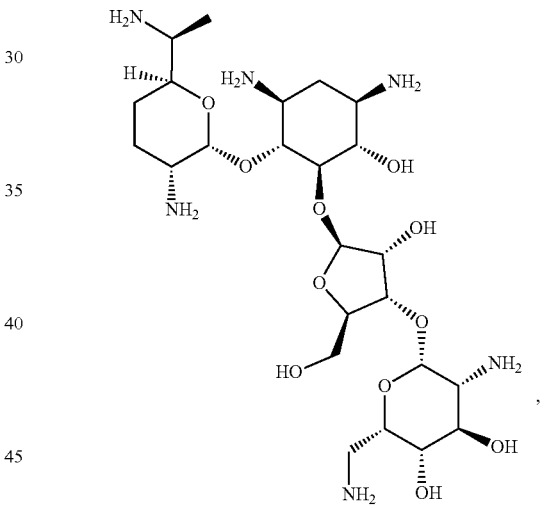
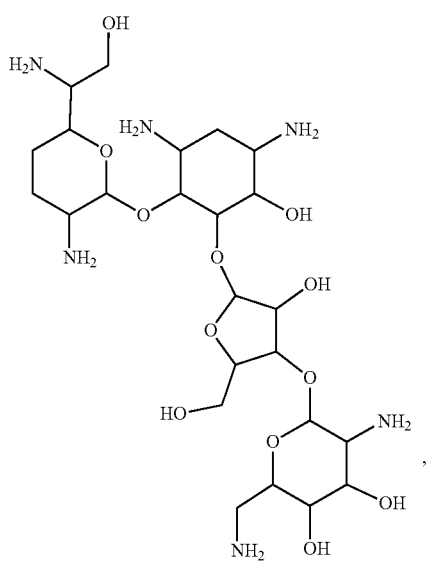
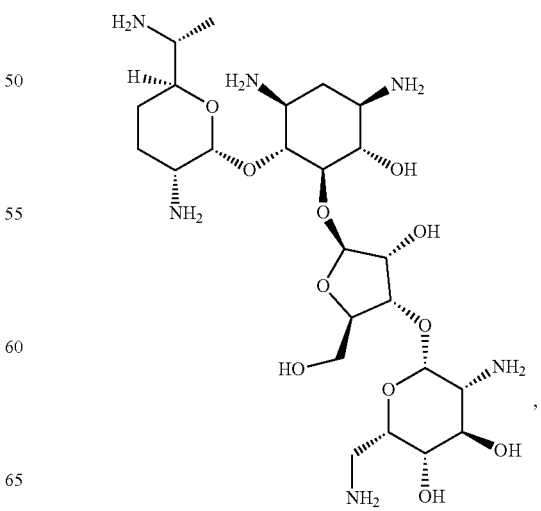

237
-continued
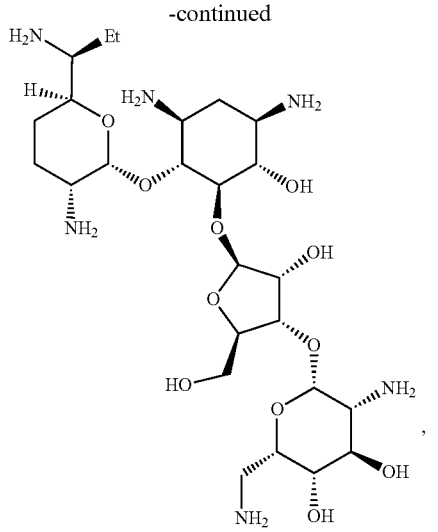
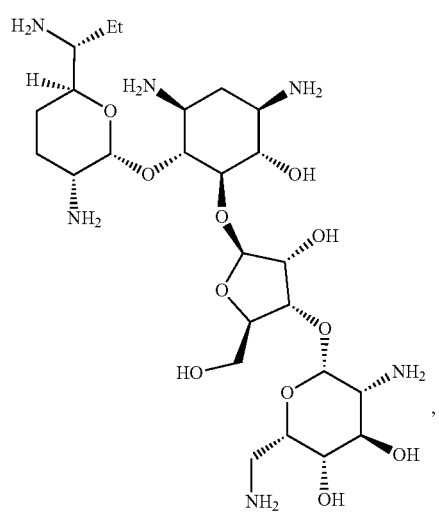
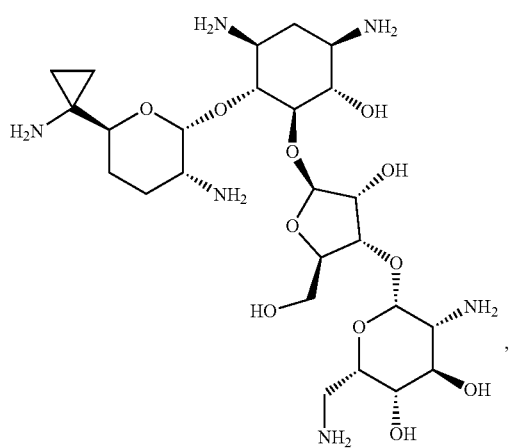
238
-continued
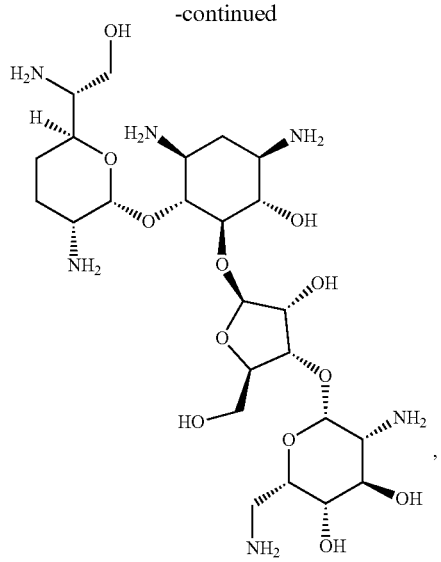
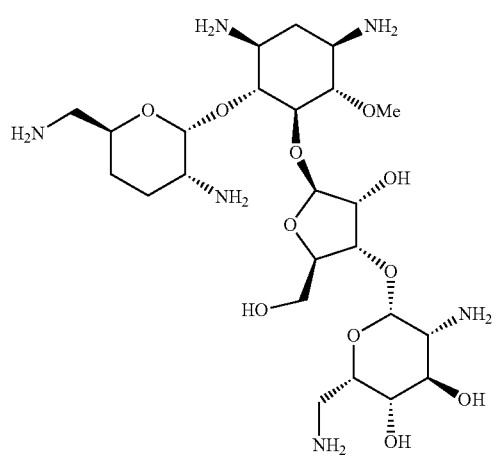
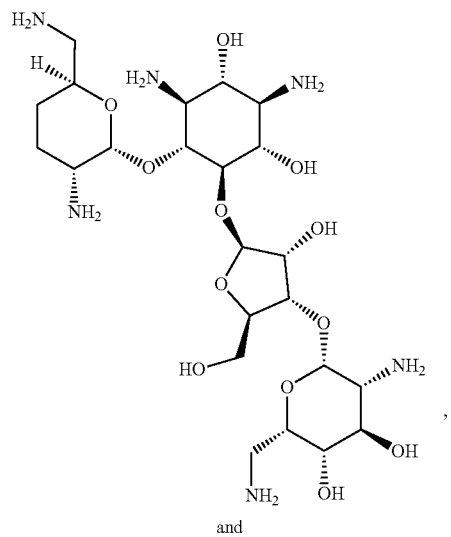
and

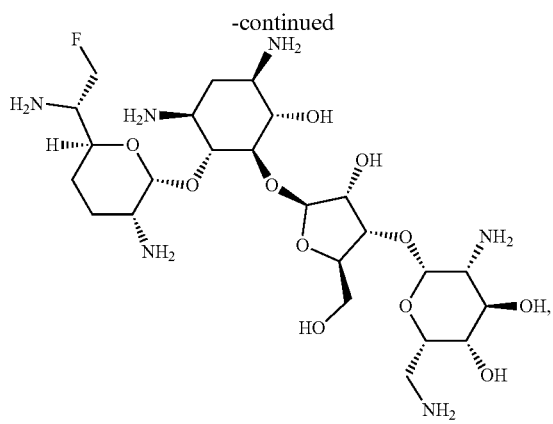

or a pharmaceutically acceptable salt, solvate, or tautomer of any of the foregoing.

In some embodiments, the compound of formula (I) is a pharmaceutically acceptable salt, solvate, stereoisomer, or tautomer. In some embodiments, the compound of formula (II) is a pharmaceutically acceptable salt, solvate, stereoisomer, or tautomer. In some embodiments, the compound of formula (III) is a pharmaceutically acceptable salt, solvate, stereoisomer, or tautomer. In some embodiments, the compound of formula (VI) is a pharmaceutically acceptable salt, solvate, stereoisomer, or tautomer. In some embodiments, the compound of formula (VIa) is a pharmaceutically acceptable salt, solvate, stereoisomer, or tautomer. In some embodiments, the compound of formula (V) is a pharmaceutically acceptable salt, solvate, stereoisomer, or tautomer. In some embodiments, the compound of formula (VI) is a pharmaceutically acceptable salt, solvate, stereoisomer, or tautomer. In some embodiments, the compound of formula (VIIa) is a pharmaceutically acceptable salt, solvate, stereoisomer, or tautomer. In some embodiments, the compound of formula (VIIb) is a pharmaceutically acceptable salt, solvate, stereoisomer, or tautomer.

The present disclosure is directed to compounds as described herein and pharmaceutically acceptable salts, solvates (e.g., hydrates), isomers (e.g., stereoisomers), and tautomers thereof, and pharmaceutical compositions comprising one or more compounds as described herein, and pharmaceutically acceptable salts, solvates (e.g., hydrates), isomers (e.g., stereoisomers), and tautomers thereof.

The disclosure is directed to compounds as described herein and pharmaceutically acceptable salts, enantiomers, diastereomers, solvates (e.g., hydrates), isomers (e.g., stereoisomers), or tautomers thereof. The use of the terms "salt," "hydrate," "solvate," and the like, is intended to equally apply to the salt, hydrate, or solvate of enantiomers, diastereomers, isomers, stereoisomers, rotamers, tautomers, positional isomers, or racemates of the disclosed compounds.

The disclosure may include pharmaceutically acceptable salts of the compounds disclosed herein. A "pharmaceutically acceptable salt" may be acceptable for use in humans or domestic animals and may refer to those salts that retain the biological effectiveness and properties of the free forms, which are not biologically or otherwise undesirable. Representative "pharmaceutically acceptable salts" may include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, 1,1-methene-bis-2-hydroxy-3-naphthoate, einbonate, pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

Pharmaceutically acceptable salts may also include both acid and base addition salts. "Pharmaceutically acceptable acid addition salt" may refer to those salts which retain the biological effectiveness and properties of the free bases, which are not biologically or otherwise undesirable, and which may be formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" may refer to those salts that retain the biological effectiveness and properties of the free acids, which are not biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. For example, inorganic salts may include, but are not limited to, ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

Compounds of the disclosure may exist as solvates. Often crystallizations produce a solvate of the compound of the disclosure. As used herein, the term "solvate" may refer to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases the compound of the disclosure may merely retain adventitious water or be a mixture of water plus some adventitious solvent.

It should be understood that all isomeric forms are included within the present disclosure, including mixtures thereof. The term "isomer" may refer to compounds that have the same composition and molecular weight but differ in physical and/or chemical properties. The structural difference may be in constitution (geometric or positional isomers) or in the ability to rotate the plane of polarized light (stereoisomers). With regard to stereoisomers, the compounds of the disclosure may have one or more asymmetric carbon atom and may occur as racemates, racemic mixtures and as individual enantiomers or diastereomers. Individual isomers of the compounds of the disclosure may, for example, be substantially free of other isomers, or may be admixed, for example, as racemates or with all other, or other selected, isomers. If the compound contains a double bond, the substituent may be in the E or Z configuration or cis or trans configuration or mixtures of any of the foregoing, unless specified otherwise. Disclosed assay results may reflect the data collected for the racemic form, the enantiomerically pure form, or any other form in terms of stereochemistry or constitution (e.g., geometric or positional isomers).

The compounds of the disclosure may contain asymmetric or chiral centers, and, therefore, exist in different stereoisomeric forms. The term "stereoisomers" may refer to the set of compounds which have the same number and type of atoms and share the same bond connectivity between those atoms, but differ in three dimensional structure. The term "stereoisomer" may refer to any member of this set of compounds. For instance, a stereoisomer may be an enantiomer or a diastereomer. It is intended that all stereoisomeric forms of the compounds of the disclosure as well as mixtures thereof, including racemic mixtures, form part of the present disclosure.

The term "enantiomers" may refer to a pair of stereoisomers which are non-superimposable mirror images of one another. The term "enantiomer" may refer to a single member of this pair of stereoisomers. The term "racemic" may refer to a 1:1 mixture of a pair of enantiomers. Each compound herein disclosed may include all the enantiomers (which may exist even in the absence of asymmetric carbons) that conform to the general structure of the compound, unless the stereochemistry is specifically indicated. The compounds may be in a racemic or enantiomerically pure form, or any other form in terms of stereochemistry. The chiral centers of the present disclosure may have the S or R configuration as defined by the IUPAC 1974 Recommendations. In some examples presented, the synthetic route may produce a single enantiomer or a mixture of enantiomers. In some embodiments of the disclosure, the compounds of the disclosure are enantiomers. In some embodiments, the compounds of the disclosure are the (S)-enantiomer. In some embodiments, the compounds of the disclosure are the (R)-enantiomer. In some embodiments, the compounds of the disclosure may be (+) or (−) enantiomers.

The term "diastereomers" may refer to the set of stereoisomers which cannot be made superimposable by rotation around single bonds. For example, cis- and trans- double bonds, endo- and exo-substitution on bicyclic ring systems, and compounds containing multiple stereogenic centers with different relative configurations may be considered to be diastereomers. The term "diastereomer" may refer to any member of this set of compounds. In some examples presented, the synthetic route may produce a single diastereomer or a mixture of diastereomers. The disclosure may include diastereomers of the compounds described herein.

Optically active (+) and (−) or (R)- and (S)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC).

Compounds of the disclosure may exist in their tautomeric form (for example, as an amide or imino ether). All such tautomeric forms are contemplated herein as part of the present disclosure. Also, for example, all keto-enol and imine-enamine forms of the compounds are included in the present disclosure. The structures have been graphically represented as one form throughout this document, but it is noted that the tautomers can exist in an equilibrium. "Tautomer" may refer to a proton shift from one atom of a molecule to another atom of the same molecule. The present disclosure may include tautomers of any said compounds.

The compounds described herein further include all pharmaceutically acceptable isotopically labeled compounds. An "isotopically" or "radio-labeled" compound may be a compound where one or more atoms are replaced or substituted by an atom having an atomic mass or mass number different from the atomic mass or mass number tyl)ically found in nature (i.e., naturally occurring). For example, in some embodiments, in the compounds described herein hydrogen atoms are replaced or substituted by one or more deuterium or tritium. Certain isotopically labeled compounds of this disclosure, for example, those incorporating a radioactive isotope, may be useful in drug and/or substrate tissue distribution studies. The radioactive isotopes tritium, i.e., $^3H$, and carbon 14, i.e., $^{14}C$, may be particularly useful for this purpose in view of their ease of incorporation and ready means of detection. Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. In some embodiments, the compound comprises at least one deuterium atom. For example, one or more hydrogen atoms in a compound of the present disclosure can be replaced or substituted by deuterium. In some embodiments, the compound comprises two or more deuterium atoms. In some embodiments, the compound comprises 1, 2, 3, 4, 5, 6, 7, 8, 9, 10, 11 or 12 deuterium atoms. Suitable isotopes that may be incorporated in compounds described herein include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$, and $^{131}$I. Substitution with positron emitting isotopes, such as $^{11}$C, $^{18}$F, $^{15}$O, and $^{13}$N, can be useful in Positron Emission Topography (PET) studies.

Isotopically labelled compounds of the compounds disclosed herein can generally be prepared by following procedures analogous to those disclosed in the Schemes and/or in the Examples herein, by substituting an appropriate isotopically labelled reagent for a non -isotopically labelled reagent.

The disclosure herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure may include compounds produced by a process comprising administering a compound of this disclosure to a subject, e.g., a mammal, for a period of time sufficient to yield a metabolic product thereof. Such products are typically identified by administering a radiolabeled compound of the disclosure in a detectable dose to subject, such as rat, mouse, guinea pig, monkey, or to human, allowing sufficient time for metabolism to occur, and isolating its conversion products from the urine, blood or other biological samples.

Preparation of Compounds

The compounds of the present disclosure can generally be prepared in a number of ways well known to those skilled in the art of organic synthesis. By way of example, compounds of the present disclosure can be synthesized using the methods described herein, together with synthetic methods known in the art of synthetic organic chemistry, or variations thereof as appreciated by those skilled in the art. Compounds of the present disclosure can be synthesized by following the steps outlined in General Scheme 1, which comprises exemplary steps 110-200, and exemplary intermediates 102-190. Starting materials are either commercially available or made by known procedures in the reported literature or as illustrated. Methods may include but are not limited to those methods described herein.

In addition, the compounds described herein may also be synthesized using the methods described in Examples 21-62 for particular compounds, but which may be adapted for the synthesis of additional compounds as described herein.

It is understood that one skilled in the art may be able to make these compounds by similar methods or by combining other methods known to one skilled in the art. It is also understood that one skilled in the art would be able to make, in a similar manner as described herein, other compounds of formula (I), (I-A), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X) or a pharmaceutically acceptable salt, solvate, stereoisomer, or tautomer of any of the foregoing, not specifically illustrated herein by using the appropriate starting components and modifying the parameters of the synthesis as needed.

General Scheme 1

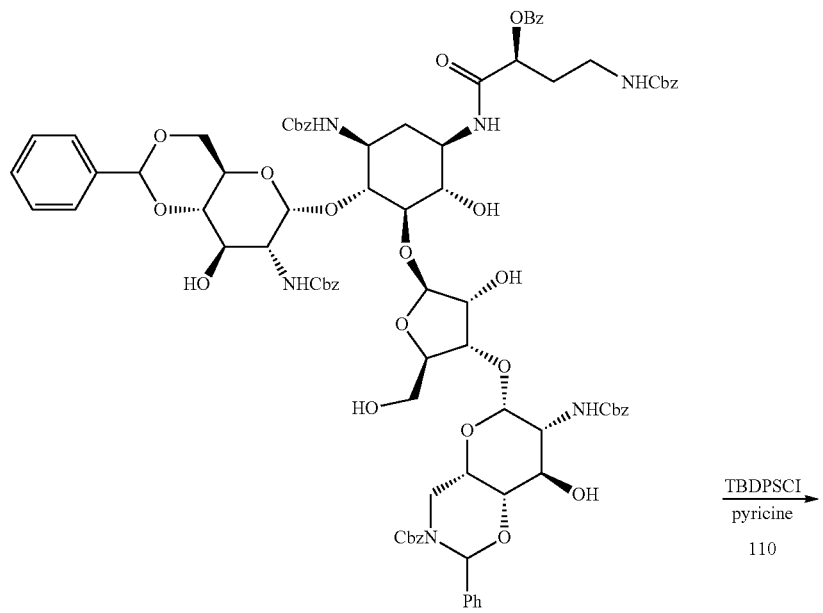

-continued
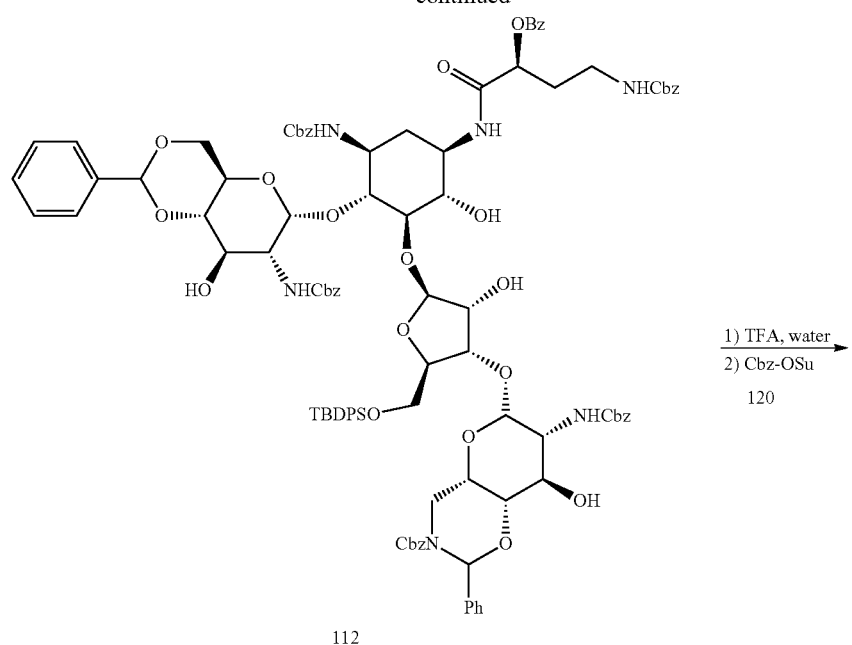
112
1) TFA, water
2) Cbz-OSu
120
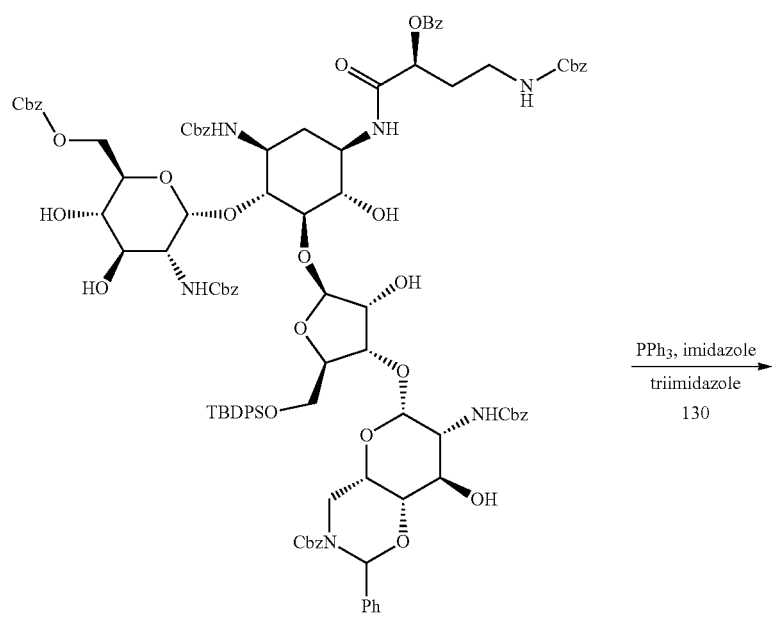
122
PPh₃, imidazole
triimidazole
130

-continued
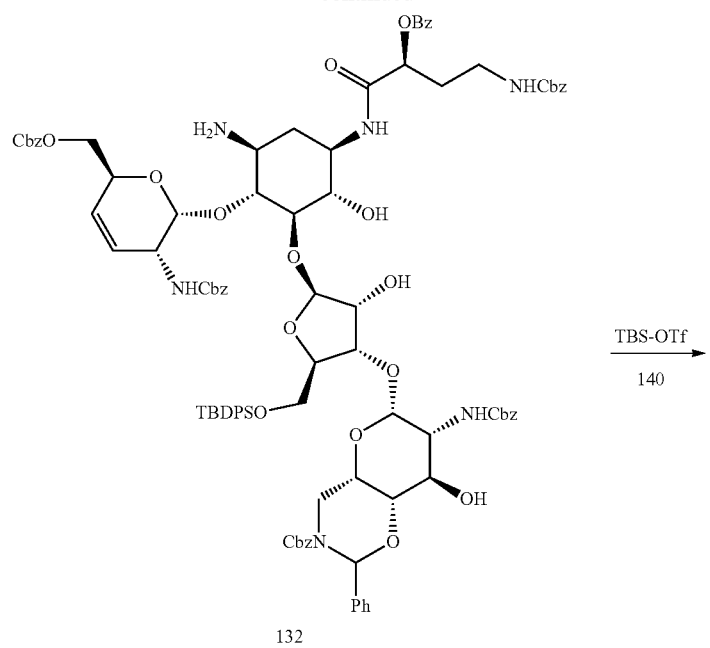
132
TBS-OTf
---------→
140
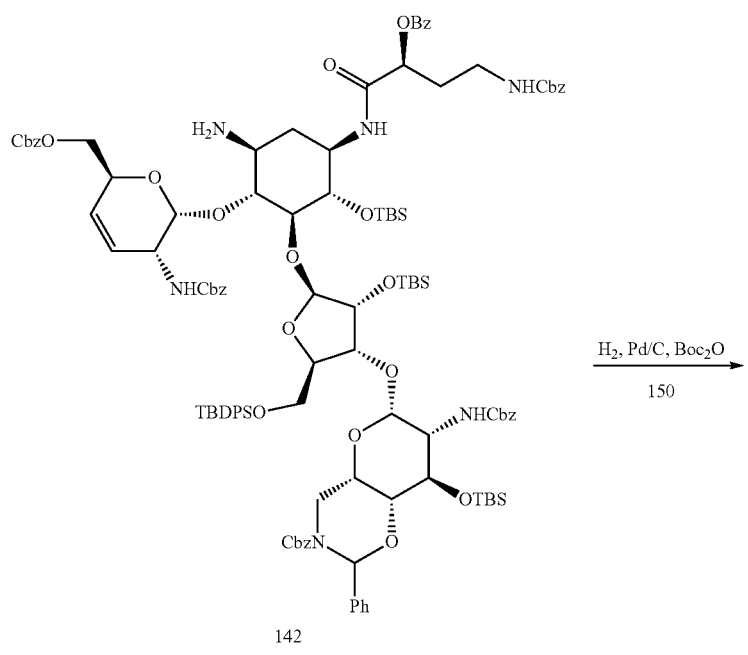
142
H₂, Pd/C, Boc₂O
-------------------→
150

-continued
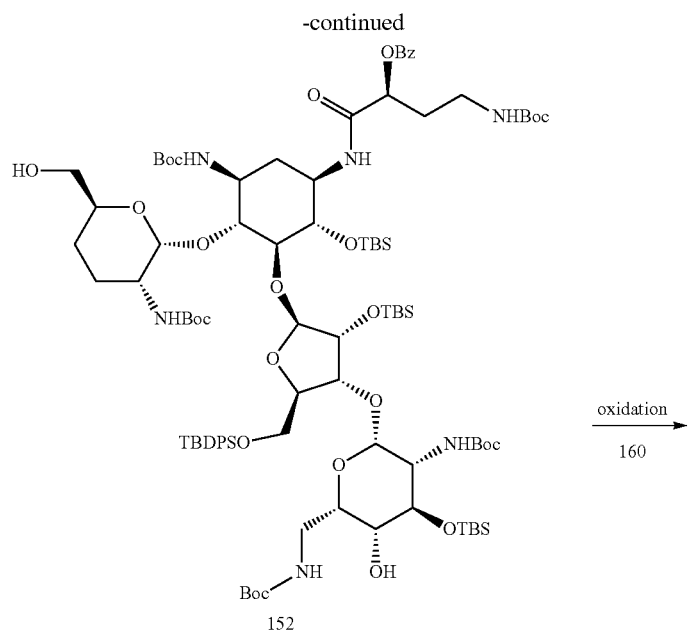
152
oxidation
160
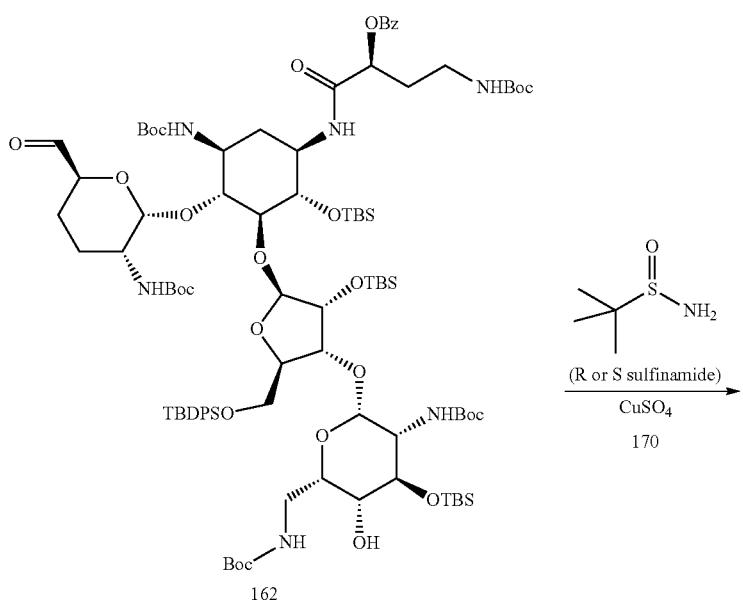
162
(R or S sulfinamide)
CuSO₄
170

-continued
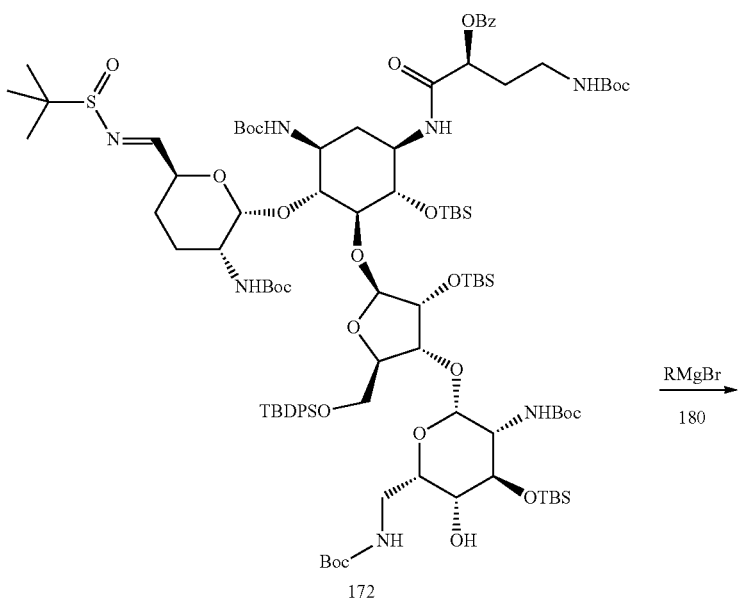
$\xrightarrow{\text{RMgBr}}$
180
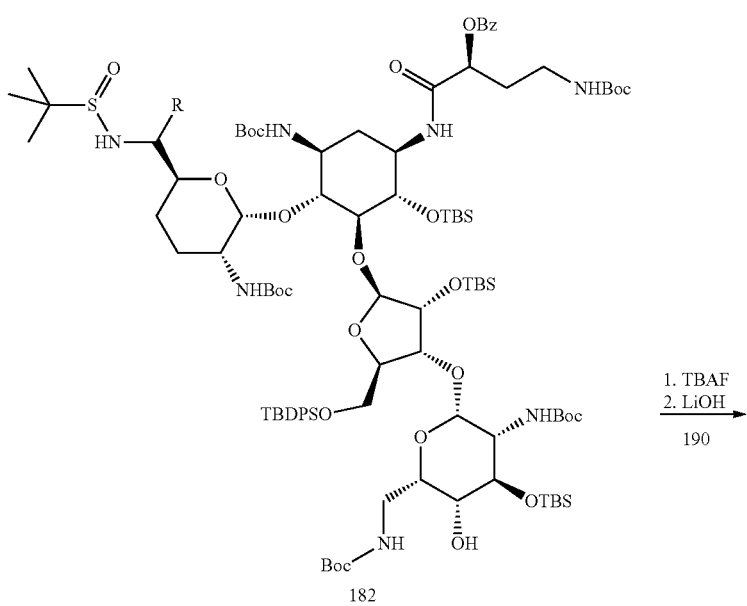
1. TBAF
2. LiOH
190

-continued

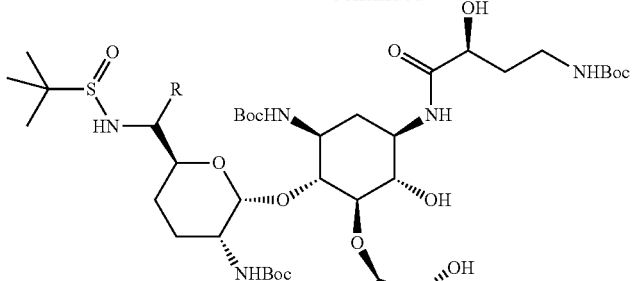

192

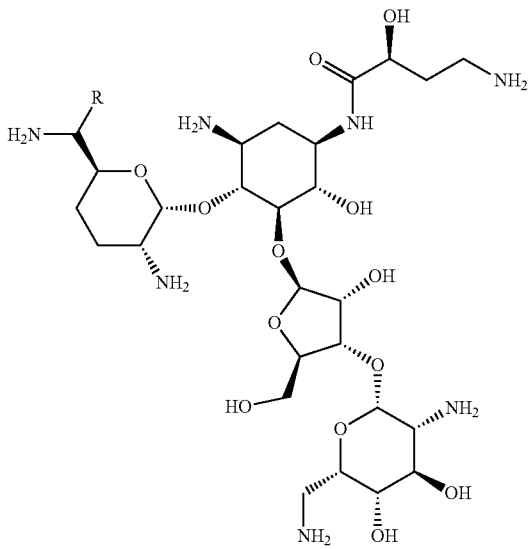

202 wherein R is $R^2$ or $R^3$ as defined herein for formula (I).

A general manner for preparing compounds of formula (I), (I-A), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X) or a pharmaceutically acceptable salt, solvate, stereoisomer, or tautomer of any of the foregoing, is outlined in General Scheme 1. In step 110, starting compound 102 is reacted with tert-butyl(chloro)diphenylsilane (TBDPSCl) in the presence of pyridine to yield compound 112. Compound 112 is then reacted with trifluoroacetic acid (TFA) in the presence of water, followed by N-(benzyloxycarbonyloxy)succinimide (Cbz-OSu) to produce compound 122 in step 120. In step 130, compound 122 is reacted with triphenyl phosphine (PPh3) in the presence of imidazole and triiodoimidazole to produce compound 132. Next, compound 132 undergoes protection with tert-butyldimethylsilyl trifluoromethanesulfonate (TBS-OTf) in step 140 to produce compound 142, which subsequently undergoes hydrogenation with $H_2$ in the presence of Pd/C and di-tert-butyl dicarbonate ($Boc_2O$) in step 150 to produce compound 152. Compound 152 is oxidized, for example in Dess Martin reaction to produce compound 162 in step 160. Compound 162 undergoes reaction with a sulfinamide in the presence of $CuSO_4$ in step 170 to produce compound 172, which then reacts in the presence of R-MgBr to produce compound 182 in step 180. In compound R-MgBr, R may be $R^2$ or $R^3$ as defined herein for formula (I), (I-A), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X). In step 190, reaction with tetra-n-butylammonium fluoride (TBAF) followed by LiOH produces compound 192 from compound 182. In the final step 202, compound 192 reacts with trifluoroacetic acid (TFA) in dichloromethane (DCM) to produce compound 202, or a pharmaceutically acceptable salt, solvate, or tautomer thereof, which is an example of a compound of formula (I), (I-A), (I-Ai), (I-Aii), (I-B), (I-Bi), (I-Bii), (II), (II-A), (III), (III-A), (IV), (IV-X), (IVa), (IVa- X), (V), (V-X), (VI), (VI-X), (VIIa), (VIIa-X), (VIIb), and (VIIb-X) wherein R is $R^2$ or $R^3$ as described herein.

General Scheme 1 is not intended to limit any aspects of the disclosure. It should be understood that some embodiments of any of the steps of General Scheme 1, additional reagents, solvents, or combinations thereof, are present. For example, in certain embodiments, one or more of the steps of General Scheme 1 occurs in the presence of one or more solvents, or in the presence of a different solvent. In certain embodiments, one or more additional steps are followed to produce a pharmaceutically acceptable salt or solvate. In certain embodiments, one or more steps of General Scheme 1 occurs in the presence of a different reagent, or is omitted. For example, oxidation may be performed using different reagents than in a Dess Martin reaction. Hydrogenation may be performed using hydrogenation catalyst other than Pd/C. In other embodiments, a stereoisomer of the compound 202, or a pharmaceutically acceptable salt, solvate, or tautomer thereof, is produced by using a stereoisomer of one of the starting materials or intermediates.

It should further be understood that while General Scheme 1 depicts a compound of formula (I-A), the scheme may generally be followed to produce other compounds of formula (I), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of the foregoing. For example, compounds of formula (I), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of the foregoing, may be produced according to General Scheme 1.

It should be further understood that in the synthesis of one or more compounds of formula (I), (I-A), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or a pharmaceutically acceptable salt, solvate, stereoisomer, or tautomer of any of these, one or more hydroxyl groups, amino groups, or additional functional groups in the compound or in an intermediate may be protected with a protecting group during one or more steps. Protecting groups are tyl)ically used selectively and/or orthogonally to protect sites during reactions at other reactive sites and can then be removed to leave the unprotected group as is or available for further reactions. Protecting groups as known in the art are described generally in Greene and Wuts, *Protective Groups in Organic Synthesis*, 3rd edition, John Wiley & Sons, New York (1999). Groups can be selectively incorporated into aminoglycosides of the disclosure as precursors. For example, an amino group can be placed into a compound of the disclosure as an azido group that can be chemically converted to the amino group at a desired point in the synthesis. Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 172.

Furthermore, compounds of the disclosure which exist in free base or acid form can be converted to their pharmaceutically acceptable salts by treatment with the appropriate inorganic or organic base or acid by methods known to one skilled in the art. Salts of the compounds of the disclosure can be converted to their free base or acid form by standard techniques.

Methods of Treating

This disclosure features methods of and uses for treating a bacterial infection comprising administering to a subject in need thereof a therapeutically effective amount of one or more compounds of the disclosure, or pharmaceutically acceptable salts, solvates, stereoisomers, or tautomers thereof, or a therapeutically effective amount of a pharmaceutical composition comprising one or more compounds of the disclosure, or pharmaceutically acceptable salts, solvates, stereoisomers, or tautomers thereof.

In certain embodiments of the methods and uses of the disclosure, the one or more compounds are compounds (or pharmaceutical composition comprising one or more compounds) of formula (I), (I-A), (I-Ai), (I-Aii), (I-B), (I-Bi), (I-Bii), (II), or (II-A), or pharmaceutically acceptable salts, solvates, stereoisomers, or tautomers of any of the foregoing. In certain embodiments of the methods and uses of the disclosure, the one or more compounds are compounds (or pharmaceutical composition comprising one or more compounds) of formula (I), (I-A), (I-Ai), (I-Aii) (I-B), (I-Bi), or (I-Bii), or pharmaceutically acceptable salts, solvates, stereoisomers, or tautomers of any of the foregoing. In certain embodiments of the methods and uses of the disclosure, the one or more compounds are compounds (or pharmaceutical composition comprising one or more compounds) of formula (II) or (II-A), or pharmaceutically acceptable salts, solvates, stereoisomers, or tautomers of any of the foregoing. In certain embodiments of the methods and uses of the disclosure, the one or more compounds are compounds (or pharmaceutical composition comprising one or more compounds) of formula (III) or (III-A), or pharmaceutically acceptable salts, solvates, stereoisomers, or tautomers of any of the foregoing. In certain embodiments of the methods and uses of the disclosure, the one or more compounds are compounds (or pharmaceutical composition comprising one or more compounds) of formula (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of the foregoing.

Provided herein are methods of using compounds of formula (I), (I-A), (I-Ai), (I -Aii), (I-B), (1-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or a pharmaceutically acceptable salt, solvate, stereoisomer, or tautomer of any of these. In particular, provided is a method of treating a bacterial infection in a subject in need thereof, comprising administering to the subject in need thereof a therapeutically effective amount of one or more compounds of formula (I), (I-A), (I -Ai), (I-Aii), (I-B), (I-Bi), (I-Bii), (II), (II-A), (III), (III-A), (IV), (IV-X), (IVa), (IVa-X), (V), (V -X), (VI), (VI-X), (VIIa), (VIIa-X), (VIIb), and (VIIb-X), or pharmaceutically acceptable salts, solvates, stereoisomers, or tautomers of any of the foregoing. Also provided is a method of treating a bacterial infection in a subject in need thereof, comprising administering to the subject in need thereof a therapeutically effective amount of a pharmaceutical composition comprising one or more compounds of formula (I), (I-A), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of the foregoing, and a pharmaceutically acceptable excipient. In some embodiments, the subject is a mammal. In certain such embodiments, the mammal is a human.

In yet a further aspect, provided herein is the use of one or more compounds described herein, or pharmaceutically acceptable salts, solvates, stereoisomers, or tautomers thereof, in the manufacture of a medicament for treating a bacterial infection in a subject in need thereof.

In still a further aspect, provided herein is one or more compounds described herein, or pharmaceutically acceptable salts, solvates, stereoisomers, or tautomers thereof, for use in a method of treating a bacterial infection in a subject in need thereof.

In yet a further aspect, provided herein is the use of one or more pharmaceutical compositions of the disclosure in the manufacture of a medicament for treating a bacterial infection in a subject in need thereof.

In still a further aspect, provided herein is one or more pharmaceutical compositions of the disclosure for use in a method of treating a bacterial infection in a subject in need thereof.

The disclosure provides for one or more compounds of formula (I), (I-A), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of the foregoing, for use as a medicament. The disclosure provides for one or more compounds of formula (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of the foregoing, for use as a medicament. The disclosure also provides for a pharmaceutical composition comprising one or more compounds of formula (I), (I-A), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of the foregoing, for use as a medicament. The disclosure also provides for a pharmaceutical composition comprising one or more compounds of formula (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of the foregoing, for use as a medicament.

The disclosure provides for use of one or more compounds described herein, or pharmaceutically acceptable salts, solvates, stereoisomers, or tautomers thereof, to treat a bacterial infection.

The disclosure provides for use of a pharmaceutical composition disclosed herein to treat a bacterial infection.

One or more of the disclosed compounds, or pharmaceutically acceptable salts, solvates, stereoisomers, or tautomers thereof, or pharmaceutical compositions of the disclosure can be administered or used in therapeutically effective amounts to treat a bacterial infection in a subject.

In some embodiments of the methods or uses of the disclosure, the subject may be a mammal. In some embodiments of the methods or uses of the disclosure, the subject is a human.

Bacterial infections susceptible to treatment according to the present disclosure may include primary infections and co-infections caused by a species of bacteria and one or more additional infectious agents such as, for example, bacteria, virus, parasite and fungus.

In some embodiments of the methods and uses of the disclosure, the bacterial infection may be a Gram-positive or Gram-negative bacterial infection. In some embodiments of the methods and uses of the disclosure, the bacterial infection may be an infection of aerobic or anaerobic bacteria. In some embodiments of the methods and uses of the disclosure, the bacterial infection may be an infection of one or more species selected from the group consisting of *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella, Francisella, Yersinia, Corynebacterium, Moraxella*, and *Enterococcus*.

In some embodiments, one or more compounds, or pharmaceutically acceptable salts, solvates, stereoisomers, or tautomers thereof, or pharmaceutical compositions of the present disclosure may be useful in the uses or methods disclosed herein for treating a bacterial infection caused by aerobic or anaerobic bacteria.

Compounds, or pharmaceutically acceptable salts, solvates, stereoisomers, or tautomers thereof, and pharmaceutical compositions of the present disclosure may possess antibacterial activity against a wide spectrum of Gram positive and Gram negative bacteria, as well as Enterobacteria and anaerobes. Representative susceptible organisms may include those Gram positive, Gram negative, aerobic, and anaerobic organisms whose growth can be inhibited by the compounds of the disclosure such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella, Francisella, Yersinia, Corynebacterium, Moraxella, Enterococcus*, and other organisms.

In some embodiments, one or more compounds or pharmaceutically acceptable salts, solvates, stereoisomers, or tautomers thereof, or pharmaceutical compositions of the present disclosure may be useful in the uses or methods disclosed herein for treating a variety of bacterial infections including, but not limited to, bacterial infections caused by *Staphylococcus* sp., *Lactobacillus* sp., *Streptococcus* sp., *Sarcina* sp., *Escherichia* sp., *Enterobacter* sp., *Klebsiella* sp., *Pseudomonas* sp., *Acinetobacter* sp., *Mycobacterium* sp., *Proteus* sp., *Campylobacter* sp., *Citrobacter* sp., *Nisseria* sp., *Baccillus* sp., *Bacteroides* sp., *Peptococcus* sp., *Clostridium* sp., *Salmonella* sp., *Shigella* sp., *Serratia* sp., *Haemophilus* sp., *Brucella* sp., *Francisella* sp., *Yersinia* sp., *Corynebacterium* sp., *Moraxella* sp., or *Enterococcus* sp.

In some embodiments, one or more compounds or pharmaceutically acceptable salts, solvates, stereoisomers, or tautomers thereof, or pharmaceutical compositions of the present disclosure may be useful in the uses or methods disclosed herein for treating a variety of bacterial infections including, but not limited to, bacterial infections caused by *Escherichia coli, Klebsiella* sp., *Klebsiella pneumoniae, Klebsiella oxytoca, Enterobacter* sp., *Enterobacter cloacae, Enterobacter aerogenes, Citrobacter* sp., *Citrobacter freundii, Citrobacter koseri, Proteus mirabilis, Bacillus anthraces, P. aeruginosa, A. baumannii, Proteus vulgaris*, or *Yersinia pestis*.

In some embodiments, one or more compounds or pharmaceutically acceptable salts, solvates, stereoisomers, or tautomers thereof, or pharmaceutical compositions of the present disclosure may be useful in the uses or methods disclosed herein for treating a bacterial infection caused by Gram-negative bacteria. In certain such embodiments, the Gram-negative bacteria may include, but are not limited to, *Escherichia* sp., *Enterobacter* sp., *Klebsiella* sp., *Pseudomonas* sp., *Acinetobacter* sp., *Proteus* sp., *Campylobacter* sp., *Citrobacter* sp., *Nisseria* sp., *Bacteroides* sp., *Salmonella* sp., *Shigella* sp., *Serratia* sp., *Haemophilus* sp., *Brucella* sp., *Francisella* sp., *Yersinia* sp., or *Moraxella* sp.

In some embodiments, one or more compounds or pharmaceutically acceptable salts, solvates, stereoisomers, or tautomers thereof, or pharmaceutical compositions of the present disclosure may be useful in the uses or methods disclosed herein for treating a bacterial infection caused by Gram-positive bacteria. In certain such embodiments, the Gram-positive bacteria may include, but are not limited to, *Staphylococcus* sp., *Lactobacillus* sp., *Streptococcus* sp., *Sarcina* sp., *Baccillus* sp., *Peptococcus* sp., *Clostridium* sp., *Corynebacterium* sp., or *Enterococcus* sp.

In some embodiments, one or more compounds or pharmaceutically acceptable salts, solvates, stereoisomers, or tautomers thereof, or pharmaceutical compositions of the present disclosure may be useful in the uses or methods disclosed herein for treating a bacterial infection caused by Methicillin-resistant *Staphylococcus aureus* (MRSA).

In some embodiments, one or more compounds or pharmaceutically acceptable salts, solvates, stereoisomers, or tautomers thereof, or pharmaceutical compositions of the present disclosure may be useful in the uses or methods disclosed herein for treating bacterial infections caused by *Enterobacteriaceae*.

In some embodiments, one or more compounds or pharmaceutically acceptable salts, solvates, stereoisomers, or tautomers thereof, or pharmaceutical compositions of the present disclosure may be useful in the uses or methods disclosed herein for treating bacterial infections caused by KPC-producing carbapenem-resistant *Enterobacteriaceae* (CRE).

In some embodiments, one or more compounds or pharmaceutically acceptable salts, solvates, stereoisomers, or tautomers thereof, or pharmaceutical compositions of the present disclosure may be useful in the uses or methods disclosed herein for treating bacterial infections caused by multidrug resistant (MDR) bacteria.

In some embodiments, one or more compounds or pharmaceutically acceptable salts, solvates, stereoisomers, or tautomers thereof, or pharmaceutical compositions of the present disclosure may be useful in the uses or methods disclosed herein for treating a bacterial infection caused by fermentative or non-fermentative Gram-negative bacteria. Examples of fermentative or non-fermentative Gram-negative bacteria include but are not limited to, *Pseudomonas aeruginosa; Stenotrophomonas maltophila; Burkholderia cepacia; Alcaligenes xylosoxidans; Enterobacteriaceae; Haemophilus; Franciscellaceae* (e.g., *Franciscella tularensis*); *Neisseria* species; and *Enterobacteriaceae*, such as *Serratia, Proteus, Klebsiella, Enterobacter, Citrobacter, Salmonella, Providencia, Yersinia* (e.g., *Yersinia pestis*), *Morganella, Cedecea, Edwardsiella* species, *Acinetobacter*, and *Escherichia coli*. In some embodiments, the Gram-negative bacteria is *Pseudomonas aeruginosa, Stenotrophomonas maltophila, Burkholderia cepacia, Alcaligenes xylosoxidans, Enterobacteriaceae, Haemophilus, Franciscellaceae* or a *Neisseria* species.

In some embodiments, one or more compounds, or pharmaceutically acceptable salts, solvates, stereoisomers, or tautomers thereof, or pharmaceutical compositions of the disclosure may be useful in the uses or methods disclosed herein for treating multidrug-resistant biothreat pathogens. In certain such embodiments, the biothreat pathogens are Gram-negative bacteria.

In some embodiments, one or more compounds, or pharmaceutically acceptable salts, solvates, stereoisomers, or tautomers thereof, or pharmaceutical compositions of the disclosure may be useful in the uses or methods disclosed herein for treating diseases or conditions caused by a bacterial infection, including, but not limited to, skin infections; pneumonia; sepsis; respiratory tract infections (e.g., lower respiratory tract or upper respiratory tract infections); lung infection in cystic fibrosis patients; acute exacerbation of chronic bronchitis; community acquired pneumonia; nosocomial pneumonia (including ventilator-associated pneumonia (VAP)); hospital or community acquired infections caused by Gram-negative bacteria; diseases of the upper airways; diffuse panbronchiolitis; tonsillitis; pharyngitis; acute sinusitis and otitis including mastoiditis; urinary tract and genital infections, for example, complicated urinary tract infections, cystitis, resistant or relapsing cystitis, urethritis, pyelonephritis, acute pyelonephritis, endometritis, prostatitis, salpingitis, and epididymitis; ocular infections such as conjunctivitis, corneal ulcer, iridocyclitis and post-operative infection in radial keratotomy surgery patients; blood infections, for example septicaemia or bacteremia; infections of the skin and soft tissues, for example infective dermatitis, infected wounds, infected burns, phlegmon, folliculitis and impetigo; bone and joint infections such as osteomyelitis and septic arthritis; gastrointestinal infections, for example dysentery, enteritis, colitis, necrotising enterocolitis and anorectal infections; intraabdominal infections, including, but not limited to, complicated intraabdominal infections, typhoid fever, infectious diarrhea, peritonitis with appendicitis, pelviperitonitis, and intra-abdominal abscesses; infections in the oral region, for example infections after dental operations; other infections, for example, meliodosis, infectious endocarditis, sexually transmitted diseases caused by Gram-negative or Gram-positive bacteria, hepatic abscesses, cholecystitis, cholangitis, mastitis as well as meningitis, and infections of the nervous systems. In some embodiments, one or more compounds or pharmaceutical compositions of the disclosure may be useful in the uses or methods disclosed herein for treating complicated intraabdominal infections. In some embodiments, one or more compounds or pharmaceutical compositions of the disclosure may be useful in the uses or methods disclosed herein for treating complicated urinary tract infections. In some embodiments, one or more compounds or pharmaceutical compositions of the disclosure may be useful in the uses or methods disclosed herein for treating resistant or relapsing cystitis. In some embodiments, one or more compounds or pharmaceutical compositions of the disclosure may be useful in the uses or methods disclosed herein for treating acute pyelonephritis. In some embodiments, one or more compounds or pharmaceutical compositions of the disclosure may be useful in the uses or methods disclosed herein for treating bacteremia. In some embodiments, one or more compounds or pharmaceutical compositions of the disclosure may be useful in the uses or methods disclosed herein for treating nosocomial pneumonia.

One or more compounds of the disclosure, such as compounds of formula (I), (I-A), (I-Ai), (I-Aii), (I-B), (1-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of these, may be administered in a therapeutically effective amount, which will vary depending upon a variety of factors including: the activity of the specific compound employed; the metabolic stability and length of action of the compound; the age, body weight, general health, sex, and diet of the subject; the mode and time of administration; the rate of excretion; the drug combination; the severity of the particular disorder or condition; and the subject undergoing therapy.

One or more compounds of the disclosure, such as compounds of formula (I), (I -A), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of these, may also be administered simultaneously with, prior to, or after administration of one or more other therapeutic agents. Such combination therapy may include administration of a single pharmaceutical dosage formulation that contains one or more compounds of the disclosure, or pharmaceutically acceptable salts, solvates, stereoisomers, or tautomers thereof, and one or more additional active agents, as well as administration of one or more compounds of the disclosure, or pharmaceutically acceptable salts, solvates, stereoisomers, or tautomers thereof, and each active agent in its own separate pharmaceutical dosage formulation. For example, one or more compounds of the disclosure, or pharmaceutically acceptable salts, solvates, stereoisomers, or tautomers thereof, and the other active agent can be administered to the subject together in a single oral dosage composition such as a tablet or capsule, or each agent administered in separate oral dosage formulations. Where separate dosage formulations are used, the one or more compounds of the disclosure, or pharmaceutically acceptable salts, solvates, stereoisomers, or tautomers thereof, and one or more additional active agents can be administered at essentially the same time, e.g., concurrently, or at separately staggered times, e.g., sequentially; combination therapy is understood to include all these regimens.

A "patient" or "subject" may encompass both mammals and non-mammals. Examples of mammals may include, but are not limited to, any member of the class Mammalia: humans; non-human primates such as chimpanzees, monkeys, baboons, or rhesus monkeys, as well as other apes and monkey species; farm animals such as cattle, horses, sheep, goats, and swine; companion animals such as rabbits, dogs, and cats; laboratory animals including rodents, such as rats, mice and guinea pigs; and the like. Examples of non-mammals include, but are not limited to, birds, fish, and the like. "Patient" or "subject" may include both human and animals. In some embodiments, the patient or subject is a human.

The terms "administered," "administration," or "administering" as used in this disclosure may refer to either directly administering one or more compounds, and pharmaceutically acceptable salts, solvates (e.g., hydrates), isomers (e.g., stereoisomers), and tautomers thereof, or pharmaceutical compositions of the disclosure to a subject.

The terms "effective amount" or "therapeutically effective amount" when used in connection with one or more compounds or pharmaceutical compositions may refer to a sufficient amount of the one or more compounds or pharmaceutical compositions to provide the desired biological result. That result can be reduction and/or alleviation of the signs, symptoms, or causes of a disorder, or any other desired alteration of a biological system. For example, an "effective amount" for therapeutic use may be the amount of the pharmaceutical composition comprising one or more compounds, or pharmaceutically acceptable salts, solvates (e.g., hydrates), isomers (e.g., stereoisomers), and tautomers thereof, as disclosed herein required to provide a clinically significant decrease in a disorder. An appropriate "effective amount" in any individual case may be determined by one of ordinary skill in the art using routine experimentation.

"Treating" or "treatment" as used herein may refer to the treatment of the disease or condition of interest in a subject, e.g., a mammal or a human, having the disease or condition of interest, and may include:
 (i) preventing the disease or condition from occurring in a subject, in particular, when such subject is predisposed to the condition but has not yet been diagnosed as having it;
 (ii) inhibiting the disease or condition, e.g., arresting its development;
 (iii) relieving the disease or condition, e.g., causing regression of the disease or condition; or
 (iv) relieving the symptoms resulting from the disease or condition, e.g., relieving pain without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The terms "antibacterial agent," "antibiotic," or "antibacterial compound" are used interchangeably herein and may refer to agents or compounds that have either bactericidal or bacteriostatic activity. The term "inhibiting the growth" may indicate that the rate of increase in the numbers of a population of a particular bacterium is reduced. Thus, the term may include situations in which the bacterial population increases but at a reduced rate, as well as situations where the growth of the population is stopped, as well as situations where the numbers of the bacteria in the population are reduced or the population even eliminated. The activity of antibacterial agents or compounds is not necessarily limited to bacteria but may also encompass general antimicrobial activity against parasites or fungi or general antiviral activity against viruses.

Pharmaceutical Compositions of the Disclosure

For the purposes of administration, the compounds of the present disclosure may be administered as a raw chemical or may be formulated as pharmaceutical compositions. Pharmaceutical compositions of the present disclosure comprise one or more compounds of formula (I), (I-A), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of these, and a pharmaceutically acceptable carrier. In some embodiments, pharmaceutical compositions of the present disclosure comprise one or more compounds of formula (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of these, and a pharmaceutically acceptable carrier. The one or more compounds of formula (I), (I-A), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa -X), (VIIb), and (VIIb-X), or pharmaceutically acceptable salts, solvates, stereoisomers, or tautomers of any of these, are present in the composition in an amount that is effective to treat a particular disease or condition of interest—for example, in an amount sufficient to treat a bacterial infection, and generally with acceptable toxicity to the subject. In some embodiments, the one or more compounds of formula (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of these, are present in the composition in an amount that is effective to treat a particular disease or condition of interest. The antibacterial activity of compounds of formula (I), (I-A), (I-Ai), (I-Aii), (I-B), (I-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of these, can be determined by one skilled in the art, for example, as described in the Examples herein. Appropriate concentrations and dosages can be readily determined by one skilled in the art.

Administration of one or more compounds of the disclosure, such as compounds of formula (I), (I-A), (I-Ai), (I-Aii), (I-B), (1-Bi), (I-Bii), (II), (II-A), (III), (III-A), (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of these, in pure form or in an appropriate pharmaceutical composition can be carried out via any of the accepted modes of administration of agents for serving similar utilities. In some embodiments, the one or more compounds of the disclosure administered are compounds of formula (IV), (IV-X), (IVa), (IVa-X), (V), (V-X), (VI), (VI-X), (VIIa), (VIIa-X), (VIIb), and (VIIb-X), or pharmaceutically acceptable salts, solvates, stereoisomers, or tautomers of any of the foregoing, in pure form or in an appropriate pharmaceutical composition.

The pharmaceutical compositions of the disclosure can be prepared by combining one or more compounds of the disclosure, or pharmaceutically acceptable salts, solvates, stereoisomers, or tautomers thereof, with an appropriate pharmaceutically acceptable carrier, and may be formulated into preparations in solid, semi solid, liquid or gaseous forms, such as tablets, capsules, powders, granules, ointments, solutions, suppositories, injections, inhalants, gels, microspheres, and aerosols. Typical routes of administering such pharmaceutical compositions may include, without limitation, oral, topical, transdermal, inhalation, parenteral, sublingual, buccal, rectal, vaginal, and intranasal. The term parenteral as used herein may include subcutaneous injections, intravenous, intramuscular, intrasternal injection or infusion techniques. Pharmaceutical compositions of the disclosure can be formulated so as to allow the active ingredients contained therein to be bioavailable upon administration of the composition to a subject. Compositions that will be administered to a subject or patient take the form of one or more dosage units, where for example, a tablet may be a single dosage unit, and a container of one or more compounds of the disclosure, or pharmaceutically acceptable salts, solvates, stereoisomers, or tautomers thereof, in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000).

A pharmaceutical composition of the disclosure may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which may be useful in, for example, inhalatory administration.

When intended for oral administration, pharmaceutical compositions of the present disclosure typically are either solid or liquid form, where semi solid, semi liquid, suspension and gel forms may be included within the forms considered herein as either solid or liquid.

As a solid composition for oral administration, the pharmaceutical compositions may be formulated into a powder, granule, compressed tablet, pill, capsule, chewing gum, wafer or the like form. Such a solid composition will tyl)ically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials disclosed herein, a liquid carrier such as polyethylene glycol or oil.

Pharmaceutical compositions of the disclosure may be in the form of a liquid, for example, an elixir, syrup, solution, emulsion or suspension. The liquid may be for oral administration or for delivery by injection, as two examples. When intended for oral administration, pharmaceutical compositions of the disclosure tyl)ically contain, in addition to one or more compounds of the disclosure, or pharmaceutically acceptable salts, solvates, stereoisomers, or tautomers thereof, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Liquid pharmaceutical compositions of the disclosure, whether they be solutions, suspensions or other like form, may include one or more of the following adjuvants: sterile diluents such as water for injection, saline solution, physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. Parenteral preparations can be enclosed in ampoules, disposable syringes or multiple dose vials made of glass or plastic. In some embodiments, the adjuvant is physiological saline. In some embodiments, the injectable pharmaceutical composition is sterile.

A liquid pharmaceutical composition of the disclosure intended for either parenteral or oral administration should contain an amount of one or more compounds of the disclosure, or pharmaceutically acceptable salts, solvates, stereoisomers, or tautomers thereof, such that a suitable dosage will be obtained.

Pharmaceutical compositions of the disclosure may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Pharmaceutical compositions of the disclosure may be intended for rectal administration, in the form, for example, of a suppository, which will melt in the rectum and release the drug. Compositions for rectal administration may contain an oleaginous base as a suitable nonirritating excipient. Such bases may include, without limitation, lanolin, cocoa butter and polyethylene glycol.

Pharmaceutical compositions of the disclosure may include various materials, which modify the physical form of a solid or liquid dosage unit. For example, the compositions may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

Pharmaceutical compositions of the disclosure in solid or liquid form may include an agent that binds to the one or more compounds of the disclosure, or pharmaceutically acceptable salts, solvates, stereoisomers, or tautomers thereof, and thereby assists in the delivery of the one or more compounds, or pharmaceutically acceptable salts, solvates, stereoisomers, or tautomers thereof. Suitable agents that may act in this capacity may include a monoclonal or polyclonal antibody, a protein or a liposome.

Pharmaceutical compositions of the disclosure may be prepared in dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of one or more compounds of the disclosure, or pharmaceutically acceptable salts, solvates, stereoisomers, or tautomers thereof, may be delivered in single phase, bi phasic, or tri phasic systems in order to deliver the active ingredient(s). Delivery of the aerosol may include the necessary container, activators, valves, subcontainers, and the like, which together may form a kit. One skilled in the art, without undue experimentation may determine preferred aerosols.

The pharmaceutical compositions of the disclosure may be prepared by methodology well known in the pharmaceutical art. For example, a pharmaceutical composition intended to be administered by injection can be prepared by combining one or more compounds of the disclosure, or pharmaceutically acceptable salts, solvates, stereoisomers, or tautomers thereof, with sterile, distilled water to form a solution. A surfactant may be added to facilitate the formation of a homogeneous solution or suspension. Surfactants are compounds that non-covalently interact with the one or more compounds of the disclosure, or pharmaceutically acceptable salts, solvates, stereoisomers, or tautomers thereof, to facilitate dissolution or homogeneous suspension of the one or more compounds or the disclosure, or pharmaceutically acceptable salts, solvates, stereoisomers, or tautomers thereof, in the aqueous delivery system.

The term "carrier," as used in this disclosure, may encompass carriers, excipients, and diluents and may mean a material, composition or vehicle, such as a liquid or solid filler, diluent, excipient, solvent or encapsulating material, involved in carrying or transporting a pharmaceutical agent, such as one or more compounds, or pharmaceutically acceptable salts, solvates (e.g, hydrates), isomers (e.g., stereoisomers), and tautomers thereof, of the disclosure, from one organ, or portion of the body, to another organ, or portion of the body of a subject. Carriers should be selected on the basis of compatibility and the release profile properties of the desired dosage form. Exemplary carrier materials may include, e.g., adjuvants, binders, suspending agents, disintegration agents, filling agents, surfactants, solubilizers, stabilizers, lubricants, wetting agents, diluents, spray-dried dispersions, and the like. See, e.g., Hoover, John E., *Remington's Pharmaceutical Sciences*, Mack Publishing Co., Easton, Pa. 1975. Exemplary carrier materials may also include without limitation any adjuvant, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The terms "pharmaceutically acceptable" or "pharmacologically acceptable" may refer to a material which is not biologically, or otherwise, undesirable—the material may be administered to an individual without causing any substantially undesirable biological effects or interacting in a deleterious manner with any of the components of the composition in which it is contained.

A "pharmaceutical composition" may refer to a formulation of a compound of the disclosure and a medium generally accepted in the art for the delivery of the biologically active compound to a subject, e.g., mammals or humans. Such a medium may include all pharmaceutically acceptable carriers therefor.

In some embodiments, pharmaceutical compositions of the disclosure may be enriched to provide predominantly one enantiomer of a compound described herein. An enantiomerically enriched mixture may comprise, for example, at least 60 mol percent of one enantiomer, or at least 75, at least 80, at least 85, at least 90, at least 95, at least 96, at least 97, at least 98, at least 99, at least 99.5 or even 100 mol percent. In some embodiments, the compositions described herein enriched in one enantiomer may be substantially free of the other enantiomer, wherein substantially free may mean that the substance in question makes up less than 10%, or less than 5%, or less than 4%, or less than 3%, or less than 2%, or less than 1% as compared to the amount of the other enantiomer, e.g., in the pharmaceutical composition or compound mixture. For example, if a pharmaceutical composition or compound mixture contains 98 grams of a first enantiomer and 2 grams of a second enantiomer, it would be said to contain 98 mol percent of the first enantiomer and only 2 mol percent of the second enantiomer.

In some embodiments, the pharmaceutical compositions of the disclosure may be enriched to provide predominantly one diastereomer of a compound disclosed herein. A diastereomerically enriched mixture may comprise, for example, at least 60 mol percent of one diastereomer, or at least 75, at least 80, at least 85, at least 90, at least 95, at least 96, at least 97, at least 98, at least 99, at least 99.5, or even 100 mol percent. In some embodiments, the compositions described herein enriched in one diastereomer may be substantially free of other diastereomers, wherein substantially free may mean that the substance in question makes up less than 10%, or less than 5%, or less than 4%, or less than 3%, or less than 2%, or less than 1% as compared to the amount of other disastereomers, e.g., in the pharmaceutical composition or compound mixture.

Diastereomeric mixtures can be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column. Also, some of the compounds of the disclosure may be atropisomers or rotameric forms and are considered as part of this disclosure.

Kits

A "kit" as used herein may include a container for containing at least one pharmaceutical composition or compound of the disclosure and may also include divided containers such as a divided bottle or a divided foil packet. The container can be in any conventional shape or form as known in the art that is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil that is opposite from the direction in which the recesses were formed. As a result, the tablets or capsules are individually sealed or collectively sealed, as desired, in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule may then be removed via said opening.

Another specific embodiment of a kit is a dispenser designed to dispense the daily doses one at a time in the order of their intended use. In some embodiments, the dispenser is equipped with a memory-aid, so as to further facilitate compliance with the regimen. An example of such a memory-aid is a mechanical counter, that indicates the number of daily doses that has been dispensed. Another example of such a memory-aid is a battery-powered micro-chip memory coupled with a liquid crystal readout, or audible reminder signal that, for example, reads out the date that the last daily dose has been taken and/or reminds one when the next dose is to be taken.

The kits of the present disclosure may also include, in addition to one or more compounds or pharmaceutical compositions of the present disclosure, one or more additional pharmaceutically active compounds or pharmaceutical compositions. For example, the additional compound may be a second antibacterial compound or the additional pharmaceutical composition may comprise a second antibacterial compound. The additional compounds or pharmaceutical compositions may be administered in the same dosage form as the one or more compounds or pharmaceutical compositions of the present disclosure or in a different dosage form. Likewise, the additional compounds or pharmaceutical compositions can be administered at the same time as the one or more compounds or pharmaceutical compositions of the present disclosure or at different times.

In some embodiments, the kit of the present disclosure has a notice in the form prescribed by a governmental agency regulating the manufacture, use or sale of pharmaceuticals or biological products, which notice reflects (a) approval by the agency of manufacture, use or sale for human administration, (b) directions for use, or both.

Testing Compounds for Antibacterial Activity

To assess the activity of the compounds of disclosure against bacterial strains, a minimum inhibitory concentration (MIC) assay may be used. The MIC can be determined by culturing microorganisms (e.g., bacteria) in liquid media or on plates of solid growth medium in the presence of a compound or pharmaceutical composition of the disclosure. A lower MIC value may indicate the antibacterial potency of a compound or pharmaceutical composition disclosed herein, as compounds or compositions with lower MIC scores are likely to be more effective antibacterial agents.

Exemplary Embodiments

Some embodiments of the disclosure are of Embodiment I.

Embodiment I-1. A compound of formula (I):

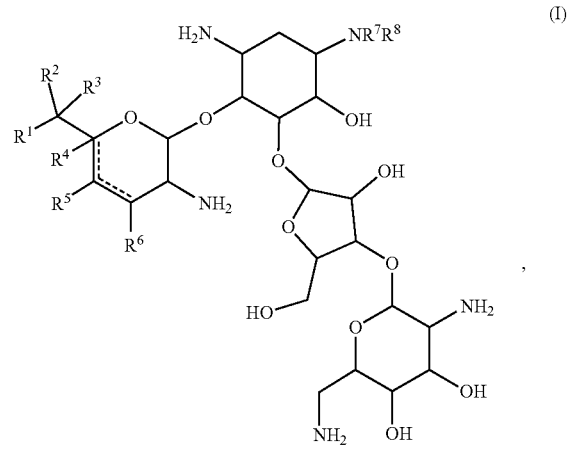

or a pharmaceutically acceptable salt, solvate, stereoisomer, or tautomer thereof, wherein:

$R^1$ is —$OR^9$ or —$NR^{10}R^{11}$, wherein $R^9$, $R^{10}$, and $R^{11}$ are independently H or $C_1$-$C_6$alkyl, wherein the alkyl is unsubstituted or substituted with one or more —OH;

R² and R³ are independently selected from the group consisting of H, alkyl, cycloalkyl, and aryl,
  wherein the alkyl, cycloalkyl, or aryl is unsubstituted or substituted with one or more substituents independently selected from the group consisting of halogen, cyano, aryl, —SR¹², —SO₂R¹³, —NR¹⁴R¹⁵, and —OR¹⁶, and
  wherein each R¹², R¹³, R¹⁴, R¹⁵, and R¹⁶ is independently H or alkyl; or
R¹ and R², together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —SR¹⁷, —SO₂R¹⁸, —NR¹⁹R²⁰, and —OR²¹, and
  wherein each R¹⁷, R¹⁸, R¹⁹, R²⁰, and R²¹ is independently H or alkyl; or
R² and R³, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, —SR²², —SO₂R²³, —NR²⁴R²⁵, and —OR²⁶, and wherein each R²², R²³, R²⁴, R²⁵, and R²⁶ is independently H or alkyl; and wherein at least one of R² and R³ is other than H; R⁴ is H or absent;

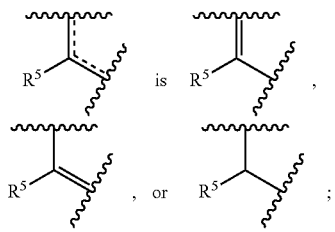

R⁵ and R⁶ are independently selected from the group consisting of H, —NR²⁸R²⁹, halogen, and alkyl, wherein each R²⁷, R²⁸, and R²⁹ is independently H or C₁-C₆alkyl;
  wherein the alkyl is unsubstituted or substituted with one or more substituents selected from the group consisting of halogen, —OR³⁰, —NR³¹R³², —SR³³, and —SO₂R³⁴; and
  wherein each R³⁰, R³¹, R³², R³³, and R³⁴ is independently H or alkyl;
R⁷ is H or C₁-C₃alkyl;
R⁸ is H or

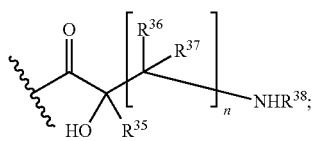

wherein n is an integer from 0 to 4,
R³⁵ is H or C₁-C₃alkyl;
each R³⁶ and R³⁷ is independently selected from the group consisting of H, alkyl, halogen, and —OH, and
R³⁸ is H, alkyl, or —C(=NH)NR³⁹R⁴⁰, wherein R³⁹ and R⁴⁰ are independently H or C₁-C₃alkyl; or
R³⁵ and R³⁸, together with the atoms to which they are attached, form a heterocycloalkyl group comprising at least one N.

Embodiment I-2. The compound of Embodiment I-1, or a pharmaceutically acceptable salt, solvate, stereoisomer, or tautomer thereof, wherein the compound is of formula (I-A):

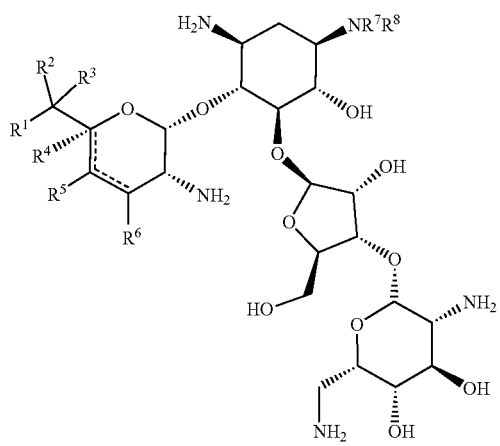

(I-A)

Embodiment I-3. The compound of Embodiment I-1 or I-2, or a pharmaceutically acceptable salt, solvate, stereoisomer, or tautomer thereof, wherein R⁷ and R⁸ are H.

Embodiment I-4. The compound of Embodiment I-1 or I-2, or a pharmaceutically acceptable salt, solvate, stereoisomer, or tautomer thereof, wherein R⁷ is H and R⁸ is:

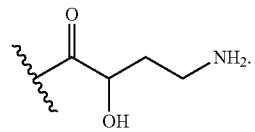 [SMILES: *C(=O)C(O)CCN]

Embodiment I-5. The compound of Embodiment I-1 or I-2, or a pharmaceutically acceptable salt, solvate, stereoisomer, or tautomer thereof, wherein R⁷ is H and R⁸ is:

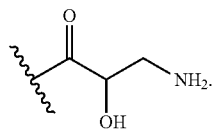 [SMILES: *C(=O)C(O)CN]

Embodiment I-6. The compound of any one of Embodiment I-1 to I-5, or a pharmaceutically acceptable salt, solvate, stereoisomer, or tautomer thereof, wherein R⁴ is H and

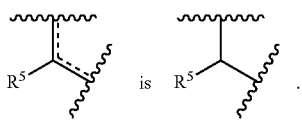

Embodiment I-7. The compound of any one of Embodiment I-1 to I-5, or a pharmaceutically acceptable salt, solvate, stereoisomer, or tautomer thereof, wherein R⁴ is H and

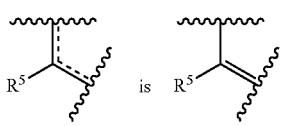

Embodiment I-8. The compound of any one of Embodiment I-1 to I-7, or a pharmaceutically acceptable salt, solvate, stereoisomer, or tautomer thereof, wherein $R^1$ is OH.

Embodiment I-9. The compound of any one of Embodiment I-1 to I-7, or a pharmaceutically acceptable salt, solvate, stereoisomer, or tautomer thereof, wherein $R^1$ is —$NR^{10}R^{11}$, wherein $R^{10}$, and $R^{11}$ are independently H, methyl, or hydroxyethyl.

Embodiment I-10. The compound of any one of Embodiment I-1 to I-9, or a pharmaceutically acceptable salt, solvate, stereoisomer, or tautomer thereof, wherein $R^2$ is unsubstituted methyl, unsubstituted ethyl, unsubstituted cyclopropyl, phenyl, or methyl substituted with one or two substituents selected from the group consisting of —$NH_2$, —OH, F, —CN, and —$S(O)_2CH_3$.

Embodiment I-11. The compound of any one of Embodiment I-1 to I-7, or a pharmaceutically acceptable salt, solvate, stereoisomer, or tautomer thereof, wherein $R^1$ and $R^2$ together with the atom to which they are attached form an unsubstituted 6-membered heterocycloalkyl group comprising one N and one O.

Embodiment I-12. The compound of any one of Embodiment I-1 to I-11, or a pharmaceutically acceptable salt, solvate, stereoisomer, or tautomer thereof, wherein $R^3$ is H or unsubstituted methyl.

Embodiment I-13. The compound of any one of Embodiment I-1 to I-9, or a pharmaceutically acceptable salt, solvate, stereoisomer, or tautomer thereof, wherein $R^2$ and $R^3$ together with the atom to which they are attached form a cyclopropyl or oxetanyl.

Embodiment I-14. The compound of any one of Embodiment I-1 to I-9, or a pharmaceutically acceptable salt, solvate, stereoisomer, or tautomer thereof, wherein $R^5$ and $R^6$ are independently H or —OH.

Embodiment I-15. The compound of any one of Embodiment I-1 to I-14, wherein the compound is selected from the group consisting of:

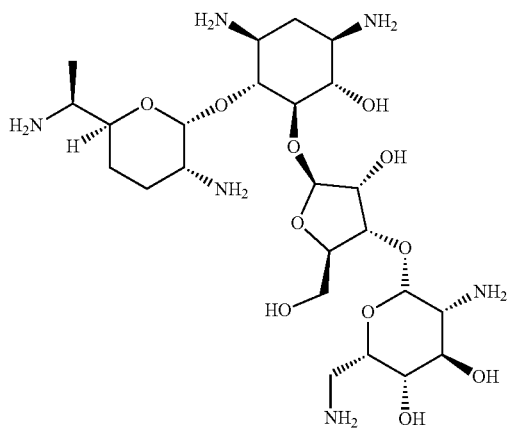

-continued

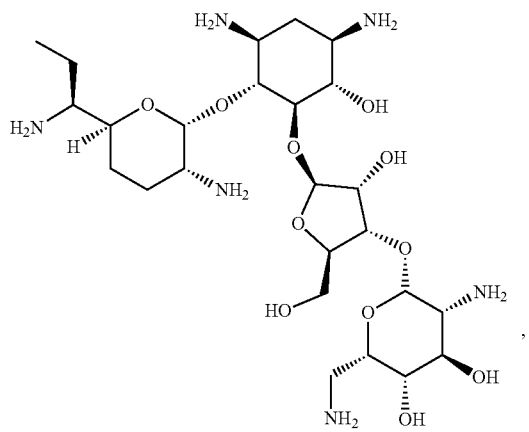

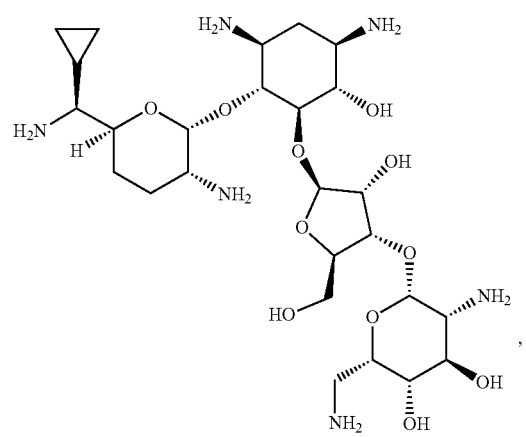

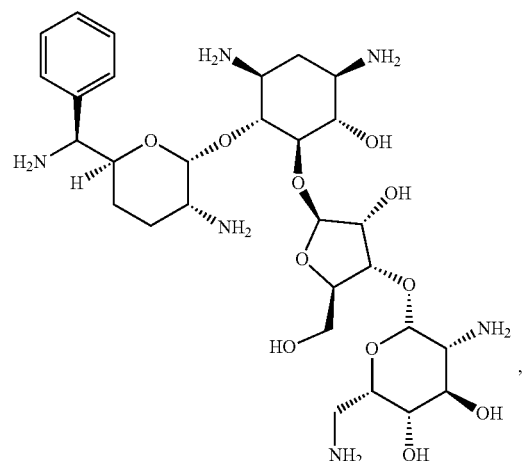

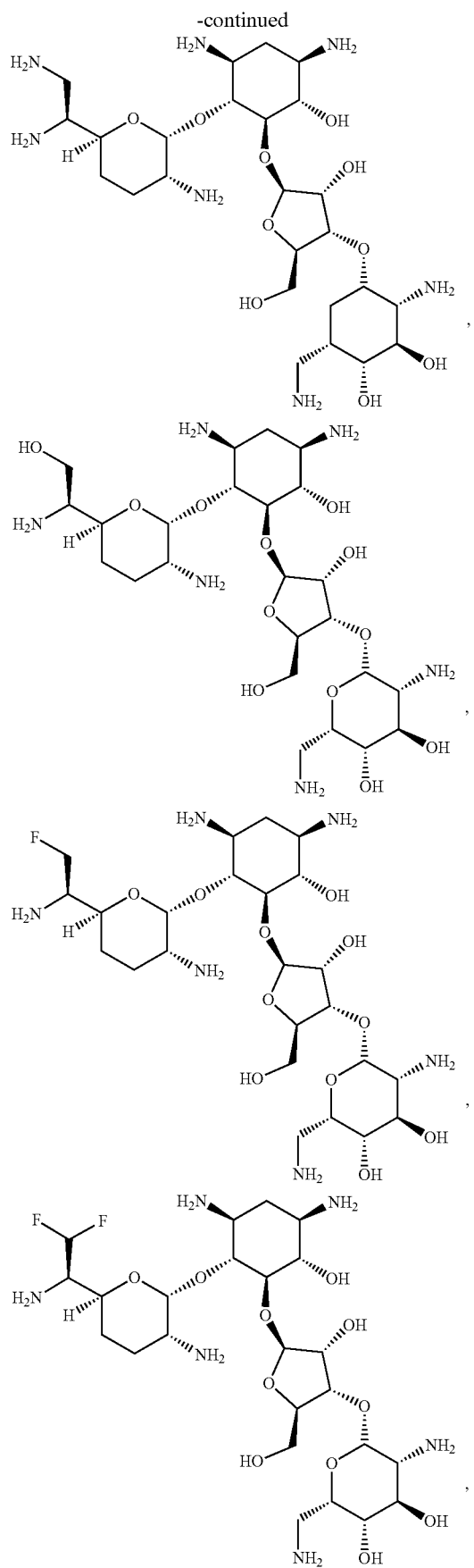
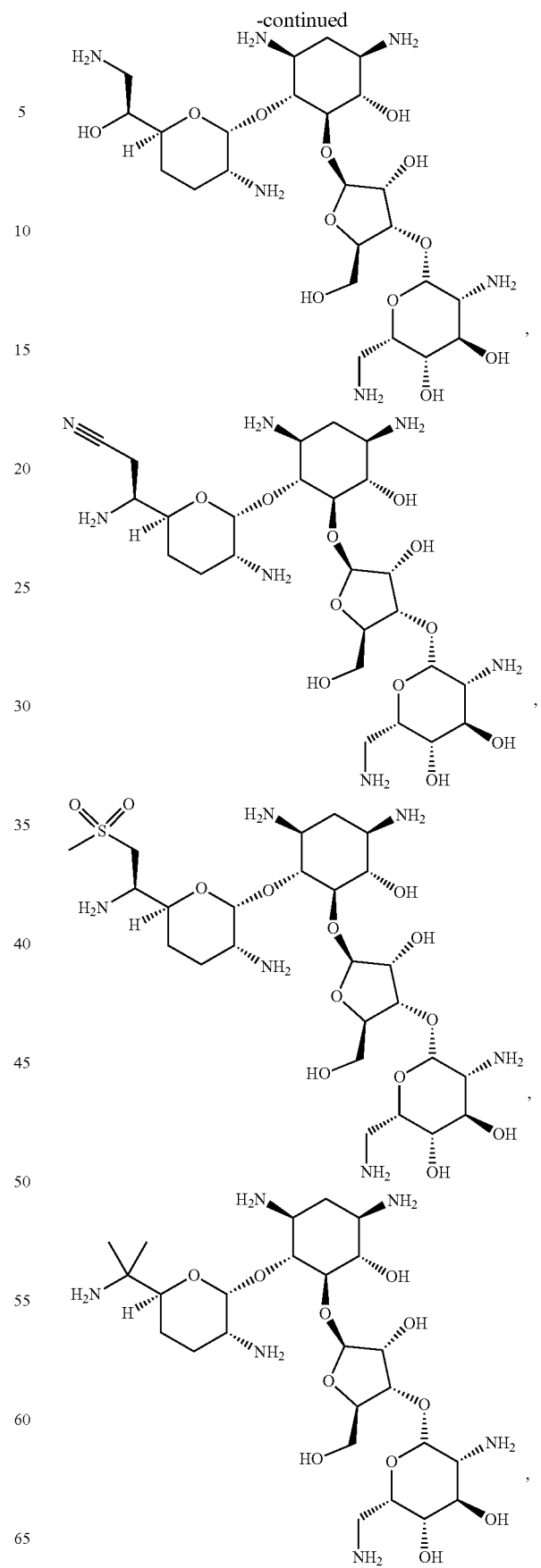

275
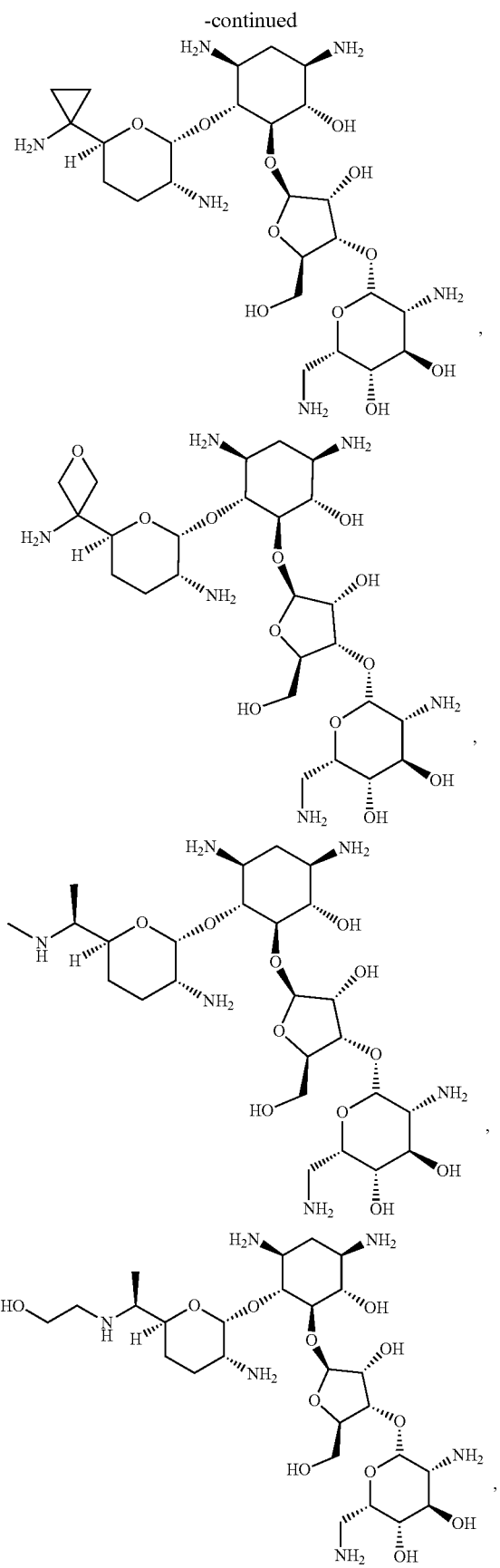
276
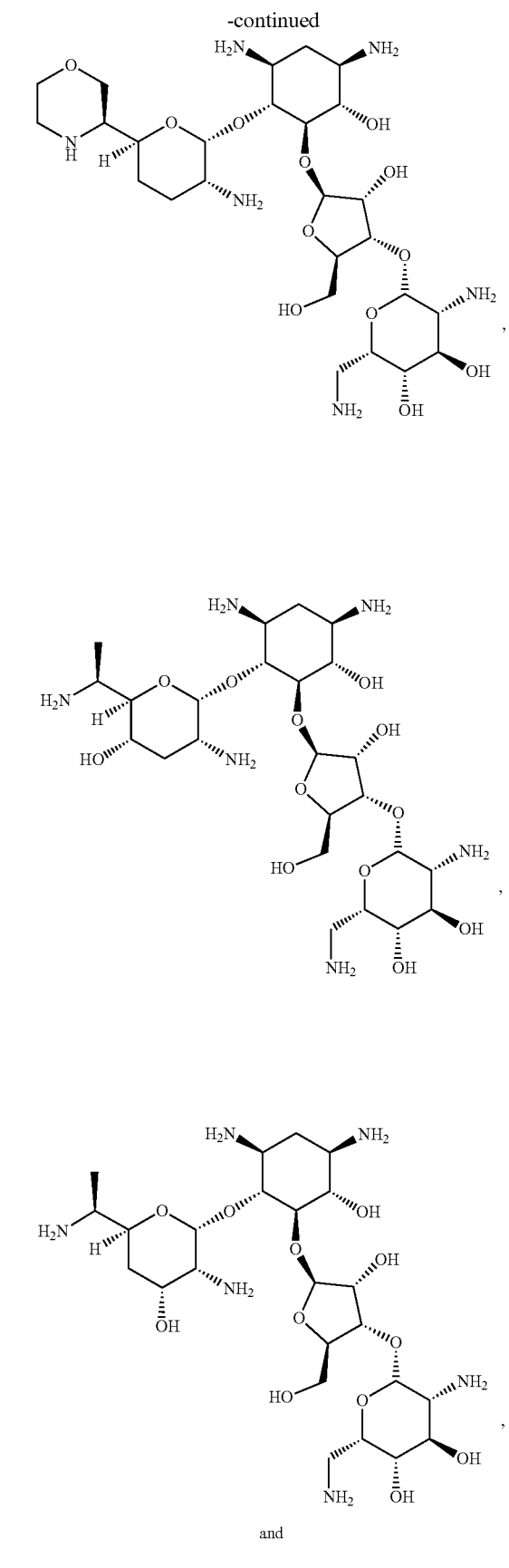
and

-continued
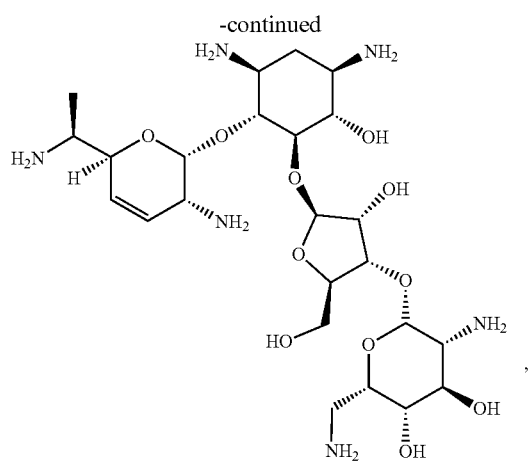
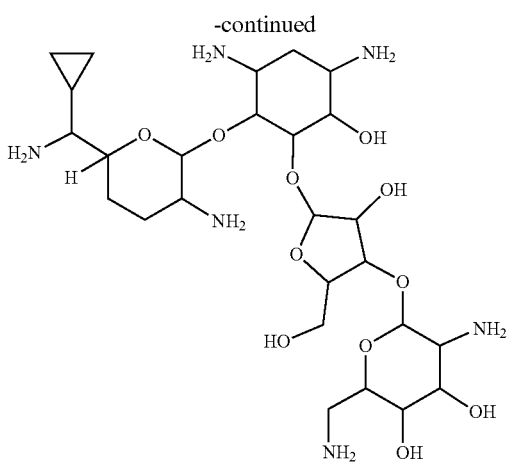
or a pharmaceutically acceptable salt, solvate, stereoisomer, or tautomer thereof.
Embodiment I-15A. The compound of any one of Embodiment I-1 to I-14, wherein the compound is selected from the group consisting of
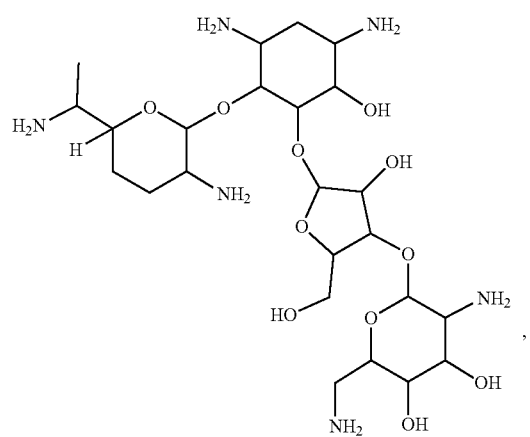
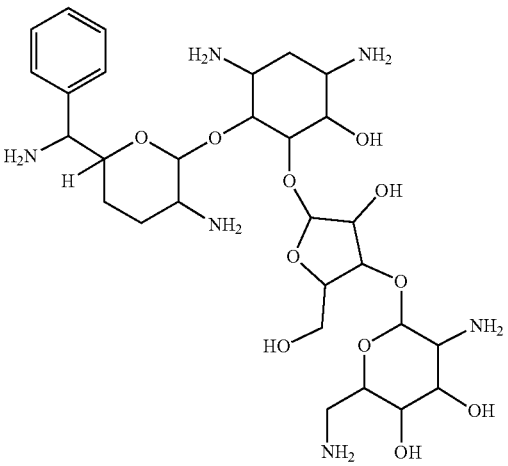
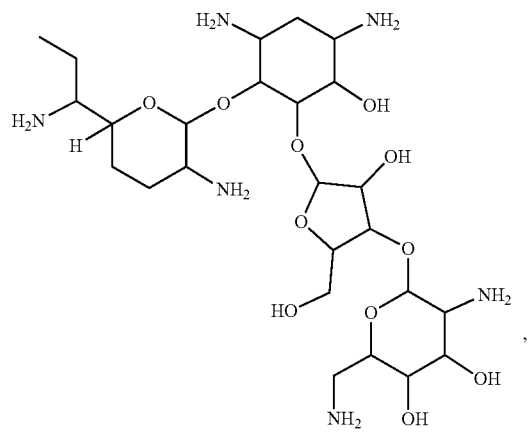
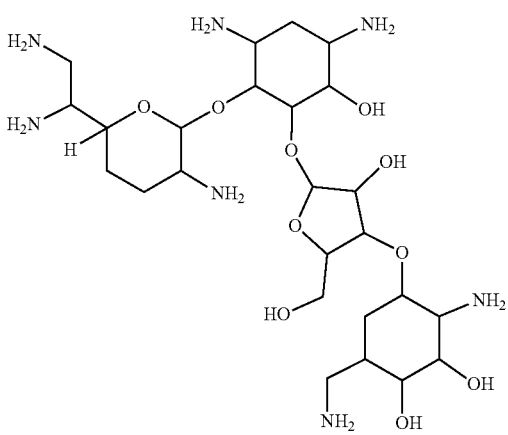

279
-continued
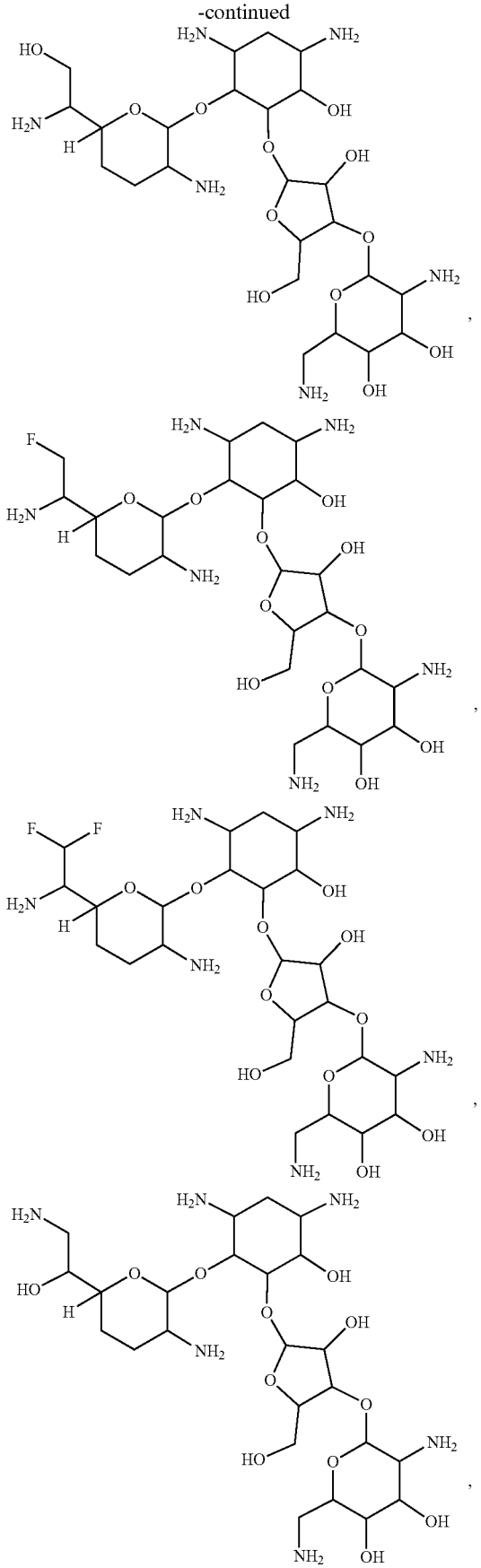
280
-continued
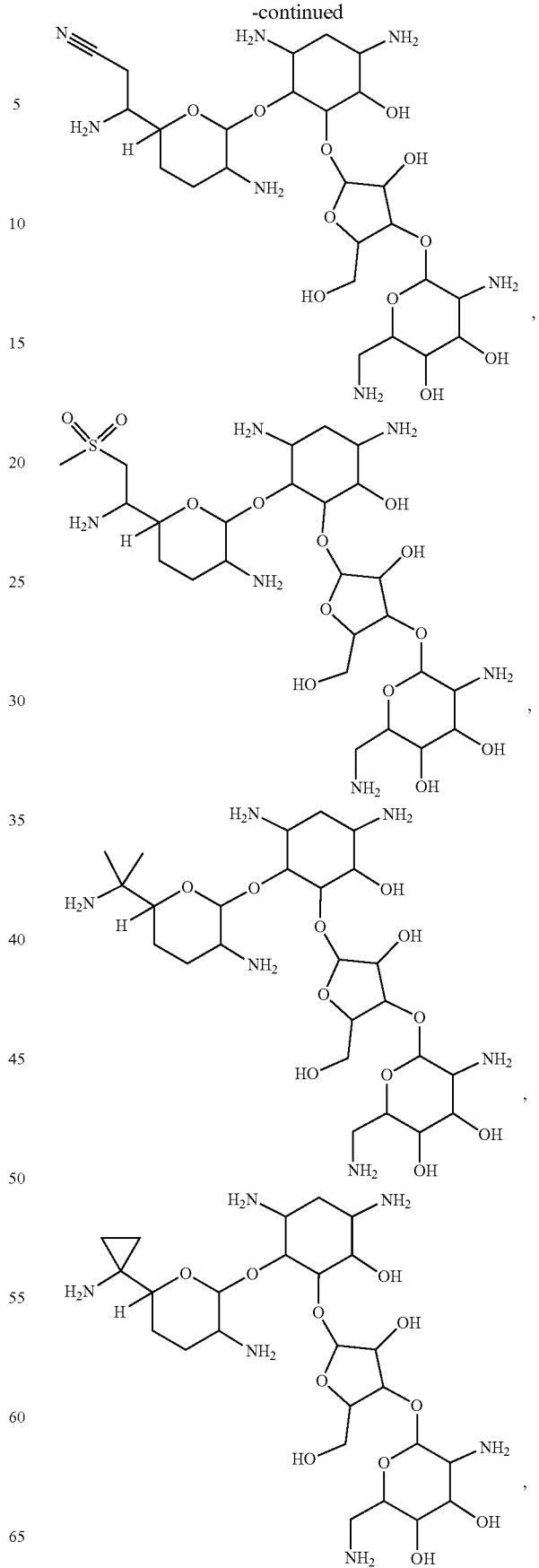

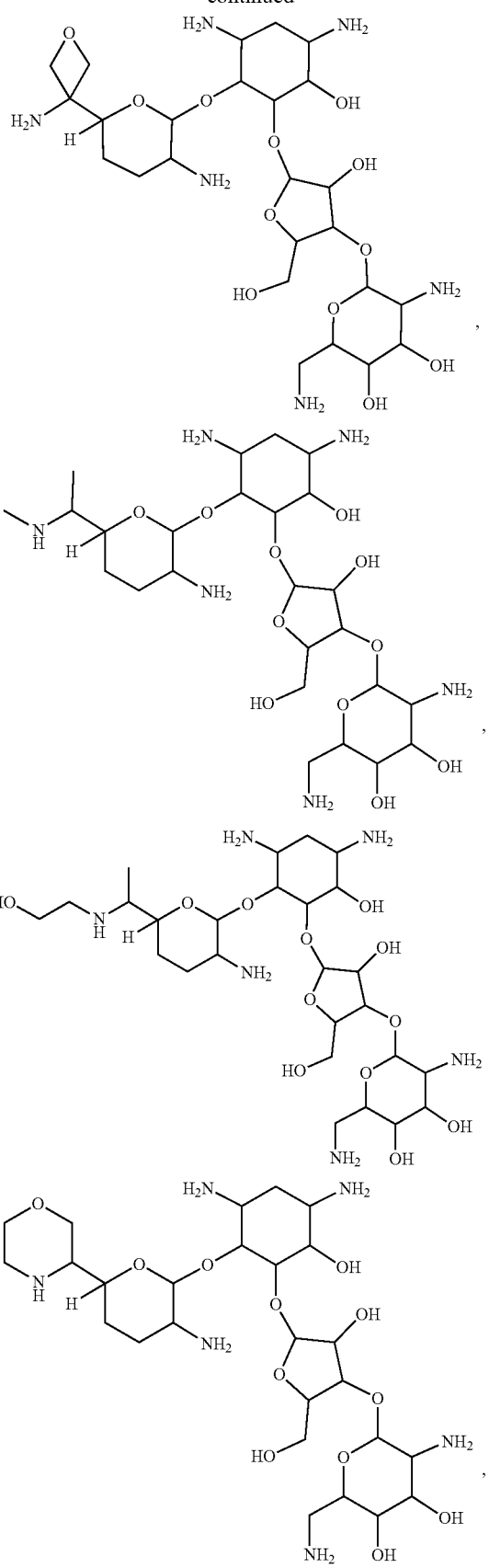

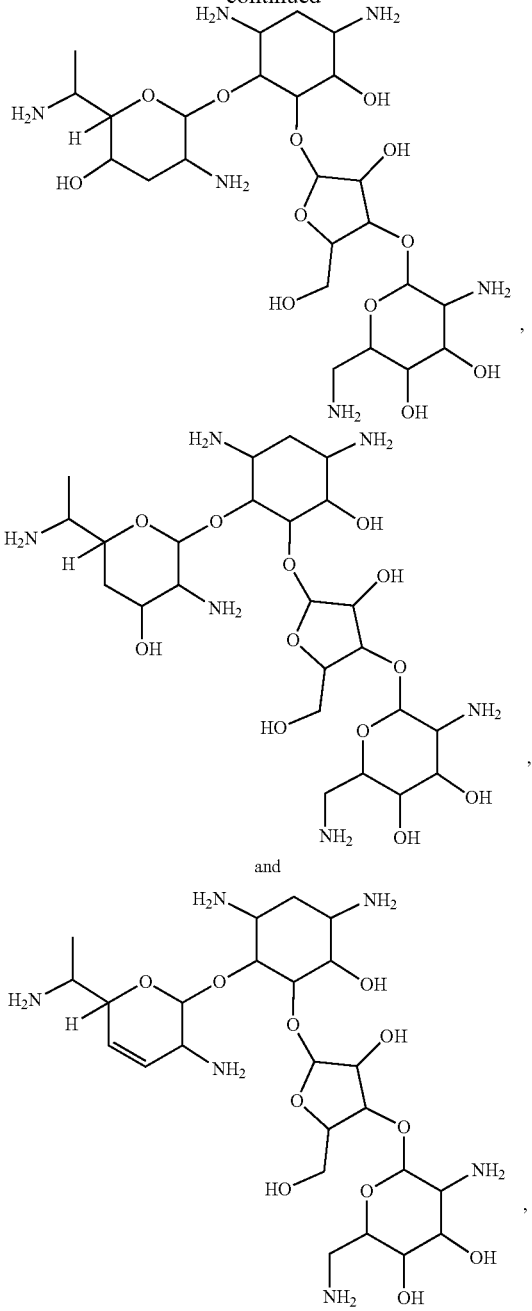

and or a pharmaceutically acceptable salt, solvate, stereoisomer, or tautomer thereof.

Embodiment I-16. A pharmaceutical composition, comprising a compound of any one of Embodiment I-1 to I-15, or a pharmaceutically acceptable salt, solvate, stereoisomer, or tautomer thereof, and a pharmaceutically acceptable carrier.

Embodiment I-17. A method for treating a bacterial infection in a subject, comprising administering to a subject in need thereof a therapeutically effective amount of a compound of any one of Embodiment I-1 to I-15, or a pharmaceutically acceptable salt, solvate, stereoisomer, or tautomer thereof.

Embodiment I-18. A method for treating a bacterial infection in a subject, comprising administering to a subject in need thereof a therapeutically effective amount of a pharmaceutical composition according to Embodiment I-16.

Embodiment I-19. The method of Embodiment I-17 or Embodiment I-18, wherein the bacterial infection is a Gram-negative bacterial infection.

Embodiment I-20. The method of Embodiment I-17 or Embodiment I-18, wherein the bacterial infection is infection of a *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella, Francisella, Yersinia, Corynebacterium, Moraxella,* or *Enterococcus* species.

Embodiment I-21. Use of a compound of any one of Embodiment I-1 to I-15, or a pharmaceutically acceptable salt, solvate, stereoisomer, or tautomer thereof., in the manufacture of a medicament for treating a bacterial infection in a subject in need thereof.

Embodiment I-22. A compound of any one of Embodiment I-1 to I-15, or a pharmaceutically acceptable salt, solvate, stereoisomer, or tautomer thereof., for use in a method of treating a bacterial infection in a subject in need thereof.

Some embodiments of the disclosure are of Embodiment II.

Embodiment II-1. A compound of formula (II):

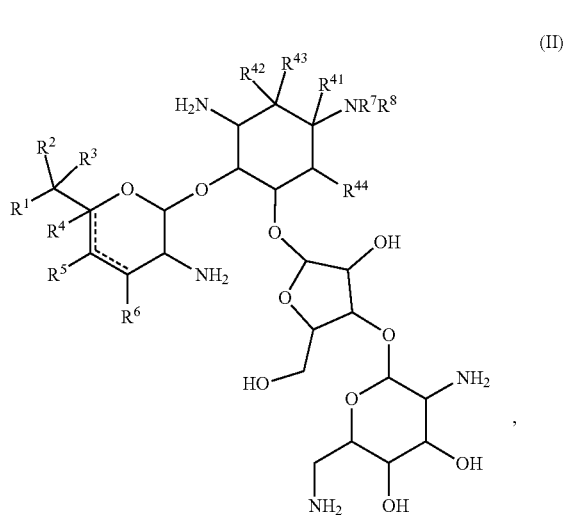

(II)

$R^1$ is —$OR^9$ or —$NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more —OH;

$R^2$ and $R^3$ are independently H, alkyl, cycloalkyl, or aryl, wherein the alkyl, cycloalkyl, or aryl is unsubstituted or substituted with one or more substituents independently selected from the group consisting of halogen, cyano, aryl, —$SR^{12}$, —$SO_{2R}^{13}$, —$OSF_2NR^{14}R^{15}$, —$NR^{14}R^{15}$, and —$OR^{16}$, and wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —$SR^{17}$, —$SO_{2R}^{18}$, —$NR^{19}R^{20}$, and —$OR^{21}$, and wherein each $R^{17}$, $R^{18}$, $R^{19}$, $R^{20}$, and $R^{21}$ is independently H or alkyl, or $R^2$ and $R^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl; and wherein at least one of $R^2$ and $R^3$ is other than H;

$R^4$ is H or absent;

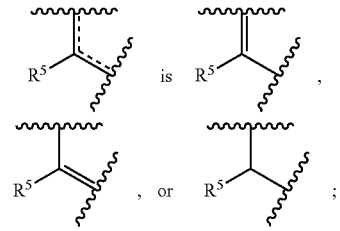

$R^5$ and $R^6$ are independently selected from the group consisting of H, —$OR^{27}$, —$NR^{28}R^{29}$, halogen, and alkyl, wherein each $R^{27}$, $R^{28}$, and $R^{29}$ is independently H or $C_1$-$C_6$alkyl;

wherein the alkyl is unsubstituted or substituted with one or more substituents selected from the group consisting of halogen, —$OR^{30}$, —$NR^{31}R^{32}$, —$SR^{33}$, and —$SO_2R^{34}$; and wherein each $R^{30}$, $R^{31}$, $R^{32}$, $R^{33}$, and $R^{34}$ is independently H or alkyl;

$R^7$ is H or $C_1$-$C_3$alkyl;

$R^8$ is H or

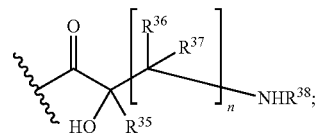

wherein n is an integer from 0 to 4, $R^{35}$ is H or $C_1$-$C_3$alkyl;

each $R^{36}$ and $R^{37}$ is independently selected from the group consisting of H, alkyl, halogen, and —OH, and $R^{38}$ is H, alkyl, or —C(=NH)$NR^{39}R^{40}$, wherein $R^{39}$ and $R^{40}$ are independently H or $C_1$-$C_3$alkyl; or $R^{35}$ and $R^{38}$, together with the atoms to which they are attached, form a heterocycloalkyl group comprising at least one N;

$R^{41}$ is H, $C_1$-$C_3$alkyl, wherein the alkyl is unsubstituted or substituted by —OH or halogen;

$R^{42}$ and $R^{43}$ are independently H, —OH, or halogen; and $R^{44}$ is H, halogen, —OH, or $C_1$-$C_3$alkoxy.

Embodiment II-2. The compound of Embodiment II-1, or a pharmaceutically acceptable salt, solvate, stereoisomer, or tautomer thereof, wherein the compound is of formula (II-A)

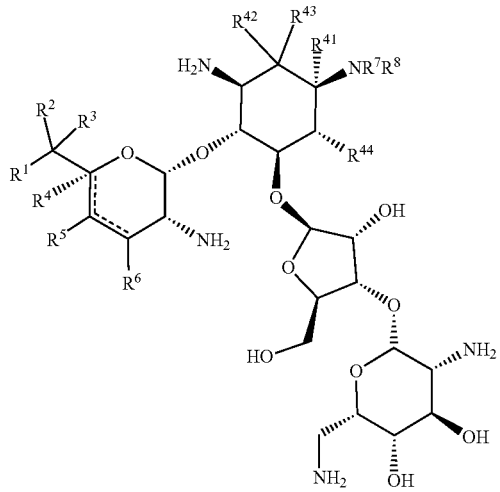

Embodiment II-3. A compound of formula (I):

(I)

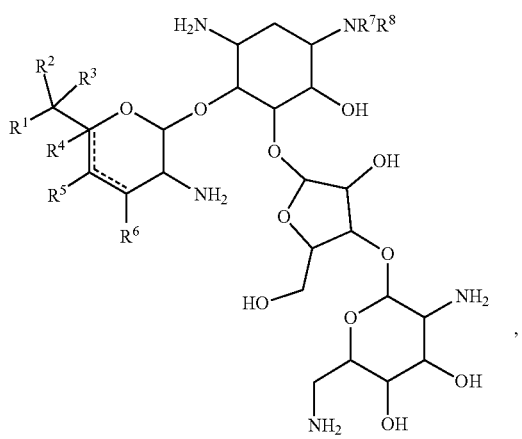

or a pharmaceutically acceptable salt, solvate, stereoisomer, or tautomer thereof, wherein:
$R^1$ is —$OR^9$ or —$NR^{10}R^{11}$, wherein $R^9$, $R^{10}$, and $R^{11}$ are independently H or $C_1$-$C_6$alkyl, wherein the alkyl is unsubstituted or substituted with one or more —OH;
$R^2$ and $R^3$ are independently selected from the group consisting of H, alkyl, cycloalkyl, and aryl,
  wherein the alkyl, cycloalkyl, or aryl is unsubstituted or substituted with one or more substituents independently selected from the group consisting of halogen, cyano, aryl, —$SR^{12}$, —$SO_2R^{13}$, —$NR^{14}R^{15}$, and —$OR^{16}$, and
  wherein each $R^{12}$, $R^{13}$, $R^{14}$, $R^{15}$, and $R^{16}$ is independently H or alkyl; or
$R^1$ and $R^2$, together with the atom to which they are attached, form a heterocycloalkyl group comprising at least one heteroatom selected from the group consisting of N and O,
  wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and
  wherein each $R^{17}$, $R^{18}$, $R^{19}$, $R^{20}$, and $R^{21}$ is independently H or alkyl; or
$R^2$ and $R^3$, together with the atom to which they are attached, form a cycloalkyl group or a heterocycloalkyl group,
  wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and
  wherein each $R^{22}$, $R^{23}$, $R^{24}$, $R^{25}$, and $R^{26}$ is independently H or alkyl; and wherein at least one of $R^2$ and $R^3$ is other than H;
$R^4$ is H or absent;

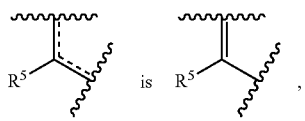 is , or $R^5$ and $R^6$ are independently selected from the group consisting of H, —$OR^{27}$, —$NR^{28}R^{29}$, halogen, and alkyl,
  wherein the alkyl is unsubstituted or substituted with one or more substituents selected from the group consisting of halogen, —$OR^{30}$, —$NR^{31}R^{32}$, —$SR^{33}$, and —$SO_2R^{34}$; and
  wherein each $R^{30}$, $R^{31}$, $R^{32}$, $R^{33}$, and $R^{34}$ is independently H or alkyl;
$R^7$ is H or $C_1$-$C_3$alkyl;
$R^8$ is H or

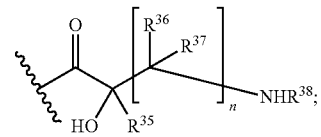

wherein n is an integer from 0 to 4,
$R^{35}$ is H or $C_1$-$C_3$alkyl;
each $R^{36}$ and $R^{37}$ is independently selected from the group consisting of H, alkyl, halogen, and —OH, and
$R^{38}$ is H, alkyl, or —C(=NH)$NR^{39}R^{40}$, wherein $R^{39}$ and $R^{40}$ are independently H or $C_1$-$C_3$ alkyl; or
$R^{35}$ and $R^{38}$, together with the atoms to which they are attached, form a heterocycloalkyl group comprising at least one N.

Embodiment II-4. The compound of Embodiment II-3, or a pharmaceutically acceptable salt, solvate, stereoisomer, or tautomer thereof, wherein the compound is of formula (I-A):

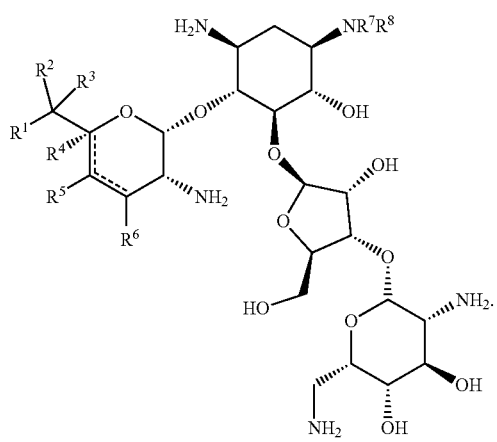

(I-A)

Embodiment II-5. The compound of any one of Embodiment II-1 to II-4, or a pharmaceutically acceptable salt, solvate, stereoisomer, or tautomer thereof, wherein $R^7$ and $R^8$ are H.

Embodiment II-6. The compound of any one of Embodiment II-1 to II-4, or a pharmaceutically acceptable salt, solvate, stereoisomer, or tautomer thereof, wherein $R^7$ is H and $R^8$ is:

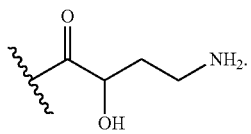 [SMILES: *C(=O)C(O)CCN]

Embodiment II-7. The compound of any one of c Embodiment II-1 to II-4, or a pharmaceutically acceptable salt, solvate, stereoisomer, or tautomer thereof, wherein $R^7$ is H and $R^8$ is:

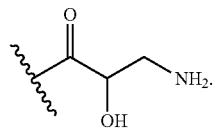 [SMILES: *C(=O)C(O)CN]

Embodiment II-8. The compound of any one of Embodiment II-1 to II-7, or a pharmaceutically acceptable salt, solvate, stereoisomer, or tautomer thereof, wherein $R^4$ is H and

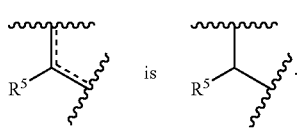

Embodiment II-9. The compound of any one of Embodiment II-1 to II-7, or a pharmaceutically acceptable salt, solvate, stereoisomer, or tautomer thereof, wherein $R^4$ is H and

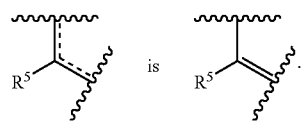

Embodiment II-10. The compound of any one of Embodiment II-1 to II-9, or a pharmaceutically acceptable salt, solvate, stereoisomer, or tautomer thereof, wherein $R^1$ is OH.

Embodiment II-11. The compound of any one of Embodiment II-1 to II-9, or a pharmaceutically acceptable salt, solvate, stereoisomer, or tautomer thereof, wherein $R^1$ is $-NR^{10}R^{11}$, wherein Rth, and $R^{11}$ are independently H, methyl, or hydroxyethyl.

Embodiment II-12. The compound of any one of Embodiment II-1 to II-11, or a pharmaceutically acceptable salt, solvate, stereoisomer, or tautomer thereof, wherein $R^2$ is unsubstituted methyl, unsubstituted ethyl, unsubstituted cyclopropyl, phenyl, or methyl substituted with one or two substituents selected from the group consisting of $-NH_2$, $-OH$, F, $-CN$, and $-S(O)_2CH_3$.

Embodiment II-13. The compound of any one of Embodiment II-1 to II-9, or a pharmaceutically acceptable salt, solvate, stereoisomer, or tautomer thereof, wherein $R^1$ and $R^2$ together with the atom to which they are attached form an unsubstituted 6-membered heterocycloalkyl group comprising one N and one O.

Embodiment II-14. The compound of any one of Embodiment II-1 to II-13, or a pharmaceutically acceptable salt, solvate, stereoisomer, or tautomer thereof, wherein $R^3$ is H or unsubstituted methyl.

Embodiment II-15. The compound of any one of Embodiment II-1 to II-11, or a pharmaceutically acceptable salt, solvate, stereoisomer, or tautomer thereof, wherein $R^2$ and $R^3$ together with the atom to which they are attached form a cyclopropyl or oxetanyl.

Embodiment II-16. The compound of any one of Embodiment II-1 to II-11, or a pharmaceutically acceptable salt, solvate, stereoisomer, or tautomer thereof, wherein $R^5$ and $R^6$ are independently H or $-OH$.

Embodiment II-17. The compound of any one of Embodiment II-1 to II-2 and II-5 to Embodiment II-16, wherein $R^{41}$ is $C_1$-$C_3$alkyl substituted by $-OH$.

Embodiment II-18. The compound of any one of Embodiment II-1 to II-2 and II-5 to II-16, wherein $R^{41}$ is $C_1$-$C_3$alkyl substituted by halogen.

Embodiment II-19. The compound of any one of Embodiment II-1 to II-2 and II-5 to II-16, wherein $R^{41}$ is $C_1$-$C_3$alkyl substituted by $-F$.

Embodiment II-20. The compound of any one of Embodiment II-1 to II-2 and II-5 to II-16, wherein $R^{41}$ is unsubstituted $C_1$-$C_3$alkyl.

Embodiment II-21. The compound of any one of Embodiment II-1 to II-2 and II-5 to II-16, wherein $R^{41}$ is H.

Embodiment II-22. The compound of any one of Embodiment II-1 to II-2 and II-5 to II-21, wherein one of $R^{42}$ and $R^{43}$ is $-OH$.

Embodiment II-23. The compound of any one of Embodiment II-1 to II-2 and II-5 to II-21, wherein one of $R^{42}$ and $R^{43}$ is halogen.

Embodiment II-24. The compound of any one of Embodiment II-1 to II-2 and II-5 to II-21, wherein $R^{42}$ is H and $R^{43}$ is $-OH$.

Embodiment II-25. The compound of any one of Embodiment II-1 to II-2 and II-5 to II-21, wherein $R^{42}$ is H and $R^{43}$ is —F.

Embodiment II-26. The compound of any one of Embodiment II-1 to II-2 and II-5 to II-21, wherein $R^{42}$ is —F and $R^{43}$ is —F.

Embodiment II-27. The compound of any one of Embodiment II-1 to II-2 and II-5 to II-21, wherein $R^{42}$ and $R^{43}$ are H.

Embodiment II-28. The compound of any one of Embodiment II-1 to II-2 and II-5 to II-27, wherein $R^{44}$ is —OCH$_3$.

Embodiment II-29. The compound of any one of Embodiment II-1 to II-2 and II-5 to II-27, wherein $R^{44}$ is —F.

Embodiment II-30. The compound of any one of Embodiment II-1 to II-2 and II-5 to II-27, wherein $R^{44}$ is —H.

Embodiment II-31. The compound of any one of Embodiment II-1 to II-30, wherein the compound is selected from the group consisting of:

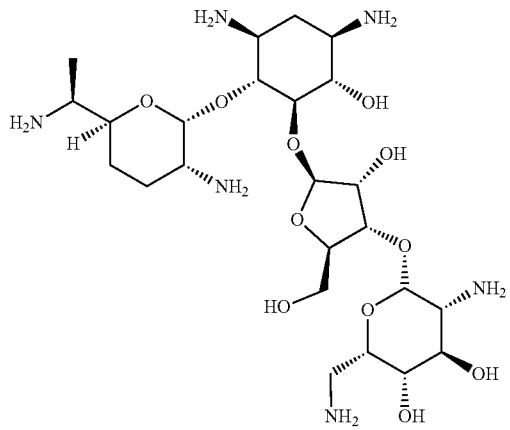

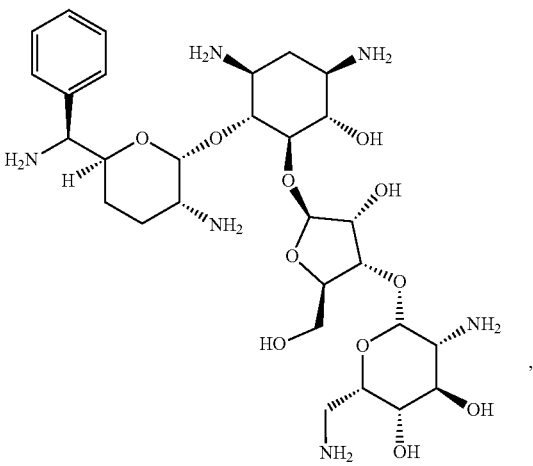

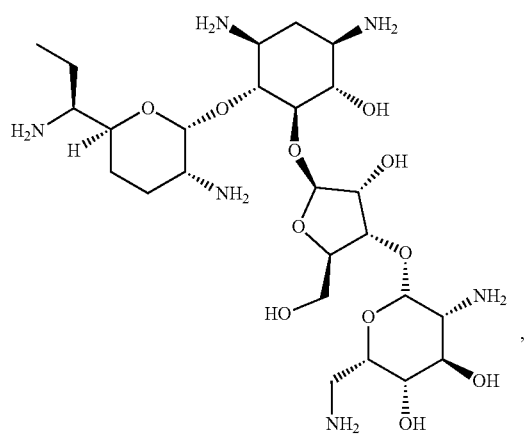

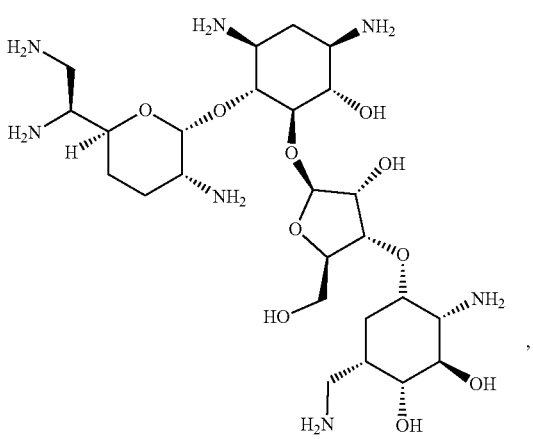

291
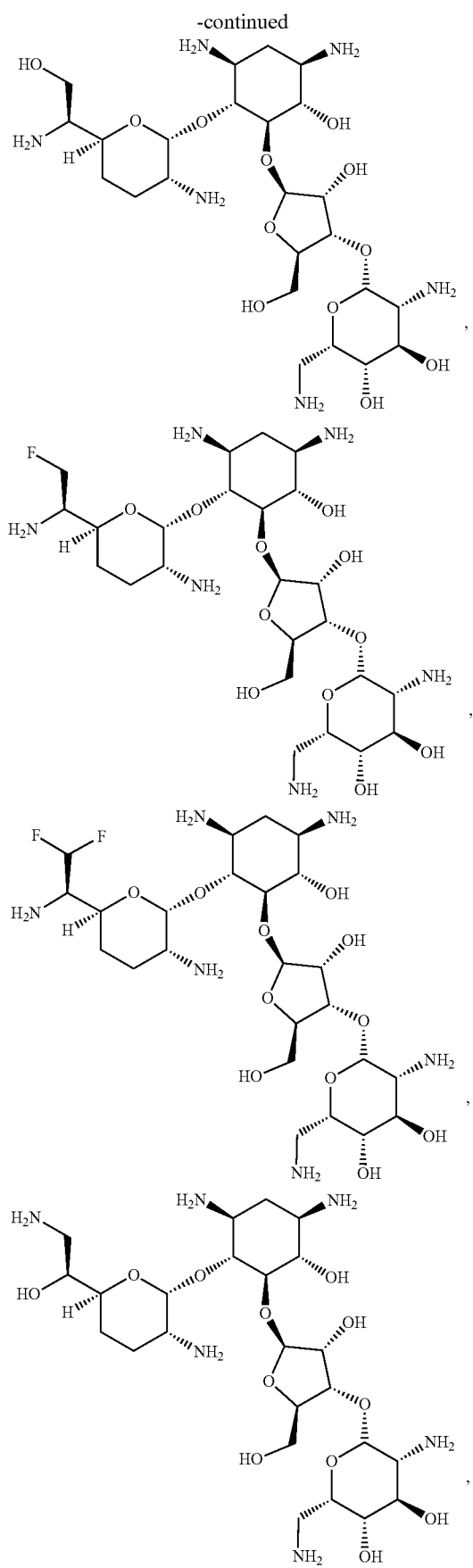
292
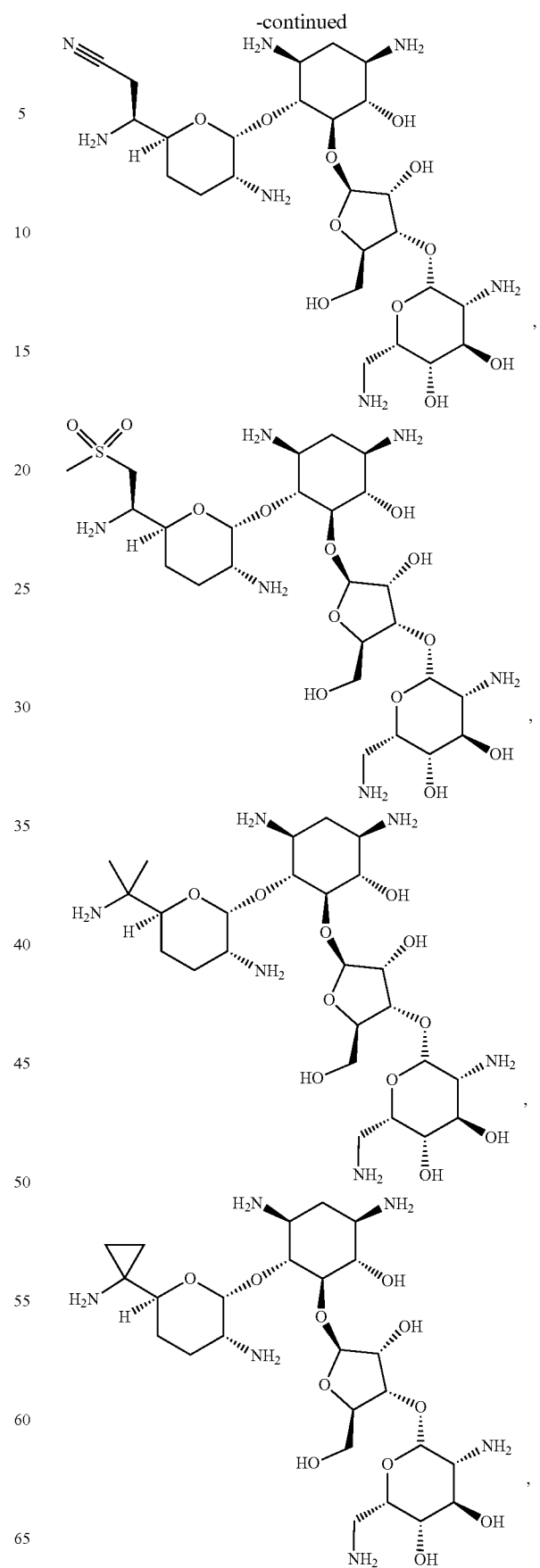

293
-continued
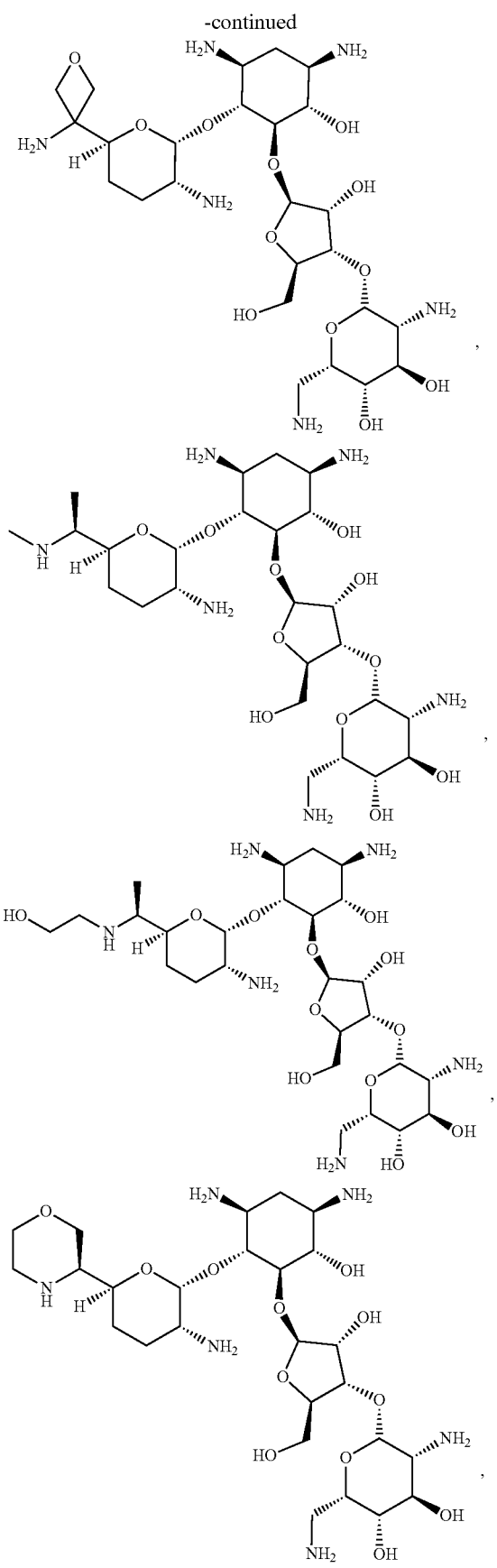
294
-continued
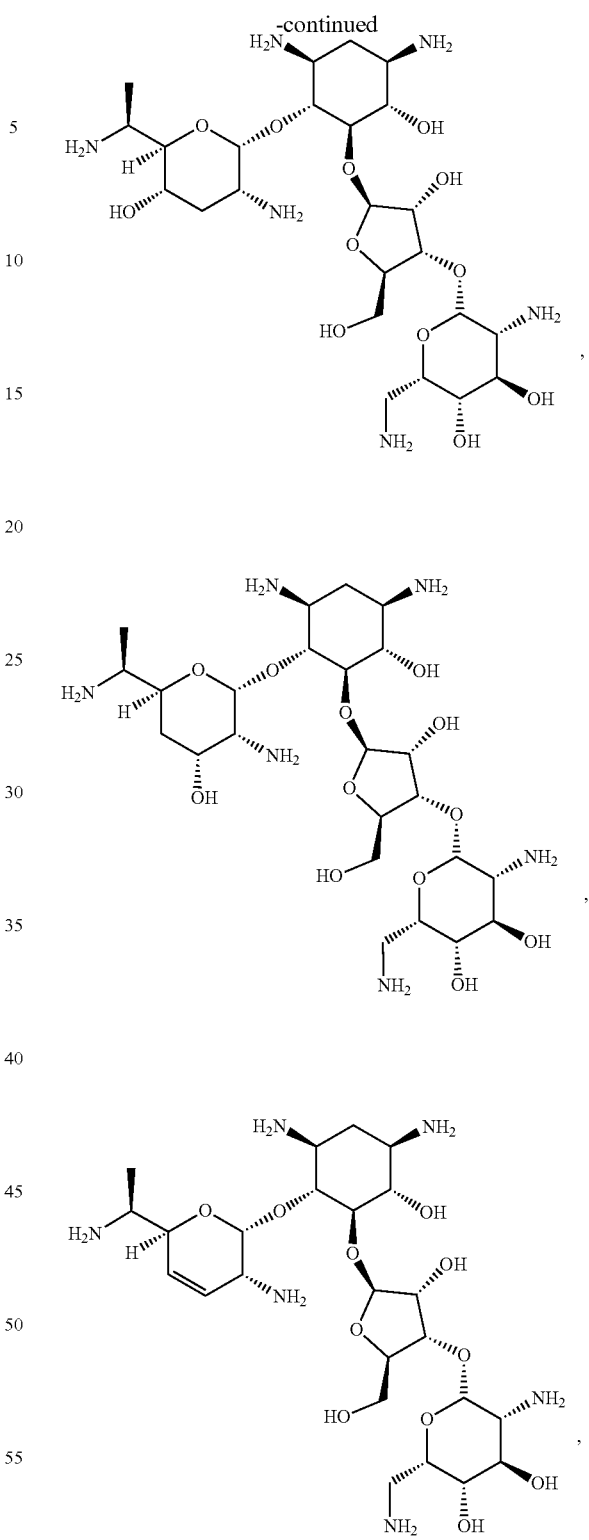
or a pharmaceutically acceptable salt, solvate, stereoisomer, or tautomer thereof.
Embodiment II-31A. The compound of any one of Embodiment II-1 to II-30, wherein the compound is selected from the group consisting of:

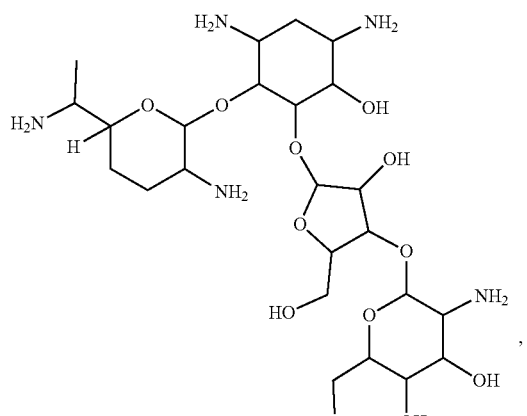
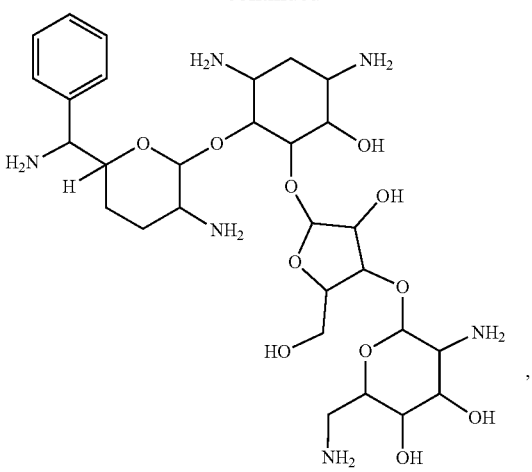
-continued
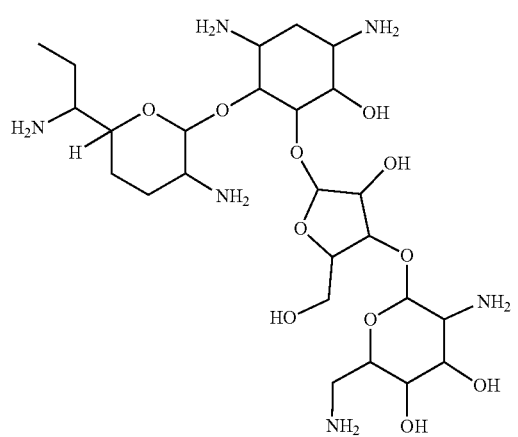
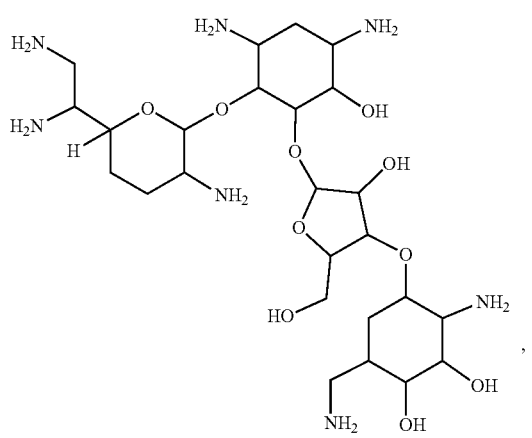
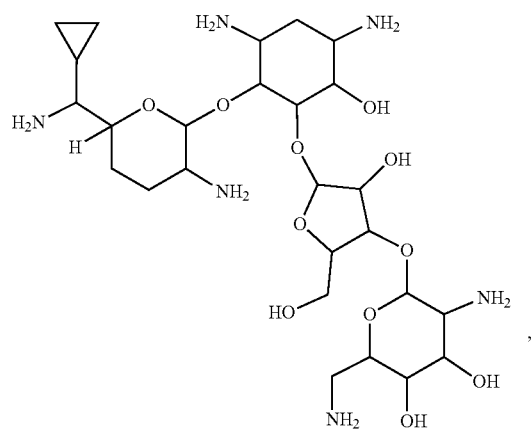
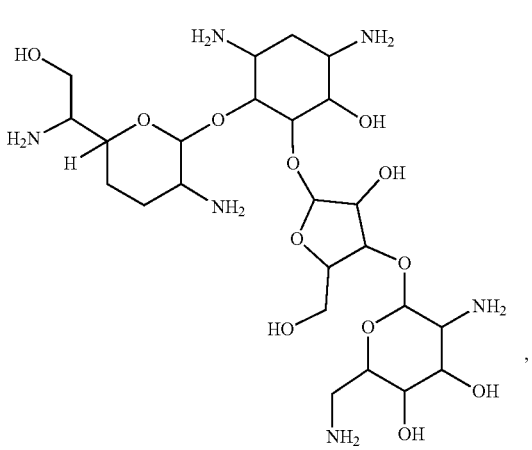

297
-continued
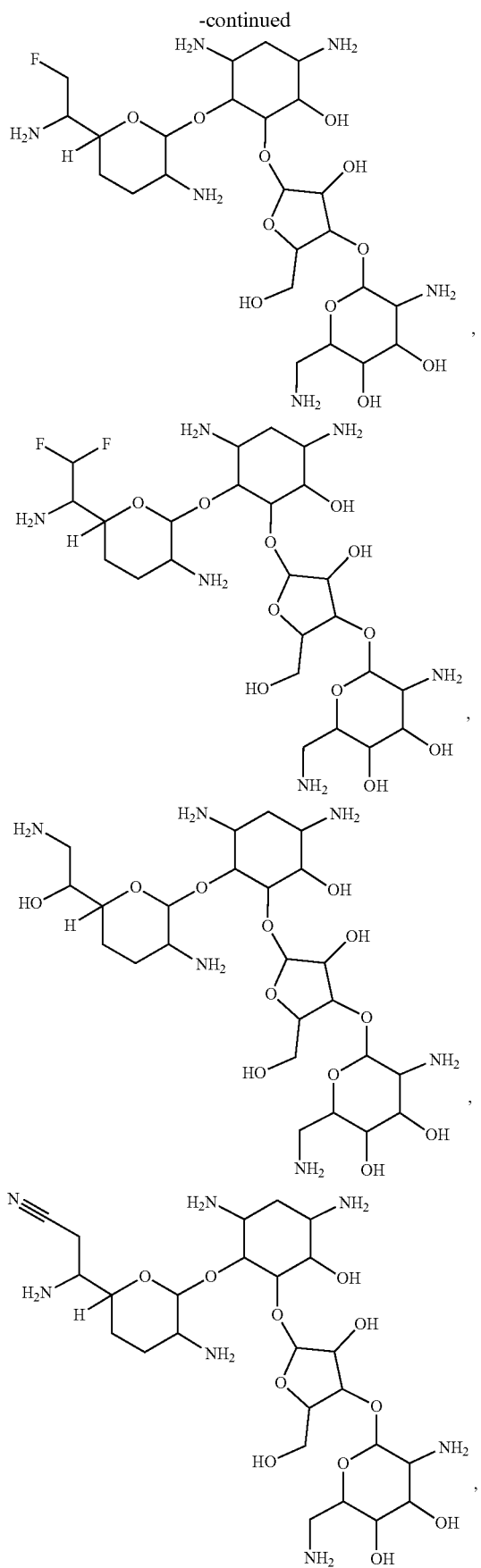
298
-continued
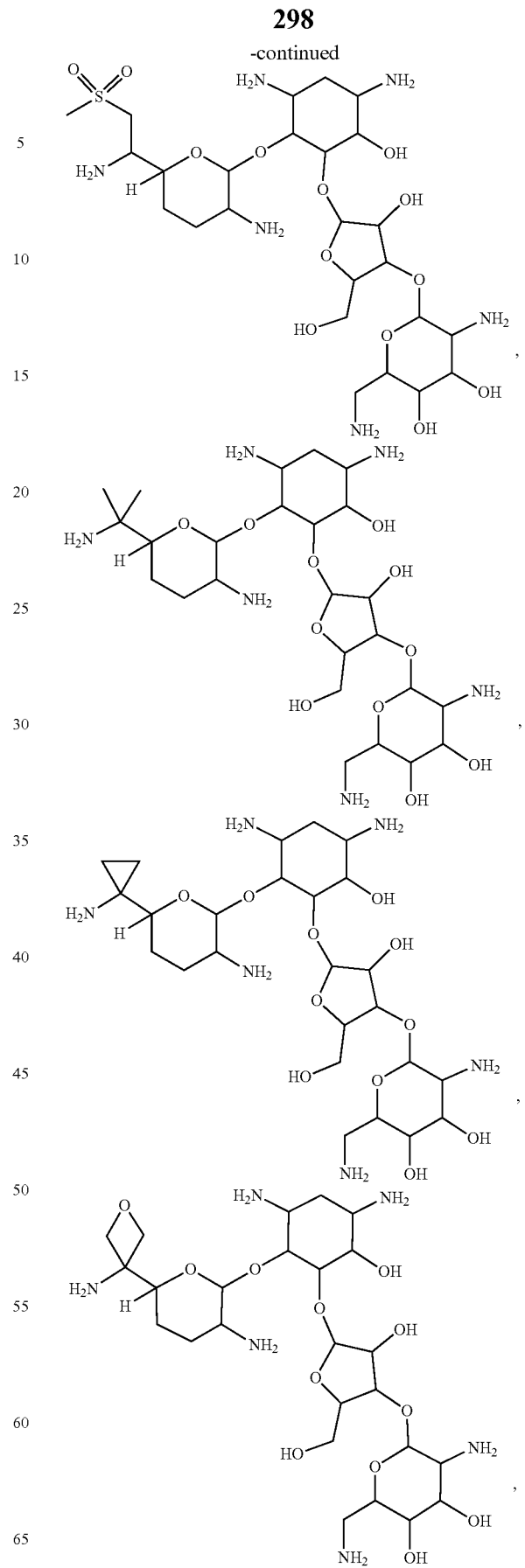

-continued

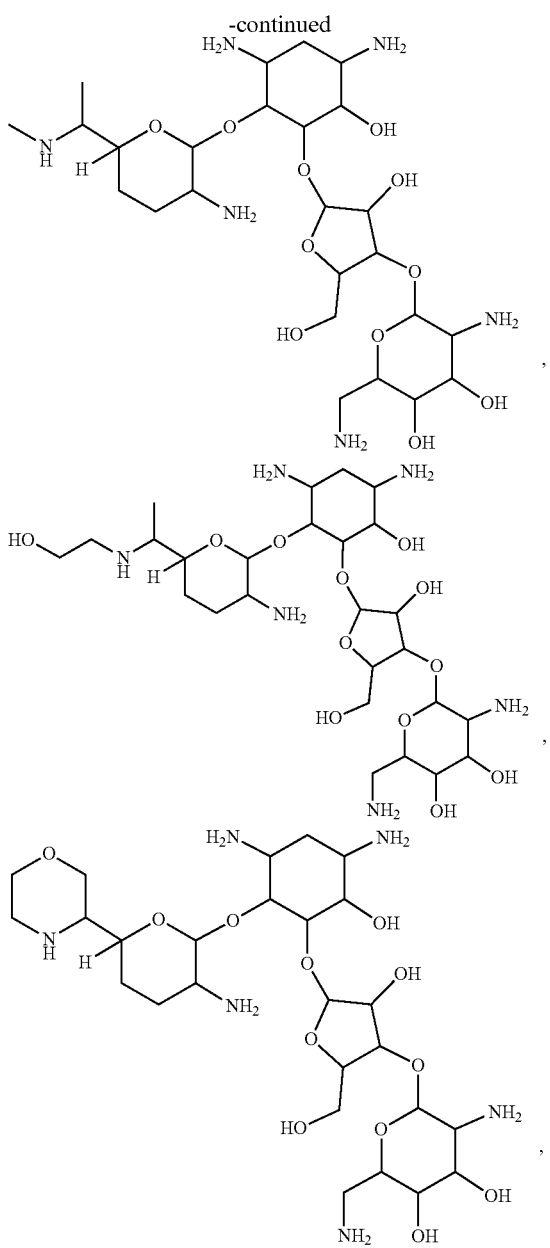

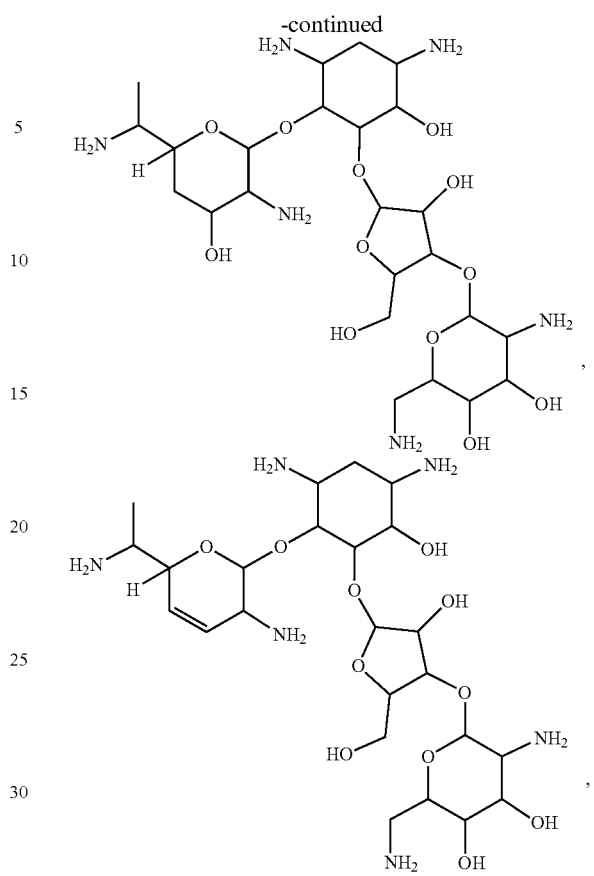

or a pharmaceutically acceptable salt, solvate, stereoisomer, or tautomer thereof.

Embodiment II-32. A pharmaceutical composition, comprising a compound of any one of Embodiment II-1 to II-31, or a pharmaceutically acceptable salt, solvate, stereoisomer, or tautomer thereof, and a pharmaceutically acceptable carrier.

Embodiment II-33. A method for treating a bacterial infection in a subject, comprising administering to a subject in need thereof a therapeutically effective amount of a compound of any one of Embodiment II-1 to II-31, or a pharmaceutically acceptable salt, solvate, stereoisomer, or tautomer thereof.

Embodiment II-34. A method for treating a bacterial infection in a subject, comprising administering to a subject in need thereof a therapeutically effective amount of a pharmaceutical composition according to Embodiment II-32.

Embodiment II-35. The method of Embodiment II-33 or Embodiment II-34, wherein the bacterial infection is a Gram-negative bacterial infection.

Embodiment II-36. The method of Embodiment II-33 or Embodiment II-34, wherein the bacterial infection is infection of a *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella, Francisella, Yersinia, Corynebacterium, Moraxella,* or *Enterococcus* species.

Embodiment II-37. Use of a compound of any one of Embodiment II-1 to I-31, or a pharmaceutically acceptable

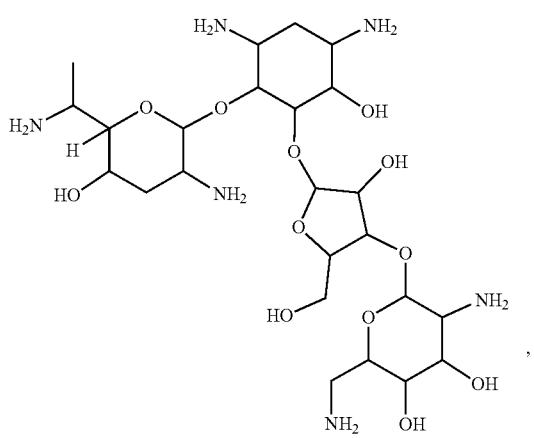

salt, solvate, stereoisomer, or tautomer thereof, in the manufacture of a medicament for treating a bacterial infection in a subject in need thereof.

Embodiment II-38. A compound of any one of Embodiment II-1 to I-31, or a pharmaceutically acceptable salt, solvate, stereoisomer, or tautomer thereof, for use in a method of treating a bacterial infection in a subject in need thereof.

Some embodiments of the disclosure are of Embodiment III.

Embodiment III-1. A compound of formula (III):

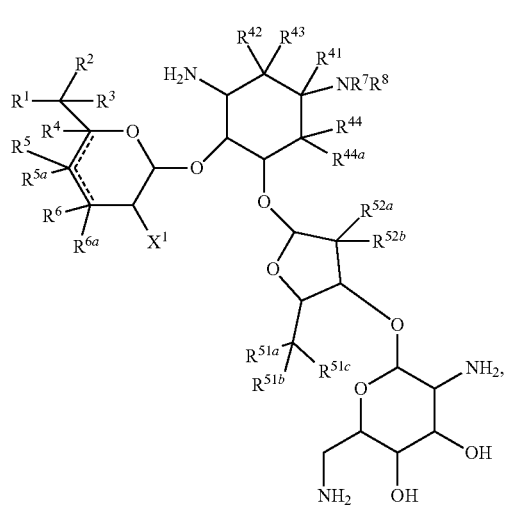

(III)

or a pharmaceutically acceptable salt, solvate, enantiomer, or diastereomer thereof, wherein $R^1$ is —$OR^9$ or —$NR^{10}R^{11}$, wherein $R^9$, $R^{10}$, and $R^{11}$ are independently H or $C_1$-$C_6$alkyl, wherein the alkyl is unsubstituted or substituted with one or more —OH;

$R^2$ and $R^3$ are independently selected from the group consisting of H, alkyl, cycloalkyl, and aryl,
  wherein the alkyl, cycloalkyl, or aryl is unsubstituted or substituted with one or more substituents independently selected from the group consisting of halogen, cyano, aryl, —$SR^{12}$, —$SO_2R^{13}$, —$OSF_2NR^{14}R^{15}$, —$NR^{14}R^{15}$, and —$OR^{16}$, and
  wherein each $R^{12}$, $R^{13}$, $R^{14}$, $R^{15}$, and $R^{16}$ is independently H or alkyl; or $R^1$ and $R^2$, together with the atom to which they are attached, form a heterocycloalkyl group comprising at least one heteroatom selected from the group consisting of N and O,
  wherein the heterocycloalkyl group is unsubstituted or substituted with one or more substituents independently selected from the group consisting of halogen, cyano, —$SO_2R^{18}$, —$NR^{19}R^{20}$, and —$OR^{21}$, and
  wherein each $R^{17}$, $R^{18}$, $R^{19}$, $R^{20}$, and $R^{21}$ is independently H or alkyl; or $R^2$ and $R^3$, together with the atom to which they are attached, form a cycloalkyl group or a heterocycloalkyl group,
  wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and wherein each $R^{22}$, $R^{23}$, $R^{24}$, $R^{25}$, and $R^{26}$ is independently H or alkyl; $R^4$ is H or absent;

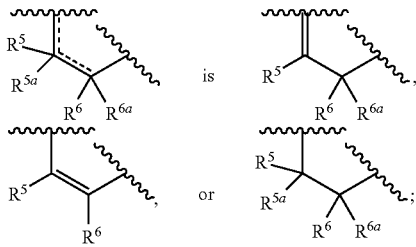

$R^5$ and $R^6$ are independently selected from the group consisting of H, —$OR^{27}$, —$NR^{28}R^{29}$, halogen, and alkyl, wherein each $R^{27}$, $R^{28}$, and $R^{29}$ is independently H or $C_1$-$C_6$alkyl,
  wherein the alkyl is unsubstituted or substituted with one or more substituents selected from the group consisting of halogen, —$OR^{30}$, —$NR^{31}R^{32}$, —$SR^{33}$, and —$SO_2R^{34}$; and
  wherein each $R^{30}$, $R^{31}$, $R^{32}$, $R^{33}$, and $R^{34}$ is independently H or alkyl; $R^{5a}$ and $R^{6a}$ are, independently, absent or independently selected from the group consisting of H, —$OR^{53}$, —$NR^{54}R^{55}$, halogen, and alkyl, wherein each $R^{53}$, $R^{54}$, and $R^{55}$ is independently H or $C_1$-$C_6$alkyl,
  wherein the alkyl is unsubstituted or substituted with one or more substituents selected from the group consisting of halogen, —$OR^{56}$, —$NR^{57}R^{58}$, —$SR^{59}$, and —$SO_2R^{60}$; and
  wherein each $R^{56}$, $R^{57}$, $R^{58}$, $R^{59}$, and $R^{60}$ is independently H or alkyl; or $R^5$ and $R^{5a}$ form an oxo group;
$R^6$ and $R^{6a}$ form an oxo group;
$R^7$ is H or $C_1$-$C_3$alkyl;

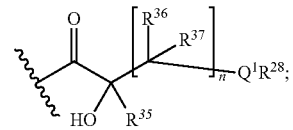

$R^8$ is H, $C_1$-$C_6$alkyl, an amino protecting group, or wherein $Q^1$ is NH, O, or S;
n is an integer from 0 to 4,
$R^{35}$ is H or $C_1$-$C_3$alkyl;
each $R^{36}$ and $R^{37}$ is independently selected from the group consisting of H, alkyl, halogen, and —OH, and
$R^{38}$ is H, alkyl, or —C(=NH)$NR^{39}R^{40}$, wherein $R^{39}$ and $R^{40}$ are independently H or $C_1$-$C_3$alkyl; or
$R^{35}$ and $R^{38}$, together with the atoms to which they are attached, form a heterocycloalkyl group comprising at least one N;

$R^{41}$ is H, —CN, —$CONH_2$ or $C_1$-$C_3$alkyl, wherein the alkyl is unsubstituted or substituted with one or more substituents selected from the group consisting of —OH, —OC(O)$CH_3$, —$NH_2$, —CN, —$CONH_2$, and halogen;

$R^{42}$ and $R^{43}$ are, independently, H, —OH, —$OR^{45}$, —$NR^{46}R^{47}$, or halogen;
  wherein each $R^{45}$, $R^{46}$, and $R^{47}$ is independently H, alkyl, —$CONH_2$, or —$COCH_3$;
  wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

R$^{44}$ and R$^{44a}$ independently H, halogen, —OH, C$_1$-C$_3$alkoxy, or —OC(O)CH$_3$;

X$^1$ is selected from the group consisting of H, NH$_2$, OH, and halogen;

R$^{51a}$, R$^{51b}$, and R$^{51c}$ are, independently, H, OH, or —OR$^{51d}$;

wherein each R$^{51d}$ is, independently, alkyl or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl;

R$^{52a}$ and R$^{52b}$ are independently H, OH, or —OR$^{52c}$, wherein each R$^{52c}$ is, independently, alkyl or —COCH$_3$; wherein the alkyl is unsubstituted or substituted with one or more substituents selected from the group consisting of —CONH$_2$, —OH, —NH$_2$, —COCH$_3$, aryl, substituted aryl, heteroaryl, or substituted heteroaryl.

Embodiment III-2. The compound of Embodiment III-1, or a pharmaceutically acceptable salt, solvate, stereoisomer, or tautomer thereof, wherein the compound is of formula (III-A):

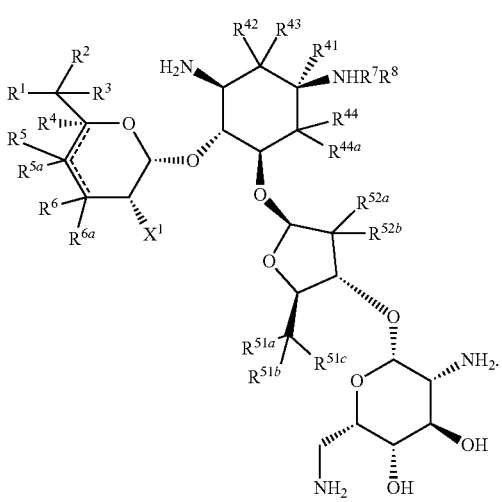

(III-A)

Embodiment III-3. The compound of any one of Embodiment III-1 to III-2, or a pharmaceutically acceptable salt, solvate, stereoisomer, or tautomer thereof, wherein R$^1$ is —NR$^{10}$R$^{11}$, wherein R$^{10}$, and R$^{11}$ are independently H, methyl, or hydroxyethyl.

Embodiment III-4. The compound of any one of Embodiment III-1 to III-2, or a pharmaceutically acceptable salt, solvate, stereoisomer, or tautomer thereof, wherein R$^1$ is OH.

Embodiment III-5. The compound of any one of Embodiment III-1 to III-4, or a pharmaceutically acceptable salt, solvate, stereoisomer, or tautomer thereof, wherein R$^2$ is alkyl, cyclopropyl, or phenyl; wherein the alkyl is unsubstituted or substituted with one, two, or three substituents selected from the group consisting of —NH$_2$, —OH, F, —CN, and —S(O)2CH$_3$.

Embodiment III-6. The compound of any one of Embodiment III-1 to III-4, or a pharmaceutically acceptable salt, solvate, stereoisomer, or tautomer thereof, wherein R$^1$ and R$^2$ together with the atom to which they are attached form an unsubstituted 6-membered heterocycloalkyl group comprising one N and one O.

Embodiment III-7. The compound of any one of Embodiment III-1 to III-6, or a pharmaceutically acceptable salt, solvate, stereoisomer, or tautomer thereof, wherein R$^3$ is H or unsubstituted methyl.

Embodiment III-8. The compound of any one of Embodiment III-1 to Embodiment III-4, or a pharmaceutically acceptable salt, solvate, stereoisomer, or tautomer thereof, wherein R$^2$ and R$^3$ together with the atom to which they are attached form a cyclopropyl or oxetanyl.

Embodiment III-9. The compound of any one of Embodiment III-1 to III-8, or a pharmaceutically acceptable salt, solvate, stereoisomer, or tautomer thereof, wherein R$^4$ is H and

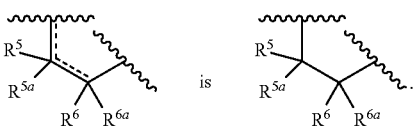

Embodiment III-10. The compound of Embodiment III-9, or a pharmaceutically acceptable salt, solvate, stereoisomer, or tautomer thereof, wherein R$^5$ and R$^{5a}$ are independently H, halogen, or —OH.

Embodiment III-11. The compound of Embodiment III-9 or III-10, or a pharmaceutically acceptable salt, solvate, stereoisomer, or tautomer thereof, wherein R$^6$ and R$^{6a}$ are independently H, halogen, or —OH.

Embodiment III-12. The compound of any one of Embodiment III-1 to Embodiment III-8, or a pharmaceutically acceptable salt, solvate, stereoisomer, or tautomer thereof, wherein R$^4$ is absent and

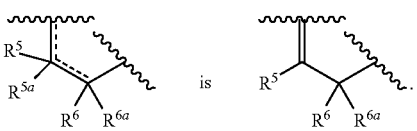

Embodiment III-13. The compound of Embodiment III-12, or a pharmaceutically acceptable salt, solvate, stereoisomer, or tautomer thereof, wherein R$^5$ is H, halogen, or —OH.

Embodiment III-14. The compound of Embodiment III-12 or III-13, or a pharmaceutically acceptable salt, solvate, stereoisomer, or tautomer thereof, wherein R$^6$ and R$^{6a}$ are independently H, halogen, or —OH.

Embodiment III-15. The compound of any one of Embodiment III-1 to Embodiment III-8, or a pharmaceutically acceptable salt, solvate, stereoisomer, or tautomer thereof, wherein R$^4$ is H and

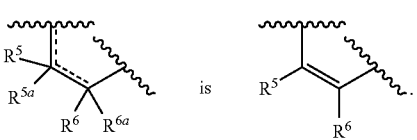

Embodiment III-16. The compound of Embodiment III-15, or a pharmaceutically acceptable salt, solvate, stereoisomer, or tautomer thereof, wherein R$^5$ is H, halogen, or —OH.

Embodiment III-17. The compound of Embodiment III-15 or III-16, or a pharmaceutically acceptable salt, solvate, stereoisomer, or tautomer thereof, wherein $R^6$ is H, halogen, or —OH.

Embodiment III-18. The compound of any one of Embodiment III-1 to III-17, or a pharmaceutically acceptable salt, solvate, stereoisomer, or tautomer thereof, wherein $X^1$ is $NH_2$.

Embodiment III-19. The compound of any one of Embodiment III-1 to III-17, or a pharmaceutically acceptable salt, solvate, stereoisomer, or tautomer thereof, wherein $X^1$ is OH.

Embodiment III-20. The compound of any one of Embodiment III-1 to III-19, or a pharmaceutically acceptable salt, solvate, enantiomer, or diastereomer thereof, wherein one of $R^{42}$ and $R^{43}$ is —OH.

Embodiment III-21. The compound of any one of Embodiment III-1 to III-19, or a pharmaceutically acceptable salt, solvate, enantiomer, or diastereomer thereof, wherein one of $R^{42}$ and $R^{43}$ is —$OR^{45}$.

Embodiment III-22. The compound of any one of Embodiment III-1 to III-19, or a pharmaceutically acceptable salt, solvate, enantiomer, or diastereomer thereof, wherein one of $R^{42}$ and $R^{43}$ is —$NR^{46}R^{47}$.

Embodiment III-23. The compound of any one of Embodiment III-1 to III-19, or a pharmaceutically acceptable salt, solvate, enantiomer, or diastereomer thereof, wherein one of $R^{42}$ and $R^{43}$ is —F.

Embodiment III-24. The compound of any one of Embodiment III-1 to III-19, or a pharmaceutically acceptable salt, solvate, enantiomer, or diastereomer thereof, wherein $R^{42}$ is —F and $R^{43}$ is —F.

Embodiment III-25. The compound of any one of Embodiment III-1 to III-19, or a pharmaceutically acceptable salt, solvate, enantiomer, or diastereomer thereof, wherein $R^{42}$ and $R^{43}$ are H.

Embodiment III-26. The compound of any one of Embodiment III-1 to III-25, or a pharmaceutically acceptable salt, solvate, enantiomer, or diastereomer thereof, wherein $R^{41}$ is H.

Embodiment III-27. The compound of any one of Embodiment III-1 to III-25, or a pharmaceutically acceptable salt, solvate, enantiomer, or diastereomer thereof, wherein $R^{41}$ is unsubstituted $C_1$-$C_3$alkyl.

Embodiment III-28. The compound of any one of Embodiment III-1 to III-25, or a pharmaceutically acceptable salt, solvate, enantiomer, or diastereomer thereof, wherein $R^{41}$ is $C_1$-$C_3$alkyl substituted by —OH.

Embodiment III-29. The compound of any one of Embodiment III-1 to III-25, or a pharmaceutically acceptable salt, solvate, enantiomer, or diastereomer thereof, wherein $R^{41}$ is $C_1$-$C_3$alkyl substituted by —$NH_2$.

Embodiment III-30. The compound of any one of Embodiment III-1 to III-25, or a pharmaceutically acceptable salt, solvate, enantiomer, or diastereomer thereof, wherein $R^{41}$ is —CN.

Embodiment III-31. The compound of any one of Embodiment III-1 to III-25, or a pharmaceutically acceptable salt, solvate, enantiomer, or diastereomer thereof, wherein $R^{41}$ is —$CONH_2$.

Embodiment III-32. The compound of any one of Embodiment III-1 to III-25, or a pharmaceutically acceptable salt, solvate, enantiomer, or diastereomer thereof, wherein $R^{41}$ is $C_1$-$C_3$alkyl substituted by one or more halogen.

Embodiment III-33. The compound of any one of Embodiment III-1 to III-25, or a pharmaceutically acceptable salt, solvate, enantiomer, or diastereomer thereof, wherein $R^{41}$ is $C_1$-$C_3$alkyl substituted by one or more —F.

Embodiment III-34. The compound of any one of Embodiment III-1 to III-25, or a pharmaceutically acceptable salt, solvate, enantiomer, or diastereomer thereof, wherein $R^{41}$ is $C_1$-$C_3$alkyl substituted by —CN.

Embodiment III-35. The compound of any one of Embodiment III-1 to III-34, or a pharmaceutically acceptable salt, solvate, enantiomer, or diastereomer thereof, wherein one of $R^{44}$ and $R^{44a}$ is —OH.

Embodiment III-36. The compound of any one of Embodiment III-1 to III-34, or a pharmaceutically acceptable salt, solvate, enantiomer, or diastereomer thereof, wherein one of $R^{44}$ and $R^{44a}$ is —$OCH_3$.

Embodiment III-37 The compound of any one of Embodiment III-1 to III-34, or a pharmaceutically acceptable salt, solvate, enantiomer, or diastereomer thereof, wherein one of $R^{44}$ and $R^{44a}$ is —F.

Embodiment III-38. The compound of any one of Embodiment III-1 to III-34, or a pharmaceutically acceptable salt, solvate, enantiomer, or diastereomer thereof, wherein $R^{44}$ and $R^{44a}$ are —F.

Embodiment III-39. The compound of any one of Embodiment III-1 to III-34, or a pharmaceutically acceptable salt, solvate, enantiomer, or diastereomer thereof, wherein $R^{44}$ and $R^{44a}$ are H.

Embodiment III-40. The compound of any one of Embodiment III-1 to III-39, or a pharmaceutically acceptable salt, solvate, stereoisomer, or tautomer thereof, wherein $R^7$ and $R^8$ are H.

Embodiment III-41. The compound of any one of Embodiment III-1 to III-39, or a pharmaceutically acceptable salt, solvate, stereoisomer, or tautomer thereof, wherein $R^7$ is H and $R^8$ is:

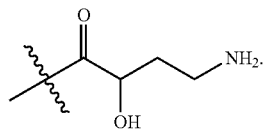 [SMILES: *C(=O)C(O)CCN]

Embodiment III-42. The compound of any one of Embodiment III-1 to III-39, or a pharmaceutically acceptable salt, solvate, stereoisomer, or tautomer thereof, wherein $R^7$ is H and $R^8$ is:

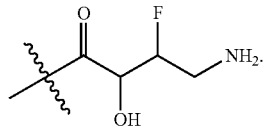 [SMILES: *C(=O)C(O)C(F)CN]

Embodiment III-43. The compound of any one of Embodiment III-1 to III-39, or a pharmaceutically acceptable salt, solvate, stereoisomer, or tautomer thereof, wherein $R^7$ is H and $R^8$ is:

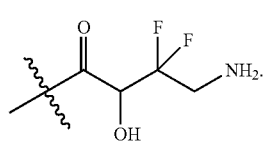 [SMILES: *C(=O)C(O)C(F)(F)CN]

Embodiment III-44. The compound of any one of Embodiment III-1 to III-39, or a pharmaceutically acceptable salt, solvate, stereoisomer, or tautomer thereof, wherein $R^7$ is H and $R^8$ is:

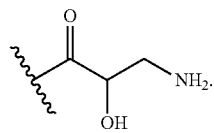 [SMILES: *C(=O)C(O)CN]

Embodiment III-45. The compound of any one of Embodiment III-1 to III-44, or a pharmaceutically acceptable salt, solvate, stereoisomer, or tautomer thereof, wherein one of $R^{51a}$, $R^{51b}$, and $R^{51c}$ is —OH.

Embodiment III-46. The compound of any one of Embodiment III-1 to III-44, or a pharmaceutically acceptable salt, solvate, stereoisomer, or tautomer thereof, wherein one of $R^{51a}$, $R^{51b}$ and $R^{51c}$ is —OR$^{51d}$.

Embodiment III-47. The compound of any one of Embodiment III-1 to III-46, or a pharmaceutically acceptable salt, solvate, stereoisomer, or tautomer thereof, wherein one of $R^{52a}$ and $R^{52b}$ is —OH.

Embodiment III-48. The compound of any one of Embodiment III-1 to III-46, or a pharmaceutically acceptable salt, solvate, stereoisomer, or tautomer thereof, wherein one of $R^{52a}$ and $R^{52b}$ is —OR$^{52c}$.

Embodiment III-49. The compound of any one of Embodiment III-1 to III-48, wherein the compound is selected from the group consisting of:

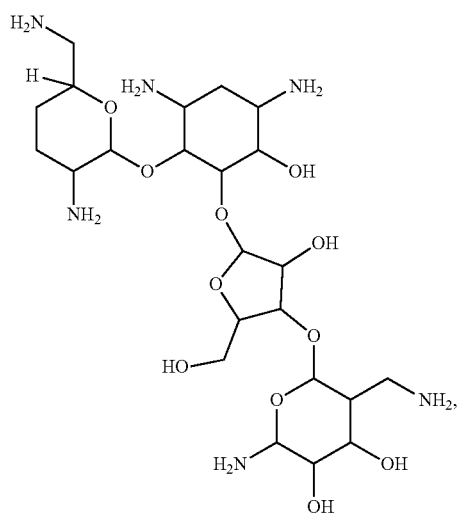

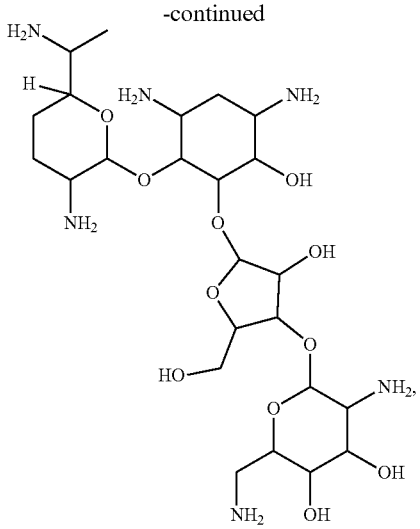

-continued

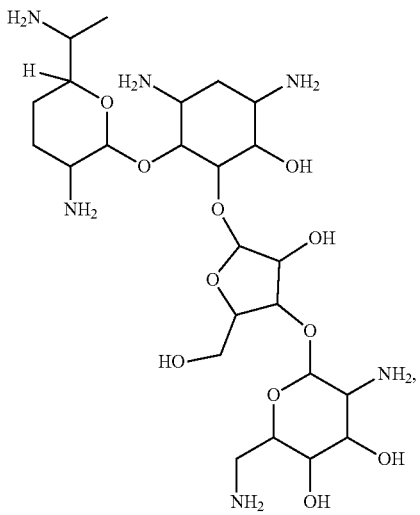

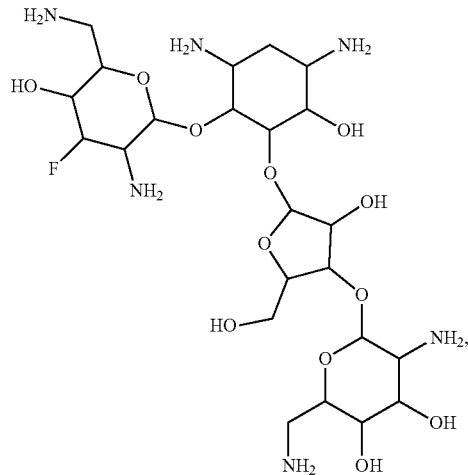

309
-continued
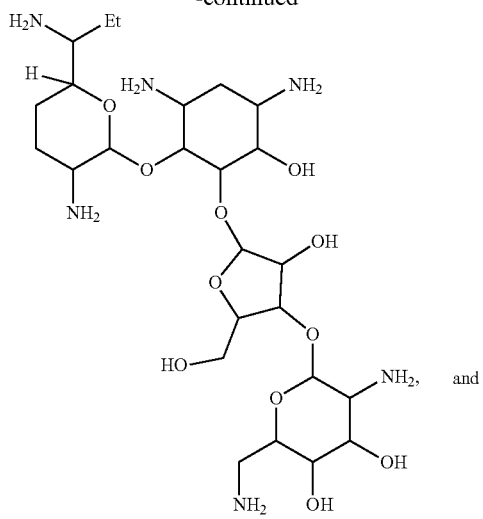
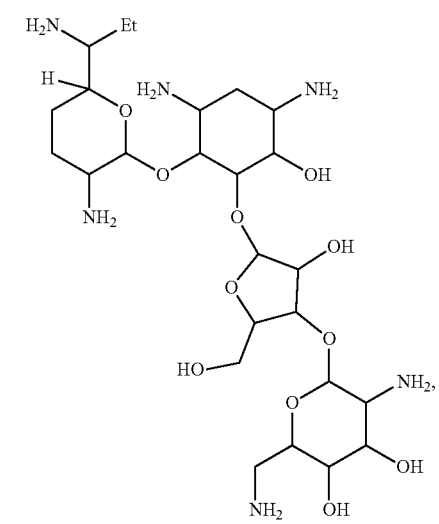
and
or a pharmaceutically acceptable salt, solvate, stereoisomer, or tautomer thereof.
Embodiment III-50. The compound of any one of Embodiment III-1 to III-48, wherein the compound is selected from the group consisting of:
310
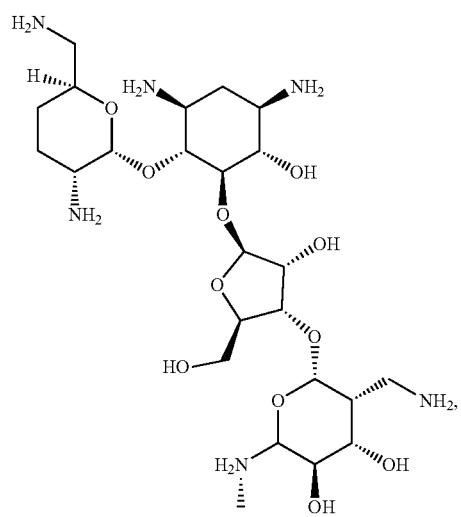
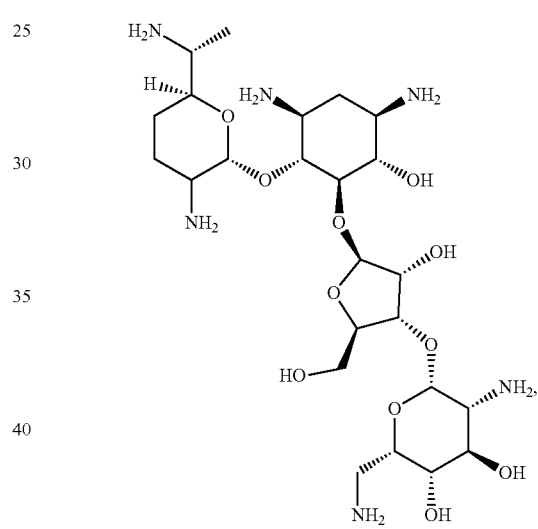
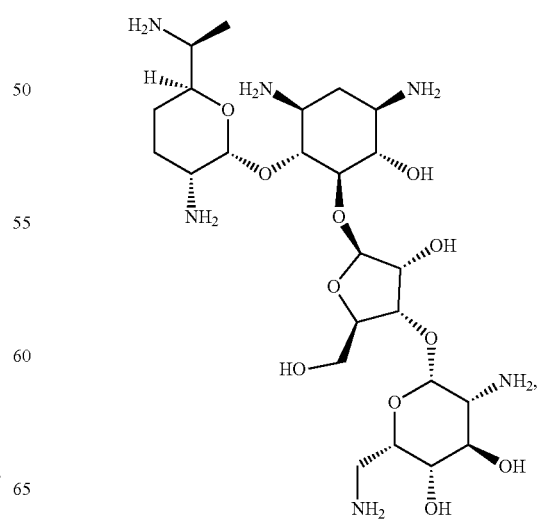

311
-continued

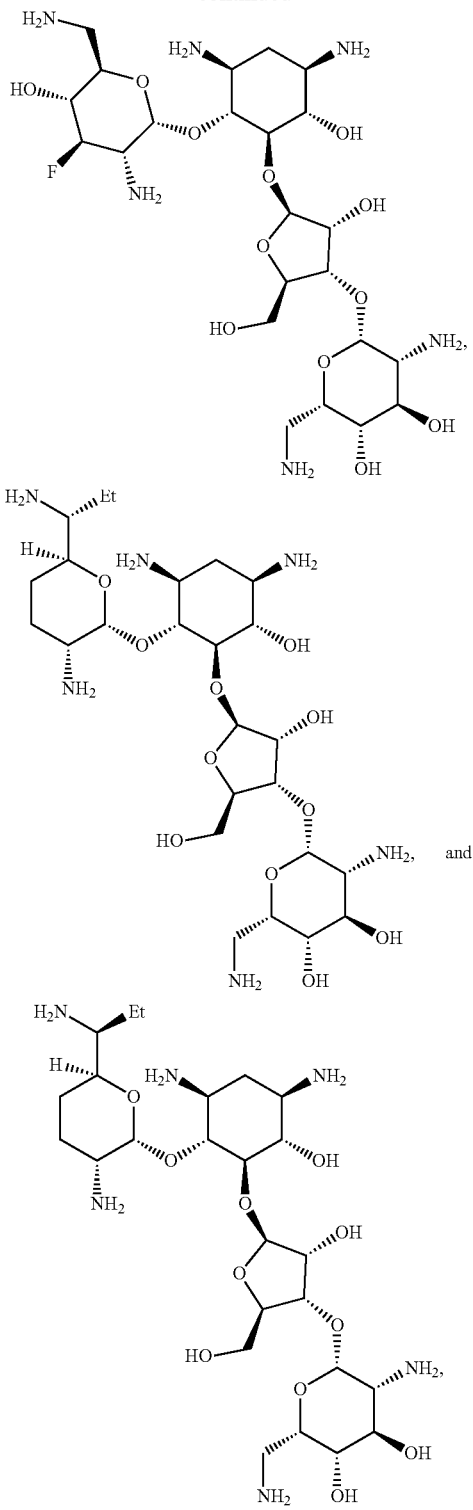

or a pharmaceutically acceptable salt, solvate, stereoisomer, or tautomer thereof.

312

Embodiment III-51. A compound of formula (II):

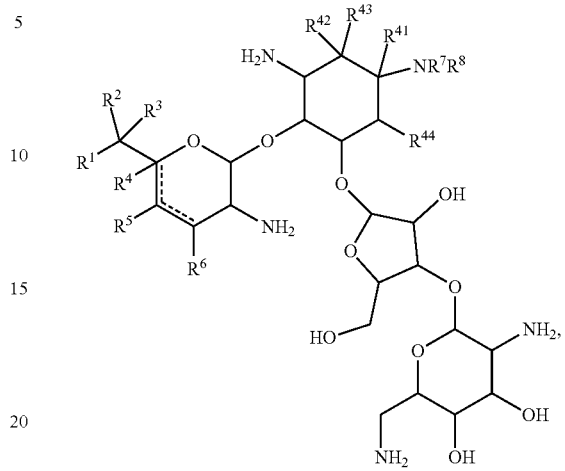

or a pharmaceutically acceptable salt, solvate, tautomer, or stereoisomer thereof, wherein as valence and stability permit, $R^1$ is —$OR^9$ or —$NR^{10}R^{11}$, wherein $R^9$, $R^{10}$, and $R^{11}$ are independently H or $C_1$-$C_6$alkyl, wherein the alkyl is unsubstituted or substituted with one or more —OH;

$R^2$ and $R^3$ are independently selected from the group consisting of H, alkyl, cycloalkyl, and aryl,
  wherein the alkyl, cycloalkyl, or aryl is unsubstituted or substituted with one or more substituents independently selected from the group consisting of halogen, cyano, aryl, —$SR^{12}$, —$SO_2R^{13}$, —$NR^{14}R^{15}$, and —$OR^{16}$, and
  wherein each $R^{12}$, $R^{13}$, $R^{14}$, $R^{15}$, and $R^{16}$ is independently H or alkyl; or $R^1$ and $R^2$, together with the atom to which they are attached, form a heterocycloalkyl group comprising at least one heteroatom selected from the group consisting of N and O,
  wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and
  wherein each $R^{17}$, $R^{18}$, $R^{19}$, $R^{20}$, and $R^{21}$ is independently H or alkyl; or $R^2$ and $R^3$, together with the atom to which they are attached, form a cycloalkyl group or a heterocycloalkyl group,
  wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and
  wherein each $R^{22}$, $R^{23}$, $R^{24}$, $R^{25}$, and $R^{26}$ is independently H or alkyl; and wherein at least one of $R^2$ and $R^3$ is other than H;

$R^4$ is H or absent;

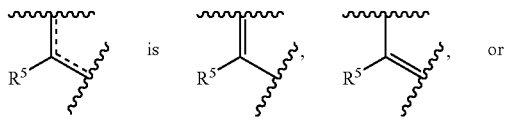 is

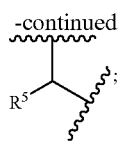

$R^5$ and $R^6$ are independently selected from the group consisting of H, —$OR^{27}$, —$NR^{28}R^{29}$, halogen, and alkyl, wherein each $R^{27}$, $R^{28}$, and $R^{29}$ is independently H or $C_1$-$C_6$alkyl,
  wherein the alkyl is unsubstituted or substituted with one or more substituents selected from the group consisting of halogen, —$OR^{30}$, —$NR^{31}R^{32}$, —$SR^{33}$, and —$SO_2R^{34}$; and
  wherein each $R^{30}$, $R^{31}$, $R^{32}$, $R^{33}$, and $R^{34}$ is independently H or alkyl;
$R^7$ is H or $C_1$-$C_3$alkyl;
$R^8$ is H or

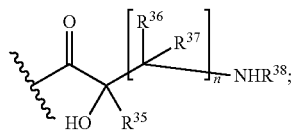

wherein n is an integer from 0 to 4,
$R^{35}$ is H or $C_1$-$C_3$alkyl;
each $R^{36}$ and $R^{37}$ is independently selected from the group consisting of H, alkyl, halogen, and —OH, and
$R^{38}$ is H, alkyl, or —C(=NH)$NR^{39}R^{49}$, wherein $R^{39}$ and $R^{40}$ are independently H or $C_1$-$C_3$alkyl; or
$R^{35}$ and $R^{38}$, together with the atoms to which they are attached, form a heterocycloalkyl group comprising at least one N;
$R^{41}$ is H, $C_1$-$C_3$alkyl, wherein the alkyl is unsubstituted or substituted by —OH or halogen;
$R^{42}$ and $R^{43}$ are, independently H, —OH, or halogen; and $R^{44}$ is H, halogen, —OH, or $C_1$-$C_3$alkoxy.

Embodiment III-52. The compound of Embodiment III-51, or a pharmaceutically acceptable salt, solvate, stereoisomer, or tautomer thereof, wherein the compound is of formula (II-A):

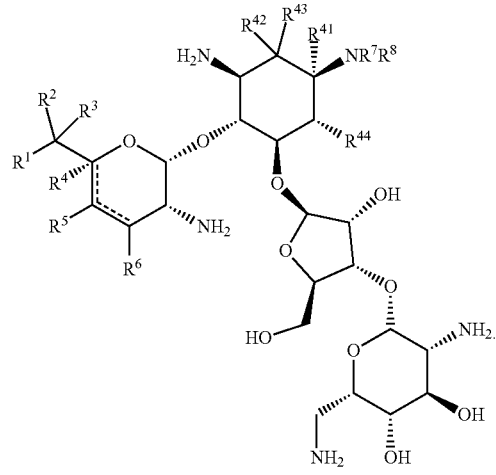

Embodiment III-53. A compound of formula (I):

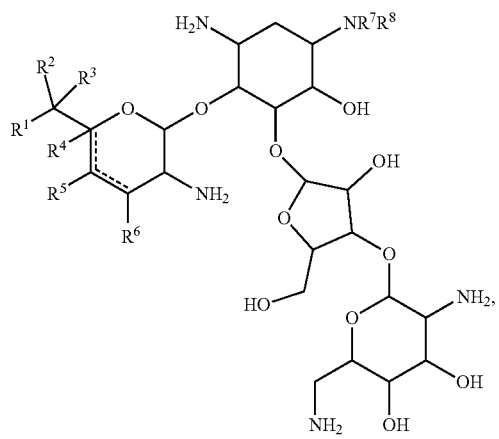

or a pharmaceutically acceptable salt, solvate, stereoisomer, or tautomer thereof, wherein:
$R^1$ is —$OR^9$ or —$NR^{10}R^{11}$, wherein $R^9$, $R^{10}$, and $R^{11}$ are independently H or $C_1$-$C_6$alkyl, wherein the alkyl is unsubstituted or substituted with one or more —OH;
$R^2$ and $R^3$ are independently selected from the group consisting of H, alkyl, cycloalkyl, and aryl,
  wherein the alkyl, cycloalkyl, or aryl is unsubstituted or substituted with one or more substituents independently selected from the group consisting of halogen, cyano, aryl, —$SR^{12}$, —$SO_2R^{13}$, —$NR^{14}R^{15}$, and —$OR^{16}$, and
  wherein each $R^{12}$, $R^{13}$, $R^{14}$, $R^{15}$, and $R^{16}$ is independently H or alkyl; or
$R^1$ and $R^2$, together with the atom to which they are attached, form a heterocycloalkyl group comprising at least one heteroatom selected from the group consisting of N and O,
  wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and
  wherein each $R^{17}$, $R^{18}$, $R^{19}$, $R^{20}$, and $R^{21}$ is independently H or alkyl; or
$R^2$ and $R^3$, together with the atom to which they are attached, form a cycloalkyl group or a heterocycloalkyl group,
  wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and
  wherein each $R^{22}$, $R^{23}$, $R^{24}$, $R^{25}$, and $R^{26}$ is independently H or alkyl; and wherein at least one of $R^2$ and $R^3$ is other than H;
$R^4$ is H or absent;

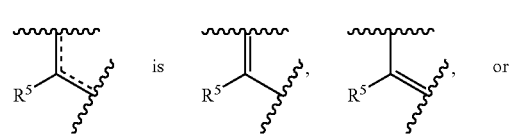

-continued

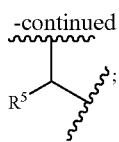

$R^5$ and $R^6$ are independently selected from the group consisting of H, —$OR^{27}$, —$NR^{28}R^{29}$, halogen, and alkyl, wherein each $R^{27}$, $R^{28}$, and $R^{29}$ is independently H or $C_1$-$C_6$alkyl, wherein the alkyl is unsubstituted or substituted with one or more substituents selected from the group consisting of halogen, —$OR^{30}$, —$NR^{31}R^{32}$, —$SR^{33}$, and —$SO_2R^{34}$; and wherein each $R^{30}$, $R^{31}$, $R^{32}$, $R^{33}$, and $R^{34}$ is independently H or alkyl;

$R^7$ is H or $C_1$-$C_3$alkyl;

$R^8$ is H or

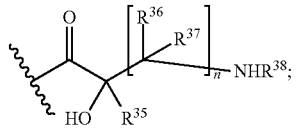

wherein n is an integer from 0 to 4, $R^{35}$ is H or $C_1$-$C_3$alkyl;

each $R^{36}$ and $R^{37}$ is independently selected from the group consisting of H, alkyl, halogen, and —OH, and $R^{38}$ is H, alkyl, or —C(=NH)$NR^{39}R^{40}$, wherein $R^{39}$ and $R^{40}$ are independently H or $C_1$-$C_3$ alkyl; or $R^{35}$ and $R^{38}$, together with the atoms to which they are attached, form a heterocycloalkyl group comprising at least one N.

Embodiment III-54. The compound of Embodiment III-53, or a pharmaceutically acceptable salt, solvate, stereoisomer, or tautomer thereof, wherein the compound is of formula (I-A):

(I-A)

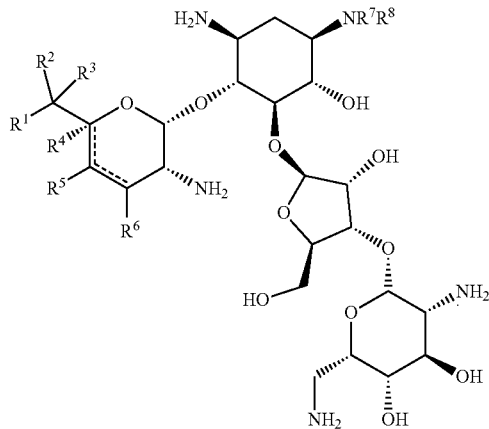

Embodiment III-55. The compound of any one of Embodiment III-51 to III-54, wherein the compound is selected from the group consisting of:

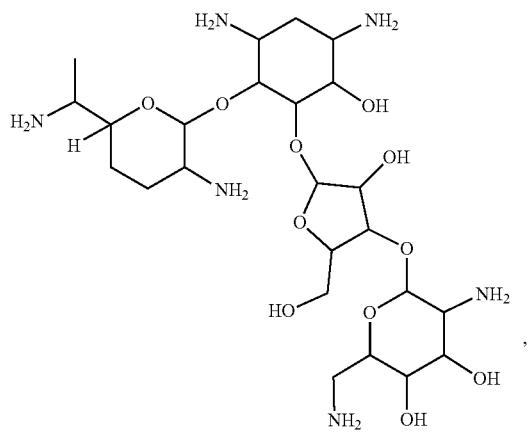

,

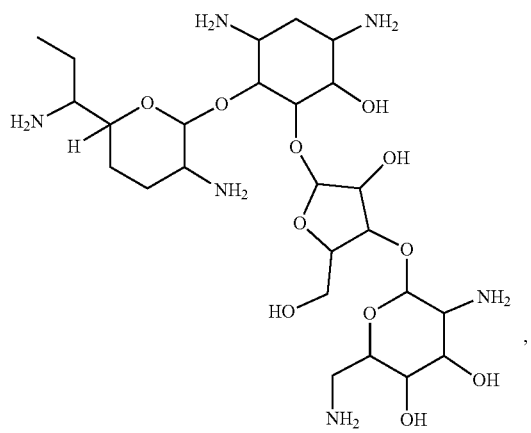

,

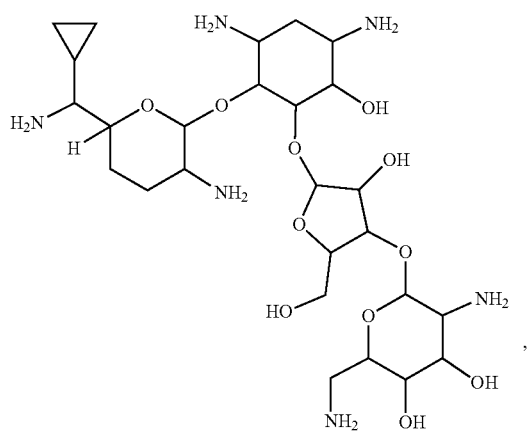

,

317
-continued
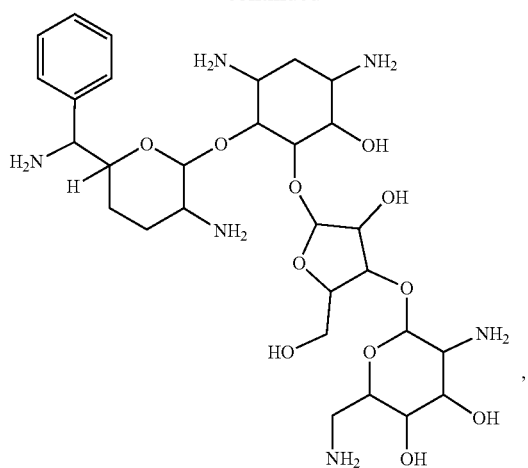
318
-continued
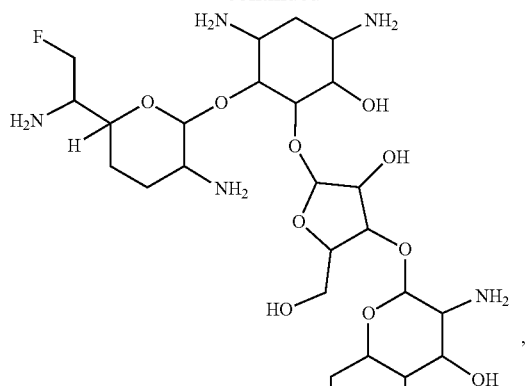
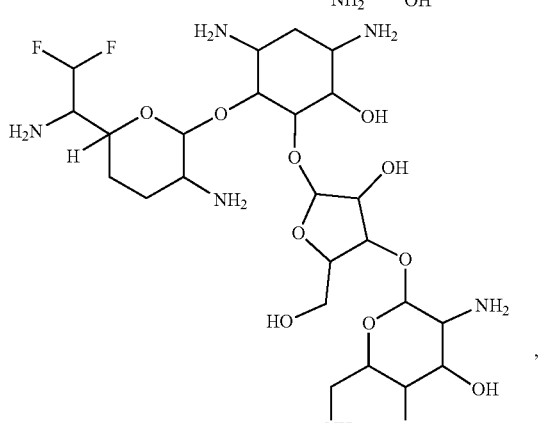
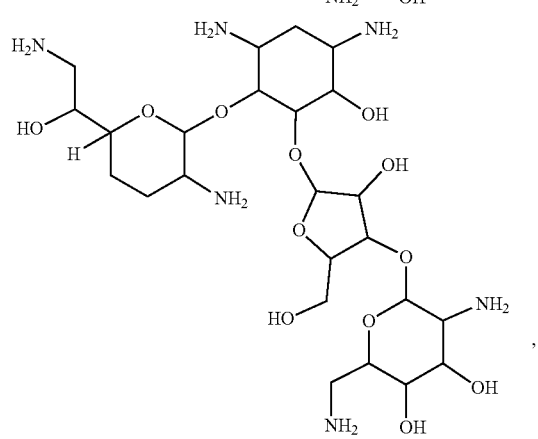
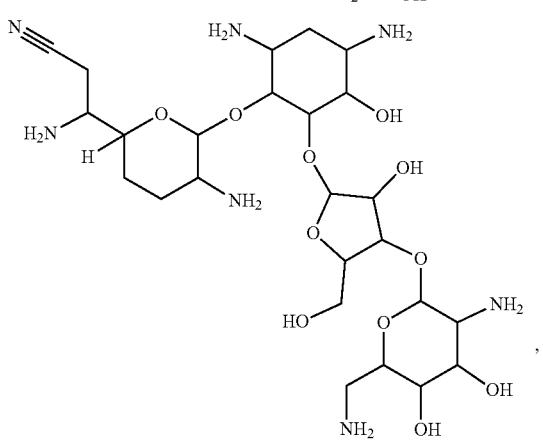

-continued
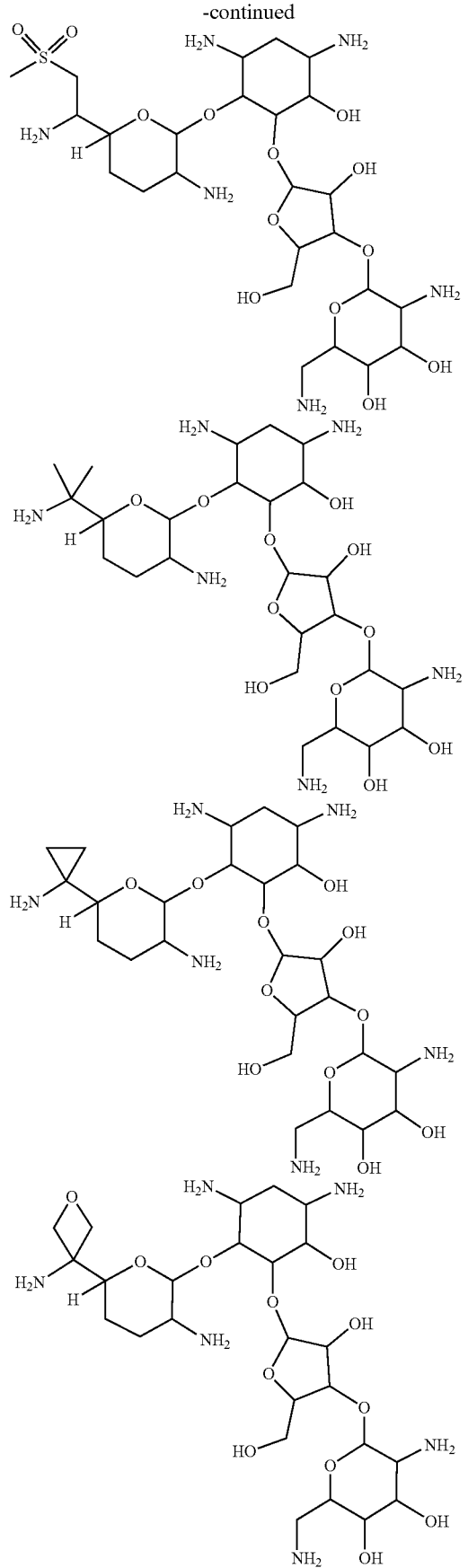
-continued
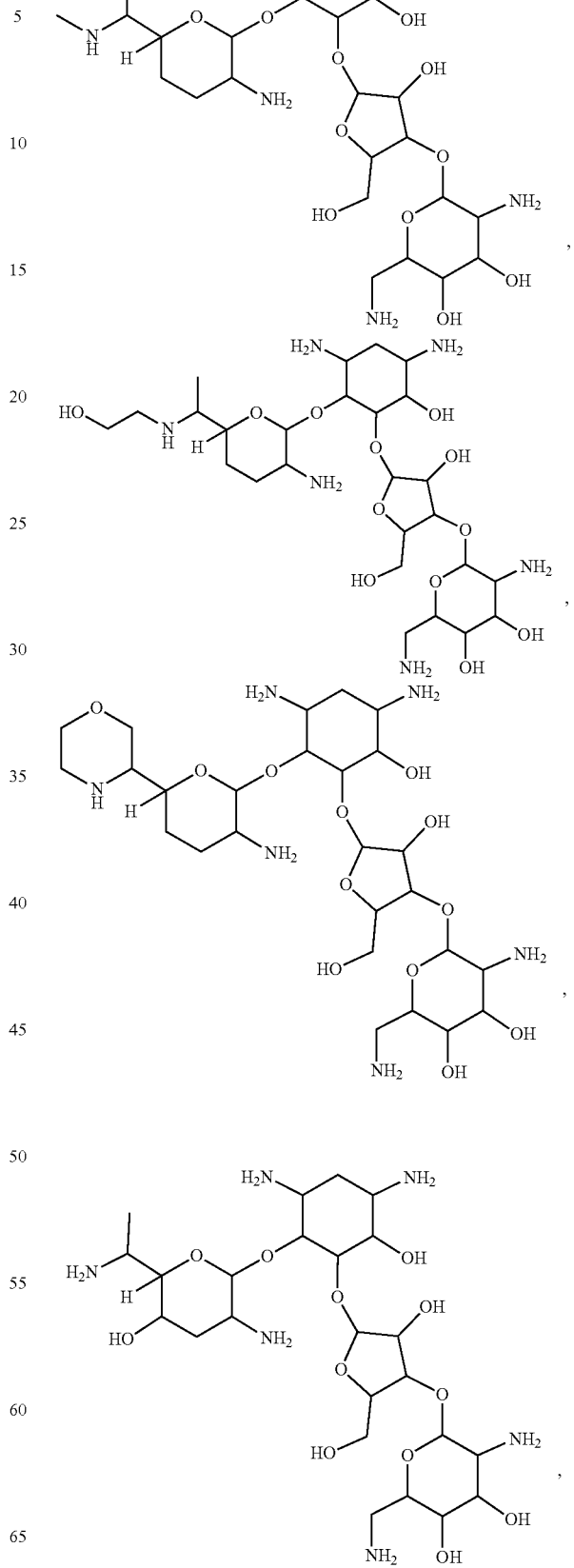

321
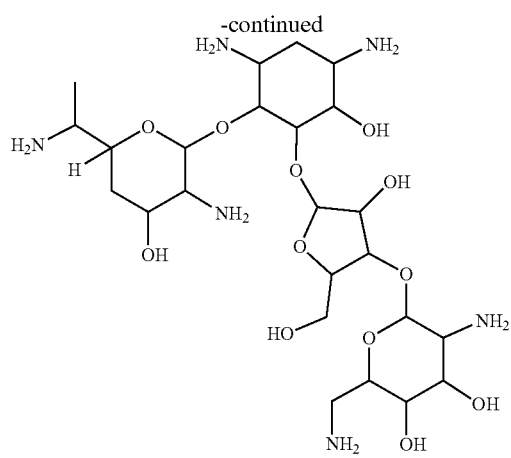
and
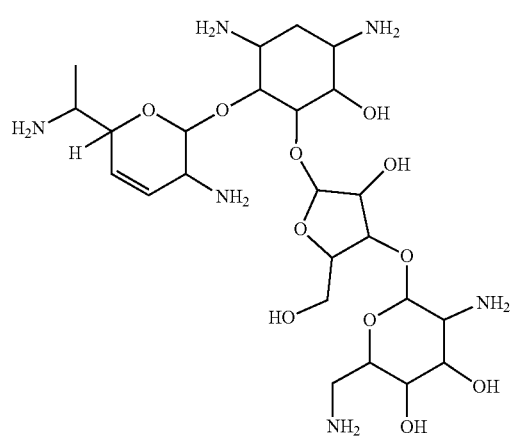
or a pharmaceutically acceptable salt, solvate, stereoisomer, or tautomer thereof.
Embodiment III-56. The compound of any one of Embodiment III-51 to III-54, wherein the compound is selected from the group consisting of:
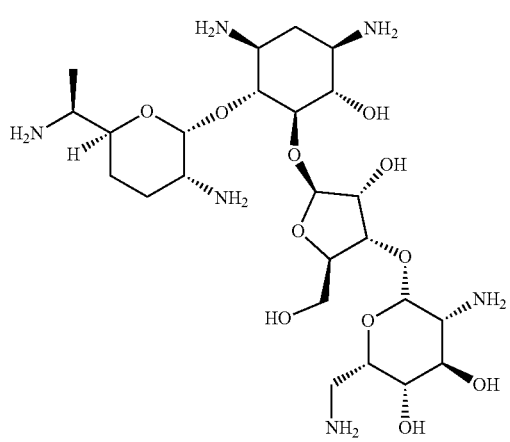
322
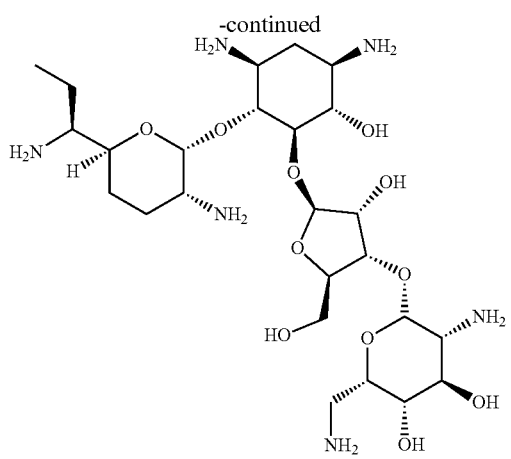
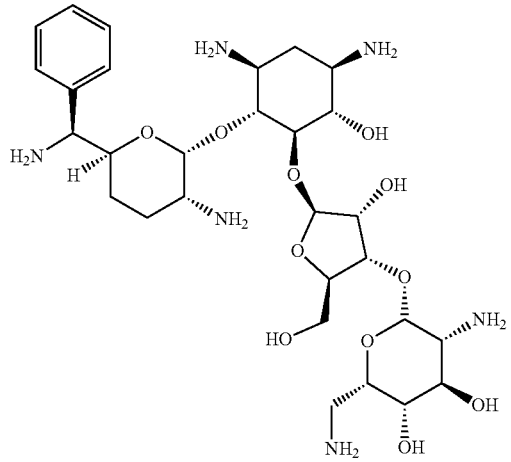

323 324
-continued -continued
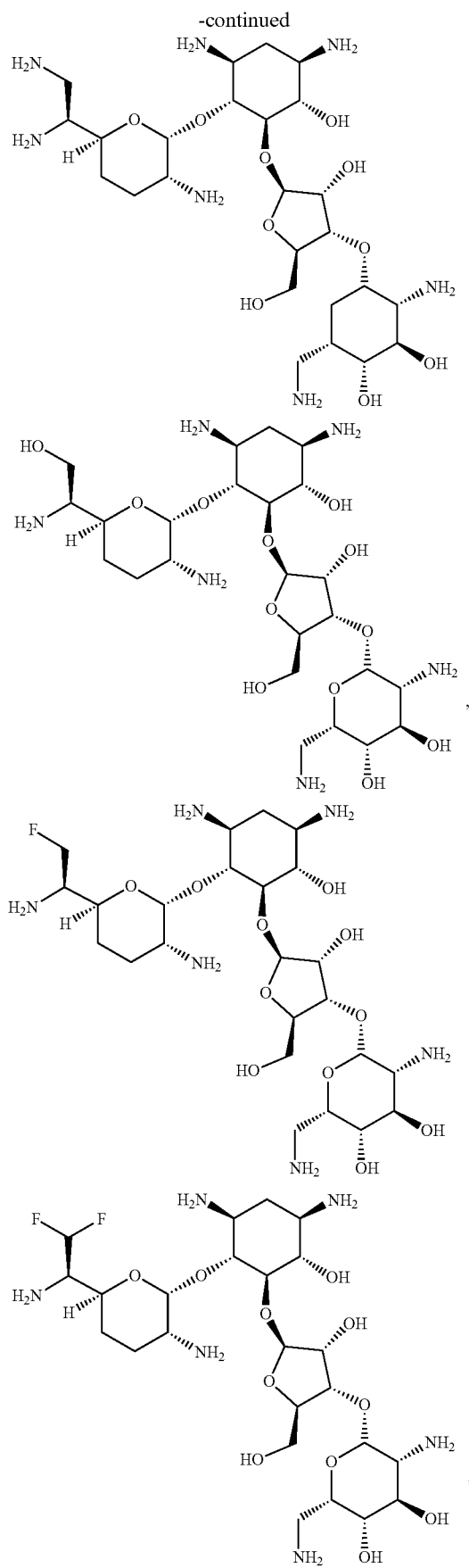
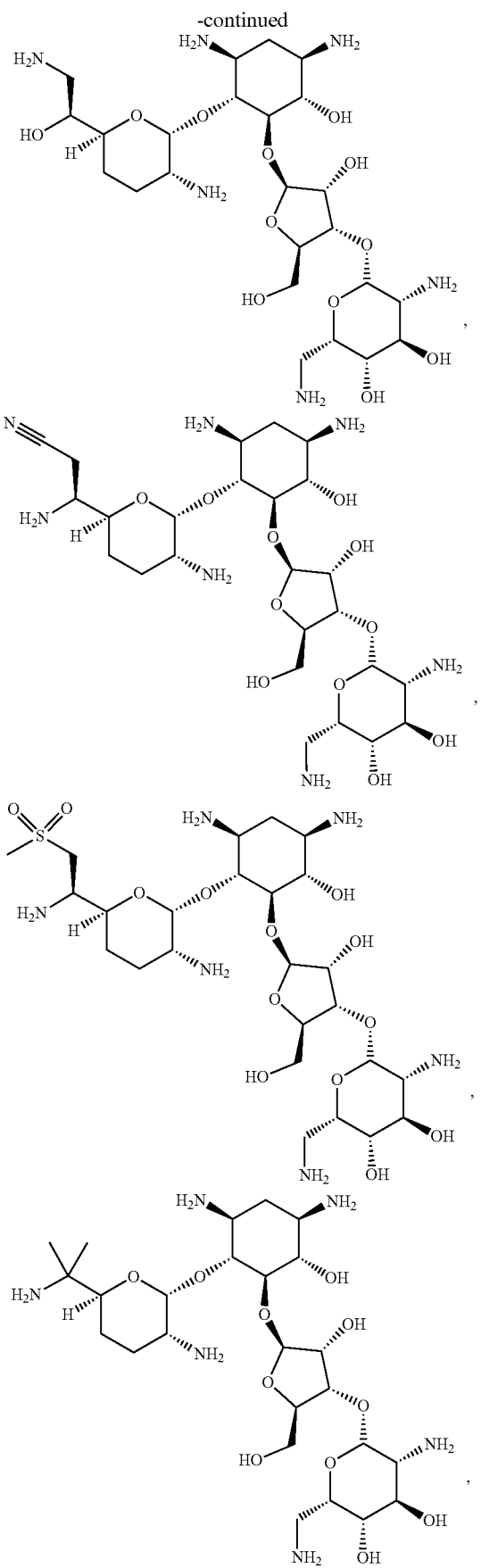

325
-continued
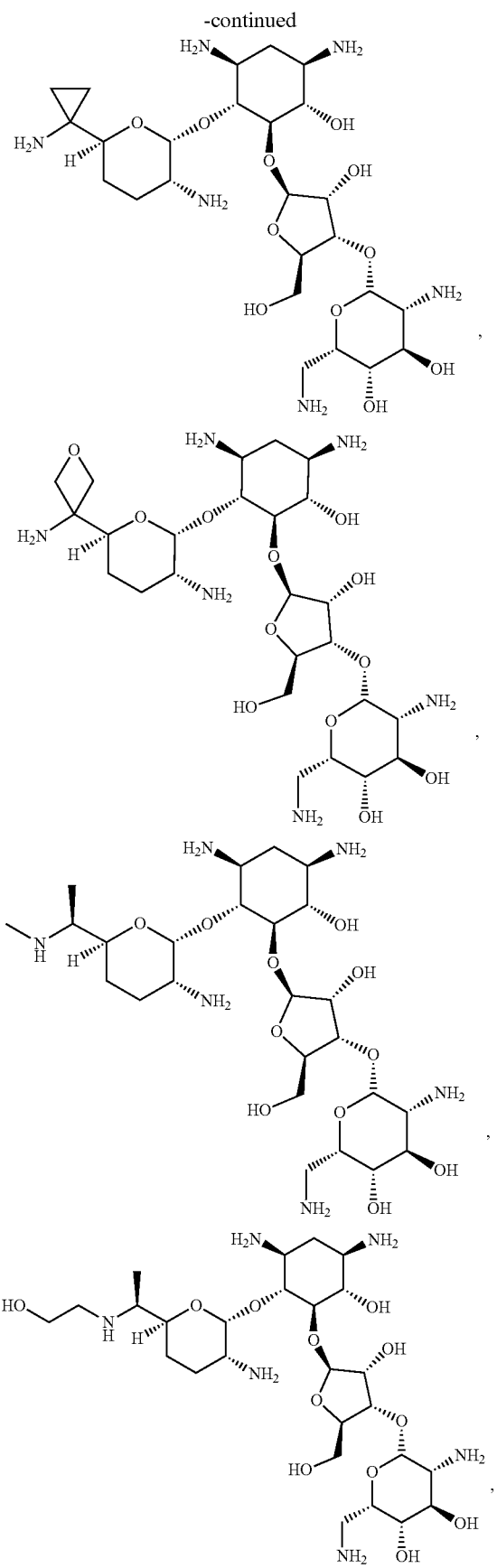
326
-continued
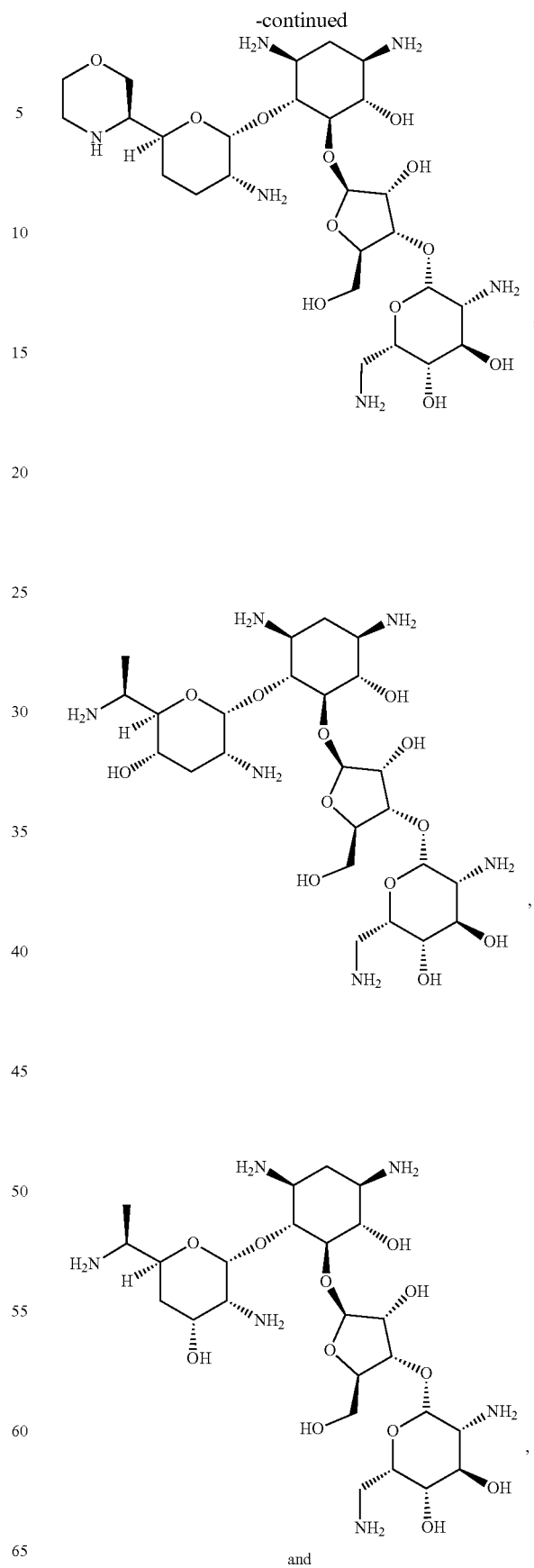
and

327
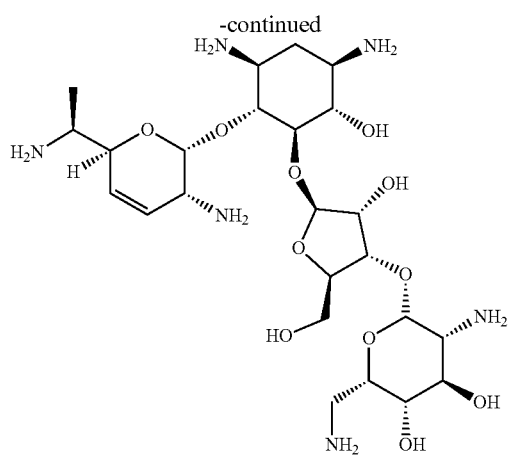
328
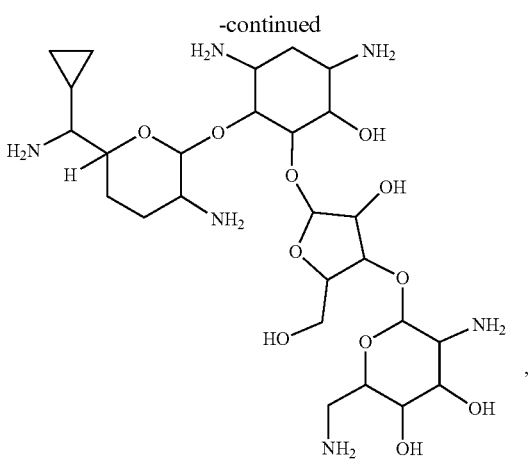
or a pharmaceutically acceptable salt, solvate, stereoisomer, or tautomer thereof.
Embodiment III-57. The compound of any one of Embodiment III-1 to III-56, wherein the compound is selected from the group consisting of:
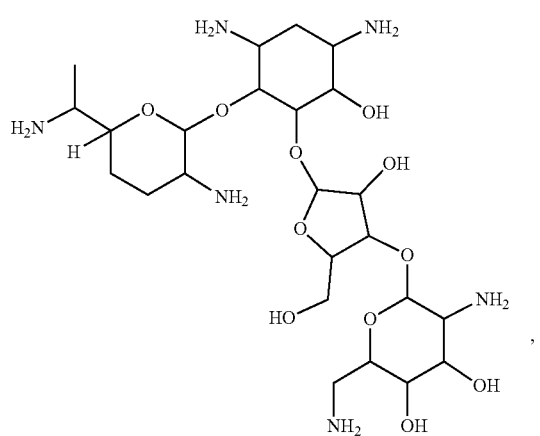
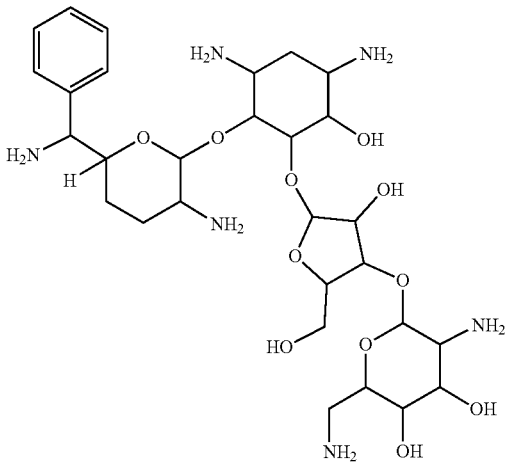
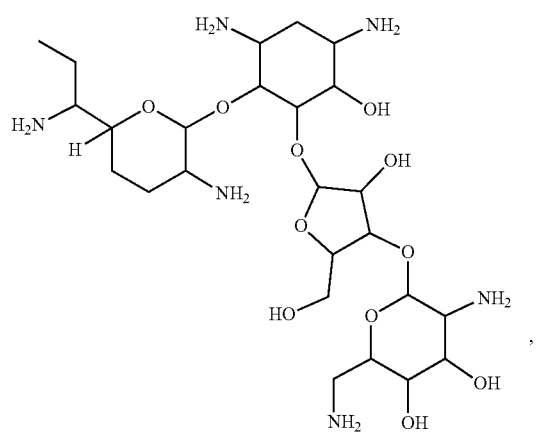
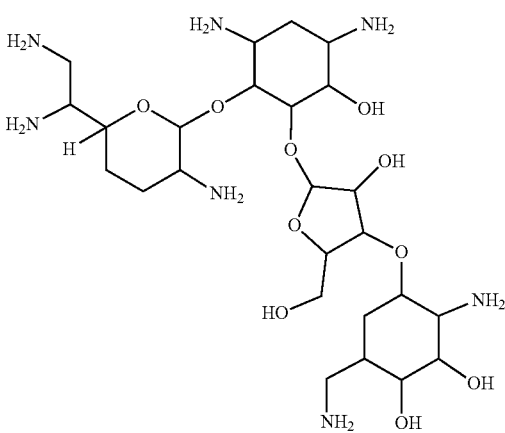

-continued
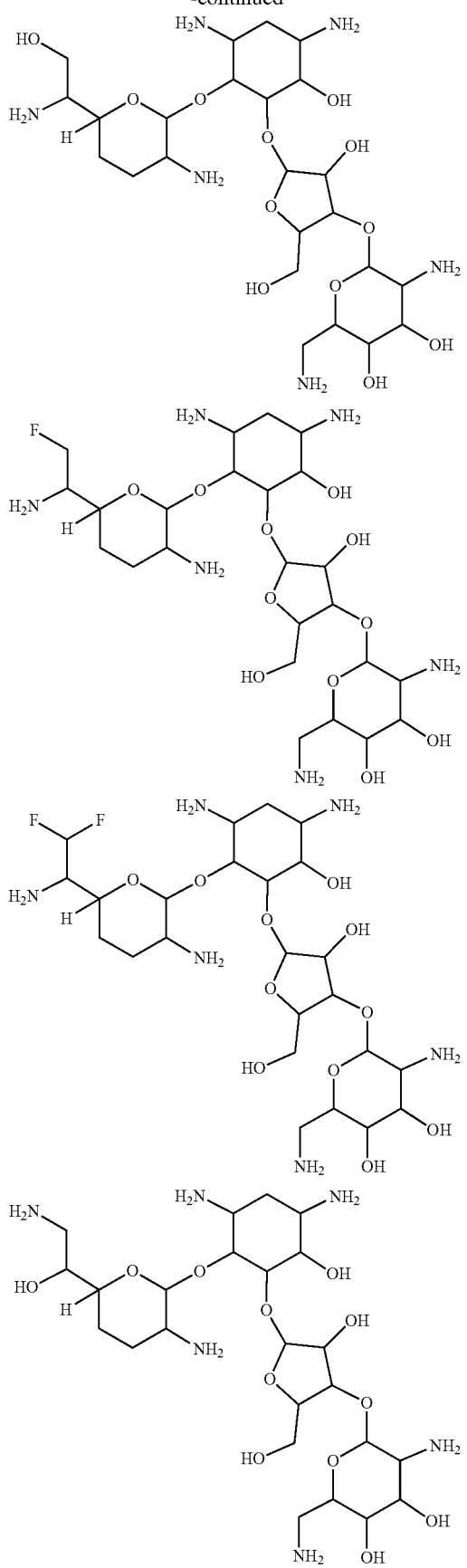

-continued
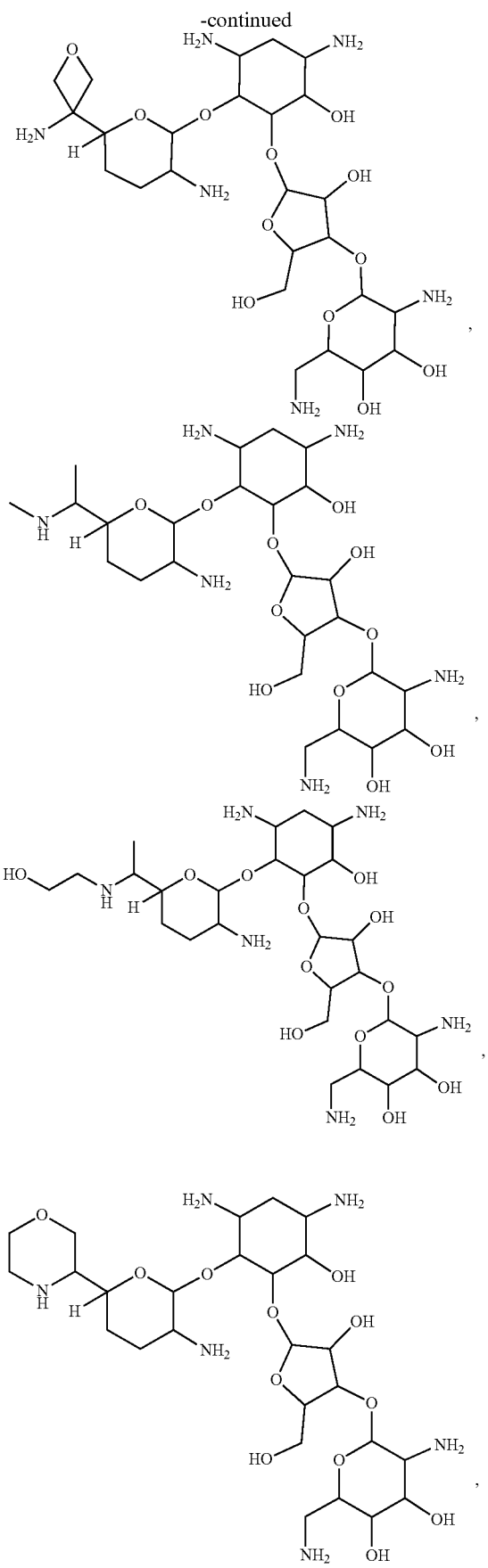
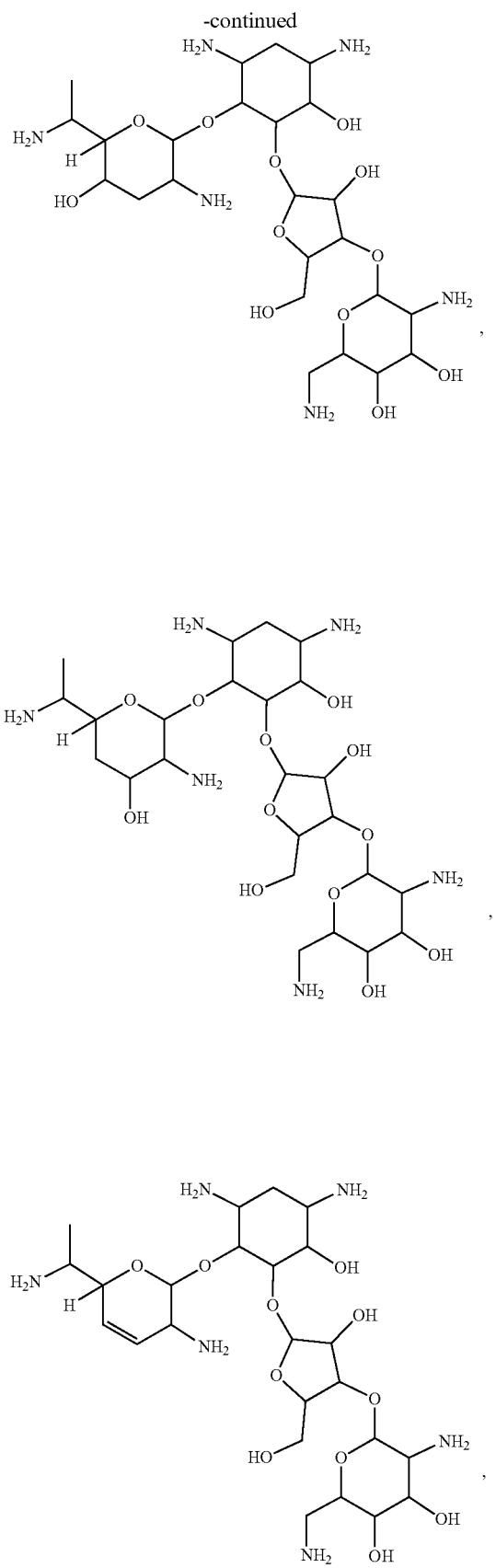

333
-continued
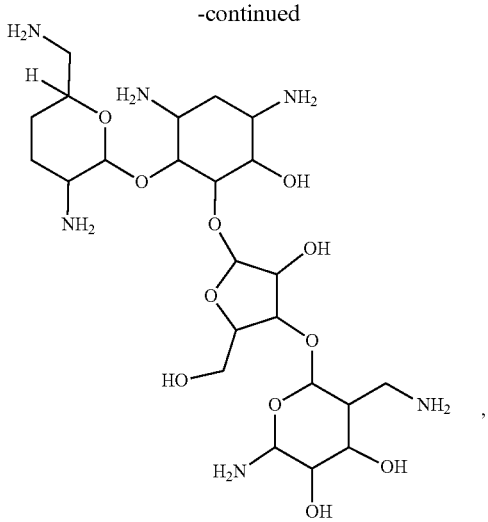
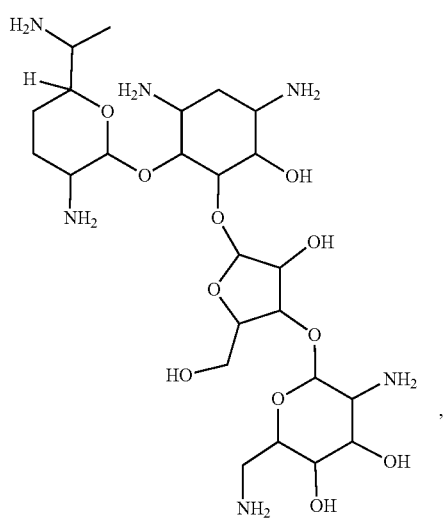
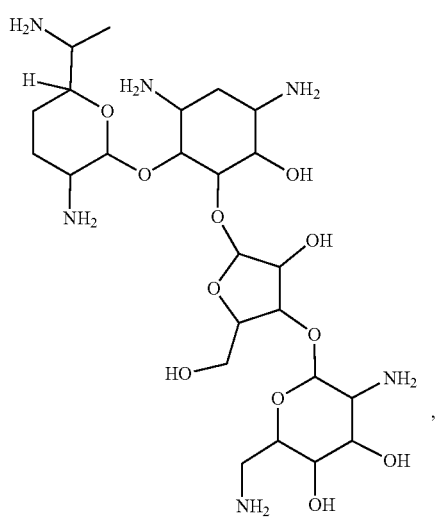
334
-continued
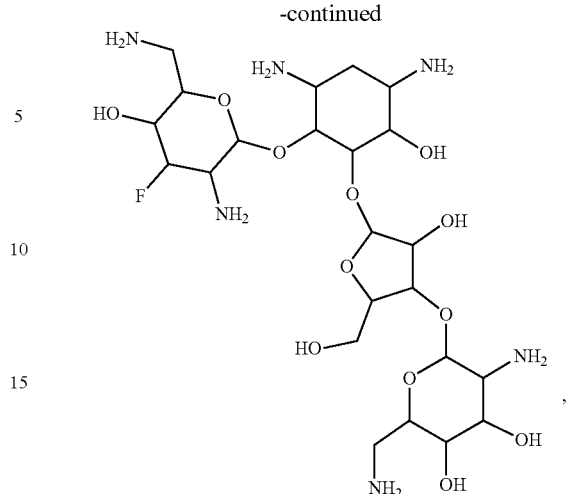
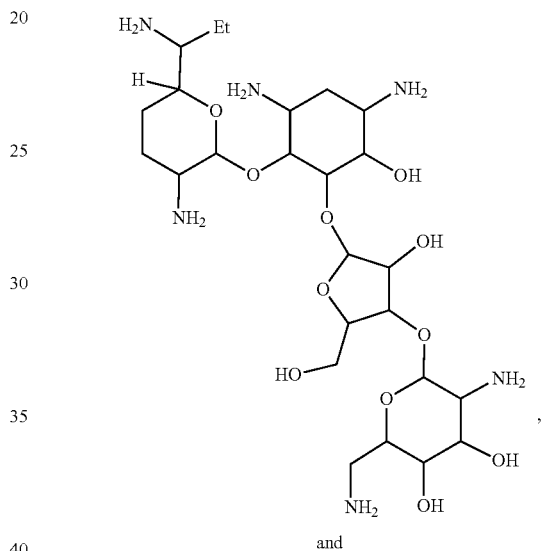
and
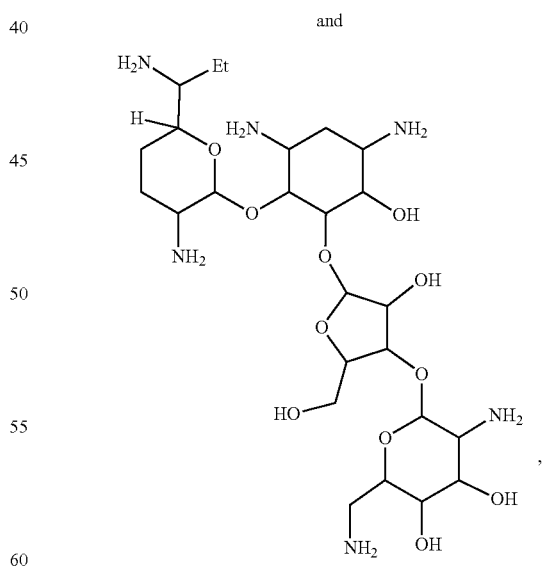
or a pharmaceutically acceptable salt, solvate, stereoisomer, or tautomer thereof.
Embodiment III-58. The compound of any one of Embodiment III-1 to III-57, wherein the compound is selected from the group consisting of:

335
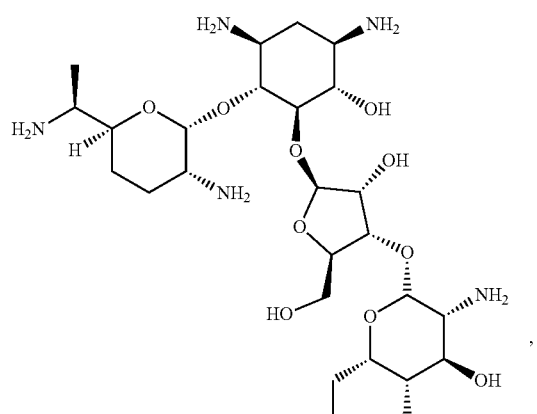
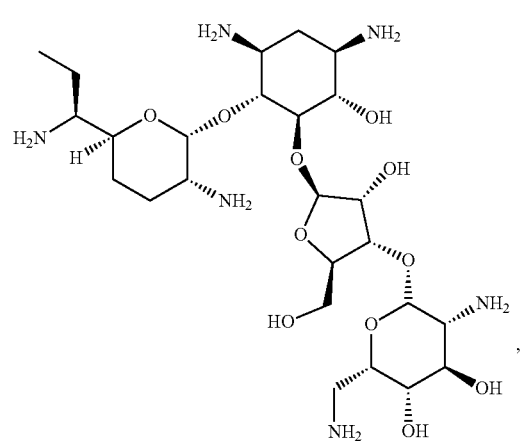
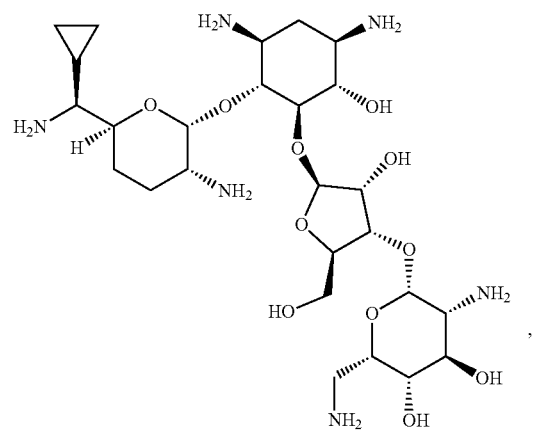
336
-continued
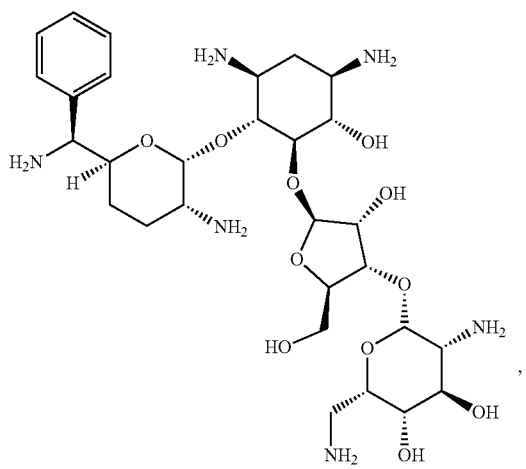
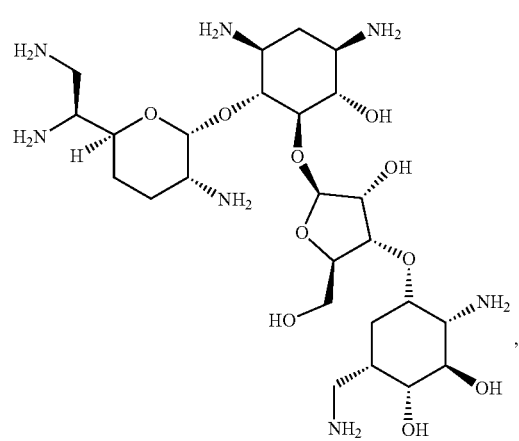
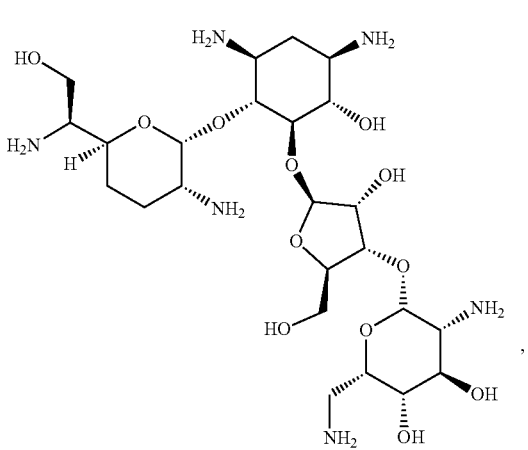

337
-continued
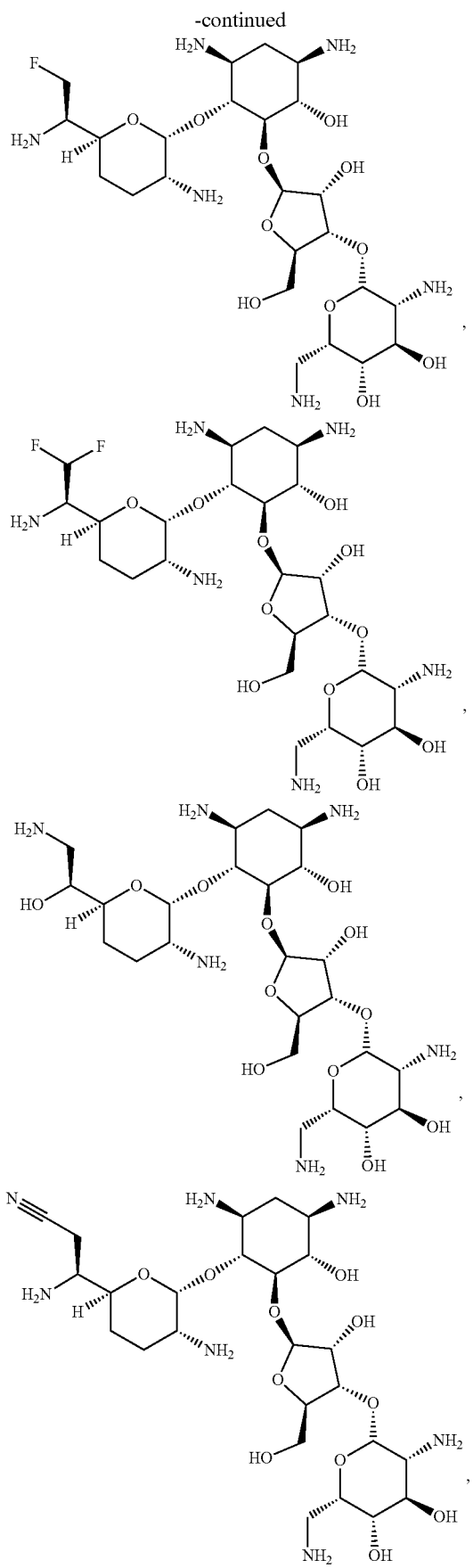
338
-continued
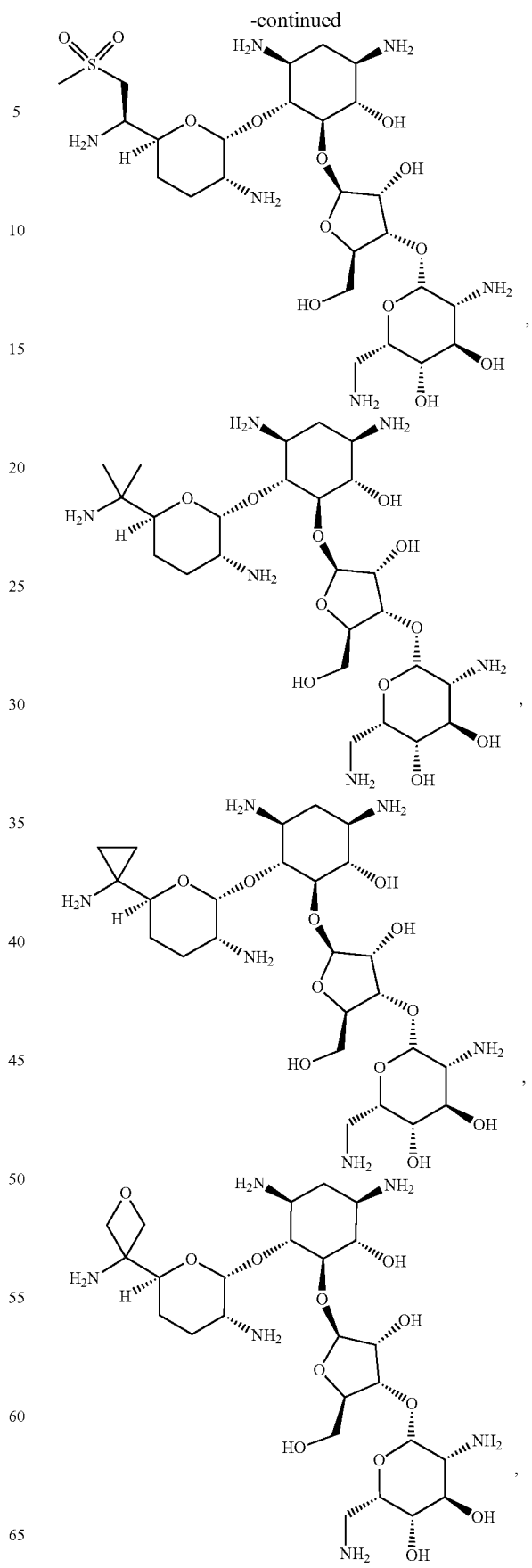

339
-continued
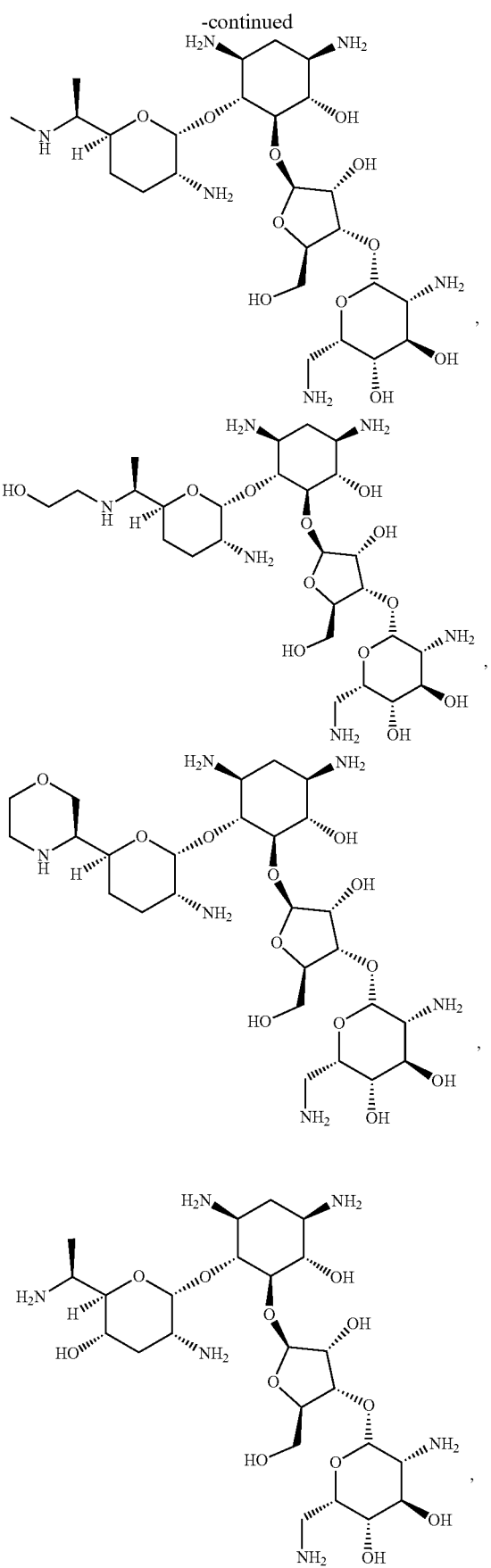
340
-continued
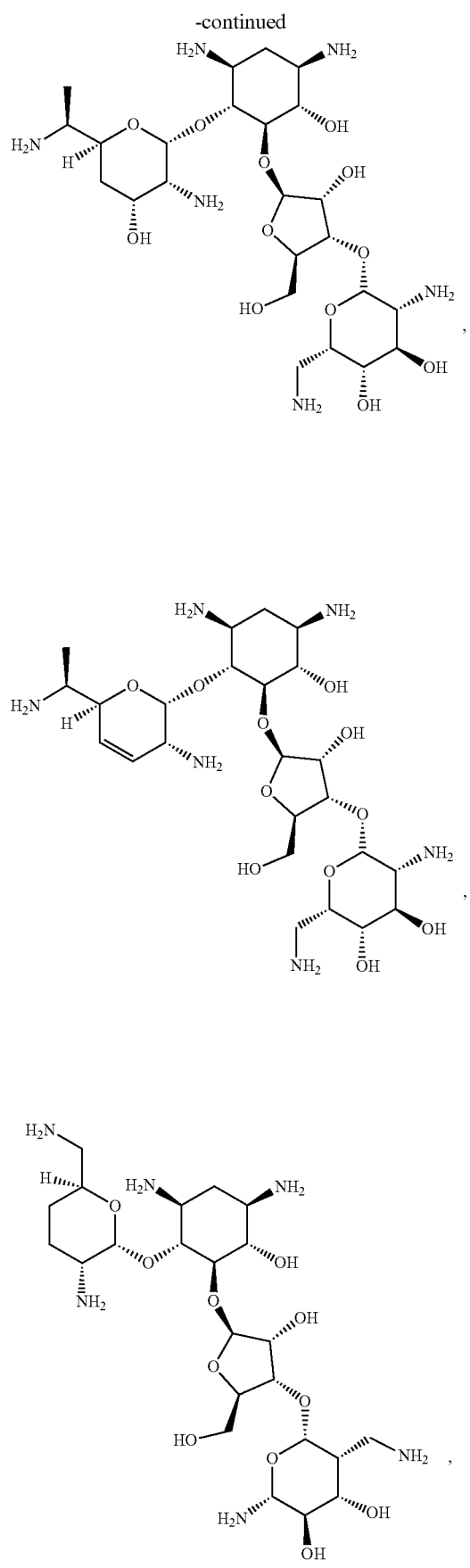

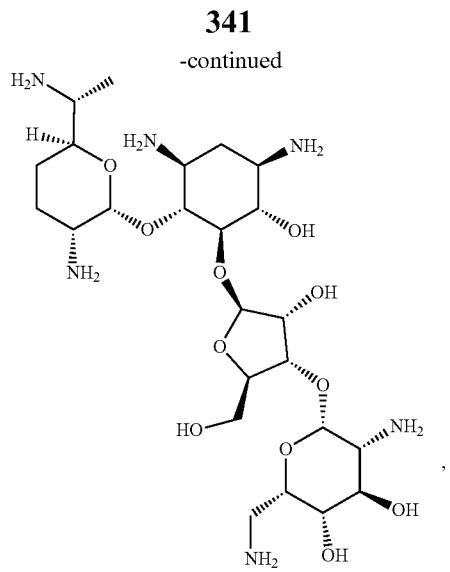

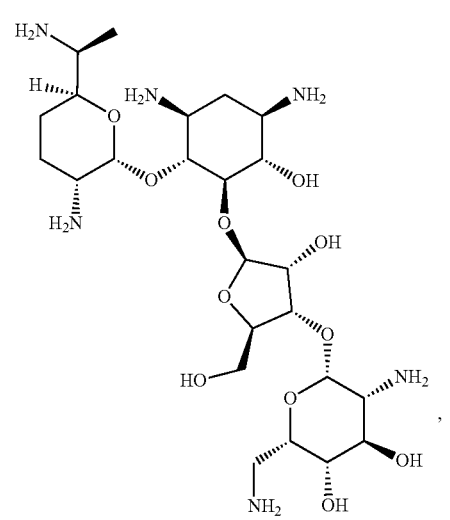

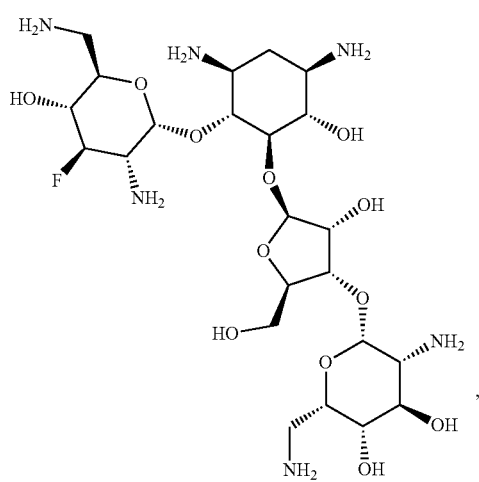

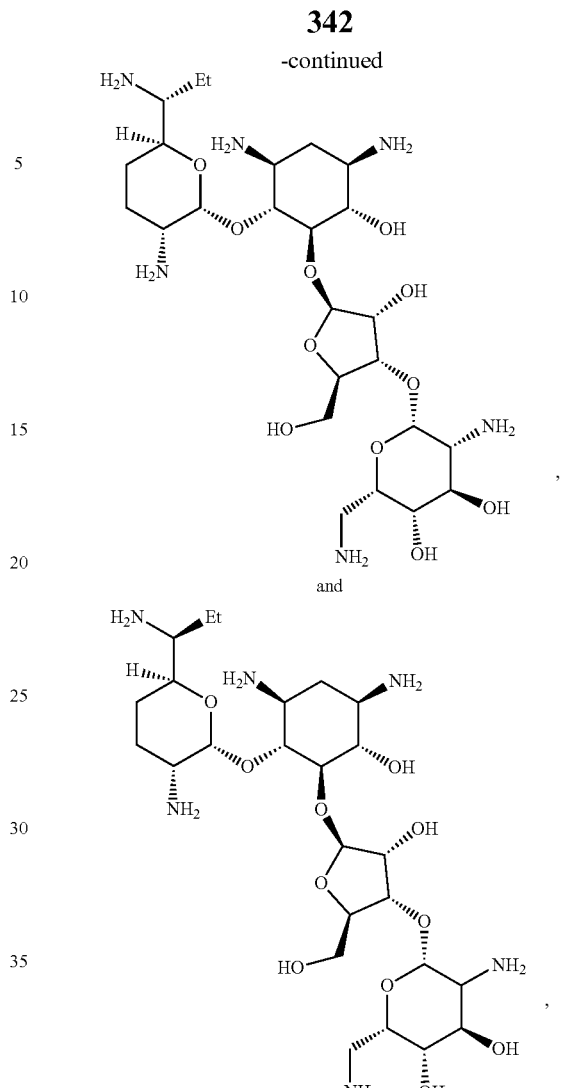

or a pharmaceutically acceptable salt, solvate, stereoisomer, or tautomer thereof.

Embodiment III-59. A pharmaceutical composition, comprising a compound of any one of Embodiment III-1 to III-58, or a pharmaceutically acceptable salt, solvate, stereoisomer, or tautomer thereof, and a pharmaceutically acceptable carrier.

Embodiment III-60. A method for treating a bacterial infection in a subject, comprising administering to a subject in need thereof a therapeutically effective amount of a compound of any one of Embodiment III-1 to III-58, or a pharmaceutically acceptable salt, solvate, stereoisomer, or tautomer thereof.

Embodiment III-61. A method for treating a bacterial infection in a subject, comprising administering to a subject in need thereof a therapeutically effective amount of a pharmaceutical composition according to Embodiment III-59.

Embodiment III-62. The method of Embodiment III-60 or Embodiment III-61, wherein the bacterial infection is a Gram-negative bacterial infection.

Embodiment III-63. The method of Embodiment III-60 or Embodiment III-61, wherein the bacterial infection is infection of a *Staphylococcus, Lactobacillus, Streptococcus, Sarcina, Escherichia, Enterobacter, Klebsiella, Pseudomo-* nas, *Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella, Francisella, Yersinia, Corynebacterium, Moraxella,* or *Enterococcus* species.

Embodiment III-64. Use of a compound of any one of Embodiment III-1 to III -58, or a pharmaceutically acceptable salt, solvate, stereoisomer, or tautomer thereof., in the manufacture of a medicament for treating a bacterial infection in a subject in need thereof Embodiment III-65. A compound of any one of Embodiment III-1 to III-58, or a pharmaceutically acceptable salt, solvate, stereoisomer, or tautomer thereof., for use in a method of treating a bacterial infection in a subject in need thereof.

EXAMPLES

The following Examples are merely illustrative and are not meant to limit any aspects of the present disclosure in any way.

Example 1: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S)-1-aminoethyl)tetrahydro -2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (1)

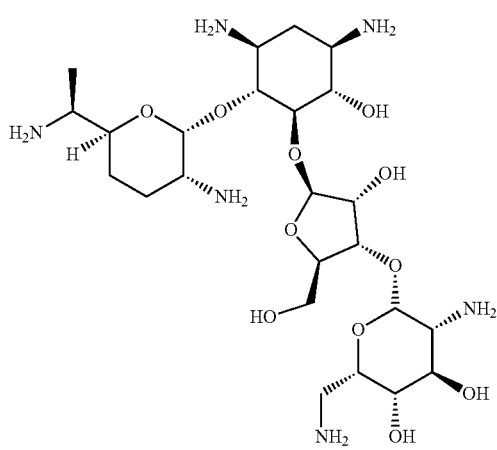

Example 2: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S)-1-aminopropyl)tetrahydro -2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (2)

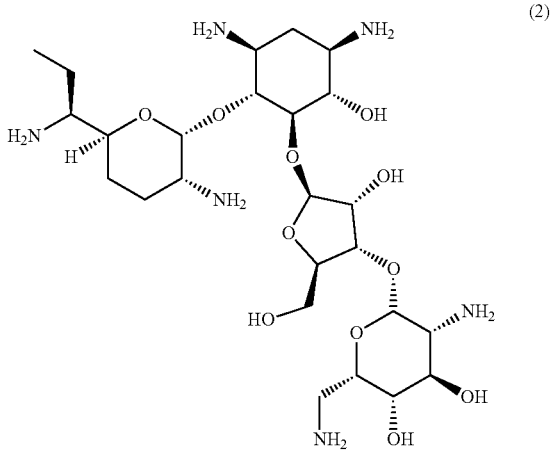

Example 3: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S) -amino(cyclopropyl)methyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (3)

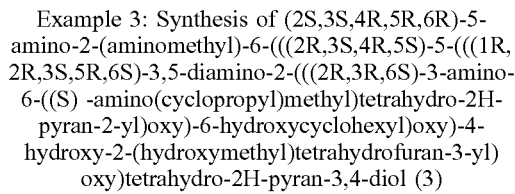

Example 4: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S)-amino(phenyl)methyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (4)

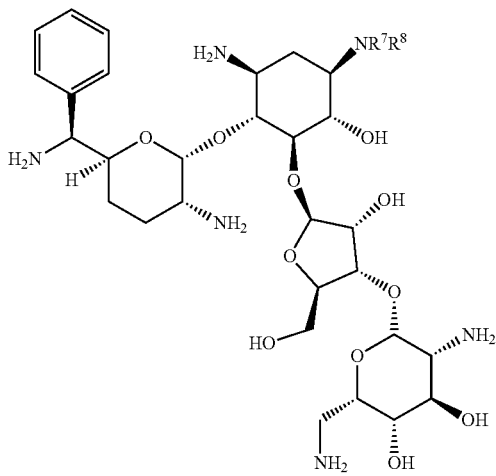

(4)

Example 5: Synthesis of (1R,2R,3R,4S,6S)-3-amino-6-(aminomethyl)-4-(((2R,3S,4R,5S)-5-(((1R,2R,3S,5R,6S)-3,5-diamino-2-(((2R,3R,6S)-3-amino-6-((S)-1,2-diaminoethyl)tetrahydro-2H-pyran-2-yl)oxy)-6-hydroxycyclohexyl)oxy)-4-hydroxy-2-(hydroxymethyl)tetrahydrofuran-3-yl)oxy)cyclohexane-1,2-diol (5)

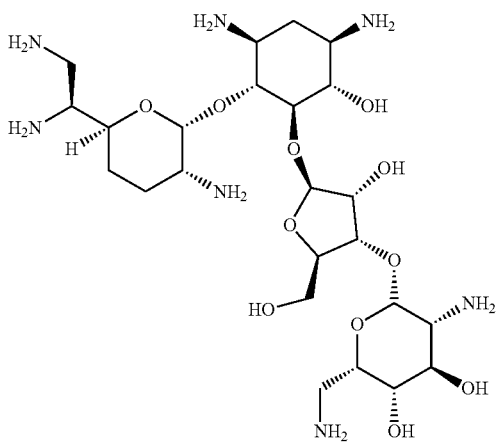

(5)

Example 6: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S)-1-amino-2-hydroxyethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (6)

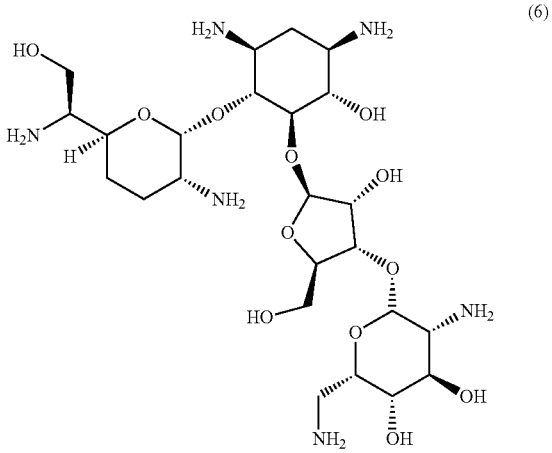

(6)

Example 7: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((R)-1-amino-2-fluoroethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (7)

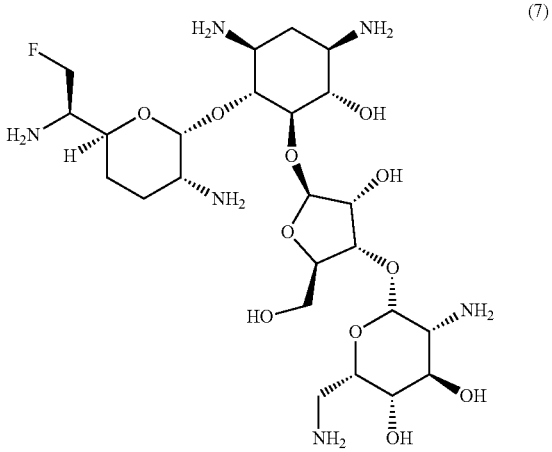

(7)

Example 8: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((R)-1-amino-2,2-difluoroethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (8)

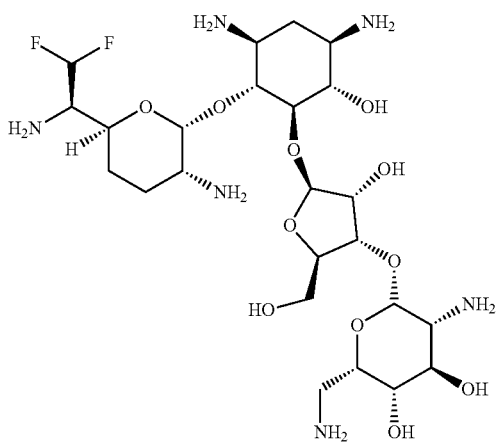

Example 9: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S)-2-amino-1-hydroxyethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (9)

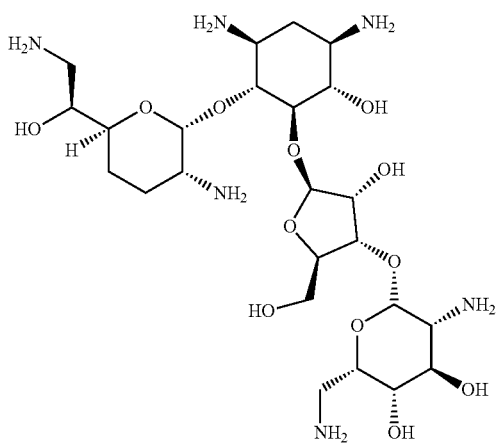

Example 10: Synthesis of (S)-3-amino-3-((2S,5R,6R)-5-amino-6-(((1R,2R,3S,4R,6S)-4,6-diamino-2-(((2S,3R,4S,5R)-4-(((2R,3R,4R,5S,6S)-3-amino-6-(aminomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)propanenitrile (10)

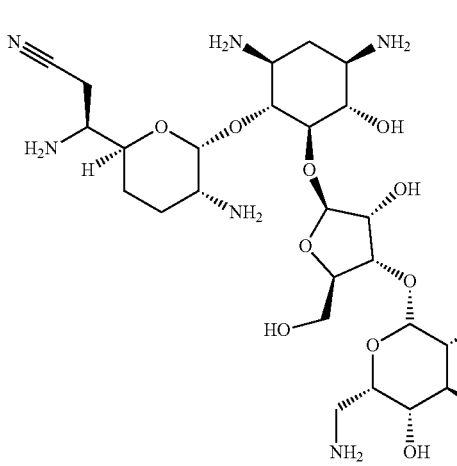

Example 11: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((R)-1-amino-2-(methylsulfonyl)ethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (11)

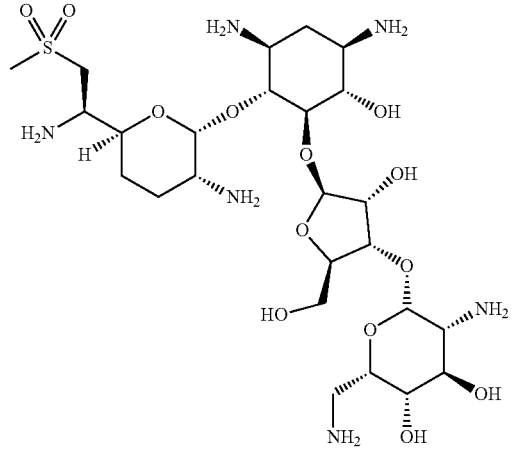

Example 12: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-(2-aminopropan-2-yl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (12)

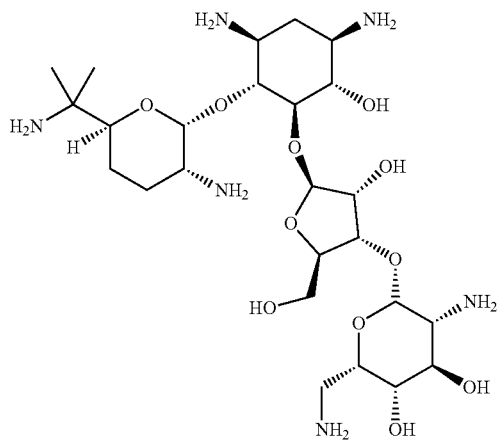

(12)

Example 13: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-(1-aminocyclopropyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (13)

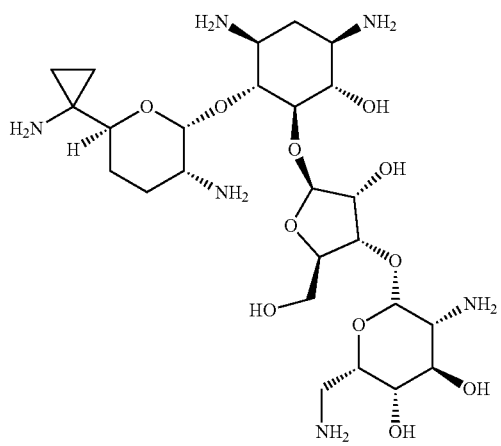

(13)

Example 14: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-(3-aminooxetan-3-yl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (14)

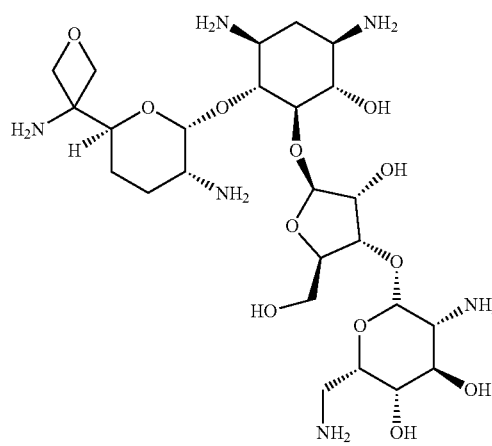

(14)

Example 15: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S)-1-(methylamino)ethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (15)

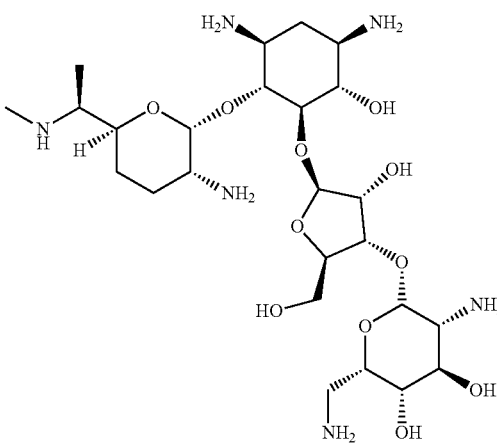

(15)

Example 16: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S)-1-((2-hydroxyethyl)amino)ethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (16)

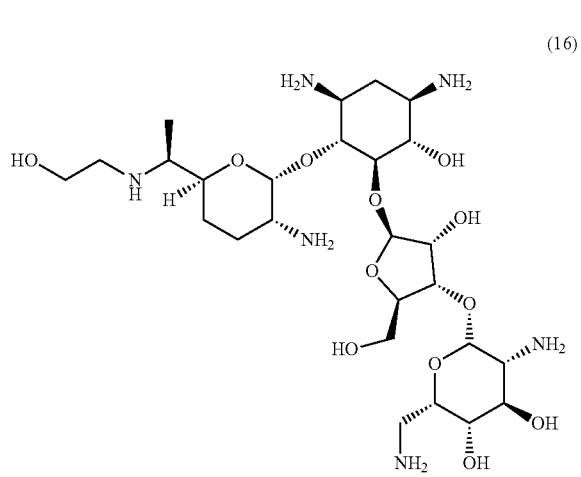

(16)

Example 18: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,5S,6R)-3-amino-6-((S)-1-aminoethyl)-5-hydroxytetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (18)

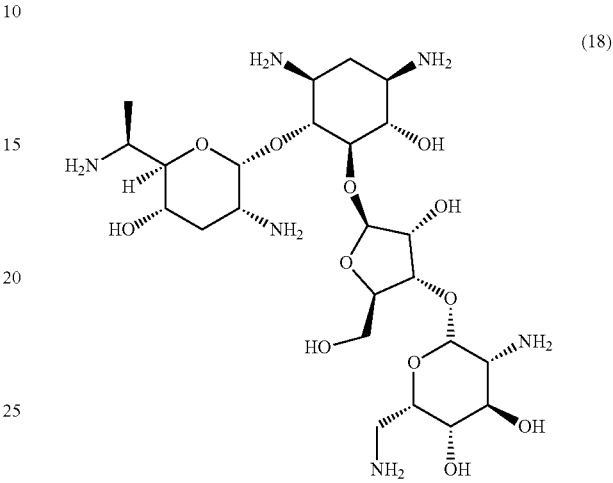

(18)

Example 17: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S)-morpholin-3-yl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (17)

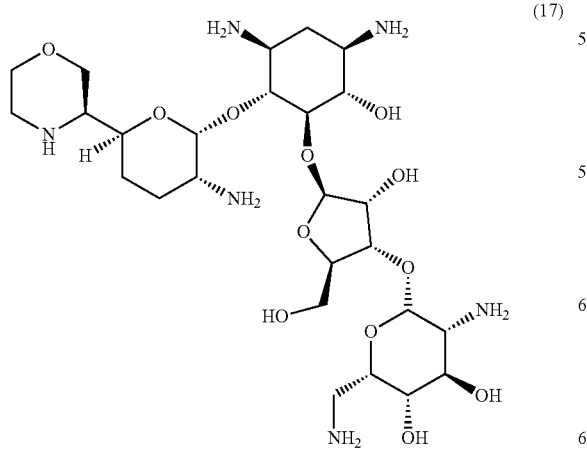

(17)

Example 19: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,4R,6S)-3-amino-6-((S)-1-aminoethyl)-4-hydroxytetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (19)

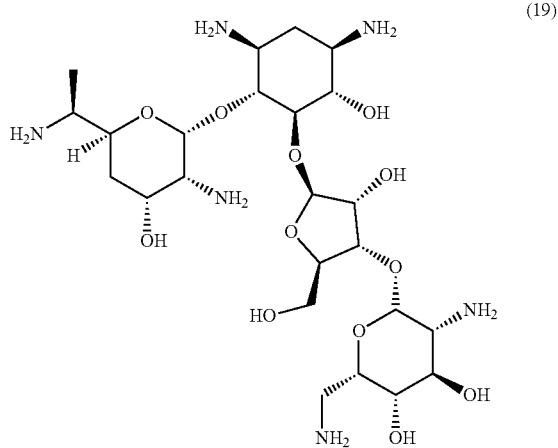

(19)

Example 20: Synthesis of (2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-((S)-1-aminoethyl)-3,6-dihydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (20)

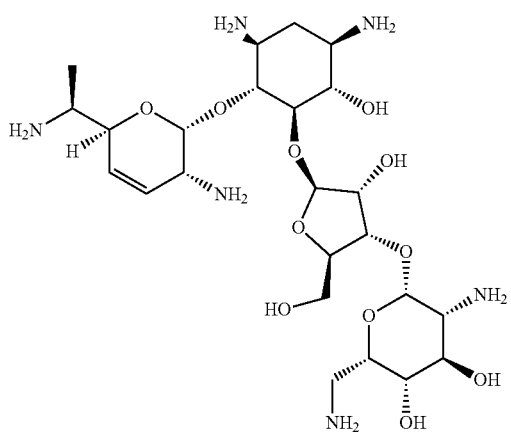

Example 21

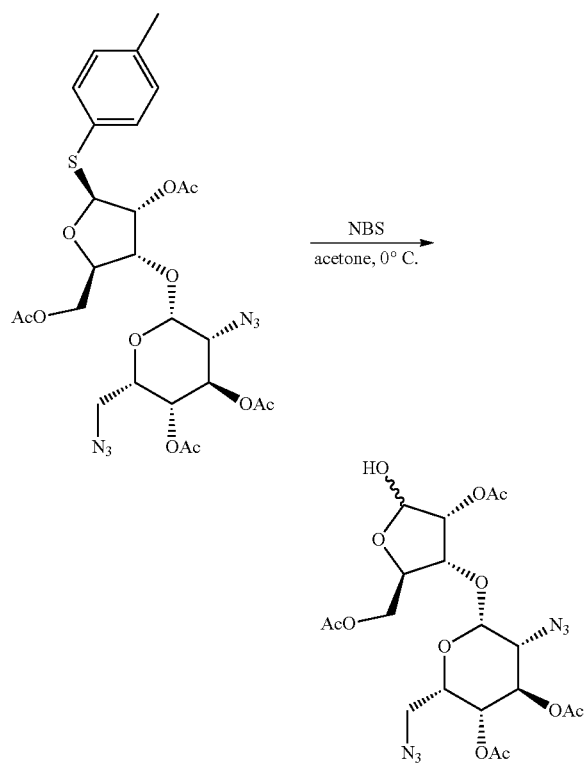

[(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate NBS (268 mg, 1.50 mmol) was added to a solution of [(2R,3R,4R,5R)-4-acetoxy-3-[(2R,3R,4R,5R,6S)-4,5-diacetoxy-3-azido-6-(azidomethyl)tetrahydropyran-2-yl]oxy-5-(p-tolylsulfanyl)tetrahydrofuran-2-yl]methyl acetate (638 mg, 1 mmol) in acetone (15.0 mL) under N$_2$ at 0° C. After 1 h, the reaction was quenched with 1:1 sat. NaHCO$_3$/Na$_2$S$_2$O$_3$ (30.0 mL) and acetone was removed under reduced pressure. The aqueous layer was extracted with DCM (3×15 mL). The combined organic layers were dried over Na$_2$SO$_4$, filtered and concentrated under reduced pressure. The material was purified on silica gel chromatography (25 g, dry loading) using 20% to 60% EtOAc in hexane to provide the title compound as a solid (diastereomers, 400 mg, 71%). LCMS m/z: ES$^+$ [M—OH]$^+$: 513.22, [M+NH$_4$]$^+$: 548.17.

Example 22

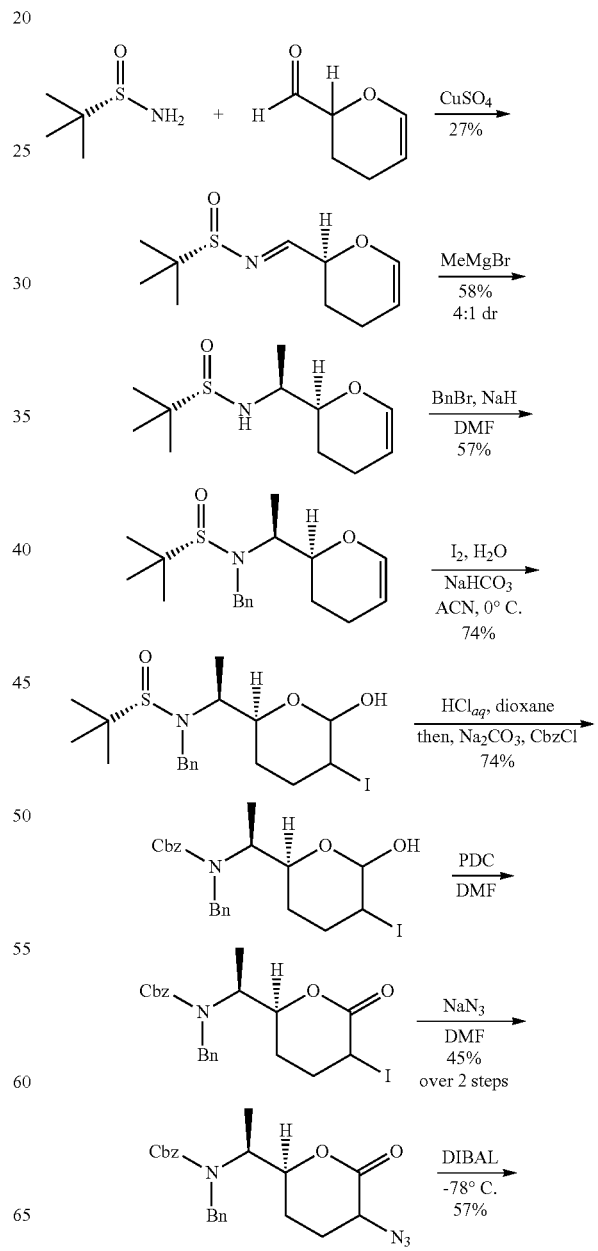

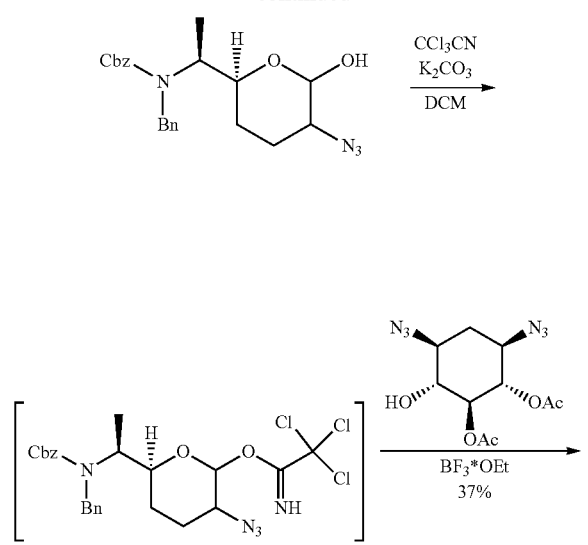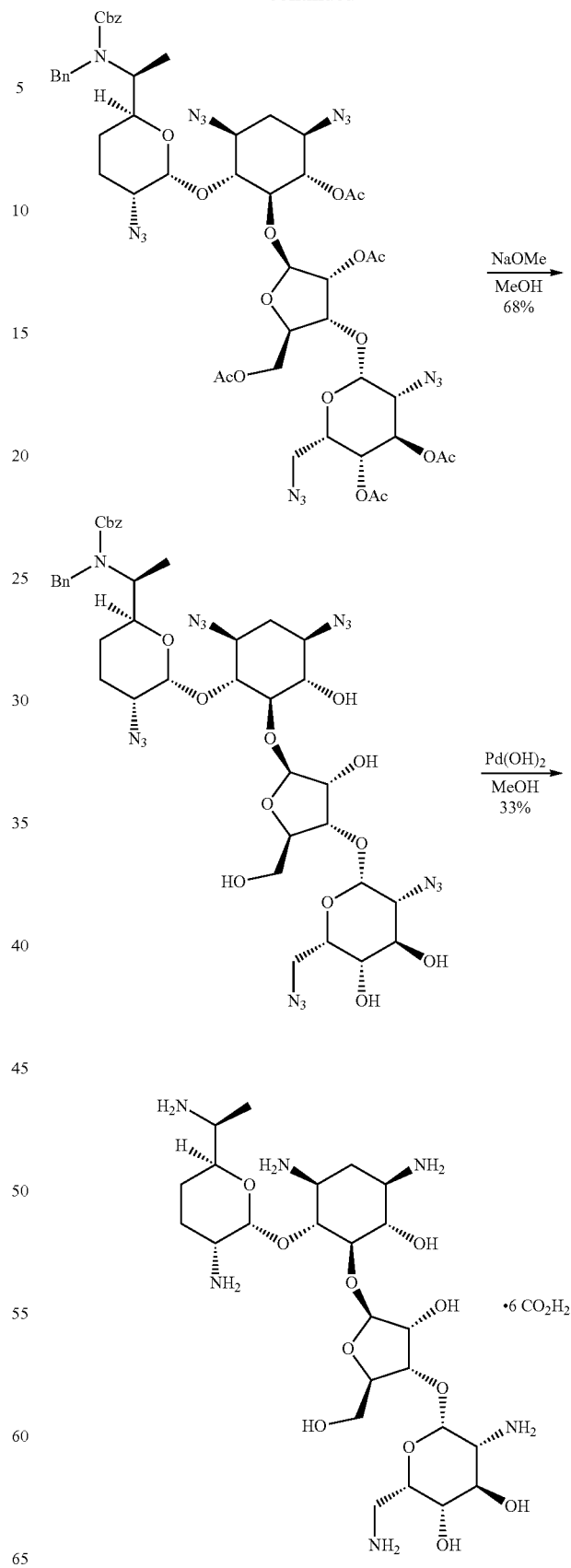

Step 1

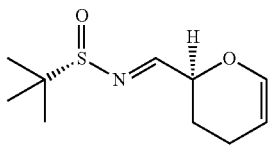

(S)-N-((E)-((S)-3,4-dihydro-2H-pyran-2-yl)methylene)-2-methylpropane-2-sulfinamide (S)-(+)-2-Methyl-2-propanesulfinamide (50 g, 412 mmol) and CuSO$_4$ (131.7 g, 825 mmol) were mixed in DCM (600.0 mL). A solution of 2-formyl-3,4-dihydro-2H-pyran (48.6 g, 433 mmol, Synthonix) in DCM (100.0 mL) was added over 20 min. The mixture was stirred at room temperature for 18 h, and then filtered through Celite and rinsed with DCM. The filtrate was evaporated under reduced pressure. The material was purified on silica gel (5×330 g, dry loading) by MPLC using 0-20% Et$_2$O in hexane as eluent to provide the title compound (23.74 g, 27%, second eluting diastereomer). $^1$H NMR (400 MHz, CDCl$_3$) δ 8.08 (d, J=3.0 Hz, 1H), 6.47 (dt, J=6.3, 1.6 Hz, 1H), 4.81-4.72 (m, 2H), 2.19-1.94 (m, 4H), 1.24 (s, 9H).

Step 2

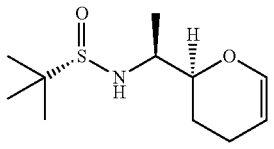

(S)-N-((S)-1-((S)-3,4-dihydro-2H-pyran-2-yl)ethyl)-2-methylpropane-2-sulfinamide (S)-N-((E)-((S)-3,4-dihydro-2H-pyran-2-yl)methylene)-2-methylpropane-2-sulfinamide (7.30 g, 33.9 mmol) was dissolved in dry DCM (100 mL) and the solution was cooled to −78° C. MeMgBr (3.0 M in Et$_2$O, 22.6 mL, 67.8 mmol) was added dropwise to the mixture and stirring was continued at low temperature for 2 hours, before allowing the mixture to warm to room temperature. Stirring was continued at room temperature for 1 hour. Concentrated aqueous NH$_4$Cl (50 mL) was added, and the mixture was extracted with DCM (3×50 mL). The combined organic layers were dried (MgSO$_4$), and concentrated in vacuo to afford a crude oil containing a mixture of diastereomers. The material was purified using silica gel chromatography (120 g cartridge) with hexanes and ethyl acetate (0-100%) to afford the title compound as an oil (4.40 g, 56%). LCMS m/z: ES$^+$ [M+H]$^+$: 232.16.

Step 3

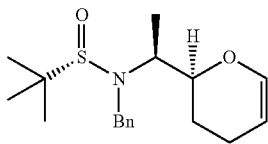 [SMILES: C[C@@H]([C@@H]1CCC=CO1)N(Cc1ccccc1)[S@@](=O)C(C)(C)C]

(S)-N-benzyl-N-((S)-1-((S)-3,4-dihydro-2H-pyran-2-yl)ethyl)-2-methylpropane-2-sulfinamide NaH (60% dispersion, 913 mg, 22.8 mmol) was added to a solution of (S)-N-((S)-1-((S)-3,4-dihydro-2H-pyran-2-yl)ethyl)-2-methylpropane-2-sulfinamide (4.40 g, 19.0 mmol) and benzyl bromide (3.39 mL, 28.5 mmol) in DMF (100 mL) at 0° C. The mixture was stirred at this temperature for 2 hours, then brine (100 mL) was added at 0° C. The aqueous layer was extracted with Et$_2$O (3×50.0 mL). The combined organic layers were dried (MgSO$_4$) and concentrated in vacuo to afford a residue that was purified using silica gel chromatography (120 g cartridge) using hexanes and ethyl acetate (0-100%). The pure fractions were concentrated in vacuo to afford the title compound as an oil (3.50 g, 57%). LCMS m/z: ES$^+$ 322.14.

$^1$H NMR (500 MHz, DMSO) δ 7.45 (d, J=7.1 Hz, 2H), 7.35-7.29 (m, 2H), 7.23 (t, J=7.3 Hz, 1H), 6.38 (d, J=6.1 Hz, 1H), 4.65 (ddd, J=6.2, 4.3, 1.4 Hz, 1H), 4.35 (d, J=16.5 Hz, 1H), 3.91 (t, J=11.4 Hz, 1H), 3.80 (td, J=9.2, 2.3 Hz, 1H), 3.22-3.11 (m, 1H), 1.97-1.92 (m, 1H), 1.89-1.78 (m, 2H), 1.53-1.42 (m, 1H), 1.19 (t, J=3.4 Hz, 3H), 1.10 (s, 8H).

Step 4

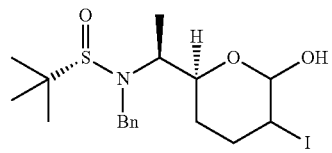 [SMILES: C[C@@H]([C@@H]1CCC(I)C(O)O1)N(Cc1ccccc1)[S@@](=O)C(C)(C)C]

(S)-N-benzyl-N-((1S)-1-((2S)-6-hydroxy-5-iodotetrahydro-2H-pyran-2-yl)ethyl)-2-methylpropane-2-sulfinamide (S)-N-benzyl-N-((S)-1-((S)-3,4-dihydro-2H-pyran-2-yl)ethyl)-2-methylpropane-2-sulfinamide (4.40 g, 13.7 mmol) and NaHCO$_3$ (3.45 g, 41.1 mmol) were dissolved in H$_2$O (75.0 mL) and ACN (75.0 mL). I$_2$ (3.82 g, 15.1 mmol) was added portionwise over 10 minutes at 0° C. The cooling bath was removed, and stirring was continued at room temperature over 90 minutes. The reaction mixture was quenched with a saturated aqueous solution of Na$_2$S$_2$O$_3$ (30.0 mL) and extracted with EtOAc (3×20.0 mL). The combined organic layers were dried (MgSO$_4$) and concentrated in vacuo to afford the title compound as a solid (4.70 g, 74%). LCMS m/z: ES$^+$ [M+H]$^+$: 466.04.

Step 5

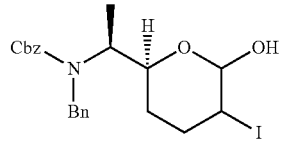 [SMILES: C[C@@H]([C@@H]1CCC(I)C(O)O1)N(Cc1ccccc1)C(=O)OCc1ccccc1]

Benzyl benzyl((1S)-1-((2S)-6-hydroxy-5-iodotetrahydro-2H-pyran-2-yl)ethyl)carbamate (S)-N-benzyl-N-((1S)-1-((2S)-6-hydroxy-5-iodotetrahydro-2H-pyran-2-yl)ethyl)-2 -methylpropane-2-sulfinamide (4.70 g, 10.1 mmol) was dissolved in 1,4-dioxane (150 mL), and an aqueous solution of 1 N HCl (25.2 mL, 25.2 mmol) was added. Stirring was continued at room temperature for 20 minutes, before solid Na$_2$CO$_3$ (8.56 g, 80.8 mmol) was added to the mixture. Stirring was continued for 20 minutes, and then CbzCl (1.72 mL, 12.1 mmol) was added dropwise. Stirring was continued for 2 hours. Water (200 mL) was added and the mixture was extracted with EtOAc (3×50 mL). The combined organic layers were dried (MgSO$_4$) and concentrated in vacuo to give a residue that was purified using silica gel chromatography (80 g cartridge) using hexanes and ethyl acetate (0-100%). The pure fractions were concentrated in vacuo to afford the title compound as an oil (3.70 g, 74%). LCMS m/z: ES+ [M+H]+ 518.04.

Step 6

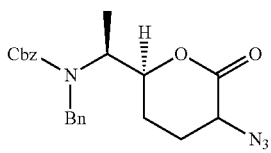 [SMILES: C[C@@H]([C@@H]1CCC(N=[N+]=[N-])C(=O)O1)N(Cc1ccccc1)C(=O)OCc1ccccc1]

Benzyl ((1S)-1-((2S)-5-azido-6-oxotetrahydro-2H-pyran-2-yl)ethyl)(benzyl)carbamate Benzyl benzyl((1S)-1-((2S)-6-hydroxy-5-iodotetrahydro-2H-pyran-2-yl)ethyl)carbamate (3.70 g, 7.47 mmol) was dissolved in DCM (350 mL). 4 Å molecular sieves (1.00 g) were suspended in the mixture, and PDC (8.43 g, 22.4 mmol) was added. Stirring was continued over 24 hours at room temperature, then filtered through a pad of celite using ethyl acetate, and concentrated in vacuo to afford crude benzyl benzyl((1S)-1-((2S)-5-iodo-6-oxotetrahydro-2H-pyran-2-yl)ethyl)carbamate as an oil, which was redissolved in DMF (50.0 mL). NaN$_3$ (971 mg, 14.9 mmol) was added as a solid, and stirring was continued for 2 hours at room temperature. The solvent was removed in vacuo, and the residue was dissolved in EtOAc (100 mL) and washed with water (3×25 mL). The organic layer was dried (MgSO$_4$) and concentrated in vacuo to afford an oil that was purified using silica gel chromatography (80 g cartridge) with ethyl acetate and hexanes (0-100%). The pure fractions were combined and concentrated in vacuo to afford the title compound as an oil (1.40 g, 46%). LCMS m/z: ES+ [M+Na]+: 431.13; calc: 431.18.

Step 7

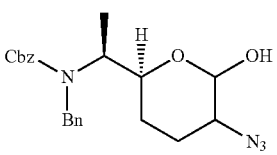 [SMILES: C[C@@H]([C@@H]1CCC(N=[N+]=[N-])C(O)O1)N(Cc1ccccc1)C(=O)OCc1ccccc1]

Benzyl ((1S)-1-((2S)-5-azido-6-hydroxytetrahydro-2H-pyran-2-yl)ethyl)(benzyl)carbamate Benzyl ((1S)-1-((2S)-5-azido-6-oxotetrahydro-2H-pyran-2-yl)ethyl)(benzyl)carbamate (1.40 g, 3.43 mmol) was dissolved in dry DCM (75.0 mL) and the mixture was cooled to −78° C. A solution of DIBAL-H (1.0 M in toluene, 6.86 mL, 6.86 mmol) was added to the mixture, and stirring was continued at low temperature for 1 hour. EtOH (2.00 mL) was added dropwise to the cold reaction mixture, which was then poured into a saturated aqueous solution of Rochelle's salt (200 mL). The mixture was stirred vigorously for 1 hour, then extracted with EtOAc (3×50.0 mL). The combined organic layers were dried (MgSO$_4$) and concentrated in vacuo to afford a residue that was purified using silica gel chromatography (80 g cartridge) with hexanes and ethyl acetate (0-70%). The pure fractions were collected and concentrated in vacuo to afford the title compound as a mixture of diastereomers (800 mg, 57%). LCMS m/z: ES+ [M+Na]+: 433.16; calc: 433.19.

Step 8

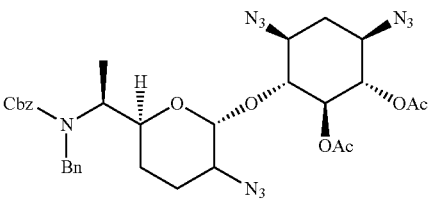

(1S,2S,3R,4S,6R)-4,6-diazido-3-(((2R,6S)-3-azido-6-((S)-1-(benzyl((benzyloxy)carbonyl)amino)ethyl)tetrahydro-2H-pyran-2-yl)oxy)cyclohexane-1,2-diyl diacetate Benzyl ((1S)-1-((2S)-5-azido-6-hydroxytetrahydro-2H-pyran-2-yl)ethyl)(benzyl)carbamate (800 mg, 1.95 mmol) and K$_2$CO$_3$ (808 mg, 5.85 mmol) were suspended in dry DCM (30.0 mL). CCl$_3$CN (0.977 mL, 9.75 mmol) was added dropwise to the mixture, and stirring was continued over two days. The reaction mixture was filtered through celite, and rinsed with DCM (25.0 mL). The filtrate was concentrated in vacuo to afford a residue that was redissolved in DCM (10.0 mL). [(1S,2S,3R,4S,6R)-2-acetoxy-4,6-diazido-3-hydroxy-cyclohexyl]acetate (814 mg, 2.73 mmol) was added. The mixture was cooled to −78° C., and BF$_3$·Et$_2$O (962 µL, 7.80 mmol) was added dropwise. Stirring was continued for 5 hours before the mixture was quenched with saturated aqueous NaHCO$_3$ (50.0 mL). The mixture was extracted with DCM (3×25.0 mL). The organic layers were combined, washed with brine (25.0 mL), dried (MgSO$_4$), and concentrated in vacuo to afford a crude residue that was purified using C18 reverse phase chromatography (120 g cartridge). The pure fractions were concentrated in vacuo to afford the title product as an oil (500 mg, 37%). LCMS m/z: ES+ [M+Na]+: 433.16; calc: 433.19.

Step 9

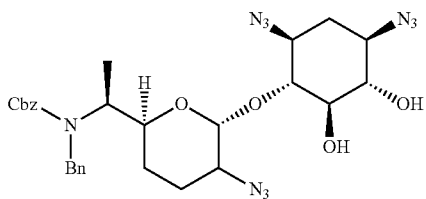 [SMILES: C[C@@H]([C@@H]1CCC(N=[N+]=[N-])[C@@H](O[C@H]2[C@H](O)[C@@H](O)[C@H](N=[N+]=[N-])C[C@@H]2N=[N+]=[N-])O1)N(Cc1ccccc1)C(=O)OCc1ccccc1]

Benzyl ((S)-1-((2S,5R,6R)-5-azido-6-4(1R,2R,3S,4R,6S)-4,6-diazido-2,3-dihydroxycyclohexyl)oxy)tetrahydro-2H-pyran-2-yl)ethyl)(benzyl)carbamate (1S,2S,3R,4S,6R)-4,6-diazido-3-(((2R,6S)-3-azido-6-((S)-1-(benzyl((benzyloxy)carbonyl)amino)ethyl)tetrahydro-2H-pyran-2-y0oxy)cyclohexane-1,2-diyl diacetate (0.500 g, 0.724 mmol) was dissolved in MeOH (25.0 mL) and NaOMe (0.235 g, 4.34 mmol) was added as a solid. Stirring was continued for 1 hour, then the mixture was quenched with AcOH (5.00 mL). The mixture was concentrated in vacuo, and submitted for SFC purification. The desired diastereomer (5.30 min. elution time) was isolated and obtained as an oil (42 mg, 13%).

Step 10

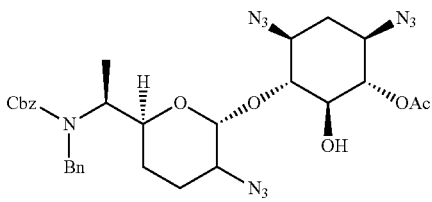 [SMILES: CC(=O)O[C@@H]1[C@@H](O)[C@H](O[C@H]2O[C@H]([C@H](C)N(Cc3ccccc3)C(=O)OCc3ccccc3)CCC2N=[N+]=[N-])[C@@H](N=[N+]=[N-])C[C@H]1N=[N+]=[N-]]

(1S,2S,3R,4S,6R)-4,6-diazido-3-(((2R,3R,6S)-3-azido-6-((S)-1-(benzyl((benzyloxy)carbonyl)amino)ethyl)tetrahydro-2H-pyran-2-yl)oxy)-2-hydroxycyclohexyl acetate Ac₂O (0.01 mL, 0.05 mmol) was added to a solution of benzyl ((S)-1-((2S,5R,6R)-5-azido-6-(((1R,2R,3S,4R,6S)-4,6-diazido-2,3-dihydroxycyclohexyl)oxy)tetrahydro-2H-pyran-2-yl)ethyl)(benzyl)carbamate (28 mg, 0.05 mmol) and pyridine (0.02 mL, 0.3 mmol) in dry DCM (3 mL) at room temperature. After 22 h, MeOH (0.5 mL) was added and the volatiles were removed under reduced pressure. The material was purified on silica gel (12 g, dry loading) by MPLC using hexane to 40% EtOAc in hexane to provide the title compound (21 mg, 70%) as a solid. M+H⁺: 649.3.

Step 11

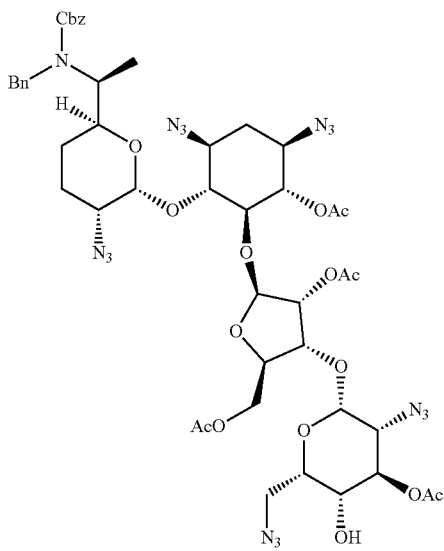 [SMILES: CC(=O)OC[C@H]1O[C@@H](O[C@@H]2[C@@H](OC(C)=O)[C@H](N=[N+]=[N-])C[C@H](N=[N+]=[N-])[C@H]2O[C@H]2O[C@H]([C@H](C)N(Cc3ccccc3)C(=O)OCc3ccccc3)CC[C@H]2N=[N+]=[N-])[C@H](OC(C)=O)[C@@H]1O[C@H]1O[C@@H](CN=[N+]=[N-])[C@@H](O)[C@H](OC(C)=O)[C@H]1N=[N+]=[N-]]

(2S,3R,4R,5R,6R)-6-(((2R,3R,4R,5S)-4-acetoxy-5-(((1S,2S,3R,5S,6R)-2-acetoxy-3,5-diazido-6-(((2R,3R,6S)-3-azido-6-((S)-1-(benzyl((benzyloxy)carbonyl)amino)ethyl)tetrahydro-2H-pyran -2-yl)oxy)cyclohexyl)oxy)-2-(acetoxymethyl)tetrahydrofuran-3-yl)oxy)-5-azido-2-(azidomethyl)tetrahydro-2H-pyran-3,4-diyl diacetate CCl₃CN (0.04 mL, 0.37 mol) was added dropwise to a mixture of [(2R,3R,4R)-4-acetoxy-3-[(2R,3R,4R,5R,6S)-4,5-diacetoxy-3-azido-6-(azidomethyl)tetrahydropyran-2-yl]oxy -5-hydroxy-tetrahydrofuran-2-yl]methyl acetate (39 mg, 0.07 mmol) and K₂CO₃ (31 mg, 0.22 mmol) in dry DCM (8 mL) at room temperature under N₂. The mixture was stirred at room temperature for 18 h, then filtered with a filter syringe and rinsed with DCM. The filtrate was concentrated under reduced pressure. (1S,2S,3R,4S,6R)-4,6-diazido-3-(((2R,3R,6S)-3-azido-6-((S)-1-(benzyl((benzyloxy)carbonyl)amino)ethyl)tetrahydro-2H-pyran-2-yl)oxy)-2-hydroxycyclohexyl acetate (16 mg, 0.03 mmol) was dissolved in DCM (8 mL) and added to the previous reaction mixture. Activated 4 Å molecular sieves were added and the mixture was cooled to −78° C., then BF₃·OEt₂ (0.02 mL, 0.12 mmol) was added dropwise. The mixture was stirred at room temperature for 5 h, then a saturated aqueous solution of NaHCO₃ (15 mL) was added. The separated aqueous layer was extracted with DCM (2×20 mL). The combined organic layer was washed with brine, dried over Na₂SO₄ and concentrated under reduced pressure. The residue was purified on C18 silica (120 g Biotage) using 50% B in A to 100% B (B=ACN 0.1% HCOOH, A=0.1% HCOOH) to provide the title compound (10 mg, 35%) as a solid. M+H⁺: 1161.7.

Step 12

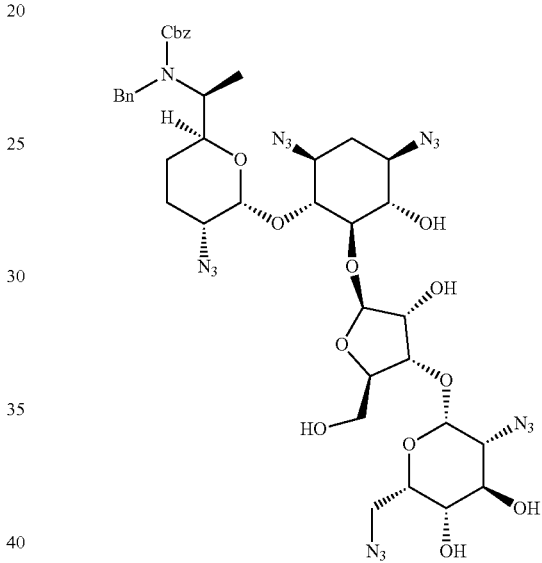

Benzyl ((S)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H -pyran-2-yl)ethyl)(benzyl)carbamate NaOMe (4.62 M in methanol, 0.01 mL, 0.06 mmol) was added dropwise to a solution of (2S,3R,4R,5R,6R)-6-(((2R,3R,4R,5S)-4-acetoxy-5-(((1S,2S,3R,5S,6R)-2-acetoxy -3,5-diazido-6-(((2R,3R,6S)-3-azido-6-((S)-1-(benzyl((benzyloxy)carbonyl)amino)ethyl)tetrahydro-2H-pyran-2-yl)oxy) cyclohexyl)oxy)-2-(acetoxymethyl)tetrahydrofuran-3-yl) oxy)-5-azido-2-(azidomethyl)tetrahydro-2H-pyran-3,4-diyl diacetate (9 mg, 0.01 mmol) in MeOH (5 mL) at room temperature. After 4 h, AcOH (4 μL, 0.07 mmol) was added to the reaction and the mixture was concentrated under reduced pressure. The residue was purified by prep-HPLC using ACN and AmFor pH 4 to provide the title compound (9 mg, 68%) as a solid. M+H⁺:951.4.

Step 13

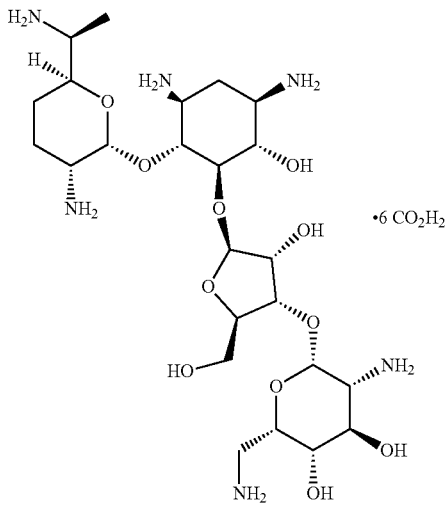 [SMILES: C[C@H](N)[C@@H]1CC[C@@H](N)[C@@H](O[C@H]2[C@H](O[C@@H]3O[C@H](CO)[C@@H](O[C@H]4O[C@@H](CN)[C@@H](O)[C@H](O)[C@H]4N)[C@H]3O)[C@@H](O)[C@H](N)C[C@@H]2N)O1]

•6 CO₂H₂

(2S,3S,4R,5R,6R)-5-Amino-2-(aminomethyl)-6-(((2R,3S,4R,5S)-5-(((1R,2R,3S,5R,6S)-3,5-diamino-2-(((2R,3R,6S)-3-amino-6-((S)-1-aminoethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol A mixture of benzyl ((S)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)ethyl)(benzyl)carbamate (5 mg, 5 μmol) and Pd(OH)₂ (20% wt, 5 mg) in MeOH (8 mL) was hydrogenated for 18 h at room temperature. The mixture was degassed with N₂ for 5 min, then filtered on 0.40 μM syringe filter. The solvent was removed under reduced pressure. The material was purified on prep-HPLC using ACN and water (0.1%) formic acid to provide the title compound (1.5 mg, 32%) as the formate salt. M+H⁺: 597.3. ¹H NMR (400 MHz, CD₃OD) δ 8.51 (br, 6H), 5.87 (s, 1H), 5.36 (s, 1H), 5.25 (s, 1H), 4.50-4.42 (m, 1H), 4.39-4.31 (m, 1H), 4.33-4.25 (m, 1H), 4.23-4.15 (m, 1H), 4.12 (s, 1H), 4.00-3.91 (m, 1H), 3.91-3.82 (m, 1H), 3.75-3.61 (m, 3H), 3.54-3.33 (m, 4H), 3.26-3.16 (m, 2H), 3.16-3.01 (m, 2H), 2.79-2.68 (m, 1H), 2.28-2.17 (m, 1H), 2.08-1.89 (m, 3H), 1.64-1.41 (m, 2H), 1.29 (d, J=6.6 Hz, 3H).

Example 23

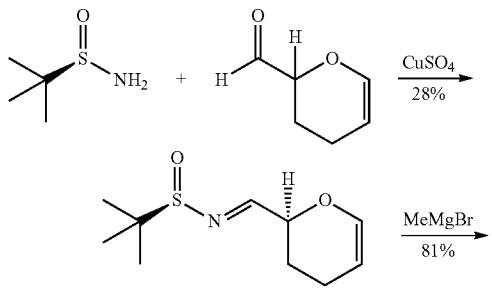

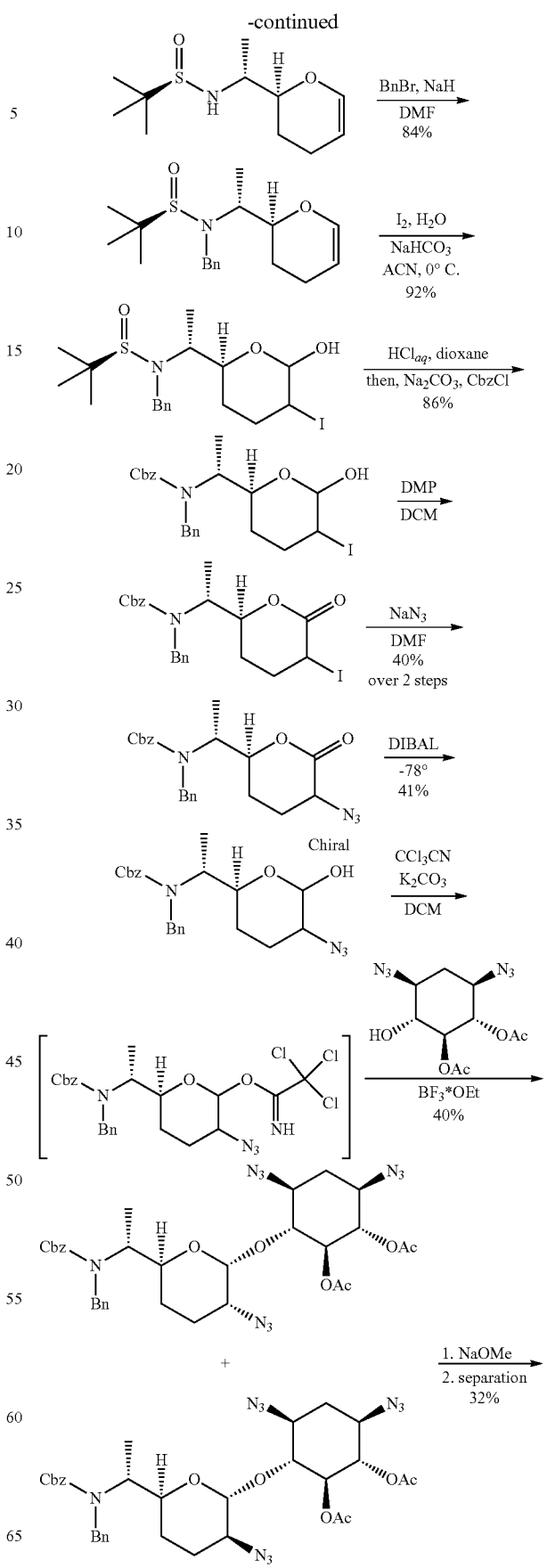

365

-continued

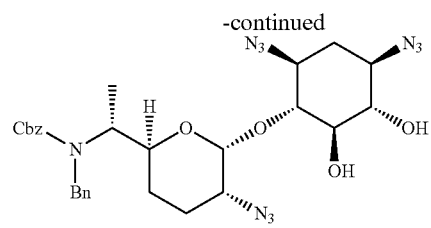

Ac₂O
Py, rt
54%

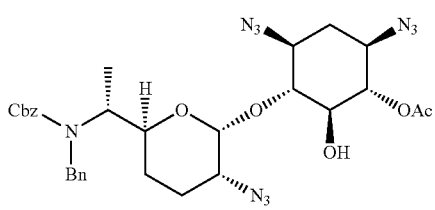

BF₃·OEt₂
−78° C. to rt
67%

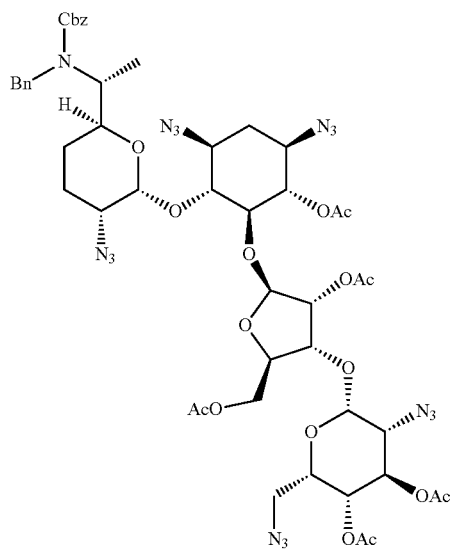

NaOMe
MeOH
70%

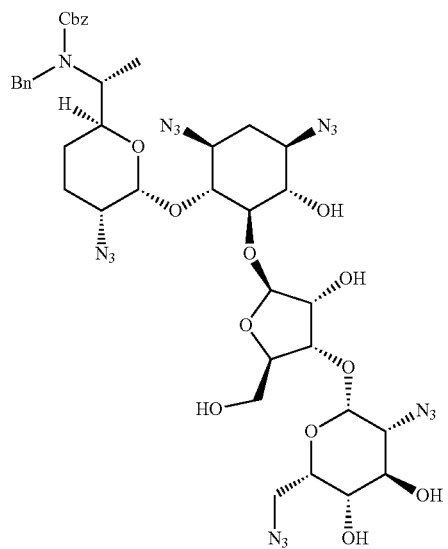

Pd(OH)₂
MeOH
68%

366

-continued

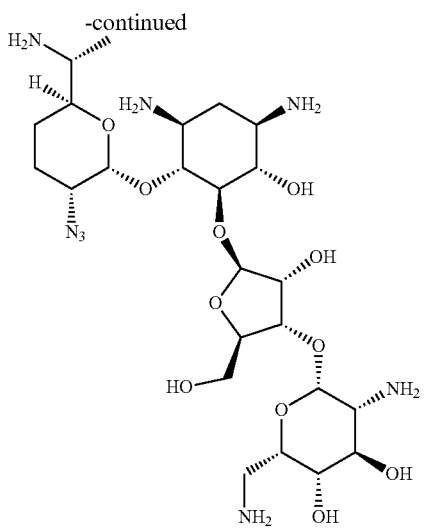

Step 1

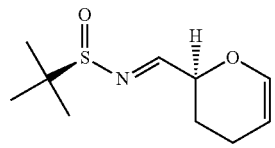

(NE)-N-[[(2S)-3,4-Dihydro-2H-pyran-2-yl]methylene]-2-methyl-propane-2-sulfinamide (R)-(+)-2-Methyl-2-propanesulfinamide (81.1 g, 669 mmol) and CuSO₄ (213.5 g, 1.34 mol) were mixed in DCM (700 mL). A solution of 2-formyl-3,4-dihydro-2H-pyran (75 g, 669 mmol) in DCM (100 mL) was added over 20 min. The mixture was stirred at room temperature for 72 h. The mixture was filtered through Celite and rinsed with DCM. The filtrate was evaporated under reduced pressure. The material was purified on silica gel (5×330 g, dry loading) by MPLC using 0-10% Et2O in hexane to provide the title compound (28 g, 19%) as a solid. ¹H NMR (400 MHz, CDCl₃) δ 8.07 (d, J=3.1 Hz, 1H), 6.40 (d, J=5.8 Hz, 1H), 4.76-4.68 (m, 1H), 4.68-4.63 (m, 1H), 2.13-1.83 (m, 4H), 1.18 (s, 9H).

Step 2

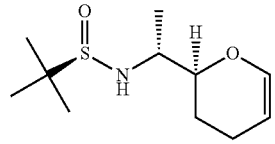

N-[(1R)-1-[(2S)-3,4-Dihydro-2H-pyran-2-yl]ethyl]-2-methyl-propane-2-sulfinamide

MeMgBr (3.0 M in Et₂O, 22.0 mL, 66.0 mmol) was added to a solution of (NE)-N-[[(2S)-3,4-dihydro-2H-pyran-2-yl]methylene]-2-methyl-propane-2-sulfinamide (7.10 g, 33.0 mmol) in dry DCM (110 mL) at −40° C. under N₂. After 2 h, the reaction was warmed to room temperature within 1 h. After another 14 h, sat. NH₄Cl (160 mL) was added dropwise (nota bene: gas evolution). Two phases were separated and the aqueous phase was extracted with DCM (3×20.0 mL). The combined organic layers were dried (Na₂SO₄), filtered and concentrated under reduced pressure. The residue was purified by silica gel chromatography (220 g cartridge) with EtOAc and hexanes (20-45%) to provide the title compound as a solid (6.00 g, 79%). ¹H NMR (500 MHz, CDCl₃) δ 6.37 (d, J=6.1 Hz, 1H), 4.75-4.61 (m, 1H), 3.93 (ddd, J=11.2, 3.3, 2.0 Hz, 1H), 3.69 (d, J=6.1 Hz, 1H), 3.56 (pd, J=6.7, 3.5 Hz, 1H), 2.16-2.06 (m, 1H), 1.99 (dtt, J=17.1, 5.6, 1.6 Hz, 1H), 1.81 (ddd, J=13.3, 6.6, 1.8 Hz, 1H), 1.66 (dtd, J=13.3, 11.4, 5.8 Hz, 1H), 1.22 (s, 9H), 1.18 (d, J=6.7 Hz, 3H).

Step 3

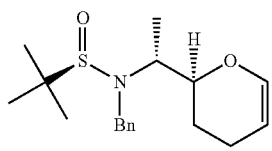 [SMILES: C[C@H]([C@@H]1CCC=CO1)N(Cc1ccccc1)[S@](=O)C(C)(C)C]

(R)-N-Benzyl-N-[(1R)-1-[(2S)-3,4-dihydro-2H-pyran-2-yl]ethyl]-2-methyl-propane-2-sulfinamide NaH (60%, 187 mg, 4.89 mmol) was added to a mixture of (R)-N-[(1R)-1-[(2S)-3,4-dihydro-2H-pyran- 2-yl]ethyl]-2-methyl-propane-2-sulfinamide (1.03 g, 4.44 mmol) and BnBr (0.79 mL, 6.67 mmol) in DMF (60 mL) at 0° C. The mixture was stirred at room temperature for 1 h, then brine (250 mL) was added at 0° C. The aqueous layer was extracted with Et₂O (3×80mL). The combined organic layer was dried over MgSO₄ and concentrated under reduced pressure. The material was purified on silica gel (40 g, dry loading) by MPLC using hexane to 60% EtOAc in hexane to provide the title compound (1.2 g, 84%) as an oil. ¹H NMR (400 MHz, cdcl3) δ 7.37 (d, J=7.5 Hz, 2H), 7.32 (t, J=7.4 Hz, 2H), 7.26 (d, J=3.8 Hz, 1H), 6.32 (d, J=6.2 Hz, 1H), 4.64 (s, 1H), 4.39 (d, J=15.3 Hz, 1H), 4.14 (d, J=15.2 Hz, 1H), 3.66-3.57 (m, 1H), 3.32-3.20 (m, 1H), 1.98-1.80 (m, 3H), 1.54-1.43 (m, 1H), 1.37 (d, J=6.8 Hz, 3H), 1.19 (s, 9H).

Step 4

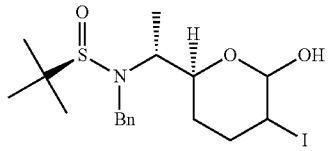 [SMILES: C[C@H]([C@@H]1CCC(I)C(O)O1)N(Cc1ccccc1)[S@](=O)C(C)(C)C]

(R)-N-Benzyl-N-[(1R)-1-[(2S)-6-hydroxy-5-iodo-tetrahydropyran-2-yl]ethyl]-2-methyl-propane -2-sulfinamide I₂ (947 mg, 3.73 mmol) was added portionwise to a suspension of (R)-N-benzyl-N -[(1R)-1-[(2S)-3,4-dihydro-2H-pyran-2-yl]ethyl]-2-methyl-propane-2-sulfinamide (1.2 g, 3.73 mmol) and NaHCO₃ (941 mg, 11.2 mmol) in ACN (50 mL) and H₂O (50 mL) at 0° C. The mixture was stirred at room temperature for 1 h, then a saturated aqueous solution of Na₂S₂O₃ (10 mL) was added. The aqueous layer was extracted with EtOAc (3×150 mL). The combined organic layer was washed with brine, dried over MgSO₄, filtered and concentrated under reduced pressure to provide the title compound (1.6 g, 92%) as a solid. M+H⁺: 466.1.

Step 5

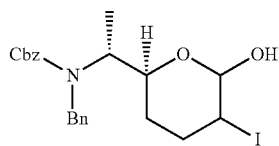 [SMILES: C[C@H]([C@@H]1CCC(I)C(O)O1)N(Cc1ccccc1)C(=O)OCc1ccccc1]

Benzyl N-benzyl-N-[(1R)-1-[(2S)-6-hydroxy-5-iodo-tetrahydropyran-2-yl]ethyl]carbamate 1N HCl (6.45 mL, 6.45 mmol) was added to a mixture of (R)-N-benzyl-N-[(1R)-1-[(2S)-6-hydroxy-5-iodo-tetrahydropyran-2-yl]ethyl]-2-methyl-propane-2-sulfinamide (1.2 g, 2.58 mmol) in dioxane (40 mL). The mixture was stirred at room temperature for 20 min, then Na₂CO₃ (2.19 g, 20.6 mmol) was added. After 20 min, CbzCl (0.51 mL, 3.61 mmol) was added dropwise. The mixture was stirred at room temperature for 2 h. Water (200 mL) was added. The separated aqueous layer was extracted with EtOAc (3×150 mL). The combined organic layer was washed with brine, dried over MgSO₄ and concentrated under reduced pressure. The material was purified on silical gel (80 g, dry loading) by MPLC using hexane to 80% EtOAc to provide the title compound (1.1 g, 86%) as a solid. M+H⁺: 496.0.

Step 6

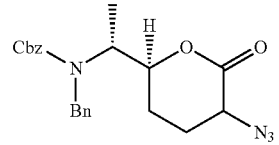 [SMILES: C[C@H]([C@@H]1CCC(N=[N+]=[N-])C(=O)O1)N(Cc1ccccc1)C(=O)OCc1ccccc1]

Benzyl N-[(1R)-1-[(2S)-5-azido-6-oxo-tetrahydropyran-2-yl]ethyl]-N-benzyl-carbamate Dess-Martin Periodinane (1.88 g, 4.44 mmol) was added to a solution of benzyl N -benzyl-N-[(1R)-1-[(2S)-6-hydroxy-5-iodo-tetrahydropyran-2-yl]ethyl]carbamate (1.10 g, 2.22 mmol) in DCM (100 mL) at 0° C. The mixture was stirred at room temperature for 5 h. Water (100 mL) was added following by a saturated aqueous solution of Na₂S₂O₃. The separated aqueous layer was extract with DCM (2×50 mL). The combined organic layer were washed with saturated aqueous NaHCO₃ (2×100 mL), brine (100 mL), dried over MgSO₄ and concentrated under reduced pressure. The residue was taken in anhydrous DMF (75 mL) and NaN₃ (217 mg, 3.33 mmol) was added. The mixture was stirred at room temperature for 15 min, then brine (300 mL) was added. The aqueous layer was extracted with Et₂O (3×100 mL). The combined organic layers were dried over MgSO₄ and concentrated under reduced pressure. The material was purified on silica gel (40 g, dry loading) by MPLC using hexane to EtOAc to provide the title compound (800 mg, 88%) as an oil. M+H⁺: 409.3.

Step 7

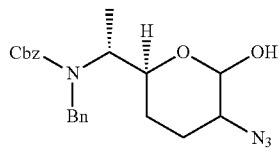

Benzyl N-[(1R)-1-[(2S)-5-azido-6-hydroxy-tetrahydropyran-2-yl]ethyl]-N-benzyl-carbamate DIBAL-H (1 M in toluene, 11.8 mL, 11.8 mmol) was added dropwise to a solution of benzyl N-[(1R)-1-[(2S)-5-azido-6-oxo-tetrahydropyran-2-yl]ethyl]-N-benzyl-carbamate (800 mg, 1.96 mmol) in DCM (60 mL) at −78° C. After 1 h at −78° C., EtOH (0.5 mL) was added dropwise. The mixture was poured into a saturated aqueous solution of Rochelle's salt (300 mL). The mixture was vigorously stirred for 1 h. The separated aqueous layer was extracted with DCM (2×75 mL). The combined organic layer was washed with brine, dried over $MgSO_4$ and concentrated under reduced pressure. The residue was purified on silica gel (40 g, dry loading) by MPLC using hexane to 60% EtOAc in hexane to provide the title compound (363 mg, 41%) as an oil. $M+H^+$: 411.2.

Step 8

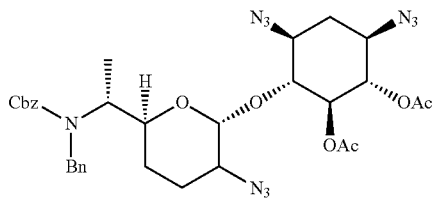

[(1S,2S,3R,4S,6R)-2-Acetoxy-4,6-diazido-3-[(2R,6S)-3-azido-6-[(1R)-1-[benzyl(benzyloxycarbonyl)amino]ethyl]tetrahydropyran-2-yl]oxy-cyclohexyl]acetate $CCl_3CN$ (0.44 mL, 4.39 mol) was added dropwise to a suspension of benzyl N-[(1R)-1-[(2S)-5-azido-6-hydroxy-tetrahydropyran-2-yl]ethyl]-N-benzyl-carbamate (360 mg, 0.88 mmol) and $K_2CO_3$ (364 mg, 2.63 mmol) in dry DCM (10 mL) at ambient temperature under $N_2$. The mixture was stirred at room temperature for 8 h, then filtered on celite and rinsed with DCM. The filtrate was concentrated under reduced pressure. The residue was taken up in DCM (10 mL) and [(1S,2S,3R,4S,6R)-2-acetoxy-4,6-diazido-3-hydroxy-cyclohexyl]acetate (654 mg, 2.19 mmol) was added. The mixture was cooled to −78° C., then $BF_3 \cdot OEt_2$ (0.43 mL, 3.51 mmol) was added dropwise. The mixture was stirred at room temperature for 5 h, then a saturated aqueous solution of $NaHCO_3$ (50 mL) was added. The separated aqueous layer was extratec with DCM (2×30 mL). The combined organic layer was washed with brine, dried over $Na_2SO_4$ and concentrated under reduced pressure. The residue was purified on C18 silica (120 g Biotage) using 45% B in A to 100% B (B=ACN 0.1% HCOOH, A=0.1% HCOOH). The mixture of diastereoisomers was used for the next step without further purification. $M+H^+$: 691.3.

Step 9

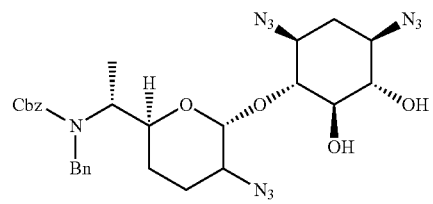

Benzyl N-[(1R)-1-[(2S,5S,6R)-5-azido-6-[(1R,2R,3S,4R,6S)-4,6-diazido-2,3-dihydroxy-cyclohexoxy]tetrahydropyran-2-yl]ethyl]-N-benzyl-carbamate NaOMe (4.62 M, 0.22 mL, 1.03 mmol) was added dropwise to a solution of [(1S,2S,3R,4S,6R)-2-acetoxy-4,6-diazido-3-[(2R,3S,6S)-3-azido-6-(benzyloxycarbonylaminomethyl)tetrahydropyran-2-yl]oxy-cyclohexyl]acetate (118 mg, 0.171 mmol) in MeOH (8 mL) at room temperature. After 60 min, AcOH (0.08 mL, 1.37 mmol) was added to the reaction and the mixture was concentrated under reduced pressure. The material was purified by chiral SFC to yield 55 mg, 53%. $M+H^+$: 607.4.

Step 10

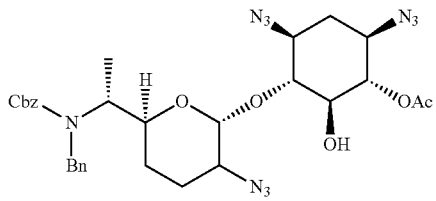 [SMILES: CC(=O)O[C@@H]1[C@@H](O)[C@H](O[C@H]2O[C@H]([C@@H](C)N(Cc3ccccc3)C(=O)OCc3ccccc3)CCC2N=[N+]=[N-])[C@@H](N=[N+]=[N-])C[C@H]1N=[N+]=[N-]]

[(1S,2S,3R,4S,6R)-4,6-Diazido-3-[(2R,3R,6S)-3-azido-6-[(1R)-1-[benzyl(benzyloxycarbonyl)amino]ethyl]tetrahydropyran-2-yl]oxy-2-hydroxy-cyclohexyl]acetate $Ac_2O$ (0.02 mL, 0.16 mmol) was added to a solution of N-[(1R)-1-[(2S,5R,6R)-5-azido-6-[(1R,2R,3S,4R,6S)-4,6-diazido-2,3-dihydroxy-cyclohexoxy]tetrahydropyran-2-yl]ethyl]-N-benzyl-carbamate (55 mg, 0.09 mmol) and pyridine (0.05 mL, 0.54 mmol) in dry DCM (5 mL) at room temperature. After 22 h, MeOH (0.5 mL) was added and the volatiles were removed under reduced pressure. The material was purified by prep-HPLC using ACN and AmFor (pH 4) to provide the title compound (32 mg, 54%) as a solid. $M+H^+$: 649.3.

Step 11

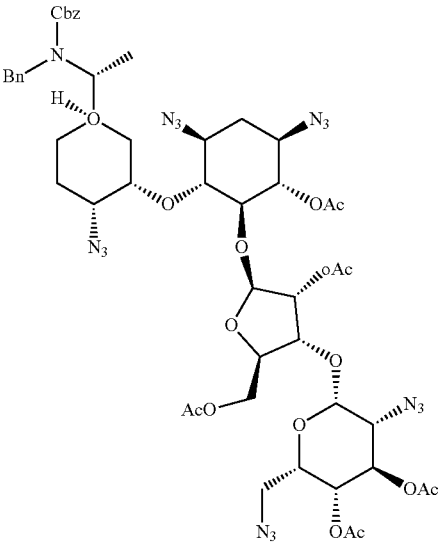

(2S,3R,4R,5R,6R)-6-(((2R,3R,4R,5S)-4-Acetoxy-5-(((1S,2S,3R,5S,6R)-2-acetoxy-3,5-diazido-6-(((2S,3S,6R)-3-azido-6-((S)-1-(benzyl((benzyloxy)carbonyl)amino)ethyl)tetrahydro-2H-pyran-2-yl)oxy)cyclohexyl)oxy)-2-(acetoxymethyl)tetrahydrofuran-3-yl)oxy)-5-azido-2-(azidomethyl)tetrahydro-2H-pyran-3,4-diyl diacetate $CCl_3CN$ (0.07 mL, 0.67 mol) was added dropwise to a mixture of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (71 mg, 0.13 mmol) and K$_2$CO$_3$ (56 mg, 0.40 mmol) in dry DCM (8 mL) at room temperature under N$_2$. The mixture was stirred at room temperature for 18 h, then filtered with a filter syringe and rinsed with DCM. The filtrate was concentrated under reduced pressure.

[(1S,2S,3R,4S,6R)-4,6-diazido-3-[(2R,3R,6S)-3-azido-6-[(1R)-1-[benzyl(benzyloxycarbonyl)amino]ethyl]tetrahydropyran-2-yl]oxy-2-hydroxy-cyclohexyl]acetate (29 mg, 0.045 mmol) was dissolved in DCM (8 mL) and added to the previous reaction mixture. 4 Å molecular sieves were added and the mixture was cooled to −78° C., then BF$_3$·OEt$_2$ (0.03 mL, 0.22 mmol) was added dropwise. The mixture was stirred at room temperature for 5 h, then a saturated aqueous solution of NaHCO$_3$ (15 mL) was added. The separated aqueous layer was extracted with DCM (2×20 mL). The combined organic layer was washed with brine, dried over Na$_2$SO$_4$ and concentrated under reduced pressure. The residue was purified on C18 silica (120 g Biotage) using 50% B in A to 100% B (B=ACN 0.1% HCOOH, A=0.1% HCOOH) to provide the title compound (35 mg, 67%) as a solid. M+H$^+$: 1161.7.

Step 12

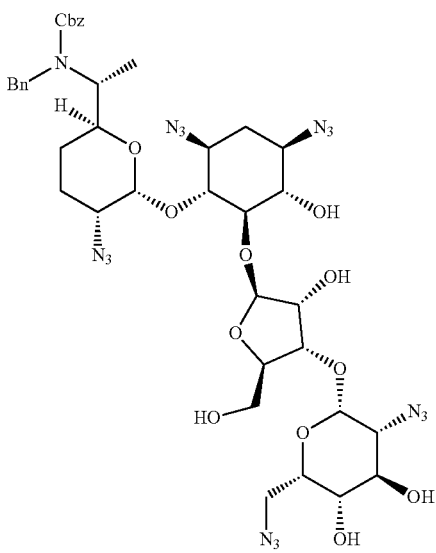 [SMILES: C[C@H]([C@@H]1CC[C@@H](N=[N+]=[N-])[C@@H](O[C@H]2[C@H](O[C@@H]3O[C@H](CO)[C@@H](O[C@H]4O[C@@H](CN=[N+]=[N-])[C@@H](O)[C@H](O)[C@H]4N=[N+]=[N-])[C@H]3O)[C@@H](O)[C@H](N=[N+]=[N-])C[C@@H]2N=[N+]=[N-])O1)N(Cc1ccccc1)C(=O)OCc1ccccc1]

Benzyl ((R)-1-((2S,5R,6R)-5-azido-6-(((1R,2R,3S,4R,6S)-4,6-diazido-2-(((2S,3R,4S,5R)-4 -(((2R,3R,4R,5S,6S)-3-azido-6-(azidomethyl)-4,5-dihydroxytetrahydro-2H-pyran-2-yl)oxy)-3 -hydroxy-5-(hydroxymethyl)tetrahydrofuran-2-yl)oxy)-3-hydroxycyclohexyl)oxy)tetrahydro-2H -pyran-2-yl)ethyl)(benzyl)carbamate NaOMe (4.62 M, 0.05 mL, 0.24 mmol) was added dropwise to a solution of (2S,3R,4R,5R,6R)-6-(((2R,3R,4R,5S)-4-acetoxy-5-(((1S,2S,3R,5S,6R)-2-acetoxy-3,5-diazido -6-(((2S,3S,6R)-3-azido-6-((S)-1-(benzyl((benzyloxy)carbonyl)amino)ethyl)tetrahydro-2H-pyran -2-yl)oxy)cyclohexyl)oxy)-2-(acetoxymethyl)tetrahydrofuran-3-yl)oxy)-5-azido-2-(azidomethyl)tetrahydro-2H-pyran-3,4-diyl diacetate (35 mg, 0.03 mmol) in MeOH (5 mL) at room temperature. After 4 h, AcOH (0.02 mL, 0.271 mmol) was added to the reaction and the mixture was concentrated under reduced pressure. The residue was purified by prep-HPLC using ACN and AmFor pH 4 to provide the title compound (20 mg, 70%) as a solid. M+H$^+$: 951.3.

Step 13

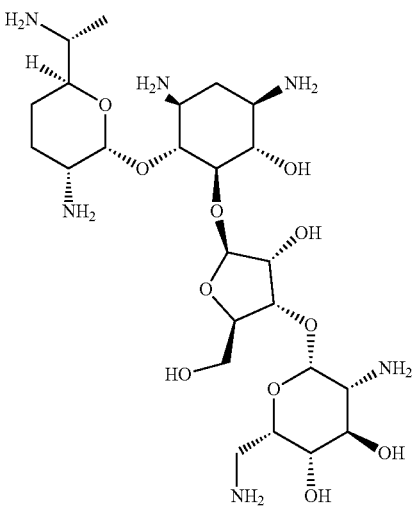 [SMILES: C[C@@H](N)[C@@H]1CC[C@@H](N)[C@@H](O[C@H]2[C@H](O[C@@H]3O[C@H](CO)[C@@H](O[C@H]4O[C@@H](CN)[C@@H](O)[C@H](O)[C@H]4N)[C@H]3O)[C@@H](O)[C@H](N)C[C@@H]2N)O1]

(2S,3S,4R,5R,6R)-5-Amino-2-(aminomethyl)-6-(((2R,3S,4R,5S)-5-(((1R,2R,3S,5R,6S)-3,5-diamino-2-(((2R,3R,6S)-3-amino-6-((R)-1-aminoethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H -pyran-3,4-diol A mixture of benzyl ((R)-1-((2S,5R,6R)-5-azido-6-(((1R,2R,3S,4R,6S)-4,6-diazido -2-(((2S,3R,4S,5R)-4-(((2R,3R,4R,5S,6S)-3-azido-6-(azidomethyl)-4,5-dihydroxytetrahydro-2H -pyran-2-yl)oxy)-3-hydroxy-5-(hydroxymethyl)tetrahydrofuran-2-yl)oxy)-3 -hydroxycyclohexyl)oxy)tetrahydro-2H-pyran-2-yl)ethyl)(benzyl)carbamate (20 mg, 0.02 mmol) and Pd(OH)$_2$ (20% wt, 10 mg, 0.02 mmol) in MeOH (8 mL) was hydrogenated for 18 h at room temperature. The mixture was degassed with N$_2$ for 5 min, then filtered on 0.40 μM syringe filter. The solvent was removed under reduced pressure to provide the title compound (8.5 mg, 68%) as a solid. M+H$^+$: 597.3 $^1$H NMR (500 MHz, MeOD) δ 5.30 (d, J=3.4 Hz, 1H), 5.23 (d, J =2.7 Hz, 1H), 4.88 (d, J=1.7 Hz, 1H), 4.32 (dd, J=6.0, 5.1 Hz, 1H), 4.14-4.11 (m, 1H), 4.03 (dt, J=6.4, 3.8 Hz, 1H), 3.90-3.80 (m, 3H), 3.78-3.70 (m, 2H), 3.66 (dd, J=12.1, 4.3 Hz, 1H), 3.50-3.45 (m, 1H), 3.45-3.43 (m, 1H), 3.35 (t, J=9.3 Hz, 1H), 3.11 (t, J=9.5 Hz, 1H), 3.00 (dd, J=13.2, 8.3 Hz, 1H), 2.97-2.90 (m, 2H), 2.87-2.74 (m, 3H), 2.59 (ddd, J=12.1, 9.8, 4.1 Hz, 1H), 1.92 (dt, J=12.9, 4.1 Hz, 1H), 1.74-1.63 (m, 3H), 1.48-1.38 (m, 1H), 1.09 (d, J=6.2 Hz, 3H).

Example 24

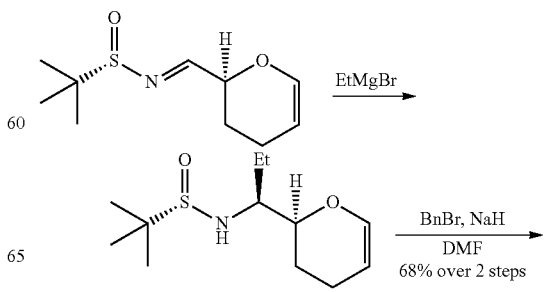

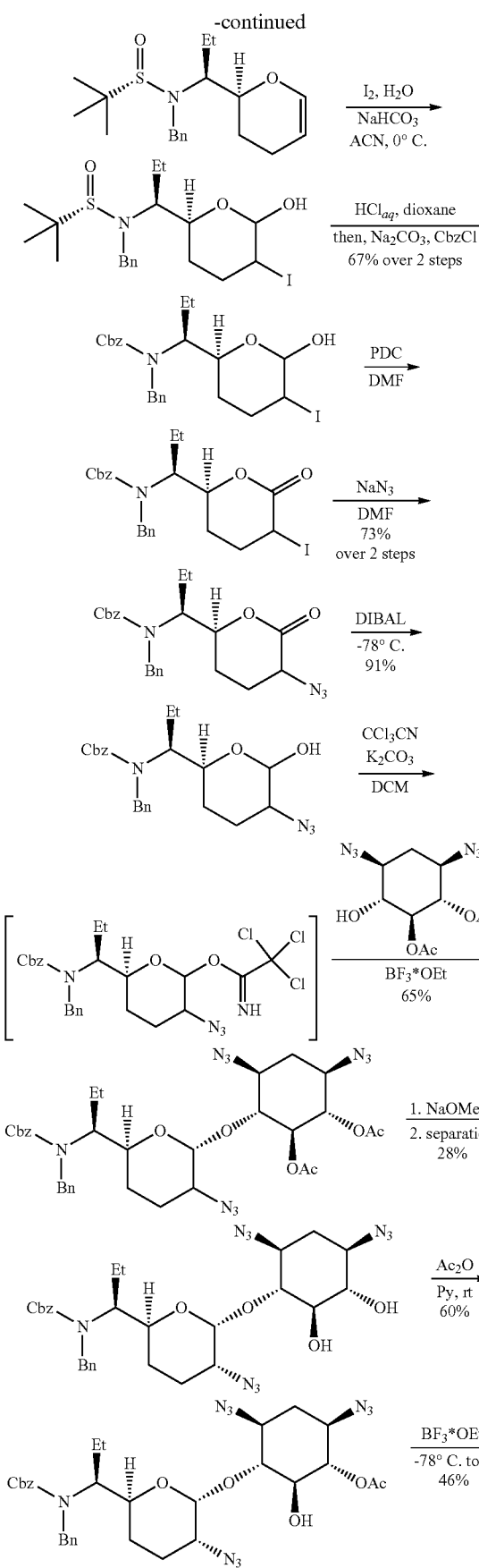
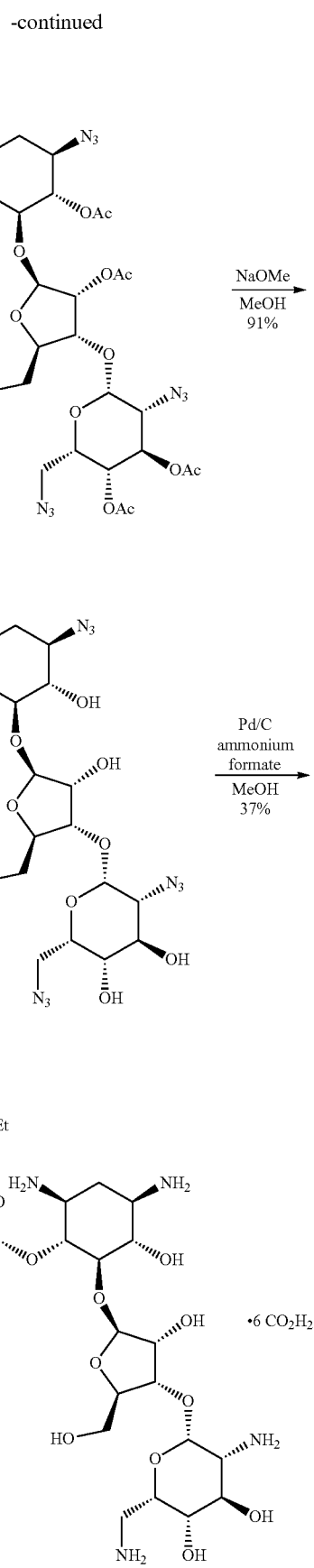

Step 1

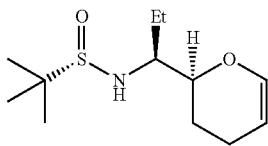 [SMILES: CC[C@H](N[S@@](=O)C(C)(C)C)[C@@H]1CCC=CO1]

(S)-N-[(1S)-1-[(2S)-3,4-Dihydro-2H-pyran-2-yl]propyl]-2-methyl-propane-2-sulfinamide EtMgBr (3.0 M in Et$_2$O, 9.29 mL, 27.9 mmol) was added to a solution of (NE,S)-N -[[(2S)-3,4-dihydro-2H-pyran-2-yl]methylene]-2-methyl-propane-2-sulfinamide (3.00 g, 13.9 mmol) in dry THF (100.0 mL) at −78° C. under N$_2$. After 1 h, the reaction was stirred at −40° C. for 1 h and then warmed to room temperature within 1 h. After 1 h, the reaction was cooled to 0° C. and sat. NH$_4$Cl (100.0 mL) was added dropwise (nota bene: gas evolution). THF was evaporated under reduced pressure and then the mixture was extracted with EtOAc (3×100.0 mL). The combined organic layers were dried (Na$_2$SO$_4$), filtered and concentrated under reduced pressure to provide the title compound as a liquid. The crude was clean and used in the next step without further purification. LCMS m/z ES$^+$ [M+Na]$^+$: 268.20, LCMS (A05) retention time=1.65 and 1.70 m.

Step 2

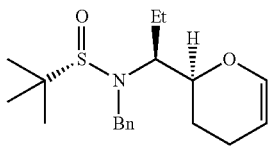 [SMILES: CC[C@@H]([C@@H]1CCC=CO1)N(Cc1ccccc1)[S@@](=O)C(C)(C)C]

(S)-N-benzyl-N-((S)-1-((S)-3,4-dihydro-2H-pyran-2-yl)propyl)-2-methylpropane-2-sulfinamide A mixture of (S)-N-[(1S)-1-[(2S)-3,4-Dihydro-2H-pyran-2-yl]propyl]-2-methyl -propane-2-sulfinamide (2.97 g, 12.1 mmol), bromomethylbenzene (2.59 mL, 21.8 mmol) in DMF (65 mL) was stirred at 0° C. NaH (0.581 g, 14.5 mmol) was then added to the reaction mixture portionwise. The mixture was allowed to stir at room temperature for 48 h. The reaction was quenched with water (200 mL) and the mixture was extract with EtOAc (3×100 mL). The organic layers were combined, washed with water and dried over sodium sulfate and then concentrated under reduced pressure. The residue was purified on silica gel (120 g) using hexane and ethyl acetate (70/30) as eluent to give the title product (2.74 g, 68%) as an oil. LCMS m/z ES$^+$ [M+Na]$^+$: 358.14, LCMS (B05) retention time=2.41 m.

Step 3

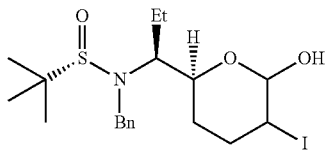 [SMILES: CC[C@@H]([C@@H]1CCC(I)C(O)O1)N(Cc1ccccc1)[S@@](=O)C(C)(C)C]

(S)-N-benzyl-N-((1S)-1-((2S)-6-hydroxy-5-iodotetrahydro-2H-pyran-2-yl)propyl)-2-methylpropane-2-sulfinamide Iodine (2.07 g, 8.17 mmol) was added portionwise to a suspension of (S)-N-benzyl -N-((S)-1-((S)-3,4-dihydro-2H-pyran-2-yl)propyl)-2-methylpropane-2-sulfinamide (2.74 g, 8.17 mmol) and NaHCO$_3$ (2.06 g, 24.5 mmol) in ACN (42.0 mL) and H$_2$O (42.0 mL) at 0° C. The mixture was stirred at 0° C. for 15 min. Then, the mixture was stirred at room temperature for 15 min. After completion, a saturated aqueous solution of Na$_2$S$_2$O$_3$ (200 mL) was added. The aqueous layer was extracted with EtOAc (3×100 mL). The combined organic layer was dried over Na$_2$SO$_4$, filtered and concentrated under reduced pressure to provide the title compound (3.92 g, 100%) as an oil. The crude was used in the next step without further purification. LCMS m/z ES$^+$ [M+Na]$^+$: 502.04, LCMS (B05) retention time=2.51 m.

Step 4

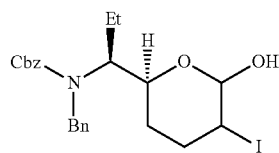 [SMILES: CC[C@@H]([C@@H]1CCC(I)C(O)O1)N(Cc1ccccc1)C(=O)OCc1ccccc1]

Benzyl benzyl((1S)-1-((2S)-6-hydroxy-5-iodotetrahydro-2H-pyran-2-yl)propyl)carbamate Aqueous HCl (1.0 M, 49.3 mL, 49.3 mmol) was dropwise added to a solution of (S) -N-benzyl-N-((1S)-1-((2S)-6-hydroxy-5-iodotetrahydro-2H-pyran-2-yl)propyl)-2-methylpropane -2-sulfinamide (3.92 g, 8.18 mmol) in dioxane (100.0 mL) with vigorous stirring. After 1 h, solid Na$_2$CO$_3$ (6.93 g, 65.4 mmol) was added. After another 10 min, CbzCl (1.97 mL, 13.8 mmol) was added dropwise. After another 30-45 min, dioxane was evaporated and the residue was partitioned in between EtOAc (150.0 mL) and H$_2$O (150.0 mL). The organic phase was dried over Na$_2$SO$_4$, filtered and concentrated under reduced pressure. The crude was purified by silica gel chromatography (120 g cartridge) using hexanes and ethyl acetate (0-30%) as eluent to give the title product (diastereomers, 2.80 g, 67%) as an oil. LCMS m/z ES$^+$ [M+Na]$^+$: 532.90, LCMS (B05) retention time=2.41, 2.50, and 2.74 m.

Step 5

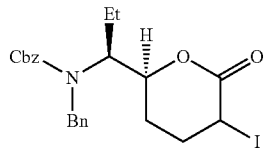 [SMILES: CC[C@@H]([C@@H]1CCC(I)C(=O)O1)N(Cc1ccccc1)C(=O)OCc1ccccc1]

Benzyl benzyl((1S)-1-((2S)-5-iodo-6-oxotetrahydro-2H-pyran-2-yl)propyl)carbamate Benzyl benzyl((1S)-1-((2S)-6-hydroxy-5-iodotetrahydro-2H-pyran-2-yl)propyl)carbamate (2.79 g, 5.48 mmol) was dissolved in DCM (120.0 mL). 4 Å molecular sieves (5.0 g) were suspended in the mixture, and PDC (6.18 g, 16.4 mmol) was added. Stirring was continued over 24 hours at room temperature, then filtered through a silica pad using ethyl acetate as eluent. The filtrate was concentrated in vacuo to afford the title compound as an oil. The crude was used in the next step without further purification. LCMS m/z: ES$^+$ [M+Na]$^+$: 530.95; (B05) retention time=2.41 m.

Step 6

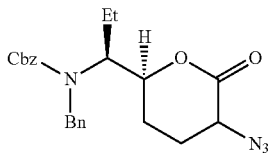

Benzyl ((1S)-1-((2S)-5-azido-6-oxotetrahydro-2H-pyran-2-yl)propyl)(benzyl)carbamate NaN$_3$ (0.413 mg, 6.36 mmol) was added to a solution of benzyl benzyl((1S)-1 -((2S)-5-iodo-6-oxotetrahydro-2H-pyran-2-yl)propyl)carbamate (2.15 g, 4.24 mmol) in DMF (50.0 mL). The mixture was stirred for 2 hours at 0° C. Water (100.0 mL) was added and the mixture was extracted with EtOAc (3×50 mL). The organic layers were combined and then washed with water (5×100 mL). The organic layer was dried over Na$_2$SO$_4$, concentrated in vacuo and purified by silica gel chromatography (80 g cartridge) to afford the title compound as an oil (1.30 g, 73%). LCMS m/z: ES$^+$ [M+Na]$^+$: 445.96; (B05) retention time=2.16 m.

Step 7

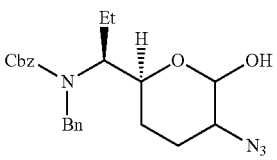 [SMILES: CC[C@@H]([C@@H]1CCC(N=[N+]=[N-])C(O)O1)N(Cc1ccccc1)C(=O)OCc1ccccc1]

Benzyl ((1S)-1-((2S)-5-azido-6-hydroxytetrahydro-2H-pyran-2-yl)propyl)(benzyl)carbamate DIBAL-H (1.00 M, 4.54 mL, 4.54 mmol) in DCM was added dropwise to a solution of benzyl ((1S)-1-((2S)-5-azido-6-oxotetrahydro-2H-pyran-2-yl)propyl)(benzyl)carbamate in DCM (75.0 mL) at −78° C. under N$_2$. After 1 h, acetone (1.00 mL) was added to the reaction mixture dropwise. After 5 min, sat. potassium sodium tartrate (100 mL) was added to the solution slowly, followed by the addition of water (100 mL). The mixture was allowed to warm to room temperature and vigorously stirred overnight in the presence of ethyl acetate. The organic layer was separated and the aqueous layer was extracted with ethyl acetate (3×100 mL). The combined organic layers were dried (Na$_2$SO$_4$), filtered and concentrated under reduced pressure to provide the title compound as an oil (diastereomers, 1.10 g, 91%). This mixture was used in the next step without further purification LCMS m/z: ES$^+$ [M+Na]$^+$: 446.93; (B05) retention time=2.31 m.

Step 8

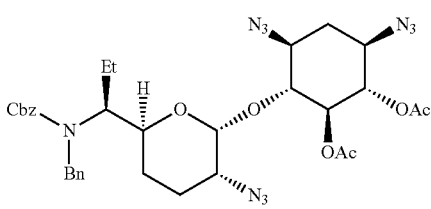 [SMILES: CC[C@@H]([C@@H]1CC[C@@H](N=[N+]=[N-])[C@@H](O[C@H]2[C@H](OC(C)=O)[C@@H](OC(C)=O)[C@H](N=[N+]=[N-])C[C@@H]2N=[N+]=[N-])O1)N(Cc1ccccc1)C(=O)OCc1ccccc1]

(1S,2S,3R,4S,6R)-4,6-diazido-3-(((2R,3R,6S)-3-azido-6-((S)-1-(benzyl((benzyloxy)carbonyl)amino)propyl)tetrahydro-2H-pyran-2-yl)oxy)cyclohexane-1,2-diyl diacetate CCl$_3$CN (0.877 mL, 8.75 mmol) was added dropwise to a suspension of benzyl ((1S)-1-((2S)-5-azido-6-hydroxytetrahydro-2H-pyran-2-yl)propyl)(benzyl)carbamate (0.734 g, 1.73 mmol) and K$_2$CO$_3$ (0.726 g, 5.25 mmol) in dry DCM (30.0 mL) at ambient temperature under N$_2$. After 12 h, the solution was filtered through Celite and the filtrate was concentrated by high-vacuum. To the crude was added [(1S,2S,3R,4S,6R)-2-acetoxy-4,6-diazido-3-hydroxy -cyclohexyl]acetate (0.418 g, 1.40 mmol) and ground 4 Å sieves (1.0 g) and the mixture was dissolved in dry DCM (30.0 mL). The suspension was stirred at ambient temperature for 25 min. The solution was cooled to 0° C. and BF$_3$·OEt$_2$ (0.864 mL, 7.00 mmol) was added dropwise with vigorous stirring. The solution was warmed to ambient temperature and stirred for another 3 hours. The reaction was quenched with sat. NaHCO$_3$ (50.0 mL). The mixture was successively extracted with DCM (3×50.0 mL) and the combined organic layer were dried (Na$_2$SO$_4$), filtered and concentrated under reduced pressure. The crude was purified by silica gel chromatography (40 g cartridge) with EtOAc and hexanes (0-30%) to produce the title compound as an oil (2 diastereomers, 0.64 g, 65%). LCMS m/z: [M+Na]$^+$: 727.13; (B05) retention time=2.61 m.

Step 9

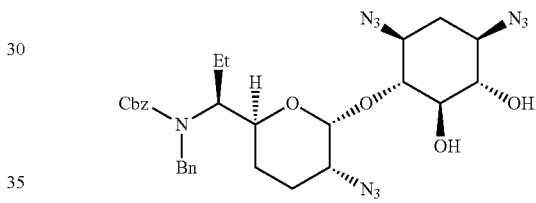

Benzyl N-[(1S)-1-[(2S,5R,6R)-5-azido-6-[(1R,2R,3S,4R,6S)-4,6-diazido-2,3-dihydroxy -cyclohexoxy]tetrahydropyran-2-yl]propyl]-N-benzyl-carbamate NaOMe (4.62 M, 737 μL, 3.41 mmol) was added dropwise to a solution of (1S,2S,3R,4S,6R)-4,6-diazido-3-(((2R,3R,6S)-3-azido-6-((S)-1-(benzyl((benzyloxy)carbonyl)amino)propyl)tetrahydro-2H-pyran-2-yl)oxy)cyclohexane-1,2-diyl diacetate (0.40 g, 0.568 mmol) in MeOH (35.0 mL) at room temperature. After 60 min, the reaction was neutralized with AcOH (260 μL, 4.54 mmol). Water (20.0 mL) was added and the mixture was extracted with DCM (3×30.0 mL). The organic layers were combined, dried over Na$_2$SO$_4$ and then concentrated under reduced pressure to provide a mixture of two diastereomers (0.280 g, 80%). ES$^+$ [M+Na]$^+$: 643.89; (B05) retention time=2.31 m. The desired isomer was separated on a Yamazen purification system using hexane and EtOAc to provide the desired diastereoisomer (100 mg, 28%) as a solid. ES$^+$ [M+Na]$^+$: 643.89.

Step 10

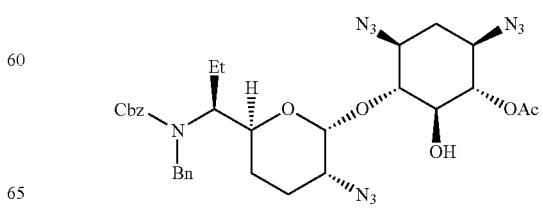

[(1S,2S,3R,4S,6R)-4,6-Diazido-3-[(2R,3R)-3-azido-6-[(1S)-1-[benzyl(benzyloxycarbonyl)amino]propyl]tetrahydropyran-2-yl]oxy-2-hydroxy-cyclohexyl]acetate Ac$_2$O (32.0 µL, 338 µmol) was added to a solution of benzyl N-[(1S)-1-[(2S,5R,6R) -5-azido-6-[(1R,2R,3S,4R,6S)-4,6-diazido-2,3-dihydroxy-cyclohexoxy]tetrahydropyran-2-yl]propyl]-N-benzyl-carbamate (70.0 mg, 113 µmol) and pyridine (54.7 µL, 677 µmol) in dry DCM (2.00 mL) at ambient temperature. After 18 h, all volatiles were removed under reduced pressure. The crude was purified by silica gel chromatography (25 g cartridge) with EtOAc and hexanes (5-40%) to produce the title compound as an oil (45.0 mg, 60%). LCMS m/z: ES$^+$ [M+Na]$^+$: 685.75; (B05), retention time=2.56 m.

Step 11

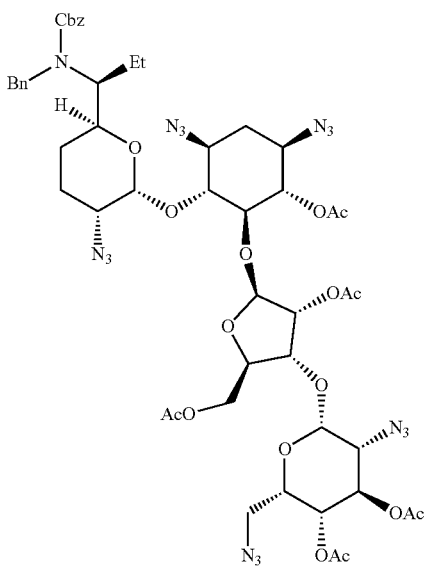 [SMILES: CC[C@@H]([C@@H]1CC[C@@H](N=[N+]=[N-])[C@@H](O[C@H]2[C@H](O[C@@H]3O[C@H](COC(C)=O)[C@@H](O[C@H]4O[C@@H](CN=[N+]=[N-])[C@@H](OC(C)=O)[C@H](OC(C)=O)[C@H]4N=[N+]=[N-])[C@H]3OC(C)=O)[C@@H](OC(C)=O)[C@H](N=[N+]=[N-])C[C@@H]2N=[N+]=[N-])O1)N(Cc1ccccc1)C(=O)OCc1ccccc1]

(2S,3R,4R,5R,6R)-6-(((2R,3R,4R,5S)-4-Acetoxy-5-(((1S,2S,3R,5S,6R)-2-acetoxy-3,5-diazido -6-(((2S,3S,6R)-3-azido-6-((S)-1-(benzyl((benzyloxy)carbonyl)amino)ethyl) tetrahydro-2H-pyran -2-yl)oxy)cyclohexyl)oxy)-2-(acetoxymethyl)tetrahydrofuran-3-yl)oxy)-5-azido-2 -(azidomethyl)tetrahydro-2H-pyran-3,4-diyl diacetate CCl$_3$CN (97.6 µL, 973 µmol) was added dropwise to a mixture of [(2R,3R,4R)-4-acetoxy-3-[(2R,3R,4R,5R,6S)-4,5-diacetoxy-3-azido-6-(azidomethyl)tetrahydropyran-2-yl]oxy -5-hydroxy-tetrahydrofuran-2-yl]methyl acetate (138 mg, 0.260 mmol) and K$_2$CO$_3$ (80.7 mg, 0.584 mmol) in dry DCM (8.00 mL) at room temperature under N$_2$. The mixture was stirred at room temperature for 16 h, then filtered through Celite and rinsed with DCM. The filtrate was concentrated under reduced pressure. The crude was dissolved in DCM (8.00 mL) and added to [(1S,2S,3R,4S,6R)-4,6-diazido-3-[(2R,3R,6S)-3-azido-6-[(1S)-1-[benzyl(benzyloxycarbonyl)amino]propyl]tetrahydropyran-2-yl]oxy-2-hydroxy-cyclohexyl]acetate (43.0 mg, 64.9 µmol). 4 Å molecular sieves (200 mg) were added and the mixture was cooled to −78° C., then BF$_3$·OEt$_2$ (40.0 µL, 324 µmol) was added dropwise. The mixture was stirred at room temperature for 5 h, then a saturated aqueous solution of NaHCO$_3$ (15.0 mL) was added. The separated aqueous layer was extracted with DCM (3×20.0 mL). The combined organic layer was washed with brine, dried over Na$_2$SO$_4$ and concentrated under reduced pressure. The residue was purified by silica gel chromatography (25 g) using hexane and ethyl acetate (0-30%) to provide the title compound (45.0 mg, 46%) as a an oil. LCMS m/z ES$^+$ [M+H]$^+$: 1175.12, LCMS (B05) retention time=2.44 m.

Step 12

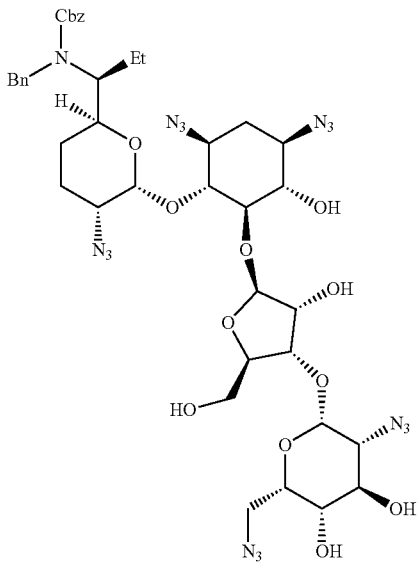 [SMILES: CC[C@@H]([C@@H]1CC[C@@H](N=[N+]=[N-])[C@@H](O[C@H]2[C@H](O[C@@H]3O[C@H](CO)[C@@H](O[C@H]4O[C@@H](CN=[N+]=[N-])[C@@H](O)[C@H](O)[C@H]4N=[N+]=[N-])[C@H]3O)[C@@H](O)[C@H](N=[N+]=[N-])C[C@@H]2N=[N+]=[N-])O1)N(Cc1ccccc1)C(=O)OCc1ccccc1]

NaOMe (25 wt %, 103 µL, 357 µmol) was added dropwise to a solution of the compound of step 11 above (35.0 mg, 298 µmol) in MeOH (5.0 mL) at ambient temperature. After 1 hour, the reaction mixture was neutralized by HOAc (~341 µL) and all volatiles were removed under reduced pressure. The crude was dissolved with EtOAc, filtered through Celite and the filtrate was concentrated under reduced pressure to produce benzyl ((S)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl) tetrahydrofuran-2-yl)oxy)-3-hydroxycyclohexyl)oxy) tetrahydro-2H-pyran-2-yl)propyl)(benzyl)carbamate as an oil (26.0 mg, 91%). LCMS m/z: ES$^+$ [M+Na]$^+$: 987.29, (B05) retention time=2.28 m.

Step 13

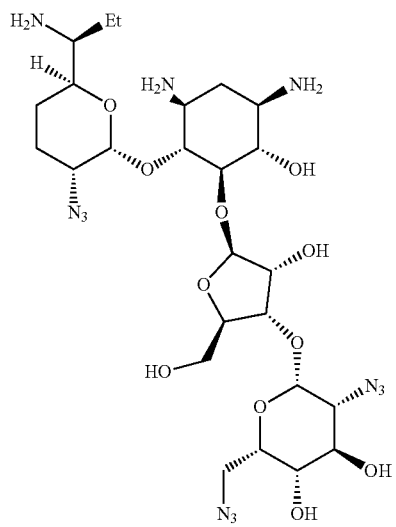 [SMILES: CC[C@H](N)[C@@H]1CC[C@@H](N=[N+]=[N-])[C@@H](O[C@H]2[C@H](O[C@@H]3O[C@H](CO)[C@@H](O[C@H]4O[C@@H](CN=[N+]=[N-])[C@@H](O)[C@H](O)[C@H]4N=[N+]=[N-])[C@H]3O)[C@@H](O)[C@H](N)C[C@@H]2N)O1]

381

(2S,3S,4R,5R,6R)-5-Amino-2-(aminomethyl)-6-(((2R,3S, 4R,5S)-5-(((1R,2R,3S,5R,6S)-3,5-diamino-2-(((2R,3R,6S)-3-amino-6-((S)-1-aminopropyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol hexaformate

In a 2 neck flask equipped with a reflux condenser were added benzyl ((S)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)propyl)(benzyl)carbamate (26 mg, 0.033 mmol) and Pd/C (10% dry on carbon, 8.6 mg, 0.01 mmol) followed by anhydrous MeOH (4 mL). Nitrogen was bubbled for 5 min, then ammonium formate (15.3 mg, 0.24 mmol) was added. The mixture was heat at 63° C. for 30 min under $N_2$, then cooled to room temperature with an ice-bath. The mixture was filtered with a filter syringe and concentrated under reduced pressure. The material was purified by prep-HPLC using 5% B in A to 100% B (A: Amfor pH 4, B: ACN) on C18 Xbridge 30×150 mm to provide the title compound (8.9 mg, 37%) as a solid. M+H$^+$: 611.3. $^1$H NMR (500 MHz, MeOD) δ 8.51 (s, 6H), 5.74 (s, 1H), 5.36 (s, 1H), 5.26 (s, 1H), 4.48 (s, 1H), 4.42-4.24 (m, 3H), 4.13-4.09 (m, 2H), 3.96-3.76 (m, 2H), 3.76-3.61 (m, 3H), 3.42 (m, 5H), 3.13 (s, 3H), 2.31-2.25 (m, 1H), 2.13-1.92 (m, 3H), 1.89-1.50 (m, 4H), 1.05 (t, J=7.4 Hz, 3H).

Example 25

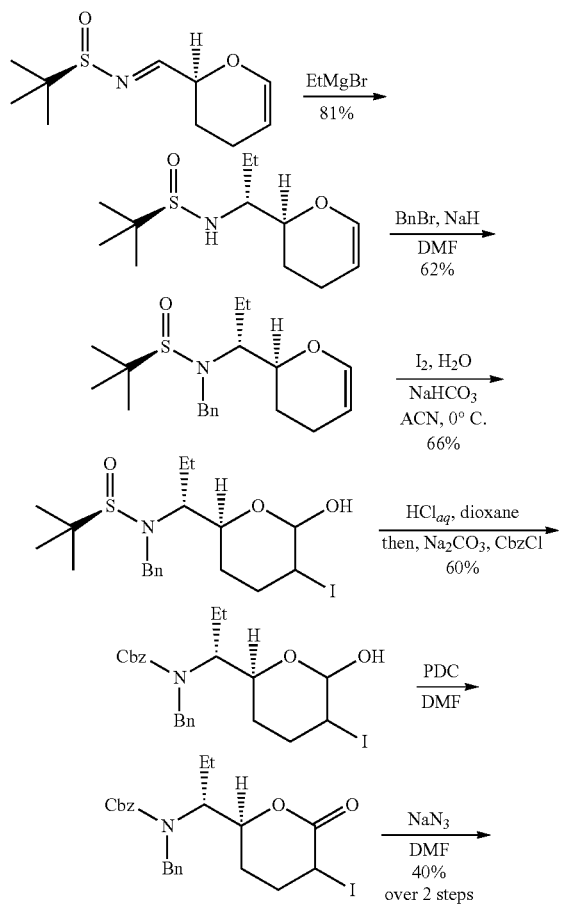

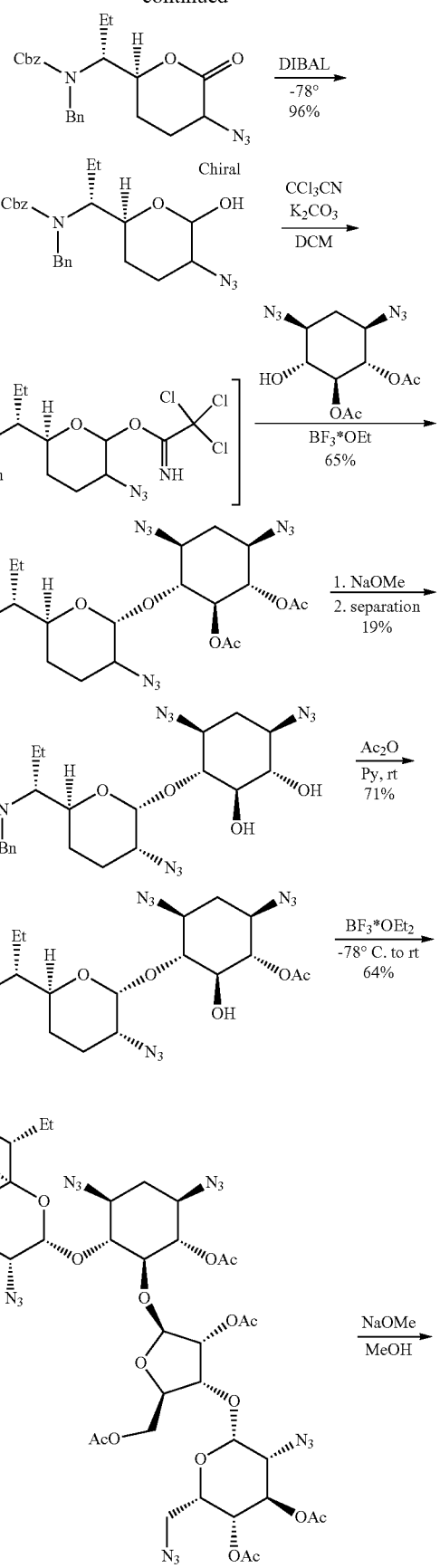

-continued

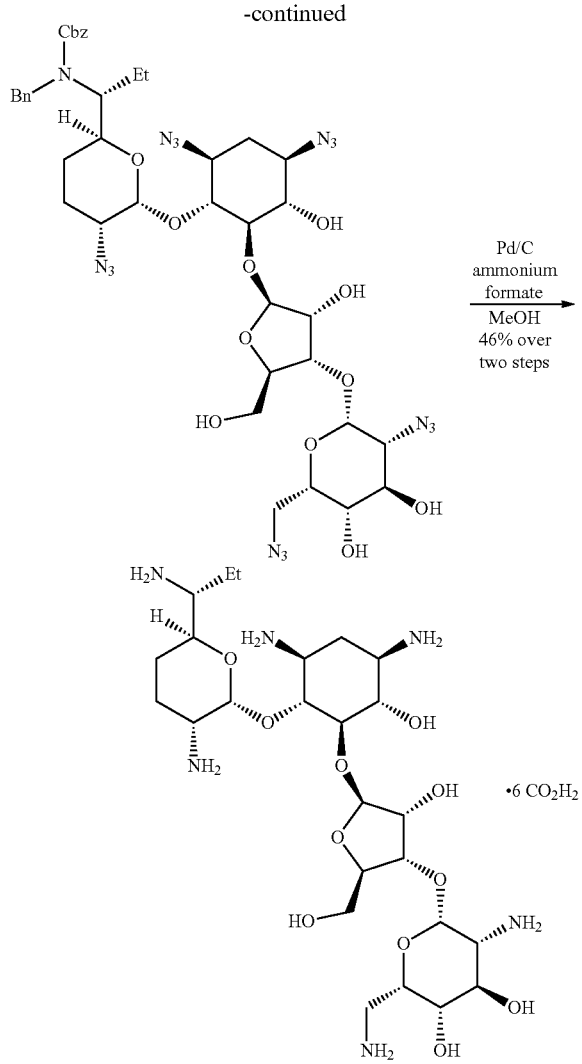

Pd/C
ammonium
formate
———————→
MeOH
46% over
two steps

·6 CO₂H₂

Step 1

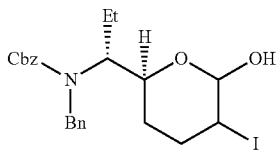

(R)-N-[(1R)-1-[(2S)-3,4-Dihydro-2H-pyran-2-yl]propyl]-2-methyl-propane-2-sulfinamide EtMgBr (3.0 M in Et₂O, 9.29 mL, 27.9 mmol) was added to a solution of (NE)-N-[[(2S)-3,4-dihydro-2H-pyran-2-yl]methylene]-2-methyl-propane-2-sulfinamide (3.00 g, 13.9 mmol) in dry THF (75.0 mL) at −78° C. under N₂. After 1 h, the reaction was stirred at −40° C. for 1 h and then warmed to room temperature within 1 h. After 1 h, the reaction was cooled to 0° C. and sat. NH₄Cl (100.0 mL) was added dropwise (nota bene: gas evolution). THF was evaporated under reduced pressure and the resulting mixture was extracted with EtOAc (3×100.0 mL). The combined organic layers were dried (Na₂SO₄), filtered and concentrated under reduced pressure to provide the title compound as a liquid. The crude was clean and used in the next step without further purification. ¹H NMR (500 MHz, CDCl₃) δ 6.35 (d, J=6.1 Hz, 1H), 4.72-4.54 (m, 1H), 4.03 (ddd, J=11.1, 3.3, 2.0 Hz, 1H), 3.64 (d, J=8.0 Hz, 1H), 3.29-3.14 (m, 1H), 2.19-2.02 (m, 1H), 2.01-1.90 (m, 1H), 1.85-1.47 (m, 4H), 1.23 (s, 9H), 0.95 (t, J=7.4 Hz, 3H). LCMS m/z ES⁺ [M+Na]: 267.94, LCMS (A05) retention time=1.65 m.

Step 2

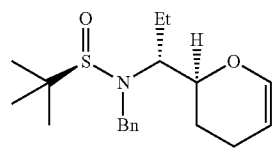 [SMILES: CC[C@H]([C@@H]1CCC=CO1)N(Cc1ccccc1)[S@](=O)C(C)(C)C]

(R)-N-benzyl-N-((R)-1-((S)-3,4-dihydro-2H-pyran-2-yl)propyl)-2-methylpropane-2-sulfinamide A mixture of (R)-N-[(1R)-1-[(2S)-3,4-Dihydro-2H-pyran-2-yl]propyl]-2-methyl-propane-2-sulfinamide (3.41 g, 13.9 mmol), bromomethylbenzene (4.28 g, 25.0 mmol) in DMF (50.0 mL) was stirred at 0° C. NaH (0.667 g, 16.7 mmol) was then added to the reaction mixture portionwise. The mixture was allowed to stir at room temperature for 48 h. The reaction was quenched with water (100 mL) and the mixture was extract with EtOAc (3×50 mL). The organic layers were combined, dried over sodium sulfate and concentrated under reduced pressure. The residue was purified on silica gel (120 g) using hexane and ethyl acetate (70/30) as eluent to give the title product (2.90 g, 62%) as a colorless oil. LCMS m/z ES⁺ [M+H]⁺: 335.94, LCMS (B05) retention time=2.12 m.

Step 3

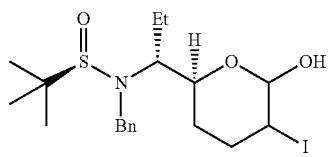 [SMILES: CC[C@H]([C@@H]1CCC(I)C(O)O1)N(Cc1ccccc1)[S@](=O)C(C)(C)C]

N-Benzyl-N-[(1R)-1-[(2S)-6-hydroxy-5-iodo-tetrahydropyran-2-yl]propyl]-2-methyl-propane-2-sulfinamide Iodine (2.33 g, 9.18 mmol) was added portionwise to a suspension of (R)-N-benzyl-N-((R)-1-((S)-3,4-dihydro-2H-pyran-2-yl)propyl)-2-methylpropane-2-sulfinamide (3.08 g, 9.18mmol) and NaHCO₃ (2.31 g, 27.5 mmol) in ACN (53 mL) and H₂O (53 mL) at 0° C. The mixture was stirred at 0° C. for 15 min, then the mixture was stirred at room temperature for 15 min. After completion, a saturated aqueous solution of Na₂S₂O₃ (100 mL) was added. The aqueous layer was extracted with EtOAc (3×100 mL). The combined organic layer was dried over Na₂SO₄, filtered, concentrated under reduced pressure to provide the title compound (2.90 g, 66%) as a yellow solid. The crude was used in the next step without further purification. LCMS m/z ES⁺ [M+Na]⁺: 502.75, LCMS (B05) retention time=1.95 and 2.93 m.

Step 4

Benzyl N-benzyl-N-[(1R)-1-[(2S)-6-hydroxy-5-iodo-tetrahydropyran-2-yl]propyl]carbamate Aqueous HCl (1.0 M, 55.3 mL, 55.3 mmol) was dropwise added to a solution of N-benzyl-N-[(1R)-1-[(2S)-6-hydroxy-5-iodo-tetrahydropyran-2-yl]propyl]-2-methyl-propane-2-sulfinamide (4.40 g, 9.18 mmol) in dioxane (130.0 mL) with vigorous stirring. After 1 h, solid Na$_2$CO$_3$ (7.78 g, 73.4 mmol) was added. After another 10 min, CbzCl (2.21 mL, 15.5 mmol) was added dropwise. After another 30-45 min, dioxane was evaporated and the residue was partitioned in between EtOAc (100.0 mL) and H$_2$O (100.0 mL). The organic phase was dried over Na$_2$SO$_4$, filtered and concentrated under reduced pressure. The crude was purified by silica gel chromatography (120 g cartridge) using hexanes and ethyl acetate (0-30%) as eluent to give the title product (diastereomers, 2.80 g, 60%) as an oil. LCMS m/z ES$^+$ [M+Na]$^+$: 531.89, LCMS (B05) retention time=2.10 and 2.15 m.

Step 5

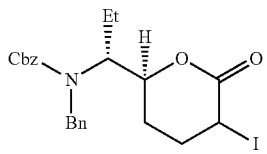 [SMILES: CC[C@H]([C@@H]1CCC(I)C(=O)O1)N(Cc1ccccc1)C(=O)OCc1ccccc1]

Benzyl N-benzyl-N-[(1R)-1-[(2S)-5-iodo-6-oxo-tetrahydropyran-2-yl]propyl]carbamate Benzyl N-benzyl-N-[(1R)-1-[(2S)-6-hydroxy-5-iodo-tetrahydropyran-2-yl]propyl]carbamate (2.80 g, 5.49 mmol) was dissolved in DCM (200.0 mL). 4 Å molecular sieves (2.0 g) were suspended in the mixture, and PDC (6.20 g, 16.4 mmol) was added. Stirring was continued over 24 hours at room temperature, then the reaction was filtered through a Silica pad using ethyl acetate as eluent. The filtrate was concentrated in vacuo to afford the title compound as an oil. The crude was used in the next step without further purification. LCMS m/z: ES$^+$ [M+H]$^+$: 507.94; (B05) retention time=2.12 m.

Step 6

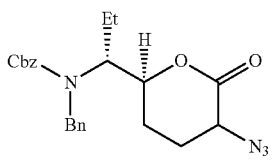 [SMILES: CC[C@H]([C@@H]1CCC(N=[N+]=[N-])C(=O)O1)N(Cc1ccccc1)C(=O)OCc1ccccc1]

Benzyl N-[(1R)-1-[(2S)-5-azido-6-oxo-tetrahydropyran-2-yl]propyl]-N-benzyl-carbamate NaN$_3$ (633 mg, 9.47 mmol) was added to a solution of benzyl N-benzyl-N-[(1R)-1-[(2S)-5-iodo-6-oxo-tetrahydropyran-2-yl]propyl]carbamate (2.47 g, 4.87 mmol) in DMF (50.0 mL). The mixture was stirred for 2 hours at room temperature. Water (100.0 mL) was added and the mixture was extracted with EtOAc (3×50 mL). The organic layers were combined and then washed with water (5×100 mL). The organic layer was dried over Na$_2$SO$_4$, concentrated in vacuo and purified by silica gel chromatography (80 g cartridge) to afford the title compound as an oil (0.825 g, 40%). LCMS m/z: ES$^+$ [M+Na]$^+$: 444.95; (B05) retention time=2.10-2.20 m.

Step 7

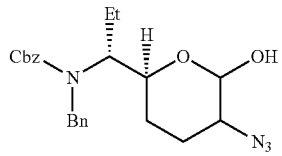 [SMILES: CC[C@H]([C@@H]1CCC(N=[N+]=[N-])C(O)O1)N(Cc1ccccc1)C(=O)OCc1ccccc1]

Benzyl((1R)-1-((2S)-5-azido-6-hydroxytetrahydro-2H-pyran-2-yl)propyl)(benzyl)carbamate DIBAL-H (1 M, 2.94 mL, 2.94 mmol) in toluene was added dropwise to a solution of benzyl N-[(1R)-1-[(2S)-5-azido-6-oxo-tetrahydropyran-2-yl]propyl]-N-benzyl-carbamate (0.777 g, 1.84 mmol) in dry DCM (50.0 mL) at −78° C. under N$_2$. After 1 h, acetone (1.0 mL) was added to the reaction mixture dropwise. After 5 min, sat. potassium sodium tartrate (100.0 mL) was added to the solution slowly, followed by the addition of water (100.0 mL). The mixture was allowed to warm to room temperature and vigorously stirred for overnight in the presence of ethyl acetate. The organic layer was separated and the aqueous layer was extracted with ethyl acetate (3×100 mL). The combined organic layers were dried (Na$_2$SO$_4$), filtered and concentrated under reduced pressure to provide the title compound as an oil (diastereomers, 0.75 g, 96%). This mixture was used in the next step without further purification LCMS m/z: ES$^+$ [M+Na]$^+$: 447.91; (B05) retention time=2.10 m.

Step 8

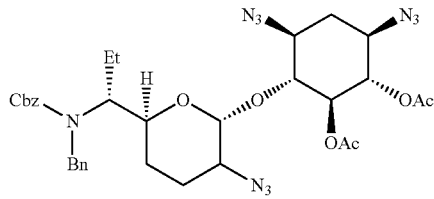 [SMILES: CC[C@H]([C@@H]1CCC(N=[N+]=[N-])[C@@H](O[C@H]2[C@H](OC(C)=O)[C@@H](OC(C)=O)[C@H](N=[N+]=[N-])C[C@@H]2N=[N+]=[N-])O1)N(Cc1ccccc1)C(=O)OCc1ccccc1]

(1S,2S,3R,4S,6R)-4,6-diazido-3-(((2R,6S)-3-azido-6-((R)-1-(benzyl((benzyloxy)carbonyl)amino)propyl)tetrahydro-2H-pyran-2-yl)oxy)cyclohexane-1,2-diyl diacetate CCl$_3$CN (0.877 mL, 8.75 mmol) was added dropwise to a suspension of benzyl ((1R)-1-((2S)-5-azido-6-hydroxytetrahydro-2H-pyran-2-yl)propyl)(benzyl)carbamate (0.767 g, 5.25 mmol) and K$_2$CO$_3$ (0.726 g, 5.25 mmol) in dry DCM (30.0 mL) at ambient temperature under N$_2$. After 12 h, the solution was filtered through Celite and the filtrate was concentrated by high-vacuum. To the crude was added [(1S,2S,3R,4S,6R)-2-acetoxy-4,6-diazido-3-hydroxy -cyclohexyl]acetate (0.418 g, 1.40 mmol) and ground 4 Å sieves (1.0 g) and the mixture was dissolved in dry DCM (30.0 mL). The suspension was stirred at ambient temperature for 25 min. The solution was cooled to 0° C. and BF$_3$·OEt$_2$ (0.864 mL, 7.0 mmol) was added dropwise with vigorous stirring. The solution was warmed to ambient temperature and stirred for another 3 hours. The reaction was quenched with sat. NaHCO$_3$ (50.0 mL). The mixture was successively extracted with DCM (3×50 mL) and the combined organic layer were dried (Na$_2$SO$_4$), filtered and concentrated under reduced pressure. The crude was purified by silica gel chromatography (40 g cartridge) with EtOAc and hexanes (0-30%) to produce the title compound as an oil (2 diastereomers, 0.64 g, 65%). LCMS m/z: [M+Na]$^+$: 727.60; (B05) retention time=2.37 m.

Step 9

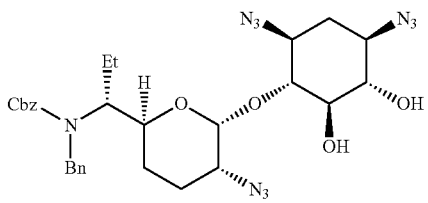 [SMILES: CC[C@H]([C@@H]1CC[C@@H](N=[N+]=[N-])[C@@H](O[C@H]2[C@H](O)[C@@H](O)[C@H](N=[N+]=[N-])C[C@@H]2N=[N+]=[N-])O1)N(Cc1ccccc1)C(=O)OCc1ccccc1]

Benzyl((R)-1-((2S,5R,6R)-5-azido-6-(((1R,2R,3S,4R,6S)-4,6-diazido-2,3-dihydroxycyclohexyl)oxy)tetrahydro-2H-pyran-2-yl)propyl)(benzyl)carbamate NaOMe (4.62 M, 1.14 mL, 5.30 mmol) was added dropwise to a solution of (1S,2S,3R,4S,6R)-4,6-diazido-3-(((2R,6S)-3-azido-6-((R)-1-(benzyl((benzyloxy)carbonyl)amino)propyl)tetrahydro-2H-pyran-2-yl)oxy)cyclohexane-1,2-diyl diacetate (0.622 g, 0.883 mmol) in MeOH (30.0 mL) at room temperature. After 60 min, AcOH (0.404 mL, 7.06 mmol) was added to the reaction. Water (30.0 mL) was added and the mixture was extracted with DCM (3×50 mL). The organic layers were combined, dried over $Na_2SO_4$ and then concentrated under reduced pressure to provide a mixture of two diastereomers (0.450 g). The diastereoisomers were separated on Yamazen purification system using hexane and EtOAc to provide the title desired diastereoisomer (105 mg, 19%) as a solid. $ES^+$ $[M+H]^+$: 621.15.

Step 10

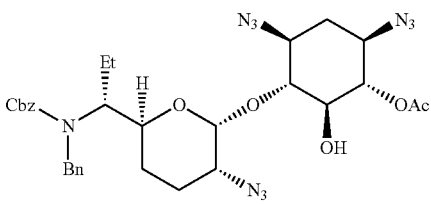 [SMILES: CC[C@H]([C@@H]1CC[C@@H](N=[N+]=[N-])[C@@H](O[C@H]2[C@H](O)[C@@H](OC(C)=O)[C@H](N=[N+]=[N-])C[C@@H]2N=[N+]=[N-])O1)N(Cc1ccccc1)C(=O)OCc1ccccc1]

(1S,2S,3R,4S,6R)-4,6-diazido-3-(((2R,3R,6S)-3-azido-6-((R)-1-(benzyl((benzyloxy)carbonyl)amino)propyl)tetrahydro-2H-pyran-2-yl)oxy)-2-hydroxycyclohexyl acetate $Ac_2O$ (14.4 µL, 152 µmol) was added to a solution of benzyl ((R)-1-((2S,5R,6R) -5-azido-6-(((1R,2R,3S,4R,6S)-4,6-diazido-2,3-dihydroxycyclohexyl)oxy)tetrahydro-2H-pyran-2-yl)propyl)(benzyl)carbamate (21.0 mg, 33.8 µmol) and pyridine (16.4 µL, 203 µmol) in dry DCM (2.0 mL) at ambient temperature. After 48 h, all volatiles were removed under reduced pressure. The crude was purified by silica gel chromatography (4 g cartridge) with EtOAc and hexanes (5-20%) to produce the title compound as an oil (16.0 mg, 71%). LCMS m/z: $ES^+$ $[M+Na]^+$: 685.17; (B05) retention time=2.31 m.

Step 11

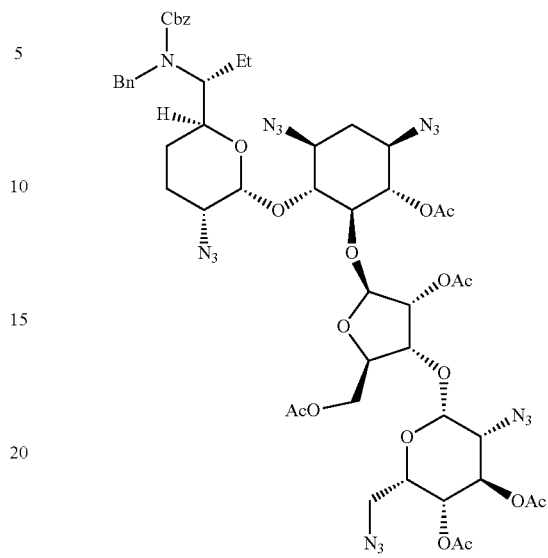

((2R,3S,4R,5S)-3-(((2R,3R,4R,5S,6S)-3-Azido-6-(azidomethyl)-4,5-dihydroxytetrahydro-2H -pyran-2-yl)oxy)-5-(((1R,2R,3S,5R,6S)-3,5-diazido-2-(((2R,3R,6S)-3-azido-6-((R)-1-(benzyl((benzyloxy)carbonyl)amino)propyl)tetrahydro-2H-pyran-2-yl)oxy)-6-hydroxycyclohexyl)oxy)-4-hydroxytetrahy drofuran-2-yl)methyl acetate $CCl_3CN$ (70.4 µL, 702 µmol) was added dropwise to a mixture of [(2R,3R,4R)-4 -acetoxy-3-[(2R,3R,4R,5R,6S)-4,5-diacetoxy-3-azido-6-(azidomethyl)tetrahydropyran-2-yl] oxy -5-hydroxy-tetrahydrofuran-2-yl]methyl acetate (74.4 mg, 0.140 mmol) and $K_2CO_3$ (58.2 mg, 0.421 mmol) in dry DCM (8.0 mL) at room temperature under Na. The mixture was stirred at room temperature for 18 h, then filtered through Celite and rinsed with DCM. The filtrate was concentrated under reduced pressure. The crude was dissolved in DCM (8 mL) and added to (1S,2S,3R,4S,6R)-4,6-diazido-3-(((2R,3R,6S)-3-azido-6-((R)-1-(benzyl((benzyloxy)carbonyl)amino)propyl)tetrahydro-2H-pyran-2-yl) oxy)-2-hydroxycyclohexyl acetate. 4 Å molecular sieves (200 mg) were added and the mixture was cooled to −78° C., then $BF_3 \cdot OEt_2$ (28.9 µL, 234 µmol) was added dropwise. The mixture was stirred at room temperature for 5 h, then a saturated aqueous solution of $NaHCO_3$ (15 mL) was added. The separated aqueous layer was extracted with DCM (3×20 mL). The combined organic layer was washed with brine, dried over $Na_2SO_4$ and concentrated under reduced pressure. The residue was purified by silica gel chromatography (25 g) using hexane and ethyl acetate (0-30%) to provide the title compound (35.0 mg, 64%) as a an oil. LCMS m/z $ES^+$ $[M+H]^+$: 1175.29, LCMS (B05) retention time=2.46 m.

Step 12

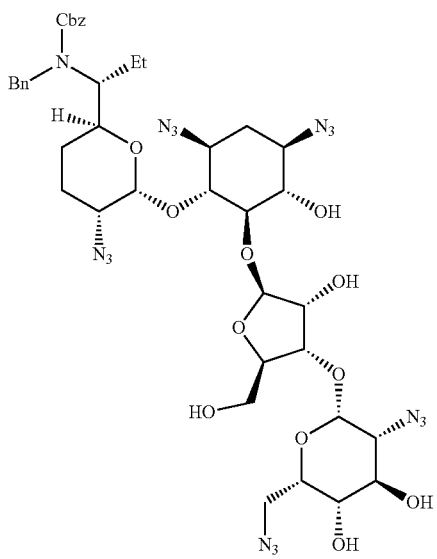 [SMILES: CC[C@H]([C@@H]1CC[C@@H](N=[N+]=[N-])[C@@H](O[C@H]2[C@H](O[C@@H]3O[C@H](CO)[C@@H](O[C@H]4O[C@@H](CN=[N+]=[N-])[C@@H](O)[C@H](O)[C@H]4N=[N+]=[N-])[C@H]3O)[C@@H](O)[C@H](N=[N+]=[N-])C[C@@H]2N=[N+]=[N-])O1)N(Cc1ccccc1)C(=O)OCc1ccccc1]

Benzyl ((R)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)propyl)(benzyl)carbamate NaOMe (25 wt %, 106 μL, 368 μmol) was added dropwise to a solution of compound ((2R,3S,4R,5S)-3-(((2R,3R,4R,5S,6S)-3-Azido-6-(azidomethyl)-4,5-dihydroxytetrahydro-2H-pyran-2-yl)oxy)-5-(((1R,2R,3S,5R,6S)-3,5-diazido-2-(((2R,3R,6S)-3-azido-6-((R)-1-(benzyl((benzyloxy)carbonyl)amino)propyl)tetrahydro-2H-pyran-2-yl)oxy)-6-hydroxycyclohexyl)oxy)-4-hydroxytetrahydrofuran-2-yl)methyl acetate (36.0 mg, 306 μmol) in MeOH (3.0 mL) at ambient temperature. After 1 hour, the reaction mixture was neutralized by HOAc (~35 μL) and all volatiles were removed under reduced pressure. The crude was dissolved with EtOAc, filtered and the filtrate was concentrated under reduced pressure to produce the title compound as an oil (29.6 mg, 100%). LCMS m/z: ES+ [M+Na]+: 987.19, (B05) retention time=2.19 m.

Step 13

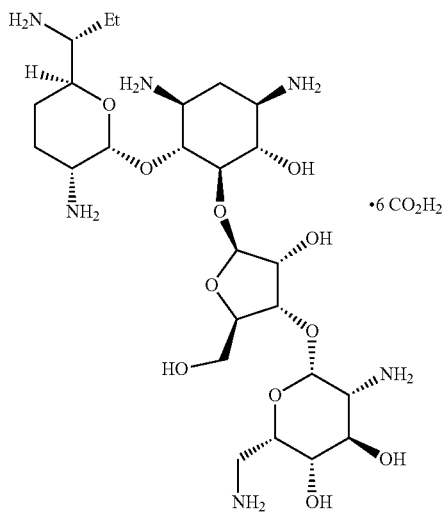 [SMILES: CC[C@@H](N)[C@@H]1CC[C@@H](N)[C@@H](O[C@H]2[C@H](O[C@@H]3O[C@H](CO)[C@@H](O[C@H]4O[C@@H](CN)[C@@H](O)[C@H](O)[C@H]4N)[C@H]3O)[C@@H](O)[C@H](N)C[C@@H]2N)O1]

(2S,3S,4R,5R,6R)-5-Amino-2-(aminomethyl)-6-(((2R,3S,4R,5S)-5-(((1R,2R,3S,5R,6S)-3,5-diamino-2-(((2R,3R,6S)-3-amino-6-((R)-1-aminopropyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol hexaformate In a 2 neck flask equipped with a reflux condenser were added benzyl ((R)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)propyl)(benzyl)carbamate (27 mg, 0.03 mmol) and Pd/C (10% dry on carbon, 8.9 mg, 0.01 mmol) following by anhydrous MeOH (4 mL). Nitrogen was bubbled for 5 min, then ammonium formate was added. The mixture was heated at 63° C. for 30 min under $N_2$, then cooled to room temperature with an ice-bath. The mixture was filtered with a filter syringe and concentrated under reduced pressure. The material was purified by prep-HPLC using 5% B in A to 100% B (A: Amfor pH 4, B: ACN) on C18 Xbridge 30×150 mm to provide the title compound (7.9 mg, 46%) as a solid. M+H+: 611.3. $^1$H NMR(400 MHz, $D_2O$) δ 8.58 (s, 6H), 6.03(d, J=3.6 Hz, 1H), 5.55 (d, J=2.6 Hz, 1H), 5.45 (s, 1H), 4.67-4.61 (m, 1H), 4.53 (dd, J=4.8, 2.8 Hz, 1H), 4.47 (t, J=5.1 Hz, 1H), 4.38 (s, 2H), 4.25 (d, J=12.2 Hz, 1H), 4.16 (t, J=9.6 Hz, 1H), 4.10-4.00 (m, 2H), 3.98 (d, J=1.5 Hz, 1H), 3.92-3.80 (m, 2H), 3.74 (s, 1H), 3.72-3.43 (m, 6H), 2.62 (dd, J=8.4, 4.3 Hz, 1H), 2.26-1.94 (m, 4H), 1.91-1.60 (m, 3H), 1.14 (t, J=7.5 Hz, 3H).

Example 26

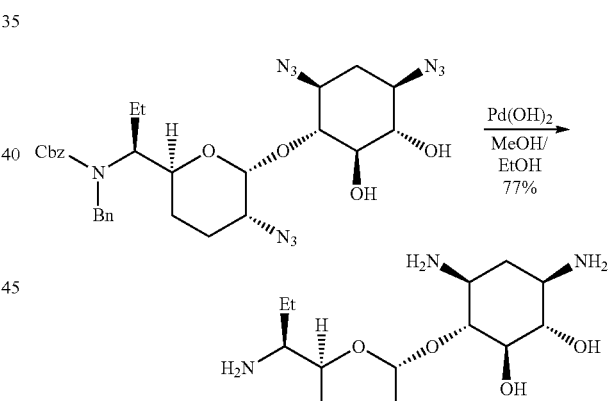

(1S,2R,3R,4S,6R)-4,6-Diamino-3-[(2R,3R,6S)-3-amino-6-[(1S)-1-aminopropyl]tetrahydropyran-2-yl]oxy-cyclohexane-1,2-diol Pd(OH)$_2$/C (20 wt %, 136 mg, 193 μmol) was added to a solution of benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]propyl]-N-benzyl-carbamate (made in Example 24, 30.0 mg, 48.3 μmol) in MeOH (2.50 mL) and EtOH (2.50 mL). $H_2$ was bubbled through the suspension. After 16 h, the solution was filtered through a frit (0.22 μm diameter) and the filtrate was concentrated under reduced pressure to give the desired product as an oil which turn into solid after lyophilization (12.1 mg, 77%). $^1$H NMR (500 MHz, MeOD) δ 5.40 (d, J=3.5 Hz, 1H), 4.14-4.07 (m, 1H), 3.47 (t, J=9.1 Hz, 1H), 3.36 (t, J=9.4 Hz, 1H), 3.23 (t, J=9.5

Hz, 1H), 3.13-3.07 (m, 1H), 3.07-3.00 (m, 1H), 2.97-2.83 (m,2H), 2.17-2.08 (m, 1H), 1.92-1.66 (m, 5H), 1.63-1.50 (m, 2H), 1.06 (t, J=7.5 Hz, 3H).

Example 27

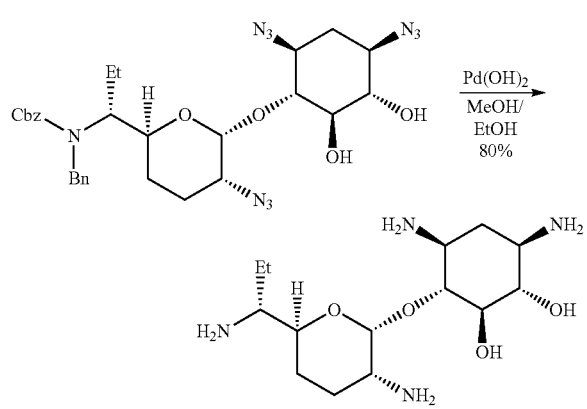

(1S,2R,3R,4S,6R)-4,6-Diamino-3-[(2R,3R,6S)-3-amino-6-[(1R)-1-aminoethyl]tetrahydropyran -2-yl]oxy-cyclohexane-1,2-diol Pd(OH)$_2$/C (20 wt %, 119 mg, 169 μmol) was added to a solution of benzyl N-[(1R) -1-[(2S,5R,6R)-5-azido-6-[(1R, 2R,3S,4R,6S)-4,6-diazido-2,3-dihydroxy -cyclohexoxy]tetrahydropyran-2-yl]propyl]-N-benzyl-carbamate (made in Example 25, 35.0 mg, 56.4 μmol) in MeOH (2.5 mL) and EtOH (2.5 mL). H$_2$ was bubbled through the suspension. After 17 h, the solution was filtered through a frit (0.22 μm diameter) and the filtrate was concentrated under reduced pressure to give the desired product as an oil which turn into solid after lyophilization (14.3 mg, 80%). $^1$H NMR (500 MHz, MeOD) δ 5.23 (d, J=3.5 Hz, 1H), 4.01-3.92 (m, 1H), 3.43 (t, J=9.1 Hz, 1H), 3.27 (t, J=9.3 Hz, 1H), 3.13 (t, J=9.4 Hz, 1H), 2.98-2.80 (m, 3H), 2.79-2.66 (m, 1H), 2.06 (dt, J=12.8, 4.2 Hz, 1H), 1.89-1.45 (m, 7H), 1.04 (t, J=7.5 Hz, 3H).

Example 28

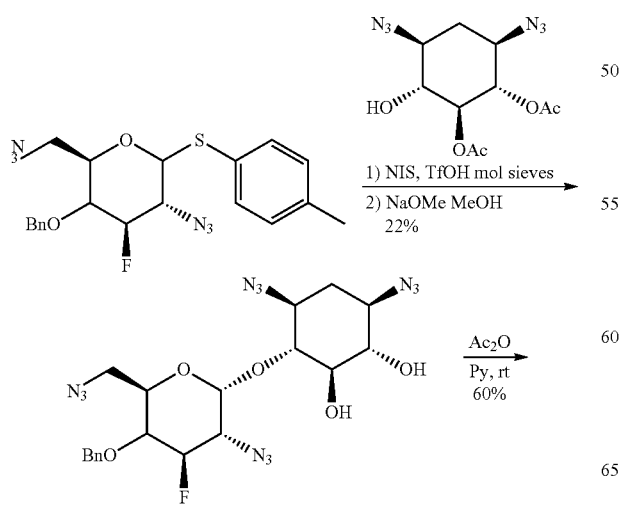

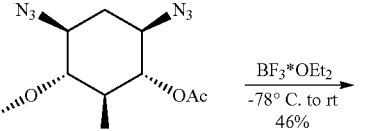

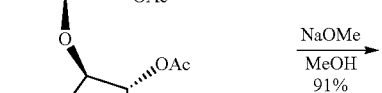

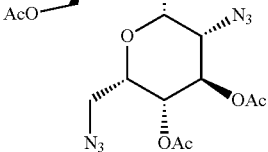

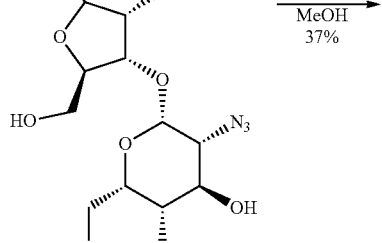

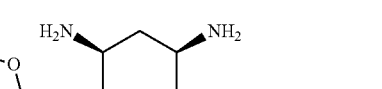

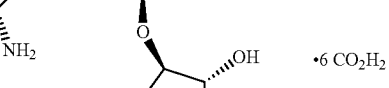

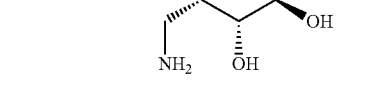

Step 1

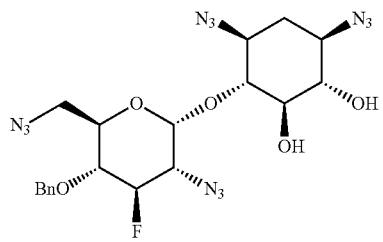 [SMILES: [N-]=[N+]=NC[C@H]1O[C@H](O[C@H]2[C@H](O)[C@@H](O)[C@H](N=[N+]=[N-])C[C@@H]2N=[N+]=[N-])[C@H](N=[N+]=[N-])[C@@H](F)[C@@H]1OCc1ccccc1]

(1S,2R,3R,4S,6R)-4,6-Diazido-3-[(2R,3S,4R,5R,6R)-3-azido-6-(azidomethyl)-5-benzyloxy-4-fluoro-tetrahydropyran-2-yl]oxy-cyclohexane-1,2-diol (2R,3R,4R,5R,6R)-5-azido-2-(azidomethyl)-3-benzyloxy-4-fluoro-6-(p-tolylsulfanyl)tetrahydropyran (preparation below, 385 mg, 0.898 mmol) and [(1S,2S,3R,4S,6R)-2-acetoxy-4,6-diazido-3-hydroxy-cyclohexyl]acetate (255 mg, 0.855 mmol) were coevaporated with dry toluene 3 times and further dried under high vacuum. Anhydrous Et$_2$O (8 mL) and DCM (4 mL) were added followed by preactivated 4 Å molecular sieves. After stirring for 30 min at room temperature, the mixture was cooled to −40° C. NIS (500 mg, 2.22 mmol) was added and the reaction mixture was stirred for 20 min at −40° C. TfOH (0.04 mL, 0.427 mmol) was added, and the reaction was warmed to −20° C. and kept stirring for 30 min. Sodium bisulfite (200 mg), NaHCO$_3$ (200 mg), and water (10 mL) were added at 0° C., and the mixture was stirred for 10 min at room temperature. The reaction mixture was diluted with DCM (50 mL), filtered through a Celite pad, and washed with a saturated solution of aqueous NaHCO$_3$ (60 mL). The aqueous layers were extracted with DCM (50 mL×3), and the combined organic phase was washed with brine, dried over MgSO$_4$, filtered, and concentrated under reduced pressure. The residue was taken up in dry MeOH (25 mL) and NaOMe (4.62 M in MeOH, 0.56 mL, 2.56 mmol) was added. The mixture was stirred at room temperature for 1 h. Water (50 mL) was added. The aqueous layer was extracted with DCM (3×50 mL). The combined organic layer was washed with brine, dried over MgSO$_4$ and concentrated under reduced pressure. The material was purified on silica gel (40 g, dry loading) by MPLC using 0% to 50% EtOAc in hexane to provide the title compound (96 mg, 22% over 2 steps). $^1$H NMR (400 MHz, CDCl$_3$) δ 7.45-7.27 (m, 5H), 5.25-5.18 (m, 1H), 5.10-4.86 (m, 2H), 4.67-4.59 (m, 1H), 4.15-4.08 (m, 1H), 3.90-3.84 (m, 1H), 3.83-3.65 (m, 2H), 3.62-3.53 (m, 1H), 3.52-3.35 (m, 3H), 3.28-3.21 (m, 1H), 2.76 (s, 1H), 2.36-2.24 (m, 1H), 1.25 (t, J=12.0 Hz, 3H).

Step 2

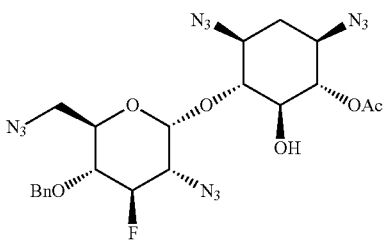 [SMILES: CC(=O)O[C@@H]1[C@@H](O)[C@H](O[C@H]2O[C@H](CN=[N+]=[N-])[C@@H](OCc3ccccc3)[C@H](F)[C@H]2N=[N+]=[N-])[C@@H](N=[N+]=[N-])C[C@H]1N=[N+]=[N-]]

[(1S,2S,3R,4S,6R)-4,6-diazido-3-[(2R,3S,4R,5R,6R)-3-Azido-6-(azidomethyl)-5-benzyloxy-4-fluoro-tetrahydropyran-2-yl]oxy-2-hydroxy-cyclohexyl]acetate Ac$_2$O (9 µL, 95 µmol) was added to a solution of (1S,2R,3R,4S,6R)-4,6-diazido-3-[(2R,3S,4R,5R,6R)-3-azido-6-(azidomethyl)-5-benzyloxy-4-fluoro-tetrahydropyran-2-yl]oxy-cyclohexane-1,2-diol (24 mg, 46 µmol) and pyridine (23 µL, 278 µmol) in dry DCM (0.80 mL) at ambient temperature. After 20 h, all volatiles were removed under reduced pressure. The crude was purified by silica gel chromatography (4 g cartridge) with EtOAc and hexanes (5-20%) to produce the title compound as an oil (21 mg, 81%). $^1$H NMR (500 MHz, CDCl$_3$) δ 7.43-7.28 (m, 5H), 5.25 (t, J=3.7 Hz, 1H), 5.10-4.85 (m, 3H), 4.63 (d, J=11.0 Hz, 1H), 4.14-4.09 (m, 1H), 3.73 (dddd, J=13.3, 11.1, 9.7, 5.7 Hz, 3H), 3.62 (td, J=9.8, 2.4 Hz, 1H), 3.57 (dt, J=13.2, 2.1 Hz, 1H), 3.54-3.44 (m, 2H), 3.38-3.32 (m, 1H), 3.27 (ddd, J=12.2, 10.0, 4.5 Hz, 1H), 2.36 (dt, J=13.3, 4.5 Hz, 1H), 2.17 (s, 3H), 1.58 (dd, J=25.7, 12.5 Hz, 1H).

Step 3

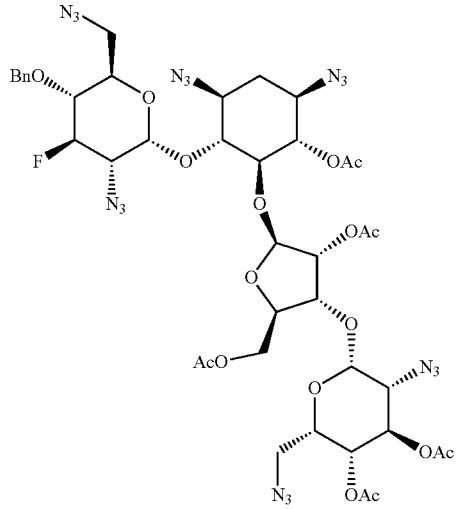 [SMILES: CC(=O)OC[C@H]1O[C@@H](O[C@@H]2[C@@H](OC(C)=O)[C@H](N=[N+]=[N-])C[C@H](N=[N+]=[N-])[C@H]2O[C@H]2O[C@H](CN=[N+]=[N-])[C@@H](OCc3ccccc3)[C@H](F)[C@H]2N=[N+]=[N-])[C@H](OC(C)=O)[C@@H]1O[C@H]1O[C@@H](CN=[N+]=[N-])[C@@H](OC(C)=O)[C@H](OC(C)=O)[C@H]1N=[N+]=[N-]]

[(2R,3R,4R,5S)-4-Acetoxy-5-[(1S,2S,3R,5S,6R)-2-acetoxy-3,5-diazido-6-[(2R,3S,4R,5R,6R)-3-azido-6-(azidomethyl)-5-benzyloxy-4-fluoro-tetrahydropyran-2-yl]oxy-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate CCl$_3$CN (38 µL, 375 µmol) was added dropwise to a suspension of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (40 mg, 75 µmol) and K$_2$CO$_3$ (31 mg, 225 µmol) in dry DCM (1.50 mL) at ambient temperature under N$_2$. After 15 h, the solution was filtered through cotton and the filtrate was concentrated under N$_2$ stream, followed by high-vacuum. To the crude was added [(1S,2S,3R,4S,6R)-4,6-diazido-3-[(2R,3S,4R,5R,6R)-3-Azido-6-(azidomethyl)-5-benzyloxy-4-fluoro-tetrahydropyran-2-yl]oxy-2-hydroxy-cyclohexyl]acetate (21 mg, 38 µmol) in DCM (3.0 mL) and all volatiles were evaporated under N$_2$ stream. To the mixture was added ground 4 Å sieves (500 mg) and the mixture was dissolved in dry DCM (1.0 mL). The suspension was stirred at ambient temperature for 1 h. The solution was cooled to 0° C. and BF$_3$·OEt$_2$ (37 µL, 300 µmol) was added. The reaction mixture was warmed to room temperature, stirred for 30 min followed by the addition of Et$_3$N (80 µL). The crude was filtered through a silica gel pad (0.30 g) with EtOAc (5.0 mL) and all volatiles were removed under reduced pressure. The crude was purified by C18 reversed phase chromatography (40 g cartridge) with ACN and 0.1% aq. formic acid (50-100%) to produce the title compound as a solid (20 mg, 60%). LCMS m/z: ES+ [M+NH4]+: 1090.32; (A50) retention time=2.03 m.

Step 4

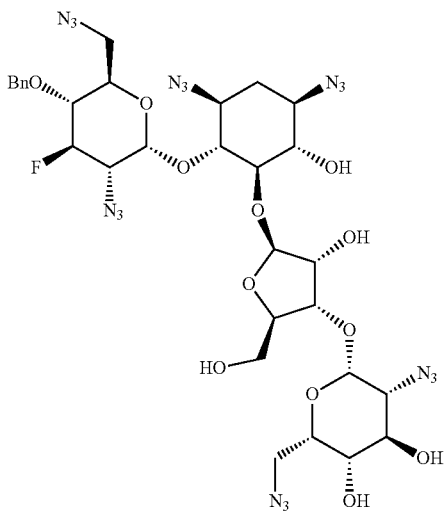 [SMILES: [N-]=[N+]=NC[C@@H]1O[C@H](O[C@H]2[C@@H](O)[C@H](O[C@@H]3[C@@H](O)[C@H](N=[N+]=[N-])C[C@H](N=[N+]=[N-])[C@H]3O[C@H]3O[C@H](CN=[N+]=[N-])[C@@H](OCc4ccccc4)[C@H](F)[C@H]3N=[N+]=[N-])O[C@@H]2CO)[C@H](N=[N+]=[N-])[C@@H](O)[C@@H]1O]

(2S,3S,4R,5R,6R)-5-Azido-2-(azidomethyl)-6-[(2R,3S,4R, 5S)-5-[(1R,2R,3S,5R,6S)-3,5-diazido -2-[(2R,3S,4R, 5R,6R)-3-azido-6-(azidomethyl)-5-benzyloxy-4-fluoro-tetrahydropyran-2-yl]oxy -6-hydroxy-cyclohexoxy]-4-hydroxy-2-(hydroxymethyl)tetrahydrofuran-3-yl]oxy-tetrahydropyran-3,4-diol NaOMe (25 wt %, 45 µL, 157 µmol) was added dropwise to a solution of [(2R,3R,4R,5S)-4-acetoxy-5-[(1S,2S,3R,5S, 6R)-2-acetoxy-3,5-diazido-6-[(2R,3S,4R,5R,6R)-3-azido-6-(azidomethyl)-5-benzyloxy-4-fluoro-tetrahydropyran-2-yl]oxy-cyclohexoxy]-3 -[(2R,3R,4R,5R,6S)-4,5-diacetoxy-3-azido-6-(azidomethyl)tetrahydropyran-2-yl]oxy - tetrahydrofuran-2-yl]methyl acetate (14 mg, 13 µmol) in MeOH (0.80 mL) at ambient temperature. After 50 min, HOAc (15 µL) was added and all volatiles were removed under reduced pressure. The crude was filtered through a silica gel pad (0.20 g) with EtOAc (6.0 mL) and the filtrate was concentrated under reduced pressure. The crude solid was washed with hexanes (3×1.0 mL) and the supernatant was decanted to produce the title compound as a solid (10 mg, 89%). 1H NMR (400 MHz, cdcl3) δ 7.41-7.29 (m, 5H), 5.70 (t, J=3.5 Hz, 1H), 5.37 (d, J=3.1 Hz, 1H), 5.11 (s, 1H), 5.10-4.93 (m, 1H), 4.91 (d, J=11.2 Hz, 1H), 4.63 (d, J=11.2 Hz, 1H), 4.45 (t, J=5.1 Hz, 1H), 4.29-4.17 (m, 3H), 4.11 (t, J=3.4 Hz, 1H), 4.05 (ddd, J=8.9, 3.7, 1.7 Hz, 1H), 3.94-3.76 (m, 3H), 3.76-3.52 (m, 6H), 3.50-3.32 (m, 7H), 3.13-3.00 (m, 2H), 2.28 (dt, J=13.1, 4.2 Hz, 1H), 1.75 (s, 1H), 1.47 (q, J=12.8 Hz, 1H). LCMS m/z: ES+ [M+NH4]+: 880.37; (A05) retention time=2.54 m.

Step 5

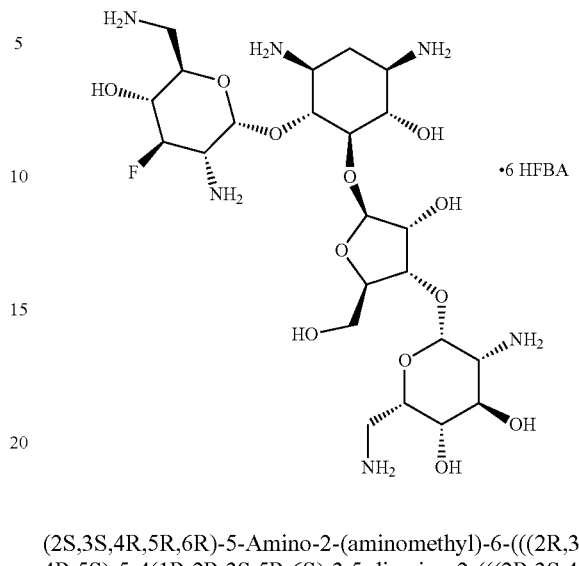

(2S,3S,4R,5R,6R)-5-Amino-2-(aminomethyl)-6-(((2R,3S, 4R,5S)-5-4(1R,2R,3S,5R,6S)-3,5-diamino-2-(((2R,3S,4R, 5R,6R)-3-amino-6-(aminomethyl)-4-fluoro-5-hydroxytetrahydro-2H -pyran-2-yl)oxy)-6-hydroxycyclohexyl)oxy)-4-hydroxy-2-(hydroxymethyl)tetrahydrofuran-3-yl)oxy) tetrahydro-2H-pyran-3,4-diol hexakis(2,2,3,3,4,4,4-heptafluorobutanoate)

Pd(OH)2/C (10 wt %, 60 mg, 43 µmol) was added to a solution of (2S,3S,4R,5R,6R) -5-azido-2-(azidomethyl)-6-[(2R,3S,4R,5S)-5-[(1R,2R,3S,5R,6S)-3,5-diazido-2-[(2R, 3S,4R,5R,6R)-3-azido-6-(azidomethyl)-5-benzyloxy-4-fluoro-tetrahydropyran-2-yl]oxy-6-hydroxy-cyclohexoxy]-4-hydroxy-2-(hydroxymethyl)tetrahydrofuran-3-yl]oxy-tetrahydropyran -3,4-diol (20 mg, 23 µmol) in MeOH/AcOH (2:1, 3.0 mL) under N2 at ambient temperature in a test tube. The tube was then placed in a hydrogenation bottle and kept agitated for 42 h under H2 (50 psi). The material was filtered through a frit (0.55 µm diameter) and the filtrate was concentrated under reduced pressure. The compound was purified by a HFBA-Coupled prep -HPLC to provide the title compound as a solid (hexa-HFBA salt, 2.2 mg, 5%). 1H NMR (500 MHz, MeOD) δ 6.11 (s, 1H), 5.47 (s, 1H), 5.31 (s, 1H), 4.52 (t, J=5.9 Hz, 1H), 4.38-4.18 (m, 4H), 4.14 (s, 1H), 4.00 (s, 1H), 3.93-3.84 (m, 2H), 3.81-3.56 (m, 6H), 3.56-3.41 (m, 5H), 3.19-3.09 (m, 2H), 2.50-2.37 (m, 1H), 2.22-1.98 (m, 2H).

Preparation of (2R,3R,4R,5R,6R)-5-azido-2-(azidomethyl)-3-benzyloxy-4-fluoro-6-(p -tolylsulfanyl)tetrahydropyran

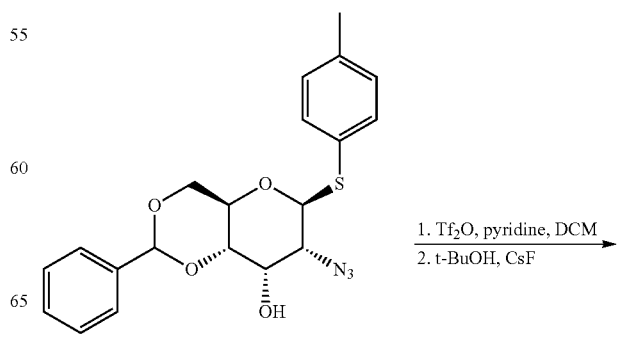

Step 1
(4aR,6S,7R,8R,8aR)-7-azido-8-fluoro-2-phenyl-6-(p-tolyl-thio)hexahydropyrano[3,2-d][1,3]dioxine

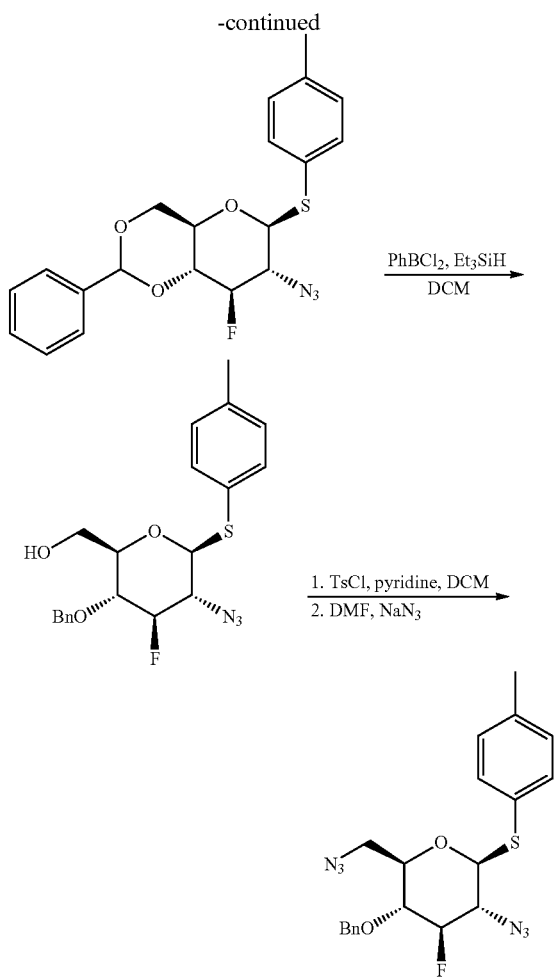

To a solution of 3.1 g of (4aR,6S,7R,8S,8aS)-7-azido-2-phenyl-6-(p-tolylthio) hexahydropyrano[3,2-d][1,3]dioxin-8-ol in 30 mL of anhydrous DCM was added 6.3 mL of pyridine and the mixture was cooled to 0° C. To this solution, 6.6 mL of triflic anhydride was added slowly and the reaction was stirred for 1 hour at the same temperature. After completion, the organic layer was diluted with DCM and washed with 1N HCl and saturated NaHCO₃. The organic layer was dried over anhydrous sodium sulfate and concentrated. The obtained crude was dissolved in 20 mL of tBuOH and 3.53 g of CsF was added and the reaction stirred at 50° C. until completion. The organic layer was diluted with EtOAc and washed with saturated NaHCO₃ and brine, then dried, filtered and concentrated. The crude was purified by flash chromatography to obtain 1.1 g of (4aR,6S,7R,8R,8aR)-7-azido-8-fluoro-2-phenyl-6-(p-tolylthio)hexahydropyrano[3,2-d][1,3]dioxine (35% yield).

Step 2
((2R,3R,4R,5R,6S)-5-azido-3-(benzyloxy)-4-fluoro-6-(p-tolylthio)tetrahydro-2H-pyran-2-yl)methanol


To the solution of 100 mg of (4aR,6S,7R,8R,8aR)-7-azido-8-fluoro-2-phenyl-6-(p-tolylthio) hexahydropyrano[3,2-d][1,3]dioxine in 5 mL of anhydrous dichloromethane was added 4 A MS and the mixture was stirred for 30 min at room temperature. The solution was cooled to −78° C. and 100 μL of triethyl silane and 84 μL of PhBCl₂ added successively and stirred at the same temperature until completion (20 min). The reaction was quenched methanol (0.2 mL) and triethyl amine (0.2 mL). The reaction was diluted with DCM and filtered. The filtrate was washed with aqueous sodium bicarbonate and the organic layer was dried, filtered and concentrated. The crude residue was purified by flash column chromatography (30% EtOAc in Hexanes) to afford 87 mg of ((2R,3R,4R,5R,6S)-5-azido-3-(benzyloxy)-4-fluoro-6-(p-tolylthio)tetrahydro-2H-pyran-2-yl)methanol (90% yield).

Step 3
(2S,3R,4R,5R,6R)-3-azido-6-(azidomethyl)-5-(benzyloxy)-4-fluoro-2-(p-tolylthio)tetrahydro-2H-pyran


To a solution of 850 mg of ((2R,3R,4R,5R,6S)-5-azido-3-(benzyloxy)-4-fluoro-6-(p-tolylthio) tetrahydro-2H-pyran-2-yl)methanol in anhydrous DCM was added 1.7 mL of Pyridine and 800 mg of tosyl chloride was added at 0° C. The reaction was stirred at the same temperature until completion (3 h). The reaction was diluted with 100 mL of DCM and washed with 1N HCl and aq NaHCO₃, then dried, filtered and concentrated. The crude was dissolved in 10 mL of anhydrous DMF and 750 mg of sodium azide was added. The reaction was stirred at 70° C. until completion. DMF was evaporated and the crude was dissolved in EtOAc and washed with water. The organic layer was dried with MgSO₄, filtered, concentrated and purified by flash chromatography to afford 700 mg of (2S,3R,4R,5R,6R)-3-azido-6-(azidomethyl)-5-(benzyloxy) -4-fluoro-2-(p-tolylthio)tetrahydro-2H-pyran (83% yield).

Example 29

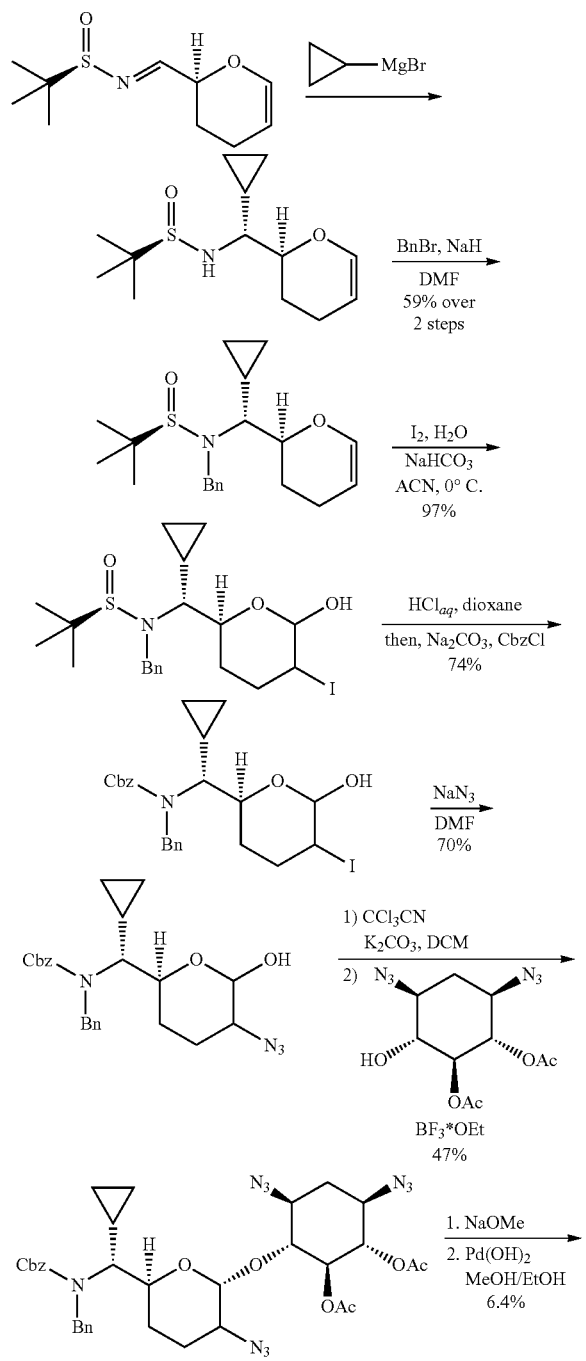

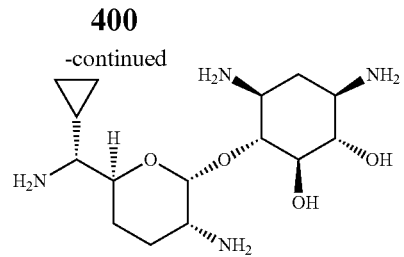

Step 1

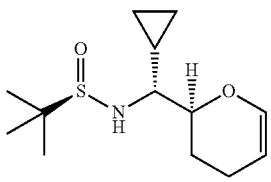 [SMILES: CC(C)(C)[S@@](=O)N[C@H](C1CC1)[C@@H]1CCC=CO1]

(R)-N-[(R)-Cyclopropyl-[(2S)-3,4-dihydro-2H-pyran-2-yl]methyl]-2-methyl-propane-2-sulfinamide Cyclopropyl MgBr (0.5 M in THF, 9.28 mL, 4.64 mmol) was added to a solution of (NE)-N-[[(2S)-3,4-dihydro-2H-pyran-2-yl]methylene]-2-methyl-propane-2-sulfinamide (500 mg, 2.32 mmol) in dry THF (15.0 mL) at −78° C. under Na. After 1 h, the reaction was stirred at −40 ° C. for 1 h and then warmed to room temperature within 1 h. After 1 h, the reaction was cooled to 0° C. and sat. NH₄Cl (20.0 mL) was added dropwise (nota bene: gas evolution). The mixture was extracted with DCM (3×15.0 mL). The combined organic layers were dried (Na₂SO₄), filtered and concentrated under reduced pressure to provide the title compound as a liquid. The ¹H NMR for crude was clean and used in the next step without further purification. ¹H NMR (400 MHz, CDCl₃) δ 6.37 (d, J=5.8 Hz, 1H), 4.68 (t, J=4.9 Hz, 1H), 4.13-3.95 (m, 1H), 3.89-3.67 (m, 1H), 2.79-2.63 (m, 1H), 2.24-1.85 (m, 4H), 1.22 (s, 9H), 0.93-0.79 (m, 1H), 0.69-0.51 (m, 2H), 0.42-0.28 (m, 1H), 0.34-0.19 (m, 1H). LCMS m/z ES⁺ [M+H]: 258.19, LCMS (B05) retention time=1.7 m.

Step 2

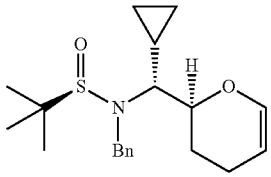 [SMILES: CC(C)(C)[S@@](=O)N(Cc1ccccc1)[C@H](C1CC1)[C@@H]1CCC=CO1]

(R)-N-Benzyl-N-[(R)-cyclopropyl(3,4-dihydro-2H-pyran-2-yl)methyl]-2-methyl-propane-2-sulfinamide A mixture of (R)-N-[(R)-cyclopropyl(3,4-dihydro-2H-pyran-2-yl)methyl]-2-methyl -propane-2-sulfinamide (0.598 g, 2.32 mmol), bromomethylbenzene (0.596 g, 3.48 mmol) in DMF (10 mL) was stirred at 0° C. NaH (92.8 mg, 2.32 mmol) was then added to the reaction mixture portionwise. The mixture was allowed to stir at room temperature for 24 h. The reaction was quenched with water and the mixture was extract with EtOAc (3×15 mL). The organic layers were combined, dried over sodium sulfate and concentrated under reduced pressure. The residue was purified on silica gel (24 g) using hexane and ethyl acetate (70/30) as eluent to give the title product as a colorless oil (473 mg, 59%). LCMS m/z ES⁺[M+H]⁺: 348.20, LCMS (B05) retention time=2.17m.

Major isomer: ¹H NMR (500 MHz, CDCl₃) δ 7.46-7.20 (m, 5H), 6.47(d, J=5.5 Hz, 1H), 4.73 (t, J=5.6 Hz, 1H), 4.59 (d, J=15.0 Hz, 1H), 4.37 (d, J=14.9 Hz, 1H), 4.04 (d, J=10.7 Hz, 1H), 2.58 (d, J=8.2 Hz, 1H), 2.14-2.02 (m, 1H), 1.96-1.93 (m, 2H), 1.72 (dd, J=12.6, 5.7 Hz, 1H), 1.33-1.20 (m, 1H), 1.12 (s, 9H), 0.71 (ddd, J=14.9, 8.1, 4.3 Hz, 1H), 0.64-0.51 (m, 1H), 0.37-0.25 (m, 1H).

Step 3

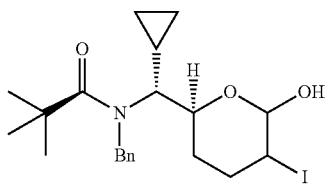

(R)-N-Benzyl-N-[(R)-cyclopropyl-[(2S)-6-hydroxy-5-iodo-tetrahydropyran-2-yl]methyl]-2-methyl-propane-2-sulfinamide Iodine (1.79 g, 7.07 mmol) was added portionwise to a suspension of (R)-N-benzyl -N-[(R)-cyclopropyl-[(2S)-3,4-dihydro-2H-pyran-2-yl]methyl]-2-methyl-propane-2-sulfinamide (2.46 g, 7.07 mmol) and NaHCO₃ (1.78 g, 21.2 mmol) in ACN (43 mL) and H₂O (43 mL) at 0° C. The mixture was stirred at 0° C. for 15 min. Then, the mixture was stirred at room temperature for 15 min. After completion, a saturated aqueous solution of Na₂S₂O₃ (100 mL) was added. The aqueous layer was extracted with EtOAc (3×100 mL). The combined organic layer was dried over Na₂SO₄, filtered and concentrated under reduced pressure to provide the title compound (3.40 g, 97%) as a yellow solid. The crude was used in the next step without further purification. LCMS m/z ES⁺ [M+H]⁺: 514.50, LCMS (B05) retention time=1.98 and 2.07 m.

Step 4

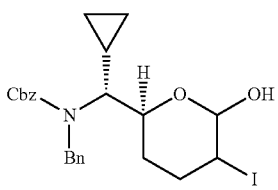 [SMILES: O=C(OCc1ccccc1)N(Cc1ccccc1)[C@H](C1CC1)[C@@H]1CCC(I)C(O)O1]

Benzyl N-benzyl-N-[(R)-cyclopropyl-[(2S)-6-hydroxy-5-iodo-tetrahydropyran-2-yl]methyl]carbamate Aqueous HCl (1.0 M, 43.6 mL, 43.6 mmol) was dropwise added to a solution of (R) -N-[(R)-[(2S)-5-azido-6-hydroxy-tetrahydropyran-2-yl]-cyclopropyl-methyl]-N-benzyl-2-methyl -propane-2-sulfinamide (3.56 g, 7.24 mmol) in dioxane (100.0 mL) with vigorous stirring. After 1 h, solid Na₂CO₃ (6.14 g, 57.9 mmol) was added. After another 10 min, CbzCl (1.74 mL, 12.2 mmol) was added dropwise. After another 30-45 min, dioxane was evaporated and the residue was partitioned in between EtOAc (100 mL) and H₂O (100 mL). The organic phase was dried over Na₂SO₄, filtered and concentrated under reduced pressure. The crude was purified by silica gel chromatography (80 g cartridge) with EtOAc and hexanes (0-35%) to produce the title compound (mixture of 4 diastereomers) as an oil (2.78 g, 74%). LCMS m/z: ES⁺ [M+Na]⁺: 544.01; (B05) retention time=2.15, 2.16, and 2.21 m.

Step 5

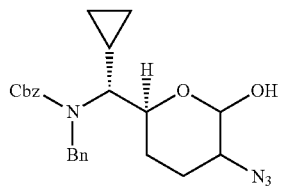 [SMILES: [N-]=[N+]=NC1CC[C@@H]([C@@H](C2CC2)N(Cc2ccccc2)C(=O)OCc2ccccc2)OC1O]

Benzyl N-[(R)-[(2S)-5-azido-6-hydroxy-tetrahydropyran-2-yl]-cyclopropyl-methyl]-N-benzyl -carbamate NaN₃ (1.04 g, 16.0 mmol) and K₂CO₃ (2.21 g, 16.0 mmol) was added to a solution of benzyl N-benzyl-N-[(R)-cyclopropyl-[(2S)-6-hydroxy-5-iodo-tetrahydropyran-2-yl] methyl]carbamate (2.78 g, 5.33 mmol) in dry DMF (30.0 mL) under N₂ at ambient temperature. After 4 h, the reaction was quenched with water (100.0 mL) and extracted with EtOAc (3×100.0 mL). The organic layer was dried over Na₂SO₄, filtered and concentrated under reduced pressure. The crude was purified by silica gel chromatography (120 g cartridge) with EtOAc and hexanes (0-30%) to produce the title compound (diastereomers) as an oil (1.63 g, 70%). ES⁺ [M+Na]⁺: 459.01; (B05) retention time=2.11 and 2.17 m.

Step 6

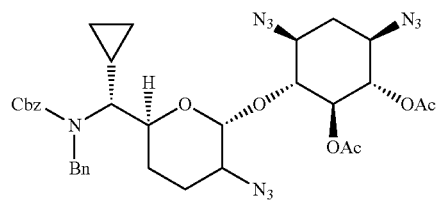 [SMILES: CC(=O)O[C@@H]1[C@@H](OC(C)=O)[C@H](N=[N+]=[N-])C[C@H](N=[N+]=[N-])[C@H]1O[C@H]1O[C@H]([C@@H](C2CC2)N(Cc2ccccc2)C(=O)OCc2ccccc2)CCC1N=[N+]=[N-]]

[(1S,2S,3R,4S,6R)-2-Acetoxy-4,6-diazido-3-[(2R,3R,6S)-3-azido-6-[(R) -[benzyl(benzyloxycarbonyl)amino]-cyclopropyl-methyl]tetrahydropyran-2-yl]oxy-cyclohexyl]acetate CCl₃CN (0.940 mL, 9.38 mmol) was added dropwise to a suspension of benzyl N -[(R)-[(2S)-5-azido-6-hydroxy-tetrahydropyran-2-yl]-cyclopropyl-methyl]-N-benzyl-carbamate (0.845 g, 1.94 mmol) and K₂CO₃ (0.777 g, 5.63 mmol) in dry DCM (30.0 mL) at ambient temperature under N₂. After 12 h, the solution was filtered through Celite and the filtrate was concentrated by high-vacuum. To the crude was added [(1S,2S,3R,4S,6R)-2-acetoxy-4,6 -diazido-3-hydroxy-cyclohexyl]acetate (0.447 mg, 1.50 mmol) and ground 4 Å sieves (1.0 g) and the mixture was dissolved in dry DCM (30.0 mL). The suspension was stirred at ambient temperature for 30 min. The solution was cooled to 0° C. and BF₃·OEt₂ (0.926 mL, 7.50 mmol) was added dropwise with vigorous stirring. The solution was warmed to ambient temperature and stirred for another 2 hours. The reaction was quenched with sat. NaHCO₃ (50.0 mL). The mixture was successively extracted with DCM (3×50 mL) and the combined organic layer were dried (Na₂SO₄), filtered and concentrated under reduced pressure. The crude was purified by silica gel chromatography (80 g cartridge) with EtOAc and hexanes (5-30%) to produce the title compound as an oil (2 diastereomers, 0.510 g, 47%). LCMS m/z: [M+Na]⁺: 739.19; (B05) retention time=2.39 m.

Step 7

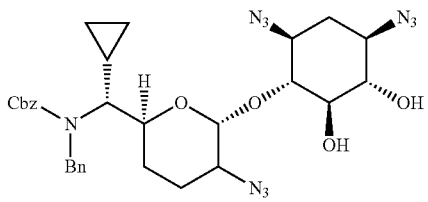

Benzyl N-[(R)-[(2S,5R,6R)-5-azido-6-[(1R,2R,3S,4R,6S)-4,6-diazido-2,3-dihydroxy -cyclohexoxy]tetrahydropyran-2-yl]-cyclopropyl-methyl]-N-benzyl-carbamate NaOMe (4.62 M, 281.0 μL, 1.29 mmol) was added dropwise to a solution of [(1S,2S,3R,4S,6R)-2-acetoxy-4,6-diazido-3-[(2R,6S)-3-azido-6-[(R) -[benzyl(benzyloxycarbonyl)amino]-cyclopropyl-methyl]tetrahydropyran-2-yl]oxy-cyclohexyl]acetate (155 mg, 0.216 mmol) in MeOH (10.0 mL) at room temperature. After 60 min, AcOH (98.9 μL, 1.73 mmol) was added to the reaction and the mixture was concentrated under reduced pressure to provide a mixture of two diastereomers. ES+ [M+Na]+: 655.09; (B05) retention time=2.23 m. The mixture was purified by SFC. The ratio by SFC was found to be 1:7 in favor of the undesired isomer. Retention time of the undesired compound is 4.69 min. Retention time of the desired compound is 7.48. 10 mg (7.3%) of the desired compound was isolated by SFC. 65 mg of the undesired compound was isolated by SFC.

Step 8

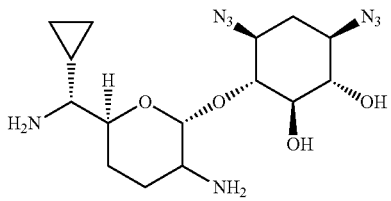 [SMILES: [N-]=[N+]=N[C@H]1C[C@@H](N=[N+]=[N-])[C@H](O)[C@@H](O)[C@@H]1O[C@H]1O[C@H]([C@H](N)C2CC2)CCC1N]

(1S,2R,3R,4S ,6R)-4,6-diamino-3-(((2R,3R,6S)-3-amino-6-((R) -amino(cyclopropyl)methyl)tetrahydro-2H-pyran-2-yl)oxy)cyclohexane-1,2-diol Pd(OH)$_2$/C (20 wt %, 102 mg, 145 μmol) was added to a solution of benzyl N-[(R) -[(2S,5S,6R)-5-azido-6-[(1R,2R,3S,4R,6S)-4,6-diazido-2,3-dihydroxy -cyclohexoxy]tetrahydropyran-2-yl]-cyclopropyl-methyl]-N-benzyl-carbamate (23.0 mg, 36.4 μmol) in MeOH (2.0 mL) and EtOH (2.0 mL). H$_2$ was bubbled through the suspension. After 24 h, the solution was filtered through a frit (0.22 μm diameter) and the filtrate was concentrated under reduced pressure to give the desired product as an oil which turn into solid after lyophilization (10.5 mg, 87%). $^1$-H NMR (500 MHz, MeOD) δ 5.33 (d, J=3.6 Hz,1H), 4.10 -4.02 (m, 1H), 3.45 (t, J=9.1 Hz, 1H), 3.30 (t, J=9.3 Hz, 1H), 3.13 (t, J=9.4 Hz, 1H), 2.98 -2.82 (m, 2H), 2.73 (ddd, J=12.2, 9.8, 4.2 Hz, 1H), 2.53-2.41 (m, 1H), 2.27 (dd, J=9.9, 3.6 Hz, 1H), 2.05 (dt, J=11.8, 4.1 Hz, 1H), 1.90-1.73 (m, 4H), 1.04-0.90 (m, 1H), 0.74-0.56 (m, 2H), 0.42-0.30 (m, 2H).

Example 30

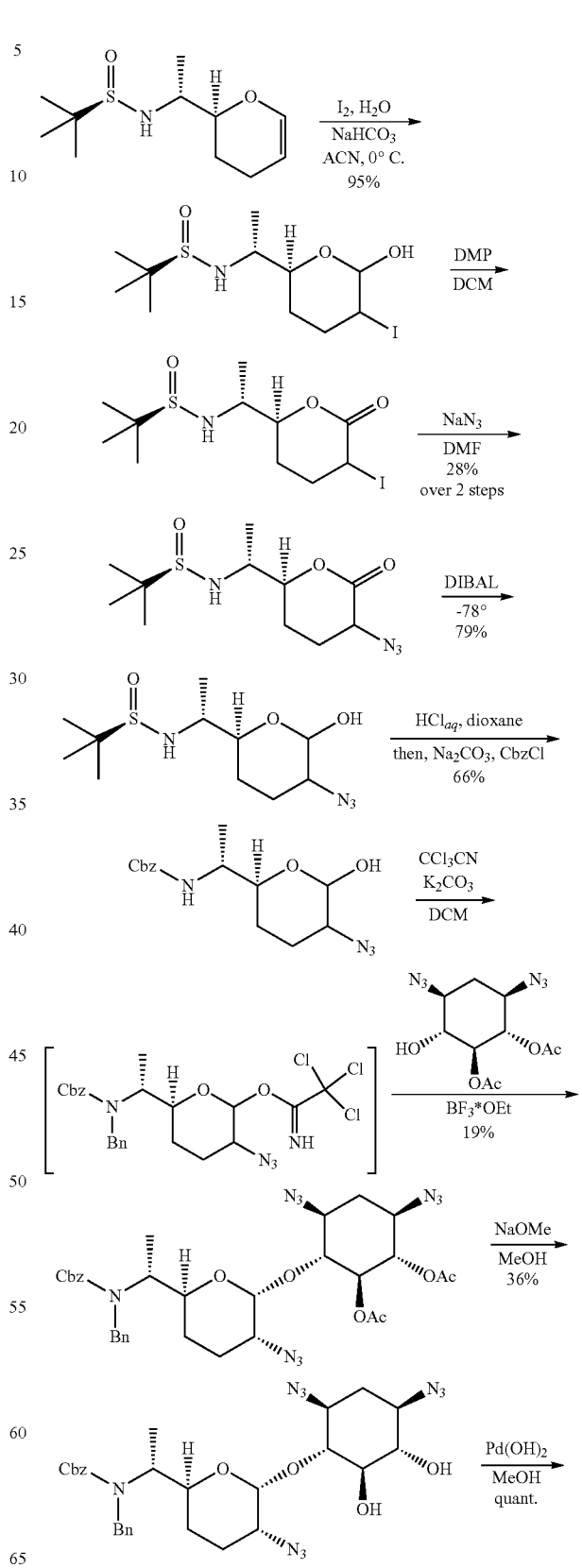

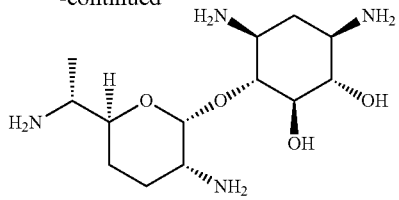

Step 1

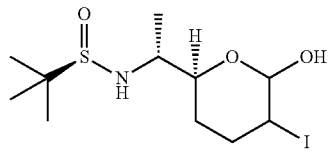 [SMILES: C[C@@H](N[S@](=O)C(C)(C)C)[C@@H]1CCC(I)C(O)O1]

(R)-N-[(1R)-1-[(2S)-6-Hydroxy-5-iodo-tetrahydropyran-2-yl]ethyl]-2-methyl-propane-2-sulfinamide Iodine (339 mg, 1.34 mmol) was added to a suspension of (R)-N-[(1R)-1-[(2S)-3,4-dihydro-2H-pyran-2-yl]ethyl]-2-methyl-propane-2-sulfinamide (303 mg, 1.31 mmol) and NaHCO$_3$ (330 mg, 3.93 mmol) in 1:1 H$_2$O/ACN (6.0 mL) at ambient temperature. After 30 min, acetonitrile was evaporated and the remaining solution was partitioned in EtOAc (25.0 mL) and water (10.0 mL). The organic layer was separated, washed with brine (10.0 mL), dried (Na$_2$SO$_4$) and filtered under reduced pressure to provide the title compounds (2 diastereomers) as a wax (490 mg, 95%). LCMS m/z: ES$^+$ [M+H]$^+$: 376.10; (A05) retention time=2.09 m. (A05) retention time=2.19 m. This material was used in the following reactions without further purifications.

Step 2

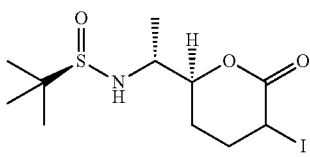 [SMILES: C[C@@H](N[S@](=O)C(C)(C)C)[C@@H]1CCC(I)C(=O)O1]

(R)-N-[(1R)-1-[(2S)-5-Iodo-6-oxo-tetrahydropyran-2-yl]ethyl]-2-methyl-propane-2-sulfinamide Dess-Martin Periodinane (631 mg, 1.48 mmol) was added to a solution of (R)-N -[(1R)-1-[(2S)-6-hydroxy-5-iodo-tetrahydropyran-2-yl]ethyl]-2-methyl-propane-2-sulfinamide (490 mg, 1.24 mmol) in DCM (15.0 mL) at ambient temperature. After 16 h, DCM was evaporated under reduced pressure and the residue was partition in between EtOAc (20.0 mL) and 1:1 sat. NaHCO$_3$/Na$_2$S$_2$O$_3$ (20.0 mL). The organic phase was successively washed with sat. NaHCO$_3$ (10.0 mL) and brine (10.0 mL), dried (Na$_2$SO$_4$), filtered and concentrated under reduced pressure to provide the title compound as an oil (463 mg, 100%). LCMS m/z: ES$^+$ [M+H]$^+$: 374.08; (A05) retention time=2.03 m.

Step 3

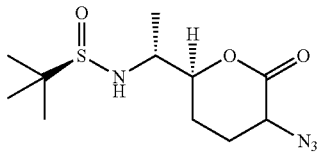 [SMILES: C[C@@H](N[S@](=O)C(C)(C)C)[C@@H]1CCC(N=[N+]=[N-])C(=O)O1]

(R)-N-[(1R)-1-[(2S)-5-Azido-6-oxo-tetrahydropyran-2-yl]ethyl]-2-methyl-propane-2-sulfinamide NaN$_3$ (282 mg, 4.34 mmol) was added to a solution of (R)-N-[(1R)-1-[(2S)-5-iodo-6 -oxo-tetrahydropyran-2-yl]ethyl]-2-methyl-propane-2-sulfinamide (463 mg, 1.24 mmol) in dry DMF (4.0 mL) at ambient temperature under N$_2$. After 16 h, the solution was filtered through a silica gel plug (4.0 g) with EtOAc (50.0 mL) and the filtrate was concentrated under reduced pressure. The crude was purified by silica gel chromatography (25 g cartridge) with EtOAc and hexanes (30%-70%) to provide the title compound as an oil (2 diastereomers, 100 mg, 28%). LCMS m/z: ES$^+$ [M+H]$^+$: 289.25; (A05) retention time=1.98-2.01 m.

Step 4

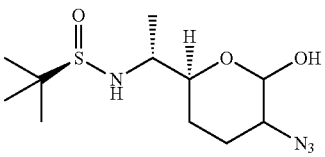 [SMILES: C[C@@H](N[S@](=O)C(C)(C)C)[C@@H]1CCC(N=[N+]=[N-])C(O)O1]

(R)-N-[(1R)-1-[(2S)-5-Azido-6-hydroxy-tetrahydropyran-2-yl]ethyl]-2-methyl-propane-2-sulfinamide DIBAL-H (1 M, 520 µL, 520 µmol) in toluene was dropwise added to a solution of (R)-N-[(1R)-1-[(2S)-5-azido-6-oxo-tetrahydropyran-2-yl]ethyl]-2-methyl-propane-2-sulfinamide (100 mg, 347 µmol) in dry DCM (4.5 mL) at −78° C. under N$_2$. After 1 h, acetone (100 µL) was added to the reaction mixture dropwise. After 5 min, sat. potassium sodium tartrate (10.0 mL) was added to the solution slowly, followed by the addition of water (10.0 mL). The mixture was allowed to warmed to room temperature and vigorously stirred for 1 h. The mixture was extracted with DCM (15.0+3×5.0 mL). The combined organic layers were dried (Na$_2$SO$_4$), filtered and concentrated under reduced pressure to provide the title compound as an oil (diastereomers, 80 mg, 79%). LCMS m/z: ES$^+$ [M+H]$^+$: 291.19; (A05) retention time=2.00 and 2.07 m. This material was used without further purifications.

Step 5

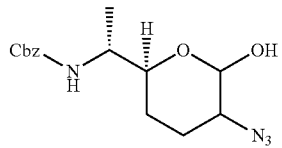 [SMILES: C[C@@H](NC(=O)OCc1ccccc1)[C@@H]1CCC(N=[N+]=[N-])C(O)O1]

Benzyl N-[(1R)-1-[(2S)-5-azido-6-hydroxy-tetrahydropyran-2-yl]ethyl]carbamate

Aqueous HCl (1.0 M, 1.37 mL, 1.37 mmol) was added dropwise to a solution of (R) -N-[(1R)-1-[(2S)-5-azido-6-hydroxy-tetrahydropyran-2-yl]ethyl]-2-methyl-propane-2-sulfinamide (80 mg, 275 µmol) in dioxane (2.0 mL) with vigorous stirring. After 1 h, solid Na$_2$CO$_3$ (234 mg, 2.20 mmol) was added. After another 15 min, CbzCl (55 µL, 386 mmol) was added dropwise. After another 3 h, dioxane was evaporated and the residue was partitioned in between EtOAc (20.0 mL) and H₂O (20.0 mL). The organic phase was washed with brine (10.0 mL), dried (Na₂SO₄), filtered and concentrated under reduced pressure. The crude was purified by silica gel chromatography (4 g cartridge) with EtOAc and hexanes (10-35%) to produce the title compound (mixture of 4 diastereomers) as a solid (58 mg, 66%). LCMS m/z: ES⁺ [M+H]⁺: 321.33; (A05) retention time=2.21, 2.24, 2.27, and 2.30 m.

Step 6

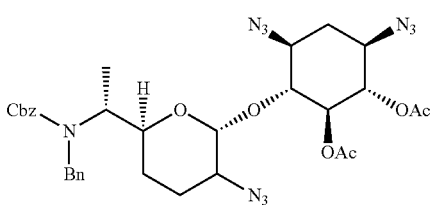

[(1S,2S,3R,4S,6R)-2-Acetoxy-4,6-diazido-3-[(2R,3R,6S)-3-azido-6-[(1R)-1-(benzyloxycarbonylamino)ethyl]tetrahydropyran-2-yl]oxy-cyclohexyl]acetate CCl₃CN (91 µL, 905 µmol) was added dropwise to a suspension of benzyl N-[(1R)-1-[(2S)-5-azido-6-hydroxy-tetrahydropyran-2-yl]ethyl]carbamate (58 mg, 181 µmol) and K₂CO₃ (75 mg, 543 µmol) in dry DCM (1.0 mL) at ambient temperature under N₂. After 64 h, the solution was filtered through cotton and the filtrate was concentrated under N₂ stream, followed by high-vacuum treatment. To the crude (96 mg) was added [(1S,2S,3R,4S,6R)-2-acetoxy-4,6-diazido-3-hydroxy-cyclohexyl]acetate (76 mg, 253 µmol) and ground 4 Å sieves (220 mg) and the mixture was dissolved in dry DCM (1.0 mL). The suspension was stirred at ambient temperature for 30 min. The solution was cooled to 0° C. and BF₃·OEt₂ (89 µL, 724 µmol) was added dropwise with vigorous stirring. The solution was warmed to ambient temperature and stirred for another 15 min. The solution was cooled to 0° C. and sat. NaHCO₃ (5.0 mL) was added. After another 15 min, the mixture was successively extracted with DCM (3×5.0 mL) and the combined organic layers were dried (Na₂SO₄), filtered and concentrated under reduced pressure. The crude was purified by silica gel chromatography (12 g cartridge) with EtOAc and hexanes (5-30%) to produce [(1S,2S,3R,4S,6R)-2-acetoxy-4,6-diazido-3-[(2R,3S,6S)-3-azido-6-[(1R)-1-(benzyloxycarbonylamino)ethyl]tetrahydropyran-2-yl]oxy-cyclohexyl]acetate as a solid (21 mg, 19%). ¹H NMR (500 MHz, CDCl₃) δ 7.37-7.28 (m, 5H), 5.21 (d, J=8.6 Hz, 1H), 5.10 (t, J=13.1 Hz, 2H), 5.05-5.00 (m, 1H), 4.92 (t, J=10.0 Hz, 1H), 4.88 (s, 1H), 4.05 (d, J=11.8 Hz, 1H), 3.77 (s, 1H), 3.61 (t, J=9.7 Hz, 1H), 3.54 (ddd, J=12.6, 10.0, 4.6 Hz, 1H), 3.44 (ddd, J=12.4, 9.9, 4.5 Hz, 1H), 3.35 (d, J=1.5 Hz, 1H), 2.28 (dt, J=12.9, 4.0 Hz, 1H), 2.07 (s, 6H), 2.05-1.96 (m, 1H), 1.84 (dd, J=14.3, 3.2 Hz,1H), 1.73-1.62 (m, 1H), 1.51-1.38 (m, 2H), 1.17 (d, J=6.8 Hz, 3H).

Step 7

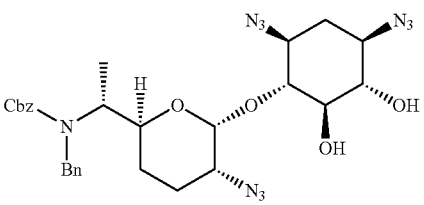 [SMILES: C[C@H]([C@@H]1CC[C@@H](N=[N+]=[N-])[C@@H](O[C@H]2[C@H](O)[C@@H](O)[C@H](N=[N+]=[N-])C[C@@H]2N=[N+]=[N-])O1)N(Cc1ccccc1)C(=O)OCc1ccccc1]

Benzyl N-[(1R)-1-[(2S,5R,6R)-5-azido-6-[(1R,2R,3S,4R,6S)-4,6-diazido-2,3-dihydroxy-cyclohexoxy]tetrahydropyran-2-yl]ethyl]carbamate NaOMe (25 wt %, 245 µL, 849 µmol) was added dropwise to a solution of [(1S,2S,3R,4S,6R)-2-acetoxy-4,6-diazido-3-[(2R,3R,6S)-3-azido-6-[(1R)-1-(benzyloxycarbonylamino)ethyl]tetrahydropyran-2-yl]oxy-cyclohexyl]acetate (85 mg, 142 µmol) in MeOH (3.0 mL) at ambient temperature. After 90 min, HOAc (245 µL, 2.55 mmol) was added to the reaction mixture dropwise and all volatiles were removed under reduced pressure. The crude was purified by silica gel chromatography (12 g cartridge) with EtOAc and hexanes (20-40%) to produce the title compound as a solid (26 mg, 36%). ¹H NMR (500 MHz, Acetone) δ 7.44-7.23 (m, 5H), 6.25 (d, J=8.6 Hz, 1H), 5.81-5.72 (m, 1H), 5.13-4.98 (m, 2H), 4.05 (ddd, J=11.9, 5.6, 2.1 Hz, 1H), 3.73-3.65 (m, 1H), 3.65-3.57 (m, 3H), 3.57-3.51 (m, 1H), 3.44-3.32 (m, 1H), 3.15 (dt, J=12.6, 4.1 Hz, 1H), 2.25 (dt, J=13.0, 4.2 Hz, 1H), 2.14-2.06 (m, 1H), 1.92-1.82 (m, 2H), 1.53 (ddt, J=10.4, 7.6, 4.0 Hz, 1H), 1.44-1.34 (m, 1H), 1.34-1.23 (m, 2H), 1.17 (d, J=6.8 Hz, 3H). LCMS m/z: ES⁺ [M+H]⁺: 517.18; (A05) retention time=2.42 m.

Step 8

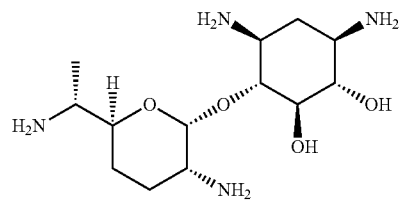 [SMILES: C[C@@H](N)[C@@H]1CC[C@@H](N)[C@@H](O[C@H]2[C@H](O)[C@@H](O)[C@H](N)C[C@@H]2N)O1]

(1S,2R,3R,4S,6R)-4,6-Diamino-3-[(2R,3R,6S)-3-amino-6-[(1R)-1-aminoethyl]tetrahydropyran-2-yl]oxy-cyclohexane-1,2-diol Pd(OH)₂/C (10 wt %, 7.5 mg, 5.4 µmol) was added to a solution of benzyl N-[(1R)-1-[(2S,5R,6R)-5-azido-6-[(1R,2R,3S,4R,6S)-4,6-diazido-2,3-dihydroxy-cyclohexoxy]tetrahydropyran-2-yl]ethyl]carbamate (11 mg, 21.3 µmol) in EtOH/MeOH (1:1, 3.0 mL) under N₂ at ambient temperature. H₂ was bubbled through the suspension for 10 min. After 17 h, the solution was filtered through a frit (0.22 µm diameter) and the filtrate was concentrated under reduced pressure, then lyophilized to provide the title compound as a solid (8.2 mg, quantitative). ¹H NMR (500 MHz, MeOD) δ 5.12 (d, J=3.6 Hz, 1H), 3.74 (ddd, J=12.0, 4.3, 2.1 Hz, 1H), 3.37 (t, J=9.1 Hz, 1H), 3.19 (t, J=9.2 Hz, 1H), 3.05 (t, J=9.4 Hz, 1H), 2.95-2.87 (m, 1H), 2.84-2.73 (m, 2H), 2.64 (ddd, J=12.0, 9.6, 4.1 Hz, 1H), 1.99 (dt, J=12.9, 4.1 Hz, 1H), 1.80-1.74 (m, 1H), 1.74-1.63 (m, 2H), 1.52-1.41 (m, 1H), 1.21 (dd, J=25.0, 12.2 Hz, 1H), 1.10 (d, J=6.7 Hz, 3H).

Example 31

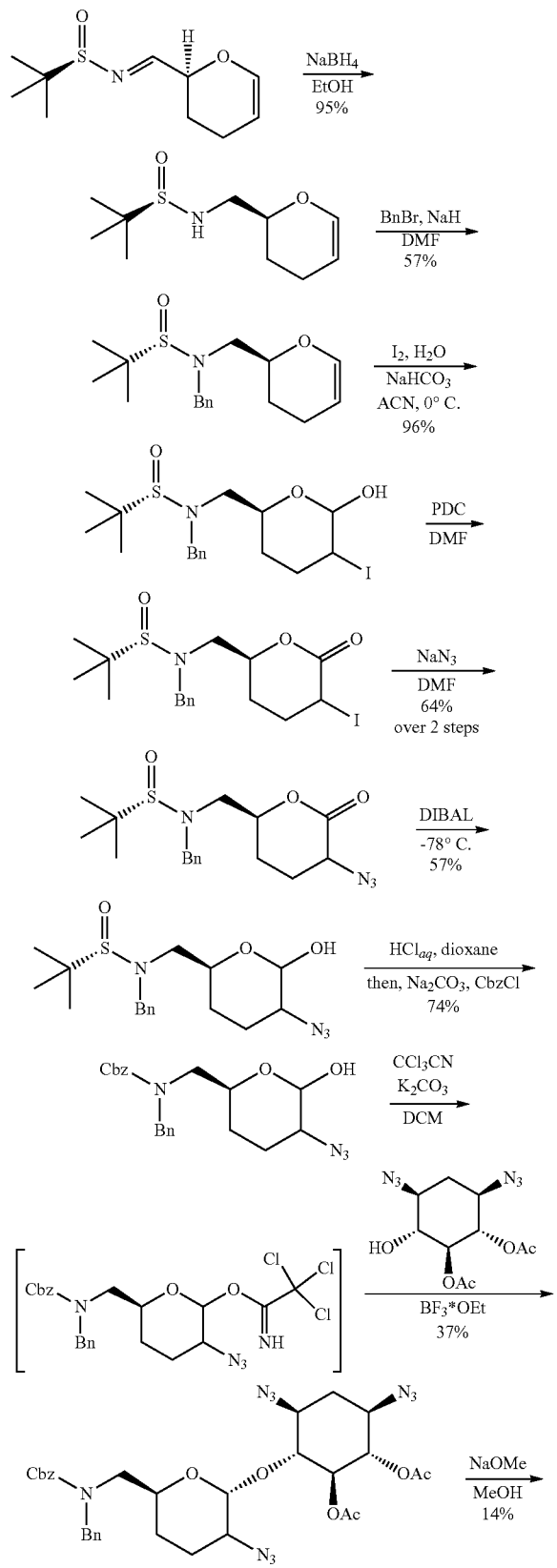

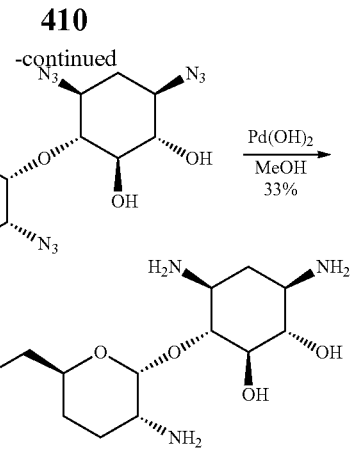

Step 1

(R)-N-[[(2S)-3,4-Dihydro-2H-pyran-2-yl]methyl]-2-methyl-propane-2-sulfinamide

NaBH$_4$ (101 mg, 2.66 mmol) was added to a solution of (NE)-N-[[(2S)-3,4-dihydro-2H-pyran-2-yl]methylene]-2-methyl-propane-2-sulfinamide (572 mg, 2.66 mmol) in reagent alcohol (10.0 mL) at 0° C. Ice bath was removed and the reaction was kept stirring for another 30 min. The reaction was cooled to 0° C. and sat. NH$_4$Cl (20.0 mL) was added (nota bene: gas evolution). EtOH was evaporated under reduced pressure and the residue was extracted with EtOAc (30.0 mL). The layers were separated and the organic phase was successively washed with water (10.0 mL) and brine (10.0 mL), dried (Na$_2$SO$_4$), filtered and concentrated under reduced pressure to provide the title compound as a solid (547 mg, 95%). LCMS m/z: ES$^+$ [M+H]$^+$: 218.20; (A05) retention time=2.04 m. This material was used in the following steps without further purifications.

Step 2

(R)-N-Benzyl-N-[[(2S)-3,4-dihydro-2H-pyran-2-yl]methyl]-2-methyl-propane-2-sulfinamide NaH (60%, 116 mg, 2.89 mmol) was added to a mixture of (R)-N-[[(2S)-3,4-dihydro-2H-pyran-2-yl]methyl]-2-methyl-propane-2-sulfinamide (547 mg, 2.52 mmol) and BnBr (448 μL, 3.78 mmol) in DMF (1.5 mL) at 0° C. The mixture was stirred at room temperature for 1 h, then cooled to 0° C. followed by addition of water (10.0 mL). The aqueous layer was extracted with EtOAc (25.0 mL) and the organic layer was successively washed with water (10.0 mL) and brine (5.0 mL), dried (Na$_2$SO$_4$), filtered and concentrated under reduced pressure. The crude was purified by silica gel chromatography (24 g cartridge) with EtOAc and Step 3

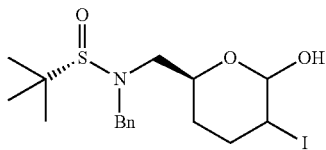 [SMILES: CC(C)(C)[S@](=O)N(Cc1ccccc1)C[C@@H]1CCC(I)C(O)O1]

(R)-N-Benzyl-N-[(1R)-1-[(2S)-6-hydroxy-5-iodo-tetrahydropyran-2-yl]ethyl]-2-methyl-propane -2-sulfinamide Iodine (272 mg, 1.07 mmol) was added to a suspension of (R)-N-benzyl-N-[(1R)-1-[(2S)-3,4-dihydro-2H-pyran-2-yl]ethyl]-2-methyl-propane-2-sulfinamide (320 mg, 1.04 mmol) and NaHCO$_3$ (262 mg, 3.12 mmol) in 1:1 H$_2$O/ACN (8.0 mL) at ambient temperature. After 30 min, MeCN was evaporated and the residue was partitioned in between EtOAc (20.0 mL) and 1:1 sat. NaHCO$_3$/sat. Na$_2$S$_2$O$_3$ (10.0 mL). The organic layer was washed with water (5.0 mL) and brine (5.0 mL), dried (Na$_2$SO$_4$), filtered and concentrated under reduced pressure to provide the title compound as a foam (4 diastereomers, 450 mg, 96%). LCMS m/z: ES$^+$ [M+H]$^+$: 452.06; (A05) retention time=2.30-2.50 m. This material was used in the following reactions without further purifications.

Step 4

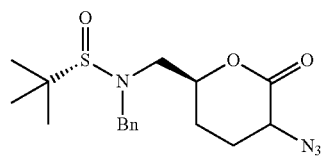 [SMILES: CC(C)(C)[S@](=O)N(Cc1ccccc1)C[C@@H]1CCC(N=[N+]=[N-])C(=O)O1]

(R)-N-[[(2S)-5-Azido-6-oxo-tetrahydropyran-2-yl]methyl]-N-benzyl-2-methyl-propane-2-sulfinamide 4 Å Sieves (500 mg) and PDC (750 mg, 1.99 mmol) was added to a solution of benzyl (R)-N-benzyl-N-[[(2S)-6-hydroxy-5-iodo-tetrahydropyran-2-yl]methyl]-2-methyl -propane-2-sulfinamide (450 mg, 997 µmol) in dry DCM (10.0 mL) under N$_2$ at ambient temperature. After 24 h, the solution was concentrated and the crude was partitioned in between EtOAc (30.0 mL) and water (15.0 mL). The organic layer was washed with water (2×10.0 mL) and brine (10.0 mL), dried (Na$_2$SO$_4$) and concentrated. The crude was dissolved in dry DMF (1.5 mL) under Na and NaN$_3$ (130 mg, 1.99 mmol) was added. After 1 h, the solution was partitioned in between EtOAc (30.0 mL) and water (15.0 mL). The organic layer was washed with water (2×10.0 mL) and brine (10.0 mL), dried (Na$_2$SO$_4$) and concentrated to provide the title compound as an oil (235 mg, 64%). LCMS m/z: ES$^+$ [M+H]$^+$: 365.17; (A05) retention time=2.37 m. This material was used in the next reactions without further purifications.

Step 5

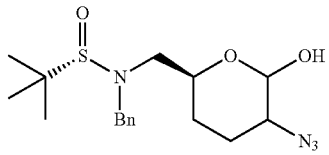

(R)-N-[[(2S)-5-Azido-6-hydroxy-tetrahydropyran-2-yl]methyl]-N-benzyl-2-methyl-propane-2-sulfinamide DIBAL-H (1 M, 1.03 mL, 1.03 mmol) in toluene was dropwise added to a solution of (R)-N-[[(2S)-5-azido-6-oxo-tetrahydropyran-2-yl]methyl]-N-benzyl-2-methyl-propane-2-sulfinamide (235 mg, 645 µmol) in dry DCM (8.0 mL) at −78° C. under N$_2$. After 100 min, sat. potassium sodium tartrate (15.0 mL) was added to the solution slowly, followed by the addition of water (15.0 mL). The mixture was allowed to warm to room temperature and vigorously stirred for 16 h. The mixture was extracted with DCM (10.0+2×5.0 mL). The combined organic layers were dried (Na$_2$SO$_4$), filtered and concentrated under reduced pressure. The crude was purified by silica gel chromatography (12 g cartridge) with EtOAc and hexanes (10%-50%) to provide the title compound as an oil (diastereomers, 195 mg, 74%). LCMS m/z: ES$^+$ [M+H]$^+$: 367.19; (A05) retention time=2.28-2.40 m.

Step 6

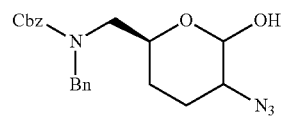 [SMILES: [N-]=[N+]=NC1CC[C@@H](CN(Cc2ccccc2)C(=O)OCc2ccccc2)OC1O]

Benzyl N-[[(2S)-5-azido-6-hydroxy-tetrahydropyran-2-yl]methyl]-N-benzyl-carbamate Aqueous HCl (1.0 M, 2.66 mL, 2.66 mmol) was dropwise added to a solution of (R) -N-[[(2S)-5-azido-6-hydroxy-tetrahydropyran-2-yl]methyl]-N-benzyl-2-methyl-propane-2 -sulfinamide (195 mg, 532 µmol) in dioxane (2.7 mL) with vigorous stirring. After 1 h, solid Na$_2$CO$_3$ (451 mg, 4.26 mmol) was added. After another 5 min, CbzCl (106 µL, 745 mmol) was added dropwise. After another 1 h, dioxane was evaporated and the residue was partitioned in between EtOAc (20.0 mL) and H$_2$O (20.0 mL). The organic phase was washed with brine (10.0 mL), dried (Na$_2$SO$_4$), filtered and concentrated under reduced pressure. The crude was purified by C18 reverse phase chromatography (80 g cartridge) with ACN and 0.1% aq. formic acid (40 -70%) to produce the title compound (mixture of 4 diastereomers) as an oil (167 mg, 79%). UPLC m/z: ES$^+$ [M−OH]$^+$: 379.21; (CSH 5 to 100% ACN/AmFor pH 4) retention time=2.12, 2.15, 2.20, and 2.22 m. A portion (40 mg) of the material was purified by prep-HPLC (CSH C18 ACN/AmForm 50-70%) to provide the a-azido as a film (20 mg, 50% recovery). UPLC m/z: (CSH 5 to 100% ACN/AmFor pH 4) retention time=2.15 and 2.22 m.

Step 7

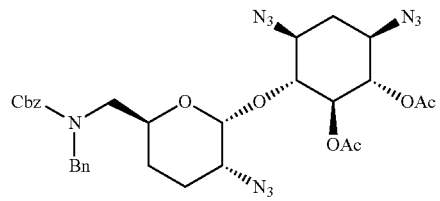 [SMILES: CC(=O)O[C@@H]1[C@@H](OC(C)=O)[C@H](N=[N+]=[N-])C[C@H](N=[N+]=[N-])[C@H]1O[C@H]1O[C@H](CN(Cc2ccccc2)C(=O)OCc2ccccc2)CC[C@H]1N=[N+]=[N-]]

[(1S,2S,3R,4S,6R)-2-Acetoxy-4,6-diazido-3-[(2R,6S)-3-azido-6-[[benzyl(benzyloxycarbonyl)amino]methyl]tetrahydropyran-2-yl]oxy-cyclohexyl]acetate CCl$_3$CN (145 µL, 1.44 mmol) was added dropwise to a suspension of benzyl N-[[(2S)-5-azido-6-hydroxy-tetrahydropyran-2-yl]methyl]-N-benzyl-carbamate (127 mg, 288 µmol) and K$_2$CO$_3$ (120 mg, 865 µmol) in dry DCM (2.0 mL) at ambient temperature under N$_2$. After 20 h, the solution was filtered through cotton and the filtrate was concentrated under N$_2$ stream, followed by high-vacuum. To the crude (92 mg) was added [(1S,2S,3R,4S,6R)-2-acetoxy-4,6-diazido-3-hydroxy-cyclohexyl]acetate (120 mg, 404 µmol) and ground 4 Å sieves (500 mg) and the mixture was dissolved in dry DCM (2.0 mL). The suspension was stirred at ambient temperature for 1 h. The solution was cooled to 0° C. and BF$_3$·OEt$_2$ (142 µL, 1.15 mmol) was added dropwise with vigorous stirring. The solution was warmed to ambient temperature and stirred for another 15 min. The reaction was quenched with sat. NaHCO$_3$ (10.0 mL). The mixture was successively extracted with DCM (3×8.0 mL) and the combined organic layer were dried (Na$_2$SO$_4$), filtered and concentrated under reduced pressure. The crude was purified by silica gel chromatography (24 g cartridge) with EtOAc and hexanes (5-25%) to produce [(1S,2S,3R,4S,6R)-2-acetoxy-4,6-diazido-3-[(2R,6S)-3-azido-6-[[benzyl(benzyloxycarbonyl)amino]methyl]tetrahydropyran-2-yl]oxy-cyclohexyl]acetate (2 diastereomers, 144 mg, 74%) as an oil. LCMS m/z: [M+H]$^+$: 677.20; (A05) retention time=2.86 m.

Step 8

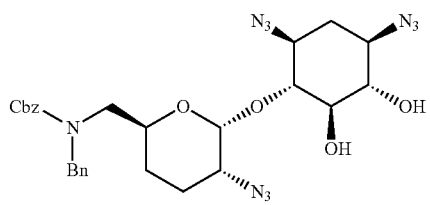 [SMILES: [N-]=[N+]=N[C@H]1C[C@@H](N=[N+]=[N-])[C@H](O)[C@@H](O)[C@@H]1O[C@H]1O[C@H](CN(Cc2ccccc2)C(=O)OCc2ccccc2)CC[C@H]1N=[N+]=[N-]]

Benzyl N-[[(2S,5R,6S)-5-azido-6-[(1R,2R,3S,4R,6S)-4,6-diazido-2,3-dihydroxy-cyclohexoxy]tetrahydropyran-2-yl]methyl]-N-benzyl-carbamate NaOMe (25 wt %, 306 µL, 1.06 mmol) was added dropwise to a solution of [(1S,2S,3R,4S,6R)-2-acetoxy-4,6-diazido-3-[(2R,6S)-3-azido-6-[[benzyl(benzyloxycarbonyl)amino]methyl]tetrahydropyran-2-yl]oxy-cyclohexyl]acetate (92 mg, 136 µmol) in MeOH (2.0 mL) at ambient temperature. After 60 min, HOAc (122 µL, 2.13 mmol) was added to the reaction mixture dropwise and all volatiles were removed under reduced pressure. The crude was purified by silica gel chromatography (24 g cartridge) with EtOAc and hexanes (10-40%) to produce the title compound as an oil (28 mg, 22%) and benzyl N-[[(2S,5S,6R)-5-azido-6-[(1R,2R,3S,4R,6S)-4,6-diazido-2,3-dihydroxy-cyclohexoxy]tetrahydropyran-2-yl]methyl]-N-benzyl-carbamate as a solid (38 mg, 30%). They has the same retention time and MS. LCMS m/z: ES$^+$ [M+H]$^+$: 379.27; (A05) retention time=2.63 m.

Step 9

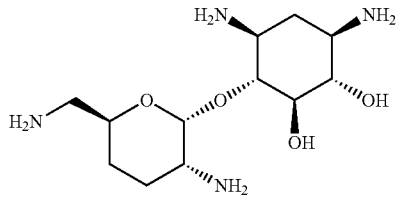 [SMILES: NC[C@@H]1CC[C@@H](N)[C@@H](O[C@H]2[C@H](O)[C@@H](O)[C@H](N)C[C@@H]2N)O1]

(1S,2R,3R,4S,6R)-4,6-Diamino-3-[(2R,3R,6S)-3-amino-6-(aminomethyl)tetrahydropyran-2-yl]oxy-cyclohexane-1,2-diol Pd(OH)$_2$/C (10 wt %, 8 mg, 5.7 µmol) was added to a solution of benzyl N-[[(2S,5R,6S)-5-azido-6-[(1R,2R,3S,4R,6S)-4,6-diazido-2,3-dihydroxy-cyclohexoxy]tetrahydropyran-2-yl]methyl]-N-benzyl-carbamate (8 mg, 13.5 µmol) in MeOH (2.5 mL) under Na at ambient temperature. H$_2$ was bubbled through the suspension for 15 min. After 17 h, the solution was filtered through a frit (0.22 µm diameter) and the filtrate was concentrated under reduced pressure, then lyophilized to provide the title compound as a wax (3.8 mg, 92%). $^1$H NMR (500 MHz, MeOD) δ 5.22 (d, J=3.6 Hz, 1H), 3.92-3.84 (m, 1H), 3.39 (t, J=9.1 Hz, 1H), 3.24 (t, J=9.3 Hz, 1H), 3.07 (t, J=9.4 Hz, 1H), 2.86-2.79 (m, 2H), 2.77 (dd, J=13.1, 3.6 Hz, 1H), 2.70-2.63 (m, 2H), 2.01 (dt, J=8.4, 3.9 Hz, 1H), 1.78-1.67 (m, 3H), 1.44-1.38 (m, 1H), 1.24 (dd, J=24.9, 12.2 Hz, 1H).

Example 32

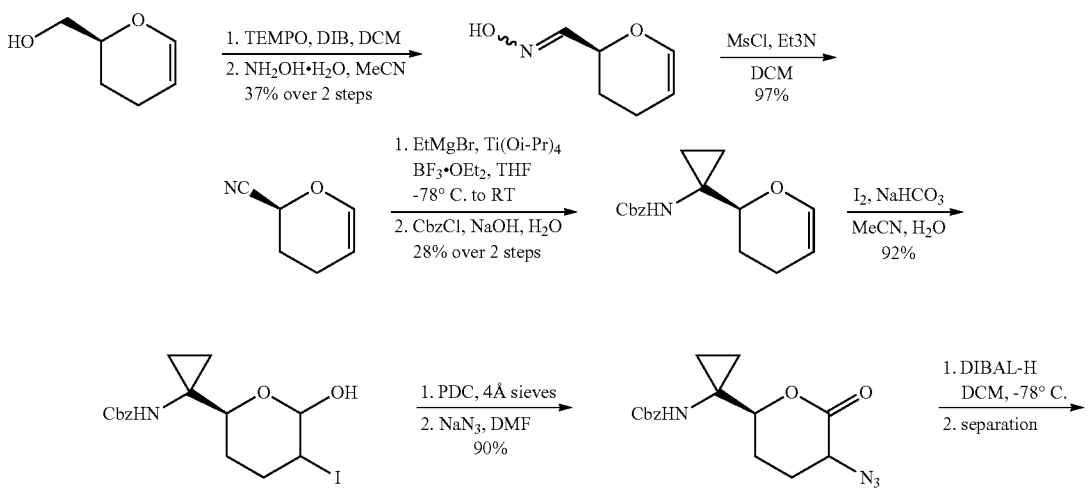

415 416
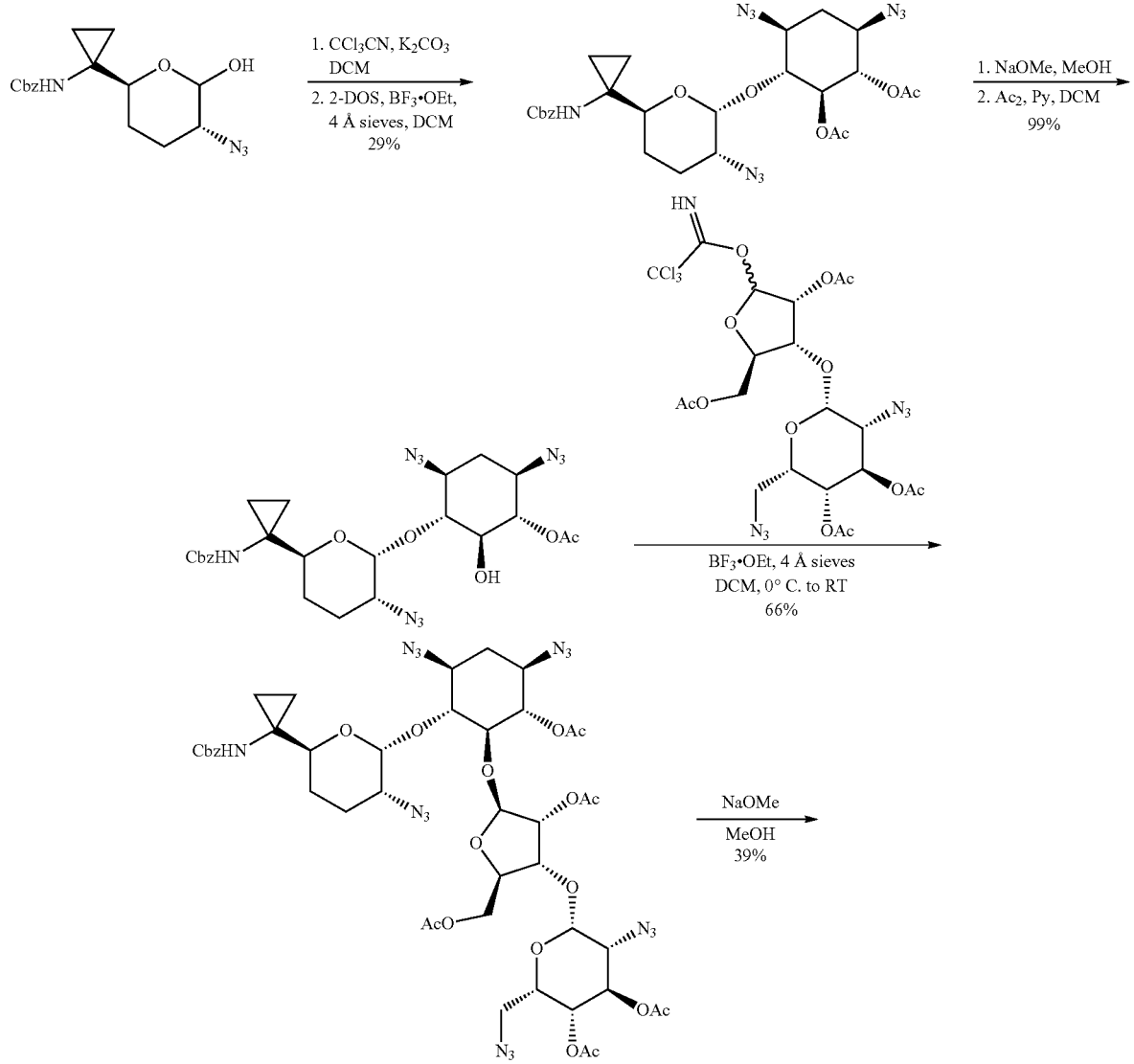
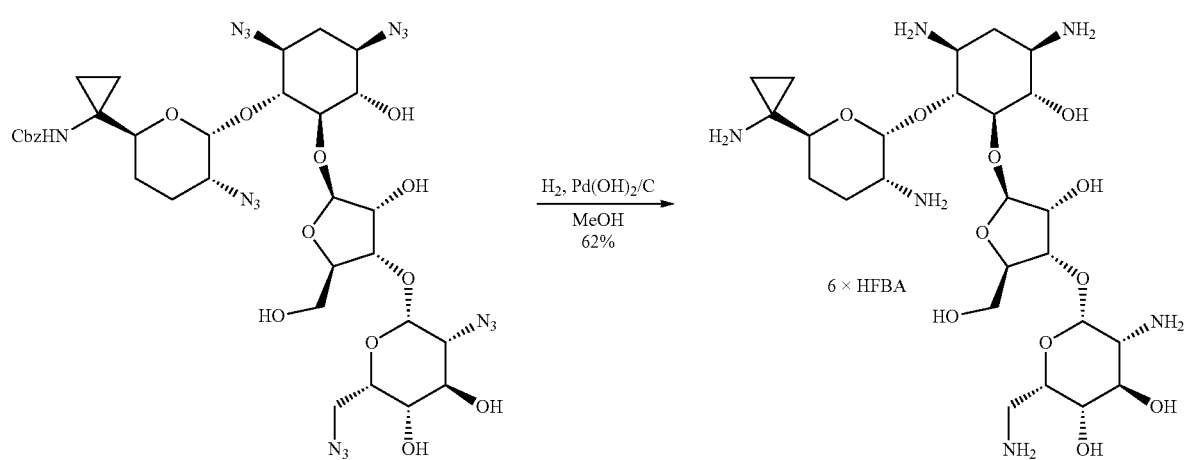

Step 1
(2S)-3,4-dihydro-2H-pyran-2-carbaldehyde oxime

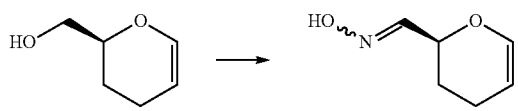 [SMILES: OC[C@@H]1CCC=CO1 ; ON=C[C@@H]1CCC=CO1]

TEMPO (137 mg, 876 μmol) was added to a suspension of (2S)-3,4-dihydro-2H-pyran-2-yl]methanol (1.0 g, 8.76 mmol) and (diacetoxyiodo)benzene (DIB) (4.23 g, 13.1 mmol) in DCM (10.0 mL) at ambient temperature. After 4.5 h, the solution was poured into a 1:1 mixture of $NaHCO_3$/$Na_2S_2O_3$ (30.0 mL) and extracted with DCM (3×15.0 mL). To the combined organic layers was added MeCN (5.0 mL) and hydroxylamine (50% aq., 1.0 mL, 16.3 mmol). After 2 h, all volatiles were removed under reduced pressure. The material was purified by silica gel chromatography (24 g cartridge) with EtOAc and hexanes (0-20%) to provide the title compound (2 oxime isomers, 436 mg, 39%) as an oil. For TEMPO/DIB oxidation: see *Tetrahedron Letters*, 2009, 50, 2693.

Step 2
(2S)-3,4-dihydro-2H-pyran-2-carbonitrile

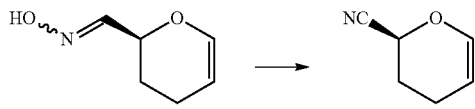 [SMILES: ON=C[C@@H]1CCC=CO1 ; N#C[C@@H]1CCC=CO1]

MsCl (398 μL, 5.14 mmol) was added dropwise (Caution: violent reaction) to a solution of (2S)-3,4-dihydro-2H-pyran-2-carbaldehyde oxime (436 mg, 3.43 mmol) and $Et_3N$ (1.67 mL, 12.0 mmol) in dry DCM (6.0 mL) under $N_2$ at 0° C. and ice bath was removed. After 30 min, the material was filtered through silica gel (5.0 g) and eluted with DCM (30 mL). The filtrate was carefully concentrated and purified by silica gel chromatography (24 g cartridge, wet loading) with DCM and the fractions were carefully concentrated to provide a solution of the title compound. $^1$H NMR (400 MHz, $CDCl_3$) δ 6.30 (dt, J=6.3, 1.7 Hz, 1H), 4.91-4.82 (m, 2H), 2.34-2.19 (m, 1H), 2.17-2.03 (m, 3H). Note: The product contains 43 wt % EtOAc from ISCO system and 28 wt % DCM by $^1$H NMR. The material was not fully concentrated because of the volatility of (2S)-3,4-dihydro-2H-pyran-2-carbonitrile.

Step 3
Benzyl N-[1-[(2S)-3,4-dihydro-2H-pyran-2-yl]cyclopropyl]carbamate

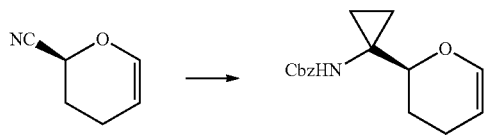 [SMILES: N#C[C@@H]1CCC=CO1 ; O=C(NC1([C@@H]2CCC=CO2)CC1)OCc1ccccc1]

Ti(OiPr)$_4$ (1.09 mL, 3.67 mmol) was added to a suspension of EtMgBr (3.0 M in ether, 2.44 mL, 7.33 mmol) in dry THF (5.0 mL) under $N_2$ at −78° C. After 30 min, a solution of (2S)-3,4-dihydro-2H-pyran-2-carbonitrile (320 mg, 2.93 mmol, carefully co-evaporated with 3×25.0 mL hexane) in dry THF (3.0 mL) was added dropwise and the mixture was warmed to room temperature. After 40 min, $BF_3·OEt_2$ (724 μL, 5.86 mmol) was added to the reaction mixture dropwise. After another 30 min, the solution was cooled to 0° C. and 1.0 M solution of NaOH (14.7 mL, 14.7 mmol) was added quickly dropwise. After another 10 min, CbzCl (625 μL, 4.40 mol) was added at ambient temperature and the reaction mixture was stirred for 1 h. The mixture was diluted with water (30.0 mL) and DCM (30.0 mL) The layers were separated, and the aqueous layer was extracted with DCM (2×10.0 mL). The combined organic layers were dried ($Na_2SO_4$), filtered and concentrated under reduced pressure. The material was purified by silica gel chromatography (25 g cartridge) using a gradient of 0-20% EtOAc in hexane as eluent to provide the title compound (225 mg, 28%) as a solid. $^1$H NMR (500 MHz, $CDCl_3$) δ 7.39-7.28 (m, 5H), 6.35 (d, J=5.4 Hz, 1H), 5.25 (s, 1H), 5.06 (s, 2H), 4.69-4.60 (m, 1H), 3.43 (d, J=10.1 Hz, 1H), 2.13-1.88 (m, 3H), 1.65 (ddd, J=25.1, 12.4, 6.2 Hz, 1H), 1.13-1.02 (m, 1H), 0.96-0.78 (m, 3H). MS ESI [M+H]$^+$274.0.

Step 4
Benzyl N-[1-[(2S)-6-hydroxy-5-iodo-tetrahydropyran-2-yl]cyclopropyl]carbamate

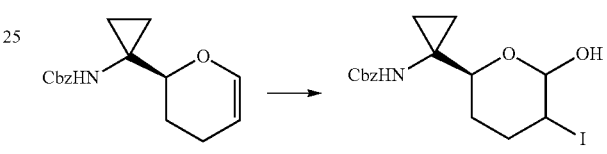

I$_2$ (71 mg, 281 μmol) was added to a suspension of N-benzyl-N-[1-[(2S)-3,4-dihydro-2H-pyran-2-yl]cyclopropyl]carbamate (100 mg, 275 μmol) and $NaHCO_3$ (46 mg, 550 mmol) in a mixture $H_2O$/MeCN (1:1) (3.0 mL) at ambient temperature. After 20 min, the volatiles were evaporated, and the residue was partitioned in between DCM (10.0 mL) and brine (10.0 mL). The aqueous layer was extracted with DCM (2×5.0 mL) and the combined organic layers were dried ($Na_2SO_4$), filtered and concentrated under reduced pressure to provide the title compound (>2 diastereomers, 140 mg, 92%) as a solid, which was used in the next step without further purification. MS ESI [M+H]$^+$ 417.9.

Step 5
Benzyl N-[1-[(2S)-5-azido-6-oxo-tetrahydropyran-2-yl]cyclopropyl]carbamate

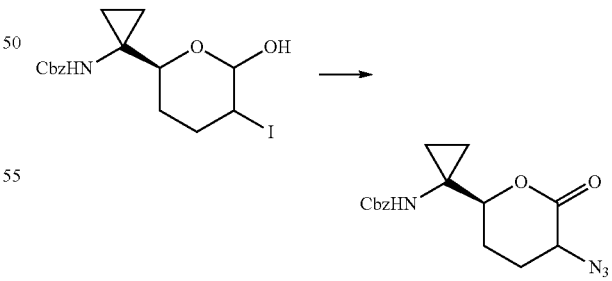

4 Å sieves (150 mg) and PDC (252 mg, 671 μmol) was added to a solution of benzyl N-[1-[(2S)-6-hydroxy-5-iodo-tetrahydropyran-2-yl]cyclopropyl]carbamate (140 mg, 336 μmol) in dry DCM (3.5 mL) under $N_2$ at ambient temperature. After 20 h, the material was filtered through a silica gel plug (1.2 mL) and was eluted with EtOAc (10.0 mL). The filtrate was concentrated under reduced pressure. The crude iodolactone (135 mg) was dissolved in dry DMF (0.40 mL) under N$_2$ and then NaN$_3$ (33 mg, 503 µmol) was added. After 1 h, the solution was filtered through a silica gel plug (1.0 mL) and eluted with EtOAc (12.0 mL). The filtrate was concentrated under reduced pressure. The mixture was re-dissolved in EtOAc and filtered through a silica gel plug (1.0 mL) and eluted with EtOAc (12.0 mL). The filtrate was concentrated under reduced pressure then lyophilized to produce the title compound (100 mg, 90%) as an oil, which was used in the next reactions without further purification. MS ESI [M+H]$^+$330.9.

Step 6
Benzyl N-[1-[(2S,5R)-5-azido-6-hydroxy-tetrahydropyran-2-yl]cyclopropyl]carbamate

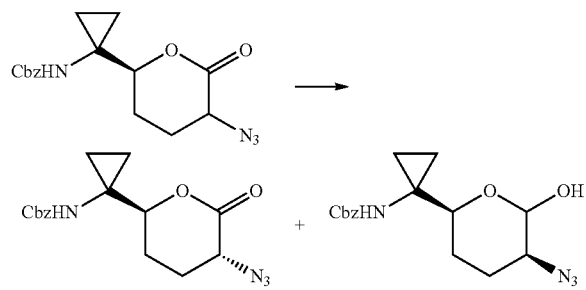

DIBAL-H (1 M, 484 µL, 484 µmol) in toluene was dropwise added to a solution of benzyl N-[1-[(2S)-5-azido-6-oxo-tetrahydropyran-2-yl]cyclopropyl]carbamate (100 mg, 303 µmol) in dry DCM (4.0 mL) at −78° C. under N$_2$ and the reaction mixture was stirred for 50 min. Acetone (150 µL) and saturated potassium sodium tartrate (5.0 mL) were added to the solution slowly. The mixture was warmed to room temperature and vigorously stirred for 16 h. The mixture was extracted with DCM (2×10 mL). The combined organic layers were dried (Na$_2$SO$_4$), filtered and concentrated under reduced pressure. The material was purified by silica gel chromatography (12 g cartridge) using a gradient of 15-40% with EtOAc and hexane as eluent and was purified by silica gel chromatography (12 g cartridge) using a gradient of 5-30% EtOAc and hexane as eluent to provide the title compound (44 mg, 44%) as a solid. MS ESI [M+Na]$^+$355.1.

Step 7
[(1S,2S,3R,4S,6R)-2-acetoxy-4,6-diazido-3-[(2R,3R,6S)-3-azido-6-[1-(benzyloxycarbonylamino)cyclopropyl]tetrahydropyran-2-yl]oxy-cyclohexyl]acetate

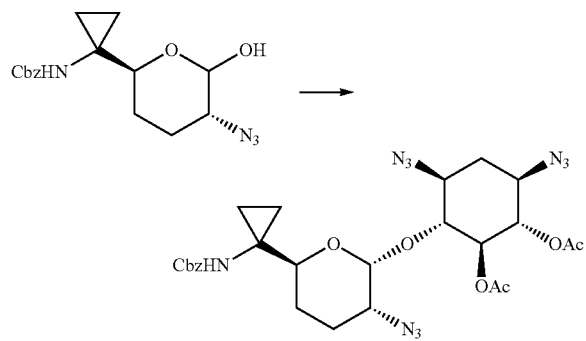

CCl$_3$CN (60 µL, 860 µmol) was added dropwise to a suspension of benzyl N-[1-[(2S,5R)-5-azido-6-hydroxy-tetrahydropyran-2-yl]cyclopropyl]carbamate (44 mg, 119 µmol) and K$_2$CO$_3$ (49 mg, 357 µmol) in dry DCM (1.0 mL) at ambient temperature under N$_2$ and the solution was stirred for 64 h. The mixture was filtered through cotton and the filtrate was concentrated under N$_2$ stream, followed by high-vacuum. To the residue was added [(1S,2S,3R,4S,6R)-2-acetoxy-4,6-diazido-3-hydroxy-cyclohexyl]acetate (50 mg, 167 µmol) and ground 4 Å sieves (300 mg) and the mixture was dissolved in dry DCM (1.0 mL). The suspension was stirred at ambient temperature for 40 min. The mixture was cooled to 0° C. and BF$_3$·OEt$_2$ (60 µL, 477 µmol) was added dropwise with vigorous stirring. The reaction mixture was warmed to ambient temperature and stirred for another 30 min. To the mixture was added Et$_3$N (100 µL) and the solution was filtered through silica gel (0.30 g) and eluted EtOAc (6.0 mL). The filtrate was concentrated and purified by preparative HPLC (BEH 30×150 mm C18 ACN/AmForm 60-70%) to provide the title compound (21 mg, 29%) as a solid. $^1$H NMR (500 MHz, CDCl$_3$) δ 7.42-7.29 (m, 5H), 5.18 (s, 1H), 5.14 (d, J=9.8 Hz, 1H), 5.11 (s, 1H), 5.05 (s, 2H), 4.91 (t, J=10.0 Hz, 1H), 3.68 (dd, J=16.4, 6.7 Hz, 2H), 3.61 (ddd, J=12.6, 10.2, 4.6 Hz, 1H), 3.54-3.41 (m, 1H), 3.00 (dt, J=6.6, 3.9 Hz, 1H), 2.34 (dt, J=13.3, 4.6 Hz, 1H), 2.07 (s, 3H), 2.07 (s, 3H), 2.03-1.92 (m, 2H), 1.92-1.85 (m, 1H), 1.57-1.45 (m, 2H), 1.10-1.02 (m, 1H), 0.91 (ddd, J=11.1, 6.6, 4.4 Hz, 1H), 0.88-0.81 (m, 1H), 0.81-0.74 (m, 1H). MS ESI [M+H]$^+$613.3.

Step 8
[(1S,2S,3R,4S,6R)-4,6-diazido-3-[(2R,3R,6S)-3-azido-6-[1-(benzyloxycarbonylamino)cyclopropyl]tetrahydropyran-2-yl]oxy-2-hydroxy-cyclohexyl]acetate

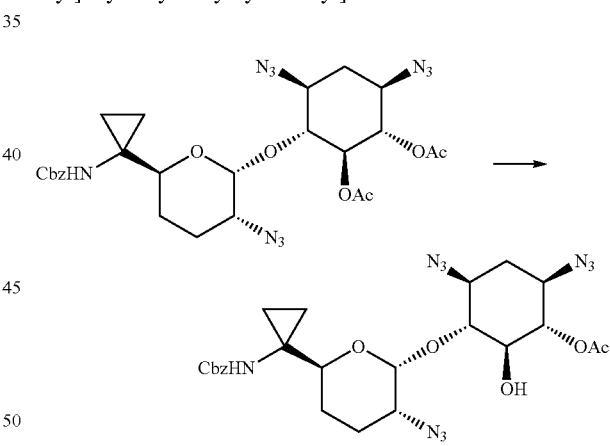

NaOMe (25 wt %, 40 µL, 173 µmol) was added dropwise to a suspension of [(1S,2S,3R,4S,6R)-2-acetoxy-4,6-diazido-3-[(2R,3R,6S)-3-azido-6-[1-(benzyloxycarbonylamino)cyclopropyl]tetrahydropyran-2-yl]oxy-cyclohexyl]acetate (21 mg, 34 µmol) in MeOH (1.0 mL) at ambient temperature and stirred for 30 min. The mixture was warmed to 40° C. and stirred for 30 min. The solution was cooled to room temperature and AcOH (20 µL, 343 µmol) was added to the reaction mixture dropwise and all volatiles were evaporated under reduced pressure. The material was filtered through silica gel (0.30 g) and eluted with EtOAc (6.0 mL). The filtrate was concentrated under reduced pressure and the residue was dissolved in dry DCM (0.50 mL) under N$_2$ and then pyridine (17 µL, 206 µmol) and Ac$_2$O (6.5 µL, 69 µmol) were added and the reaction mixture was stirred for 20 h. MeOH (100 µL) was added and all volatiles were evaporated under reduced pressure. The material was lyophilized to afford the title compound (20 mg, 99%) as a solid, which was used in the next step without further purification. $^1$H NMR (500 MHz, CDCl$_3$) δ 7.39-7.28 (m, 5H), 5.34-5.23 (m, 2H), 5.16-5.01 (m, 2H), 4.90 (dd, J=13.6, 6.3 Hz, 1H), 3.70-3.57 (m, 2H), 3.52-3.41 (m, 2H), 3.40-3.27 (m, 2H), 2.35-2.25 (m, 1H), 2.16 (s, 3H), 1.99-1.88 (m, 3H), 1.57-1.47 (m, 2H), 1.11-1.01 (m, 1H), 0.93-0.81 (m, 2H), 0.81-0.74 (m, 1H). MS ESI [M+H]$^+$571.2.

Step 9

[(2R,3R,4R,5S)-4-acetoxy-5-[(1S,2S,3R,5S,6R)-2-acetoxy-3,5-diazido-6-[(2R,3R,6S)-3-azido-6-[1-(benzyloxycarbonylamino)cyclopropyl]tetrahydropyran-2-yl]oxy-cyclohexoxy]-3-[(2R,3R,4R,5R,6S)-4,5-diacetoxy-3-azido-6-(azidomethyl)tetrahydropyran-2-yl]oxy -tetrahydrofuran-2-yl]methyl acetate stream. To the mixture was added ground 4 Å sieves (300 mg) and the mixture was dissolved in dry DCM (1.0 mL). The suspension was stirred at ambient temperature for 30 min, then cooled to 0° C., followed by the addition of BF$_3$·OEt$_2$ (43 µL, 351 µmol) and the mixture was stirred at ambient temperature for another 1 h. Et$_3$N (100 µL) was added and the mixture was filtered through a silica gel pad (0.30 g) and eluted with EtOAc (5.0 mL). All volatiles were evaporated under reduced pressure and the material was purified by reversed phase chromatography (C18, 12 g cartridge) with ACN and 0.1% aqueous formic acid (50-100%) to afford the title compound (25 mg, 66%) as a solid. $^1$H NMR (500 MHz, CDCl$_3$) δ 7.40-7.30 (m, 5H), 5.76 (d, J=2.8 Hz, 1H), 5.35 (d, J=2.5 Hz, 2H), 5.06 (d, J=4.0 Hz, 2H), 5.02 (t, J=2.8 Hz, 1H), 4.93 (dd, J=12.1, 6.5 Hz, 2H), 4.87 (d, J=1.8 Hz, 1H), 4.71-4.68 (m, 1H), 4.44-4.37 (m, 2H), 4.33 (td, J=6.1, 2.1 Hz, 1H), 4.21 (dd, J=12.0, 5.7 Hz,

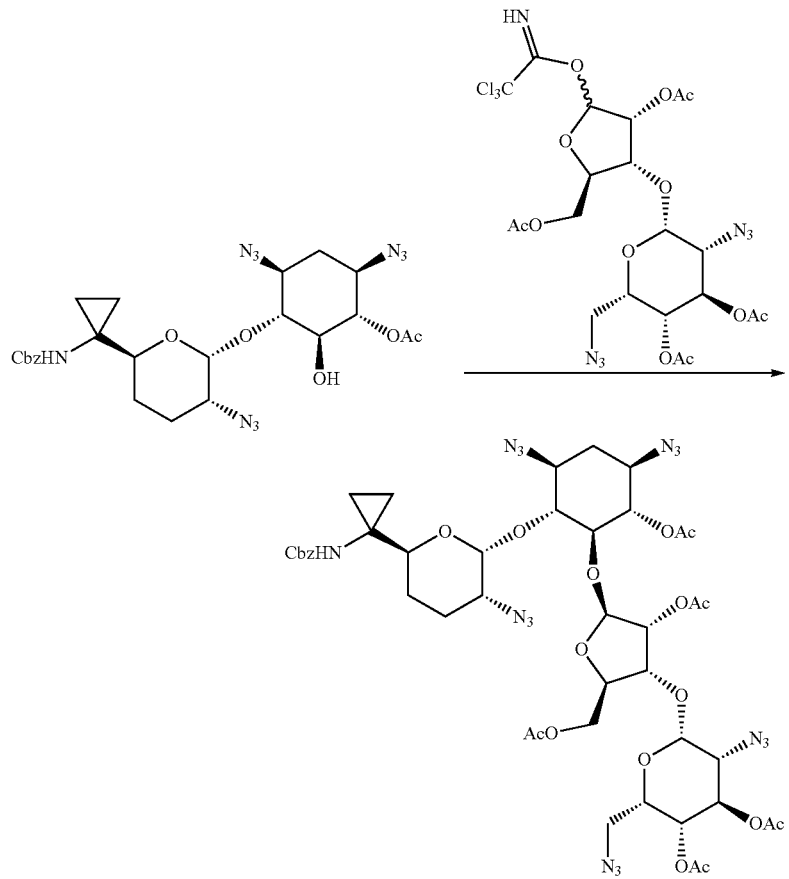

CCl$_3$CN (44 µL, 438 µmol) was added dropwise to a suspension of [(2R,3R,4R) -4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (46 mg, 87 µmol) and K$_2$CO$_3$ (36 mg, 263 µmol) in dry DCM (1.0 mL) at ambient temperature under N$_2$ and stirred for 64 h. The solution was filtered through cotton and the filtrate was concentrated under N$_2$ stream, and then dried under reduced pressure. To the crude was added [(1S,2S,3R,4S,6R)-4,6-diazido-3-[(2R,3R,6S) -3-azido-6-[1-(benzyloxycarbonylamino)cyclopropyl]tetrahydropyran-2-yl]oxy-2-hydroxy -cyclohexyl]acetate (20 mg, 35 µmol) in DCM (3.0 mL) and all volatiles were evaporated under N$_2$ 1H), 4.08 (ddd, J=8.1, 4.2, 1.8 Hz, 1H), 3.88 (t, J=8.6 Hz, 1H), 3.72 (t, J=8.7 Hz, 1H), 3.63-3.53 (m, 2H), 3.49-3.39 (m, 2H), 3.32 (s, 1H), 3.23 (dd, J=12.6, 4.3 Hz, 1H), 2.89 (dt, J=7.8, 3.1 Hz, 1H), 2.32-2.21 (m, 1H), 2.17 (s, 3H), 2.15 (s, 6H), 2.12 (s, 3H), 2.06-2.00 (m, 1H), 1.98-1.82 (m, 2H), 1.50-1.41 (m, 2H), 1.13-1.02 (m, 1H), 0.91-0.76 (m, 4H). MS ESI [M+H]$^+$1083.4.

Step 10

Benzyl N-[1-[(2S,5R,6R)-5-azido-6-[(1R,2R,3S,4R,6S)-4,6-diazido-2-[(2S,3R,4S,5R)-4-[(2R,3R,4R,5S,6S)-3-azido-6-(azidomethyl)-4,5-dihydroxy-tetrahydropyran-2-yl]oxy-

423

3-hydroxy-5-(hydroxymethyl)tetrahydrofuran-2-yl]oxy-3-hydroxy-cyclohexoxy]tetrahydropyran -2-yl]cyclopropyl]carbamate

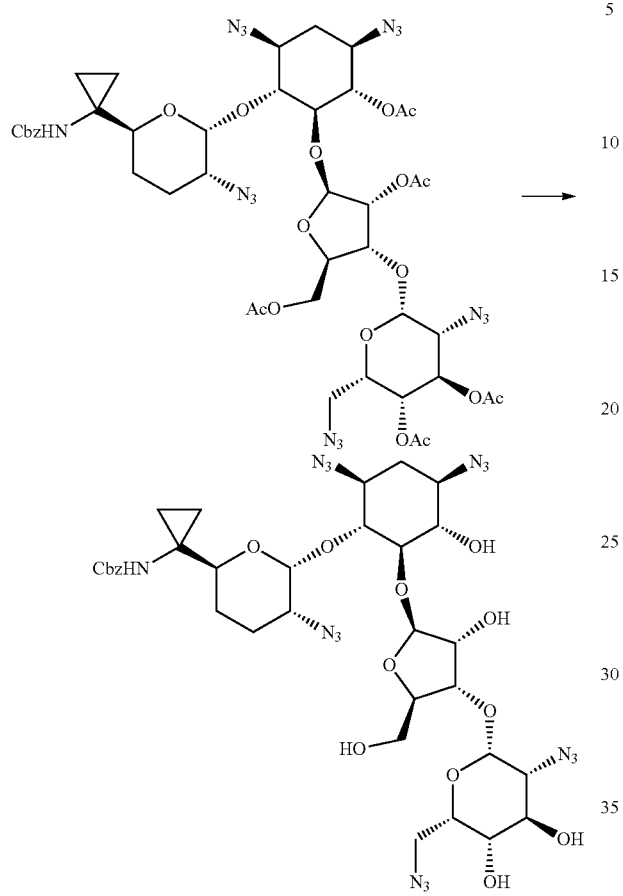

NaOMe (25 wt %, 63 µL, 277 µmol) was added dropwise to a solution of [(2R,3R,4R,5S)-4-acetoxy-5-[(1S,2S,3R,5S,6R)-2-acetoxy-3,5-diazido-6-[(2R,3R,6S)-3-azido-6-[1-(benzyloxycarbonylamino)cyclopropyl]tetrahydropyran-2-yl]oxy-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate (25 mg, 23 µmol) in MeOH (1.0 mL) at ambient temperature and stirred for 75 min. AcOH (24 µL, 416 µmol) was added dropwise and all volatiles were evaporated under reduced pressure. The material was filtered through silica gel (0.30 g) and eluted with EtOAc (6.0 mL). The filtrate was concentrated under reduced pressure and the maerial was purified by silica gel chromatography (4 g cartridge) using a gradient of 50-100% EtOAc in hexane as eluent and was further purified by supercritical fluid chromatography (Lux Cellulose-2 10×250 mm −25 ACN-EtOH −10 mL/min) to provide the title compound (8 mg, 39%) as a solid. MS ESI [M+NH$_4$]$^{+}$890.3; MS ESI [M+Na]$^{+}$895.3.

Step 11
(2S,3S,4R,5R,6R)-5-amino-2-(aminomethyl)-6-[(2R,3S,4R,5S)-5-[(1R,2R,3S,5R,6S)-3,5-diamino-2-[(2R,3R,6S)-3-amino-6-(1-aminocyclopropyl)tetrahydropyran-2-yl]oxy-6-hydroxy -cyclohexoxy]-4-hydroxy-2-(hydroxymethyl) tetrahydrofuran-3-yl]oxy-tetrahydropyran-3,4-diol;2,2,3,3,4,4,4-heptafluorobutanoic acid

424

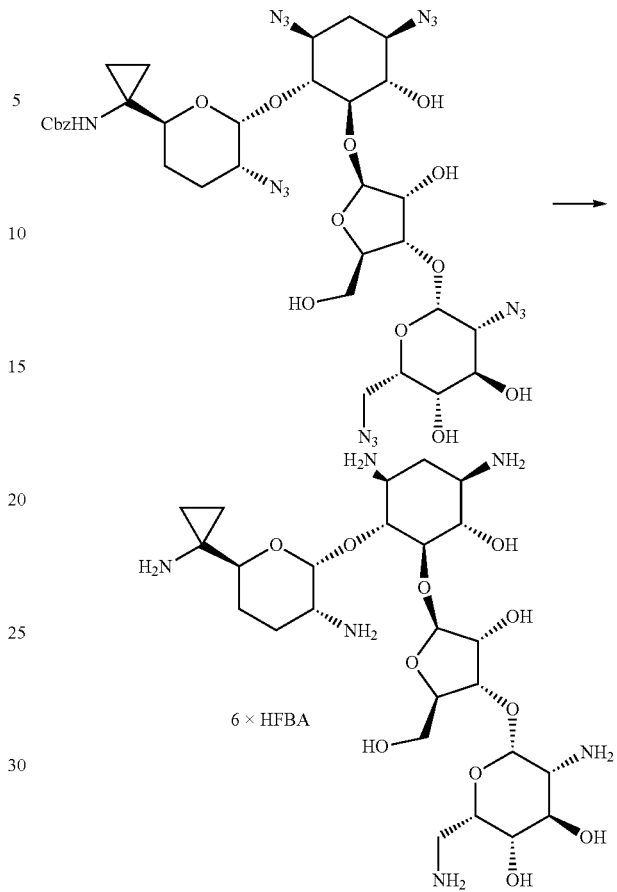

Pd(OH)$_2$/C (10 wt %, 2.6 mg, 1.8 µmol) was added to a solution of benzyl N-[1-[(2S,5R,6R)-5-azido-6-[(1R,2R,3S,4R,6S)-4,6-diazido-2-[(2S,3R,4S,5R)-4-[(2R,3R,4R,5S,6S) -3-azido-6-(azidomethyl)-4,5-dihydroxy-tetrahydropyran-2-yl]oxy-3-hydroxy-5-(hydroxymethyl)tetrahydrofuran-2-yl]oxy-3-hydroxy-cyclohexoxy]tetrahydropyran-2-yl]cyclopropyl]carbamate (8 mg, 9 µmol) in MeOH (3.0 mL) under N$_2$ at ambient temperature. H$_2$ was bubbled into the solution for 15 min and the suspension was hydrogenated for 21 h. The material was filtered through a frit (0.45 µm diameter) and the filtrate was concentrated under reduced pressure. The material was purified by a HFBA-coupled preparative HPLC to provide the title compound (hexa-HFBA salt, 10.8 mg, 62%) as a solid. $^1$H NMR (500 MHz, MeOD) δ 5.91 (d, J=3.4 Hz, 1H), 5.47 (d, J=3.0 Hz, 1H), 5.31 (d, J=1.4 Hz, 1H), 4.49 (t, J=5.3 Hz, 1H), 4.31 (dd, J=4.8, 3.1 Hz, 1H), 4.30-4.27 (m, 1H), 4.22 (td, J=5.3, 3.0 Hz, 1H), 4.17-4.10 (m, 2H), 3.99 (dd, J=12.0, 2.3 Hz, 1H), 3.91-3.83 (m, 2H), 3.74 (dd, J=12.1, 5.2 Hz, 1H), 3.70-3.66 (m, 1H), 3.66-3.60 (m, 1H), 3.55 (ddd, J=12.9, 10.4, 4.0 Hz, 1H), 3.49 (dt, J =12.9, 4.1 Hz, 1H), 3.46-3.42 (m, 1H), 3.37 (dd, J=13.4, 7.2 Hz, 1H), 3.29-3.22 (m, 2H), 2.48 (dt, J=12.4, 4.1 Hz, 1H), 2.16-2.02 (m, 2H), 1.97-1.88 (m, 1H), 1.81 (dd, J=13.3, 2.3 Hz, 1H), 1.64-1.52 (m, 1H), 1.08-0.91 (m, 4H). MS (ESI) [M+H]$^{+}$609.4.

Example 33

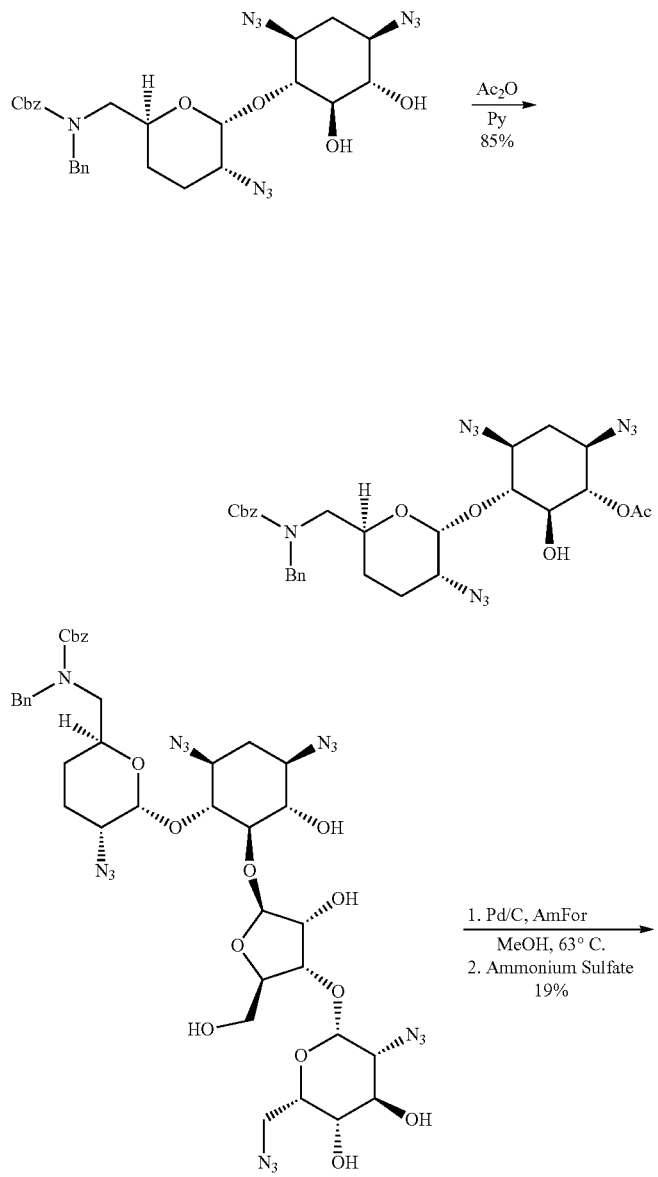

Step 1

[(1S,2S,3R,4S,6R)-4,6-diazido-3-[(2R,3R,6S)-3-azido-6-[[benzyl(benzyloxycarbonyl) amino]methyl]tetrahydropyran-2-yl]oxy-2-hydroxy-cyclohexyl]acetate

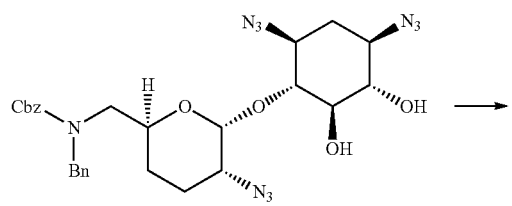

To a solution of benzyl N-[[(2S,5R,6R)-5-azido-6-[(1R,2R,3S,4R,6S)-4,6-diazido-2,3-dihydroxy-cyclohexoxy]tetrahydropyran-2-yl]methyl]-N-benzyl-carbamate (see Example 31 for synthesis, 4.4 g, 4.42 mmol) and pyridine (3.60 mL, 44.5 mmol) in dry DCM (400 mL) at room temperature was added $Ac_2O$ (3.51 mL, 37.1 mmol) and the reaction mixture was stirred for 20 h. MeOH (5 mL) was added, and the volatiles were removed under reduced pressure. The material was purified by MPLC on silica gel (220 g, liquid loading with toluene) using a gradient of 0-35% EtOAc in hexane as eluent to provide the title compound (4.0 g, 85%) as a solid. MS (ESI) [M+H]$^+$635.3.

Step 2
Benzyl ((R)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)ethyl)(benzyl)carbamate

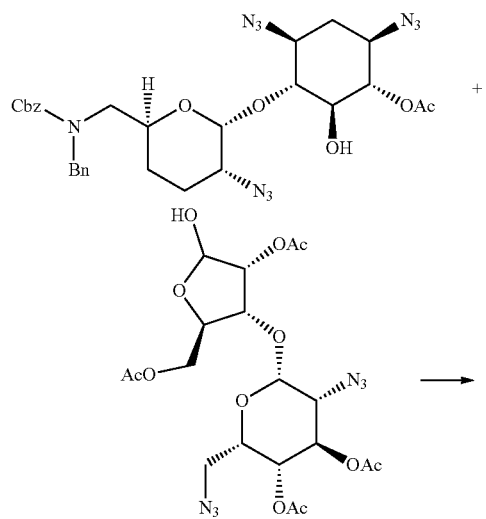

To a mixture of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (3.08 g, 5.80 mmol) and K$_2$CO$_3$ (2.79 g, 20.2 mmol) in DCM (500 mL) was added CCl$_3$CN (2.53 mL, 25.2 mmol) at room temperature. The mixture was stirred at room temperature for 18 h, then filtered on Celite, rinsed with DCM and concentrated under reduced pressure. To the above material in dry DCM (500 mL) was added [(1S,2S,3R,4S,6R)-4,6-diazido-3-[(2R,3R,6S)-3-azido-6-[(1R)-1-[benzyl(benzyloxycarbonyl)amino]ethyl]tetrahydropyran-2-yl]oxy-2-hydroxy -cyclohexyl]acetate (3.20 g, 5.04 mmol) followed by activated 3 Å sieves (5 g). The mixture was cooled to −78° C. and then BF$_3$·OEt$_2$ (1.56 mL, 12.6 mmol) was added dropwise. The acetone-dry ice bath was removed, and the reaction mixture was slowly warmed to room temperature, and then saturated NaHCO$_3$ (40 mL) was added. The separated aqueous layer was extracted with DCM (3×150 mL). The combined organic layers were washed with brine, then dried (MgSO$_4$), filtered and concentrated under reduced pressure. The residue was dissolved in MeOH (200 mL) then NaOMe (4.62 M in MeOH, 3.62 mL, 16.7 mmol) was added at room temperature and the resulting mixture was stirred for 1 h. The mixture was diluted with saturated NH$_4$Cl (300 mL) and the separated aqueous layer was extracted with DCM (3×300 mL). The combined organic layers were washed with brine, then dried (MgSO$_4$), filtered and concentrated under reduced pressure. The material was purified on C18 silica (120 g) by MPLC using a gradient of 30-100% B in A (A: 10 mm AmFor pH 3.8, B: acetonitrile) to provide the title compound (1.90 g, 41%) as a solid. MS (ESI) [M+Na]$^+$959.4.

Step 3
(2S,3S,4R,5R,6R)-5-amino-2-(aminomethyl)-6-(((2R,3S,4R,5S)-5-(((1R,2R,3S,5R,6S)-3,5-diamino-2-(((2R,3R,6S)-3-amino-6-(aminomethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H -pyran-3,4-diol tris(sulfate)

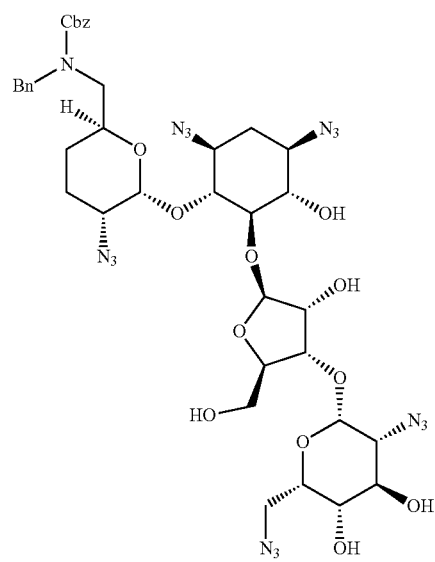

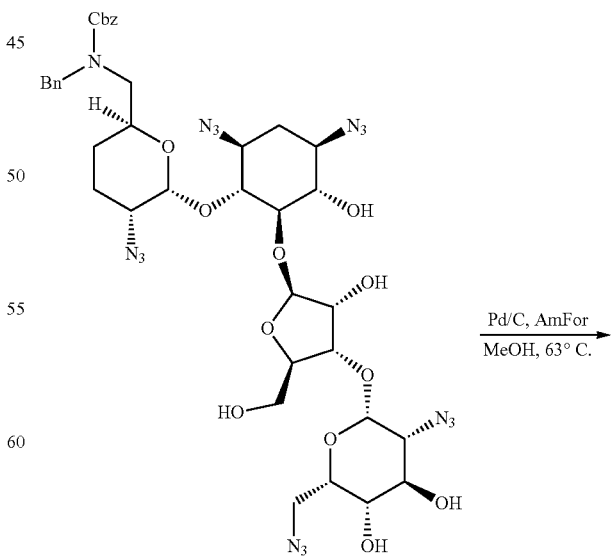

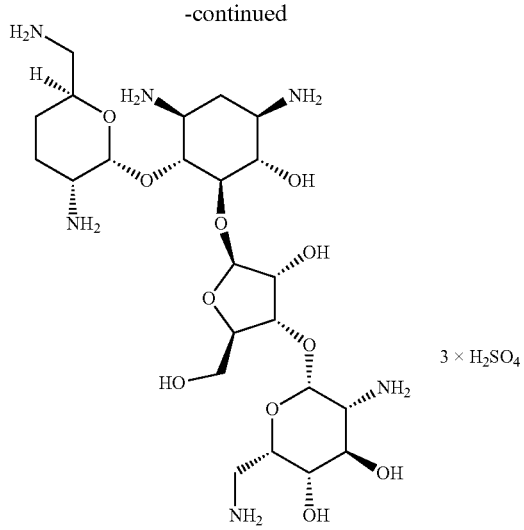

3 × H₂SO₄

Example 34

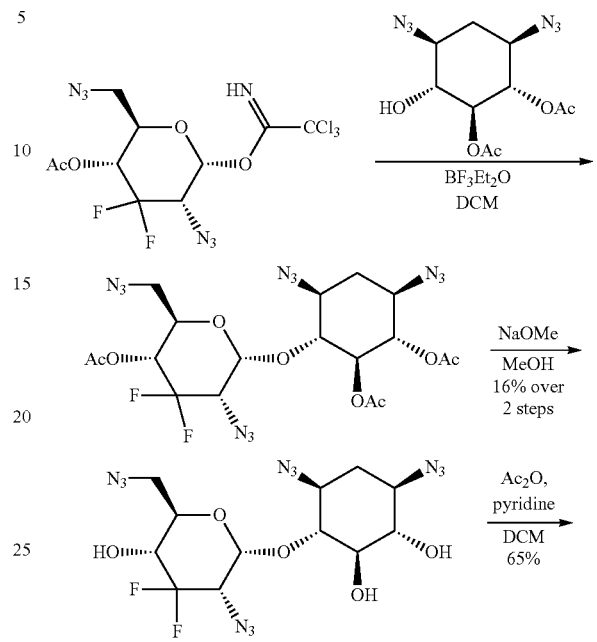

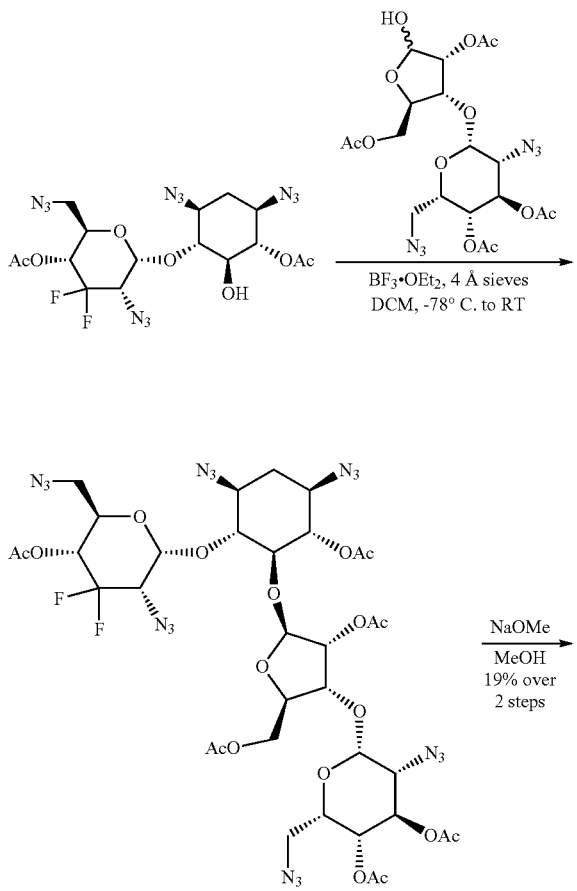

In a 2 neck flask equipped with a reflux condenser were benzyl (((2S,5R,6R)-5-azido-6-(((1R,2R,3S,4R,6S)-4,6-di-azido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl) tetrahydrofuran-2-yl)oxy)-3-hydroxycyclohexyl)oxy)tetrahydro-2H-pyran-2-yl)methyl)(benzyl) carbamate (1.60 g , 0.04 mmol) and Pd/C (10% dry on carbon, 727 mg, 0.683 mmol) following by anhydrous MeOH (500 mL). Nitrogen was bubbled for 5 min, then ammonium formate (1.62 g, 25.6 mmol) was added. The mixture was heated at 63° C. for 5 h under $N_2$, then cooled to room temperature with an ice-bath. The mixture was filtered over Celite, rinsed with MeOH and concentrated under reduced pressure. The material was purified by preparative HPLC using a gradient 27-37% B in A over 6.9 min (A: 0.3% HCOOH, 0.3% HFBA, B: 0.3% HFBA in ACN) on C18 Gemini-NX 30×150 mm provide the title compound (850 mg, 27%) as a 6×HFBA salt. The salt was dissolved in water (10 mL), then the pH was adjusted to 7 using 0.1 N aqueous $NH_4OH$. Ammonium sulfate (3 eq, 180 mg, 1.37 mmol) was then added. The mixture was stirred at room temperature for 5 min, then filtered with 0.40 μM syringe filter and added dropwise to MeOH (450 mL) under vigorous stirring. The suspension was filter on Fine frit and rinsed with MeOH (20mL). The mother liquor was discarded and the solid was dissolved in water (50 mL) and lyophilized to provide the title compound (282 mg, 19%) as a solid. $^1$H NMR (500 MHz, $D_2O$) δ 5.94 (d, J=3.6 Hz, 1H), 5.44 (d, J=2.3 Hz, 1H), 5.33 (d, J=1.7 Hz, 1H), 4.56 (dd, J=6.7, 4.8 Hz, 1H), 4.47 (dd, J=4.8, 2.3 Hz, 1H), 4.36 (ddd, J=7.0, 3.8, 1.4 Hz, 1H), 4.29-4.24 (m, 2H), 4.16 (dd, J=12.6, 6.6 Hz, 2H), 3.98-3.90 (m, 2H), 3.86-3.84 (m, 1H), 3.81-3.74 (m, 2H), 3.64-3.61 (m, 1H), 3.61-3.55 (m, 1H), 3.54-3.44 (m, 2H), 3.42-3.35 (m, 2H), 3.26 (dd, J=13.4, 3.3 Hz, 1H), 3.10 (dd, J=13.5, 8.2 Hz, 1H), 2.74-2.43 (m, 1H), 2.12-1.91 (m, 4H), 1.66-1.54 (m, 1H). MS (ESI) [M+H]⁺ 583.5.

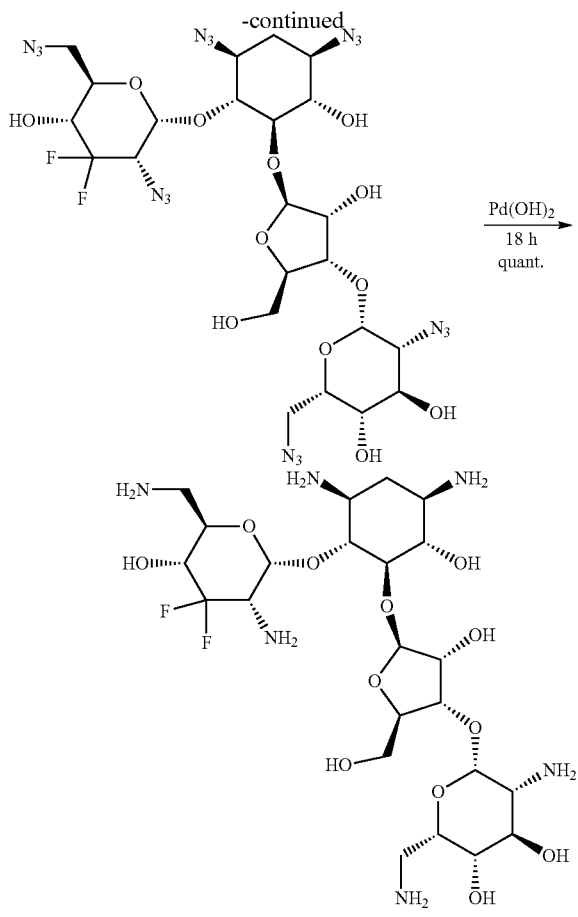

Step 1
(1S,2R,3R,4S,6R)-4,6-diazido-3-[(2R,3S,5R,6R)-3-azido-6-(azidomethyl)-4,4-difluoro-5-hydroxy-tetrahydropyran-2-yl]oxy-cyclohexane-1,2-diol

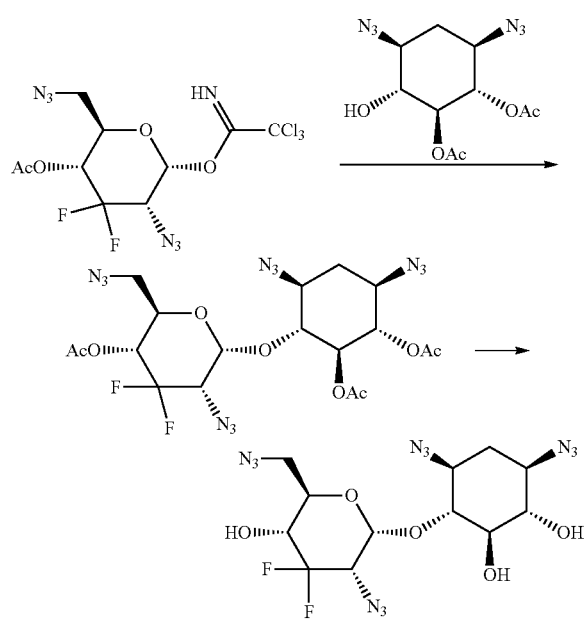

[(2R,3R,5S,6S)-5-azido-2-(azidomethyl)-4,4-difluoro-6-hydroxy-tetrahydropyran-3-yl]acetate (preparation below, 250 mg, 0.57 mmol), [(1S,2S,3R,4S,6R)-2-acetoxy-4,6-diazido-3-hydroxy-cyclohexyl]acetate (384 mg, 1.29 mmol) and grounded 4 Å molecular sieves were added to a dry round bottom flask. The mixture was dissolved in dry DCM (8.0 mL) and the suspension was stirred at ambient temperature for 45 min under $N_2$. The solution was cooled to −78° C. and then $BF_3·Et_2O$ (0.53 mL, 4.29 mmol) was added dropwise with vigorous stirring and the reaction was stirred at −78° C. for 1 h. The solution was warmed to ambient temperature and stirred for another 3 h. The reaction was quenched with saturated $NaHCO_3$ (50.0 mL) and the aqueous layer was extracted with DCM (3×50 mL). The combined organic layers were dried ($Na_2SO_4$), filtered and concentrated under reduced pressure.

Step 2

NaOMe (25 wt %, 0.56 mL, 2.58 mmol) was added dropwise to a solution of the crude in MeOH (2.0 mL) at ambient temperature. After 70 min, AcOH (0.26 mL, 4.58 mmol) was added and the volatiles were removed under reduced pressure. The material was purified by silica gel chromatography (24 g, dry loading) using a gradient of 0-40% EtOAc in hexane as eluent to provide the title compound (60.2 mg, 24%). $^1$H NMR (400 MHz, $CD_3OD$) δ 5.81 (t, J=4.2 Hz, 1H), 4.50 (ddd, J=10.1, 4.5, 2.8 Hz, 1H), 3.84-3.70 (m, 1H), 3.62-3.40 (m, 7H), 3.29 (t, J=9.5 Hz, 1H), 2.31 (dt, J=12.9, 4.4 Hz, 1H), 1.47 (dd, J=24.8, 12.2 Hz, 1H).

Step 3

[(1S,2S,3R,4S,6R)-3-[(2R,3S,5R,6R)-5-acetoxy-3-azido-6-(azidomethyl)-4,4-difluoro -tetrahydropyran-2-yl]oxy-4,6-diazido-2-hydroxy-cyclohexyl]acetate

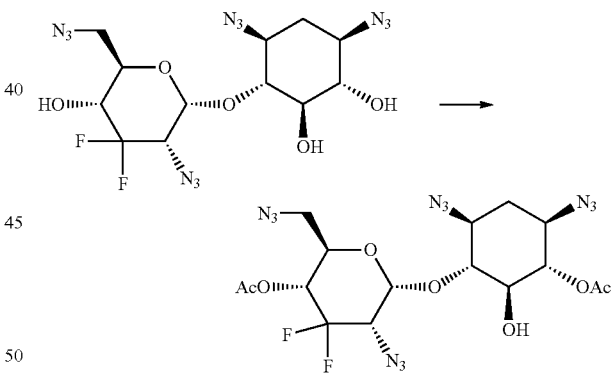

To a solution of (1S,2R,3R,4S,6R)-4,6-diazido-3-[(2R, 3S,5R,6R)-3-azido-6 -(azidomethyl)-4,4-difluoro-5-hydroxy-tetrahydropyran-2-yl]oxy-cyclohexane-1,2-diol (60 mg, 134 μmol) in dry DCM (2 mL) at ambient temperature, was added pyridine (87 μL, 1.08 mmol) followed by $Ac_2O$ (76 μL, 807 μmol) and the reaction mixture was stirred for 20 h. The volatiles were evaporated under reduced pressure and the material was purified silica gel chromatography (4 g, dry loading) using a gradient of 10-30% EtOAc in hexane as eluent to provide the title compound (56.9 mg, 80%). $^1$H NMR (400 MHz, $CDCl_3$) δ 5.53 (t, J=4.3 Hz, 1H), 5.17 (ddd, J =19.5, 10.4, 4.0 Hz, 1H), 4.86 (t, J=9.9 Hz, 1H), 4.52-4.43 (m, 1H), 3.71 (td, J=9.3, 4.2 Hz, 1H), 3.62 (dt, J=23.3, 4.2 Hz, 1H), 3.55-3.22 (m, 6H), 2.36 (dt, J=13.1, 4.3 Hz, 1H), 2.21-2.11 (m, 6H), 1.62-1.53 (m, 1H).

Step 4
[(2R,3R,4R,5S)-4-acetoxy-5-[(1S,2S,3R,5S,6R)-2-acetoxy-6-[(2R,5R,6R)-5-acetoxy-3-azido-6-(azidomethyl)-4,4-difluoro-tetrahydropyran-2-yl]oxy-3,5-diazido-cyclohexoxy]-3-[(2R,4R,5R,6S)-4,5-diacetoxy-3-azido-6-(azidomethyl) tetrahydropyran-2-yl]oxy -tetrahydrofuran-2-yl]methyl acetate

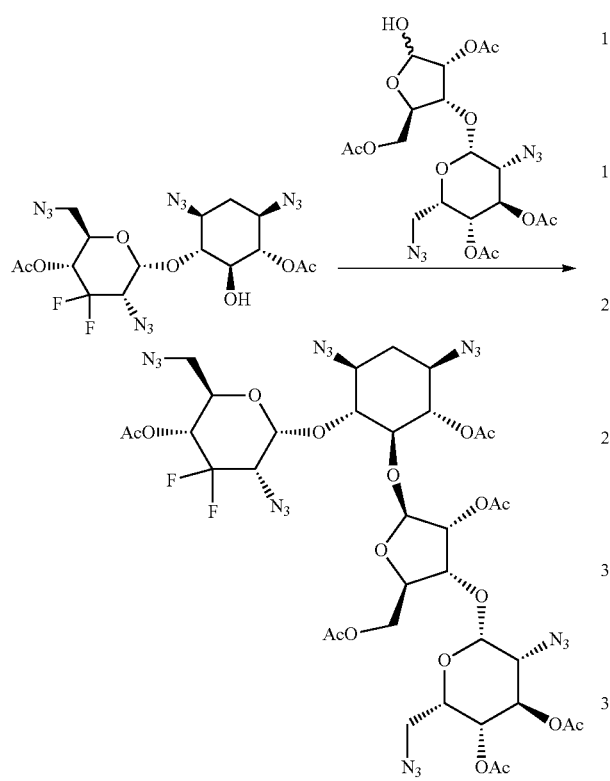

CCl₃CN (0.16 mL, 1.64 mmol) was added dropwise to a mixture of [(2R,3R,4R) -4-acetoxy-3-[(2R,3R,4R,5R,6S)-4,5-diacetoxy-3-azido-6-(azidomethyl)tetrahydropyran-2-yl] oxy-5-hydroxy-tetrahydrofuran-2-yl]methyl acetate (174 mg, 0.33 mmol) and K₂CO₃ (136 mg, 0.98 mmol) in dry DCM (10 mL) at room temperature under N₂. The mixture was stirred at room temperature for 18 h, then filtered with a filter syringe and rinsed with DCM. The filtrate was concentrated under reduced pressure and the crude imidate was used directly in the next step.

To a solution of [(1S,2S,3R,4S,6R)-3-[(2R,3S,5R,6R)-5-acetoxy-3-azido-6-(azidomethyl)-4,4-difluoro-tetrahydro-pyran-2-yl]oxy-4,6-diazido-2-hydroxy-cyclohexyl]acetate (58 mg, 0.11 mmol) in DCM (10 mL) was added the crude imidate followed by 4 Å molecular sieves and the mixture was stirred for 2 h and then cooled to −78° C. BF₃·OEt₂ (0.068 mL, 0.55 mmol) was added dropwise. The mixture was stirred at −78° C. for 2 h and then at room temperature for 2 h. The mixture was diluted with saturated NaHCO₃ (10 mL) and the separated aqueous layer was extracted with DCM (2×10 mL). The combined organic layers were washed with brine, dried (Na₂SO₄), filtered and concentrated under reduced pressure to afford the title compound. MS ESI [M+NH₄]⁺ 1060.4.

Step 5
(2S,3S,4R,5R,6R)-5-azido-2-(azidomethyl)-6-[(2R,3S,4R,5S)-5-[(1R,2R,3S,5R,6S)-3,5-diazido -2-[(2R,3S,5R,6R)-3-azido-6-(azidomethyl)-4,4-difluoro-5-hydroxy-tetrahydro-pyran-2-yl]oxy-6-hydroxy-cyclohexoxy]-4-hydroxy-2-(hydroxymethyl)tetrahydrofuran-3-yl]oxy-tetrahydropyran -3,4-diol

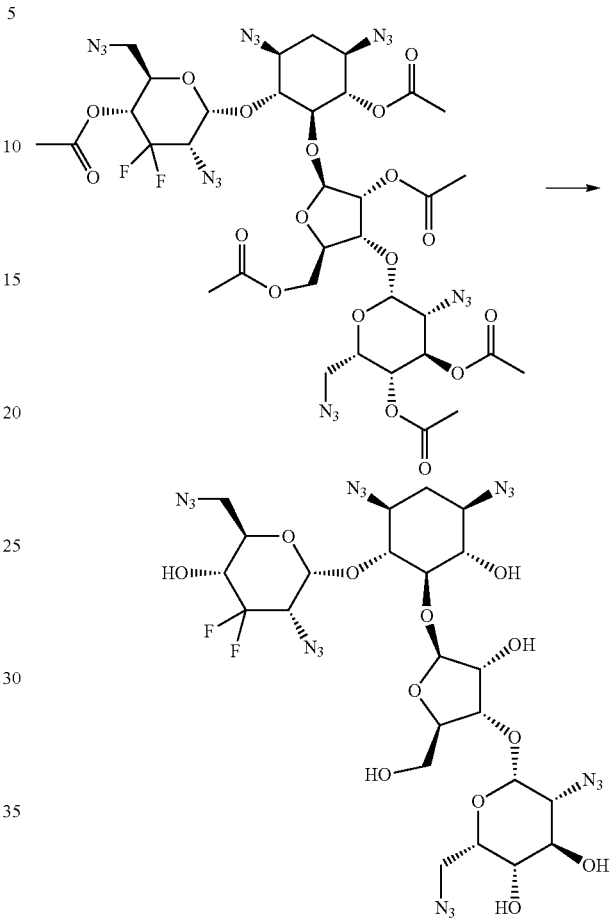

To a solution of crude [(2R,3R,4R,5S)-4-acetoxy-5-[(1S,2S,3R,5S,6R)-2-acetoxy -6-[(2R,5R,6R)-5-acetoxy-3-azido-6-(azidomethyl)-4,4-difluoro-tetrahydropyran-2-yl] oxy-3,5-diazido-cyclohexoxy]-3-[(2R,4R,5R,6S)-4,5-diacetoxy-3-azido-6-(azidomethyl)tetrahydropyran -2-yl] oxy-tetrahydrofuran-2-yl]methyl acetate (114 mg, 109 µmol) in MeOH (2 mL) at ambient temperature, was added NaOMe (25 wt %, 337 µL, 1.31 mmol) dropwise and the reaction mixture was stirred for 50 min. The mixture was diluted with AcOH (125 mL, 2.18 mmol) and the volatiles were evaporated under reduced pressure. The material was purified by silica gel chromatography (12 g cartridge) using a gradient of 5-35% EtOAc and hexane as eluent and was further purified by reverse phase (C18, 120 g Biotage) using 50% B in A to 100% B (B=ACN 0.1% HCOOH, A=H₂O 0.1% HCOOH) to provide the title compound. The material purified with preparative HPLC (ACN, AmFor, CSH column) to give the title compound (16 mg, 19%, 2 steps from [(1S,2S,3R,4S,6R)-3-[(2R,3S,5R,6R)-5-acetoxy-3-azido-6-(azidomethyl)-4,4-difluoro-tetrahydropyran-2-yl]oxy-4,6-diazido-2-hydroxy-cyclohexyl]acetate). ¹H NMR (400 MHz, CD₃OD) δ 5.92 (t, J=4.1 Hz, 1H), 5.32 (d, J=2.0 Hz, 1H), 5.10 (d, J=1.8 Hz, 1H), 4.46 (ddd, J=10.2, 4.7, 2.6 Hz, 1H), 4.37 (dd, J=6.6, 4.6 Hz, 1H), 4.29 (dd, J=4.5, 2.0 Hz, 1H), 4.11 (td, J=6.1, 2.7 Hz, 1H), 3.99 (ddd, J=8.5, 4.4, 1.9 Hz, 1H), 3.90 (t, J=3.4 Hz, 1H), 3.82 (dd, J=11.9, 2.7 Hz, 1H), 3.74-3.29 (m, 14H), 2.23 (dt, J=12.8, 4.0 Hz, 1H), 1.46-1.32 (m, 1H). MS ESI [M+NH$_4$]$^{+808.2}$.

Step 6

(2S,3S,4R,5R,6R)-5-amino-2-(aminomethyl)-6-[(2R,3S,4R,5S)-5-[(1R,2R,3S,5R,6S)-3,5-diamino-2-[(2R,3S,5R,6R)-3-amino-6-(aminomethyl)-4,4-difluoro-5-hydroxy-tetrahydropyran -2-yl]oxy-6-hydroxy-cyclohexoxy]-4-hydroxy-2-(hydroxymethyl)tetrahydrofuran-3-yl]oxy -tetrahydropyran-3,4-diol

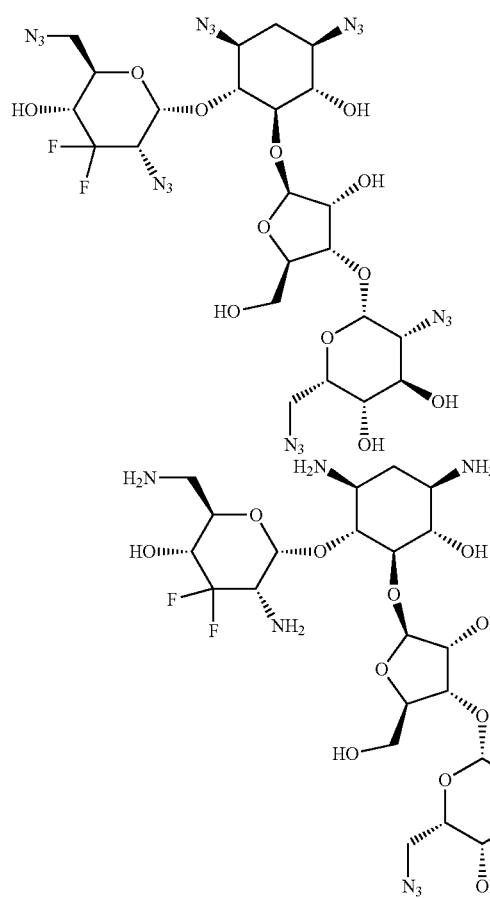

To (2S,3S,4R,5R,6R)-5-azido-2-(azidomethyl)-6-[(2R,3S,4R,5S)-5-[(1R,2R,3S,5R,6S)-3,5-diazido-2-[(2R,3S,5R,6R)-3-azido-6-(azidomethyl)-4,4-difluoro-5-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol (8.0 mg, 10.1 µmol) under N$_2$ at ambient temperature was added Pd(OH)$_2$/C (10 wt %, 5.0 mg, 3.5 µmol) followed by MeOH (3.0 mL) and the resulting suspension was bubbled with H$_2$ for 10 min. The mixture was hydrogenated under hydrogen atmosphere (1 atm, balloon) for 16 h. The suspension was filtered through a nylon filter (0.45 µm), rinsed with MeOH and the filtrate was concentrated under reduced pressure to give the title compound. The procedure was repeated to give the title compound (9.5 mg with 74% yield in total). $^1$H NMR (500 MHz, CD$_3$OD) δ 5.72 (s, 1H), 5.38 (d, J=2.1 Hz, 1H), 4.97 (d, J=1.6 Hz, 1H), 4.45 (dd, J=6.6, 5.0 Hz, 1H), 4.19 (dd, J=4.9, 2.2 Hz, 1H), 4.09 (dd, J=6.7, 3.3 Hz, 1H), 4.00-3.93 (m, 2H), 3.89 (dd, J=12.2, 5.4 Hz, 1H), 3.83 (dd, J=12.3, 2.8 Hz, 1H), 3.74 (dd, J=12.2, 3.6 Hz, 1H), 3.63 (t, J=9.2 Hz, 2H), 3.54-3.49 (m, 2H), 3.26 (t, J=9.5 Hz, 1H), 3.22-3.10 (m, 3H), 3.02 (s, 1H), 2.96 (dd, J=13.3, 3.8 Hz, 1H), 2,86 (dt, J=17.5. 8.7 Hz, 2H), 2.73-2.66 (m, TH), 2.00 (dt, J=12.9, 4.1 Hz, 1H), 1.28 (m, 1H). MS ESI [M+H]$^+$635.4.

Preparation of [(2R,3R,5S,6S)-5-azido-2-(azidomethyl)-4,4-difluoro-6-hydroxy-tetrahydropyran -3-yl]acetate

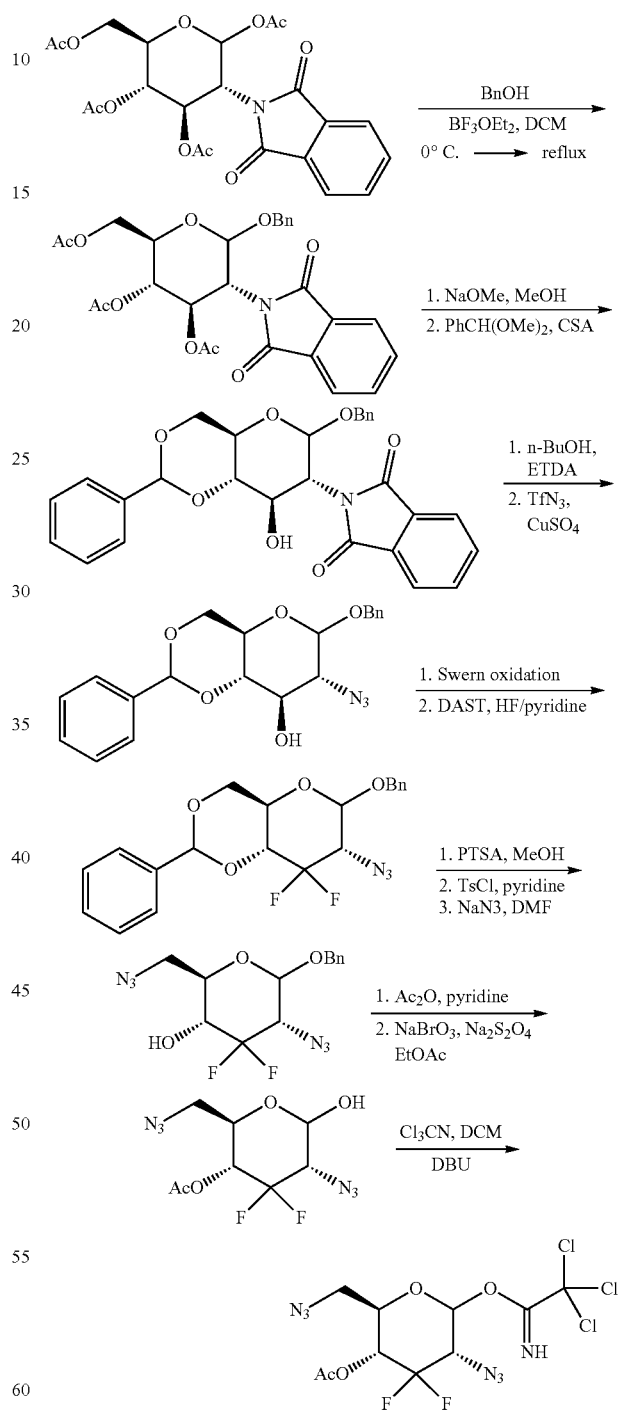

Step 1

(2R,3S,4R,5R)-(acetoxymethyl)-6-(benzyloxy)-5-(1,3-dioxoisoindolin-2-yl)tetrahydro-2H -pyran-3,4-diyl diacetate

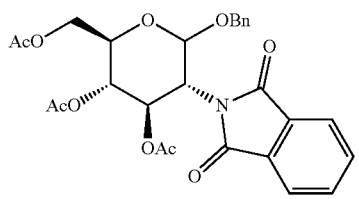 [SMILES: CC(=O)OC[C@H]1OC(OCc2ccccc2)[C@H](N2C(=O)c3ccccc3C2=O)[C@@H](OC(C)=O)[C@@H]1OC(C)=O]

To a solution of 23 g (3R,4R,5S,6R)-6-(acetoxymethyl)-3-(1,3-dioxoisoindolin-2-yl)tetrahydro-2H-pyran-2,4,5-triyl triacetate and 10.4 g of benzyl alcohol in 100 mL of anhydrous DCM was added 29.7 mL of $BF_3 \cdot OEt_2$ at 0° C. The temperature was raised to 35° C. and stirred for 12 hours until completion. The reaction was diluted with 250 mL of DCM and washed with 2×250 mL ice cold water and 1×250 mL aqueous sodium bicarbonate. The organic layer was dried, filtered, concentrated and purified by flash chromatography to yield 22.3 g of (3R,4R,5S,6R)-6-(acetoxymethyl)-3-(1,3-dioxoisoindolin-2-yl)tetrahydro-2H-pyran-2,4,5-triyltriacetate (88% yield).

Step 2
2-((4aR,7R,8R,8aS)-6-(benzyloxy)-8-hydroxy-2-phenylhexahydropyrano[3,2-d][1,3]dioxin-7-yl)isoindoline-1,3-dione

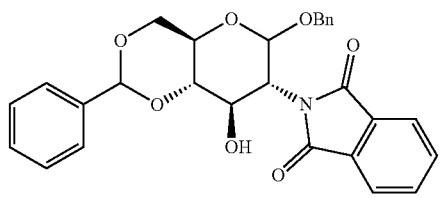

A solution of 55 g of (2R,3S,4R,5R)-2-(acetoxymethyl)-6-(benzyloxy)-5-(1,3-dioxoisoindolin-2-yl)tetrahydro-2H-pyran-3,4-diyl diacetate in 500 mL of methanol/DCM (3:2) was cooled to −10° C. 160 mL of 0.3 M sodium methoxide (in methanol) was added and the reaction continued stirring at 0° C. for two hours. The reaction was neutralized with amberlyst resin, filtered and concentrated. The concentrated residue was dissolved in 500 mL acetonitrile and 23.75 g of benzaldehyde dimethyl acetal was added, followed by 3.6 g of CSA. The reaction stirred at room temperature for one hour until completion. The reaction was quenched with triethylamine, concentrated and purified by flash chromatography (20% EtOAc in hexanes) to afford 2-((4aR,7R,8R,8aS)-6-(benzyloxy)-8-hydroxy-2-phenylhexahydropyrano [3,2-d][1,3]dioxin-7-yl)isoindoline-1,3-dione (78% yield).

Step 3
(4aR,7R,8R,8aS)-7-azido-6-(benzyloxy)-2-phenylhexahydropyrano[3,2-d][1,3]dioxin-8-ol

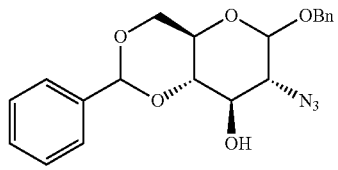

2-((4aR,7R,8R,8aS)-6-(benzyloxy)-8-hydroxy-2-phenylhexahydropyrano[3,2-d][1,3]dioxin-7-yl)isoindoline-1,3-dione was dissolved in n-BuOH and ethylene diamine. The solution was heated to 90° C. for 12 hours. The reaction was concentrated in vacuo, taken up in EtOAc, and washed with an equal volume of water. The organic layer was concentrated and used in the next step without further purification. 5 grams of the crude intermediate was added to a solution of 300 mL of water/methanol (1:2) containing 100 mg $CuSO_4$ and 3.85 g $K_2CO_3$. To the mixture was added 5 equivalents of $TfN_3$ in DCM at room temperature for 12 hours. 10 g of glycine was then added and the reaction stirred an additional 12 hours. The solid was filtered and washed with methanol. The filtrate was concentrated to 40% original volume and additional precipitate formed and was filtered and dissolved in DCM and dried over sodium sulfate. The dried organic portion was filtered and concentrated to yield pure (4aR,7R,8R,8aS)-7-azido-6-(benzyloxy)-2-phenylhexahydropyrano [3,2-d][1,3]dioxin-8-ol (92% yield).

Step 4
(4aR,7S,8aR)-7-azido-6-(benzyloxy)-8,8-difluoro-2-phenylhexahydropyrano[3,2-d][1,3]dioxine

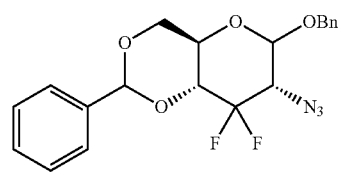

To a solution of 500 mg of (4aR,7R,8R,8aS)-7-azido-6-(benzyloxy)-2-phenylhexahydropyrano [3,2-d][1,3]dioxin-8-ol in 5 mL of DCM was added 520 μL of DAST and 15 μL of HF/Py at 0° C. and the reaction was refluxed until completion. The reaction was quenched with aqueous $NaHCO_3$ at 0° C. and the diluted with DCM. The organic layer was washed with aqueous $NaHCO_3$, dried, filtered and concentrated. The crude thus obtained was purified by column chromatography to yield 183 mg of (4aR,7S,8aR)-7-azido-6-(benzyloxy)-8,8-difluoro-2-phenylhexahydropyrano[3,2-d][1,3]dioxine (36% yield).

Step 5
(2R,3R,5S)-5-azido-2-(azidomethyl)-6-(benzyloxy)-4,4-difluorotetrahydro-2H-pyran-3-ol

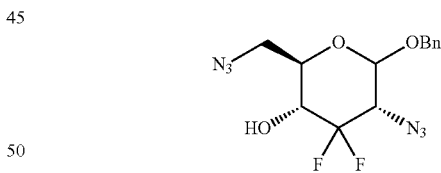

3.4 g of (4aR,7S,8aR)-7-azido-6-(benzyloxy)-8,8-difluoro-2 -phenylhexahydropyrano[3,2-d][1,3]dioxine was dissolved in 20 mL of methanol and 219 mg of p-toluene sulfonic acid was added. The reaction was heated at 40° C. for 1 hour until completion. The reaction was quenched with 0.1 equivalents of $Et_3N$ and concentrated to dryness. The crude was purified by flash chromatography. 2.5 g of the diol was dissolved in 24 mL of DCM/pyridine (5:3) and 1.80 g of tosyl chloride was added at 0° C. The reaction was allowed to warm to room temperature and stirred for 3 hours, then diluted with DCM and washed with 1 N HCl and saturated aqueous $NaHCO_3$. The organic portion was dried, filtered and concentrated to dryness. The crude concentrate was dissolved in 30 mL of anhydrous DMF and 2.3 g of $NaN_3$ and the reaction heated at 70° C. for several hours.

The reaction was then diluted into EtOAc and washed with water. The organic portion was dried, filtered, concentrated and purified by flash chromatography to yield 2.2 g of (2R,3R,5S)-5-azido-2-(azidomethyl)-6-(benzyloxy)-4,4-difluorotetrahydro-2H-pyran-3-ol (77% yield).

Step 6
(2R,3R,5S)-5-azido-2-(azidomethyl)-6-(benzyloxy)-4,4-difluorotetrahydro-2H-pyran-3-yl acetate

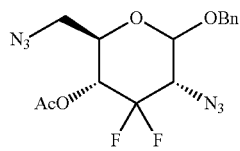 [SMILES: [N-]=[N+]=NC[C@H]1OC(OCc2ccccc2)[C@H](N=[N+]=[N-])C(F)(F)[C@@H]1O]

(2R,3R,5S)-5-azido-2-(azidomethyl)-6-(benzyloxy)-4,4-difluorotetrahydro-2H -pyran-3-ol was dissolved in pyridine and cooled to 0° C. in an ice water bath. Acetic anhydride was added and the reaction was allowed to warm to room temperature and stir overnight. The reaction was then concentrated in vacuo, dissolved in EtOAc, and washed with 1 N HCl aq and NaHCO₃, then dried, filtered and concentrated. 100 mg of the crude was dissolved in 3.8 mL of EtOAc and 3 mL of aqueous sodium bromate (179 mg/3 mL) added in one portion. Next aqueous sodium dithionate (212 mg/6 mL) was added dropwise and the reaction stirred vigorously until completion. The reaction was diluted with EtOAc and washed with 1:1 aqueous NaHCO₃ and sodium thiosulfate. The organic layer was dried, filtered and concentrated, then purified by flash chromatography (20% EtOAc in Hexanes) to yield 70 mg of (2R,3R,5S)-5-azido-2-(azidomethyl)-6-(benzyloxy)-4,4-difluorotetrahydro-2H-pyran-3-yl acetate (93% yield).

Step 7
(2R,3R,5S)-5-azido-2-(azidomethyl)-4,4-difluoro-6-hydroxytetrahydro-2H-pyran-3-yl acetate

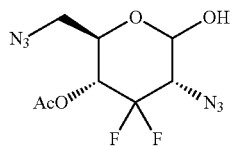 [SMILES: CC(=O)O[C@@H]1[C@@H](CN=[N+]=[N-])OC(O)[C@H](N=[N+]=[N-])C1(F)F]

1.4 grams of (2R,3R,5S)-5-azido-2-(azidomethyl)-6-(benzyloxy)-4,4-difluorotetrahydro-2H-pyran-3-yl acetate was dissolved in 54 mL EtOAc. 42 mL of aqueous sodium bromate (60 mg/mL) was added at once to the EtOAc solution, followed by 84 mL of aqueous sodium dithionate (35.3 mg/mL) was added slowly dropwise over 15 min and stirred vigorously until completion. The reaction was diluted with EtOAc and washed with 1:1 aq NaHCO₃ and sodium thiosulfate. The organic layer was concentrated and purified by flash column chromatography to afford 1 g of (2R,3R,5S)-5-azido-2-(azidomethyl)-4,4-difluoro-6-hydroxytetrahydro-2H-pyran-3-yl acetate (94% yield).

Step 8
(2R,3R,5S,6S)-5-azido-2-(azidomethyl)-4,4-difluoro-6-(2,2,2-trichloro-1-iminoethoxy) tetrahydro-2H-pyran-3-yl acetate

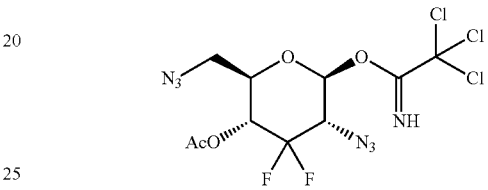

To a solution of 700 mg of (2R,3R,5S)-5-azido-2-(azidomethyl)-4,4-difluoro-6 -hydroxytetrahydro-2H-pyran-3-yl acetate in 25 mL of anhydrous DCM was added 720 µL of trichloroacetonitrile at 0° C. To this solution, 103 µL of DBU was slowly added at the same temperature. The reaction was stirred until completion at room temperature. The reaction was diluted with DCM and washed with 1 N HCl, brine and the organic layer was concentrated. The crude thus obtained was purified by flash column chromatography (20% EtOAc in hexanes) to afford 750 mg of (2R,3R,5S,6S)-5-azido-2-(azidomethyl)-4,4-difluoro-6-(2,2,2-trichloro-1-iminoethoxy) tetrahydro-2H-pyran-3-yl acetate (75% yield).

Example 35

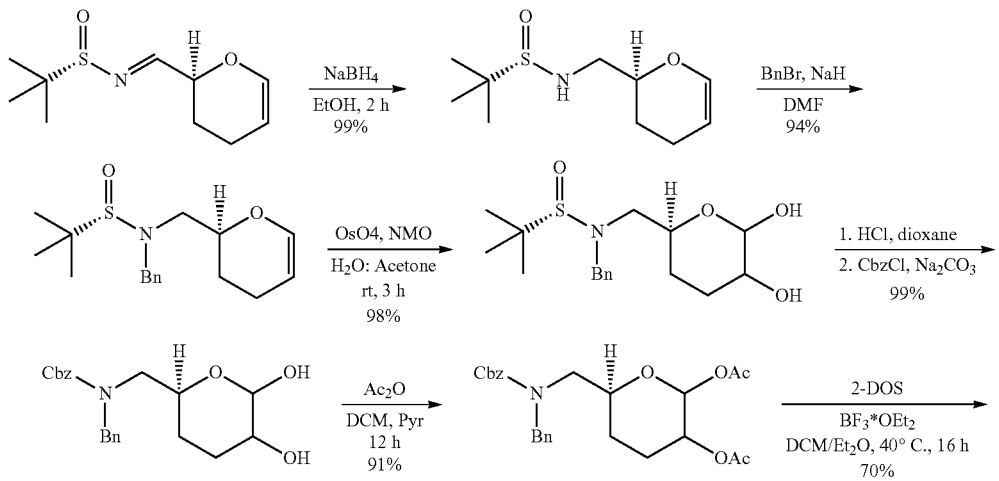

441 442
-continued
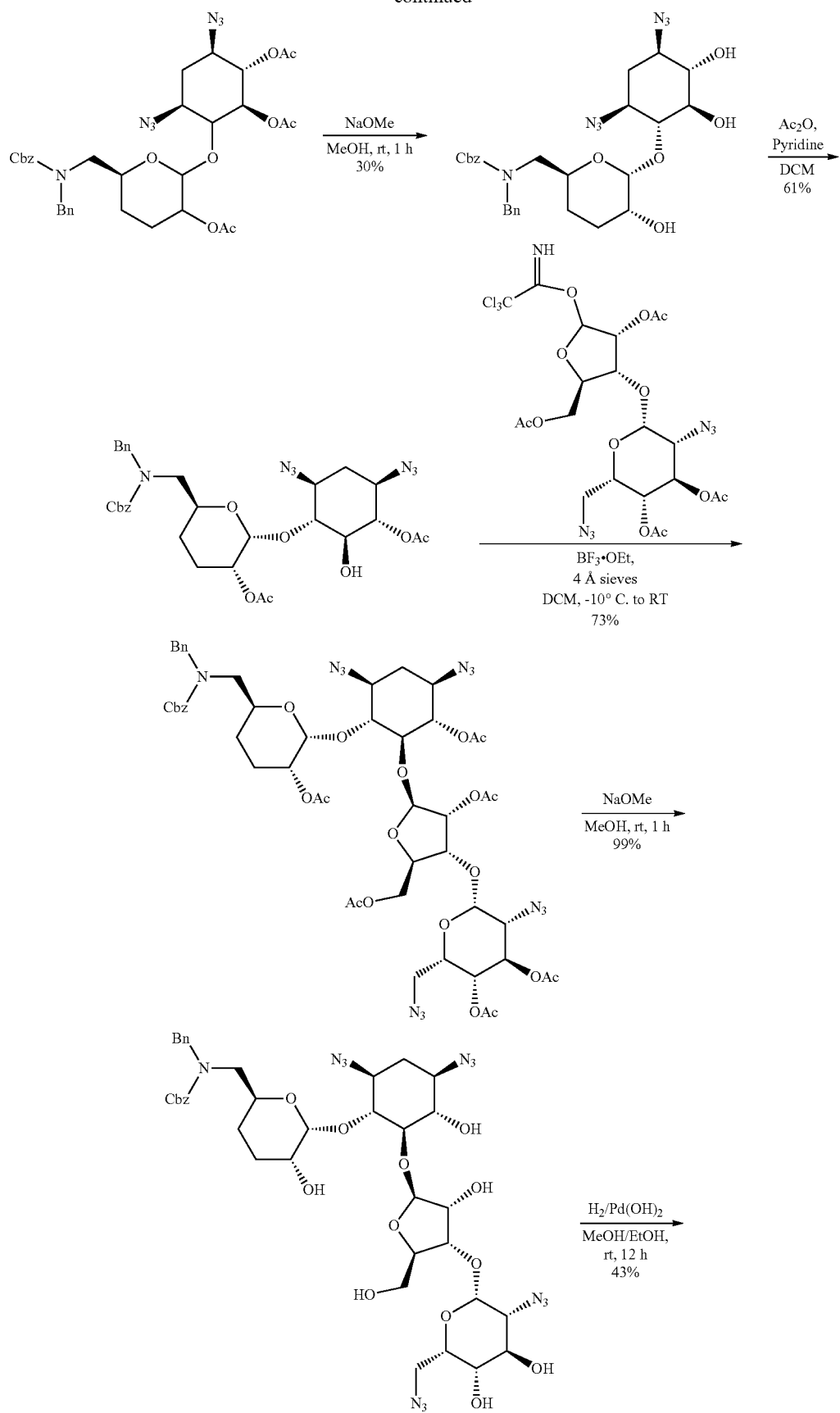

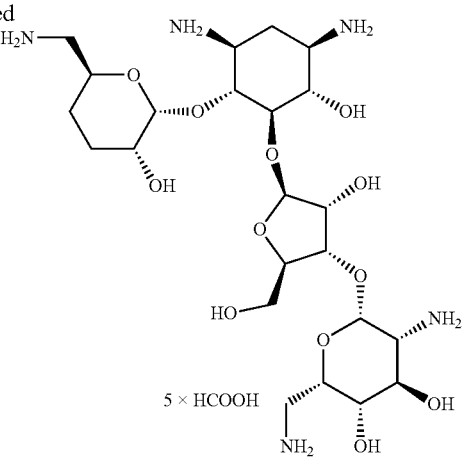

5 × HCOOH

Step 1
(S)-N-[[(2S)-3,4-dihydro-2H-pyran-2-yl]methyl]-2-methyl-propane-2-sulfinamide

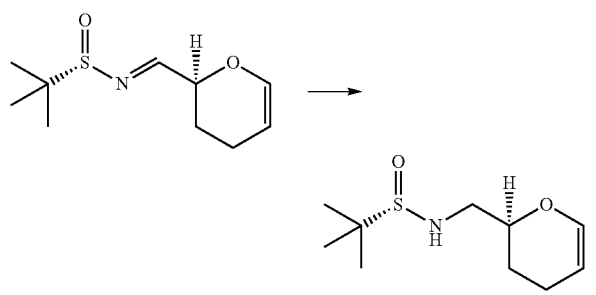

To a solution of (NE,S)-N-[[(2S)-3,4-dihydro-2H-pyran-2-yl]methylene]-2-methyl-propane-2-sulfinamide (3.00 g, 13.9 mmol) in ethanol (60.0 mL) at 0° C., was added NaBH$_4$ (0.527 g, 13.9 mmol) and the ice bath was removed and the reaction mixture was stirred 30 min. The reaction was cooled to 0° C. and saturated NH$_4$Cl (40.0 mL) was added (CAUTION: gas evolution). The volatiles were evaporated under reduced pressure and the residue was extracted with EtOAc (3×40.0 mL). The combined organic layers were dried (Na$_2$SO$_4$), filtered and concentrated under reduced pressure to provide the title compound (3.00 g, 99%) as a solid, which was in the next step without further purification. MS (ESI) [M+H]$^+$218.0.

Step 2
(S)-N-benzyl-N-[[(2S)-3,4-dihydro-2H-pyran-2-yl]methyl]propane-2-sulfinamide

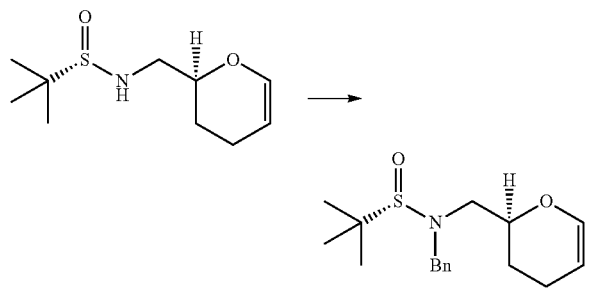

NaH (60%, 0.635 g, 15.9 mmol) was added to a mixture of (S)-N-[[(2S)-3,4-dihydro-2H-pyran-2-yl]methyl]-2-methyl-propane-2-sulfinamide (3.00 g, 13.8 mmol) and BnBr (2.46 mL, 20.7 mmol) in DMF (10.0 mL) at 0° C. and the reaction mixture was stirred at room temperature for 3 h. The mixture was cooled to 0° C. and then water was added (20.0 mL). The aqueous layer was extracted with EtOAc (3×25.0 mL) and the combined organic layers were washed with water (5×20.0 mL), then dried (Na$_2$SO$_4$), filtered and concentrated under reduced pressure. The material was purified by silica gel chromatography (80 g cartridge) using a gradient of EtOAc and hexane (0-40%) to afford the title compound (4.00 g, 94%) as an oil. MS (ESI) [M+Na]$^+$330.2.

Step 3
(S)-N-benzyl-N-[[(2S)-5,6-dihydroxytetrahydropyran-2-yl]methyl]-2-methyl-propane-2-sulfinamide

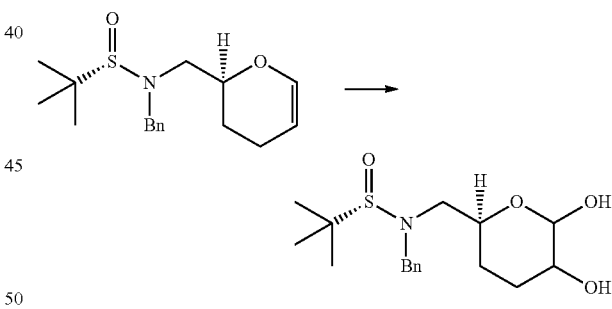

O$_s$O$_4$ (4% solution in water, 3.91 mL, 0.615 mmol) was added to a solution of (S)-N-benzyl-N-[[(2S)-3,4-dihydro-2H-pyran-2-yl]methyl]propane-2-sulfinamide (3.78 g, 12.3 mmol) and NMO (2.97 g, 24.6 mmol) in a mixture acetone and H$_2$O (100 mL, 5:1) at ambient temperature and the reaction mixture was stirred at room temperature for 3 h. The volatiles were removed under reduced pressure (CAUTION: O$_s$O$_4$ is volatile) and the residue was diluted with saturated solution of sodium thiosulfate (200 mL). The aqueous layer was then extracted with EtOAc (3×100 mL). The combined organic layers were dried (Na$_2$SO$_4$), filtered and evaporated under reduced pressure. The material was purified by silica gel chromatography (80 g cartridge) using a gradient of EtOAc and hexane (10-50%) as eluent to produce the title compound (mixture of diastereomers) (4.10 g, 98%) as an oil. MS (ESI) [M+Na]$^+$364.9.

Step 4

Benzyl N-benzyl-N-[[(2S)-5,6-dihydroxytetrahydropyran-2-yl]methyl]carbamate

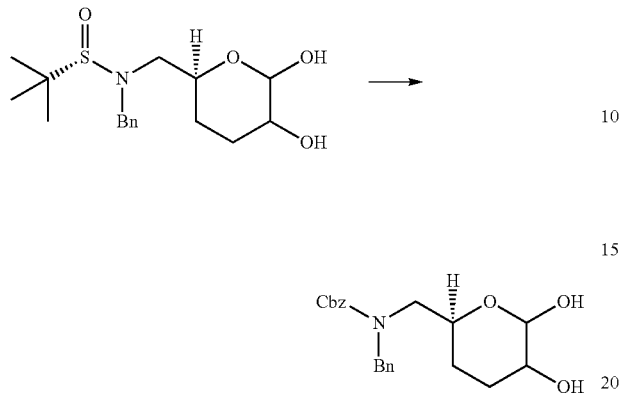

Aqueous HCl (1.0 M, 74.4 mL, 72.4 mmol) was dropwise added to a solution of N-benzyl-N-[[(2S)-5,6-dihydroxytetrahydropyran-2-yl]methyl]-2-methyl-propane-2 sulfinamide (4.10 g, 12.0 mmol) in dioxane (100.0 mL) with vigorous stirring. After 1 h, solid $Na_2CO_3$ (10.2 g, 96.1 mmol) was added. After another 10 min, CbzCl (2.89 mL, 20.3 mmol) was added dropwise and the reaction mixture was stirred for 3 h. The volatiles were evaporated, and the residue was partitioned in between EtOAc (150 mL) and $H_2O$ (150 mL). The layers were separated, and the organic phase was dried ($Na_2SO_4$), filtered and concentrated under reduced pressure. The material was purified by silica gel chromatography (120 g cartridge) using a gradient of ethyl acetate in hexane (0-40%) as eluent to afford the title compound (diastereomers, 4.40 g, 99%) as an oil. MS (ESI) [M+Na]$^+$394.8.

Step 5

[(6S)-2-acetoxy-6-[[benzyl(benzyloxycarbonyl)amino]methyl]tetrahydropyran-3-yl]acetate

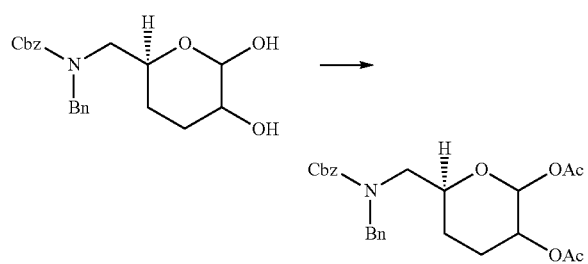

To a solution of benzyl N-benzyl-N-[[(2S)-5,6-dihydroxytetrahydropyran-2-yl]methyl]carbamate (4.40 g, 11.8 mmol) in a mixture pyridine (10 mL) and DCM (75.0 mL) at 0° C., was added acetic anhydride (5.60 mL, 59.2 mmol) and the reaction mixture was stirred at room temperature for 48 h. The mixture was diluted with 5% of sulfuric acid (100 mL) and the aqueous layer was extracted with EtOAc (3×100 mL). The combined organic layers were dried ($Na_2SO_4$), filtered and concentrated under reduced pressure. The material was purified by silica gel chromatography (120 g cartridge) using a gradient ethyl acetate of hexane (0-30%) as eluent to afford the title compound (diastereomers, 4.90 g, 91%) as an oil. MS (ESI) [M+Na]$^+$478.8.

Step 6

[(2R,3R,6S)-6-[[benzyl(benzyloxycarbonyl)amino]methyl]-2-[(1R,2S,3S,4R,6S)-2,3-diacetoxy -4,6-diazido-cyclohexoxy]tetrahydropyran-3-yl]acetate

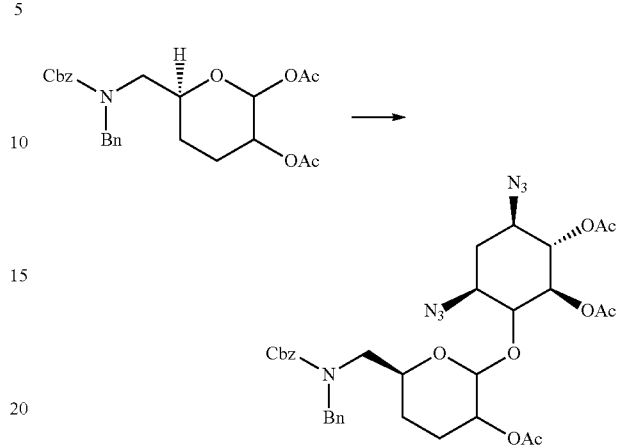

A microwave tube was charged with [(6S)-2-acetoxy-6 -[[benzyl(benzyloxycarbonyl)amino]methyl]tetrahydropyran-3-yl]acetate (0.70 g, 0.154 mmol), [(1S,2S,3R,4S,6R)-2-acetoxy-4,6-diazido-3-hydroxy-cyclohexyl]acetate (0.504 g, 1.69 mmol) and 4 Å molecular sieves (3.00 g) and then a mixture of solvent (DCM/Ether; 5:1, 10.0 mL) was added followed $BF_3 \cdot Et_2O$ (0.948 mL, 7.68 mmol). The reaction mixture was stirred at 50° C. for 24 h. The mixture was quenched with saturated $NaHCO_3$, and the aqueous layer was extracted with DCM (3×20.0 mL). The organic combined layers were dried ($Na_2SO_4$), filtered and concentrated under reduced pressure. The material was purified by silica gel chromatography (180 g) using a gradient of ethyl acetate in hexane (0-50%) as eluent to provide the title compound (0.750 g, 70%) as mixture of diastereomers. MS (ESI) [M+Na]$^+$716.1.

Step 7

Benzyl N-benzyl-N-[[(2S,5R,6R)-6-[(1R,2R,3S,4R,6S)-4,6-diazido-2,3-dihydroxy -cyclohexoxy]-5-hydroxy-tetrahydropyran-2-yl]methyl]carbamate

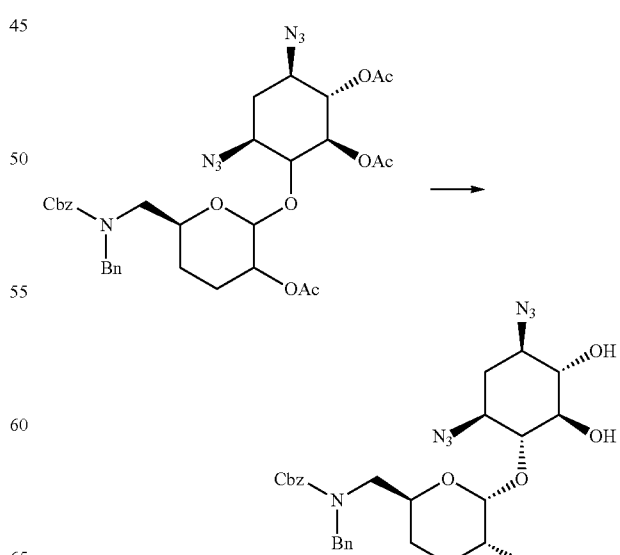

NaOMe (25 wt %, 1.59 mL, 5.54 mmol) was added dropwise to a solution of [(2R,3R,6S)-6-[[benzyl(benzyloxycarbonyl)amino]methyl]-2-[(1R,2S,3S,4R,6S)-2,3-diacetoxy -4,6-diazido-cyclohexoxy]tetrahydropyran-3-yl]acetate (0.640 g, 0.923 mmol) in MeOH (25.0 mL) at ambient temperature and the reaction mixture was stirred for 60 min. The mixture was neutralized by AcOH (0.950 mL, 16.6 mmol) and the volatiles were removed under reduced pressure. The material was purified by silica gel chromatography (120 g) using a mixture MeOH (2%) in DCM as eluent to afford the title compound (second eluting, 156 mg, 30%) as an oil. Note: three spots appeared on TLC plate and the middle spot corresponds to the desired diastereomer benzyl N-benzyl-N [[(2S,5R,6R)-6-[(1R,2R,3S,4R,6S)-4,6-diazido-2,3-dihydroxy -cyclohexoxy]-5-hydroxy-tetrahydropyran-2-yl]methyl]carbamate. $^1$H NMR (500 MHz, MeOD) δ 7.55-7.13 (m, 10H), 5.38-5.11 (m, 3H), 4.83 (dd, J=15.7, 4.3 Hz, 1H), 4.60 (d, J=15.7 Hz, 1H), 4.39-4.19 (m, 1H), 3.76-3.62 (m, 6H), 3.58-3.31 (m, 1H), 3.18 (dt, J=14.2, 7.1 Hz, 1H), 2.23 (dt, J=12.8, 4.1 Hz, 1H), 1.99-1.56 (m, 3H), 1.48-1.24 (m, 2H). MS (ESI) [M+Na]$^+$590.1.

Step 8
[(2R,3R,6S)-2-[(1R,2S,3S,4R,6S)-3-acetoxy-4,6-diazido-2-hydroxy-cyclohexoxy]-6-[[benzyl(benzyloxycarbonyl) amino]methyl]tetrahydropyran-3-yl]acetate

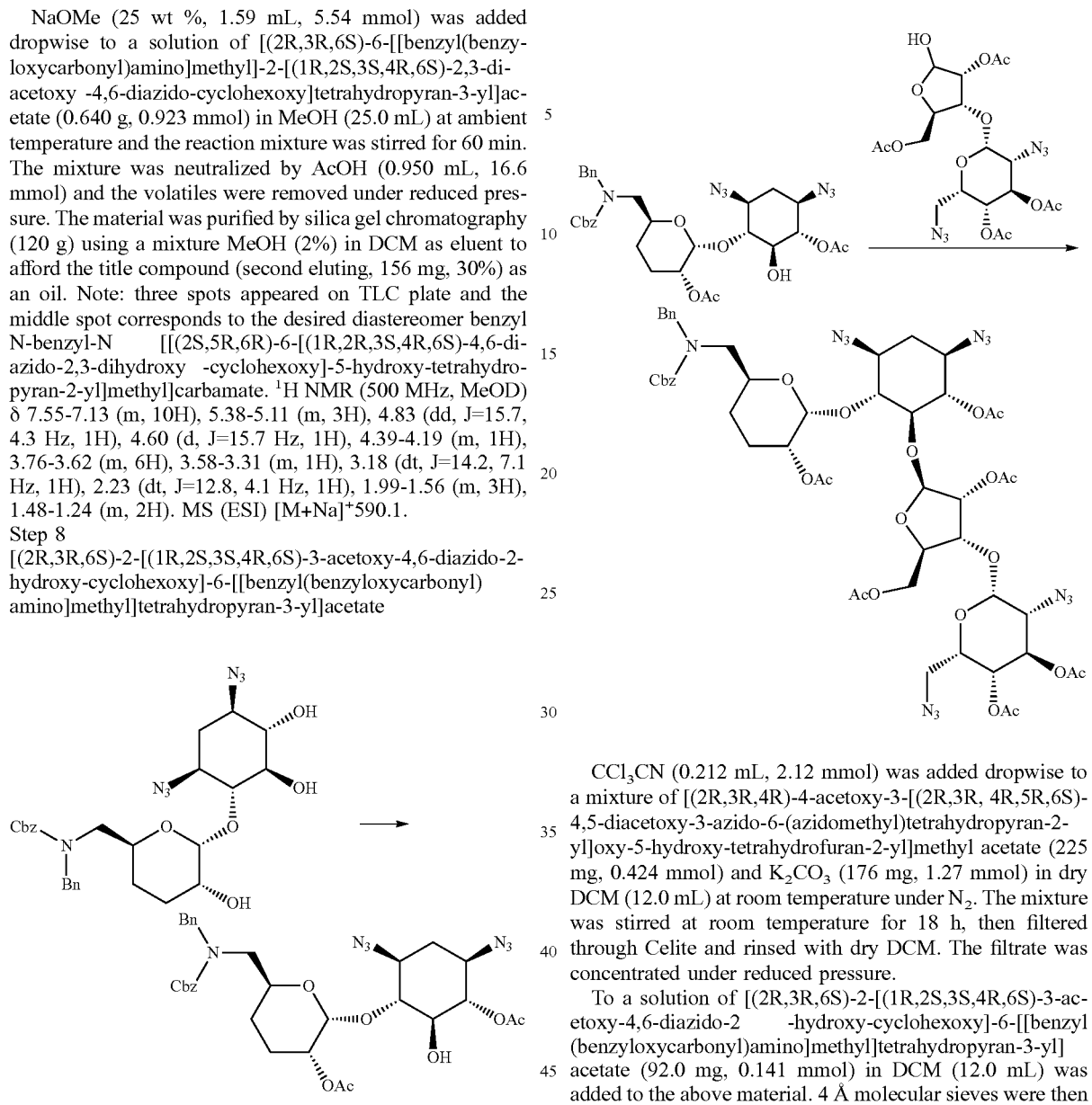

To a solution of benzyl N-benzyl-N [[(2S,5R,6R)-6-[(1R, 2R,3S,4R,6S)-4,6 -diazido-2,3-dihydroxy-cyclohexoxy]-5-hydroxy-tetrahydropyran-2-yl]methyl]carbamate (132 mg, 233 μmol) in dry DCM (6.00 mL) at ambient temperature, was added Ac$_2$O (55.0 μL, 581 μmol) and the reaction mixture was stirred for 18 h. The volatiles were removed under reduced pressure and the residue was purified by silica gel chromatography (40 g) using a gradient of EtOAc in hexane (0-70%) as eluent to provide compound [(2R,3R, 4R)-4-acetoxy-3-[(2R,3R, 4R,5R,6S)-4,5-diacetoxy-3-azido-6-(azidomethyl)tetrahydropyran-2-yl]oxy-5-hydroxy -tetrahydrofuran-2-yl]methyl acetate (90.0 mg, 61%). MS (ESI) [M+Na]$^+$651.9.

Step 9
[(2R,3R,4R,5S)-4-acetoxy-5-[(1S,2S,3R,5S,6R)-2-acetoxy-6-[(2R,3R,6S)-3-acetoxy-6-[[benzyl(benzyloxycarbonyl) amino]methyl]tetrahydropyran-2-yl]oxy-3,5-diazido-cyclohexoxy]-3-[(2R,3R,4R,5R,6S)-4,5-diacetoxy-3-azido-6-(azidomethyl)tetrahydropyran-2-yl]oxy -tetrahydrofuran-2-yl]methyl acetate CCl$_3$CN (0.212 mL, 2.12 mmol) was added dropwise to a mixture of [(2R,3R,4R)-4-acetoxy-3-[(2R,3R, 4R,5R,6S)-4,5-diacetoxy-3-azido-6-(azidomethyl)tetrahydropyran-2-yl]oxy-5-hydroxy-tetrahydrofuran-2-yl]methyl acetate (225 mg, 0.424 mmol) and K$_2$CO$_3$ (176 mg, 1.27 mmol) in dry DCM (12.0 mL) at room temperature under N$_2$. The mixture was stirred at room temperature for 18 h, then filtered through Celite and rinsed with dry DCM. The filtrate was concentrated under reduced pressure.

To a solution of [(2R,3R,6S)-2-[(1R,2S,3S,4R,6S)-3-acetoxy-4,6-diazido-2 -hydroxy-cyclohexoxy]-6-[[benzyl (benzyloxycarbonyl)amino]methyl]tetrahydropyran-3-yl] acetate (92.0 mg, 0.141 mmol) in DCM (12.0 mL) was added to the above material. 4 Å molecular sieves were then added and the mixture was cooled to −10° C. and then BF$_3$·Et$_2$O (87.1 μL, 0.706 mmol) was added dropwise. The mixture warmed slowly at room temperature and stirred for 5 h. The mixture was diluted with saturated NaHCO$_3$ (10.0 mL) and the separated aqueous layer was extracted with DCM (3×20.0 mL). The combined organic layers were washed with brine, then dried (Na$_2$SO$_4$), filtered and concentrated under reduced pressure. The material was purified by silica gel chromatography (40 g) using gradient of EtOAc in hexane (0-40%) as eluent to provide title product [(2R, 3R,4R,5S)-4-acetoxy-5-[(1S,2S,3R,5S,6R)-2-acetoxy-6-[(2R,3R,6S)-3-acetoxy-6-[[benzyl(benzyloxycarbonyl) amino]methyl]tetrahydropyran -2-yl]oxy-3,5-diazido-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate (120 mg, 73%) as an oil. MS (ESI) [M+Na]$^+$1186.0.

Step 10
Benzyl N-benzyl-N-[[(2S,5R,6R)-6-[(1R,2R,3S,4R,6S)-4, 6-diazido-2-[(2S,3R,4S,5R)-4-[(2R,3R,4R,5S,6S)-3-azido-6-(azidomethyl)-4,5-dihydroxy-tetrahydropyran-2-yl]oxy-

449

3-hydroxy-5-(hydroxymethyl)tetrahydrofuran-2-yl]oxy-3-hydroxy-cyclohexoxy]-5-hydroxy -tetrahydropyran-2-yl]methyl]carbamate

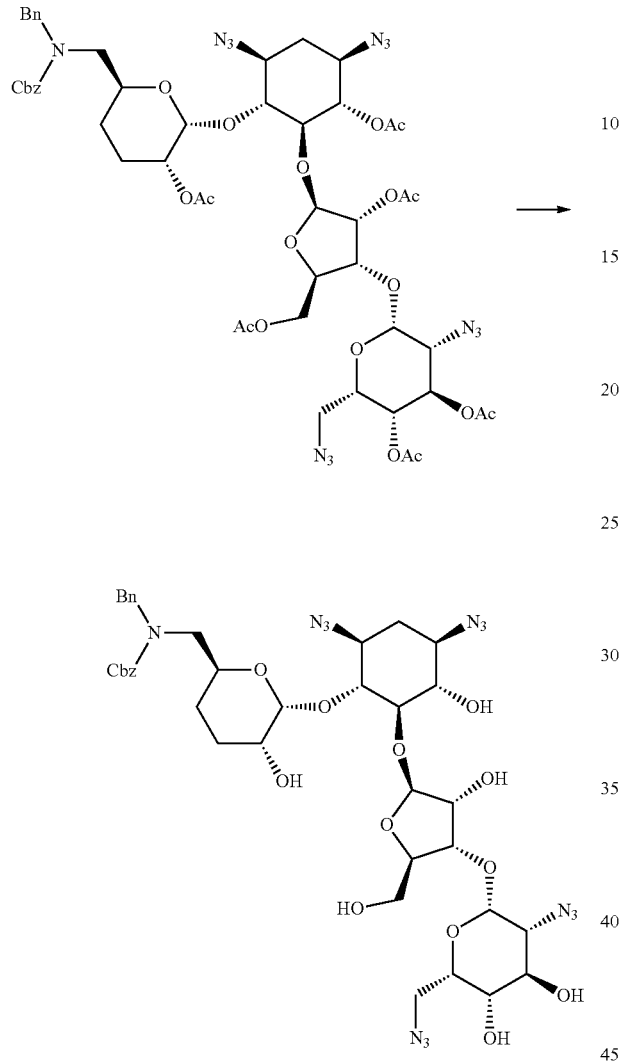

NaOMe (25 wt %, 356 μL, 124 μmol) was added dropwise to a solution of [(2R,3R,4R,5S)-4-acetoxy-5-[(1S,2S,3R,5S,6R)-2-acetoxy-6-[(2R,3R,6S)-3-acetoxy-6-[[benzyl(benzyloxycarbonyl)amino]methyl]tetrahydropyran-2-yl]oxy-3,5-diazido-cyclohexoxy]-3-[(2R,3R,4R,5R,6S)-4,5-diacetoxy-3-azido-6-(azidomethyl)tetrahydropyran-2-yl]
oxy -tetrahydrofuran-2-yl]methyl acetate (120 mg, 103 μmol) in MeOH (5.00 mL) at ambient temperature and the reaction mixture was stirred for 1 h. The mixture was neutralized by AcOH (~118 μL) and the volatiles were removed under reduced pressure. The material was dissolved with EtOAc, filtered through silica gel pad and the filtrate was concentrated under reduced pressure to produce the title compound (90.0 mg, 96%) as an oil. MS (ESI) [M+Na]$^+$934.1.

Step 11

(2S,3S,4R,5R,6R)-5-amino-2-(aminomethyl)-6-[(2R,3S,4R,5S)-5 [(1R,2R,3S,5R,6S)-3,5-diamino-2-[(2R,3R,6S)-6-(aminomethyl)-3-hydroxy-tetrahydropyran-2-yl]oxy-6-hydroxy -cyclohexoxy]-4-hydroxy-2-(hydroxymethyl)tetrahydrofuran-3-yl]oxy-tetrahydropyran-3,4-diol; formate

450

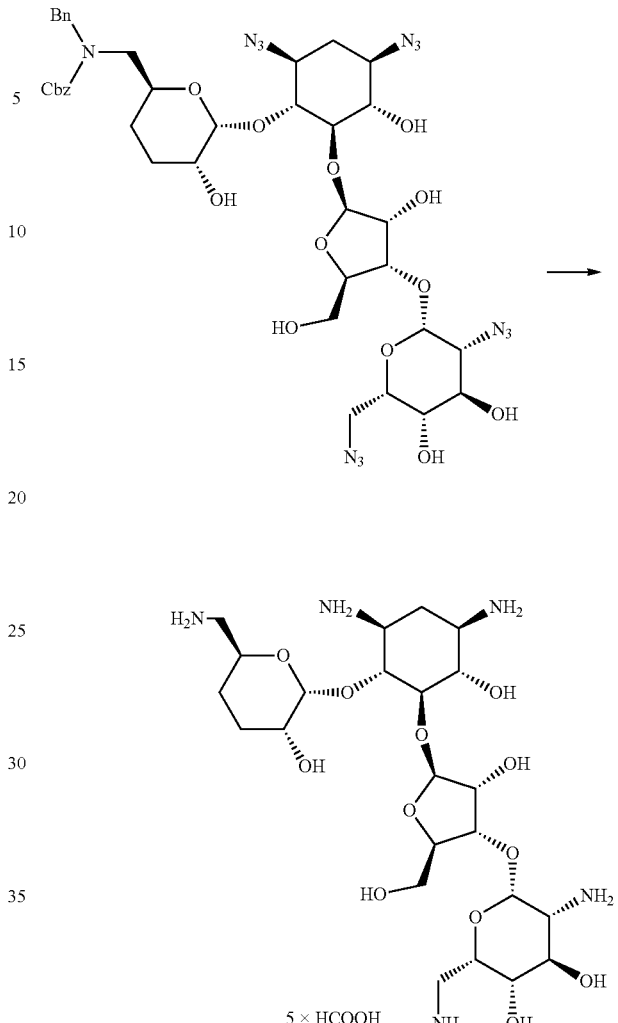

Pd(OH)$_2$/C (20 wt %, 194 mg, 276 μmol) was added to a solution of benzyl N -benzyl-N-[[(2S,5R,6R)-6-[(1R,2R,3S,4R,6S)-4,6-diazido-2-[(2S,3R,4S,5R)-4 -[(2R,3R,4R,5S,6S)-3-azido-6-(azidomethyl)-4,5-dihydroxy-tetrahydropyran-2-yl]oxy-3 -hydroxy-5-(hydroxymethyl)tetrahydrofuran-2-yl]oxy-3-hydroxy-cyclohexoxy]-5-hydroxy -tetrahydropyran-2-yl]methyl]carbamate (42.0 mg, 46.1 μmol) in MeOH (3.60 mL) and EtOH (3.60 mL). H$_2$ was bubbled and the suspension was hydrogenated under hydrogen atmosphere for 16 h. The mixture was filtered through a frit (0.22 μm diameter) and the filtrate was concentrated under reduced pressure. The material was purified by preparative HPLC to provide the title compound (12.5 mg, 43%) as a formate salt. $^1$H NMR (400 MHz, MeOD) δ 8.46 (s, 5H), 5.46 (d, J=3.2 Hz, 1H), 5.33 (d, J=2.1 Hz, 1H), 5.22 (s, 1H), 4.57-4.48 (m, 1H), 4.32-4.20 (m, 2H), 4.16-4.04 (m, 3H), 3.87-3.52 (m, 7H), 3.41-3.30 (m, 2H), 3.13-3.05 (m, 4H), 2.92 (dd, J=13.1, 8.5 Hz, 1H), 2.27 (d, J=11.6 Hz, 1H), 1.97-1.61 (m, 4H), 1.43 (dd, J=25.9, 14.0 Hz, 1H). MS (ESI) [M+Na]$^+$606.8.

Example 36
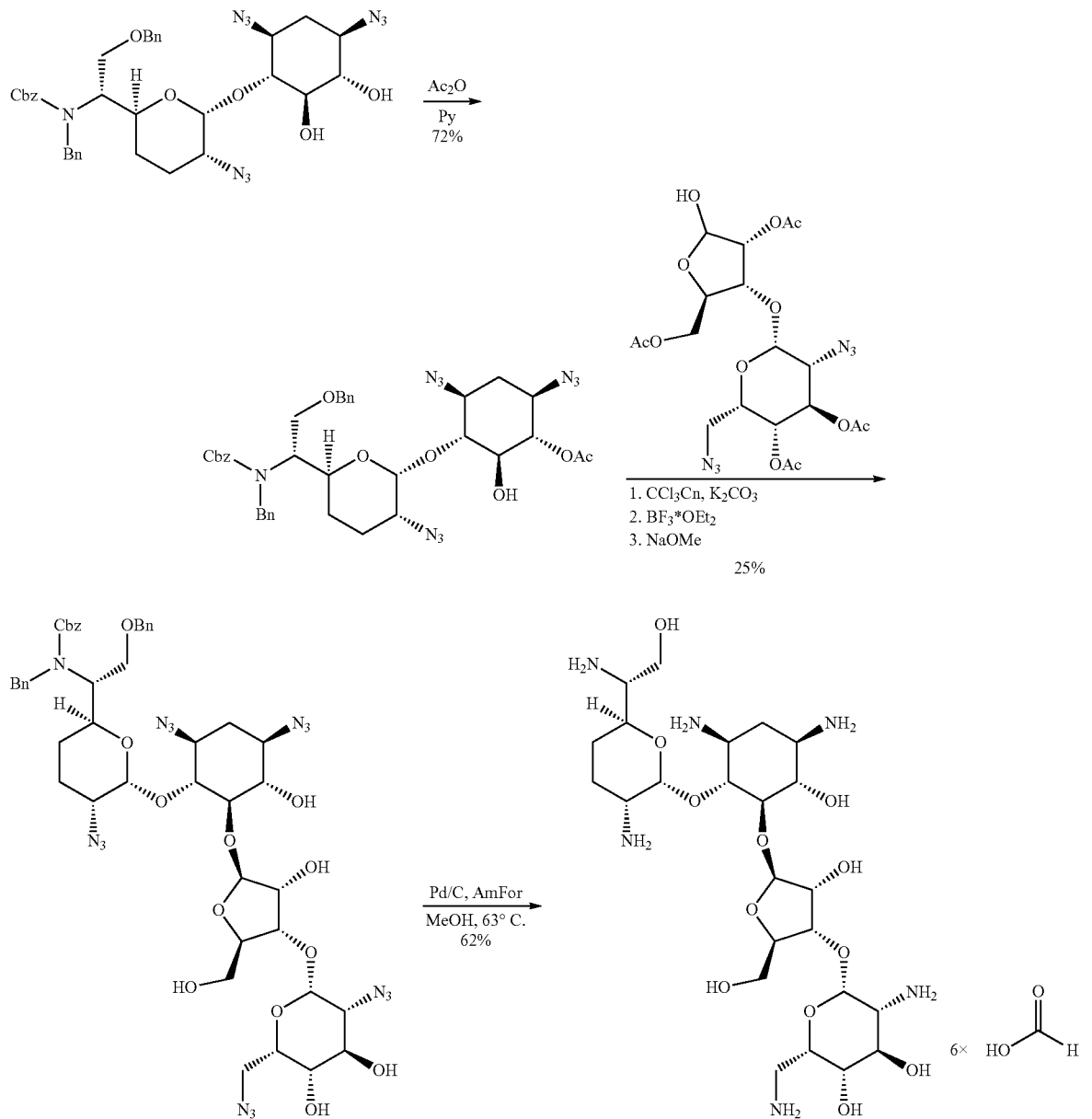
Step 1
Benzyl N-[(1R)-1-[(2S,5R,6R)-5-azido-6-[(1R,2R,3S,4R,6S)-4,6-diazido-2,3-dihydroxy-cyclohexoxy]tetrahydropyran-2-yl]-2-benzyloxy-ethyl]-N-benzyl-carbamate
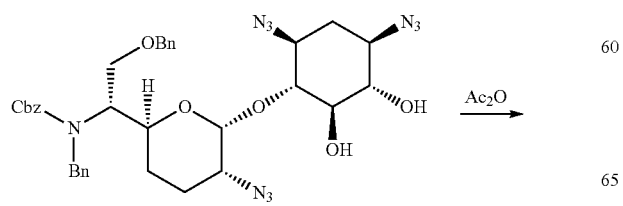
-continued
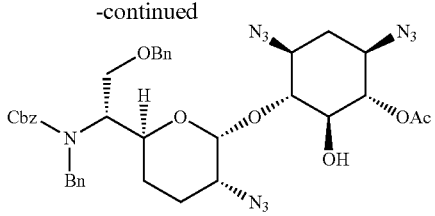
To a solution of benzyl N-[(1R)-1-[(2S,6R)-5-azido-6-[(1R,2R,3S,4R,6S)-4,6-diazido-2,3-dihydroxy-cyclohexoxy]tetrahydropyran-2-yl]-2-benzyloxy-ethyl]-N-benzyl-carbamate (see Example 56 for synthesis, 134 mg, 0.19 mmol) and pyridine (9 μL, 1.13 mmol) in dry DCM (5.0 mL) at room temperature was added Ac$_2$O (9 μL, 94 μmol) and the reaction mixture was stirred for 20 h. The volatiles were removed under reduced pressure. The material was purified by MPLC on silica gel (40 g, liquid loading with toluene) using a gradient of 0-45% EtOAc in hexane as eluent to provide the title compound (72 mg, 96%) as a solid. MS (ESI) [M+H]$^+$755.4.

Step 2

Benzyl ((R)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl) tetrahydrofuran-2-yl)oxy)-3-hydroxycyclohexyDoxy)tetrahydro-2H -pyran-2-yl)-2-(benzyloxy) ethyl)(benzyl)carbamate

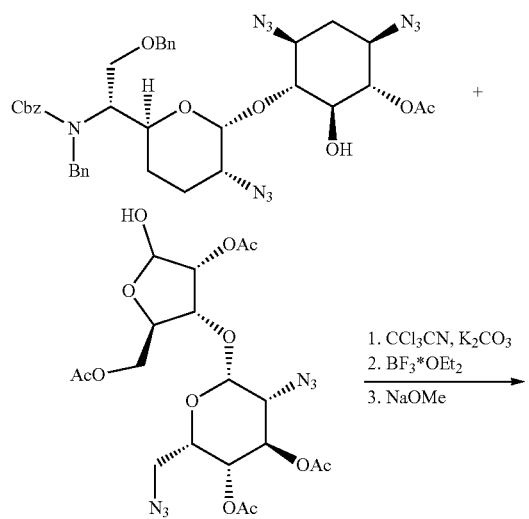

To a mixture of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (155 mg, 0.29 mmol) and K$_2$CO$_3$ (88 mg, 0.64 mmol) in DCM (5.0 mL) was added CCl$_3$CN (0.08 mL, 0.76 mmol) at room temperature. The mixture was stirred at room temperature for 18 h, then filtered on Celite, rinsed with DCM and concentrated under reduced pressure. To the above material in dry DCM (20 mL) was added [(1S,2S,3R,4S,6R)-4,6-diazido-3-[(2R,3R,6S) -3-azido-6-[(1R)-1-[benzyl(benzyloxycarbonyl) amino]-2-benzyloxy-ethyl]tetrahydropyran-2-yl]oxy-2-hydroxy-cyclohexyl]acetate (96 mg, 0.13 mmol) followed by activated 3 Å sieves (1 g). The mixture was cooled to −78° C. and then BF$_3$·OEt$_2$ (0.06 mL, 0.51 mmol) was added dropwise. The acetone-dry ice bath was removed, and the reaction mixture was slowly warmed to room temperature, and then saturated NaHCO$_3$ (10 mL) was added. The separated aqueous layer was extracted with DCM (3×15 mL). The combined organic layers were washed with brine, dried (MgSO$_4$), filtered and concentrated under reduced pressure. The residue was taken in MeOH (10 mL) then NaOMe (4.62 M in MeOH, 0.39 mL, 1.78 mmol) was added at room temperature and the reaction mixture was stirred for 1 h. The mixture was diluted with saturated NH$_4$Cl (10 mL) and the separated aqueous layer was extracted with DCM (3×15 mL). The combined organic layers were washed with brine, dried (MgSO$_4$), filtered and concentrated under reduced pressure. The material was purified by preparative HPLC to provide the title compound (47 mg, 35%) as a solid. MS (ESI) [M+Na]$^+$1079.4.

Step 3

(2S,3S,4R,5R,6R)-5-amino-2-(aminomethyl)-6-(((2R,3S,4R,5S)-5-(((1R,2R,3S,5R,6S)-3,5 -diamino-2-(((2R,3R,6S)-3-amino-6-((R)-1-amino-2-hydroxyethyl)tetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol

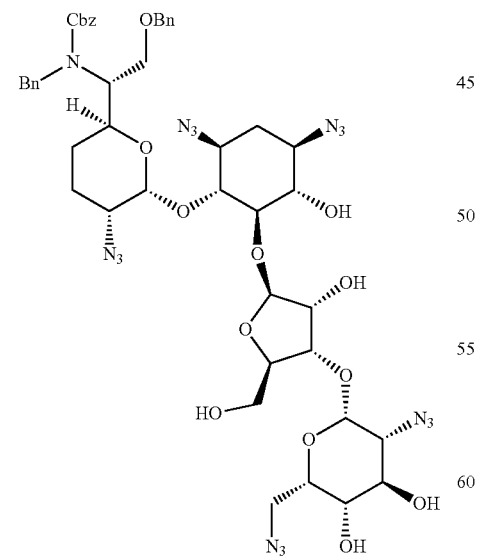

-continued

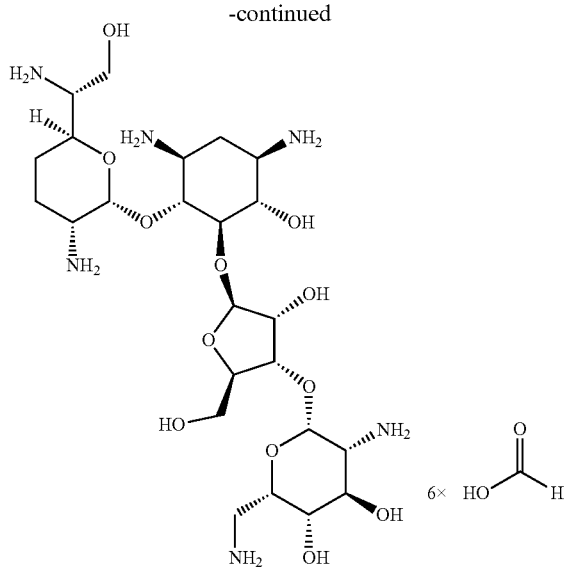

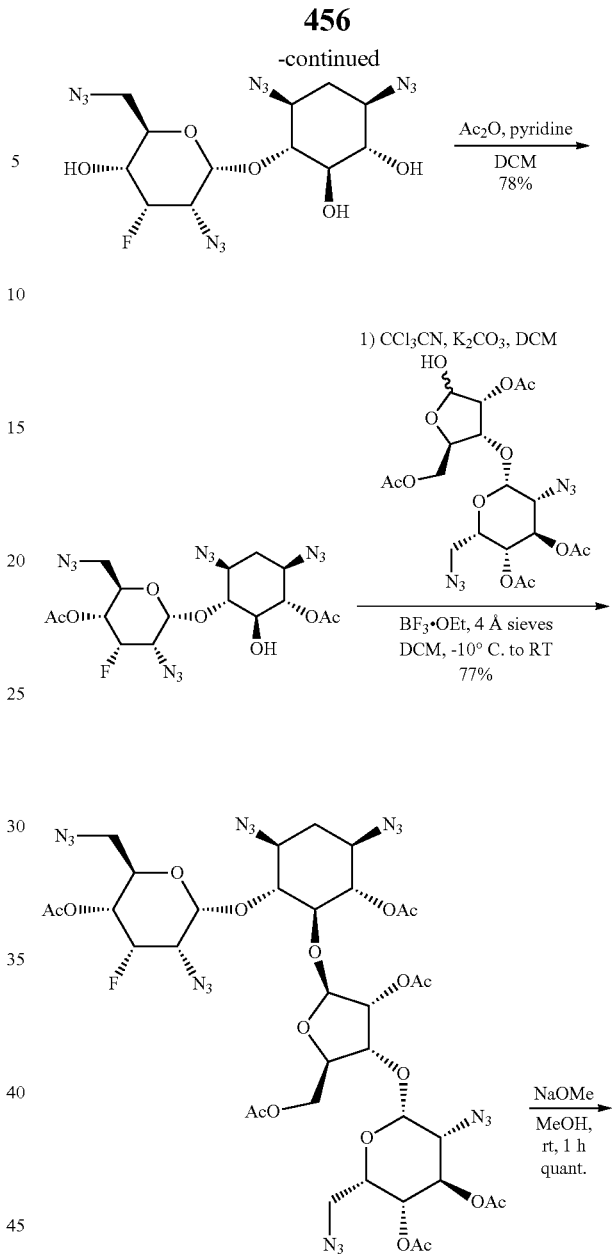

In a 2 neck flask equipped with a reflux condenser were added benzyl ((R)-1-((2S,5R,6R)-5-azido-6-(((1R,2R,3S,4R,6S)-4,6-diazido-2-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3-hydroxycyclohexyl)oxy)tetrahydro-2H-pyran-2-yl)-2-(benzyloxy) ethyl)(benzyl)carbamate (43 mg, 0.04 mmol) and Pd/C (10% dry on carbon, 19.5 mg, 0.02 mmol) following by anhydrous MeOH (8 mL). Nitrogen was bubbled for 5 min, then ammonium formate (44 mg, 0.69 mmol) was added. The mixture was heated at 63 °C. for 5 h under $N_2$, then cooled to room temperature with an ice-bath. The mixture was filtered with a filter syringe and concentrated under reduced pressure. The material was purified by preparative HPLC using isocratic 10% B in A (A: Amfor pH 4, B: ACN) on C18 Xbridge 30×150 mm to provide the title compound (22.3 mg, 62%) as a solid. $^1$H NMR (500 MHz, MeOD) δ 8.41 (s, 6H), 5.48 (s, 1H), 5.15 (s, 1H), 5.09 (d, J=1.5 Hz, 1H), 4.39-4.34 (m, 1H), 4.30-4.17 (m, 3H), 4.10-3.99 (m, 3H), 3.81-3.71 (m, 3H), 3.68-3.53 (m, 2H), 3.50-3.42 (m, 3H), 3.32-3.24 (m, 3H), 3.16-2.99 (m, 3H), 2.26-2.14 (m, 2H), 1.87-1.78 (m, 1H), 1.71-1.57 (m, 3H). MS (ESI) [M+H]$^+$613.4.

Example 37

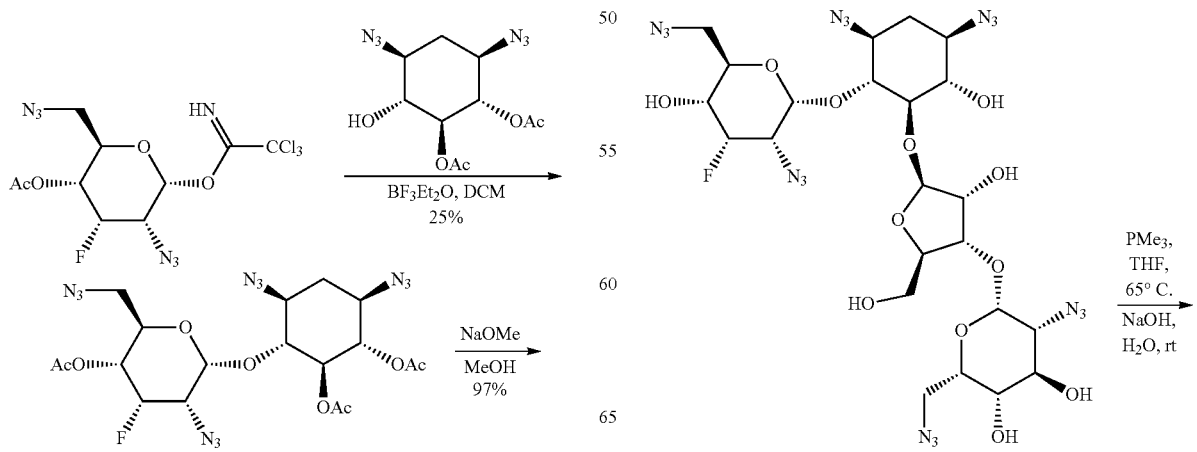

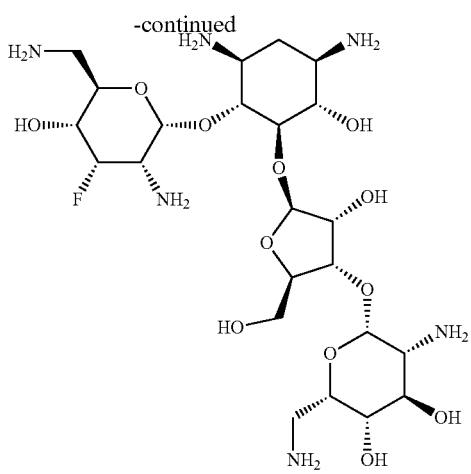

Step 1
(1S,2R,3R,4S,6R)-4,6-diazido-3-[(2R,3S,4S,5R,6R)-3-azido-6-(azidomethyl)-4-fluoro-5-hydroxy-tetrahydropyran-2-yl]oxy-cyclohexane-1,2-diol

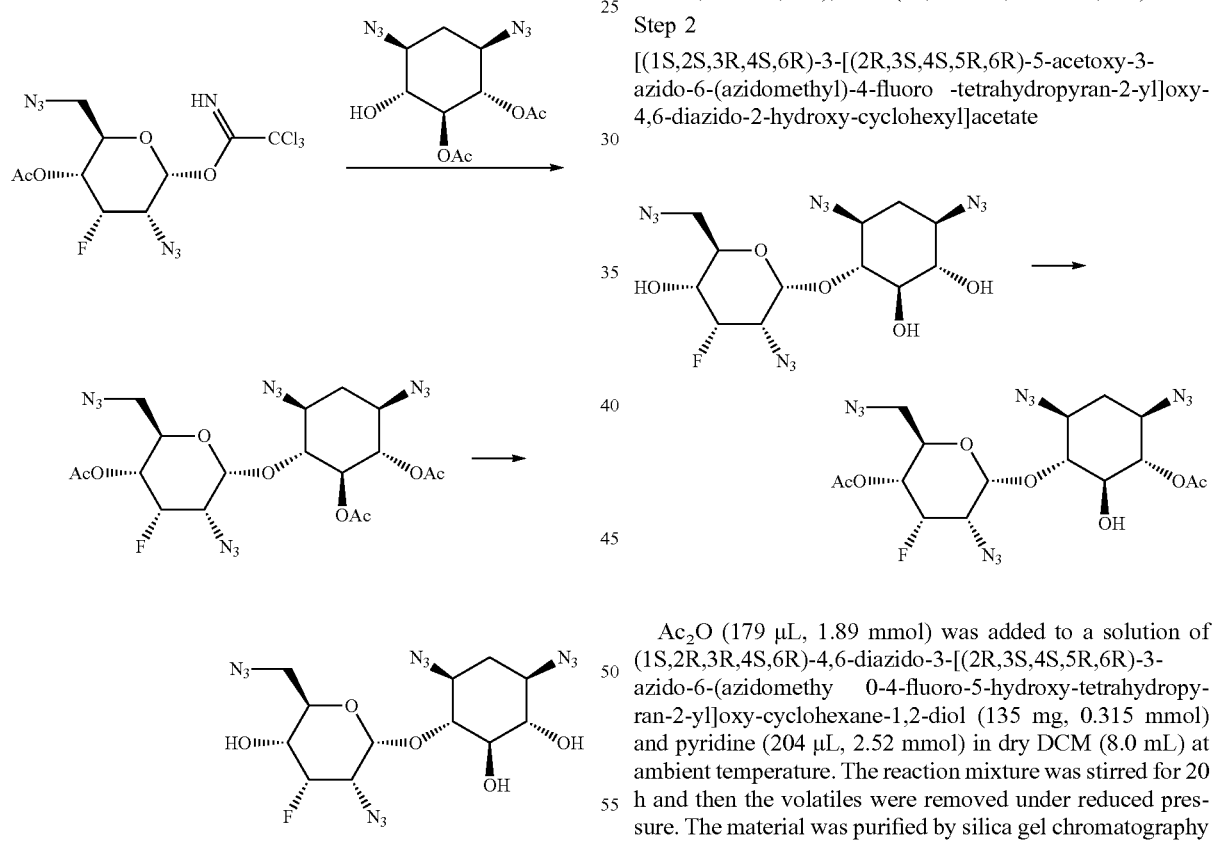

To (2R,3R,4S,5S)-5-azido-2-(azidomethyl)-4-fluoro-6-(2,2,2-trichloro-1-iminoethoxy) tetrahydro-2H-pyran-3-yl acetate (preparation below, 1.00 g, crude) was added [(1S,2S,3R,4S,6R)-2-acetoxy-4,6-diazido-3-hydroxy-cyclohexyl]acetate (500 mg, 1.68 mmol) and grounded 4 Å sieves (3.70 g). Dry DCM (18.0 mL) was added and the suspension was stirred at ambient temperature for 30 min. The mixture was cooled to −10° C. and then BF₃·Et₂O (1.18 mL, 9.56 mmol) was added dropwise with vigorous stirring. The solution was warmed to ambient temperature slowly and stirred for another 5 h. The reaction was quenched with saturated NaHCO₃ (10.0 mL) and the aqueous layer was extracted with DCM (3×20.0 mL). The combined organic layers were dried (Na₂SO₄), filtered and concentrated under reduced pressure. The material was purified by silica gel chromatography (80 g) using a gradient of EtOAc in hexane (0-30%) as eluent to provide the title compound as an oil (220 mg, 25%). MS (ESI) [M+Na]⁺576.9.

NaOMe (25 wt %, 686 µL, 2.38 mmol) was added dropwise to a solution of [(1S,2S,3R,4S,6R)-2-acetoxy-3-[(2R,3S,4S,5R,6R)-5-acetoxy-3-azido-6-(azidomethyl)-4-fluoro -tetrahydropyran-2-yl]oxy-4,6-diazido-cyclohexyl] acetate (220 mg, 397 µmol) in MeOH (15.0 mL) at ambient temperature and the reaction mixture was stirred for 60 min. The mixture was neutralized with AcOH (408 µL, 7.14 mmol) and the volatiles were removed under reduced pressure. The material was filtered through a silica gel pad and eluted with EtOAc to afford the title compound (165 mg, 97%) as a solid. ¹H NMR (500 MHz, MeOD) δ 5.75 (d, J=4.5 Hz, 1H), 5.12 (dt, J=53.8, 2.2 Hz, 1H), 4.59 (ddd, J=10.1, 5.1, 2.4 Hz, 1H), 3.72-3.43 (m, 7H), 3.32 (t, J=9.5 Hz, 1H), 3.18 (ddd, J=35.0, 4.4, 2.4 Hz, 1H), 2.34 (dt, J=13.0, 4.3 Hz, 1H), 1.50 (dd, J=24.7, 12.3 Hz, 1H).

Step 2
[(1S,2S,3R,4S,6R)-3-[(2R,3S,4S,5R,6R)-5-acetoxy-3-azido-6-(azidomethyl)-4-fluoro -tetrahydropyran-2-yl]oxy-4,6-diazido-2-hydroxy-cyclohexyl]acetate Ac₂O (179 µL, 1.89 mmol) was added to a solution of (1S,2R,3R,4S,6R)-4,6-diazido-3-[(2R,3S,4S,5R,6R)-3-azido-6-(azidomethy 0-4-fluoro-5-hydroxy-tetrahydropyran-2-yl]oxy-cyclohexane-1,2-diol (135 mg, 0.315 mmol) and pyridine (204 µL, 2.52 mmol) in dry DCM (8.0 mL) at ambient temperature. The reaction mixture was stirred for 20 h and then the volatiles were removed under reduced pressure. The material was purified by silica gel chromatography (40 g cartridge) using a gradient of EtOAc in hexane (0-30%) as eluent to afford the title compound (126 mg, 78%) as an oil. MS (ESI) [M+Na]⁺535.0.

Step 3
(2S,3R,4R,5R,6R)-6-(((2R,3R,4R,5S)-4-acetoxy-5-(((1S,2S,3R,5S,6R)-2-acetoxy-6-(((2R,3S,4S,5R,6R)-5-acetoxy-3-azido-6-(azidomethyl)-4-fluorotetrahydro-2H-pyran-2-yl)oxy) -3,5-diazidocyclohexyl)oxy)-2-(acetoxymethyl) tetrahydrofuran-3-yl)oxy)-5-azido-2-(azidomethyl) tetrahydro-2H-pyran-3,4-diyl diacetate

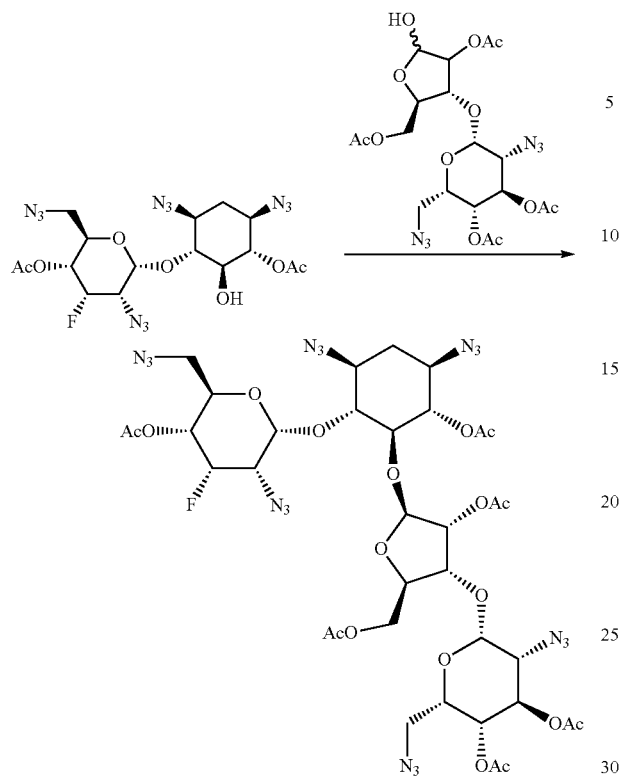

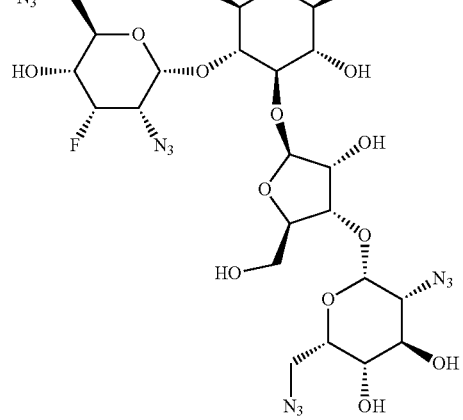

CCl₃CN (0.370 mL, 3.69 mmol) was added dropwise to a mixture of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (391 mg, 0.738 mmol) and K₂CO₃ (306 mg, 2.21 mmol) in dry DCM (15.0 mL) at room temperature under N₂. The reaction mixture was stirred at room temperature for 18 h, then filtered through Celite pad and washed with dry DCM. The filtrate was concentrated under reduced pressure and used in the next step without purification.

To a solution of [(1S,2S,3R,4S,6R)-3-[(2R,3S,4S,5R,6R)-5-acetoxy-3-azido-6-(azidomethyl)-4-fluoro-tetrahydropyran-2-yl]oxy-4,6-diazido-2-hydroxy-cyclohexyl]acetate (126 mg, 0.246 mmol) in dry DCM (15.0 mL), was added the above material followed by molecular sieves 4 Å and the mixture was cooled to −10° C. BF·OEt₂ (0.152 mL, 1.23 mmol) was then added dropwise and the reaction mixture was warmed slowly at room temperature and then stirred for 5 h. The mixture was diluted with saturated NaHCO₃ (10.0 mL) and the separated aqueous layer was extracted with DCM (3×20.0 mL). The combined organic layer was washed with brine, then dried (Na₂SO₄), filtered and concentrated under reduced pressure. The material was purified on silica gel chromatography (40 g cartridge) using a gradient of EtOAc in hexane (0-40%) as eluent to provide the title compound (194 mg, 77%) as a solid. MS (ESI) [M+Na]⁺ 1047.9.

Step 4
(2S,3S,4R,5R,6R)-5-azido-2-(azidomethyl)-6-(((2R,3S,4R,5S)-5-(((1R,2R,3S,5R,6S)-3,5-diazido-2-4(2R,3S,4S,5R,6R)-3-azido-6-(azidomethyl)-4-fluoro-5-hydroxytetrahydro-2H-pyran -2-yl)oxy)-6-hydroxycyclohexyl)oxy)-4-hydroxy-2-(hydroxymethyl)tetrahydrofuran-3-yl)oxy) tetrahydro-2H-pyran-3,4-diol NaOMe (25 wt %, 0.654 mL, 2.27 mmol) was added dropwise to a solution of (2S,3R,4R,5R,6R)-6-(((2R,3R,4R,5 S)-4-acetoxy-5-(((1S,2S,3R,5S,6R)-2-acetoxy-6 -(((2R,3S,4S,5R,6R)-5-acetoxy-3-azido-6-(azidomethyl)-4-fluorotetrahydro-2H-pyran-2-yl)oxy) -3,5-diazidocyclohexyl)oxy)-2-(acetoxymethyl)tetrahydrofuran-3-yl)oxy)-5-azido-2 -(azidomethyl)tetrahydro-2H-pyran-3,4-diyl diacetate (194 mg, 0.189 mmol) in MeOH (6.00 mL) at ambient temperature and the reaction mixture was stirred for 60 min. The mixture was neutralized with AcOH (217 µL, 3.79 mmol) and then the volatiles were removed under reduced pressure. The material was purified on silica gel pad using EtOAc as eluent to provide the title compound (145 mg, 99%) as a solid. MS (ESI) [M+Na]⁺795.2.

Step 5
(2S,3S,4R,5R,6R)-5-amino-2-(aminomethyl)-6-[(2R,3S,4R,5S)-5-[(1R,2R,3S,5R,6S)-3,5-diamino-2-[(2R,3S,4S,5R,6R)-3-amino-6-(aminomethyl)-4-fluoro-5-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol

461

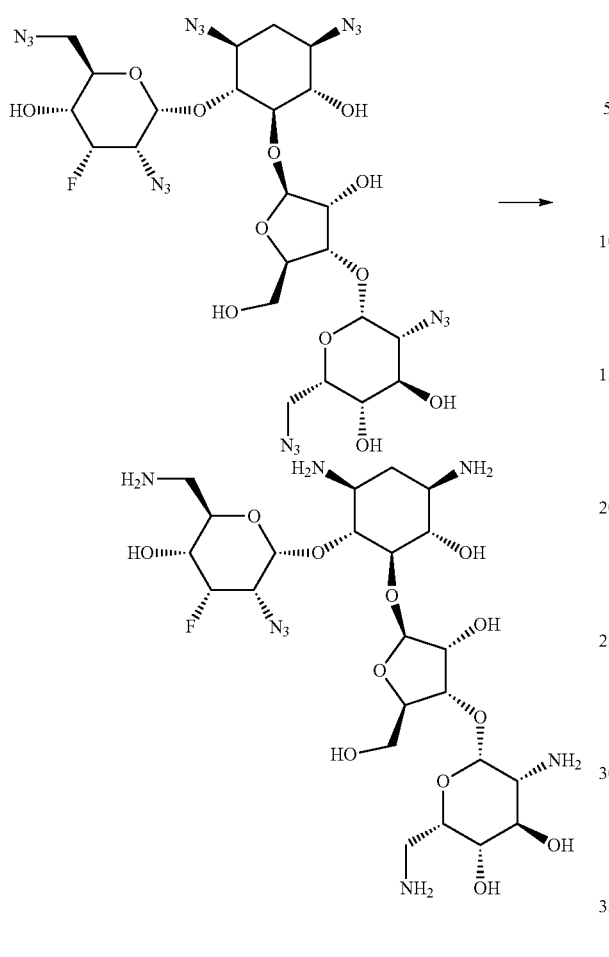

To a solution of (2S,3S,4R,5R,6R)-5-azido-2-(azidomethyl)-6-(((2R,3S,4R,5S)-5-(((1R,2R,3S,5R,6S)-3,5-diazido-2-(((2R,3S,4S,5R,6R)-3-azido-6-(azidomethyl)-4-fluoro-5-hydroxytetrahydro-2H-pyran-2-yl)oxy)-6-hydroxycyclohexyl)oxy)-4-hydroxy-2-(hydroxymethyl)tetrahydrofuran-3-yl)oxy)tetrahydro-2H-pyran-3,4-diol (15.0 mg, 19.4 μmol) in THF (2.00 mL) was added trimethylphosphine (777μL, 777 μmol) at ambient temperature and the reaction mixture was stirred at room temperature for 16 h. The mixture was diluted with water (2.00 mL) and then NaOH (0.3 mL, 0.1 M) were added. The resulting mixture was then stirred for 3 h at ambient temperature, concentrated under reduced pressure. The material was purified by Sephadex C-25 column using water and ammonium hydroxide (0.25%) as eluent to afford the title compound (6.90 mg, 58%) as a white solid after lyophilization. $^1$H NMR(400 MHz, MeOD) δ 5.57 (d, J=4.4 Hz, 1H), 5.28 (s, 1H), 4.93 (d, J=1.5 Hz, 1H), 4.75 (d, J=53.4 Hz, 1H), 4.22 (t, J=4.7 Hz, 1H), 4.12 (dt, J=8.9, 4.6 Hz, 2H), 3.91 (t, J=3.1 Hz, 1H), 3.85-3.60 (m, 4H), 3.47 (dtt, J=28.5, 19.0, 9.4 Hz, 5H), 3.19 (t, J=9.3 Hz, 1H), 3.01 (ddd, J=21.8, 13.4, 5.5 Hz, 3H), 2.90-2.67 (m, 3H), 2.60 (dd, J=16.9, 8.7 Hz, 1H), 1.96 (dd, J=8.3, 3.4 Hz, 1H), 1.31-1.16 (m, 1H). MS (ESI) [M+Na]$^+$ 639.1.

462

Preparation of (2R,3R,4S,5S)-5-azido-2-(azidomethyl)-4-fluoro-6-(2,2,2-trichloro-1-iminoethoxy)tetrahydro-2H-pyran-3-yl acetate

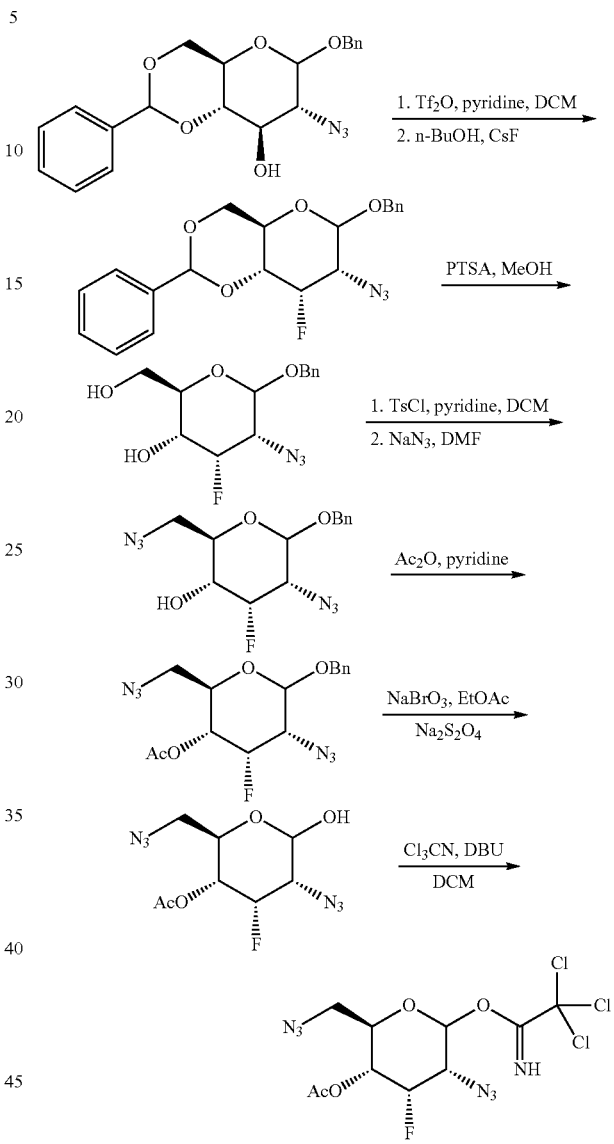

Step 1
(4aR,7S,8S,8aR)-7-azido-6-benzyloxy)-8-fluoro-2-phenylhexahydropyrano[3,2-d][1,3]dioxine

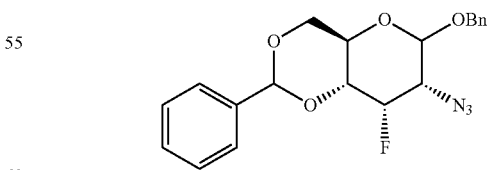

To a solution of 7.7 g of (4aR,7S,8S,8aR)-7-azido-6-(benzyloxy)-8-fluoro-2-phenylhexa-hydropyrano[3,2-d][1,3]dioxine in 60 mL of anhydrous DCM was added 16.1 mL of pyridine and the reaction was cooled to 0° C. To this solution, 6.8 mL of Triflic anhydride was added slowly and the reaction stirred for 1 hour at the same temperature. After completion, the organic layer was diluted with DCM and washed with 1 N HCl and saturated NaHCO$_3$. The organic layer was dried over anhydrous sodium sulfate, filtered and concentrated. The obtained crude was dissolved in 50 mL BuOH and 30 mL of toluene and 9.1 g of CsF was added and the reaction stirred at 70° C. until completion. The organic layer was diluted with EtOAc and washed with saturated NaHCO$_3$, brine and concentrated. The crude was purified by column chromatography (20% EtOAc, in hexanes) to afford 5.5 g of (4aR,7S,8S,8aR)-7-azido-6-(benzyloxy)-8-fluoro-2-phenylhexahydropyrano[3,2-d][1,3]dioxine 72% yield).

Step 2
(2R,3R,4S,5S)-5-azido-6-(benzyloxy)-4-fluoro-2-(hydroxymethyl)tetrahydro-2H-pyran-3-ol

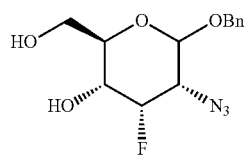 [SMILES: [N-]=[N+]=N[C@H]1C(OCc2ccccc2)O[C@H](CO)[C@@H](O)[C@H]1F]

To a solution of 6.2 g of (4aR,7S,8S,8aR)-7-azido-6-(benzyloxy)-8-fluoro-2-phenylhexahydro-pyrano[3,2-d][1,3]dioxine in 100 mL of MeOH was added 420 mg of p-toluenesulfonic acid at room temperature. The reaction was stirred at room temperature until completion (4 hours). The reaction was quenched with 0.1 eq of Et$_3$N and concentrated. The crude was purified by flash column chromatography (EtOAc/Hexanes 2:3) to afford 4.5 g of (2R,3R,4S,5S)-5-azido-6-(benzyloxy)-4-fluoro-2-(hydroxymethyl)tetrahydro-2H-pyran-3-ol (95% yield).

Step 3
(2R,3R,4S,5S)-5-azido-2-(azidomethyl)-6-(benzyloxy)-4-fluorotetrahydro-2H-pyran-3-ol

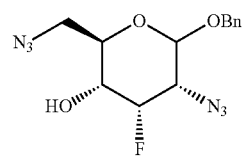 [SMILES: [N-]=[N+]=NC[C@H]1OC(OCc2ccccc2)[C@H](N=[N+]=[N-])[C@H](F)[C@@H]1O]

To a solution of 4.5 g of (2R,3R,4S,5S)-5-azido-6-(benzyloxy)-4-fluoro-2-(hydroxymethyl)tetrahydro-2H-pyran-3-ol in anhydrous DCM/pyridine (5:3), 3.75 g of Tosyl Chloride was added at 0° C. The reaction was stirred at the same temperature until completion (3 h). The reaction was diluted with 100 mL of DCM and washed with 1 N HCl and aqueous NaHCO$_3$, dried, filtered and concentrated. The crude was dissolved in anhydrous DMF and 4.9 g of sodium azide was added. The reaction was further stirred at 70° C. until completion. DMF was evaporated and the residue was dissolved in EtOAc and washed with water. The organic layer was dried, filtered, concentrated and purified by flash chromatography to afford 2.9 g of (2R,3R,4S,5S)-5-azido-2-(azidomethyl)-6-(benzyloxy)-4-fluorotetrahydro-2H-pyran-3-ol (60% yield).

Step 4
(2R,3R,4S,5S)-5-azido-2-(azidomethyl)-6-(benzyloxy)-4-fluorotetrahydro-2H-pyran-3-yl acetate

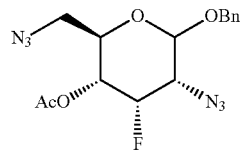 [SMILES: CC(=O)O[C@H]1[C@@H](F)[C@@H](N=[N+]=[N-])C(OCc2ccccc2)O[C@@H]1CN=[N+]=[N-]]

(2R,3R,4S,5S)-5-azido-2-(azidomethyl)-6-(benzyloxy)-4-fluorotetrahydro-2H-pyran-3-ol was dissolved in anhydrous pyridine and the solution was cooled to 0° C. Acetic anhydride was slowly added and the reaction was allowed to warm to room temperature and stirred overnight. The reaction was concentrated to dryness, resuspended in EtOAc, and washed with aqueous NaHCO$_3$ and brine. The organic portion was dried, filtered, concentrated and purified by flash chromatography to yield (2R,3R,4S,5S)-5-azido-2-(azidomethyl)-6-(benzyloxy)-4-fluorotetrahydro-2H-pyran-3-yl acetate (89% yield).

Step 5
(2R,3R,4S,5S)-5-azido-2-(azidomethyl)-4-fluoro-6-hydroxytetrahydro-2H-pyran-3-yl acetate

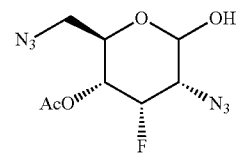 [SMILES: CC(=O)O[C@H]1[C@@H](F)[C@@H](N=[N+]=[N-])C(O)O[C@@H]1CN=[N+]=[N-]]

1.5 g of (2R,3R,4S,5S)-5-azido-2-(azidomethyl)-6-(benzyloxy)-4-fluorotetrahydro-2H-pyran-3-yl acetate was dissolved in 38 mL of EtOAc. 30 mL of aqueous sodium bromate (0.62 M) was added at once to the EtOAc solution. 60 mL aqueous sodium dithionate (0.27 M) was added slowly dropwise over 15 min and the reaction was stirred vigorously until completion. The reaction was then diluted with EtOAc and washed with 1:1 aq NaHCO$_3$ and sodium thiosulfate. The organic layer was dried, filtered, concentrated and purified by flash column chromatography (30% EtOAc in hexanes) to afford 921 mg of (2R,3R,4S,5S)-5-azido-2-(azidomethyl)-4-fluoro-6-hydroxytetrahydro-2H-pyran-3-yl acetate (82% yield).

Step 6
(2R,3R,4S,5S)-5-azido-2-(azidomethyl)-4-fluoro-6-(2,2,2-trichloro-1-iminoethoxy) tetrahydro -2H-pyran-3-yl acetate

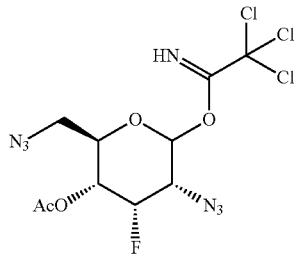 [SMILES: CC(=O)O[C@H]1[C@@H](F)[C@@H](N=[N+]=[N-])C(OC(=N)C(Cl)(Cl)Cl)O[C@@H]1CN=[N+]=[N-]]

To a solution of 950 mg of (2R,3R,4S,5S)-5-azido-2-(azidomethyl)-4-fluoro-6-hydroxytetrahydro-2H-pyran-3-yl acetate in 20 mL of anhydrous DCM was added 970 µL of trichloroacetonitrile at 0° C. To this solution, 143 μL of DBU was slowly added at the same temperature. The reaction was stirred until completion at room temperature (~5 minutes). The reaction was diluted with DCM and washed with 1N HCl, brine and the organic layer was dried, filtered and concentrated. The crude thus obtained was purified by flash column chromatography (20% EtOAc in hexanes) to afford 1.04 g of (2R,3R,4S,5S)-5-azido-2-(azidomethyl)-4-fluoro-6-(2,2,2-trichloro-1-iminoethoxy) tetrahydro-2H-pyran-3-yl acetate (78% yield).

Example 38

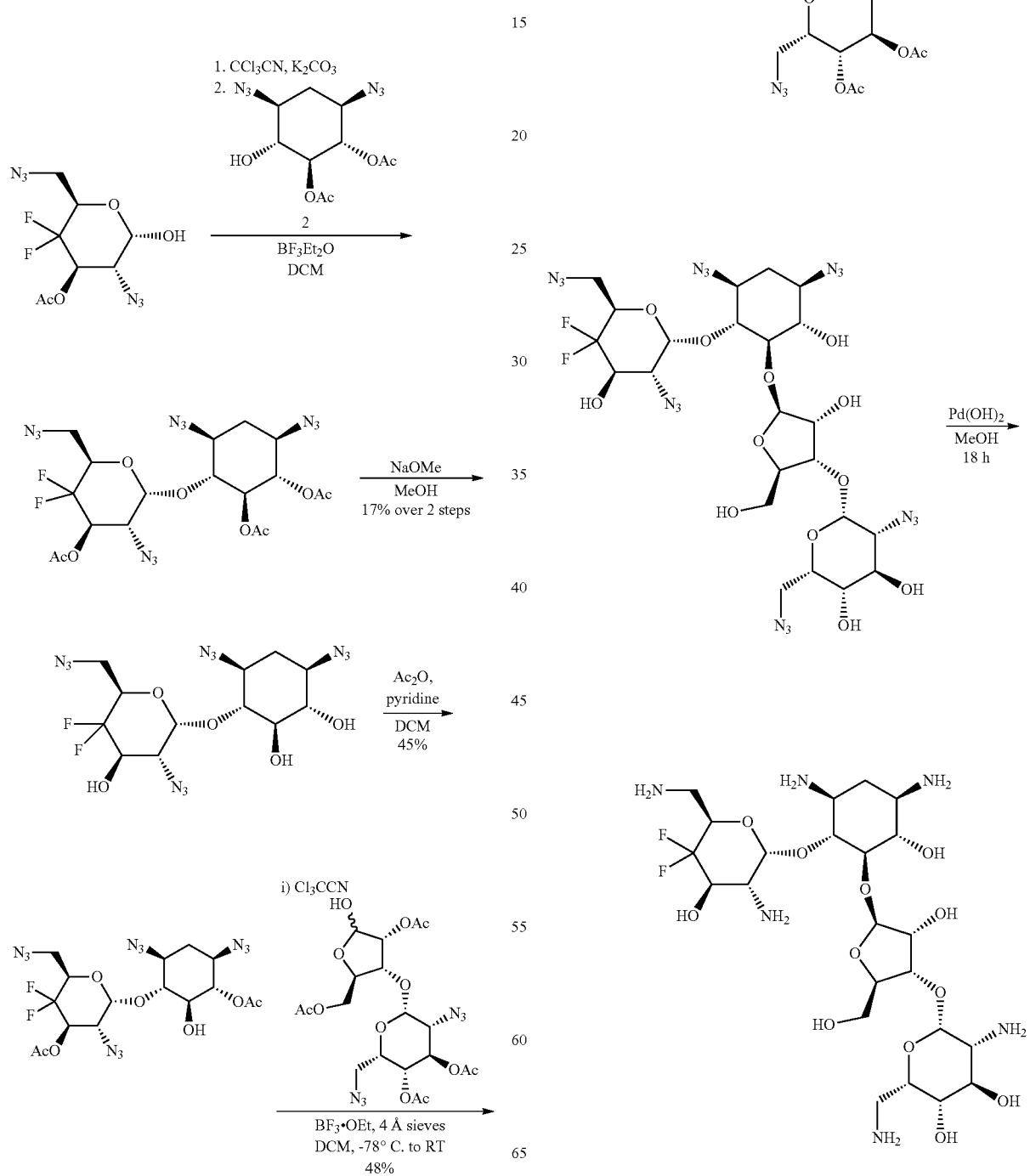

Step 1

(1S,2R,3R,4S,6R)-4,6-diazido-3-[(2S,3R,4R,6R)-3-azido-6-(azidomethyl)-5,5-difluoro-4-hydroxy-tetrahydropyran-2-yl]oxy-cyclohexane-1,2-diol

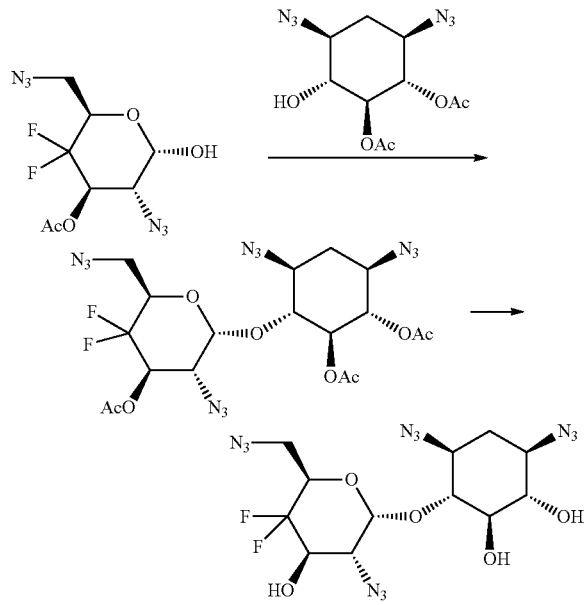

CCl₃CN (0.34 mL, 3.42 mmol) was added dropwise to a suspension of [(2R,4R,5R)-5-azido-2-(azidomethyl)-3,3-difluoro-6-hydroxy-tetrahydropyran-4-yl]acetate (preparation below, 200 mg, 0.68 mmol) and K₂CO₃ (284 mg, 2.05 mmol) in dry DCM (20 mL) at ambient temperature under N₂. After 72 h, the solution was filtered through cotton and the filtrate was concentrated under N₂ stream, followed by high-vacuum.

To the above material was added [(1S,2S,3R,4S,6R)-2-acetoxy-4,6-diazido-3-hydroxy-cyclohexyl]acetate (408 mg, 1.37 mmol) and ground 4 Å sieves and then dry DCM (20 mL) was added. The suspension was stirred at ambient temperature for 1 h. The solution was cooled to −78° C. and BF₃·Et₂O (0.34 mL, 2.74 mmol) was added dropwise with vigorous stirring and the resulting mixture was stirred at −78° C. for 1 h. The mixture was warmed to ambient temperature and stirred for another hour. The reaction was diluted with saturated NaHCO₃ (100.0 mL) and the aqueous layer mixture was extracted with DCM (3×50 mL). The combined organic layers were dried (Na₂SO₄), filtered and concentrated under reduced pressure to afford an acetylated dimer.

NaOMe (25 wt %, 0.44 mL, 2.05 mmol) was added dropwise to a solution of the crude acetylated dimer in MeOH (2.0 mL) at ambient temperature and the reaction mixture was stirred for 70 min. The mixture was diluted with AcOH (0.23 mL, 4.11 mmol) and the volatiles were removed under reduced pressure. The residue was purified by silica gel chromatography (24 g cartridge) using a gradient of EtOAc in hexane (0-50%) as eluent to afford the title compound (49.5 mg, 16%, 3 steps).

Step 2

[(1S,2S,3R,4S,6R)-3-[(2S,3R,4R,6R)-4-acetoxy-3-azido-6-(azidomethyl)-5,5-difluoro-tetrahydropyran-2-yl]oxy-4,6-diazido-2-hydroxy-cyclohexyl]acetate

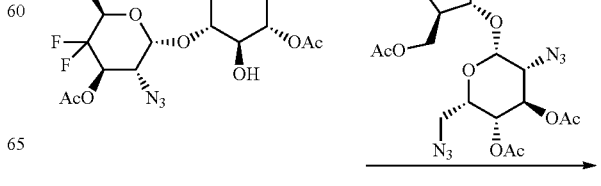

Ac₂O (62 μL, 659 μmol) was added to a solution of (1S,2R,3R,4S,6R)-4,6-diazido-3-[(2S,3R,4R,6R)-3-azido-6-(azidomethyl)-5,5-difluoro-4-hydroxy-tetrahydropyran-2-yl]oxy-cyclohexane-1,2-diol (49 mg, 110 μmol) and pyridine (71 μL, 878 mmol) in dry DCM (2 mL) at ambient temperature and the reaction mixture was stirred for 20 h. The mixture was diluted with MeOH and then the volatiles were removed under reduced pressure. The materail was purified by silica gel chromatography (12 g cartridge) using a gradient of EtOAc and hexane (5-25%) as eluent to afford the title compound as an oil along with beta anomer (~25%). The mixture was repurified by silica gel chromatography (12 g cartridge) using a gradient of EtOAc and hexane (15-30%) as eluent to afford the title compound (26.0 mg, 45%) as an oil. ¹H NMR (500 MHz, CDCl₃) δ 5.61-5.50 (m, 1H), 5.42-5.37 (m, 1H), 4.84 (t, J=9.9 Hz, 1H), 4.46 (ddd, J=24.0, 8.1, 2.9 Hz, 1H), 3.70 (dd, J=10.9, 3.6 Hz, 1H), 3.62 (td, J=9.4, 3.8 Hz, 1H), 3.56-3.32 (m, 7H), 2.38-2.32 (m, 1H), 2.16 (s, 3H), 2.11 (s, 3H), 1.65-1.52 (m, 1H).

Step 3

(2S,3S,4R,5R,6R)-5-azido-2-(azidomethyl)-6-[(2R,3S,4R,5S)-5-[(1R,2R,3S,5R,6S)-3,5-diazido-2-[(2S,3R,4R,6R)-3-azido-6-(azidomethyl)-5,5-difluoro-4-methyl-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol

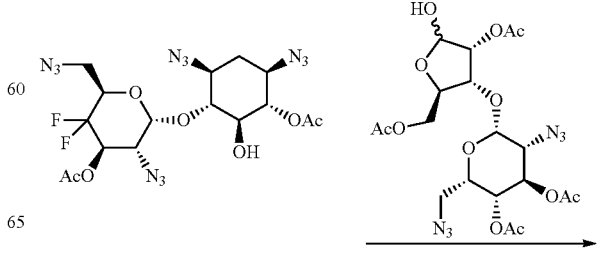

-continued

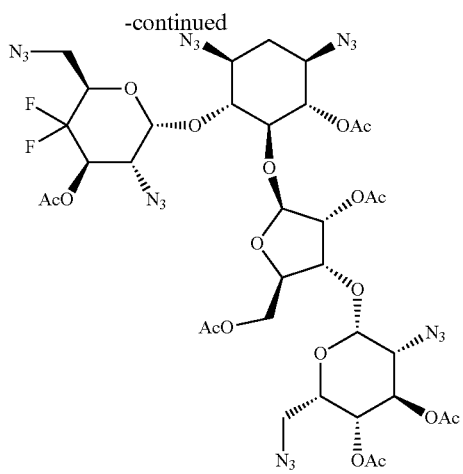

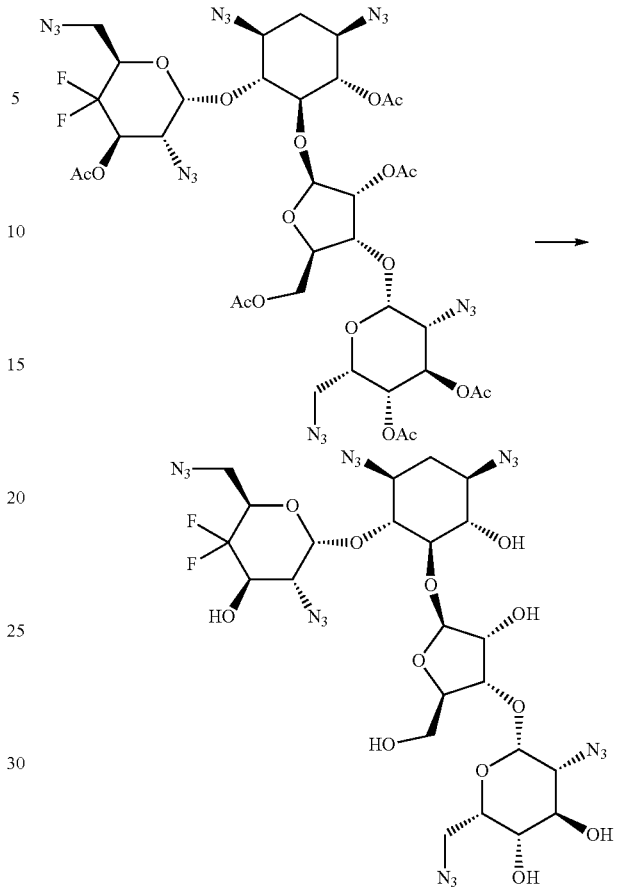

CCl$_3$CN (0.074 mL, 0.74 mmol) was added dropwise to a mixture of [(2R,3R,4R)-4-acetoxy-3-[(2R,3R,4R,5R,6S)-4,5-acetoxy-3-azido-6 -(azidomethyl)tetrahydropyran-2-yl]oxy-5-hydroxy-tetrahydrofuran-2-yl]methyl acetate (78 mg, 0.15 mmol) and K$_2$CO$_3$ (61 mg, 0.44 mmol) in dry DCM (5 mL) at room temperature under N$_2$. The mixture was stirred at room temperature for 18 h, then filtered through a 45 μm nylon filter and rinsed with DCM. The filtrate was concentrated under reduced pressure and used in the next step without further purification.

To a solution of [(1S,2S,3R,4S,6R)-3-[(2S,3R,4R,6R)-4-acetoxy-3-azido-6-(azidomethyl)-5,5-difluoro-tetrahydropyran-2-yl]oxy-4,6-diazido-2-hydroxy-cyclohexyl]acetate (26 mg, 0.049 mmol) in DCM (5 mL) was added the above material followed 4 Å molecular sieves and the mixture was cooled to −78° C. BF$_3$·Et$_2$O (0.030 mL, 0.25 mmol) was then added dropwise and the reaction mixture was stirred at room temperature for 4 h. The mixture was diluted with saturated NaHCO$_3$ (8 mL) and the separated aqueous layer was extracted with DCM (2×8 mL). The combined organic layer was washed with brine, then dried (Na$_2$SO$_4$), filtered and concentrated under reduced pressure. The material was purified by flash column chromatography (12 g) using a gradient of EtOAc in hexane (0-45%) as eluent to afford the title compound (24.5 mg, 48%). $^1$H NMR (500 MHz, CDCl$_3$) δ 6.04 (d, J=2.6 Hz, 1H), 5.57 (ddd, J=19.6, 11.2, 4.6 Hz, 1H), 5.33 (d, J=2.6 Hz, 1H), 5.02 (t, J=2.8 Hz, 1H), 4.95 (t, J=9.8 Hz, 1H), 4.92-4.85 (m, 2H), 4.73-4.63 (m, 2H), 4.45-4.38 (m, 2H), 4.32-4.25 (m, 2H), 4.10-4.06 (m, 1H), 3.89 (t, J=9.0 Hz, 1H), 3.72-3.67 (m, 1H), 3.60-3.40 (m, 5H), 3.33-3.25 (m, 3H), 2.40 (dt, J=13.2, 4.5 Hz, 1H), 2.21 (s, 3H), 2.17-2.14 (m, 9H), 2.11 (s, 3H), 2.09 (s, 3H), 1.70-1.62 (m, 1H). MS (ESI) [M+NH$_4$]$^{+1060.4}$.

Step 4

(2S,3S,4R,5R,6R)-5-azido-2-(azidomethyl)-6-[(2R,3S,4R,5S)-5-[(1R,2R,3S,5R,6S)-3,5-diazido -2-[(2S,3R,4R,6R)-3-azido-6-(azidomethyl)-5,5-difluoro-4-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran -3,4-diol NaOMe (25 wt %, 41 μL, 0.14 mmol) was added dropwise to a solution of (2S,3S,4R,5R,6R)-5-azido-2-(azidomethyl)-6-[(2R,3S,4R,5S)-5-[(1R,2R,3S,5R,6S)-3,5-diazido -2-[(2S,3R,4R,6R)-3-azido-6-(azidomethyl)-5,5-difluoro-4-methyl-tetrahydropyran-2-yl]oxy-6-hydroxy-cyclohexoxy]-4-hydroxy-2-(hydroxymethyl)tetrahydrofuran-3-yl]oxy-tetrahydropyran -3,4-diol (24.5 mg, 0.024 mmol) in MeOH (2 mL) at ambient temperature and the reaction mixture was stirred for 75 min. The mixture was diluted with AcOH (0.013 mL, 0.24 mmol) and the volatiles were removed under reduced pressure. The residue was diluted in EtOAc and the organic layer was washed with saturated NaHCO$_3$ and brine, then dried (Na$_2$SO$_4$), filtered and concentrated under reduced pressure to give the title compound (18.0 mg, 97%). $^1$H NMR (500 MHz, MeOD) δ 5.91 (s, 1H), 5.29 (d, J=2.1 Hz, 1H), 5.04 (d, J=1.7 Hz, 1H), 4.49-4.36 (m, 1H), 4.31 (dd, J=6.3, 4.7 Hz, 1H), 4.21 (dd, J=4.5, 2.2 Hz, 1H), 4.10-4.01 (m, 2H), 3.92 (ddd, J=8.4, 4.5, 1.9 Hz, 1H), 3.84 (t, J=3.3 Hz, 1H), 3.78-3.71 (m, 1H), 3.64-3.24 (m, 13H), 2.18-2.09 (m, 1H), 1.32-1.25 (m, 1H).

Step 5

(2S,3S,4R,5R,6R)-5-amino-2-(aminomethyl)-6-[(2R,3S,4R,5S)-5-[(1R,2R,3S,5R,6S)-3,5-diamino-2-[(2S,3R,4R,6R)-3-amino-6-(aminomethyl)-5,5-difluoro-4-hydroxy-tetrahydropyran -2-yl]oxy-6-hydroxy-cyclohexoxy]-4-hydroxy-2-(hydroxymethyl)tetrahydrofuran-3-yl] oxy -tetrahydropyran-3,4-diol

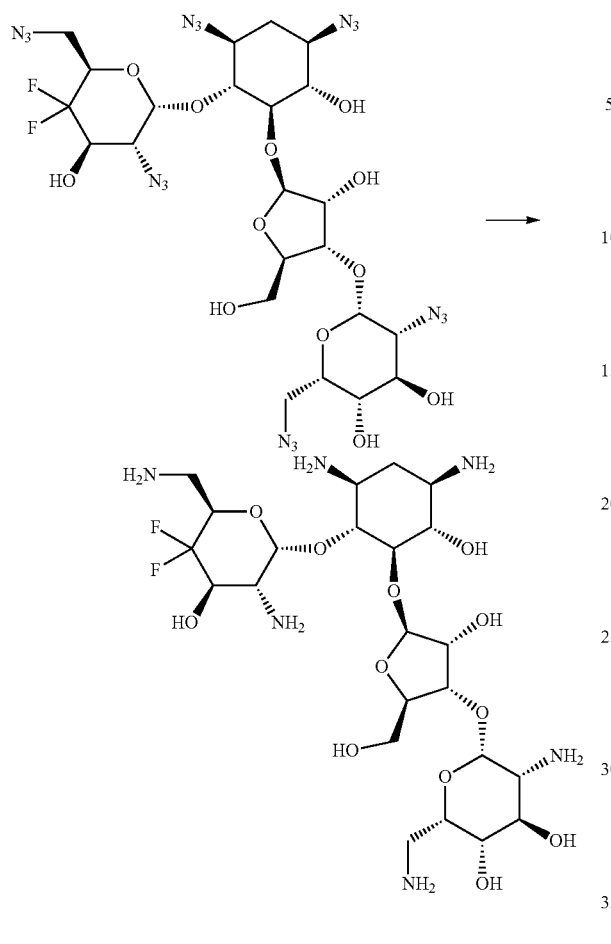

Pd(OH)$_2$ (2.8 mg, 2.0 µmol) was added to a solution of (2S,3S,4R,5R,6R)-5-azido-2-(azidomethyl)-6-[(2R,3S,4R,5S)-5-[(1R,2R,3S,5R,6S)-3,5-diazido-2-[(2S,3R,4R,6R)-3-azido-6-(azidomethyl)-5,5-difluoro-4-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol (4.5 mg, 5.7 µmol) in MeOH (3.0 mL) under N$_2$ at ambient temperature. The suspension was bubbled with H$_2$ for 10 min and then hydrogenated for 16 h under hydrogen atmosphere (1 atm, balloon). The mixture was filtered through a frit (nylon, 0.45 µm diameter), rinsed with MeOH and the filtrate was concentrated under reduced pressure to give the title compound. Note: the exact procedure was repeated (on 13.5 mg, 17.1 µmol scale) to give the title compound (16.4 mg overall amount). $^1$H NMR (500 MHz, MeOD) δ 5.54 (s, 1H), 5.35 (d, J=2.8 Hz, 1H), 4.98 (d, J=1.7 Hz, 1H), 4.43-4.39 (m, 1H), 4.19-4.07 (m, 3H), 4.01-3.93 (m, 3H), 3.86-3.81 (m, 1H), 3.74 (dd, J=12.3, 3.9 Hz, 1H), 3.61 (t, J=9.2 Hz, 1H), 3.54-3.47 (m, 2H), 3.25 (t, J=9.5 Hz, 1H), 3.15 (dd, J=13.2, 8.4 Hz, 1H), 3.06-3.00 (m, 2H), 2.98-2.90 (m, 3H), 2.90-2.84 (m, 1H), 2.68 (ddd, J=12.2, 9.8, 4.1 Hz, 1H), 2.04-1.96 (m, 1H), 1.30-1.20 (m, 1H).

Preparation of [(2R,4R,5R-5-azido-2-(azidomethyl)-3,3-difluoro-6-hydroxy-tetrahydropyran-4-yl]acetate

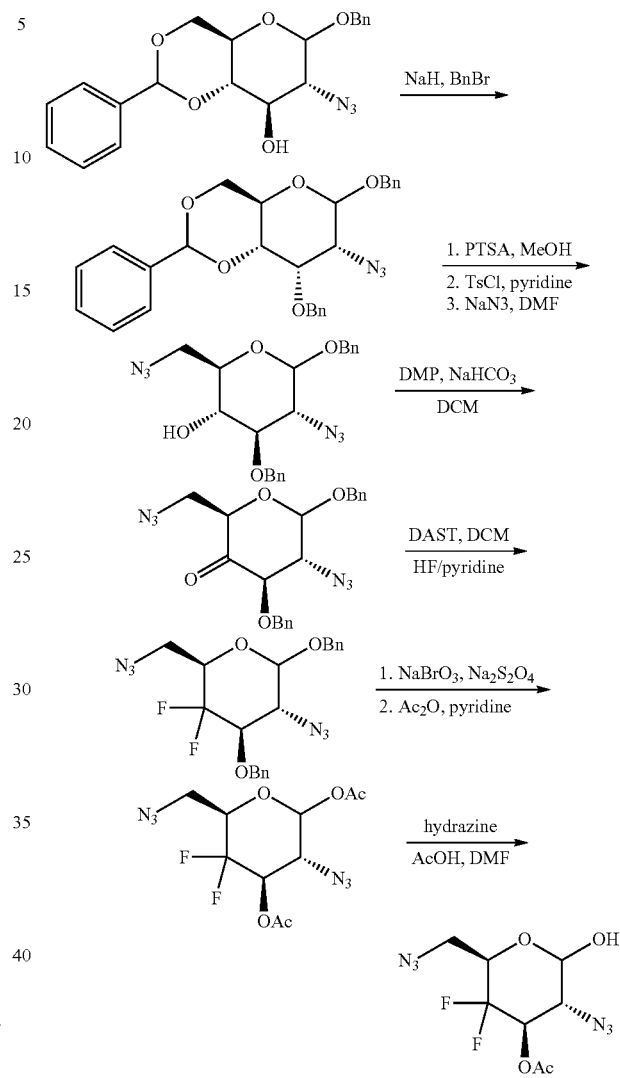

Step 1
(4aR,7R,8R,8aS)-7-azido-6,8-bis(benzyloxy)-2-phenyl-hexahydropyrano[3,2-d][1,3]dioxine

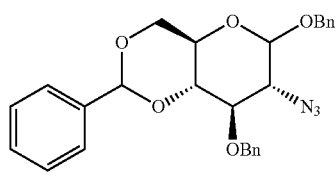

To a solution of 4.8 g of (4aR,7R,8R,8aS)-7-azido-6-(benzyloxy)-2-phenylhexahydropyrano[3,2-d][1,3]dioxin-8-ol in 50 mL of anhydrous DMF at 4° C., was added 750 mg of NaH in several portions. The reaction was stirred at 0° C. for 30 minutes. 2.2 g of benzyl bromide was added to the reaction and the vessel was removed from the ice bath and allowed to warm to room temperature. After completion, the reaction was quenched with cold water and concentrated in vacuo. The concentrate was dissolved in DCM and

473 washed with equal volumes of 1 N HCl and brine. The organic portion was dried, filtered and concentrated to dryness. The residue was then purified by flash chromatography (10% EtOAc in hexanes) to yield 5.7 g of (4aR,7R,8R,8aS)-7-azido-6,8-bis(benzyloxy)-2-phenylhexahydropyrano[3,2-d][1,3]dioxine (96% yield).

Step 2
(2R,3R,4R,5R)-5-azido-2-(azidomethyl)-4,6-bis(benzyloxy)tetrahydro-2H-pyran-3-ol

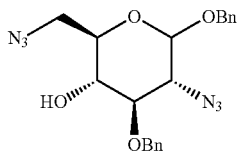 [SMILES: [N-]=[N+]=NC[C@H]1OC(OCc2ccccc2)[C@H](N=[N+]=[N-])[C@@H](OCc2ccccc2)[C@@H]1O]

To a solution of 15 g of (4aR,7R,8R,8aS)-7-azido-6,8-bis(benzyloxy)-2-phenylhexa-hydropyrano[3,2-d][1,3]dioxine in 100 mL of methanol, was added 540 mg of p-toluenesulfonic acid at room temperature. The reaction was stirred at room temperature for 4 hours until completion. The reaction was then quenched with 0.1 equivalent of triethylamine, concentrated, and purified by flash chromatography (10% EtOAC in DCM) to yield 5.6 g of the diol intermediate. The diol was dissolved in 15 mL of DCM, cooled to 0° C., and 9 mL of pyridine was added, followed by 3.6 g of Tosyl chloride. The reaction was stirred at 0° C. for 3 hours until completion. The reaction was then diluted with 100 mL of DCM and washed with an equal volume of 1 N HCl followed by aqueous sodium bicarbonate. The organic portion was dried, filtered and concentrated. The crude concentrate was dissolved in mL DMF, 4.7 g of sodium azide was added, and the reaction heated at 70° C. for hours. The DMF was removed by evaporation and the crude was dissolved in EtOAc and washed with water. The organic portion was dried, filtered, and concentrated then purified by flash chromatography to yield 5.8 g of (2R,3R,4R,5R)-5-azido-2-(azidomethyl)-4,6-bis(benzyloxy)tetrahydro-2H-pyran-3-ol (97% yield).

Step 3
(2R,4R,5R)-5-azido-2-(azidomethyl)-4,6-bis(benzyloxy)dihydro-2H-pyran-3(4H)-one

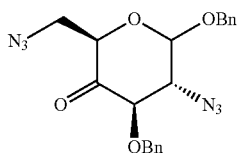 [SMILES: [N-]=[N+]=NC[C@H]1OC(OCc2ccccc2)[C@H](N=[N+]=[N-])[C@@H](OCc2ccccc2)C1=O]

To a solution of 5.9 g of the alcohol (2R,3R,4R,5R)-5-azido-2-(azidomethyl)-4,6-bis(benzyloxy)tetrahydro-2H-pyran-3-ol in 50 mL of DCM was added 1.57 g of NaHCO$_3$ and 7.93 g of DMP at 0° C. and the reaction was allowed to warm to room temperature and stirred until completion. The reaction was quenched with aqueous sodium bicarbonate, diluted with DCM, and washed with an equal volume of aqueous sodium bicarbonate. The organic portion was dried, filtered, concentrated, and purified by flash chromatography to yield a white solid. The solid was washed with Et$_2$O to obtain 5.0 g of pure product (85% yield).

474

Step 4
(2R,4R,5R)-5-azido-2-(azidomethyl)-4,6-bis(benzyloxy)-3,3-difluorotetrahydro-2H-pyran

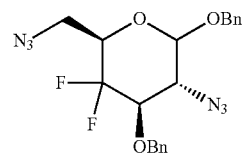 [SMILES: [N-]=[N+]=NC[C@H]1OC(OCc2ccccc2)[C@H](N=[N+]=[N-])[C@@H](OCc2ccccc2)C1(F)F]

To a solution of 2.6 g of (2R,4R,5R)-5-azido-2-(azidomethyl)-4,6-bis(benzyloxy)dihydro-2H-pyran-3(4H)-one in 30 mL DCM was added 3.5 g of DAST and 291 mg HF/pyridine at 0° C. The reaction was then heated to reflux until the reaction was complete.

The reaction was then cooled to 0° C. and quenched with aqueous sodium bicarbonate, then diluted with DCM and washed with an equal volume of aqueous sodium bicarbonate. The organic portion was dried, filtered and concentrated, then purified by flash chromatography (15:85 EtOAc/Hexanes) to yield 1.8 grams of (2R,4R,5R)-5-azido-2-(azidomethyl)-4,6-bis(benzyloxy)-3,3-difluorotetrahydro-2H-pyran (66% yield).

Step 5
(3R,4R,6R)-3-azido-6-(azidomethyl)-5,5-difluorotetrahydro-2H-pyran-2,4-diyl diacetate

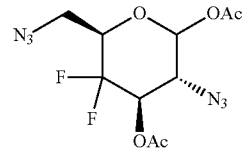

The starting material, (2R,4R,5R)-5-azido-2-(azidomethyl)-4,6-bis(benzyloxy)-3,3-difluorotetrahydro-2H-pyran, was dissolved in 7.2 mL EtOAc. 6 mL of aqueous sodium bromate (69 mM) was added to the reaction in one portion. Next, aqueous sodium dithionate was slowly added dropwise over 15 minutes and the reaction stirred vigorously until completion. The reaction was diluted with EtOAc and and washed with 1:1 aqueous sodium bicarbonate and sodium thiosulfate. The organic layer was concentrated and dissolved in 10 mL anhydrous pyridine. 3 mL of acetic anhydride was added slowly and the reaction stirred at room temperature until completion. The reaction was concentrated to dryness, dissolved in 100 mL DCM, and washed with 1 N HCl aq, followed by saturated aqueous sodium bicarbonate. The organic portion was concentrated, dissolved in DCM, and purified by flash chromatography (3:7 EtOAc/Hexanes) to yield 135 mg of (3R,4R,6R)-3-azido-6-(azidomethyl)-5,5-difluorotetrahydro-2H-pyran-2,4-diyl diacetate (88% yield).

Step 6
(2R,4R,5R)-5-azido-2-(azidomethyl)-3,3-difluoro-6-hydroxytetrahydro-2H-pyran-4-yl acetate

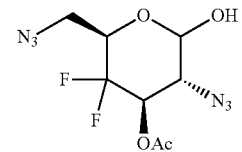 [SMILES: CC(=O)O[C@@H]1[C@@H](N=[N+]=[N-])C(O)O[C@H](CN=[N+]=[N-])C1(F)F]

To a solution of 140 mg (3R,4R,6R)-3-azido-6-(azidomethyl)-5,5-difluorotetrahydro-2H-pyran-2,4-diyl diacetate in 2 mL of anhydrous DMF, was added 40 mg of hydrazine acetate. The reaction was heated at 50° C. for 1 hour. The reaction was concentrated to dryness and the residue taken up in 100 mL DCM. The organic layer was washed with 1 N HCl and aqueous sodium bicarbonate. The washed organic portion was concentrated and purified by flash chromatography (3:7 EtOAc/Hexanes). 110 mg of (2R,4R,5R)-5-azido-2-(azidomethyl) -3,3-difluoro-6-hydroxytetrahydro-2H-pyran-4-yl acetate was isolated (92% yield).

Example 39

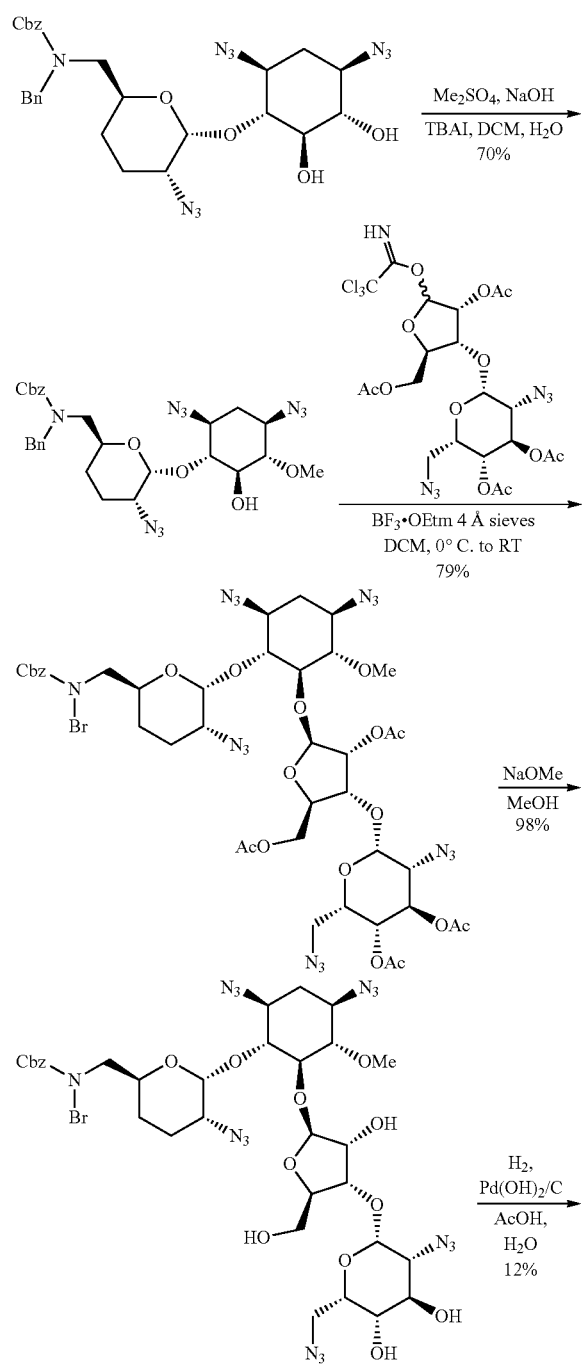

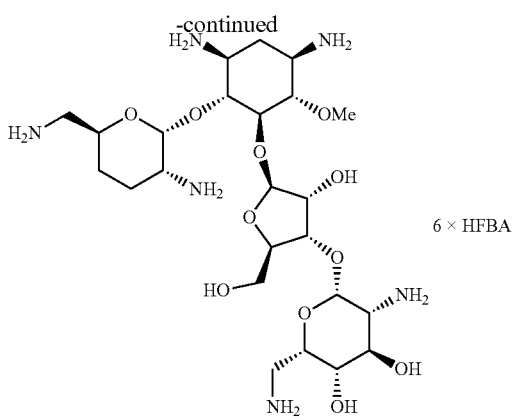

Step 1
Benzyl N-[[(2S, 5R,6R)-5-azido-6-[(1R,2R,3S,4R,6S)-4,6-diazido-2-hydroxy-3-methoxy -cyclohexoxy]tetrahydropyran-2-yl]methyl]-N-benzyl-carbamate

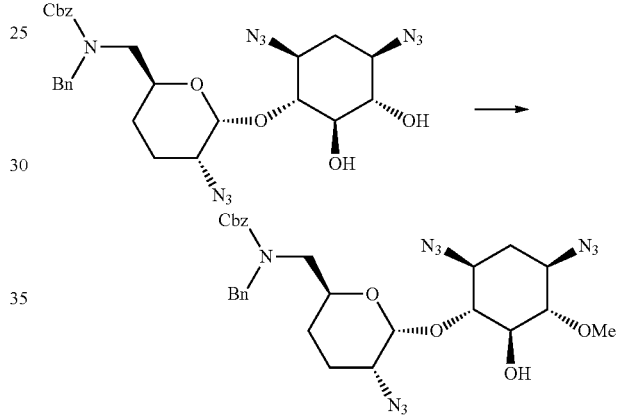

Me$_2$SO$_4$ (128 µL, 1.35 mmol) was added to a vigorously stirring suspension of benzyl N-[[(5R,6R)-5-azido-6-[(1R,2R,3S,4R,6S)-4,6-diazido-2,3-dihydroxy -cyclohexoxy]tetrahydropyran-2-yl]methyl]-N-benzyl-carbamate (see Example 31 for synthesis, 100 mg, 169 µmol) and TBAI (9 mg, 25 µmol) in DCM (2.5 mL) and NaOH solution (1.0 M aq., 2.5 mL, 2.5 mmol) at ambient temperature. After 2 h, concentrated NH$_4$OH (300 µL) was added and the mixture was partitioned in between water (10.0 mL) and DCM (10.0 mL). The aqueous layer was extracted with DCM (2×5.0 mL). The combined organic layers were dried (Na$_2$SO$_4$), filtered and concentrated under reduced pressure. The residue was filtered through silica gel (0.30 g) and eluted with EtOAc (6.0 mL). The filtrate was concentrated under reduced pressure and the material was purified by preparative HPLC (BEH 30×150 mm C18 ACN/AmForm 70-80%) to provide the title compound (rotamers, 72 mg, 70%) as a solid. $^1$H NMR (500 MHz, CDCl$_3$) δ 7.39-7.13 (m, 10H), 5.34-5.08 (m, 3H), 4.81-4.69 (m, 1H), 4.56-4.45 (m, 1H), 4.27 (d, J=43.5 Hz, 1H), 3.69 (s, 3H), 3.61-3.14 (m, 8H), 2.99 (t, J=9.5 Hz, 1H), 2.22 (dt, J=13.2, 4.5 Hz, 1H), 2.08-1.96 (m, 1H), 1.96-1.87 (m, 1H), 1.87-1.68 (m, 1H), 1.50-1.30 (m, 2H). MS ESI [M+H]$^+$607.3.

Step 2
[(2R,3R,4R,5S)-4-acetoxy-3-[(2R,3R,4R,5R,6S)-4,5-diacetoxy-3-azido-6-(azidomethyl)tetrahydropyran-2-yl]oxy-5-

[(1R,2R,3S,5R,6S)-3,5-diazido-2-[(2R,3R,6S)-3-azido-6-[[benzyl(benzyloxycarbonyl)amino]methyl]tetrahydropyran-2-yl]oxy-6-methoxy -cyclohexoxy]tetrahydrofuran-2-yl]methyl acetate

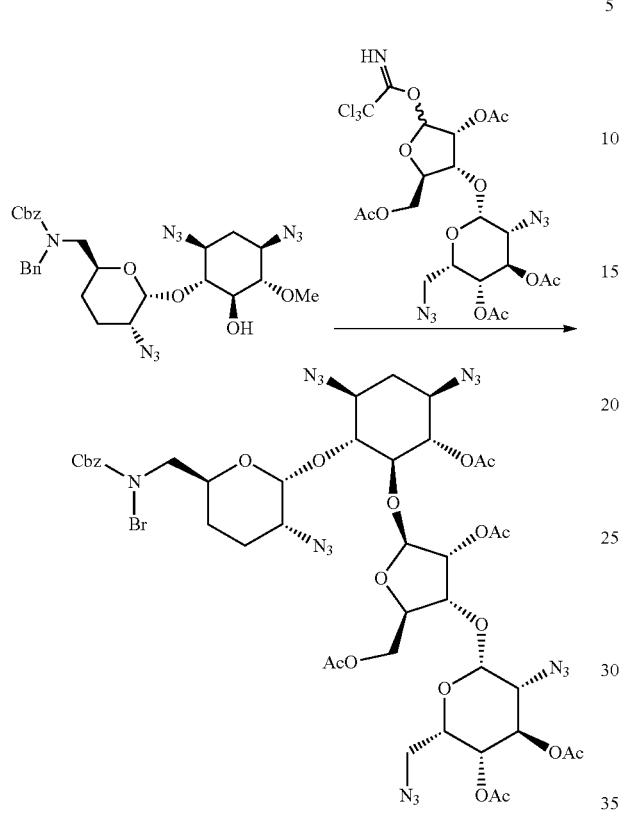

hydroxy-5-(hydroxymethyl)tetrahydrofuran-2-yl]oxy-3-methoxy-cyclohexoxy]tetrahydropyran -2-yl]methyl]-N-benzyl-carbamate

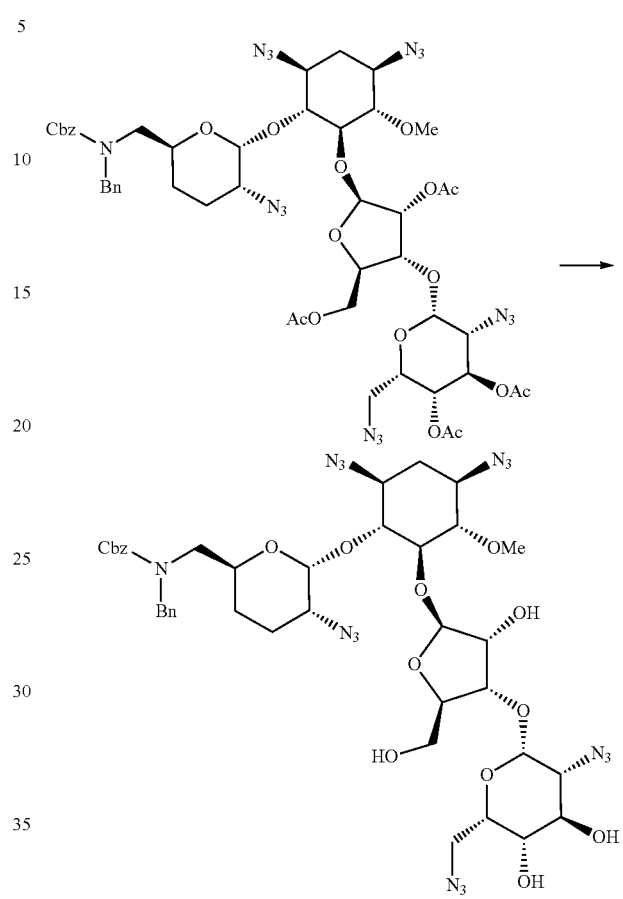

CCl$_3$CN (119 µL, 1.19 mmol) was added dropwise to a suspension of [(2R,3R,4R)-4-acetoxy-3-[(2R,3R,4R,5R,6S)-4,5-diacetoxy-3-azido-6 -(azidomethyl)tetrahydropyran-2-yl]oxy-5-hydroxy-tetrahydrofuran-2-yl]methyl acetate (126 mg, 237 µmol) and K$_2$CO$_3$ (98 mg, 712 µmol) in dry DCM (2.0 mL) at ambient temperature under N$_2$. After 18 h, the solution was filtered through cotton and the filtrate was concentrated under N$_2$ stream, followed by high-vacuum. To the crude material was added a solution of benzyl N -[[(2S,5R,6R)-5-azido-6-[(1R,2R,3S,4R,6S)-4,6-diazido-2-hydroxy-3-methoxy -cyclohexoxy]tetrahydropyran-2-yl]methyl]-N-benzyl-carbamate (72 mg, 119 µmol) in DCM (3.0 mL) and then all volatiles were evaporated under N$_2$ stream. To the mixture was added ground 4 Å sieves (500 mg) and the mixture was dissolved in dry DCM (2.0 mL). The suspension was stirred at ambient temperature for 60 min, then cooled to 0° C., and then BF$_3$·OEt$_2$ (43 µL, 351 µmol) was added. The mixture was stirred at ambient temperature for 1 h and then Et$_3$N (200 µL) was added. The mixture was filtered through a silica gel pad (0.50 g) and eluted with EtOAc (10.0 mL). The volatiles were evaporated under reduced pressure and the material was purified by reversed phase chromatography (C18, 30 g cartridge) with ACN and 0.1% aqueous formic acid (50-100%) to produce the title compound (105 mg, 79%) as a solid. MS ESI [M+H]$^+$1019.4.

Step 3
Benzyl N-[[(2S,5R,6R)-5-azido-6-[(1R,2R,3S,4R,6S)-4,6-diazido-2-[(2S,3R,4S,5R)-4-[(2R,3R,4R,5S,6S)-3-azido-6-(azidomethyl)-4,5-dihydroxy-tetrahydropyran-2-yl]oxy-3-

NaOMe (25 wt %, 77 µL, 336 µmol) was added dropwise to a solution of [(2R,3R,4R,5S)-4-acetoxy-3-[(2R,3R,4R,5R,6S)-4,5-diacetoxy-3-azido-6-(azidomethyl)tetrahydropyran-2-yl]oxy-5-[(1R,2R,3S,5R,6S)-3,5-diazido-2-[(2R,3R,6S)-3-azido-6-[[benzyl(benzyloxycarbonyl)amino]methyl]tetrahydropyran-2-yl]oxy-6-methoxy -cyclohexoxy]tetrahydrofuran-2-yl]methyl acetate (47 mg, 42 µmol) in MeOH (1.0 mL) at ambient temperature and the reaction mixture was stirred for 75 min. AcOH (29 µL, 504 µmol) was added dropwise and all volatiles were evaporated under reduced pressure. The material was filtered through silica gel (0.30 g) and eluted with EtOAc (8.0 mL) to provide the title compound (rotamers, 39 mg, 98%) as a solid. $^1$H NMR (500 MHz, CDCl$_3$) δ 7.39-7.25 (m, 9H), 7.18 (d, J=7.1 Hz, 1H), 5.73 (d, J=25.1 Hz, 1H), 5.40 (d, J=4.6 Hz, 1H), 5.30-5.07 (m, 3H), 4.85-4.65 (m, 1H), 4.59-4.46 (m, 1H), 4.39-4.22 (m, 2H), 4.16 (s, 1H), 4.11-4.08 (m, 1H), 4.02 (ddd, J=8.5, 4.5, 1.9 Hz, 1H), 3.99 (dd, J=5.8, 4.8 Hz, 1H), 3.88 (dd, J=12.6, 2.3 Hz, 1H), 3.83-3.73 (m, 3H), 3.69-3.60 (m, 4H), 3.52 (t, J=9.5 Hz, 1H), 3.47-3.33 (m, 5H), 3.28-3.13 (m, 1H), 3.12-2.88 (m, 3H), 2.23-2.15 (m, 1H), 2.15-2.09 (m, 1H), 1.93-1.69 (m, 2H).

Step 4
(2S,3S,4R,5R,6R)-5-amino-2-(aminomethyl)-6-[(2R,3S,4R,5S)-5-[(1R,2R,3S,5R,6S)-3,5 -diamino-2-[(2R,3R,6S)-3-amino-6-(aminomethyl)tetrahydropyran-2-yl]oxy-6-methoxy -cyclohexoxy]-4-hydroxy-2-(hydroxymethyl)

tetrahydrofuran-3-yl]oxy-tetrahydropyran-3,4-diol;2,2,3,3,4,4,4-heptafluorobutanoic acid Example 40

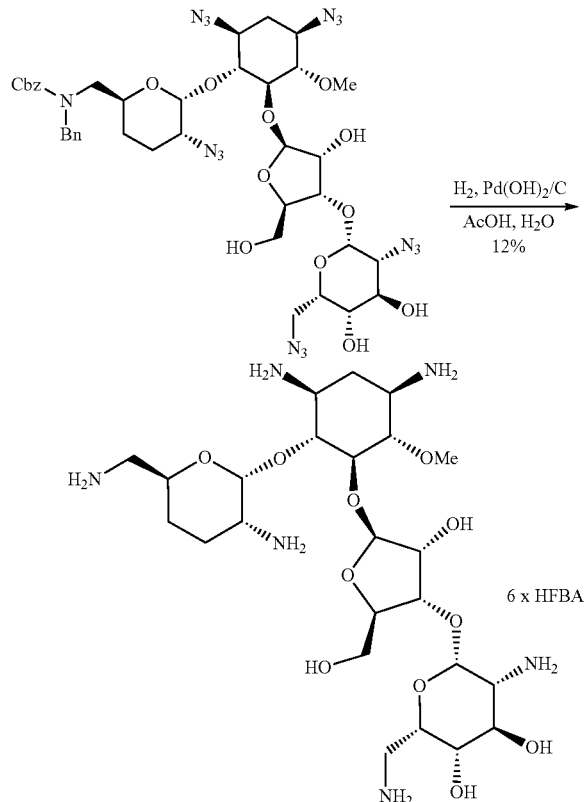

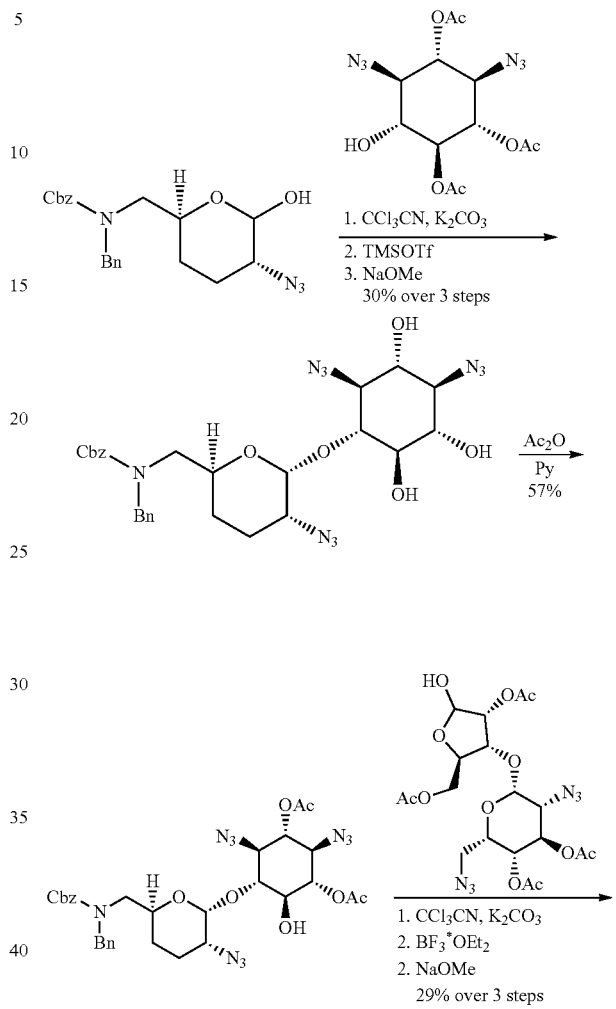

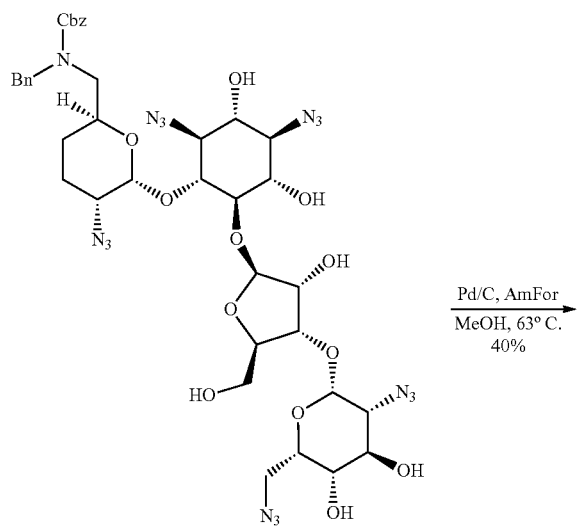

Pd(OH)$_2$/C (10 wt %, 18 mg, 13 µmol) was added to a solution of benzyl N-[[(2S,5R,6R)-5-azido-6-[(1R,2R,3S,4R,6S)-4,6-diazido-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-3-methoxy-cyclohexoxy]tetrahydropyran-2-yl]methyl]-N-benzyl-carbamate (18 mg, 19 µmol) in 4:1 AcOH/H$_2$O (0.50 mL) under N$_2$ at ambient temperature. H$_2$ was bubbled into the solution for 20 min and the resulting mixture was for 20 h. The mixture was filtered through a frit (0.45 µm diameter), washed with water (5.0 mL) and the filtrate was lyophilized. The material was purified by a HFBA-coupled preparative HPLC to provide the title compound (4.4 mg, 12%) as a solid. $^1$H NMR (500 MHz, MeOD) δ 6.08 (d, J=3.5 Hz, 1H), 5.40 (d, J=3.9 Hz, 1H), 5.32 (d, J=1.3 Hz, 1H), 4.40 (t, J=5.7 Hz, 1H), 4.29 (dd, J=6.0, 4.1 Hz, 1H), 4.24 (t, J=9.5 Hz, 1H), 4.16-4.07 (m, 4H), 3.95 (t, J=8.9 Hz, 1H), 3.90 (dd, J=12.2, 2.4 Hz, 1H), 3.76 (dd, J=12.1, 5.3 Hz, 1H), 3.69-3.67 (m, 1H), 3.67 (s, 3H), 3.56-3.46 (m, 3H), 3.41-3.35 (m, 3H), 3.26 (dd, J=13.4, 3.9 Hz, 1H), 3.15 (dd, J=13.2, 2.4 Hz, 1H), 2.95 (dd, J=13.2, 8.6 Hz, 1H), 2.46 (dt, J=12.1, 3.7 Hz, 1H), 2.23-2.08 (m, 2H), 1.96-1.83 (m, 2H), 1.57-1.46 (m, 1H). MS (ESI) [M+H]$^+$ 597.4.

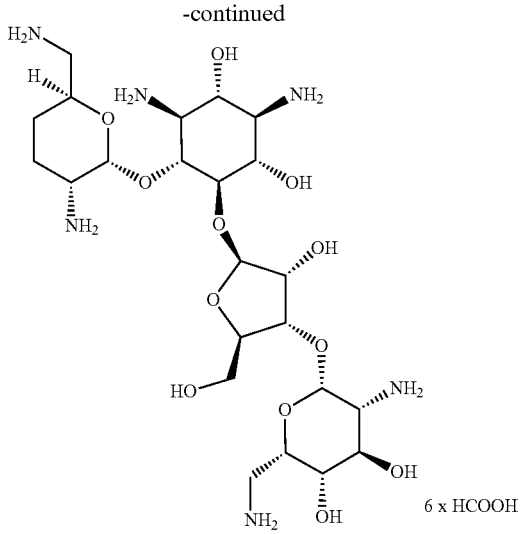

6 x HCOOH

Step 1
Benzyl N-[[(2S,5R,6R)-5-azido-6-[(1R,2S,3R,4R,5S,6R)-2,4-diazido-3,5,6-trihydroxy -cyclohexoxy]tetrahydropyran-2-yl]methyl]-N-benzyl-carbamate

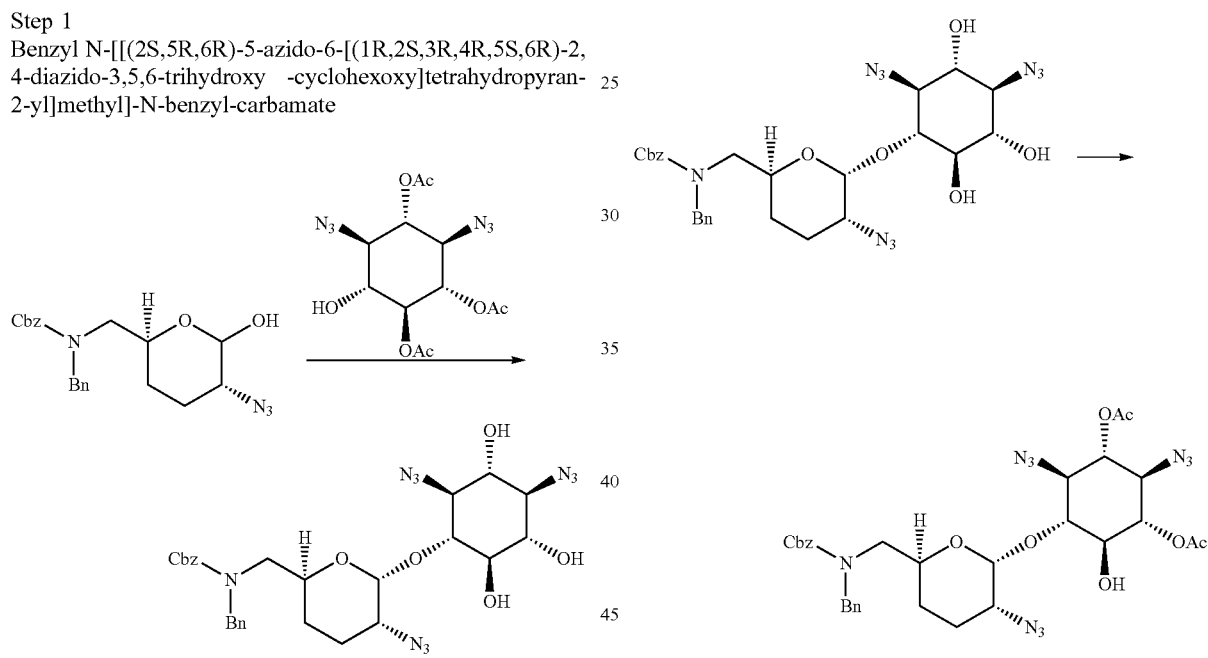

To a suspension of benzyl N-[[(2S,5R)-5-azido-6-hydroxy-tetrahydropyran-2 -yl]methyl]-N-benzyl-carbamate (see Example 31 for synthesis, 101 mg, 0.26 mmol) and K₂CO₃ (155 mg, 1.12 mmol) in DCM (3 mL) was added CCl₃CN (0.14 mL, 1.40 mmol). The mixture was stirred at room temperature for 18 h, then filtered on Celite, rinsed with DCM and concentrated under reduced pressure. [(1S,2R,3S,4S,5R,6R)-3,4-diacetoxy-2,6-diazido-5 -hydroxy-cyclohexyl]acetate (70 mg, 0.20 mmol) was added to the above material, and the mixture was co-evaporated with anhydrous toluene (3×10 mL) and then was dried under reduced pressure for 2 h. To a solution of above material in anhydrous Et₂O (10 mL) were added activated 3 Å (0.5 g) and 4 Å sieves (0.5 g). The mixture was stirred at room temperature for 1 h, then cooled to −45° C. TMSOTf (0.01 mL, 0.06 mmol) was added dropwise and the mixture was stirred at −40° C. for 2 h, then warmed to room temperature. A saturated solution of NaHCO₃ (20 mL) was added and the separated aqueous layer was extracted with EtOAc (3×30 mL). The combined organic layers were dried (MgSO₄), filtered and concentrated under reduced pressure. To a solution of above material in MeOH (6 mL), NaOMe (4.62 M in MeOH, 0.34 mL, 1.57 mmol) was added and the mixture was stirred at room temperature for 1 h. The volatiles were evaporated under reduced pressure. The residue was dissolved in DCM (25 mL) and a saturated solution of NH₄Cl (25 mL) was added. The separated aqueous layer was extracted with DCM (2×30 mL). The combined organic layers were dried (MgSO₄), filtered and concentrated under reduced pressure. The material was purified by MPLC on silica (24 g, liquid loading with toluene) using a gradient of 0-50% EtOAc in hexane as eluent to provide the title compound (70 mg, 59% over 3 steps) as a solid. MS (ESI) [M+H]⁺609.2

Step 2
[(1S,2R,3S,4S,5R,6S)-3-acetoxy-2,6-diazido-5-[(2R,3R,6S)-3-azido-6-[[benzyl (benzyloxy carbonyl)amino]methyl]tetrahydropyran-2-yl]oxy-4-hydroxy-cyclohexyl]acetate To a solution of benzyl N-[[(2S,5R,6R)-5-azido-6-[(1R,2S,3R,4R,5S,6R)-2,4 -diazido-3,5,6-trihydroxy-cyclohexoxy]tetrahydropyran-2-yl]methyl]-N-benzyl-carbamate (70 mg, 0.115 mmol) in DCM (3 mL) was added pyridine (0.07 mL, 0.81 mmol) followed by Ac₂O (0.07 mL, 0.69 mmol) and the reaction mixture was stirred at room temperature for 18 h. MeOH (1 mL) was then added and the mixture was concentrated under reduced pressure. The material was purified by MPLC on silica gel (24 g, liquid loading with toluene) using a gradient of 0-45% EtOAc in hexane as eluent to provide the title compound (45 mg, 57%) as a solid.

Step 3
Benzyl (((2S,5R,6R)-5-azido-6-(((1R,2S,3R,4R,5S,6R)-2,4-diazido-6-(((2S,3R,4S,5R)-4-(((2R,3R,4R,5S,6S)-3-azido-6-(azidomethyl)-4,5-dihydroxytetrahydro-2H-pyran-2-yl)oxy)-3-hydroxy-5-(hydroxymethyl)tetrahydrofuran-2-yl)oxy)-3,5-dihydroxycyclohexyl)oxy)tetrahydro -2H-pyran-2-yl)methyl)(benzyl)carbamate

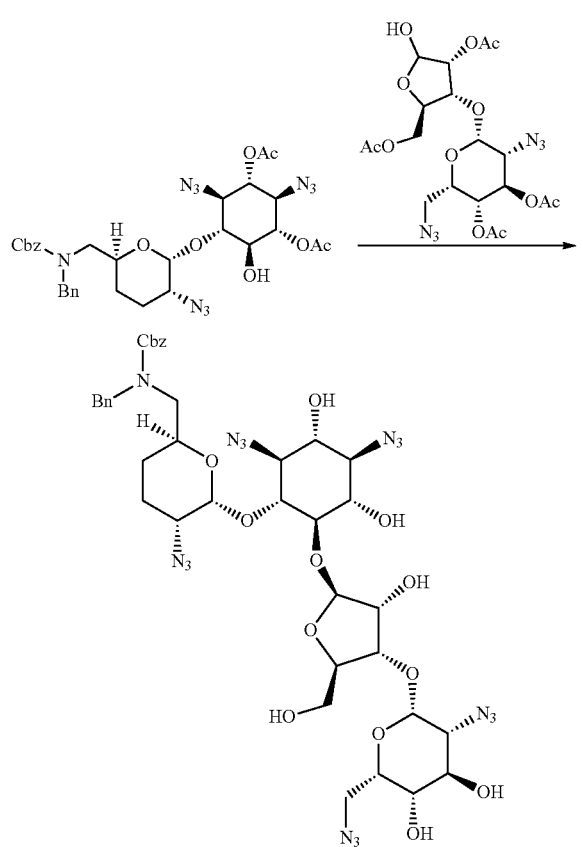

Step 4
(2S,3S,4R,5R,6R)-5-amino-2-(aminomethyl)-6-(((2R,3S,4R,5S)-5-(((1R,2R,3S,4R,5R,6S)-3,5-diamino-2-(((2R,3R,6S)-3-amino-6-(aminomethyl)tetrahydro-2H-pyran-2-yl)oxy)-4,6-dihydroxycyclohexyl)oxy)-4-hydroxy-2-(hydroxymethyl) tetrahydrofuran-3-yl)oxy)tetrahydro -2H-pyran-3,4-diol; 6 HCOOH

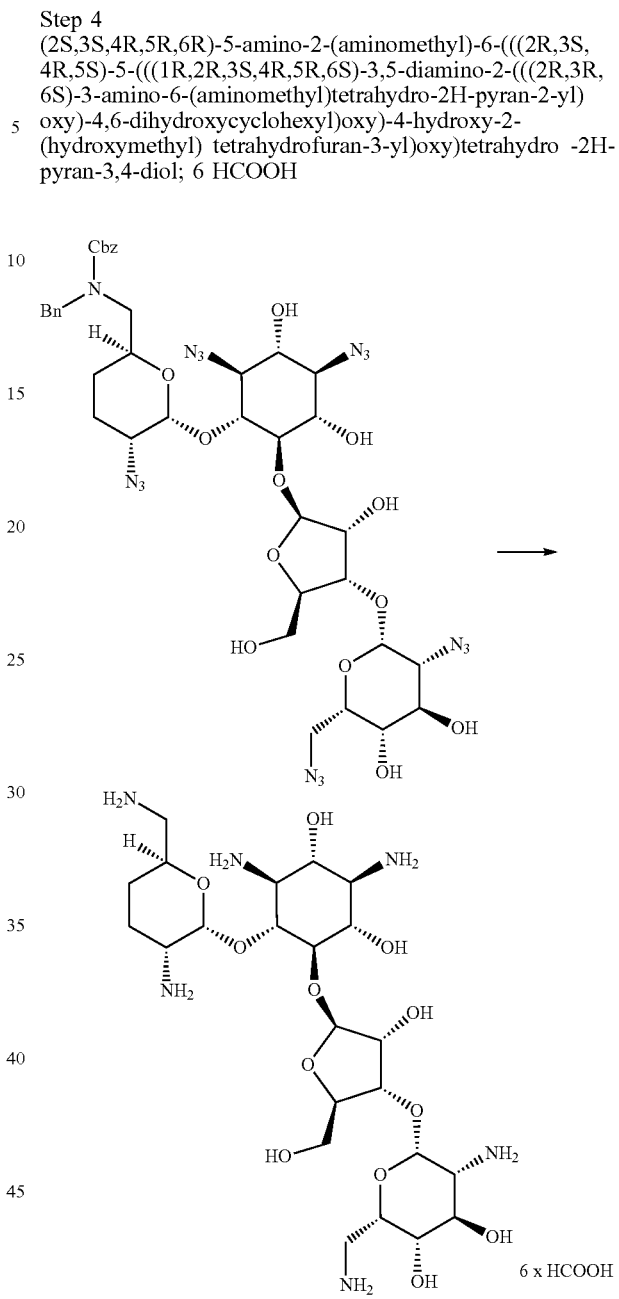

To a mixture of [(2R,3R,4R)-4-acetoxy-3-[(2R,3R,4R,5R,6S)-4,5-diacetoxy-3 -azido-6-(azidomethyl) tetrahydropyran-2-yl]oxy-5-hydroxy-tetrahydrofuran-2-yl]methyl acetate (76 mg, 0.14 mmol) and $K_2CO_3$ (54 mg, 0.07 mmol) in DCM (10 mL) was added $CCl_3CN$ (0.05 mL, 0.52 mmol) at room temperature. The mixture was stirred at room temperature for 18 h, then filtered on Celite, rinsed with DCM and concentrated under reduced pressure. To the above material in dry DCM (10 mL) was added (1S,2R,3S,4S,5R,6S)-2,4-diazido-5-(((2R,3R,6S)-3-azido-6-((benzyl ((benzyloxy)carbonyl)amino)methyl)tetrahydro-2H-pyran-2-yl)oxy)-6-hydroxycyclohexane-1,3-diyl diacetate (45 mg, 0.07 mmol) followed by activated 3 Å sieves (1 g). The mixture was cooled to −78° C. and then $BF_3·OEt_2$ (0.03 mL, 0.23 mmol) was added dropwise. The acetone-dry ice bath was removed, and the reaction mixture was slowly warmed to room temperature, and then saturated $NaHCO_3$ (10 mL) was added. The separated aqueous layer was extracted with DCM (3×15 mL). The combined organic layers were washed with brine, dried ($MgSO_4$), filtered and concentrated under reduced pressure. To a solution of the above material in MeOH (10 mL), NaOMe (4.62 M in MeOH, 0.14 mL, 0.65 mmol) was added at room temperature and the reaction mixture was stirred for 1 h. The mixture was diluted with saturated $NH_4Cl$ (10 mL) and the separated aqueous layer was extracted with DCM (3×15 mL). The combined organic layers were washed with brine, dried ($MgSO_4$), filtered and concentrated under reduced pressure. The material was purified by preparative HPLC to provide the title compound (18 mg, 29% over 3 steps) as a solid. MS (ESI) [M+Na]⁺ 953.3.

MeOH (5.0 mL) was added to a mixture of Pd/C (10% on carbon, 8.0 mg, 0.01 mmol) and benzyl (((2S,5R,6R)-5-azido-6-(((1R,2S,3R,4R,5S,6R)-2,4-diazido-6 -(((2S,3R,4S,5R)-4-(((2R,3R,4R,5S,6S)-3-azido-6-(azidomethyl)-4,5-dihydroxytetrahydro-2H -pyran-2-yl)oxy)-3-hydroxy-5-(hydroxymethyl)tetrahydrofuran-2-yl)oxy)-3,5 -dihydroxycyclohexyl)oxy)tetrahydro-2H-pyran-2-yl)methyl)(benzyl)carbamate (18 mg, 0.02 mmol) under $N_2$. The suspension was degassed for 5 min, then ammonium formate (18 mg, 0.28 mmol) was added. The septum was replaced by a reflux condenser, followed by 3 vacuum/nitrogen cycles and the reaction mixture was heated at 63° C. for 5 h, then cooled to room temperature. The mixture was filtered with a syringe filter and concentrated under reduced pressure. The material was purified by preparative HPLC (Waters XBridge C18, 30×150 mm; 40 mL/min) using isocratic 10% acetonitrile in water (10 mM AmForm pH 3.8) over 7 min to provide the title compound (6.60 mg, 40%) as a solid. ¹H NMR (500 MHz, D₂O) δ 8.47 (br, 6H), 5.91 (d, J=3.3 Hz, 1H), 5.44 (d, J=2.5 Hz, 1H), 5.33 (s, 1H), 4.51 (t, J=5.5 Hz, 1H), 4.42-4.39 (m, 1H), 4.36-4.33 (m, 1H), 4.28-4.18 (m, 3H), 4.05-3.91 (m, 3H), 3.87-3.84 (m, 1H), 3.80-3.71 (m, 3H), 3.64-3.61 (m, 1H), 3.60-3.55 (m, 1H), 3.49-3.38 (m, 2H), 3.34-3.23 (m, 3H), 3.11 (dd, J=13.5, 7.6 Hz, 1H), 2.12-1.99 (m, 2H), 1.98-1.91 (m, 1H), 1.66-1.55 (m, 1H). MS (ESI) [M+H]⁺599.4.
Example 41
Step 1
(3aR,5R,6S,6aS)-5-[(4R)-2,2-dimethyl-1,3-dioxolan-4-yl]-6-fluoro-2,2-dimethyl-3a,5,6,6a-tetrahydrofuro[2,3-d][1,3]dioxole
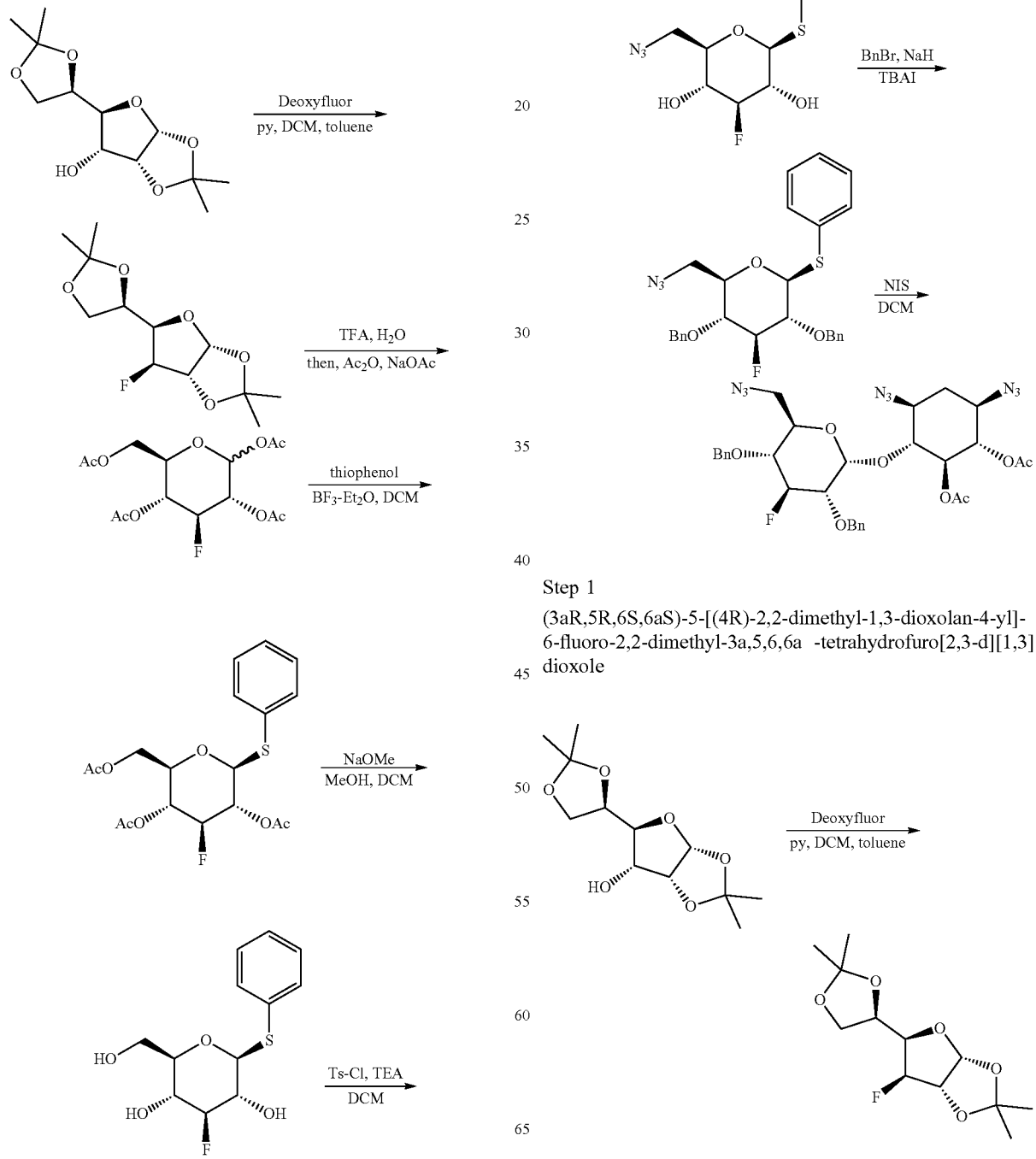

Allofuranose diacetonide (10 g, 38.4 mmol) was dissolved in 35 mL of dry DCM and pyridine at −78° C. To the cold solution, 2.7 M Deoxyfluor in toluene (20 mL, 54 mmol) was added dropwise. The reaction was stirred for 7 days at 40° C. The reaction was quenched with sat NaHCO$_3$, and the aqueous phase was extracted with DCM (3×50 mL). Combined organic phases were washed with NaHCO$_3$ (100 mL) and dried with Na$_2$SO$_4$. The crude material was purified by MPLC to afford the title compound (9.54 g, 36.4 mmol, 95%). Acetonides fragment on mass spec: MS (ESI) [M-both acetonides+Na]$^+$=205.1.

Step 2

[(2R)-2-[(3aR,5R,6S,6aS)-6-fluoro-2,2-dimethyl-3a,5,6,6a-tetrahydrofuro[2,3-d][1,3]dioxol-5-yl]-2-acetoxy-ethyl]acetate; [(2R,3R,4S,5S)-3,5,6-triacetoxy-4-fluoro-tetrahydropyran-2-yl]methyl acetate

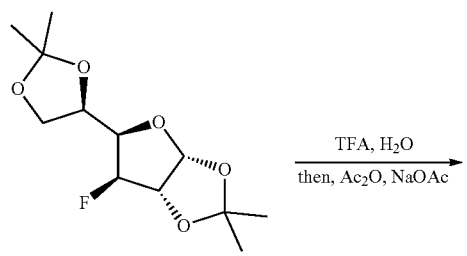

Fluorinated allofuranose diacetonide (9.5 g, 36.2 mmol) was dissolved in 10 mL of THF and 100 mL of 5% TFA in water was added to the solution. The reaction was stirred for 14 hours at room temperature. The solution was rotovaped and co-evaporated with toluene (100 mL). Then dissolved in 40 mL of acetic anhydride and refluxed for 30 min with 6 equiv (1.3 g) of sodium acetate. After that the reaction was cooled to room temperature. and quenched with sat NaHCO$_3$/CH$_2$Cl$_2$=300 mL/300 mL twice. The organic phase was washed with brine and aqueous phase was backwashed with EtOAc 300 mL. Combined org phases were dried over Na$_2$SO$_4$ and reduced to an oil which was purified by MPLC to afford the title compound (7.66 g, 11.7 mmol, 60%) MS (ESI) [M+NH$_4$]$^{+=368.1.}$ Step 3

[(2R,3R,4S,5R,6S)-3,5-diacetoxy-4-fluoro-6-phenylsulfanyl-tetrahydropyran-2-yl]methyl acetate

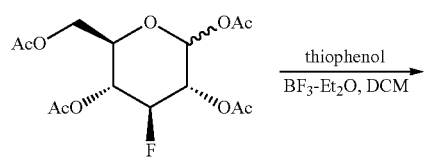

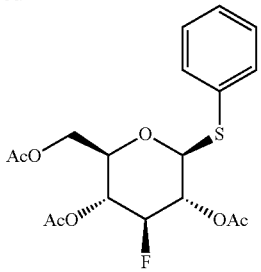

3-deoxy-3-fluoro-allopyranose tetracetate (7.7 g, 22.0 mmol) and thiophenol (4.85 g, 4.50 mmol) were dissolved in DCM (100 mL) with 10 g of activated 4 Å molecular sieves and stirred for at least 24 hours at room temperature under dry nitrogen. The suspension was treated with BF$_3$·Et$_2$O and the reaction suspension was stirred overnight. The crude material was purified by MPLC to afford the title compound (2.5 g, 6.24 mmol, 28%) MS (ESI) [M+NH$_4$]$^{+=418.2.}$ Step 4

(2R,3R,4S,5R,6S)-4-fluoro-2-(hydroxymethyl)-6-phenylsulfanyl-tetrahydropyran-3,5-diol

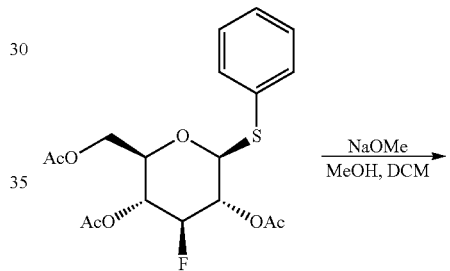

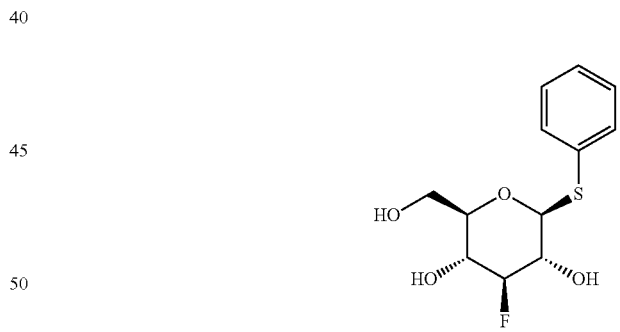

1-phenylthio-3-deoxy-3-fluoro-allopyranoside peracetate (2.5 g, 6.24 mmol) was dissolved in 25 mL of 4:1=MeOH:DCM mixture and treated with 5 mL of 25% NaOMe in MeOH. The reaction was stirred for 1h at room temperature. The reaction was quenched with Amberlyst 15 resin which was filtered and washed with 20 mL of MeOH, solvent was evaporated and the crude material was used in the next step without any further purification. MS (ESI) [M+NH$_4$]+=292.3.

Step 5
[(2R,3R,4S,5R,6S)-4-fluoro-3,5-dihydroxy-6-phenylsulfanyl-tetrahydropyran-2-yl]methyl 4-methylbenzenesulfonate

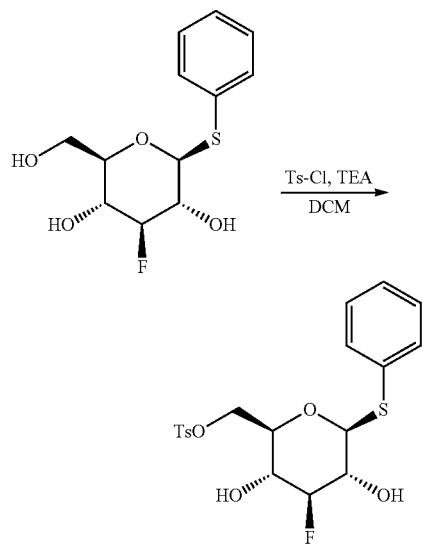

1-phenylthio-3-deoxy-3-fluoro-allopyranoside (2.28 g, 8.31 mmol) was dissolved in 5 mL of DCM at 0° C. and Et$_3$N (4.20 g, 41.6 mmol) with TsCl (1.91 g, 10 mmol) were added sequentially. After 3 hours the crude reaction in DCM was purified by MPLC to afford the title compound (1.92 g, 4.62 mmol, 38%) MS (ESI) [M+NH$_4$]+=446.1.

Step 6
(2R,3R,4S,5R,6S)-2-(azidomethyl)-4-fluoro-6-phenylsulfanyl-tetrahydropyran-3,5-diol

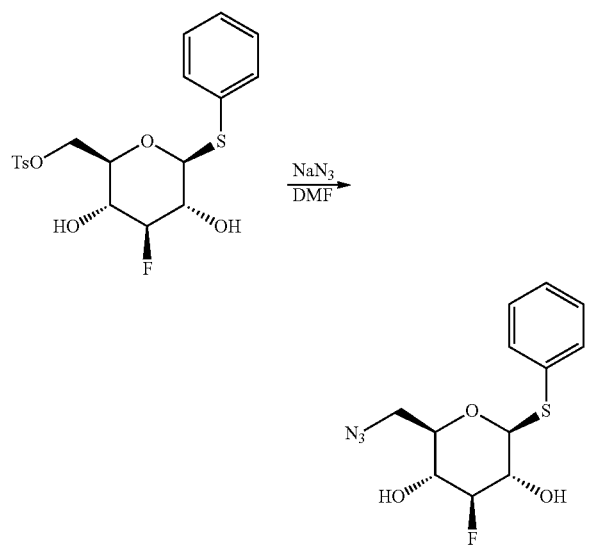

1-phenylthio-3-deoxy-3-fluoro-6-OTs-allopyranoside (1.98 g, 4.62 mmol) was dissolved in 17 mL of DMF and NaN$_3$ (0.36 g, 5.54 mmol) was added. The reaction was stirred at 80° C. for 5 hours. The reaction was washed with NaHCO$_3$ (7 mL) and extracted with EtOAc (3×10 mL) and the combined organic phases were washed with brine, and dried with Na$_2$SO$_4$. The crude was used in the next step without further purification (1.36 g, 4.54 mmol, 98%).

Step 7
(2R,3R,4S,5R,6S)-2-(azidomethyl)-3,5-dibenzyloxy-4-fluoro-6-phenylsulfanyl-tetrahydropyran

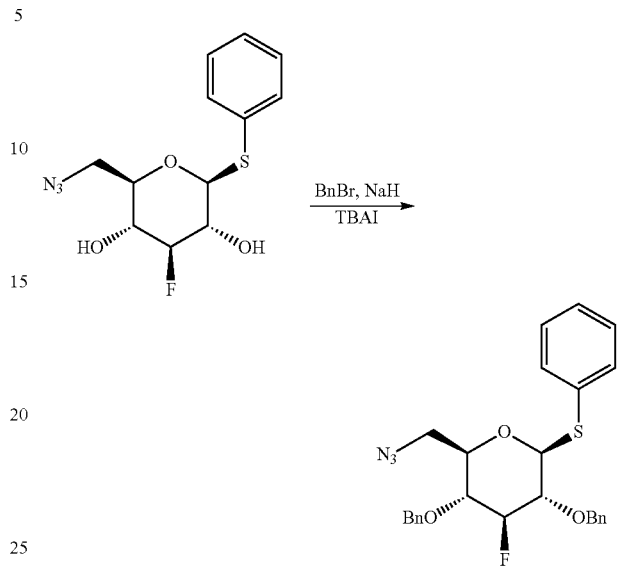

1-phenylthio-3-deoxy-3-fluoro-6-azido-allopyranoside (1.36 g, 4.54 mmol) and BnBr (2.33 g, 13.6 mmol) were dissolved in 16 mL of DMF with catalytic TBAI (0.18 g, 0.45 mmol). Dry NaH (0.44 g, 18.2 mmol) was added to the mixture at 0° C. The reaction was stirred at room temperature for 3 hours after which the reaction was quenched with 5 M NH$_4$Cl and extracted with Et$_2$O (3×100 mL), which washed with brine. The crude was purified by MPLC to provide the title compound (1.37 g, 2.86 mmol, 63%) MS (ESI) [M+Na]+=497.2.

Step 8
[(1S,2S,3R,4S,6R)-2-acetoxy-4,6-diazido-3-[(2R,3S,4S,5R,6R)-6-(azidomethyl)-3,5-dibenzyloxy-4-fluoro-tetrahydropyran-2-yl]oxy-cyclohexyl]acetate

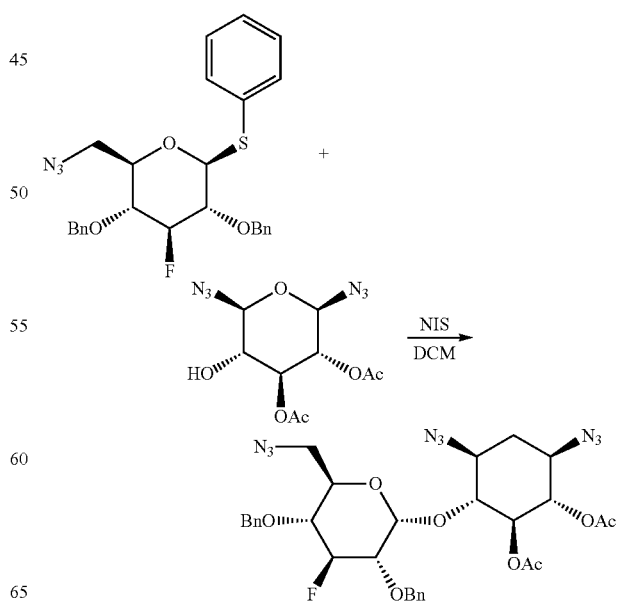

1-phenylthio-3-deoxy-3-fluoro-6-N₃-allopyranoside and 1,3-N₃-5,6-Ac-2-DOS were coevaporated with toluene (3×5 mL) and dried in high vacuum, were dissolved in DCM (12 mL) with 2 g of activated 4 Å mol sieves. The suspension was stirred at room temperature for 14 hours and cooled to −78° C. followed by a quick addition of NIS (dried in high vacuum for 12 hours). The reaction was allowed to stir for 30 min at −78° C. and catalytic TfOH was added. The reaction was stirred at −78° C. for 1 hour and allowed to warm up to room temperature over 2 hours. The reaction turned to dark brown-purple color. TLC showed product formation with Rf ~0.55 in 20% EtOAc in hexanes as a single spot. The reaction was quenched with Et₃N and filtered and the molecular sieves were washed on filter with 50 mL of DCM. Organic phase was washed with 30 mL of sat. NaHCO₃ and 50 mL of water. Aqueous phases were dried with Na₂SO₄ and crude after concentration was taken up in 3 mL of DCM and purified by MPLC to afford the title compound (0.82 g, 1.23 mmol, 88%. MS (ESI) [M+Na]⁺=690.3.

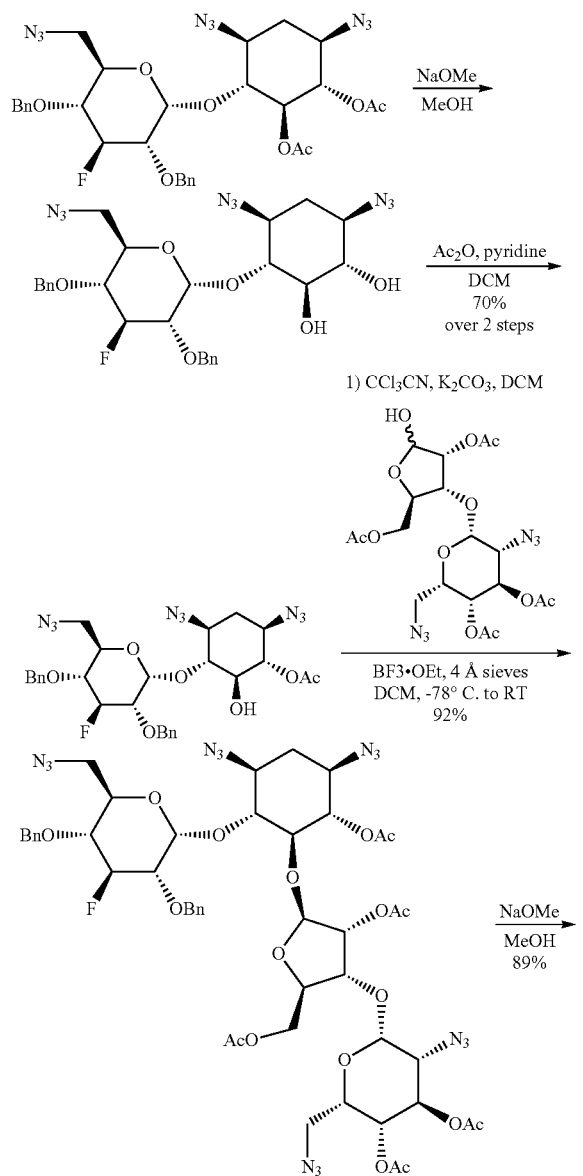

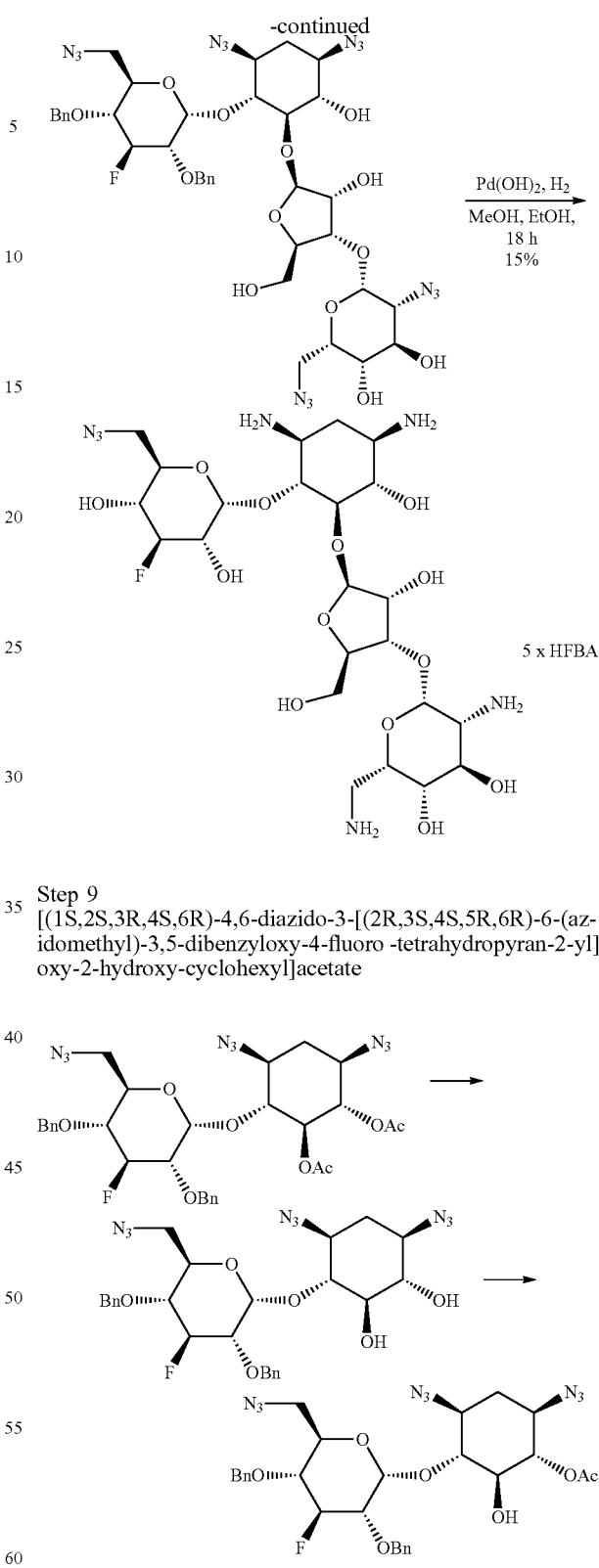

Step 9
[(1S,2S,3R,4S,6R)-4,6-diazido-3-[(2R,3S,4S,5R,6R)-6-(azidomethyl)-3,5-dibenzyloxy-4-fluoro-tetrahydropyran-2-yl]oxy-2-hydroxy-cyclohexyl]acetate NaOMe (25 wt %, 518 µL, 1.80 mmol) was added dropwise to a solution of [(1S,2S,3R,4S,6R)-2-acetoxy-4,6-diazido-3-[(2R,3S,4S,5R,6R)-6-(azidomethyl)-3,5-dibenzyloxy-4-fluoro-tetrahydropyran-2-yl]oxy-cyclohexyl]acetate (200 mg, 300 µmol) in MeOH (15.0 mL) at ambient temperature and the reaction mixture was stirred for 60 min. The mixture was neutralized with AcOH (308 μL, 5.39 mmol) and the volatiles were removed under reduced pressure. The material was purified through a silica gel plug using EtOAc as eluent to afford the title compound, which was used in the next without further purification. MS (ESI) [M+Na]$^+$606.9.

Ac$_2$O (162 82 L, 1.72 mmol) was added to a solution of (1S,2R,3R,4S,6R)-4,6-diazido-3-[(2R,3S,4S,5R,6R)-6-(azidomethyl)-3,5-dibenzyloxy-4-fluoro-tetrahydropyran-2-yl]oxy-cyclohexane-1,2-diol (167 mg, 0.286 mmol) and pyridine (185 μL, 2.29 mmol) in dry DCM (10.0 mL) at ambient temperature and the reaction mixture was stirred for 16 h. The volatiles were removed under reduced pressure and the material was purified by silica gel chromatography (40 g cartridge) using a gradient of EtOAc in hexane (0-30%) as eluent to afford the title compound (128 mg, 70%) as an oil. MS (ESI) [M+Na]$^+$648.1.

Step 10
[(2R,3R,4R,5S)-4-acetoxy-5-[(1S,2S,3R,5S,6R)-2-acetoxy-3,5-diazido-6-[(2R,3S,4S,5R,6R)-6-(azidomethyl)-3,5-dibenzyloxy-4-fluoro-tetrahydropyran-2-yl]oxy-cyclohexoxy]-3-[(2R,3R,4R,5R,6S)-4,5-diacetoxy-3-azido-6-(azidomethyl)tetrahydropyran-2-yl]oxy -tetrahydrofuran-2-yl]methyl acetate tetrahydropyran-2-yl]oxy-2-hydroxy-cyclohexyl]acetate (128 mg, 0.205 mmol) in DCM (15.0 mL) was added the above material followed molecular sieves 4 Å were added and the mixture was cooled to −10° C. BF$_3$·OEt$_2$ (0.126 mL, 1.02 mmol) was then added dropwise and the mixture was warmed slowly at room temperature and stirred for 4 h. The mixture was diluted with saturated NaHCO$_3$ (10.0 mL) and the separated aqueous layer was extracted with DCM (3×20.0 mL). The combined organic layer was washed with brine, then dried (Na$_2$SO$_4$), filtered and concentrated under reduced pressure. The material was purified on silica gel chromatography (40 cartridge) using a gradient of EtOAc in hexane (0-40%) as eluent to provide the title compound (213 mg, 92%) as an oil. $^1$H NMR (400 MHz, CDCl$_3$) δ 7.45-7.26 (m, 10H), 5.83 (t, J=3.5 Hz, 1H), 5.26 (s, 1H), 5.08-5.01 (m, 2H), 4.99 (d, J=4.5 Hz, 1H), 4.95-4.86 (m, 3H), 4.85 (d, J=1.8 Hz, 1H), 4.77 (q, J=11.2 Hz, 2H), 4.72 —4.67 (m, 1H), 4.61 (d, J=11.3 Hz, 1H), 4.46 (dd, J=12.1, 2.4 Hz, 1H), 4.41 (dd, J=7.5, 4.6 Hz, 1H), 4.27-4.04 (m, 5H), 3.79-3.24 (m, 12H), 2.31 (dt, J=13.2, 4.6 Hz, 1H), 2.17 (s, 6H), 2.07 (s, 3H), 2.04 (s, 3H), 1.58 (dd, J=24.7, 12.3 Hz, 1H). MS (ESI) [M+Na]$^+$1161.3.

Step 11
(2S,3S,4R,5R,6R)-5-azido-2-(azidomethyl)-6-[(2R,3S,4R,5S)-5-[(1R,2R,3S,5R,6S)-3,5-diazido -2-[(2R,3S,4S,5R,6R)-6-(azidomethyl)-3,5-dibenzyloxy-4-fluoro-tetrahydropyran-2-yl]oxy-6-hydroxy-cyclohexoxy]-4-hydroxy-2-(hydroxymethyl)tetrahydrofuran-3-yl]oxy-tetrahydropyran -3,4-diol

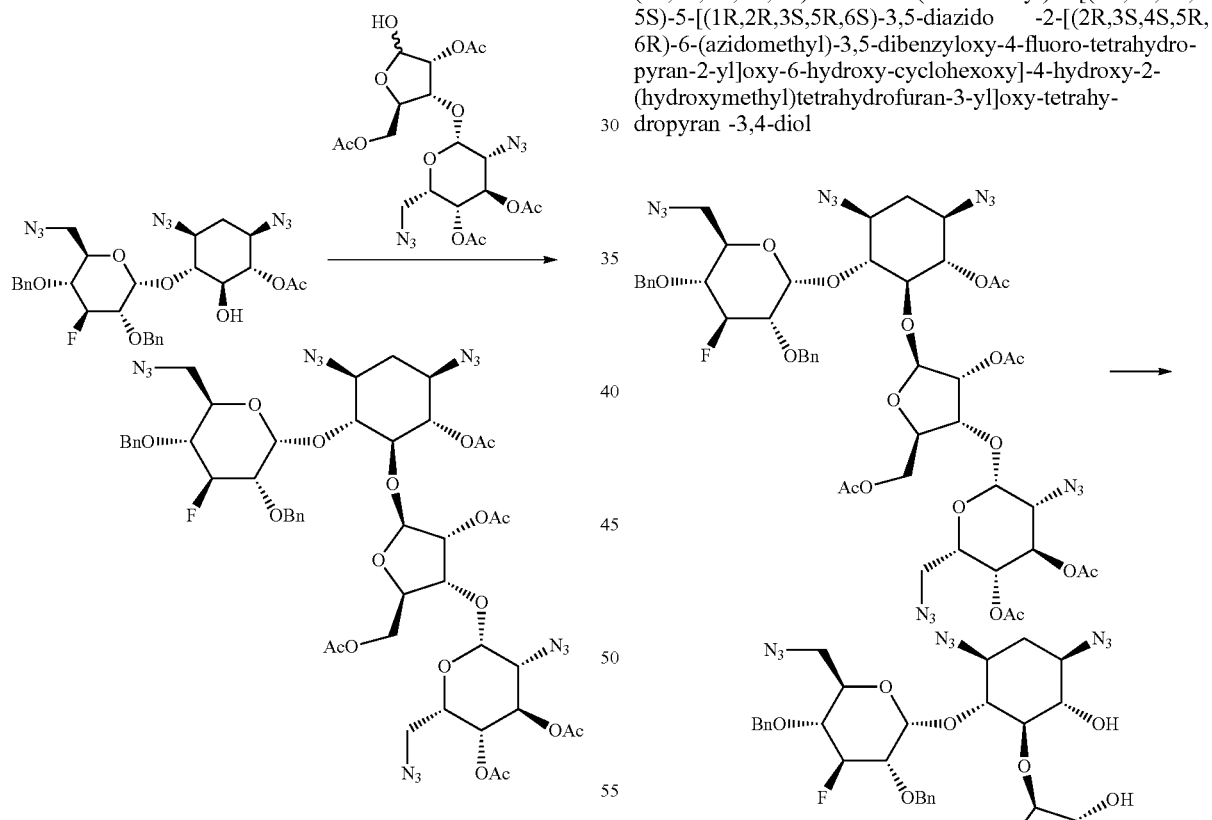

CCl$_3$CN (0.308 mL, 3.07 mol) was added dropwise to a mixture of [(2R,3R,4R) -4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (326 mg, 0.614 mmol) and K$_2$CO$_3$ (254 mg, 1.84 mmol) in dry DCM (15.0 mL) at room temperature under N$_2$. The reaction mixture was stirred at room temperature for 18 h, then filtered through a Celite pad, washed with dry DCM and the filtrate was concentrated under reduced pressure.

To a solution of [[(1S,2S,3R,4S,6R)-4,6-diazido-3-[(2R,3S,4R,5R,6R)-6 -(azidomethyl)-3,5-dibenzyloxy-4-fluoro- NaOMe (25 wt %, 0.647 mL, 2.25 mmol) was added dropwise to a solution of [(2R,3R,4R,5S)-4-acetoxy-5-[(1S, 2S,3R,5S,6R)-2-acetoxy-3,5-diazido-6-[(2R,3S,4S,5R,6R)-6-(azidomethyl)-3,5-dibenzyloxy-4-fluoro-tetrahydropyran-2-yl]oxy-cyclohexoxy]-3-[(2R,3R,4R,5R,6S)-4,5-diacetoxy-3-azido-6-(azidomethyl)tetrahydropyran-2-yl]oxy-tetrahydrofuran-2-yl]methyl acetate (213 mg, 0.187 mmol) in MeOH (10.0 mL) at ambient temperature and the reaction mixture was stirred for 60 min. The mixture was neutralized by adding AcOH (214 µL, 3.74 mmol) and the volatiles were removed under reduced pressure. The material was purified on silica plug using EtOAc as eluent to provide the title compound (155 mg, 89%) as a solid. $^1$H NMR (500 MHz, MeOD) δ 7.73-7.22 (m, 10H), 6.22 (t, J=3.5 Hz, 1H), 5.39 (d, J=1.9 Hz, 1H), 5.15 (d, J=1.8 Hz, 1H), 5.07-4.91 (m, 3H), 4.76 (d, J=11.2 Hz, 1H), 4.68 (d, J=11.4 Hz, 1H), 4.44 (dd, J=6.5, 4.5 Hz, 1H), 4.35 (dd, J=4.5, 1.9 Hz, 1H), 4.20 (td, J=6.2, 2.8 Hz, 2H), 4.04 (ddd, J=8.2, 4.8, 2.0 Hz, 1H), 3.99 (t, J=3.4 Hz, 1H), 3.88 (dd, J=11.9, 2.8 Hz, 1H), 3.83-3.76 (m, 1H), 3.75-3.54 (m, 8H), 3.53—3.40 (m, 5H), 2.26-2.15 (m, 1H), 1.37 (m, 1H). MS (ESI) [M+Na]$^+$ 950.8.

Step 12

(2S,3S,4R,5R,6R)-5-amino-2-(aminomethyl)-6-[(2R,3S,4R,5S)-5-[(1R,2R,3S,5R,6S)-3,5-diamino-2-[(2R,3S,4S,5R,6R)-6-(aminomethyl)-4-fluoro-3,5-dihydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol Pd(OH)$_2$ (20 wt %, 109 mg, 155 µmol) was added to a solution of (2S,3S,4R,5R,6R)-5-azido-2-(azidomethyl)-6-[(2R,3S,4R,5S)-5-[(1R,2R,3S,5R,6S)-3,5-diazido-2-[(2R,3S,4S,5R,6R)-6-(azidomethyl)-3,5-dibenzyloxy-4-fluoro-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol (24.0 mg, 25.9 µmol) in a mixture MeOH (2.00 mL) and EtOH (2.00 mL). H$_2$ was bubbled for 5 min and the suspension was hydrogenated for 16 h. The mixture was filtered through a frit (0.22 µm diameter) and the filtrate was concentrated under reduced pressure. The material was purified by preparative HPLC to provide (2S,3S,4R,5R,6R)-5-amino-2-(aminomethyl)-6-[(2R,3S,4R,5S)-5-[(1R,2R,3S,5R,6S)-3,5-diamino-2-[(2R,3S,4S,5R,6R)-6-(aminomethyl)-4-fluoro-3,5-dihydroxy-tetrahydropyran-2-yl]oxy-6-hydroxy-cyclohexoxy]-4-hydroxy-2-(hydroxymethyl)tetrahydrofuran-3-yl]oxy-tetrahydropyran-3,4-diol (13.4 mg, 15%) as HFBA salt. $^1$H NMR(400 MHz, MeOD) δ 5.67 (t, J=3.5 Hz, 1H), 5.37 (d, J=2.4 Hz, 1H), 5.25 (d, J=1.6 Hz, 1H), 4.60 (dt, J=52.2, 8.2 Hz, 1H), 4.52-4.46 (m, 1H), 4.29 (dd, J=4.9, 2.4 Hz, 1H), 4.27-4.21 (m, 1H), 4.17-4.09 (m, 3H), 3.98 (ddd, J=10.2, 6.7, 3.9 Hz, 1H), 3.85 (dd, J=15.0, 5.8 Hz, 1H), 3.81-3.71 (m, 3H), 3.69-3.47 (m, 4H), 3.43-3.30 (m, 2H), 3.25-3.08 (m, 4H), 2.49-2.35 (m, 1H), 1.91 (dd, J=25.0, 12.5 Hz, 1H). MS (ESI) [M+H]$^{30}$ 618.4.

Example 42

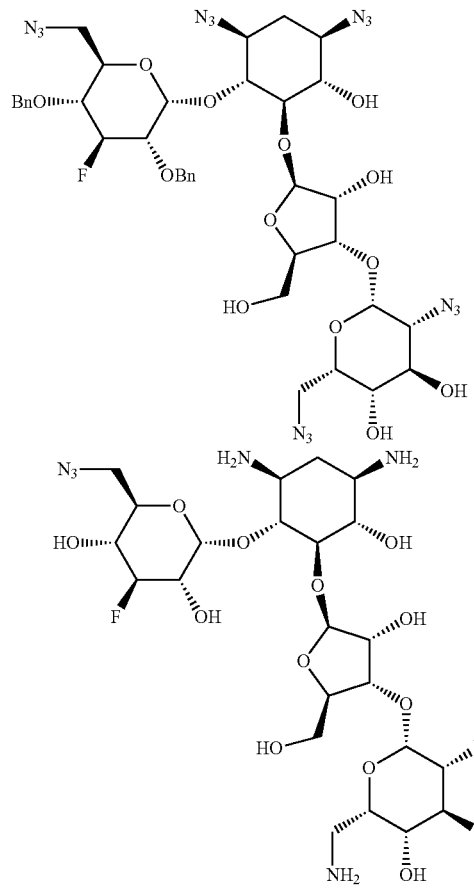

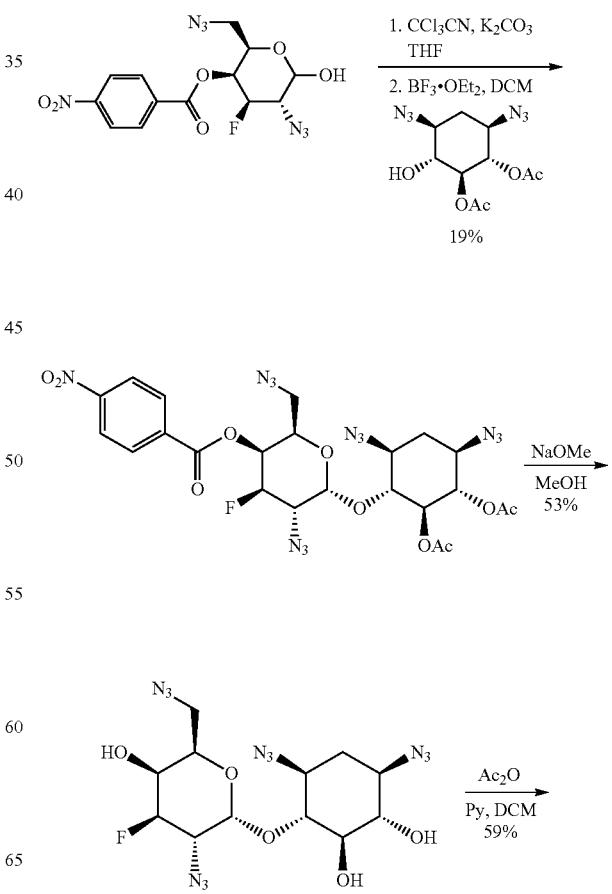

497

-continued

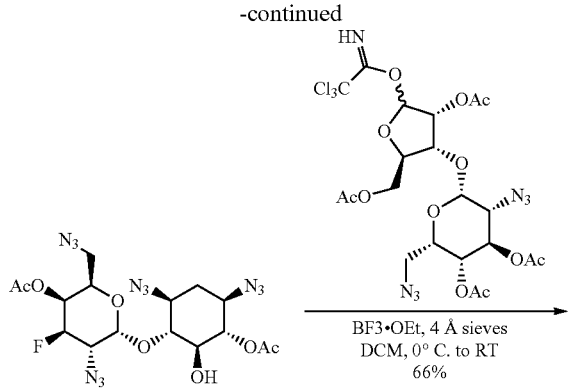

498

-continued

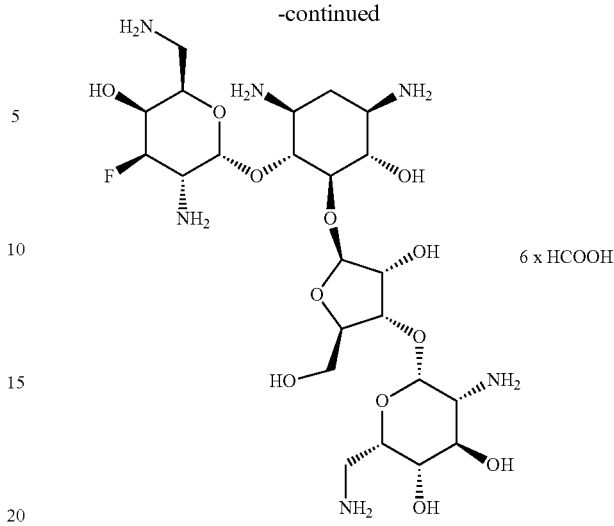

Step 1
[(2R,3S,4R,5R,6R)-5-azido-2-(azidomethyl)-4,6-difluoro-tetrahydropyran-3-yl]4-nitrobenzoate

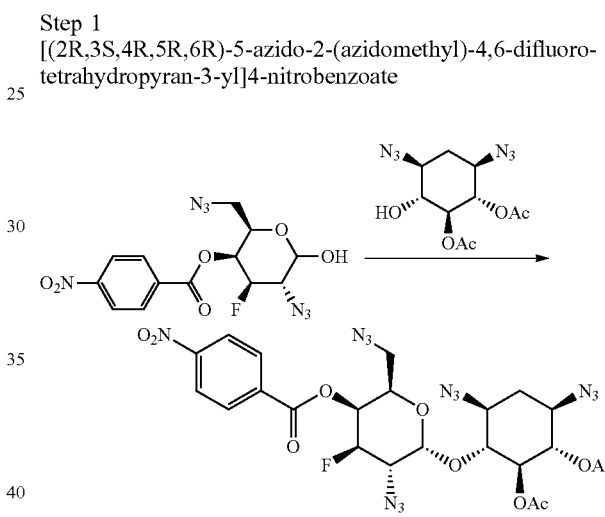

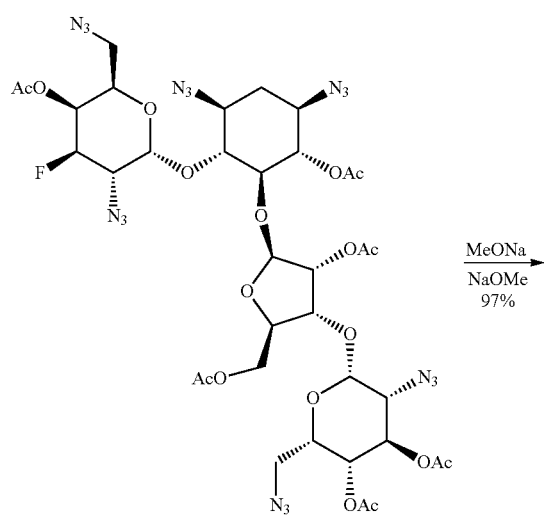

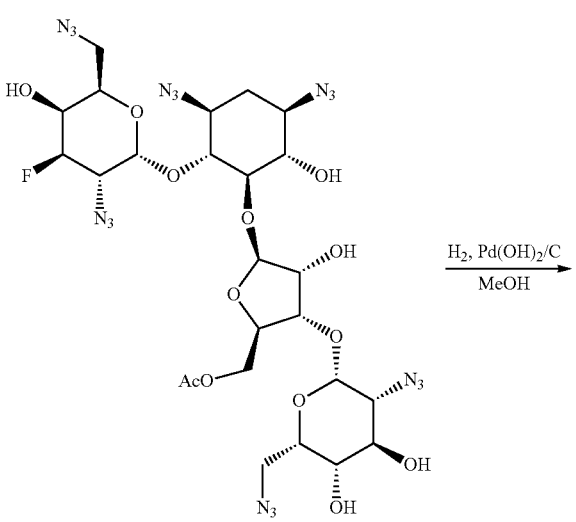

CCl$_3$CN (241 µL, 2.40 mmol) was added dropwise to a suspension of [(2R,3S,4R,5S)-5-azido-2-(azidomethyl)-4-fluoro-6-hydroxy-tetrahydropyran-3-yl]4-nitrobenzoate (preparation below, 183 mg, 480 µmol) and K$_2$CO$_3$ (199 mg, 1.44 mmol) in dry THF (2.0 mL) at ambient temperature under N$_2$ and the reaction mixture was stirred for 18 h. The mixture was filtered through cotton and the filtrate was concentrated under N$_2$ stream, and then dried under high-vacuum. To the above material was added [(1S,2S,3R,4S,6R)-2-acetoxy -4,6-diazido-3-hydroxy-cyclohexyl]acetate (2-DOS, 179 mg, 600 µmol) and ground 4 Å sieves (750 mg) and the mixture was dissolved in dry DCM (2.5 mL). The suspension was stirred at ambient temperature for 60 min. The mixture was cooled to 0° C. and BF$_3$·OEt$_2$ (237 µL, 1.92 mmol) was added dropwise with vigorous stirring. The reaction mixture was warmed to ambient temperature and stirred for another 60 min. The reaction was quenched with saturated NaHCO$_3$ (5.0 mL) and the aqueous layer was extracted with DCM (3×5.0 mL). The combined organic layers were dried (Na$_2$SO$_4$), filtered and concentrated under reduced pressure. The material was purified by silica gel chromatography (25 g cartridge) using a gradient of with EtOAc and hexane (5-50%) as eluent to provide the title compound (60 mg, 19%) as a solid. $^1$H NMR (500 MHz, CDCl$_3$) δ 8.34 (d, J=9.0 Hz, 2H), 8.24 (d, J=9.0 Hz, 2H), 5.92-5.85 (m, 1H), 5.31 (t, J=4.2 Hz, 1H), 5.22-5.05 (m, 2H), 4.96 (t, J=10.0 Hz, 1H), 4.64 (t, J=5.9 Hz, 1H), 3.84 (td, J=10.2, 3.9 Hz, 1H), 3.73-3.61 (m, 2H), 3.57-3.45 (m, 2H), 3.31 (dd, J=13.0, 5.3 Hz, 1H), 2.46 (dt, J=13.4, 4.6 Hz, 1H), 2.12 (s, 3H), 2.10 (s, 3H), 1.65 (dd, J=25.9, 12.5 Hz, 1H).

Step 2

(1S,2R,3R,4S,6R)-4,6-diazido-3-[(2R,3S,4R,5S,6R)-3-azido-6-(azidomethyl)-4-fluoro-5-hydroxy-tetrahydropyran-2-yl]oxy-cyclohexane-1,2-diol

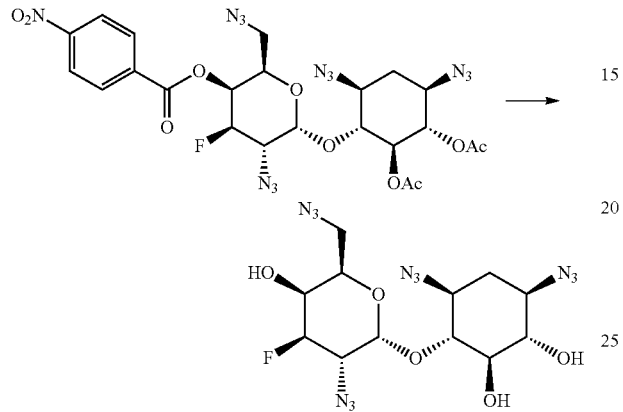

NaOMe (25 wt %, 138 µL, 605 µmol) was added dropwise to a solution of [(2R,3S,4R,5S,6R)-5-azido-2-(azidomethyl)-6-[(1R,2S,3S,4R,6S)-2,3-diacetoxy-4,6-diazido -cyclohexoxy]-4-fluoro-tetrahydropyran-3-yl]4-nitrobenzoate (80 mg, 121 µmol) in MeOH (1.0 mL) at ambient temperature. The solution was warmed to 50° C. and stirred for 60 min. The solution was cooled to ambient temperature and the volatiles were evaporated under reduced pressure. The residue was diluted with saturated NaHCO₃ (5.0 mL) and DCM (5.0 mL). The separated aqueous layer was extracted with DCM (5.0 mL). The combined organic layers were dried (Na₂SO₄), filtered and concentrated under reduced pressure. The material was purified by C18 reverse phase chromatography (12 g cartridge) using a gradient of ACN and 0.1% formic acid (10-45%) to provide the title compound (30 mg, 53%) as a solid. ¹H NMR (500 MHz, CDCl₃) δ 5.34 (t, J=4.2 Hz, 1H), 4.93 (ddd, J=49.4, 10.1, 3.2 Hz, 1H), 4.31-4.21 (m, 2H), 4.12 (td, J=10.4, 3.8 Hz, 1H), 3.84 (s, 1H), 3.63 (dd, J=12.3, 6.6 Hz, 1H), 3.53-3.37 (m, 4H), 3.35-3.26 (m, 2H), 2.87 (s, 1H), 2.39 (s, 1H), 2.36-2.26 (m, 1H), 1.57-1.46 (m, 1H). MS (ESI) [M−H]⁻ 427.3.

Step 3

[(1S,2S,3R,4S,6R)-3-[(2R,3S,4R,5S ,6R)-5-acetoxy-3-azido-6-(azidomethyl)-4-fluoro -tetrahydropyran-2-yl]oxy-4,6-diazido-2-hydroxy-cyclohexyl]acetate

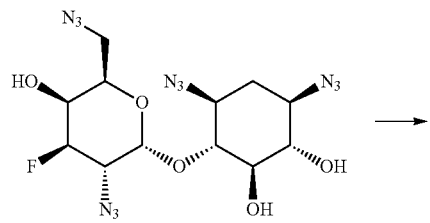

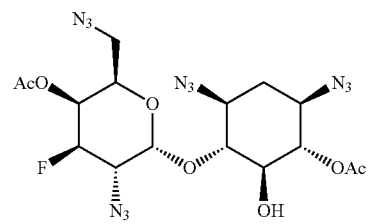

Ac₂O (17 µL, 180 µmol) was added to a solution of (1S,2R,3R,4S,6R)-4,6-diazido-3-[(2R,3S,4R,5S,6R)-3-azido-6-(azidomethyl)-4-fluoro-5-hydroxy-tetrahydropyran-2-yl]oxy-cyclohexane-1,2-diol (17 mg, 40 µmol) and pyridine (32 µL, 397 µmol) in dry DCM (1.0 mL) at ambient temperature and the reaction mixture was stirred for 18 h. MeOH (100 µL) was added and the volatiles were evaporated under reduced pressure. The material was purified by C18 reverse phase chromatography (4 g cartridge) using a gradient of ACN and 0.1% aq formic acid (20-70%) to provide the title compound (12 mg, 59%) as a solid. ¹H NMR (500 MHz, CDCl₃) δ 5.64-5.54 (m, 1H), 5.41 (t, J=4.2 Hz, 1H), 5.08-4.89 (m, 2H), 4.37 (dd, J=6.9, 5.4 Hz, 1H), 4.01 (td, J=10.3, 3.8 Hz, 1H), 3.65 (dd, J=11.7, 5.3 Hz, 2H), 3.52 (ddd, J=12.5, 10.0, 4.6 Hz, 1H), 3.48-3.38 (m, 2H), 3.34 (ddd, J=12.2, 10.0, 4.5 Hz, 1H), 3.25 (dd, J=12.9, 5.1 Hz, 1H), 2.38 (dt, J=13.3, 4.5 Hz, 1H), 2.19 (s, 3H), 2.18 (s, 3H), 1.64-1.56 (m, 1H).

Step 4

[(2R,3R,4R,5S)-4-acetoxy-5-[(1S,2S,3R,5S,6R)-2-acetoxy-6-[(2R,3S,4R,5S,6R)-5-acetoxy-3-azido-6-(azidomethyl)-4-fluoro-tetrahydropyran-2-yl]oxy-3,5-diazido-cyclohexoxy]-3-[(2R,3R,4R,5R,6S)-4,5-diacetoxy-3-azido-6-(azidomethyl)tetrahydropyran-2-yl]oxy -tetrahydrofuran-2-yl]methyl acetate

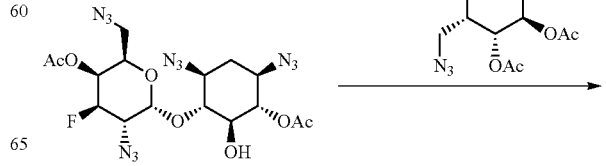

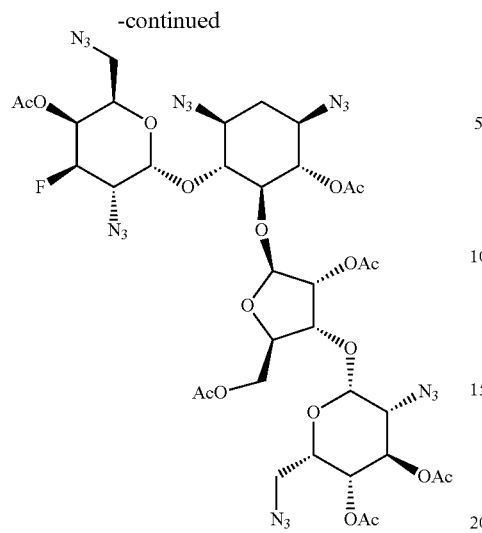

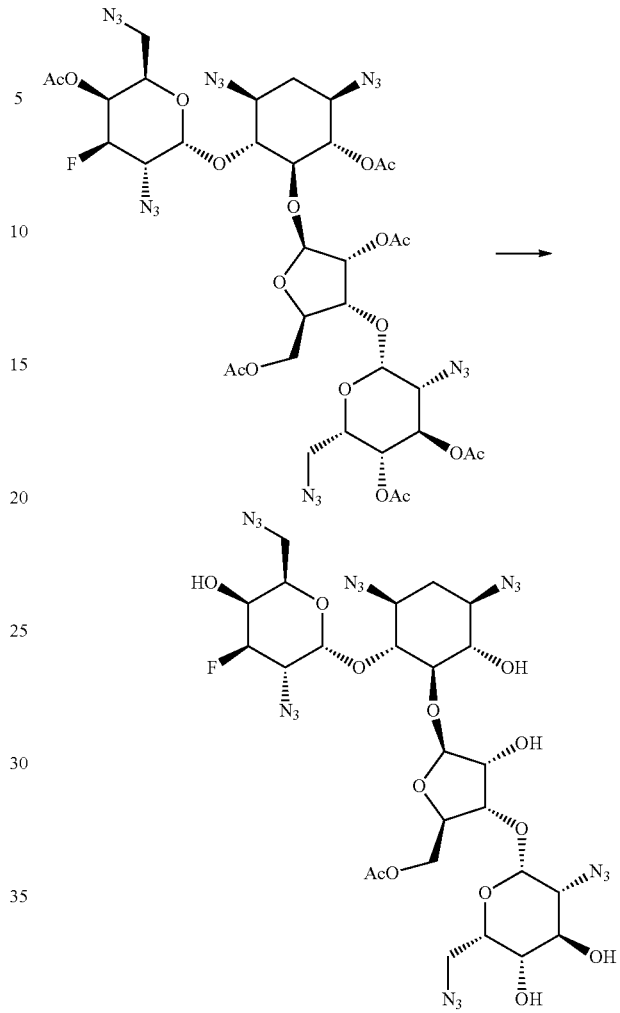

CCl$_3$CN (94 µL, 940 µmol) was added dropwise to a suspension of [(2R,3R,4R) -4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (99 mg, 187 µmol) and K$_2$CO$_3$ (78 mg, 562 µmol) in dry DCM (1.5 mL) at ambient temperature under N$_2$ and the reaction mixture was stirred for 18 h. The mixture was filtered through a Celite pad and the filtrate was concentrated under N$_2$ stream, and then dried under high-vacuum. To the above material was added [(1S,2S,3R,4S,6R)-3-[(2R,3S,4R,5S,6R)-5-acetoxy-3-azido-6-(azidomethyl)-4-fluoro -tetrahydropyran-2-yl]oxy-4,6-diazido-2-hydroxy-cyclohexyl] acetate (48 mg, 94 µmol) in DCM (3.0 mL) and the volatiles were evaporated under N$_2$ stream. To the mixture was added ground 4 Å sieves (300 mg) followed by dry DCM (1.5 mL). The suspension was stirred at ambient temperature for 90 min, then cooled to 0° C. BF$_3$·OEt$_2$ (92 µL, 749 µmol) was added and the reaction mixture was stirred at ambient temperature for another 1 h. Et$_3$N (200 µL) was added and the mixture was filtered through a silica gel pad (0.30 g) and eluted with EtOAc. The filtrate was evaporated under reduced pressure and the material was purified by C18 reversed phase chromatography (12 g cartridge) using a gradient of ACN and 0.1% aq. formic acid (50-100%) as eluent to afford the title compound (63 mg, 66%) as a solid. $^1$H NMR (500 MHz, CDCl$_3$) δ 6.05 (t, J=4.0 Hz, 1H), 5.56 (dd, J=5.7, 3.6 Hz, 1H), 5.34 (d, J=2.5 Hz, 1H), 5.03-4.86 (m, 5H), 4.73-4.66 (m, 1H), 4.49-4.39 (m, 3H), 4.33-4.28 (m, 1H), 4.24 (dd, J=12.2, 4.9 Hz, 1H), 4.09 (ddd, J=8.0, 4.4, 1.7 Hz, 1H), 3.87 (t, J=9.0 Hz, 1H), 3.70-3.65 (m, 1H), 3.65-3.55 (m, 2H), 3.49 (ddd, J=12.6, 9.9, 4.5 Hz, 1H), 3.45-3.36 (m, 2H), 3.34-3.29 (m, 1H), 3.28 (dd, J=13.0, 4.4 Hz, 1H), 3.21 (dd, J=12.9, 4.2 Hz, 1H), 2.35 (dt, J=13.2, 4.5 Hz, 1H), 2.17 (s, 3H), 2.16 (s, 3H), 2.15 (s, 3H), 2.15 (s, 3H), 2.12 (s, 3H), 2.11 (s, 3H), 1.59 (dd, J=25.7, 12.7 Hz, 1H). MS (ESI) [M+NH$_4$]$^+$1042.2.

Step 5

(2S,3S,4R,5R,6R)-5-azido-2-(azidomethyl)-6-[(2R,3S,4R,5S)-5-[(1R,2R,3S,5R,6S)-3,5-diazido -2-[(2R,3S,4R,5S,6R)-3-azido-6-(azidomethyl)-4-fluoro-5-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran -3,4-diol NaOMe (25 wt %, 141 µL, 615 µmol) was added dropwise to a solution of [(2R,3R,4R,5S)-4-acetoxy-5-[(1S,2S,3R,5S,6R)-2-acetoxy-6-[(2R,3S,4R,5S,6R)-5-acetoxy-3-azido-6-(azidomethyl)-4-fluoro-tetrahydropyran-2-yl]oxy-3,5-di-azido-cyclohexoxy]-3-[(2R,3R,4R,5R,6S)-4,5-diacetoxy-3-azido-6-(azidomethyl)tetrahydropyran-2-yl]oxy -tetrahydrofuran-2-yl]methyl acetate (63 mg, 62 µmol) in MeOH (2.0 mL) at ambient temperature and the reaction mixture was stirred for 90 min. AcOH (53 µL, 922 µmol) was added and the volatiles were evaporated under reduced pressure. The material was filtered through silica gel (0.50 g) and eluted with EtOAc (10.0 mL). The filtrate was concentrated under reduced pressure to provide the title compound (46 mg, 97%) as a solid, which was used in the next step without further purification. MS (ESI) [M+NH$_4$]$^+$790.3.

Step 6

(2S,3S,4R,5R,6R)-5-amino-2-(aminomethyl)-6-[(2R,3S,4R,5S)-5-[(1R,2R,3S,5R,6S)-3,5-diamino-2-[(2R,3S,4R,5S,6R)-3-amino-6-(azidomethyl)-4-fluoro-5-hydroxy-tetrahydropyran-2-yl]oxy-6-hydroxy-cyclohexoxy]-4-hydroxy-2-(hydroxymethyl)tetrahydrofuran-3-yl] oxy -tetrahydropyran-3,4-diol; formic acid

503

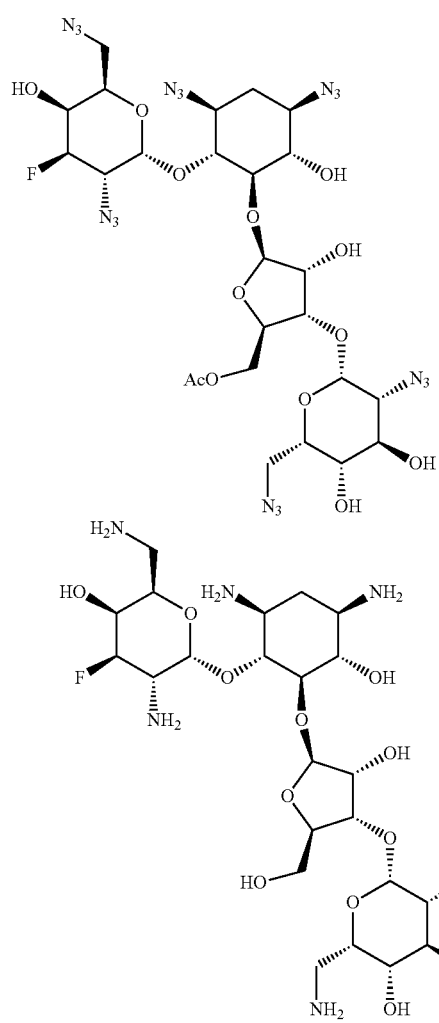

Pd(OH)$_2$/C (10 wt %, 7.6 mg, 5.4 μmol) was added to a solution of (2S,3S,4R,5R,6R)-5-azido-2-(azidomethyl)-6-[(2R,3S,4R,5S)-5-[(1R,2R,3S,5R,6S)-3,5-diazido -2-[(2R,3S,4R,5S,6R)-3-azido-6-(azidomethyl)-4-fluoro-5-hydroxy-tetrahydropyran-2-yl]oxy-6-hydroxy-cyclohexoxy]-4-hydroxy-2-(hydroxymethyl)tetrahydrofuran-3-yl]oxy-tetrahydropyran -3,4-diol (21 mg, 27 μmol) in MeOH (3.0 mL) under N$_2$ at ambient temperature. H$_2$ was bubbled into the solution for 15 min and then the suspension was hydrogenated under hydrogen atmosphere for 18 h. The mixture was filtered through a frit (0.45 μm diameter) and then formic acid (40 μL) was added to the filtrate. The filtrate was concentrated under reduced pressure and then lyophilization to provide the title compound (hexa-formate salt, 20.5 mg, 82%) as a solid. $^1$H NMR (500 MHz, MeOD) δ 8.49 (s, 6H), 6.01 (t, J=4.2 Hz, 1H), 5.41 (d, J=2.1 Hz, 1H), 5.27 (d, J=1.5 Hz, 1H), 5.09 (ddd, J=49.5, 10.9, 3.0 Hz, 1H), 4.51 (dd, J=6.7, 4.7 Hz, 1H), 4.40-4.33 (m, 2H), 4.30 (ddd, J=4.7, 3.4, 0.8 Hz, 1H), 4.22 (dd, J=8.5, 1.9 Hz, 1H), 4.20-4.17 (m, 1H), 4.16 (t, J=3.1 Hz, 1H), 3.94-3.86 (m, 2H), 3.82 (t, J=9.5 Hz, 1H), 3.78-3.71 (m, 2H), 3.69-3.66 (m, 1H), 3.56-3.50 (m, 1H), 3.43-3.40 (m, 1H), 3.40-3.33 (m, 2H), 3.26-3.13 (m, 4H), 2.31 (dt, J=12.5, 4.2 Hz, 1H), 1.79-1.68 (m, 1H). MS (ESI) [M+H]$^+$617.51.

504

Preparation of [(2R,3S,4R,5S)-5-azido-2-(azidomethyl)-4-fluoro-6-hydroxy-tetrahydropyran-3-yl]4-nitrobenzoate

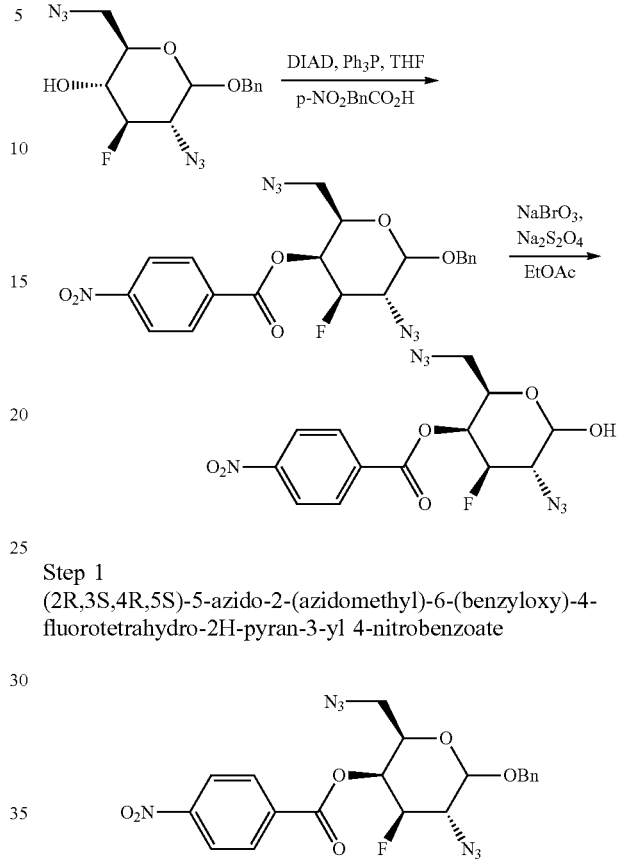

Step 1
(2R,3S,4R,5S)-5-azido-2-(azidomethyl)-6-(benzyloxy)-4-fluorotetrahydro-2H-pyran-3-yl 4-nitrobenzoate

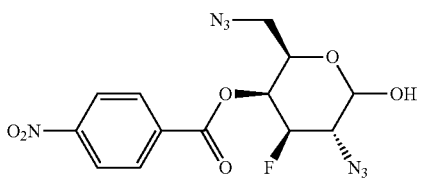 [SMILES: [N-]=[N+]=NC[C@H]1OC(O)[C@H](N=[N+]=[N-])[C@@H](F)[C@H]1OC(=O)c1ccc([N+](=O)[O-])cc1]

To a solution of 4.52 g of DIAD in 30 mL of THF was added 5.13 g of triphenylphosphine at 0° C. and stirred for 1 h at the same temperature. To this solution, was added p-nitrobenzoic acid at the same temperature and stirred for 1 hour. To this solution, (2R,3R,4R,5S,6R)-5-azido-2-(azidomethyl)-6-(benzyloxy)-4-fluorotetrahydro-2H-pyran-3-ol in 30 mL of anhydrous THF was slowly added at 0° C. and the reaction allowed to reach room temperature. The reaction mixture was stirred until completion of the reaction. The reaction was purified by flash chromatography (30% EtOAc in Hexanes) to afford 1.85 g of (2R,3S,4R,5S)-5-azido-2-(azidomethyl)-6-(benzyloxy)-4-fluorotetrahydro-2H-pyran-3-yl 4-nitrobenzoate (74% yield).
Step 2
(2R,3S,4R,5S)-5-azido-2-(azidomethyl)-4-fluoro-6-hydroxytetrahydro-2H-pyran-3-yl 4-nitrobenzoate To a solution of 2 g of (2R,3S,4R,5S)-5-azido-2-(azidomethyl)-6-(benzyloxy)-4-fluorotetrahydro-2H-pyran-3-yl 4-nitrobenzoate in EtOAc was added 3 g of NaBrO$_3$ dissolved in 30 mL of water. To this mixture, 3.14 g sodium dithionate dissolved in 60 mL of water was added over 30 min. The reaction mixture was vigorously stirred until completion (3-6 h). The organic layer was separated and washed with 200 mL of 1:1 mixture of aqueous sodium thiosulfate (5%) and saturated aqueous NaHCO₃. The organic layer was dried over anhydrous sodium sulfate and concentrated. The obtained crude was purified by flash chromatography (EtOAc/Hexanes 1:3) to afford 1 g of (2R,3S,4R,5S)-5-azido-2-(azidomethyl)-4-fluoro-6-hydroxytetrahydro-2H-pyran-3-yl 4-nitrobenzoate (63% yield).

Example 43

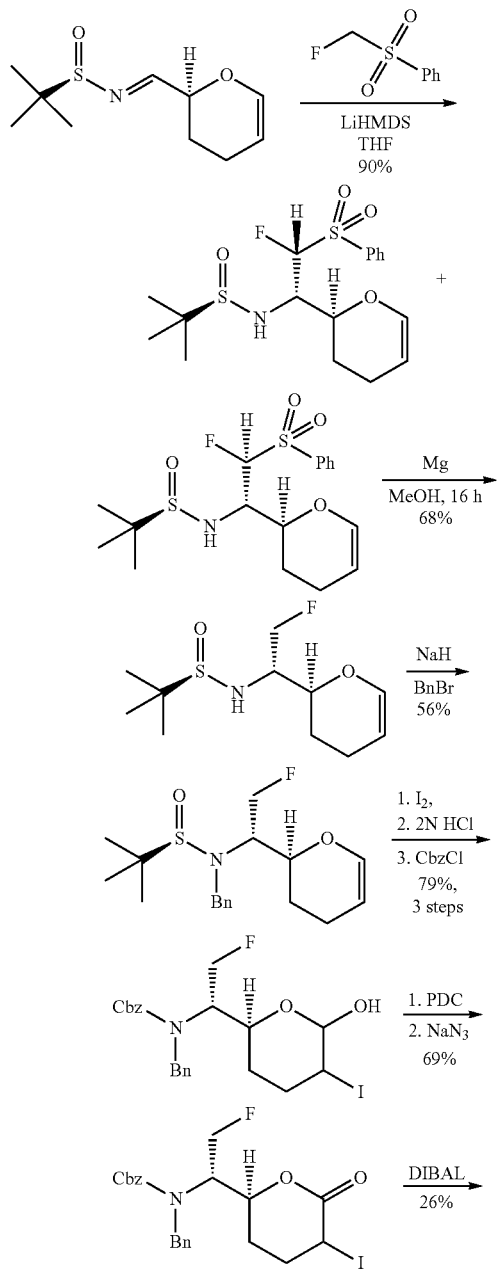

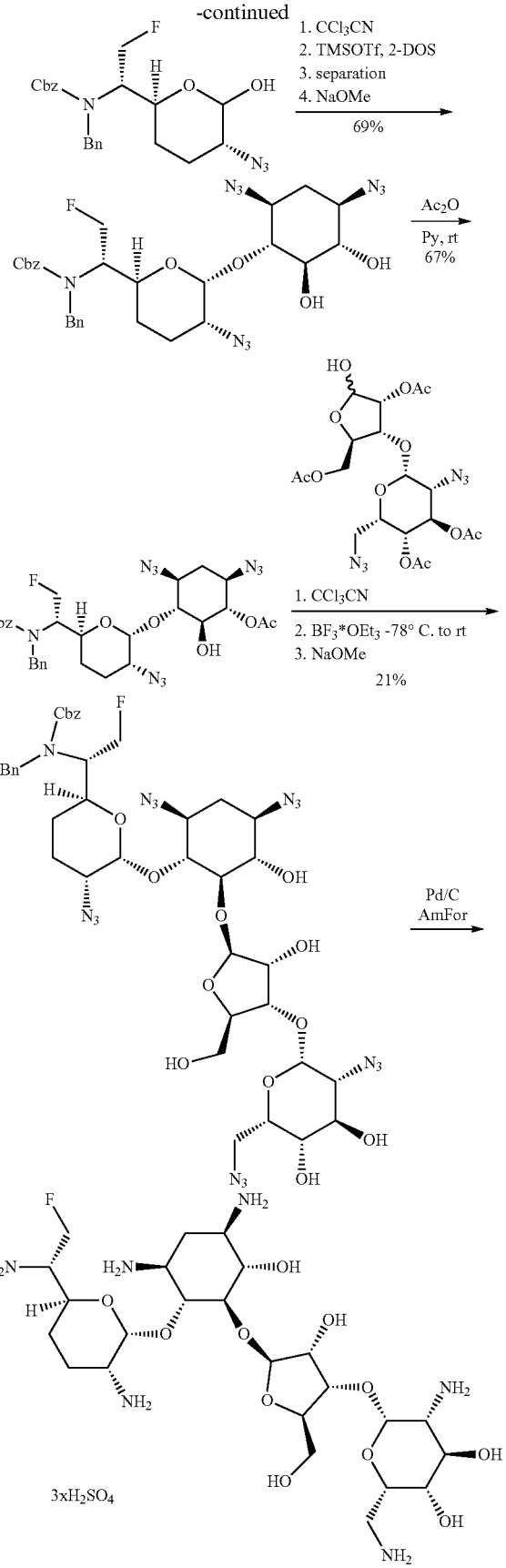

Step 1
(R)-N-[(1S,2R)-2-(benzenesulfonyl)-1-[(2S)-3,4-dihydro-2H-pyran-2-yl]-2-fluoro-ethyl]-2-methyl-propane-2-sulfinamide

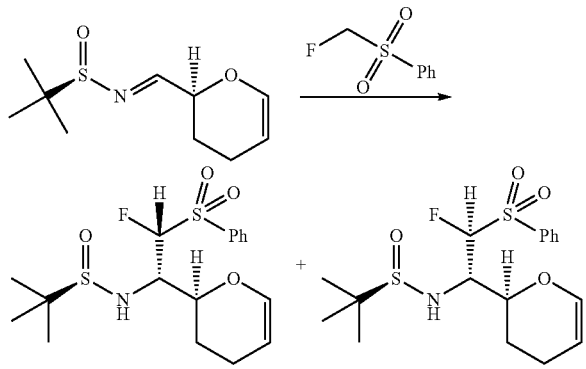

To a solution of (NE,R)-N-[[(2S)-3,4-dihydro-2H-pyran-2-yl]methylene]-2-methyl-propane-2-sulfinamide (4.82 g, 22.4 mmol) and fluoromethylsulfonylbenzene (3.90 g, 22.4 mmol) in anhydrous THF (100 mL), at −78° C. was added LiHMDS (1.00 M in THF, 23.5 mL, 23.5 mmol) and the reaction mixture was stirred at −78° C. for 1 h. The mixture was warmed to 20° C. and quenched with saturated NaHCO₃ (50 mL). The mixture was diluted with EtOAc (150 mL) and water (100 mL). The separated organic phase was dried (Na₂SO₄), filtered and concerted under reduced pressure. The material was purified by column chromatography on silica gel (120 g, dry pack) using a gradient of 20-50% EtOAc in hexane as eluent to afford the title compound (7.84 g, 90%, 1:1 mixture). MS (ESI) [M+Na]⁺412.3.

Step 2
(R)-N-[(1S)-1-[(2S)-3,4-dihydro-2H-pyran-2-yl]-2-fluoro-ethyl]-2-methyl-propane-2-sulfinamide

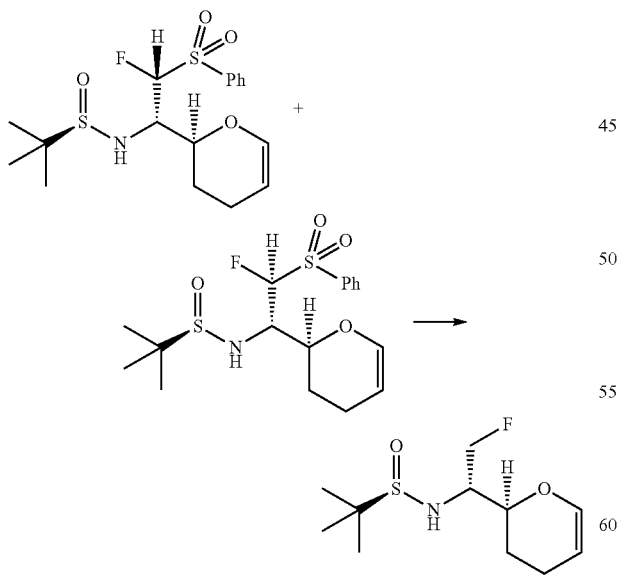

To a solution of (R)-N-[(1S)-2-(benzenesulfonyl)-1-[(2S)-3,4-dihydro-2H-pyran -2-yl]-2-fluoro-ethyl]-2-methyl-propane-2-sulfinamide (8.4 g, 21.6 mmol) in MeOH (75 mL), was added Mg (2.10 g, 86 mmol) in 4 portions over 1 h (bubbles) and the reaction mixture was stirred overnight at room temperature. The mixture was concentrated under reduced pressure and then saturated NH₄Cl and Et₂O was added. The separated organic phase was washed with brine (100 mL), then dried (Na₂SO₄), filtered and concentrated under reduced pressure to provide title product (R)-N-[(1S)-1-[(2S)-3,4-dihydro-2H-pyran-2-yl]-2-fluoro-ethyl]-2-methyl-propane-2-sulfinamide (3.65 g, 68%). ¹H NMR (400 MHz, CDCl₃) δ 6.31-6.26 (m, 1H), 4.67 (tdd, J=6.3, 3.1, 2.0 Hz, 1H), 4.54 (dd, J=4.9, 1.4 Hz, 1H), 4.42 (dd, J=4.9, 1.3 Hz, 1H), 3.98 (dd, J=10.2, 5.5 Hz, 1H), 3.68 (d, J=8.3 Hz, 1H), 3.59-3.45 (m, 1H), 2.08-1.91 (m, 3H), 1.76-1.63 (m, 1H), 1.18 (s, 9H). MS (ESI) [M+H]⁺250.4.

Step 3
(R)-N-benzyl-N-[(1S)-1-[(2S)-3,4-dihydro-2H-pyran-2-yl]-2-fluoro-ethyl]-2-methyl-propane-2-sulfinamide

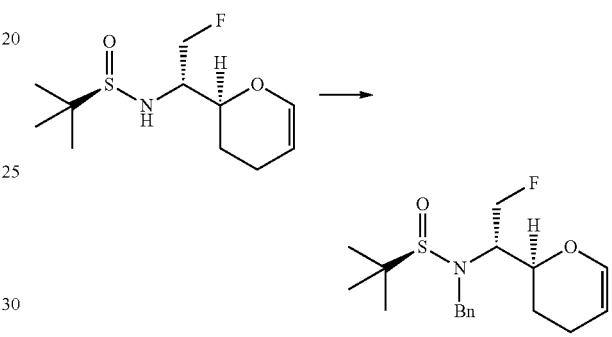

To a solution of (R)-N-[(1S)-1-[(2S)-3,4-dihydro-2H-pyran-2-yl]-2-fluoro-ethyl]-2-methyl-propane-2-sulfinamide (3.65 mg, 14.6 mmol) and benzyl bromide (2.61 mL, 22.0 mmol) in DMF (30 mL) at 0° C., was added sodium hydride (60.0%, 703 mg, 17.6 mmol) and the reaction mixture was stirred at 20° C. for 1 h. The mixture was quenched with brine (100 mL) and the aqueous layer was extracted with EtOAc (150 mL). The organic phase was dried (Na₂SO₄), filtered and concentrated under reduced pressure. The material was purified by column chromatography on silica gel (120 g) using a gradient of 0-40% EtOAc in hexane as eluent to afford the title compound (2.76 g, 56%). MS (ESI) [M+Na]⁺362.4.

Step 4
Benzyl-N-benzyl-N-[(1S)-2-fluoro-1-[(2S)-6-hydroxy-5-iodo-tetrahydropyran-2 -yl]ethyl]carbamate

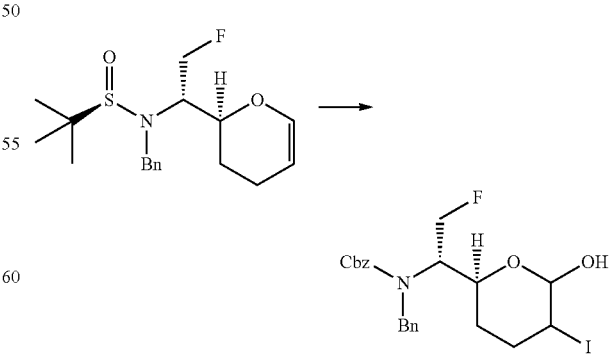

To a suspension of (R)-N-benzyl-N-[(1S)-1-[(2S)-3,4-dihydro-2H-pyran-2-yl]-2 -fluoro-ethyl]-2-methyl-propane-2-sulfinamide (2.78 g, 8.19 mmol) and NaHCO₃ (2.06 g, 24.6 mmol) in a mixture of ACN (30 mL) and H$_2$O (30 mL) at 0° C., was added 12 (3.12 g, 12.3 mmol) portionwise and the reaction mixture was stirred at 20° C. for 90 min. The mixture was diluted with saturated aqueous solution of Na$_2$S$_2$O$_3$ (100 mL) and the aqueous layer was extracted with EtOAc (100 mL). The organic layer was dried (Na$_2$SO$_4$), filtered, and concentrated under reduced pressure to provide the iodolactol. MS (ESI) [M+Na]$^+$506.2.

To a solution of above material (3.96 g, 8.19 mmol) in dioxane (100 mL) with vigorous stirring, was added 1.0 M aqueous HCl (32.8 mL, 32.8 mmol) and the reaction mixture was stirred for 1 h. Solid Na$_2$CO$_3$ (6.94 g, 65.5 mmol) was then added and the mixture was stirred for 10 min. CbzCl (1.63 mL, 11.5 mmol) was added dropwise and the reaction mixture was stirred for 30 min. The mixture was partitioned in between EtOAc (50 mL) and H$_2$O (50 mL). The aqueous layer was extracted with EtOAc (50 mL) and the combined organic layers were combined were dried (Na$_2$SO$_4$), filtered and concentrated under reduced pressure. The material was purified by column chromatography on silica gel (120 g) using a gradient of 0-55% EtOAc in hexane as eluent to provide the title compound (3.30 g, 79%). MS (ESI) [M+Na]$^+$536.2.

Step 5
Benzyl N-[(1S)-1-[(2S)-5-azido-6-oxo-tetrahydropyran-2-yl]-2-fluoro-ethyl]-N-benzyl-carbamate

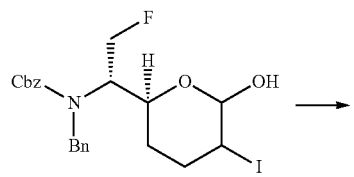

To a solution of benzyl N-benzyl-N-[(1S)-2-fluoro-1-[(2S)-6-hydroxy-5-iodo-tetrahydropyran-2-yl]ethyl]carbamate (3.30 g, 6.43 mmol) in DCM (200 mL), was added 4 Å molecular sieves (2.00 g) followed by PDC (10.9 g, 28.9 mmol) and the suspension was stirred for 18 h. The mixture was filtered on a silica pad, rinsed with EtOAc and concentrated under reduced pressure. The residue material was dissolved in DMF (30 mL) and then cooled at 0° C. NaN$_3$ (0.46 g, 7.07 mmol) was added and the reaction mixture was stirred for 1 h at room temperature. The mixture was diluted with brine (250 mL) and the separated aqueous layer was extracted with Et$_2$O. The combined organic layers were dried over (Na$_2$SO$_4$), filtered and concentrated under reduced pressure to provide the title compound as a mixture of diastereomers (1.9 g, 69%), which was used in the next step without further purification. MS (ESI) [M+Na]$^+$449.3.

Step 6
Benzyl N-[(1S)-1-[(2S,5R)-5-azido-6-hydroxy-tetrahydropyran-2-yl]-2-fluoro-ethyl]-N-benzyl-carbamate

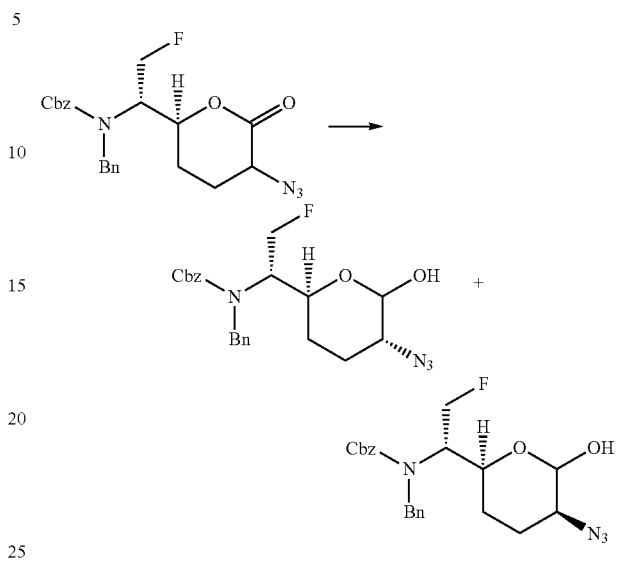

DIBAL-H (1 M in toluene, 8.96 mL, 8.96 mmol) was added dropwise to a solution of benzyl N-[(1S)-1-[(2S)-5-azido-6-oxo-tetrahydropyran-2-yl]-2-benzyloxy-ethyl]-N-benzyl-carbamate (1.91 g, 4.48 mmol) in DCM (50 mL) at −78° C. and the reaction mixture was stirred at room temperature for 1 h. EtOH (1 mL) was added dropwise and the mixture was poured into a saturated aqueous solution of Rochelle's salt (300 mL) and then was stirred vigorously stirred for 1 h. The separated aqueous layer was extracted with DCM (2×75 mL). The combined organic layer was washed with brine, then dried (Na$_2$SO$_4$), filtered and concentrated under reduced pressure. The material was purified flash chromatography on silica gel (120 g) using a gradient of 25-70% Et$_2$O in hexane to provide benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]-2-fluoro-ethyl]-N-benzyl-carbamate (first eluting, 489 mg, 26%) and a diastereomer (second eluting, 283 mg, 15%). MS (ESI) [M+Na]$^+$451.1. (5.69 and 5.86 min are the first eluting diastereomer; 5.57 and 5.78 min are the first eluting diastereomer).

Step 7
(1S,2R,3R,4S,6R)-4,6-diazido-3-[(2R,3R,6S)-3-azido-6-[(1S)-1-[benzyl(methyl)amino]-2-fluoro-ethyl]tetrahydropyran-2-yl]oxy-cyclohexane-1,2-diol

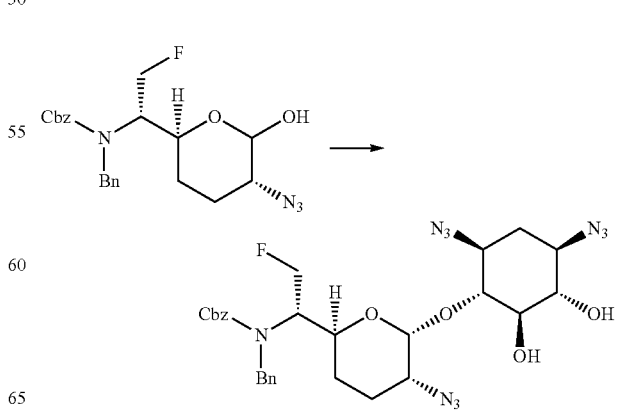

To a suspension of benzyl N-[(1S)-1-[(2S,5R,6R)-5-azido-6-[(1R,2R,3S,4R,6S) -4,6-diazido-2,3-dihydroxy-cyclohexoxy]tetrahydropyran-2-yl]-2-fluoro-ethyl]-N-benzyl -carbamate (150 mg, 0.58 mmol) and K₂CO₃ (174 mg, 1.26 mmol) in DCM (5 mL) under N₂ was added CCl₃CN (0.20 mL, 2.01 mmol). The mixture was stirred at room temperature for 66 h, then the filtered through Celite, rinsed with DCM and concentrated under reduced pressure.

[(1S,2S,3R,4S,6R)-2-acetoxy-4,6-diazido-3-hydroxy-cyclohexyl]acetate (150 mg, 0.50 mmol) was added to the above material, and the mixture was co-evaporated with anhydrous toluene (2×10 mL) and then was dried under reduced pressure for 2 h. The material was dissolved in anhydrous Et₂O (5 mL) and then grounded activated 3 Å (0.5 g) and 4 Å sieves (0.5 g) were added. The mixture was stirred at room temperature for 1 h, then cooled to −40° C. TMSOTf (0.027 mL, 0.15 mmol) was then added dropwise and the mixture was stirred at −40° C. for 2 h, then warmed to room temperature. A saturated solution of NaHCO₃ (200 mL) was added and the separated aqueous layer was extracted with EtOAc (3×200 mL). The combined organic layers were dried (MgSO₄), filtered and concentrated under reduced pressure. The material was purified by flash chromatography (24 g, liquid loading) using a gradient of 0-40% EtOAc in hexane as eluent to afford intermediate A (minor, first eluting) and intermediate B (major, second eluting). MS (ESI) [M+Na]⁺731.5.

To a solution of intermediate B in MeOH (5 mL), NaOMe (4.62 M in MeOH, 0.87 mL, 4.02 mmol) was added and the reaction mixture was stirred at room temperature for 1 h. The mixture was concentrated under reduced pressure and the residue was dissolved in DCM (25 mL) and then a saturated solution of NH₄Cl (25 mL) was added. The separated aqueous layer was extracted with DCM (2×20 mL). The combined organic layers were dried (MgSO₄), filtered and concentrated under reduced pressure to provide the title compound (70.0 mg, 22%) MS (ESI) [M+Na]⁺647.5.

Step 8

Benzyl N-[(1S)-1-[(2S,5R,6R)-5-azido-6-[(1R,2R,3S,4R, 6S)-4,6-diazido-2,3-dihydroxy -cyclohexoxy]tetrahydropyran-2-yl]-2-fluoro-ethyl]-N-benzyl-carbamate

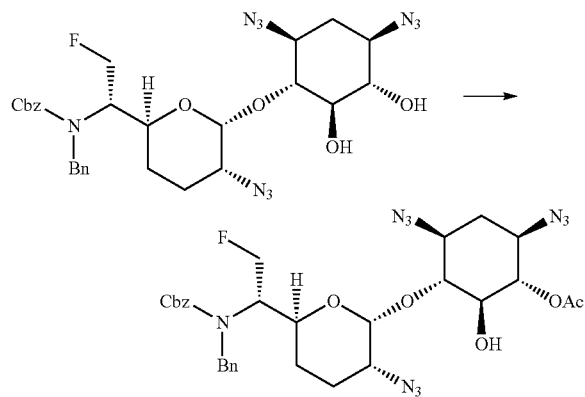

To a solution of benzyl N-[(1S)-1-[(2S,6R)-5-azido-6-[(1R,2R,3S,4R,6S)-4,6-diazido-2,3-dihydroxy-cyclohexoxy]tetrahydropyran-2-yl]-2-fluoro-ethyl]-N-benzyl-carbamate (88.0 mg, 0.14 mmol) in dry DCM (8 mL), was added pyridine (67 µL, 0.85 mmol) followed by Ac₂O (67 µL, 0.70 mmol) at room temperature and the reaction mixture was stirred for 20 h. MeOH was added and the volatiles were evaporated under reduced pressure. The material was purified by flash chromatography (12 g, liquid loading with toluene) using a gradient 0-45% EtOAc in hexane as eluent to provide the title compound (63 mg, 67%). MS (ESI) [M+H]⁺667.7.

Step 9

Benzyl-N-[(1S)-1-[(2S,5R,6R)-5-azido-6-[(1R,2R,3S,4R, 6S)-4,6-diazido-2-[(2S,3R,4S,5R)-4-[(2R,3R,4R,5S,6S)-3-azido-6-(azidomethyl)-4,5-dihydroxy-tetrahydropyran-2-yl] oxy-3-hydroxy-5-(hydroxymethyl)tetrahydrofuran-2-yl] oxy-3-hydroxy-cyclohexoxy]tetrahydropyran -2-yl]-2-fluoro-ethyl]-N-benzyl-carbamate

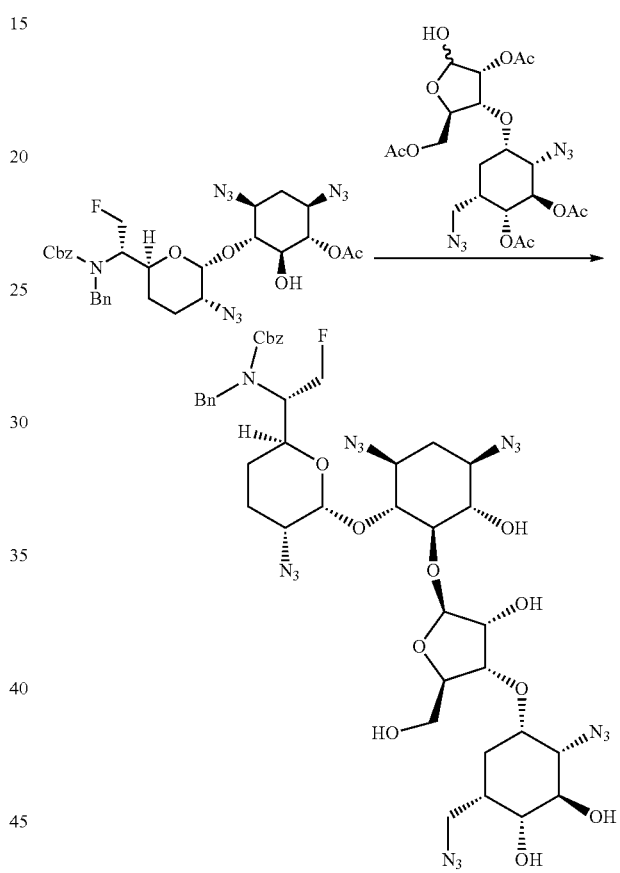

To a suspension of [(2R,3R,4R)-4-acetoxy-3-[(2R,3R,4R, 5R,6S)-4,5-diacetoxy-3-azido-6-(azidomethyl)tetrahydropyran-2-yl]oxy-5-hydroxy-tetrahydrofuran-2-yl]methyl acetate (150 mg, 0.28 mmol) and K₂CO₃ (78.4 mg, 0.57 mmol) in dry DCM (5.0 mL) at ambient temperature under N₂, was added CCl₃CN (0.095 mL, 0.95 mmol) dropwise and the reaction mixture was stirred for 15 h. The mixture was filtered through 45 µm nylon filter and the volatiles were evaporated under reduced pressure.

To the above material was added a solution of [(1S,2S, 3R,4S,6R)-4,6-diazido-3 -[(2R,3R,6S)-3-azido-6-[(1S)-1-[benzyl(benzyloxycarbonyl)amino]-2-fluoro -ethyl]tetrahydropyran-2-yl]oxy-2-hydroxy-cyclohexyl]acetate (63.0 mg, 0.095 mmol) in DCM (1.0 mL) and the volatiles were evaporated under reduced pressure. To the residue was added ground 4 Å sieves (200 mg) followed by dry DCM (5.0 mL). The suspension was stirred at ambient temperature for 1 h. The solution was cooled to 0° C. and then BF₃·Et₂O (0.093 mL, 0.76 mmol) was added. The reaction mixture was stirred for 2 h, and then the reaction was quenched with NaHCO$_3$. The layers were separated, and the aqueous layer was extracted with EtOAc (5.0 mL). The organic phase was dried (Na$_2$SO$_4$), filtered and concentrated under reduced pressure. The material was purified by reversed phase chromatography on C18 (80 g) using ACN in water and 0.1% aqueous. formic acid (40-100%) to afford the title compound. MS (ESI) [M+Na]$^+$1201.8.

To a solution of the above material in MeOH (1.0 mL) at ambient temperature, was added NaOMe (25 wt %, 0.33 mL, 1.13 mmol) dropwise and the reaction mixture was stirred for 45 min. The volatiles were removed under reduced pressure. The residue was diluted with EtOAc and the organic layer was washed with saturated NH$_4$Cl and brine, then dried (Na$_2$SO$_4$), filtered, and concentrated under reduced pressure. The material was purified by preparative HPLC (CSH ACN/AmForm 60-80%) to afford the title compound (19 mg, 21%, 3 steps). MS (ESI) [M+H]$^+$969.7.

Step 10

(2S,3S,4R,5R,6R)-5-amino-2-(aminomethyl)-6-[(2R,3S,4R,5S)-5-[(1R,2R,3S,5R,6S)-3,5-diamino-2-[(2R,3R,6S)-3-amino-6-[(1S)-1-amino-2-fluoro-ethyl]tetrahydropyran-2-yl]oxy-6-hydroxy-cyclohexoxy]-4-hydroxy-2-(hydroxymethyl)tetrahydrofuran-3-yl]oxy-tetra-hydropyran -3,4-diol; Sulfate tetrahydrofuran-2-yl]oxy-3-hydroxy -cyclohexoxy] tetrahydropyran-2-yl]-2-fluoro-ethyl]-N-benzyl-carbamate (19 mg, 0.020 mmol) and Pd/C (10% dry on carbon, 10.4 mg, 0.0098 mmol) following by anhydrous MeOH (1 mL). Nitrogen was bubbled for 5 min, then ammonium formate (18.5 mg, 0.29 mmol) was added and the mixture was heated at 63° C. for 6 h. The mixture was then cooled and filtered through a nylon filter (45 μm) and the volatiles were evaporated under reduced pressure to provide the title compound (7.7 mg, 64%). The material was purified by preparative HPLC (with A: 0.3% HFBA, 0.3% HCOOH in water B: 0.3% HFBA Acetonitrile; Flow rate: 40 mL/min; Column : C18, 30×150 mm, 27% B in A to 37% B in A over 7 minutes provided 8 mg of the title compound as a HFBA salt. The salt swap with ammonium sulfate provided the title product (0.7 mg, 6%). $^1$H NMR (500 MHz, D20) δ 5.86 (d, J=3.5 Hz, 1H), 5.35 (d, J=2.3 Hz, 1H), 5.24 (d, J=1.7 Hz, 1H), 4.83-4.74 (m, 1H), 4.68-4.63 (m, 1H), 4.47 (dd, J=6.7, 4.9 Hz, 1H), 4.38 (dd, J=4.8, 2.3 Hz, 1H), 4.30-4.25 (m, 1H), 4.22-4.14 (m, 3H), 4.00 (s, 1H), 3.88-3.82 (m, 2H), 3.79-3.64 (m, 4H), 3.56-3.52 (m, 1H), 3.52-3.46 (m, 1H), 3.43-3.24 (m, 4H), 2.36 (dt, J=6.9, 4.6 Hz, 1H), 2.02-1.93 (m, 2H), 1.93-1.83 (m, 2H), 1.70-1.58 (m, 1H). MS (ESI) [M+H]$^+$615.0.

Example 44

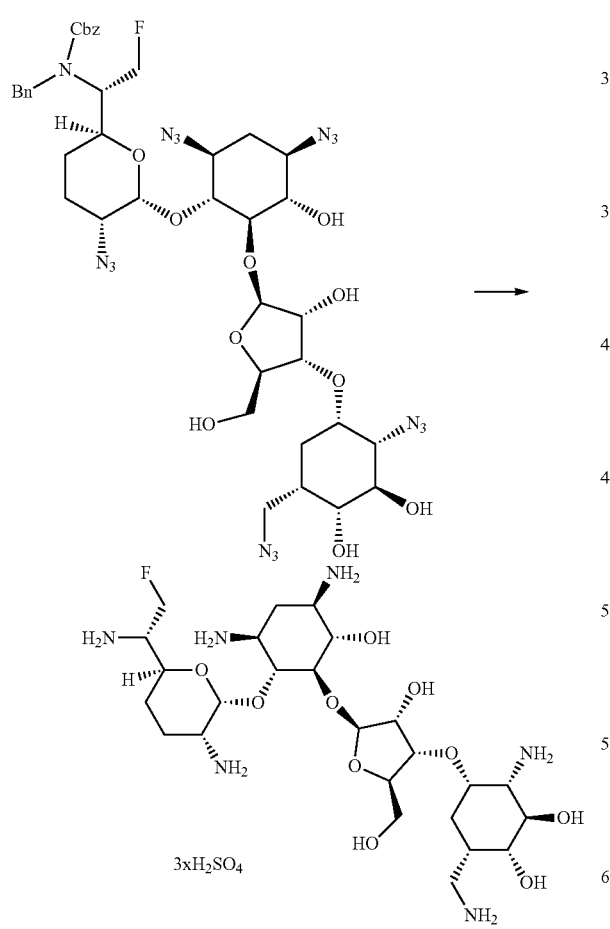

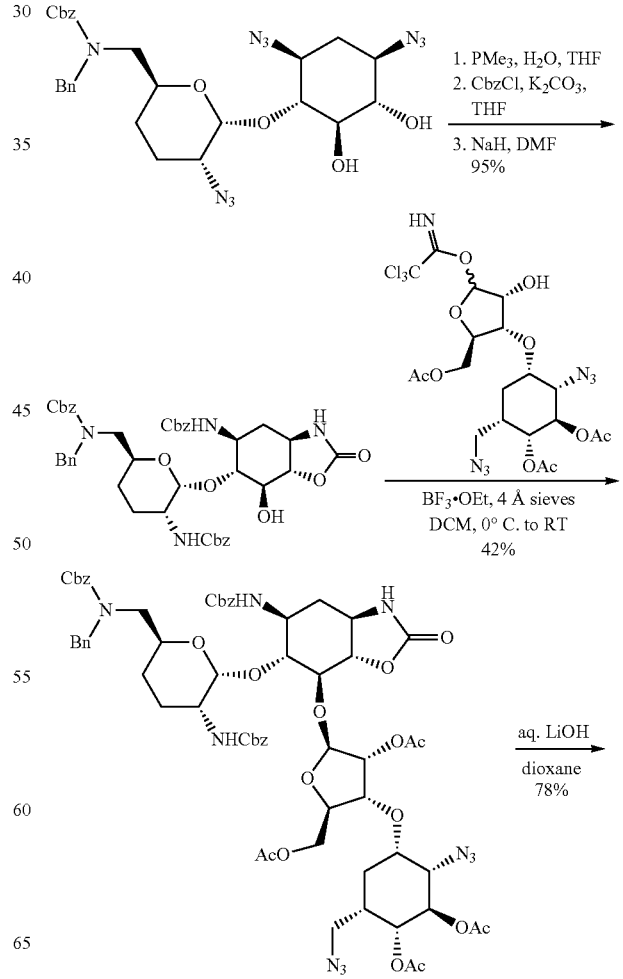

To a solution of benzyl N-[(1S)-1-[(2S,5R,6R)-5-azido-6-[(1R,2R,3S,4R,6S)-4,6-diazido-2-[(2S,3R,4S,5R)-4-[(2R,3R,4R,5S,6S)-3-azido-6-(azidomethyl)-4,5-dihydroxy -tetrahydropyran-2-yl]oxy-3-hydroxy-5-(hydroxymethyl)

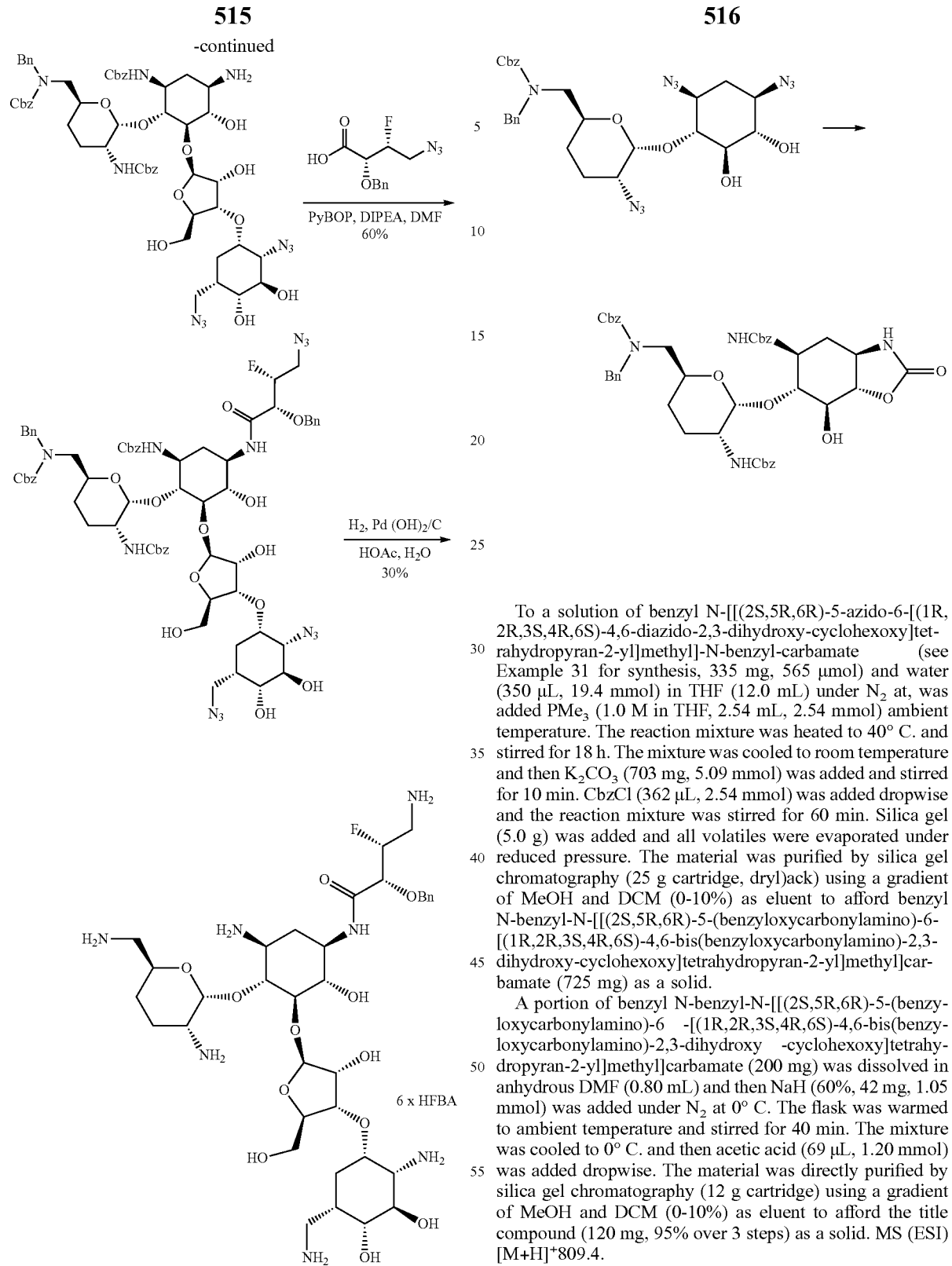

Step 1
Benzyl N-[[(2S,5R,6R)-6-[[(3aR,5S,6R,7S,7aS)-5-(benzyloxycarbonylamino)-7-hydroxy-2-oxo -3a,4,5,6,7,7a-hexahydro-3H-1,3-benzoxazol-6-yl]oxy]-5-(benzyloxycarbonylamino)tetrahydropyran-2-yl]methyl]-N-benzyl-carbamate To a solution of benzyl N-[[(2S,5R,6R)-5-azido-6-[(1R,2R,3S,4R,6S)-4,6-diazido-2,3-dihydroxy-cyclohexoxy]tetrahydropyran-2-yl]methyl]-N-benzyl-carbamate (see Example 31 for synthesis, 335 mg, 565 µmol) and water (350 µL, 19.4 mmol) in THF (12.0 mL) under $N_2$ at, was added $PMe_3$ (1.0 M in THF, 2.54 mL, 2.54 mmol) ambient temperature. The reaction mixture was heated to 40° C. and stirred for 18 h. The mixture was cooled to room temperature and then $K_2CO_3$ (703 mg, 5.09 mmol) was added and stirred for 10 min. CbzCl (362 µL, 2.54 mmol) was added dropwise and the reaction mixture was stirred for 60 min. Silica gel (5.0 g) was added and all volatiles were evaporated under reduced pressure. The material was purified by silica gel chromatography (25 g cartridge, dryl)ack) using a gradient of MeOH and DCM (0-10%) as eluent to afford benzyl N-benzyl-N-[[(2S,5R,6R)-5-(benzyloxycarbonylamino)-6-[(1R,2R,3S,4R,6S)-4,6-bis(benzyloxycarbonylamino)-2,3-dihydroxy-cyclohexoxy]tetrahydropyran-2-yl]methyl]carbamate (725 mg) as a solid.

A portion of benzyl N-benzyl-N-[[(2S,5R,6R)-5-(benzyloxycarbonylamino)-6 -[(1R,2R,3S,4R,6S)-4,6-bis(benzyloxycarbonylamino)-2,3-dihydroxy -cyclohexoxy]tetrahydropyran-2-yl]methyl]carbamate (200 mg) was dissolved in anhydrous DMF (0.80 mL) and then NaH (60%, 42 mg, 1.05 mmol) was added under $N_2$ at 0° C. The flask was warmed to ambient temperature and stirred for 40 min. The mixture was cooled to 0° C. and then acetic acid (69 µL, 1.20 mmol) was added dropwise. The material was directly purified by silica gel chromatography (12 g cartridge) using a gradient of MeOH and DCM (0-10%) as eluent to afford the title compound (120 mg, 95% over 3 steps) as a solid. MS (ESI) [M+H]$^+$809.4.

Step 2
[(2R,3R,4R,5S)-5-[[(3aR,5S,6R,7S,7aS)-6-[(2R,3R,6S)-6-[[benzyl(benzyloxycarbonyl)amino]methyl]-3-(benzyloxycarbonylamino)tetrahydropyran-2-yl]oxy-5-(benzyloxycarbonylamino)-2-oxo-3a,4,5,6,7,7a-hexahydro-3H-1,3-benzoxazol-7-yl]oxy]-4-acetoxy-3-[(2R,3R,4R,5R,6S)-4,5-diacetoxy-3-azido-6-(azidomethyl)tetrahydropyran -2-yl]oxy-tetrahydrofuran-2-yl]methyl acetate

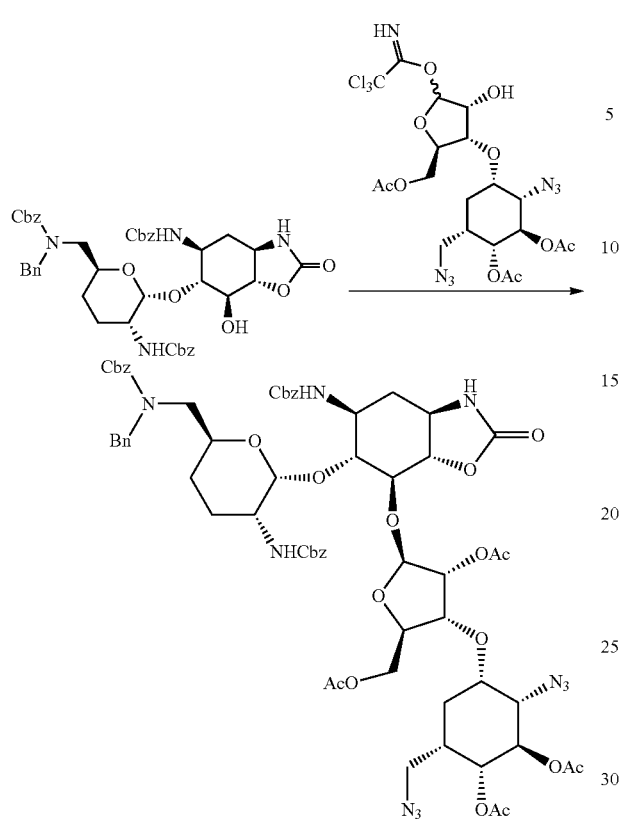

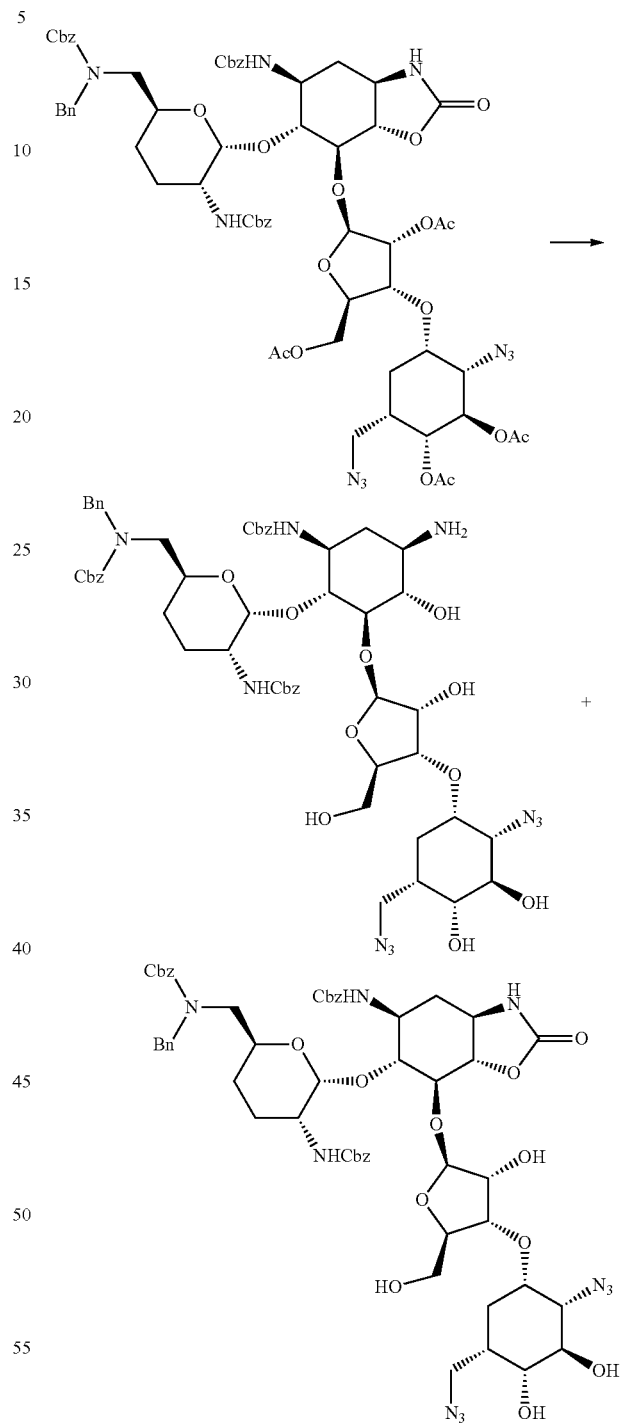

CCl$_3$CN (149 µL, 1.48 mmol) was added dropwise to a suspension of [(2R,3R,4R)-4-acetoxy-3-[(2R,3R,4R,5R,6S)-4,5-diacetoxy-3-azido-6-(azidomethyl)tetrahydropyran-2-yl]oxy-5-hydroxy-tetrahydrofuran-2-yl]methyl acetate (157 mg, 297 µmol) and K$_2$CO$_3$ (123 mg, 890 µmol) in dry DCM (1.8 mL) at ambient temperature under N$_2$. After 17 h, the solution was filtered through a Celite pad and the filtrate was concentrated under N$_2$ stream, and then dried under high-vacuum. To the above material was added benzyl N -[[(2S,5R,6R)-6-[[(3aR,5S,6R,7S,7aS)-5-(benzyloxycarbonylamino)-7-hydroxy-2-oxo -3a,4,5,6,7,7a-hexahydro-3H-1,3-benzoxazol-6-yl]oxy]-5-(benzyloxycarbonylamino)tetrahydropyran-2-yl]methyl]-N-benzyl-carbamate (120 mg, 148 µmol) in DCM (1.8 mL) and all volatiles were evaporated under N$_2$ stream. To the mixture was added ground 4 Å sieves (450 mg) and the mixture was dissolved in dry DCM (1.8 mL). The suspension was stirred at ambient temperature for 90 min, and then cooled to 0° C. BF$_3$·OEt$_2$ (146 µL, 1.19 mmol) was added and then stirred at ambient temperature for another 1 h. Et$_3$N (300 µL) was added and the mixture was filtered through a silica gel pad (0.30 g) and washed with EtOAc (20.0 mL). The volatiles were evaporated under reduced pressure and the material was purified by silica gel chromatography (12 g cartridge) using a gradient of MeOH and DCM (0-5%) as eluent and was further purified by C18 reversed phase chromatography (30 g cartridge) using ACN and 0.1% aq. formic acid (40-100%) to provide the title compound (83 mg, 42%) as a solid. MS (ESI) [M+H]$^+$1322.8.

Step 3
Benzyl N-[[(2S,5R,6R)-6-[(1R,2R,3S,4R,6S)-4-amino-2-[(2S,3R,4S,5R)-4-[(2R,3R,4R,5S,6S) -3-azido-6-(azidomethyl)-4,5-dihydroxy-tetrahydropyran-2-yl]oxy-3-hydroxy-5-(hydroxymethyl)tetrahydrofuran-2-yl]oxy-6-(benzyloxycarbonylamino)-3-hydroxy -cyclohexoxy]-5-(benzyloxycarbonylamino)tetrahydropyran-2-yl]methyl]-N-benzyl-carbamate LiOH·H$_2$O (12 mg, 280 µmol) was added to a suspension of [(2R,3R,4R,5S)-5-[[(3aR,5S,6R,7S,7aS)-6-[(2R,3R,6S)-6-[[benzyl(benzyloxycarbonyl)amino]methyl]-3-(benzyloxycarbonylamino)tetrahydropyran-2-yl]oxy-5-(benzyloxycarbonylamino)-2-oxo -3a,4,5,6,7,7a-hexahydro-3H-1,3-benzoxazol-7-yl]oxy]-4-acetoxy-3-[(2R,3R,4R,5R,6S)-4,5-diacetoxy-3-azido-6-(azidomethyl)tetrahydropyran-2-yl]oxy-tetrahydrofuran-2-yl]methyl acetate (37 mg, 28 µmol)

in a mixture dioxane and water (2.0 mL, 1:1) at ambient temperature. After 2 h, LiOH·H$_2$O (12 mg, 280 µmol) was added and the reaction mixture was stirred for 18 h. All volatiles were removed under reduced pressure and the material was purified by silica gel chromatography (4 g cartridge) using a gradient of MeOH and DCM (0-20%) as eluent to provide the title compound (21 mg, 66%) as a solid. MS (ESI) [M+H]$^+$1127.8.

Also from the same chromatography, benzyl N-[[(2S,5R,6R)-6 -[[(3aR,5S,6R,7S,7aS)-7-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl) tetrahydrofuran-2-yl]oxy-5 -(benzyloxycarbonylamino)-2-oxo-3a,4,5,6,7,7a-hexahydro-3H-1,3-benzoxazol-6-yl]oxy]-5-(benzyloxycarbonylamino)tetrahydropyran-2-yl]methyl]-N-benzyl-carbamate (8 mg, 25%). MS (ESI) [M+H]$^+$1154.6.

To a suspension of [(2R,3R,4R,5S)-5-[[(3aR,5S,6R,7S,7aS)-6-[(2R,3R,6S)-6-[[benzyl(benzyloxycarbonyl)amino] methyl]-3-(benzyloxycarbonylamino)tetrahydropyran-2-yl] oxy-5-(benzyloxycarbonylamino)-2-oxo-3a,4,5,6,7,7a-hexahydro-3H-1,3-benzoxazol-7-yl]oxy]-4-acetoxy-3-[(2R,3R,4R,5R,6S)-4,5-diacetoxy-3-azido-6-(azidomethyl) tetrahydropyran -2-yl]oxy-tetrahydrofuran-2-yl]methyl acetate (45 mg, 34 µmol) and benzyl N-[[(2S,5R,6R)-6-[[(3aR,5S,6R,7S,7aS)-7-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl) tetrahydrofuran-2-yl]oxy-5 -(benzyloxycarbonylamino)-2-oxo-3a,4,5,6,7,7a-hexahydro-3H-1,3-benzoxazol-6-yl]oxy]-5-(benzyloxycarbonylamino)tetrahydropyran-2-yl]methyl]-N-benzyl-carbamate (8 mg, 7 µmol) in a mixture dioxane and water (1:1; 2.0 mL) at ambient temperature was added LiOH·H$_2$O (43 mg, 1.02 mmol) and the reaction mixture was stirred for 18 h.

All volatiles were evaporated under reduced pressure and the material was purified by silica gel chromatography (12 g cartridge) using a gradient of MeOH and DCM (0 -20%) as eluent to provide the title compound (34 mg, 74%) as a solid. MS (ESI) [M+H]$^+$1127.8.

Overall, the hydrolysis of [(2R,3R,4R,5S)-5-[[(3aR,5S,6R,7S,7aS)-6-[(2R,3R,6S)-6-[[benzyl(benzyloxycarbonyl) amino]methyl]-3-(benzyloxycarbonylamino)tetrahydropyran-2-yl]oxy-5-(benzyloxycarbonylamino)-2-oxo -3a,4,5,6,7,7a-hexahydro-3H-1,3-benzoxazol-7-yl]oxy]-4-acetoxy-3-[(2R,3R,4R,5R,6S)-4,5-diacetoxy-3-azido-6-(azidomethyl) tetrahydropyran-2-yl]oxy-tetrahydrofuran-2-yl]methyl acetate (82 mg, 62 µmol) afforded the title compound (55 mg) with 78% yield.

Step 4
Benzyl N-[[(2S,5R,6R)-6-[(1R,2R,3S,4R,6S)-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-4-[[(2R,3R)-4-azido-2-benzyloxy-3-fluoro -butanoyl]amino]-6-(benzyloxycarbonylamino)-3-hydroxy-cyclohexoxy]-5-(benzyloxycarbonylamino)tetrahydropyran-2-yl]methyl]-N-benzyl-carbamate

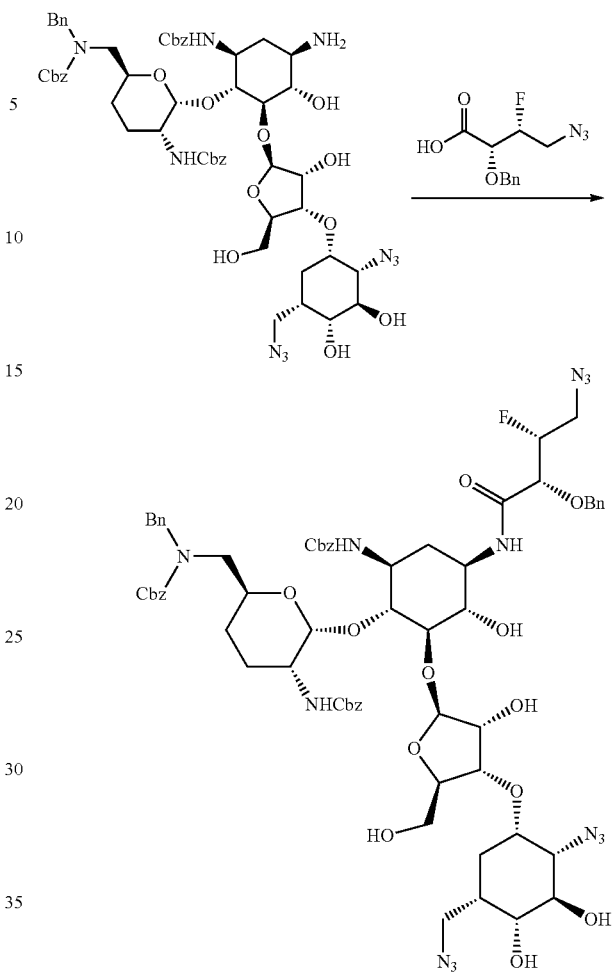

PyBOP (30 mg, 59 µmol) was added to a solution of benzyl N-[[(2S,5R,6R)-6 -[(1R,2R,3S,4R,6S)-4-amino-2-[(2S,3R,4S,5R)-4-[(2R,3R,4R,5S,6S )-3-azido-6-(azidomethyl) -4,5-dihydroxy-tetrahydropyran-2-yl]oxy-3-hydroxy-5-(hydroxymethyl)tetrahydrofuran-2-yl]oxy -6-(benzyloxycarbonylamino)-3-hydroxy-cyclohexoxy]-5 -(benzyloxycarbonylamino)tetrahydropyran-2-yl]methyl]-N-benzyl-carbamate (55 mg, 49 µmol), (2R,3R)-4-azido-2-benzyloxy-3-fluoro-butanoic acid (14 mg, 56 µmol) and DIPEA (20 µL, 146 µmol) in dry DMF (0.40 mL) under N$_2$ and the reaction mixture was stirred for 60 min. The mixture was directly purified by C18 reverse phase chromatography (12 g cartridge) using ACN and 0.1% aq formic acid (30-100%) as eluent to provide the title compound (40 mg, 60%) as a solid. MS (ESI) [M+H]$^+$1363.9.

Step 5
(2R,3R)-4-amino-N-[(1R,2S,3R,4R,5S)-5-amino-3-[(2S,3R,4S,5R)-4-[(2R,3R,4R,5S,6S)-3-amino-6-(aminomethyl)-4,5-dihydroxy-tetrahydropyran-2-yl]oxy-3-hydroxy-5-(hydroxymethyl)tetrahydrofuran-2-yl]oxy-4-[(2R,3R,6S)-3-amino-6-(aminomethyl)tetrahydropyran-2-yl]oxy-2-hydroxy-cyclohexyl]-3-fluoro-2-hydroxy -butanamide,2,2,3,3,4,4,4-heptafluorobutanoic acid

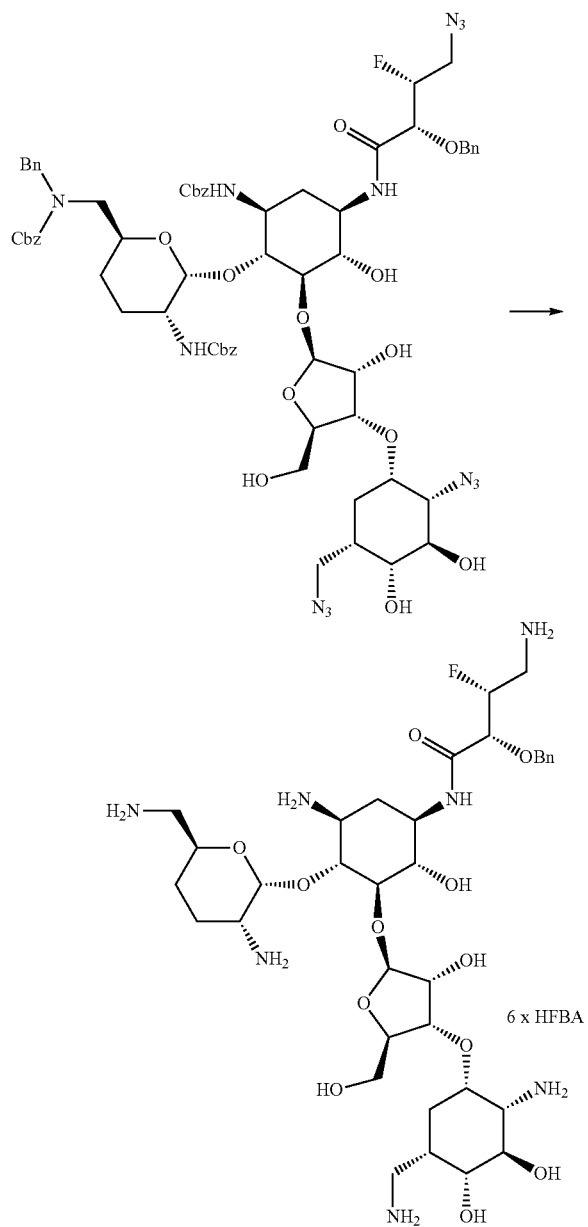

Pd(OH)$_2$/C (10 wt %, 82 mg, 59 μmol) was added to a solution of benzyl N -[[(2S,5R,6R)-6-[(1R,2R,3S,4R,6S)-2-[(2S,3R,4S,5R)-4-[(2R,3R,4R,5S,6S)-3-azido-6-(azidomethyl)-4,5-dihydroxy-tetrahydropyran-2-yl]oxy-3-hydroxy-5-(hydroxymethyl)tetrahydrofuran-2-yl]oxy-4-[[(2R,3R)-4-azido-2-benzyloxy-3-fluoro -butanoyl]amino]-6-(benzyloxycarbonylamino)-3-hydroxy-cyclohexoxy]-5-(benzyloxycarbonylamino)tetrahydropyran-2-yl]methyl]-N-benzyl-carbamate (21 mg, 27 μmol) in a mixture 4:1 AcOH/H$_2$O (2.0 mL) under N$_2$ at ambient temperature. H$_2$ was bubbled into the solution for 15 min and the suspension was hydrogenated under hydrogen atmosphere for 18 h. The material was filtered through a frit (0.45 μm diameter) and concentrated under reduced pressure. The material was purified by preparative HPLC (BEH 30×100 mm ACN/AmForm 10 -15%) and was further purified by HFBA-coupled preparative HPLC (HFBA 25-40%) to provide the title compound (hexa-HFBA salt, 17.5 mg, 30%) as a solid.

$^1$H NMR (500 MHz, D$_2$O) δ 5.91 (d, J=3.3 Hz, 1H), 5.42 (d, J=1.8 Hz, 1H), 5.37-5.21 (m, 2H), 4.52-4.41 (m, 2H), 4.38 (dd, J=4.5, 2.1 Hz, 1H), 4.33 (t, J=4.4 Hz, 1H), 4.27-4.21 (m, 2H), 4.17-4.10 (m, 1H), 4.08-3.97 (m, 2H), 3.95 (dd, J=12.3, 2.5 Hz, 1H), 3.90 (t, J=9.1 Hz, 1H), 3.86 (s, 1H), 3.76 (dd, J=12.2, 5.4 Hz, 1H), 3.67 (t, J=9.8 Hz, 1H), 3.61 (s, 1H), 3.59-3.53 (m, 2H), 3.53-3.37 (m, 4H), 3.27 (dd, J=13.5, 3.1 Hz, 1H), 3.12 (dd, J=13.5, 7.0 Hz, 1H), 2.34-2.26 (m, 1H), 2.11-2.01 (m, 2H), 1.99-1.91 (m, 1H), 1.89-1.78 (m, 1H), 1.68-1.56 (m, 1H). MS (ESI) [M+H]$^+$702.4.

Example 45

(1S,2R,3R,4S,6R)-4,6-diamino-3-(((2R,3R,6S)-3-amino-6-((S)-1-aminoethyl)tetrahydro-2H -pyran-2-yl)oxy)cyclohexane-1,2-diol

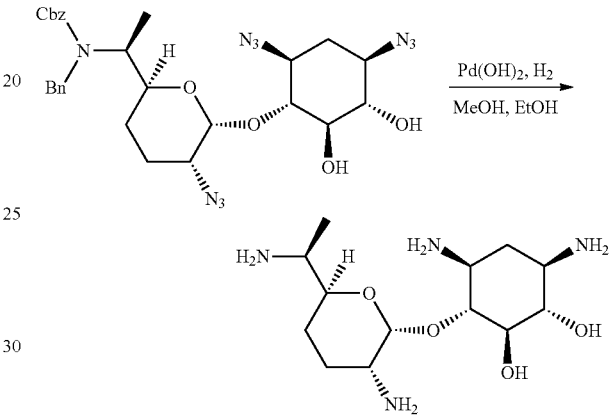

Pd(OH)$_2$/C (20 wt %, 145 mg, 206 μmol) was added to a solution of benzyl N -[(1S)-1-[(2S,5R,6R)-5-azido-6-[(1R,2R,3S,4R,6S)-4,6-diazido-2,3-dihydroxycyclohexoxy]tetrahydropyran-2-yl]ethyl]-N-benzyl-carbamate (see Example 22 for synthesis, 25.0 mg, 41.2 μmol) in MeOH (2.50 mL) and EtOH (2.50 mL). H$_2$ was bubbled and the suspension was hydrogenated under hydrogen atmosphere for 16 h. The mixture was filtered through a frit (0.22 μm diameter) and the filtrate was concentrated under reduced pressure to afford the title compound (11.0 mg, 88%) as a solid. $^1$H NMR (500 MHz, MeOD) δ 5.47 (d, J=3.5 Hz, 1H), 3.75-3.68 (m, 1H), 3.43 (t, J=9.1 Hz, 1H), 3.37-3.31 (m, 1H), 3.12 (t, J=9.5 Hz, 1H), 3.07-3.00 (m, 1H), 2.95-2.86 (m, 2H), 2.79-2.72 (m,1H), 2.06-2.00 (m, 1H), 1.87-1.73 (m, 3H), 1.46-1.36 (m, 1H), 1.28-1.14 (m, 4H). MS (ESI) [M+H]$^+$ 305.0.

Example 46

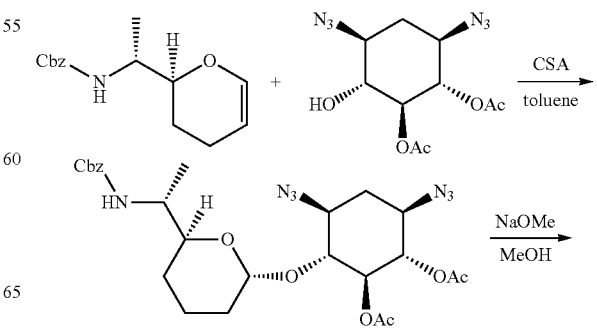

-continued

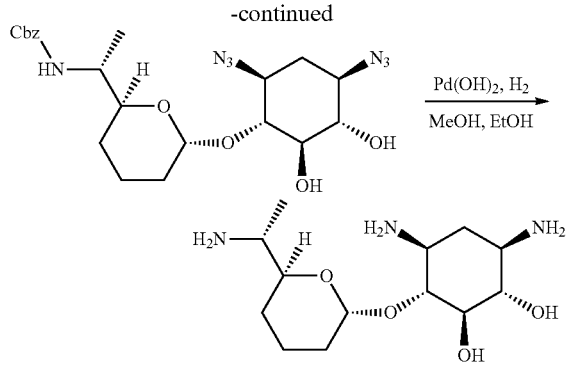

Step 1
[(1S,2S,3R,4S,6R)-2-acetoxy-4,6-diazido-3-[(6S)-6-[(1R)-1-(benzyloxycarbonylamino)ethyl]tetrahydropyran-2-yl]oxy-cyclohexyl]acetate

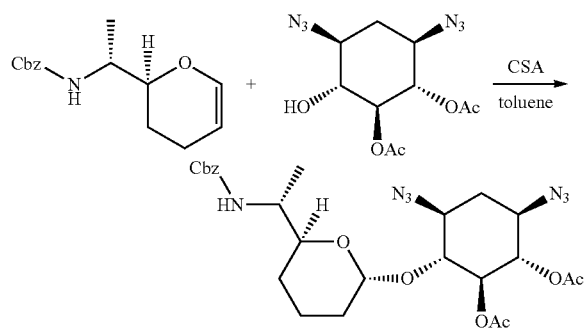

CSA (97.8 mg, 0.42 mmol) was added to a solution of benzyl N-[(1R)-1-[(2S) -3,4-dihydro-2H-pyran-2- yl]ethyl]carbamate (see Example 47, 100 mg, 0.38 mmol) and DL -[(1S,2S,3R,4S,6R)-2-acetoxy-4,6-diazido-3- hydroxy-cyclohexyl]acetate (126 mg, 0.42 mmol) in toluene (5 mL) at room temperature. The mixture was stirred at room temperature for 5 h, then a saturated aqueous solution of NaHCO$_3$ (5 mL) was added. The aqueous layer was extracted with DCM. The combined organic layer was drier over MgSO$_4$ and concentrated under reduced pressure. The material was purified by prep HPLC (ACN, AmFor, BEH column) to provide the title compound (103 mg) with 48% as a solid. 1H NMR (500 MHz, CDCl$_3$) δ 7.33-7.23 (m, 5H), 5.08-5.02 (m, 2H), 4.96-4.88 (m, 3H), 4.53 (dd, J=9.5, 1.8 Hz, 1H), 3.74-3.63 (m, 1H), 3.58-3.50 (m, 1H), 3.50-3.42 (m, 2H), 3.26 (dd, J=11.0, 4.5 Hz, 1H), 2.20 (dt, J=13.4, 4.5 Hz, 1H), 2.01 (s, 3H), 1.95 (s, 3H), 1.84-1.74 (m, 2H), 1.45-1.34 (m, 3H), 1.27-1.17 (m, 2H), 1.13 (d, J=6.7 Hz, 3H).

Step 2
Benzyl N-[(1R)-1-[(2S,6R)-6-[(1R,2R,3S,4R,6S)-4,6-diazido-2,3-dihydroxy -cyclohexoxy]tetrahydropyran-2-yl]ethyl]carbamate

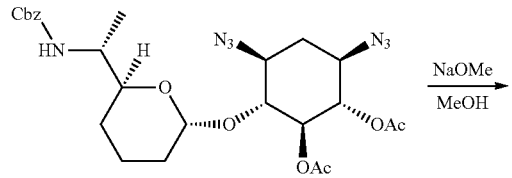

-continued

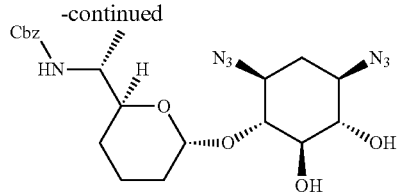

A MeONa solution (0.50 M, 1.47 mL, 736 μmol) in MeOH was added dropwise to a solution of [(1S,2S,3R,4S,6R)-2-acetoxy-4,6-diazido-3-[(2R,6S)-6-[(1R)-1-(benzyloxycarbonylamino)ethyl]tetrahydropyran-2-yl]oxy-cyclohexyl]acetate (103 mg, 184 μmol) in methanol (4.6 mL). After 1 h, AcOH (63 μL, 1.10 mmol) was added to the solution. All volatiles were evaporated, and the crude was purified by silica gel chromatography (4 g cartridge) with EtOAc and hexanes (10-50%) to provide the title compound, which was further purified by prep-HPLC to produce the title compound as a solid (29 mg, 32%). $^1$H NMR (500 MHz, DMSO) δ 7.40-7.26 (m, 5H), 7.11 (d, J=8.9 Hz, 1H), 5.51 (t, J=4.4 Hz, 2H), 5.29 (d, J =5.6 Hz, 1H), 5.01 (d, J=12.5 Hz, 1H), 4.97 (d, J=12.5 Hz, 1H), 3.81-3.73 (m, 1H), 3.56-3.44 (m, 2H), 3.44-3.34 (m, 2H), 3.27-3.20 (m, 1H), 3.14 (td, J=9.4, 5.5 Hz, 1H), 2.03 (dt, J =12.5, 4.4 Hz, 1H), 1.76-1.61 (m, 2H), 1.52 (ddd, J=18.9, 16.5, 8.5 Hz, 3H), 1.18 (dd, J=24.8, 12.4 Hz, 2H), 1.06 (d, J=6.8 Hz, 3H). LCMS m/z: ES$^+$[M+H]$^+$: 476.24; (A05) retention time=2.35 m.

Step 3

(1S,2R,3R,4S,6R)-4,6-diamino-3-[(2R,6S)-6-[(1R)-1-aminoethyl]tetrahydropyran-2-yl]oxy -cyclohexane-1,2-diol

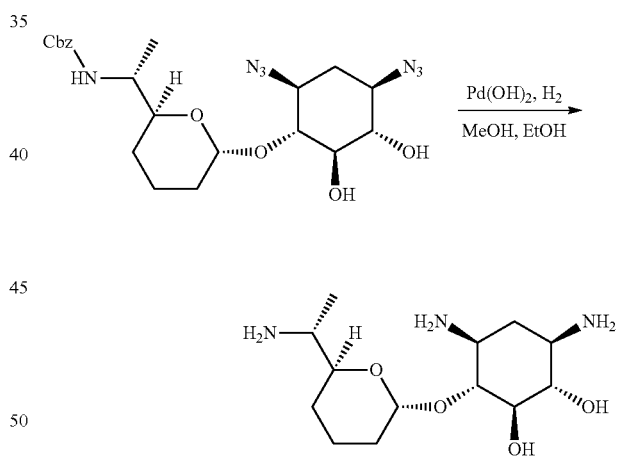

A solution of benzyl N-[(1R)-1-[(2S,6R)-6-[(1R,2R,3S,4R,6S)-4,6-diazido-2,3 -dihydroxy-cyclohexoxy]tetrahydropyran-2-yl]ethyl]carbamate (8.5 mg, 0.02 mmol) and 20% wt Pd(OH)$_2$ (2.5 mg, 0.004 mmol) in MeOH/EtOH (5 mL, 1:1) was hydrogenated at room temperature for 18 hours. The mixture was degassed with N$_2$ and filtered on celite. The mixture was concentrated under reduced pressure to provide the title compound (4.66 mg, 90%) as a solid. M+Na+: 312.1. $^1$H NMR (500 MHz, MeOD) δ 5.50 (d, J=3.0 Hz, 1H), 3.94-3.89 (m, 1H), 3.26-3.19 (m, 2H), 3.12-3.06 (m, 1H), 3.02-2.97 (m, 1H), 2.80-2.73 (m, 1H), 2.62 (ddd, J=12.0, 9.7, 4.2 Hz, 1H), 1.94 (dt, J=12.8, 4.2 Hz, 1H), 1.85-1.78 (m, 2H), 1.65-1.53 (m, 3H), 1.35 (qd, J=12.2, 3.7 Hz, 1H), 1.23-1.18 (m, 1H), 1.15 (d, J=5.2 Hz, 3H).

Example 47

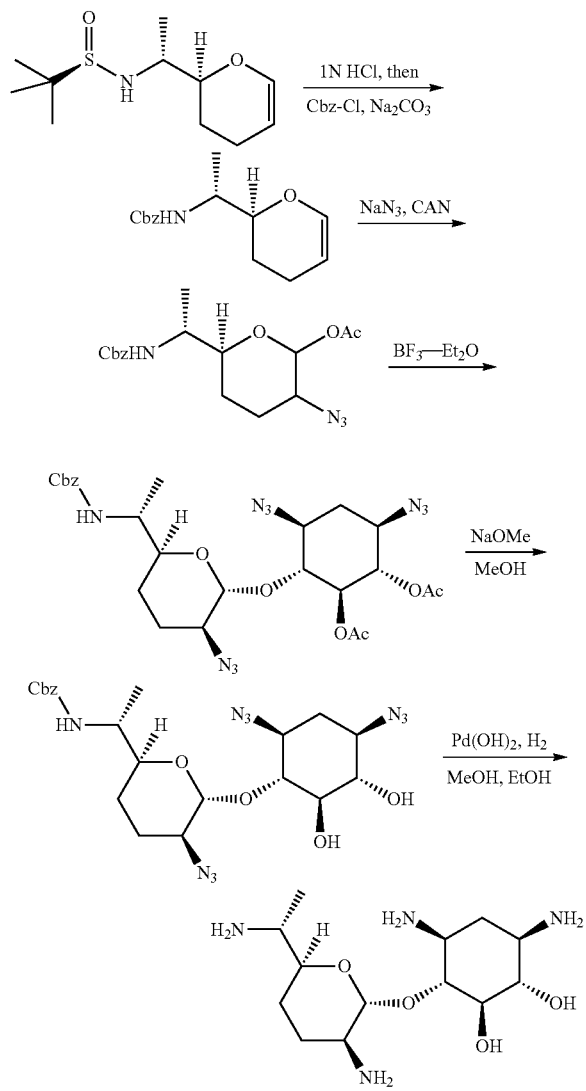

Step 1
Benzyl N-[(1R)-1-[(2S)-3,4-dihydro-2H-pyran-2-yl]ethyl]carbamate

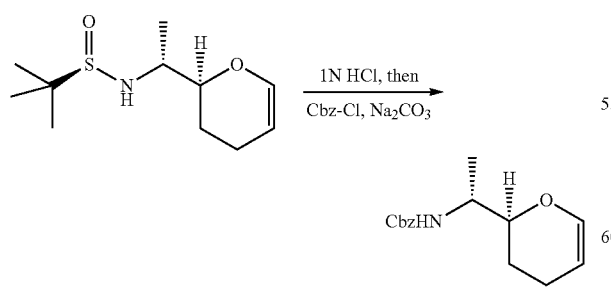

HCl (4 M, 842 µL, 3.37 mmol) was added dropwise into a solution of N-[(1R)-1 -[(2S)-3,4-dihydro-2H-pyran-2-yl]ethyl]-2-methyl-propane-2-sulfinamide (780 mg, 3.37 mmol) and isopropanol (309 µL, 4.05 mmol) in EtOAc (7.0 mL) at ambient temperature. After 90 min, triethylamine (600 µL, 4.30 mmol) was added and all volatiles were removed under reduced pressure. The crude was dissolved in THF (12.0 mL) and water (3.0 mL) followed by the addition of $K_2CO_3$ (932 mg, 6.74 mmol). After 15 min, CbzCl (575 µL, 4.05 mmol) was dropwise added to the solution. After another 2 h, THF was evaporated and the remainder was partitioned in between EtOAc (20.0 mL) and water (20.0 mL). The organic layer was washed with brine (10.0 mL), dried ($Na_2SO_4$), filtered and concentrated under reduced pressure. The crude was purified by silica gel chromatography (25 g cartridge) with EtOAc and hexanes (5% -20%) to provide the title compound as a solid (125 mg, 13%). LCMS m/z: $ES^+$ $[M+H]^+$: 262.16; (A05) retention time=2.44 m.

Step 2
[(6S)-3-azido-6-[(1R)-1-(benzyloxycarbonylamino)ethyl]tetrahydropyran-2-yl]acetate

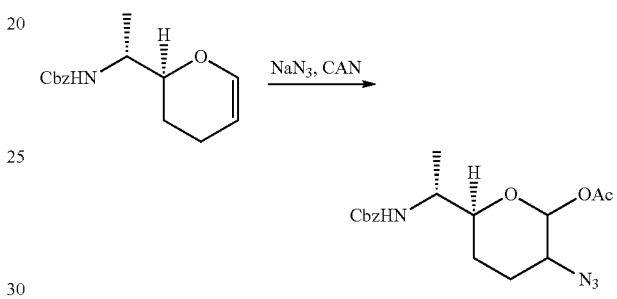

A solution of benzyl N-[(1R)-1-[(2S)-3,4-dihydro-2H-pyran-2-yl]ethyl]carbamate (112 mg, 429 µmol) in dry MeCN (1.0 mL) was added to solid CAN (0.705 g, 1.29 mmol) and $NaN_3$ (56 mg, 857 µmol) at −20° C. dropwise under $N_2$. After the addition, dry MeCN (0.50+0.50 mL) was used to transfer all material. The solution was kept within −25~−15° C. for 7 h. The solution was diluted with water (20.0 mL) and $Et_2O$ (20.0 mL) and the organic layer was successively washed with water (10.0 mL) and brine (5.0 mL), dried ($Na_2SO_4$), filtered and concentrated under reduced pressure. The crude was dissolved in HOAc (2.0 mL) and was added NaOAc (11 mg, 129 µmol). After 20 h, all solvents were removed under reduced pressure and the crude was purified by silica gel chromatography (4 g cartridge) with EtOAc and hexanes (10-40%) to produce the title compound (mixture of diastereomers) as an oil (79 mg, 48%). LCMS m/z: ES+ $[M+H]^+$: 363.04, $[M-OAc]^+$: 303.27; (A05) retention time=2.40 and 2.44 m.

Step 3
[(1S,2S,3R,4S,6R)-2-acetoxy-4,6-diazido-3-[(2R,3S,6S)-3-azido-6-[(1R)-1-(benzyloxycarbonylamino)ethyl]tetrahydropyran-2-yl]oxy-cyclohexyl]acetate

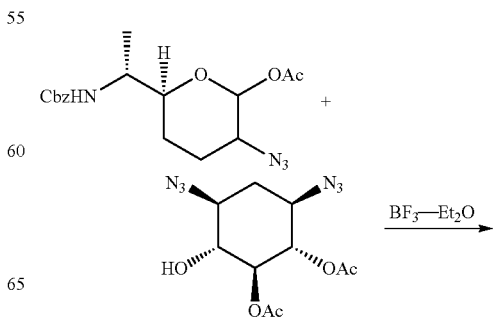

-continued

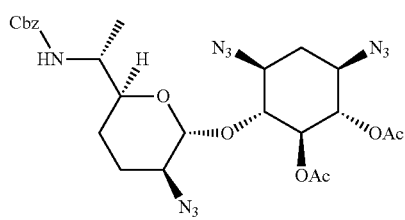

Dry DCM (2.0 mL) was added into a solid mixture of [(6S)-3-azido-6-[(1R)-1 -(benzyloxycarbonylamino)ethyl]tetrahydropyran-2-yl]acetate (75 mg, 207 µmol), [(1S,2S,3R,4S,6R)-2-acetoxy-4,6-diazido-3-hydroxy-cyclohexyl]acetate (80 mg, 268 µmol) and pulverized 4 Å molecular sieves (600 mg) under $N_2$. After 1 h, the solution was cooled to 0° C. and $BF_3 \cdot OEt_2$ (89 µL, 717 µmol) was added dropwise with rapid stirring. After 1 h, the solution was warmed to room temperature. After another 22 h, another portion of $BF_3 \cdot OEt_2$ (89 µL, 717 µmol) was added dropwise with rapid stirring. After another 6 h, sat, $NaHCO_3$ (5.0 mL) was added to the reaction mixture. The mixture was extracted by EtOAc (10.0 mL) and the organic layer was successively washed with water (5.0 mL) and brine (5.0 mL). The crude was purified by silica gel chromatography (12 g cartridge) with EtOAc and hexanes (5-30%) to provide the title compound as a solid (12 mg, 10%). LCMS m/z: $ES^+[M+H]^+$: 601.28, $[M-DOS]^+$: 303.24; (A05) retention time=2.69 m.

Step 4
Benzyl N-[(1R)-1-[(2S,5S,6R)-5-azido-6-[(1R,2R,3S,4R,6S)-4,6-diazido-2,3-dihydroxy -cyclohexoxy]tetrahydropyran-2-yl]ethyl]carbamate

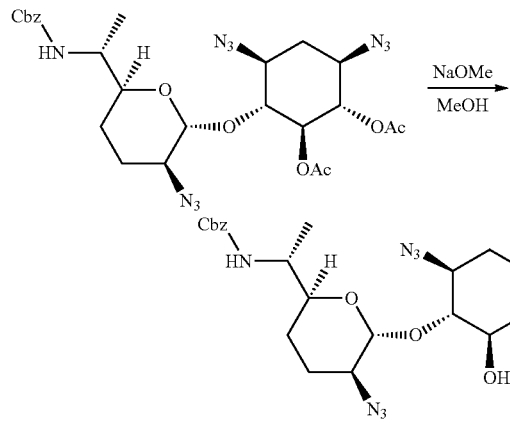

A MeONa solution (25 wt %, 23 µL, 100 µmol ) in MeOH was added dropwise to a solution of [(1S,2S,3R,4S,6R)-2-acetoxy-4,6-diazido-3-[(2R,6S)-6-[(1R)-1-(benzyloxycarbonylamino)ethyl]tetrahydropyran-2-yl]oxy-cyclohexyl]acetate (12 mg) in methanol (1.0 mL). After 1 h, HOAc (30 µL, 525 mmol) was added to the solution. All volatiles were evaporated and the crude was purified by silica gel chromatography (4 g cartridge) with EtOAc and hexanes (20-50%) to provide the title compound as a film (7 mg, 66%). $^1$H NMR (500 MHz, MeOD) δ 7.45-7.22 (m, 5H), 5.50 (s, 1H), 5.16-5.04 (m, 2H), 4.16-4.03 (m, 1H), 3.75-3.66 (m, 1H), 3.64 (s, 1H), 3.55-3.45 (m, 2H), 3.43-3.35 (m, 2H), 3.23 (t, J=9.5 Hz, 1H), 2.22-2.08 (m, 2H), 1.85 (dd, J=14.0, 2.6 Hz, 1H), 1.66 (qd, J=13.2, 3.7 Hz, 1H), 1.46 (d, J=13.7 Hz, 1H), 1.24 (dt, J =12.8, 9.4 Hz, 1H), 1.19 (d, J=6.9 Hz, 3H). LCMS m/z: $ES^+[M+H]^+$: 517.25; (A05) retention time =2.39

Step 5
(1S,2R,3R,4S,6R)-4,6-diamino-3-[(2R,3S,6S)-3-amino-6-[(1R)-1-aminoethyl]tetrahydropyran-2-yl]oxy-cyclohexane-1,2-diol

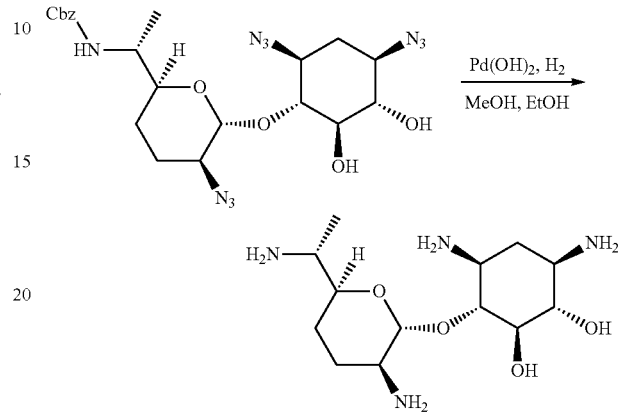

$Pd(OH)_2$/C (10 wt %, 4.5 mg, 3.3 µmol) was added to a solution of benzyl N -[(1R)-1-[(2S,5S,6R)-5-azido-6-[(1R,2R,3S,4R,6S)-4,6-diazido-2,3-dihydroxy -cyclohexoxy]tetrahydropyran-2-yl]ethyl]carbamate (7 mg, 13.6 µmol) in EtOH/MeOH (1:1, 3.0 mL) under $N_2$ at ambient temperature. $H_2$ was bubbled through the suspension for 10 min. After 17 h, the solution was filtered through a frit (0.22 µm diameter) and the filtrate was concentrated under reduced pressure, then lyophilized to provide the title compound as a solid (4.7 mg, 114%). $^1$H NMR (500 MHz, MeOD) δ 5.06 (d, J=1.9 Hz, 1H), 3.87-3.79 (m, 1H), 3.30 (t, J=9.1 Hz, 1H), 3.23 (t, J=9.2 Hz, 1H), 3.05 (t, J=9.4 Hz, 1H), 3.02-2.98 (m, 1H), 2.96 (dd, J=6.2, 3.8 Hz, 1H), 2.76 (ddd, J=12.2, 9.4, 4.2 Hz, 1H), 2.64 (ddd, J=12.0, 9.6, 4.1 Hz, 1H), 2.12 -2.04 (m, 1H), 2.01 (dt, J=12.9, 4.2 Hz, 1H), 1.75-1.62 (m, 2H), 1.51-1.44 (m, 1H), 1.28 -1.22 (m, 1H), 1.15 (d, J=6.7 Hz, 3H). LCMS m/z: $[M+H]^+$: 305.19; $[M+Na]^+$: 327.14.

Example 48

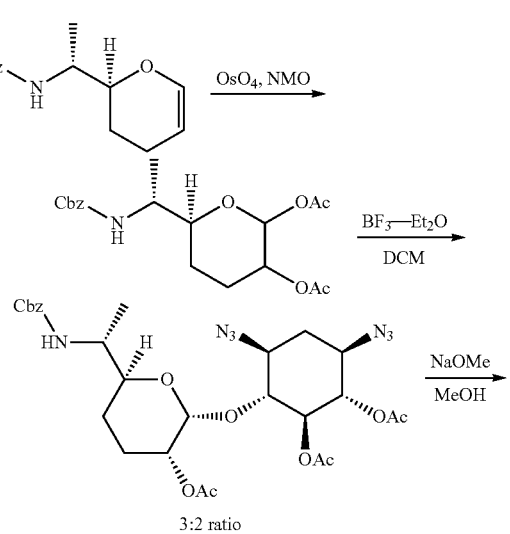

3:2 ratio

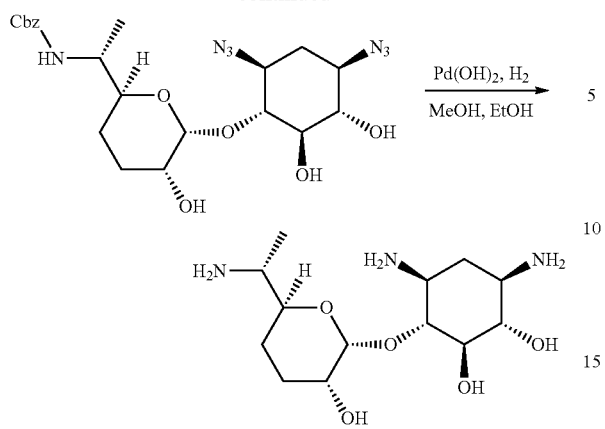

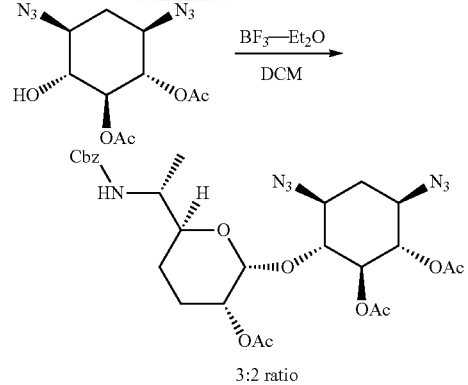

3:2 ratio

BF₃·OEt₂ (0.09 mL, 0.7 mL) was added to a mixture of [rac-(6S)-2-acetoxy-6 -[rac-(1R)-1-(benzyloxycarbonylamino)ethyl]tetrahydropyran-3-yl]acetate (180 mg, 0.474 mmol) and [(1S,2S,3R,4S,6R)-2-acetoxy-4,6-diazido-3-hydroxy-cyclohexyl]acetate (283 mg, 0.95 mmol) in DCM (50 mL) at −78° C. The acetone/dry ice bath was removed, and the mixture was stirred 6 h at room temperature. A saturated aqueous solution of NaHCO₃ (50 mL) was added. The aqueous layer was extracted with DCM. The combined organic layers were dried over Na₂SO₄ and concentrated under reduced pressure. The product was purified by prep HPLC and provided a mixture of 3 diastereoisomers. 195 mg (2 dia)-32% yield.

Step 3
Benzyl N-[(1R)-1-[(2S,5R,6R)-6-[(1R,2R,3S,4R,6S)-4,6-diazido-2,3-dihydroxy-cyclohexoxy]-5-hydroxy-tetrahydropyran-2-yl]ethyl]carbamate Step 1
[(6S)-2-acetoxy-6-[(1R)-1-(benzyloxycarbonylamino)ethyl]tetrahydropyran-3-yl]acetate

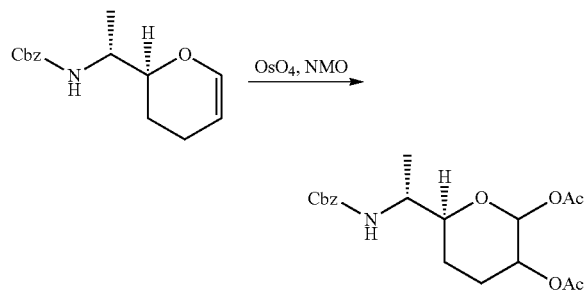

OsO₄ (4.0 mg, 0.02 mmol) was added to a solution of benzyl N-[(1R)-1-[(2S)-3,4-dihydro-2H-pyran-2-yl]ethyl]carbamate (210 mg, 0.80 mmol) and NMO (235 mg, 2.01 mmol) in acetone (10 mL). The mixture was stirred at room temperature for 18 h, then filtered on Florisil, rinsed with EtOAc and concentrated under reduced pressure. The residue was taken in dry pyridine (10 mL) and acetic anhydride (0.30 mL, 3.21 mmol) was added. The mixture was stirred at room temperature for 18 h, then water (50 mL) was added. The separated aqueous layer was extracted with DCM. The combined organic was washed with brine, dried over MgSO₄ and concentrated under reduced pressure. The material was purified on silica gel (40 g, dry loading) by MPLC using 0% to 50% EtOAc in hexane to provide the title compound (280 mg, 92%) as a mixture of 3 diastereoisomers.

Step 2
[(6S)-6-[(1R)-1-(benzyloxycarbonylamino)ethyl]-2-[(1R,2S,3S,4R,6S)-2,3-diacetoxy-4,6-diazido-cyclohexoxy]tetrahydropyran-3-yl]acetate

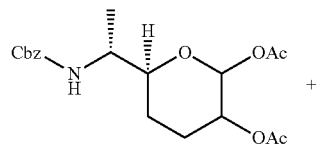

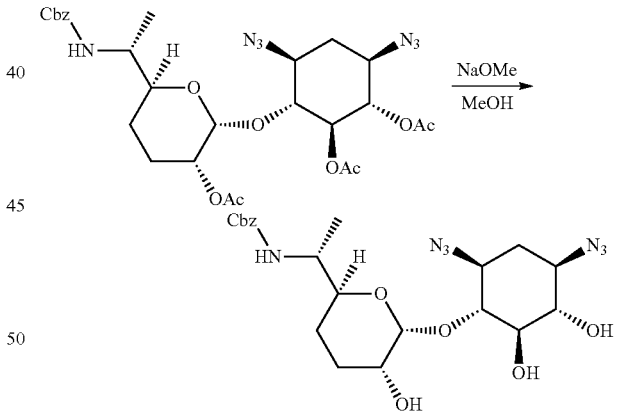

Sodium methoxide (4.62 M in methanol, 0.17 mL, 0.77 mmol) was added to a solution of [(6S)-6-[(1R)-1-(benzyloxycarbonylamino)ethyl]-2-[(1R,2S,3S,4R,6S)-2,3 -diacetoxy-4,6-diazido-cyclohexoxy]tetrahydropyran-3-yl]acetate (95 mg, 0.157 mmol) in dry MeOH (6.0 mL). The mixture was stirred at room temperature for 4 h, then AcOH (0.05 mL, 0.923 mmol) was added. The mixture was concentrated under reduced pressure. The material was purified by prep-HPLC to provide the desired compound (major anomer : 37 mg, 48%) ¹H NMR (500 MHz, MeOD) δ 7.44-7.23 (m, 5H), 5.28 (d, J=3.1 Hz, 1H), 4.01-3.87 (m, 1H), 3.70-3.56 (m, 2H), 3.52-3.43 (m, 2H), 3.43-3.34 (m, 2H), 3.30-3.24 (m, 1H), 2.24-2.13 (m, 1H), 1.89-1.80 (m, 1H), 1.80-1.72 (m, 1H), 1.69 (d, J=12.8 Hz, 1H), 1.50-1.36 (m, 1H), 1.36-1.26 (m, 1H), 1.14 (d, J=6.7 Hz, 3H).

Step 4
(1S,2R,3R,4S,6R)-4,6-diamino-3-[(2R,3R,6S)-6-[(1R)-1-aminoethyl]-3-hydroxy -tetrahydropyran-2-yl]oxy-cyclohexane-1,2-diol

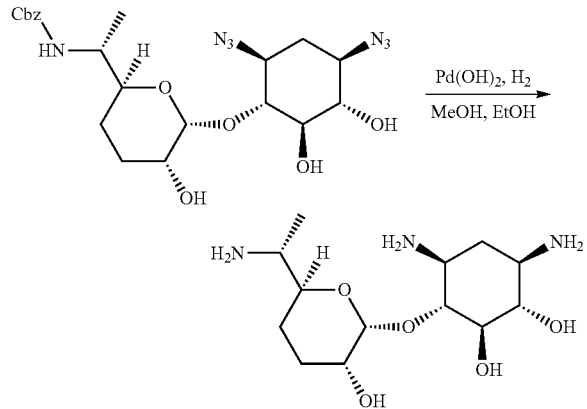

A mixture of benzyl N-[(1R)-1-[(2S,5R,6R)-6-[(1R,2R,3S,4R,6S)-4,6-diazido -2,3-dihydroxy-cyclohexoxy]-5-hydroxy-tetrahydropyran-2-yl]ethyl]carbamate (12 mg, 0.024 mmol) and Pd(OH)$_2$ (20% on dry support, 3.5 mg, 0.005 mmol) in MeOH/EtOH (5 mL, 1:1) was hydrogenated at room temperature for 18 h. The mixture was filtered with a 0.45 μM filter syringe and the solvent was removed under reduced pressure to provide the title compound (5.66 mg, 76%) as a solid. M+Na$^+$: 329.7 $^1$H NMR (500 MHz, D$_2$O) δ 5.31 (d, J=3.5 Hz, 1H), 4.03 -3.97 (m, 1H), 3.85-3.77 (m, 1H), 3.55 (t, J=9.3 Hz, 1H), 3.40-3.32 (m, 2H), 3.26 (t, J=9.6 Hz, 1H), 2.96 (ddd, J=12.1, 9.7, 4.3 Hz, 1H), 2.86 (ddd, J=12.1, 9.9, 4.2 Hz, 1H), 2.07 (dt, J=12.9, 4.2 Hz, 1H), 1.92-1.88 (m, 1H), 1.87-1.78 (m, 2H), 1.58-1.47 (m, 1H), 1.35-1.27 (m, 1H), 1.23 (d, J=6.8 Hz, 3H).

Example 49

Step 1
Benzyl ((R)-1-((2S,5S,6R)-6-4(1R,2R,3S,4R,6S)-4,6-diazido-2,3-dihydroxycyclohexyl)oxy)-5-hydroxytetrahydro-2H-pyran-2-yl)ethyl)carbamate

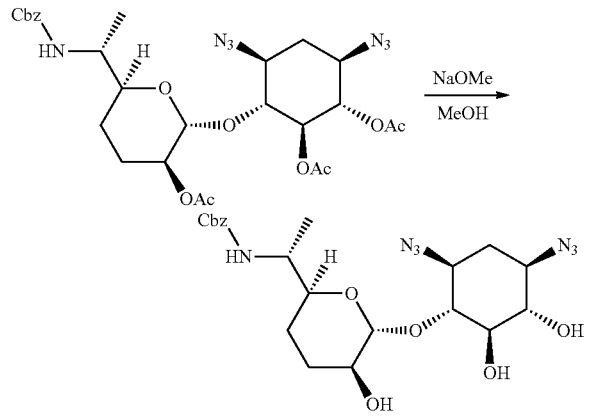

Sodium methoxide (4.62 M in methanol, 0.05 mL, 0.22 mmol) was added to a solution of [(6S)-6-[(1R)-1-(benzyloxycarbonylamino)ethyl]-2-[(1R,2S,3S,4R,6S)-2,3-diacetoxy-4,6-diazido-cyclohexoxy]tetrahydropyran-3-yl]acetate (as made in Example 48, 23 mg, 0.037 mmol) in dry MeOH (6.0 mL). The mixture was stirred at room temperature for 4 h, then AcOH (0.02 mL, 0.261 mmol) was added. The mixture was concentrated under reduced pressure. The material was purified by prep-HPLC to provide the title compound (11 mg, 59%) as a solid. M+H$^+$492.34.

Step 2
(1S,2R,3R,4S ,6R)-4,6-diamino-3-[(2R,3S,6S)-6-[(1R)-1-aminoethyl]-3-hydroxy -tetrahydropyran-2-yl]oxy-cyclohexane-1,2-diol

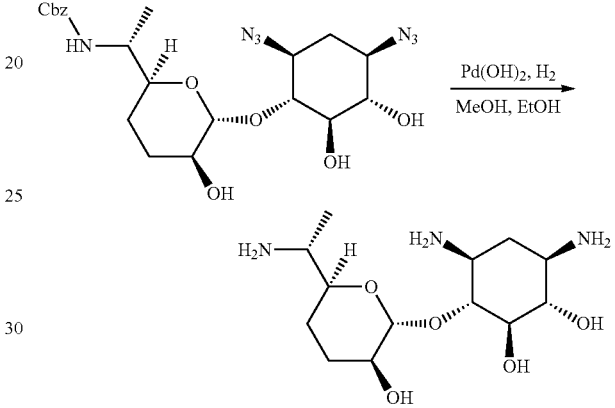

A mixture of benzyl N-[(1R)-1-[(2S,5S,6R)-6-[(1R,2R,3S,4R,6S)-4,6-diazido -2,3-dihydroxy-cyclohexoxy]-5-hydroxy-tetrahydropyran-2-yl]ethyl]carbamate (8 mg, 0.016 mmol) and Pd(OH)$_2$ (20% on dry support, 2.3 mg, 0.003 mmol) in MeOH/EtOH (5 mL, 1:1) was hydrogenated at room temperature for 18 h. The mixture was filtered with a 0.45 uM filter syringe and the solvent was removed under reduced pressure to provide the title compound (3.64 mg, 73%) as a solid. M+H$^+$: 306.2. $^1$H NMR (500 MHz, D$_2$0) δ 5.19 (s, 1H), 4.05 (dt, J=12.0, 2.9 Hz, 1H), 3.86-3.80 (m, 1H), 3.49-3.37 (m, 4H), 3.18-3.10 (m, 1H), 3.10-3.01 (m, 1H), 2.21 (dt, J=12.5, 4.0 Hz, 1H), 1.99-1.90 (m, 1H), 1.81-1.75 (m, 1H), 1.69-1.43 (m, 3H), 1.22 (d, J=6.9 Hz, 3H).

Example 50

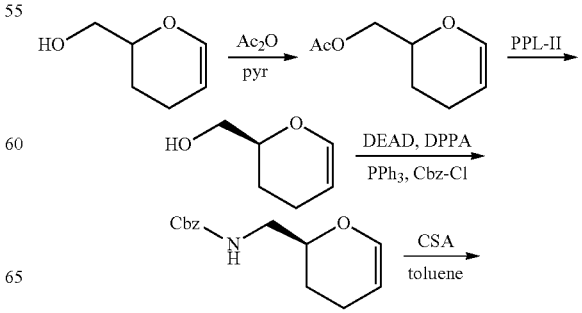

533

-continued

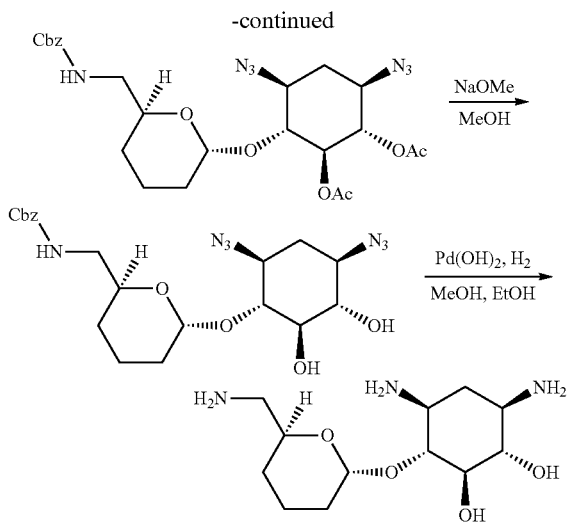

Step 1
3,4-Dihydro-2H-pyran-2-ylmethyl acetate

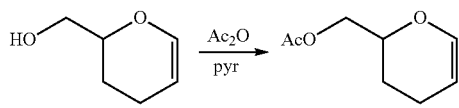

Ac$_2$O (10.0 mL, 106 mmol) was added to a solution of 3,4-dihydro-2H-pyran-2-ylmethanol (5.00 g, 43.8 mmol) in dry pyridine (20.0 mL). After 30 min, most of volatiles were removed under reduced pressure, then MeOH (10.0 mL) was added. All volatiles were removed under reduced pressure to yield the title compound as a liquid (7.80 g, 93%). This material was used in the next steps without further purification. $^1$H NMR (400 MHz, CDCl$_3$) δ 6.35 (d, J=5.9 Hz, 1H), 4.76-4.63 (m, 1H), 4.21-4.08 (m, 2H), 4.08-3.98 (m, 1H), 2.10-1.93 (m, 7H), 1.88-1.77 (m, 1H), 1.73-1.60 (m, 1H).

Step 2
[(2S)-3,4-dihydro-2H-pyran-2-yl]methanol

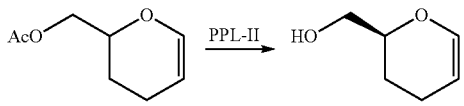

A solution of DL-3,4-dihydro-2H-pyran-2-ylmethyl acetate (3.20 g, 19.5 mmol) in acetone (10.0 mL) was added to a pH 7.4 phosphate buffer (0.010 M, 1.10 L, containing 343 mg NaH$_2$PO$_4$·H$_2$O and 1210 mg Na$_2$HPO$_4$) with vigorous stirring in an Erlenmeyer flask. More acetone (3×9.0 mL) was used to quantitatively transfer all material. PPL-II (300 mg) was added to the reaction mixture and the solution was stirred at ambient temperature (20° C.) for 16 h. The reaction mixture was then successively extracted with EtOAc (200+100+100+100 mL). The combined organic layers were dried (Na$_2$SO$_4$), filtered and concentrated under reduced pressure. The crude was purified by silica gel chromatography (80 g cartridge) with EtOAc and hexanes (40-50%) to provide the title compound as a volatile oil (540 mg, 72%). This material was used in the next step without further purification.

534

Step 3
Benzyl N-[[(2S)-3,4-dihydro-2H-pyran-2-yl]methyl]carbamate

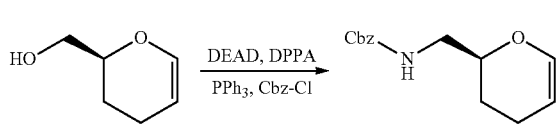

DEAD (922 μL, 5.68 mmol) was added to a solution of [(2S)-3,4-dihydro-2H-pyran-2-yl]methanol (540 mg, 4.73 mmol) and PPh$_3$ (1.49 g, 5.68 mmol) in dry THF (19.0 mL) dropwise at 0° C. under N$_2$. Then DPPA (1.22 mL, 5.68 mmol) was added to the reaction mixture dropwise. The solution was warmed to ambient temperature and stirred for 16 h. PPh$_3$ (1.49 g, 5.68 mmol) was added to the reaction mixture (CAUTION: gas evolution). After 30 min, deionized water (1.6 mL, 90.0 mmol) was added to the solution and the reaction was warmed to 50° C. under a refluxing condenser. After another 4 h, the solution was cooled to room temperature and K$_2$CO$_3$ (1.31 g, 9.46 mmol) was added. After another 30 min, CbzCl (0.81 mL, 5.68 mmol) was added dropwise. After another 60 min, THF was evaporated under reduced pressure and the residue was diluted with sat. NaHCO$_3$ (20.0 mL), successively extracted with ether (30.0+20.0+20.0 mL). The combined organic layer was dried (Na$_2$SO$_4$), filtered and concentrated under reduced pressure. The residue was purified by silica gel chromatography (25 g cartridge) with EtOAc and hexanes (5-20%) to produce the title compound as a solid (860 mg, 73%). LCMS m/z: ES+ [M+H]+: 248.33; (A05) retention time=2.37 m.

Step 4
(1S,2S,3R,4S,6R)-2-acetoxy-4,6-diazido-3-[(2R,6S)-6-(benzyloxycarbonylaminomethyl)tetrahydropyran-2-yl]oxy-cyclohexyl]acetate

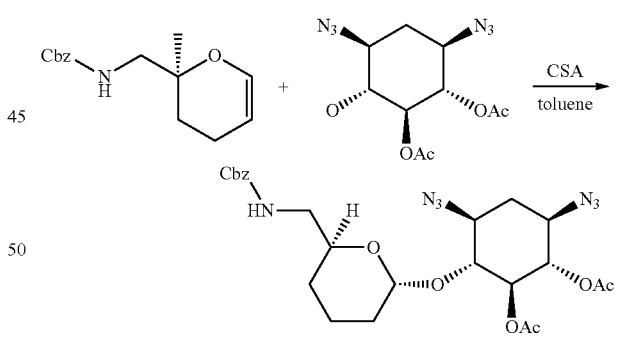

CSA (207 mg, 0.89 mmol) was added to a solution of benzyl N-[[(2S)-3,4-dihydro-2H-pyran-2-yl]methyl]carbamate (200 mg, 0.81 mmol) and DL-[(1S,2S,3R,4S,6R)-2-acetoxy-4,6-diazido-3-hydroxy-cyclohexyl]acetate (265 mg, 0.89 mmol) in toluene (15 mL) at room temperature. The mixture was stirred at room temperature for 4 h, then a saturated aqueous solution of NaHCO$_3$ (10 mL) was added. The aqueous layer was extracted with DCM. The combined organic layer was dried over MgSO$_4$ and concentrated under reduced pressure. The crude was purified by prep HPLC (ACN, AmFor, BEH column) to provide the title compound (along with some water left).

Step 5
Benzyl N-[[(2S,6R)-6-[(1R,2R,3S,4R,6S)-4,6-diazido-2,3-dihydroxy -cyclohexoxy]tetrahydropyran-2-yl]methyl]carbamate

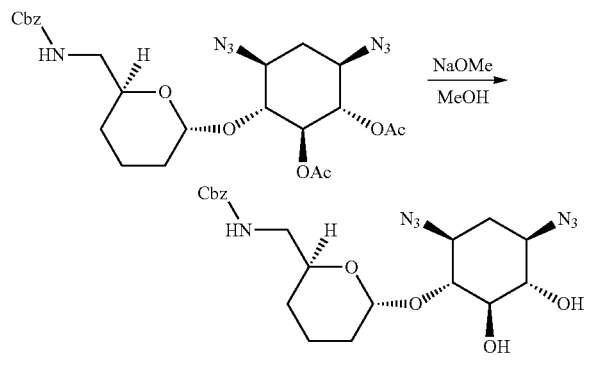

Sodium methoxide (4.62 M in methanol, 0.86 mL, 4.04 mmol) was added to a solution of [(1S,2S,3R,4S,6R)-2-acetoxy-4,6-diazido-3-[(2R,6S)-6-(benzyloxycarbonylaminomethyl)tetrahydropyran-2-yl]oxy-cyclohexyl]acetate (441 mg, 0.81 mmol) in dry methanol (10.0 mL). After 1 h, HOAc (1.21 mL, 21.2 mmol) was added to the solution. All volatiles were evaporated, and the crude was purified by quick silica gel chromatography (4 g cartridge) with EtOAc and hexanes (20-70%) to give the product with slight impurity (60 mg) followed by prep HPLC (ACN, AmFor, BEH column) to give the title product (30 mg, 8% over two steps). LCMS m/z: ES$^+$ [M+H]$^+$: 462.16; ES$^+$ [M-2DOS+H]$^+$: 248.16. (A05) retention time=2.3 min. $^1$H NMR (500 MHz, MeOD) δ 7.30-7.11 (m, 5H), 5.41 (s, 1H), 4.97 (s, 2H), 4.00 (dd, J=14.2, 7.1 Hz, 1H), 3.39-3.05 (m, 7H), 2.92 (dd, J=13.8, 7.7 Hz, 1H), 2.03 (ddd, J=8.2, 6.8, 3.6 Hz, 1H), 1.89 (s, 2H), 1.84-1.71 (m, 1H), 1.71-1.60 (m, 1H), 1.53-1.43 (m, 3H), 1.22-1.08 (m, 3H).

Step 6
(1S,2R,3R,4S,6R)-4,6-diamino-3-[(2R,6S)-6-(aminomethyl)tetrahydropyran-2-yl]oxy -cyclohexane-1,2-diol

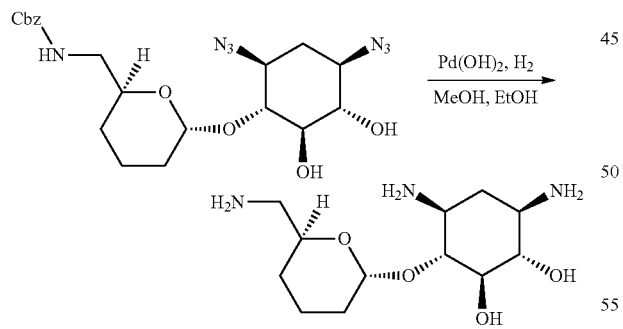

Pd(OH)$_2$/C (10 wt %, 7.6 mg, 5.4 μmol) was added to a flask containing benzyl benzyl N-[[(2S,6R)-6-[(1R,2R,3S,4R,6S)-4,6-diazido-2,3-dihydroxy -cyclohexoxy]tetrahydropyran-2-yl]methyl]carbamate (10 mg, 21.7 μmol) under N$_2$ at ambient temperature. EtOH/MeOH (1:1, 2.0 mL) was added after which H$_2$ was bubbled through the suspension for 10 min. After 17 h under hydrogen atmosphere (1 atm, balloon), the solution was filtered through a frit (0.45 μm diameter), rinsed with MeOH and the filtrate was concentrated under reduced pressure, then lyophilized to provide the title product (6.9 mg). $^1$H NMR (500 MHz, D2O) δ 5.41 (s, 1H), 4.05-3.96 (m, 1H), 3.36-3.30 (m, 2H), 3.15-3.08 (m, 1H), 2.93 (dd, J=13.3, 3.6 Hz, 1H), 2.87-2.76 (m, 2H), 2.76-2.67 (m, 1H), 1.95 (dt, J=13.0, 4.2 Hz, 1H), 1.78-1.59 (m, 5H), 1.35-1.25 (m, 1H), 1.25-1.15 (m, 1H).

Example 51

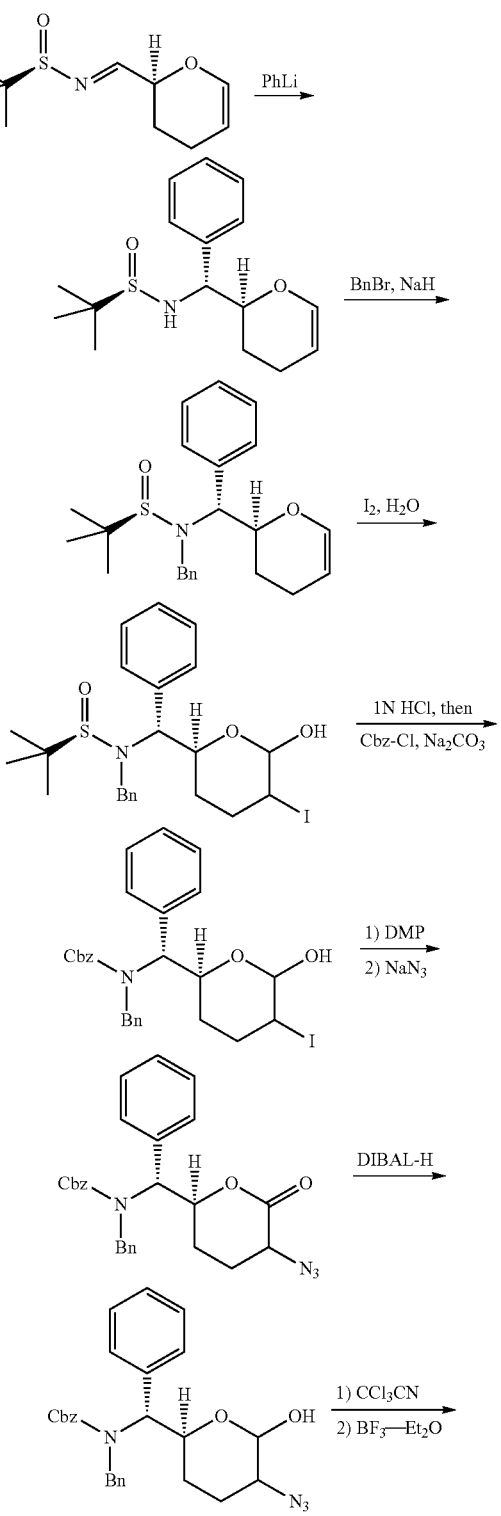

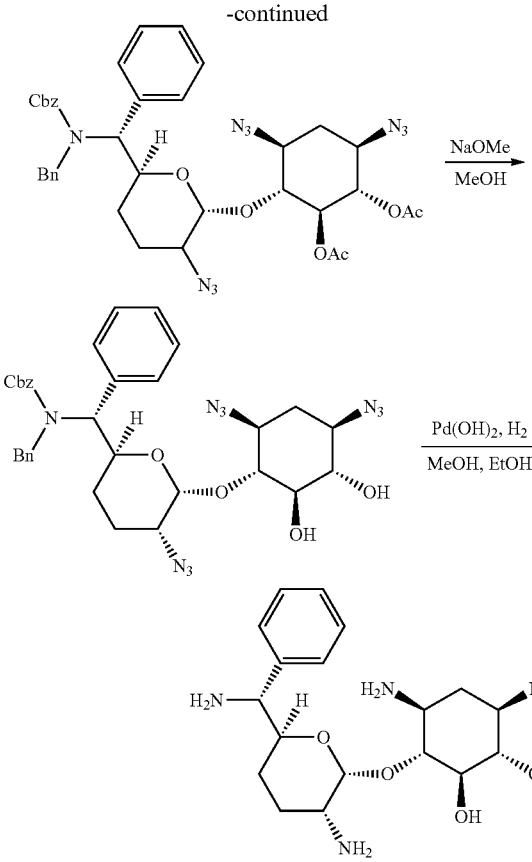

Step 1
(R)-N-[(R)-[(2S)-3,4-dihydro-2H-pyran-2-yl]-phenyl-methyl]-2-methyl-propane-2-sulfinamide

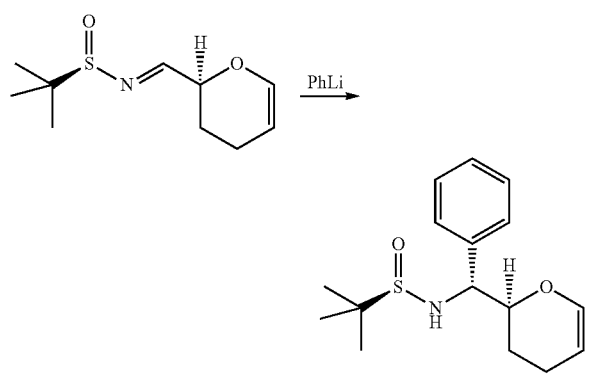

PhLi (1.9 M in dibutyl ether, 12.2 mL, 23.22 mmol) was added to a solution of (NE,R)-N-[[(2S)-3,4-dihydro-2H-pyran-2-yl]methylene]-2-methyl-propane-2-sulfinamide (2.50 g, 11.61 mmol) in dry Toluene (100 mL) at −78° C. under N₂. After 3 h, the reaction was warmed to −30° C. The reaction was quenched with adding sat. NH₄Cl dropwise dropwise (CAUTION: gas evolution). Two phases were separated, and the aqueous phase was extracted with DCM. The combined organic layers were dried (Na₂SO₄), filtered and concentrated under reduced pressure. Purified by flash chromatography (80 g cartridge, 20-50% EtOAc in hexanes as eluent) to give the title product (3.55 g total, 87% based on both reactions). LCMS m/z: ES⁺ [M+H]⁺: 294.09 (A05) retention time=2.41 min.

¹H NMR (400 MHz, cdcl3) δ 7.41-7.24 (m, 5H), 6.35 (d, J=5.8 Hz, 1H), 4.73-4.56 (m, 2H), 4.14-3.96 (m, 3H), 2.00-1.83 (m, 2H), 1.76-1.67 (m, 1H), 1.52-1.40 (m, 1H), 1.20 (s, 9H).

Step 2
(R)-N-benzyl-N-[(R)-[(2S)-3,4-dihydro-2H-pyran-2-yl]-phenyl-methyl]-2-methyl-propane-2 -sulfinamide

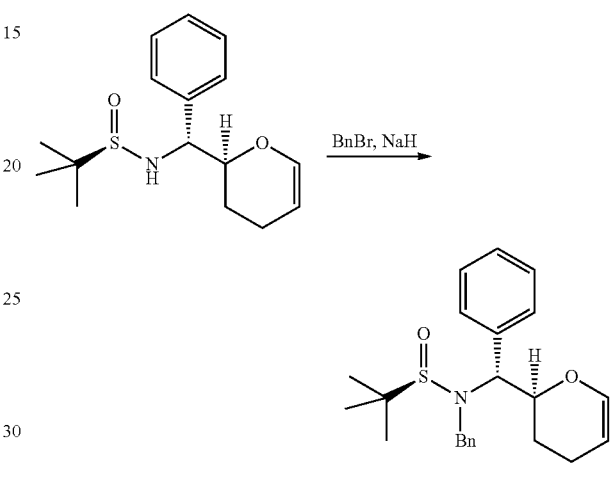

NaH (60%, 367 mg, 9.19 mmol) was added to a mixture of (R)-N-[(R)-[(2S)-3,4 -dihydro-2H-pyran-2-yl]-phenyl-methyl]-2-methyl-propane-2-sulfinamide (2.45 g, 8.35 mmol) and BnBr (1.49 mL, 12.52 mmol) in DMF (100 mL) at 0° C. The mixture was stirred at room temperature for 1 h, then brine (250 mL) was added at 0° C. The aqueous layer was extracted with Et₂O (3×80 mL). The combined organic layer was dried over MgSO₄ and concentrated under reduced pressure. The material was purified on silica gel (80 g cartridge, 10-40% EtOAc in hexane) to provide the title compound (2.18 g, 68%) as a sticky foam. LCMS m/z: ES⁺ [M+H]⁺: 384.18. (A05) retention time=2.77 min. ¹H NMR (400 MHz, cdcl3) δ 7.46-7.17 (m, 9H), 6.21 (d, J=6.0 Hz, 1H), 4.63 (d, J=13.0 Hz, 1H), 4.36 (d, J=15.9 Hz, 1H), 4.25 (t, J=8.5 Hz, 1H), 4.13-3.99 (m, 1H), 3.83 (d, J=15.9 Hz, 1H), 2.16-2.04 (m, 1H), 2.04-1.92 (m, 1H), 1.85 (d, J=16.9 Hz, 1H), 1.59-1.42 (m, 1H), 1.24 (s, 9H).

Step 3
(R)-N-benzyl-N-[(R)-[(2S)-6-hydroxy-5-iodo-tetrahydro-pyran-2-yl]-phenyl-methyl]-2-methyl -propane-2-sulfinamide

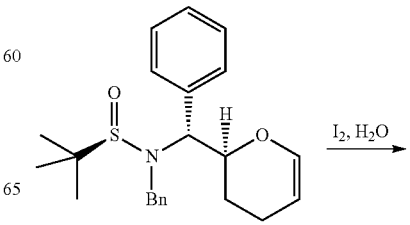

-continued

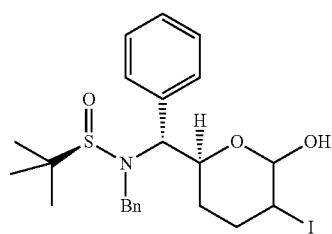

I₂ (1.59 g, 6.25 mmol) was added portionwise to a suspension of (R)-N-benzyl-N-[(R)-[(2S)-3,4-dihydro-2H-pyran-2-yl]-phenyl-methyl]-2-methyl-propane-2-sulfinamide (2.18 g, 5.68 mmol) and NaHCO₃ (1.43 g, 17.05 mmol) in ACN (25 mL) and H₂O (25 mL) at 0° C. The mixture was stirred at room temperature for 90 min, then a saturated aqueous solution of Na₂S₂O₃ (10 mL) was added. The aqueous layer was extracted with EtOAc (3×20 mL). The combined organic layer was washed with brine, dried over Na₂SO₄, filtered and concentrated under reduced pressure to provide the title compound. M+Na⁺ m/z: 550.02 (A05), retention time =2.6 min.

Step 4
benzyl N-benzyl-N-[(R)-[(2S)-6-hydroxy-5-iodo-tetrahydropyran-2-yl]-phenyl-methyl]carbamate

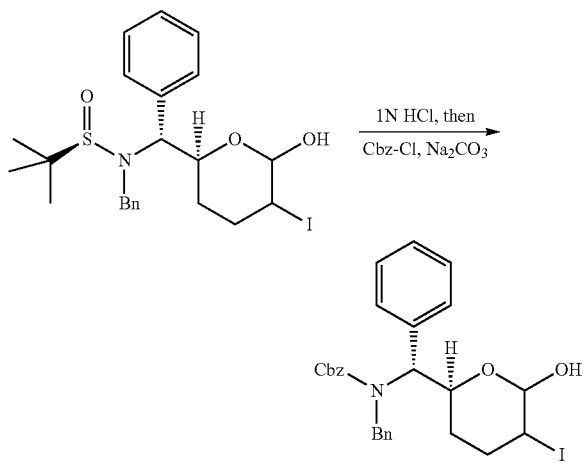

1 N HCl (11.3 mL, 11.36 mmol) was added to a mixture of (R)-N-benzyl-N-[(R)-[(2S)-6-hydroxy-5-iodo-tetrahydropyran-2-yl]-phenyl-methyl]-2-methyl-propane-2-sulfinamide (3.0 g, 5.68 mmol) in dioxane (80 mL). The mixture was stirred at room temperature for 20 min, LCMS indicated no starting material. Na₂CO₃ (4.8 g, 45.44 mmol) and water (10 mL) was added. After 20 min, CbzCl (1.1 mL, 7.95 mmol) was added dropwise. The mixture was stirred at room temperature overnight. Water (100 mL) was added. The separated aqueous layer was extracted with EtOAc (3×50 mL). The combined organic layer was washed with brine, dried over MgSO₄ and concentrated under reduced pressure. The material was purified on silica gel (80 g, dry loading) by MPLC using hexane to 60% EtOAc to provide the title compound (1.69 g, 53%, over 3 steps) as a solid. [M+Na+] m/z: 580.04. (A05) retention time=~2.8 min, several diastereomers.

Step 5
benzyl N-[(R)-[(2S)-5-azido-6-oxo-tetrahydropyran-2-yl]-phenyl-methyl]-N-benzyl-carbamate

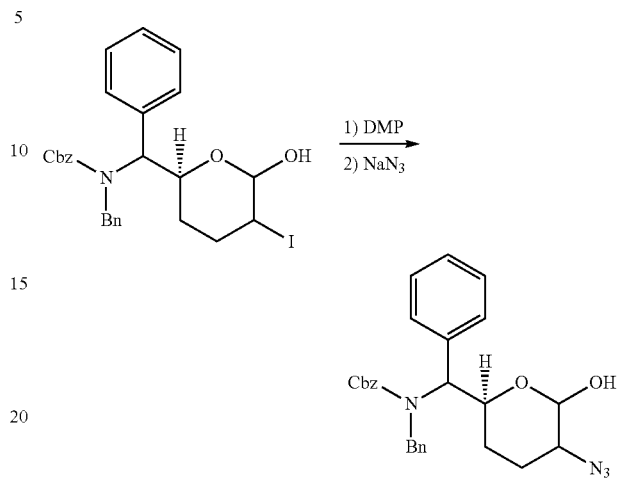

Dess-Martin Periodinane (1.93 g, 4.55 mmol) was added to a solution of benzyl N-benzyl-N-[(R)-[(2S)-6-hydroxy-5-iodo-tetrahydropyran-2-yl]-phenyl-methyl]carbamate (1.69 g, 3.03 mmol, includes impurity) in DCM (100 mL) at 0° C. The mixture was stirred at room temperature for 5 h. Water (100 mL) was added following by a saturated aqueous solution of Na₂S₂O₃. The separated aqueous layer was extract with DCM (2×50 mL). The combined organic layer were washed with saturated aqueous NaHCO₃ (2×100 mL), brine (100 mL), dried over MgSO₄ and concentrated under reduced pressure.

The residue was taken in anhydrous DMF (75 mL) and NaN₃ (296 mg, 4.55 mmol) was added. The mixture was stirred at room temperature for 15 min, then brine (300 mL) was added. The aqueous layer was extracted with EtOAc (3×100 mL). The combined organic layers was dried over MgSO₄ and concentrated under reduced pressure. The material was purified on silica gel (40 g, dry loading) by MPLC using hexane to EtOAc to provide the title compound (603 mg, 42%) as an yellow oil. M+H+: 471 and/or M+Na 493.

Step 6
Benzyl N-[(R)-[(2S)-5-azido-6-hydroxy-tetrahydropyran-2-yl]-phenyl-methyl]-N-benzyl-carbamate

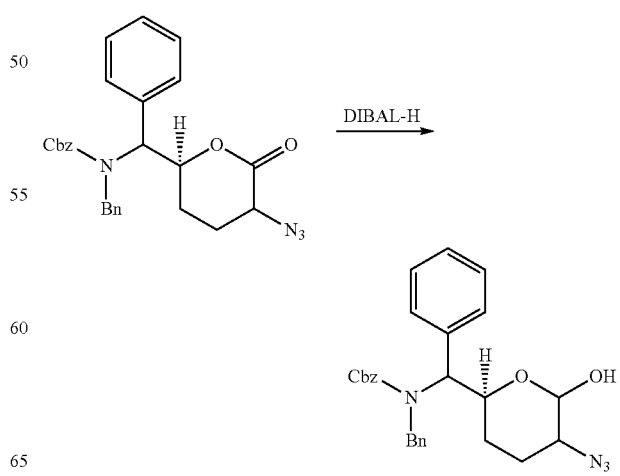

DIBAL-H (1 M in toluene, 7.65 mL, 7.65 mmol) was added dropwise to a solution of benzyl N-[(R)-[(2S)-5-azido-6-oxo-tetrahydropyran-2-yl]-phenyl-methyl]-N-benzyl-carbamate (600 mg, complex mixture) in DCM (60 mL) at −78° C. After 1 h at −78° C., EtOH (0.5 mL) was added dropwise. The mixture was poured into a saturated aqueous solution of Rochelle's salt (300 mL). The mixture was vigorously stirred for 1.5 h. The separated aqueous layer was extracted with DCM (2×75 mL). The combined organic layer was washed with brine, dried over MgSO4 and concentrated under reduced pressure. The residue was purified on silica gel (24 g, dry loading) by MPLC using hexane to 60% EtOAc in hexane to provide the title compound (482 mg, 72%). [M+H+] m/z: 473.11 retention time=2.71 min.

Step 7

[(1S,2S,3R,4S,6R)-2-acetoxy-4,6-diazido-3-[(2R,6S)-3-azido-6-[(R) -[benzyl(benzyloxycarbonyl)amino]-phenyl-methyl]tetrahydropyran-2-yl]oxy-cyclohexyl]acetate

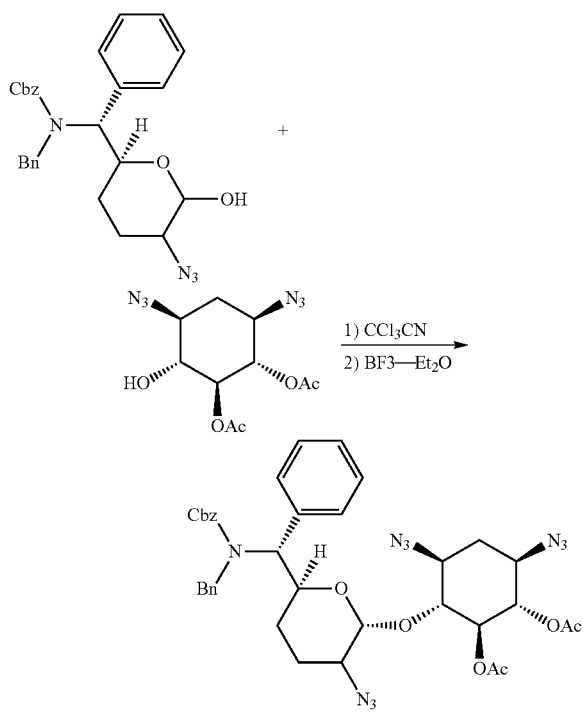

CCl3CN (0.44 mL, 4.39 mol) was added dropwise to a suspension of benzyl N -[(R)-[(2S)-5-azido-6-hydroxy-tetrahydropyran-2-yl]-phenyl-methyl]-N-benzyl-carbamate (360 mg, 0.88 mmol) and K2CO3 (364 mg, 2.63 mmol) in dry DCM (10 mL) at ambient temperature under N2. The mixture was stirred at room temperature for 8 h, then filtered on celite and rinsed with DCM. The filtrate was concentrated under reduced pressure. The residue was taken in DCM (10 mL) and [(1S,2S,3R,4S,6R)-2-acetoxy-4,6-diazido-3-hydroxy-cyclohexyl]acetate (654 mg, 2.19 mmol) was added. The mixture was cooled to −78° C., then BF3·OEt2 (0.43 mL, 3.51 mmol) was added dropwise. The mixture was stirred at room temperature for 5 h, then a saturated aqueous solution of NaHCO3 (50 mL) was added. The separated aqueous layer was extracted with DCM (2×30 mL). The combined organic layer was washed with brine, dried over Na2SO4 and concentrated under reduced pressure. The residue was purified on C18 silica (120 g Biotage) using 50% B in A to 100% B (B=ACN 0.1% HCOOH, A=H2O 0.1% HCOOH); out at 90% to give the title products (19 mg, 5%).LCMS m/z: ES+[M+H]+: 753.34. (A05) retention time=3.02 min.

Step 8

Benzyl N-[(R)-[(2S,5R,6R)-5-azido-6-[(1R,2R,3S,4R,6S)-4,6-diazido-2,3-dihydroxy -cyclohexoxy]tetrahydropyran-2-yl]-phenyl-methyl]-N-benzyl-carbamate

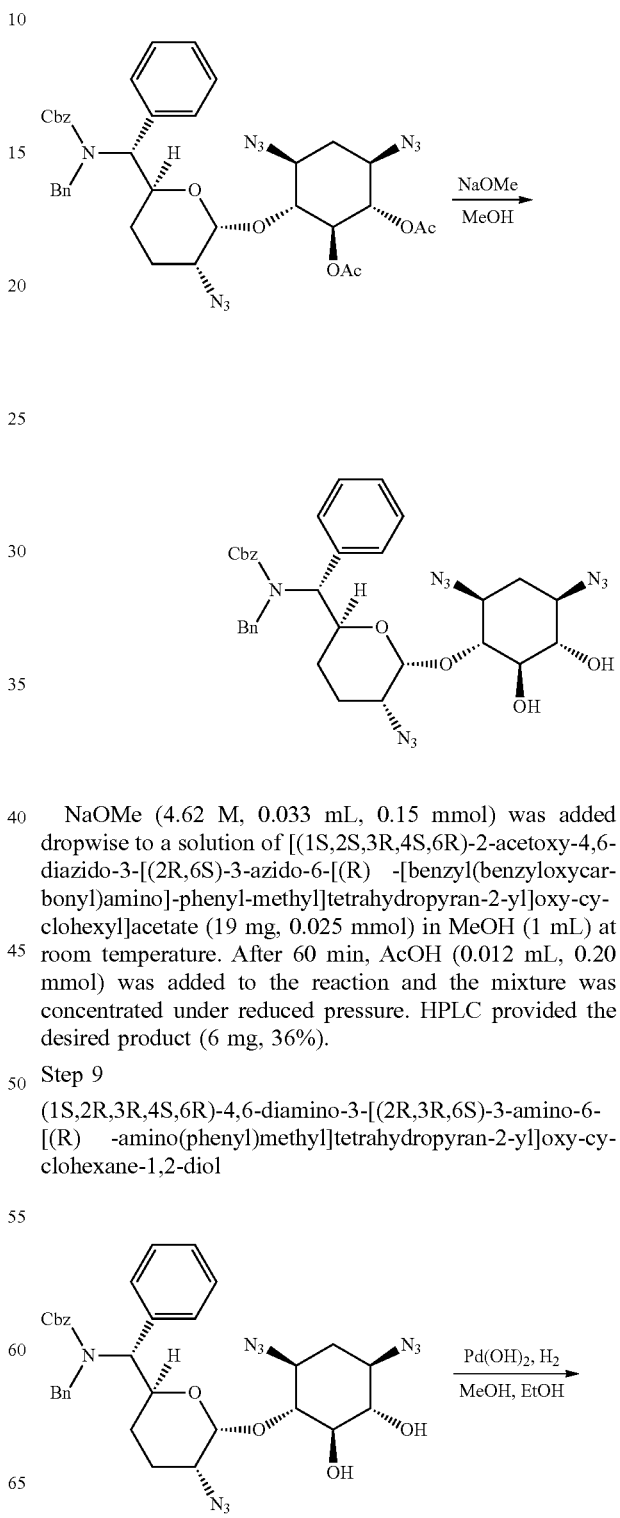

NaOMe (4.62 M, 0.033 mL, 0.15 mmol) was added dropwise to a solution of [(1S,2S,3R,4S,6R)-2-acetoxy-4,6-diazido-3-[(2R,6S)-3-azido-6-[(R) -[benzyl(benzyloxycarbonyl)amino]-phenyl-methyl]tetrahydropyran-2-yl]oxy-cyclohexyl]acetate (19 mg, 0.025 mmol) in MeOH (1 mL) at room temperature. After 60 min, AcOH (0.012 mL, 0.20 mmol) was added to the reaction and the mixture was concentrated under reduced pressure. HPLC provided the desired product (6 mg, 36%).

Step 9

(1S,2R,3R,4S,6R)-4,6-diamino-3-[(2R,3R,6S)-3-amino-6-[(R) -amino(phenyl)methyl]tetrahydropyran-2-yl]oxy-cyclohexane-1,2-diol

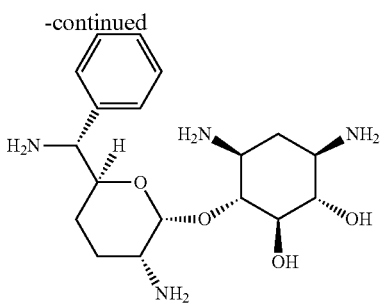

Pd(OH)₂/C (10 wt %, 18.6 mg, 13.3 μmol) was added to a flask containing benzyl N-[(R) -[(2S,5R,6R)-5-azido-6-[(1R,2R,3S,4R,6S)-4,6-diazido-2,3-dihydroxy -cyclohexoxy]tetrahydropyran-2-yl]-phenyl-methyl]-N-benzyl-carbamate (6.0 mg, 89.7 umol) under N₂ at ambient temperature. MeOH (3.0 mL) was added after which H₂ was bubbled through the suspension for 10 min. After 16 h under hydrogen atmosphere (1 atm, balloon), the solution was filtered through a frit (0.45 μm), rinsed with MeOH and the filtrate was concentrated under reduced pressure to give the title product (2.7 mg, 82%). ¹H NMR (500 MHz, D₂O) δ 7.55-7.42 (m, 5H), 4.91 (s, 1H), 4.25-4.16 (m, 1H), 4.10 (d, J=8.1 Hz, 1H), 3.40-3.34 (m, 1H), 3.21 (t, J=9.7 Hz, 1H), 3.12 (s, 1H), 2.95-2.88 (m, 2H), 2.68 (t, J=8.7 Hz, 1H), 2.16-2.06 (m, 1H), 2.05-1.95 (m, 1H), 1.90-1.67 (m, 3H), 1.20-1.08 (m, 1H).

Example 52

(1S,2R,3R,4S,6R)-4,6-diamino-3-(((2R,3S,6S)-3-amino-6-((R) -amino(cyclopropyl)methyl)tetrahydro-2H-pyran-2-yl)oxy)cyclohexane-1,2-diol

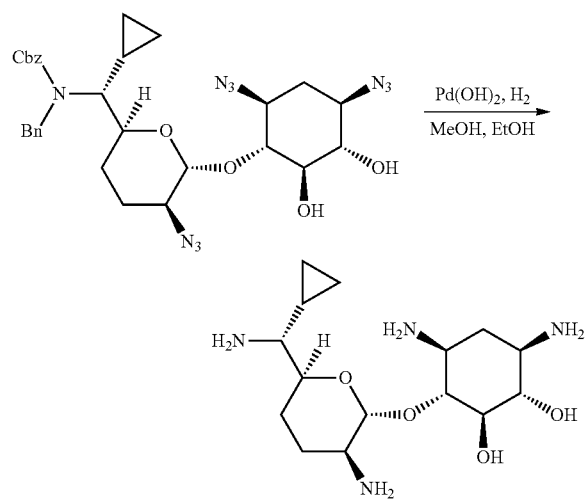

Pd(OH)₂ (20 wt %, 133 mg, 190 μmol) was added to a solution of benzyl N-[(R) -[(2S,5S,6R)-5-azido-6-[(1R,2R,3S,4R,6S)-4,6-diazido-2,3-dihydroxy -cyclohexoxy]tetrahydropyran-2-yl]-cyclopropyl-methyl]-N-benzyl-carbamate (prepared in Example 29, 40.0 mg, 63.2 μmol) in MeOH (2.5 mL) and EtOH (2.5 mL). H₂ was bubbled through the suspension. After 17 h, the solution was filtered through a frit (0.22 μm diameter) and the filtrate was concentrated under reduced pressure to give the desired product as an oil which turn into solid after lyophilization (19.0 mg, 91%). ¹H NMR (500 MHz, MeOD) δ 5.10 (s, 1H), 4.09-4.04 (m, 1H), 3.34-3.24 (m, 2H), 3.07 (t, J=9.3 Hz, 1H), 3.01 (d, J=2.0 Hz, 1H), 2.83-2.71 (m, 1H), 2.66 (ddd, J=12.1, 9.7, 4.1 Hz, 1H), 2.17-2.09 (m, 2H), 2.03 (d, J=13.0 Hz, 1H), 1.99-1.86 (m, 2H), 1.74-1.63 (m, 1H), 1.60-1.48 (m, 1H), 1.00-0.82 (m, 1H), 0.60 (dq, J=17.9, 8.8 Hz, 2H), 0.39-0.24 (m, 2H).

Example 53

(1S,2R,3R,4S,6R)-4,6-diamino-3-(((2R,3S,6S)-3-amino-6-((R)-1-aminopropyl)tetrahydro-2H -pyran-2-yl)oxy)cyclohexane-1,2-diol

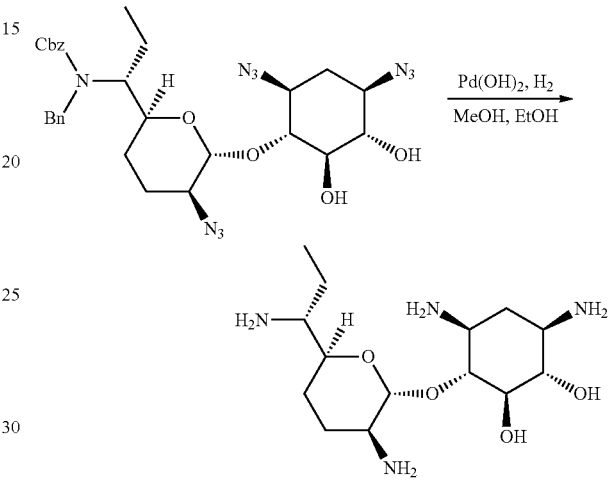

Pd(OH)₂/C (wet, 20 wt %, 249 mg, 354 μmol) was added to a solution of benzyl N-[(1R)-1-[(2S,5S,6R)-5-azido-6-[(1R,2R,3S,4R,6S)-4,6-diazido-2,3-dihydroxy -cyclohexoxy]tetrahydropyran-2-yl]propyl]-N-benzyl-carbamate (made in Example 25, 55.0 mg, 88.6 μmol) in MeOH (3.0 mL) and EtOH (3.0 mL). H₂ was bubbled through the suspension. After 24 h, the solution was filtered through a frit (0.22 μm diameter) and the filtrate was concentrated under reduced pressure to give the desired product as an oil which turned into a solid after lyophilization (26.1 mg, 93%). ¹H NMR (500 MHz, MeOD) δ 4.97 (d, J=1.4 Hz, 1H), 3.91-3.84 (m, 1H), 3.19-3.08 (m, 2H), 2.95 (t, J=9.3 Hz, 1H), 2.89 (dd, J=5.8, 3.6 Hz, 1H), 2.83-2.74 (m, 1H), 2.66 (ddd, J=12.2, 9.4, 4.3 Hz, 1H), 2.60-2.49 (m, 1H), 1.99-1.84 (m, 2H), 1.66-1.45 (m, 3H), 1.39-1.26 (m, 3H), 0.90 (t, J=7.5 Hz, 3H).

Example 54

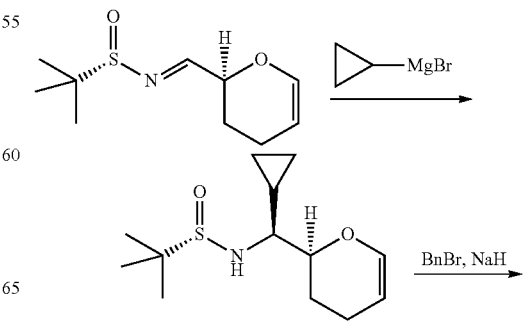

545

-continued

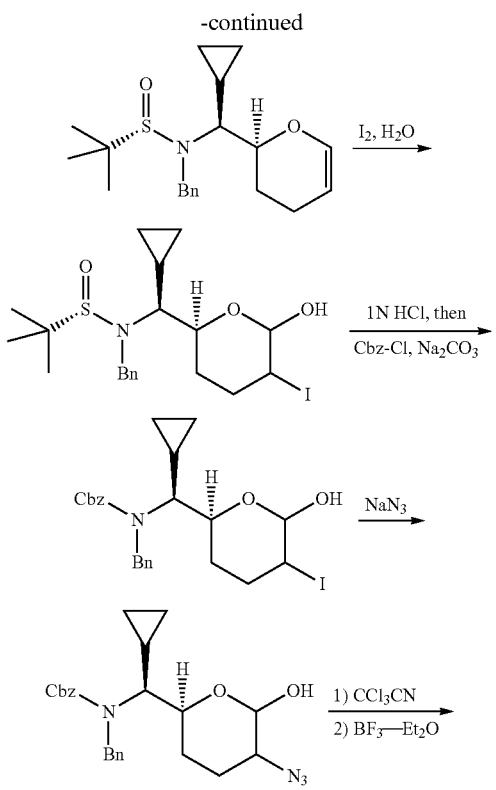

546

Step 1
(S)-N-[(5)-cyclopropyl-[(2S)-3,4-dihydro-2H-pyran-2-yl]methyl]-2-methyl-propane-2-sulfinamide

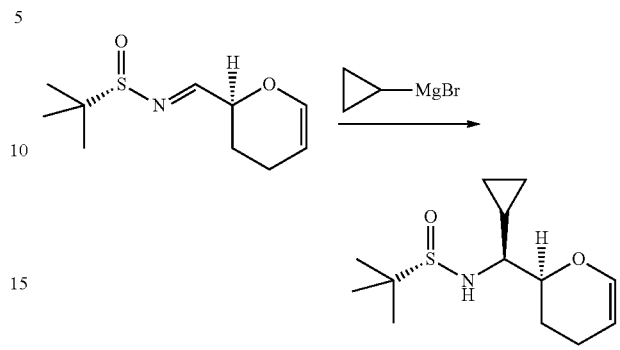

Cyclopropyl MgBr (0.5 M in THF, 55.7 mL, 27.8 mmol) was added to a solution of ((NE,S)-N-[[(2S)-3,4-dihydro-2H-pyran-2-yl]methylene]-2-methyl-propane-2-sulfinamide (3.00 g, 13.9 mmol) in dry THF (100.0 mL) at −78° C. under N$_2$. After 1 h, the reaction was stirred at −40° C. for 1 h and then warmed to room temperature within 1 h. After 1 h, the reaction was cooled to 0° C. and sat. NH$_4$Cl (100.0 mL) was added dropwise (CAUTION: gas evolution). THF was evaporated under reduced pressure and then the mixture was extracted with DCM (3×50 mL). The combined organic layers were dried (Na$_2$SO$_4$), filtered and concentrated under reduced pressure to provide the title compound as a liquid. The $^1$H NMR for crude was clean and used in the next step without further purification. $^1$H NMR (500 MHz, CDCl$_3$) δ 6.37 (d, J=6.1 Hz, 1H), 4.76-4.60 (m, 1H), 3.96-3.86 (m, 1H), 3.43 (d, J=6.1 Hz, 1H), 2.56 (ddd, J=9.6, 6.2, 3.2 Hz, 1H), 2.19-1.75 (m, 4H), 1.22 (s, 9H), 1.09-0.97 (m, 1H), 0.74-0.56 (m, 2H), 0.46-0.39 (m, 2H). LCMS m/z ES$^+$[M+H]$^+$: 258.19, LCMS (B05) retention time=1.78 m.

Step 2
(S)-N-benzyl-N-[(S)-cyclopropyl(3,4-dihydro-2H-pyran-2-yl)methyl]-2-methyl-propane-2-sulfinamide

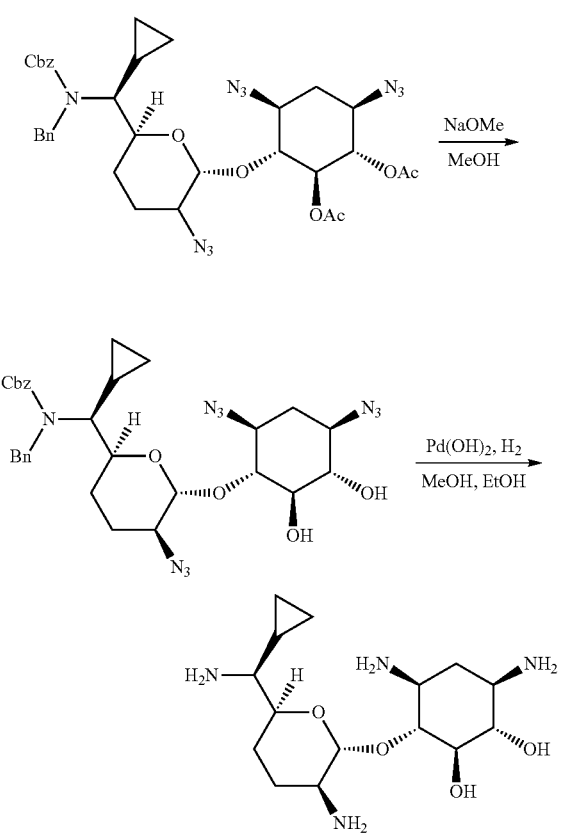

A mixture of (S)-N-[(S)-cyclopropyl(3,4-dihydro-2H-pyran-2-yl)methyl]-2-methyl-propane-2-sulfinamide (3.58 g, 13.9 mmol), bromomethylbenzene (2.97 mL, 25.0 mmol) in DMF (50.0 mL) was stirred at 0° C. NaH (0.667 g, 16.7 mmol) was then added to the reaction mixture portionwise. The mixture was stirred at room temperature for 12 h. The reaction was quenched with water (100 mL) and the mixture was extract with EtOAc (3×50 mL). The organic layers were combined, washed with water and dried over sodium sulfate and then concentrated under reduced pressure. The residue was purified on silica gel (120 g) using hexane and ethyl-acetate (70/30) as eluent to give the title product (2.88 g, 60%) as an oil. LCMS m/z ES⁺[M'H]⁺: 348.16, LCMS (B05) retention time=2.10 m.

Step 3
(S)-N-benzyl-N-[(S)-cyclopropyl-[(2S)-6-hydroxy-5-iodo-tetrahydropyran-2-yl]methyl]-2-methyl-propane-2-sulfinamide

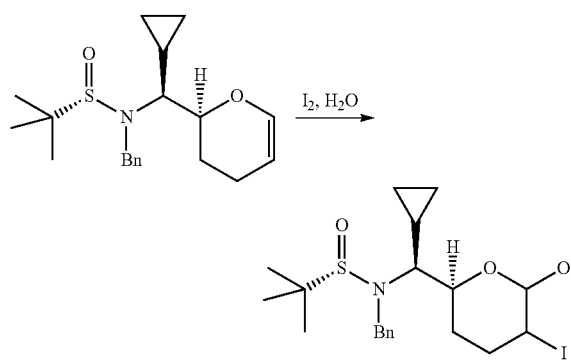

I₂ (1.59 g, 6.30 mmol) was added portionwise to a suspension of N-benzyl-N -[(S)-cyclopropyl-[(2S)-3,4-di-hydro-2H-pyran-2-yl]methyl]-2-methyl-propane-2-sulfinamide (2.19 g, 6.30 mmol) and NaHCO₃ (1.58 g, 18.9 mmol) in ACN (38 mL) and H₂O (38 mL) at 0° C. The mixture was stirred at 0° C. for 15 min. Then, the mixture was stirred at room temperature for 15 min. After completion, a saturated aqueous solution of Na₂S₂O₃ (100 mL) was added. The aqueous layer was extracted with EtOAc (3×100 mL). The combined organic layer was dried over Na₂SO₄, filtered and concentrated under reduced pressure to provide the title compound (2.90 g, 94%) as an yellow solid. The crude was used in the next step without further purification. LCMS m/z ES⁺ [M+Na]⁺: 514.50, LCMS (B05) retention time=2.10 and 2.21 m.

Step 4
Benzyl N-benzyl-N-[(5)-cyclopropyl-[(2S)-6-hydroxy-5-iodo-tetrahydropyran-2-yl]methyl]carbamate

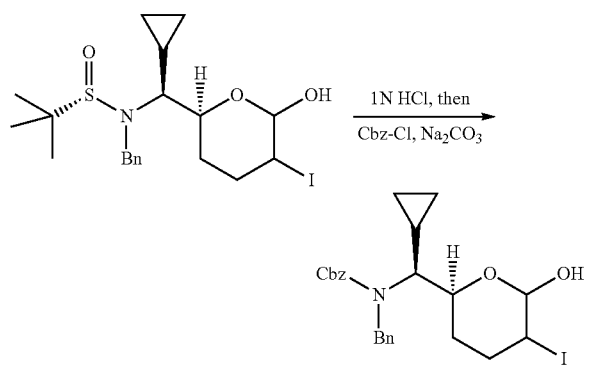

Aqueous HCl (1.0 M, 35.3 mL, 35.3 mmol) was dropwise added to a solution of N-benzyl-N-[(5)-cyclopropyl-[(2S)-6-hydroxy-5-iodo-tetrahydropyran-2-yl]methyl]-2-methyl -propane-2-sulfinamide (2.88 g, 5.86 mmol) in dioxane (82.0 mL) with vigorous stirring. After 1 h, solid Na₂CO₃ (4.96 g, 46.8 mmol) was added. After another 10 min, CbzCl (1.41 mL, 9.91 mmol) was added dropwise.

After another 30-45 min, dioxane was evaporated and the residue was partitioned in between EtOAc (100.0 mL) and H₂O (100.0 mL). The organic phase was dried over Na₂SO₄, filtered and concentrated under reduced pressure. The crude was purified by silica gel chromatography (120 g cartridge) using hexanes and ethyl acetate (0-30%) as eluent to give the title product (diastereomers, 1.50 g, 49%) as an oil. LCMS m/z ES⁺ [M+Na]⁺: 544.01, LCMS (B05) retention time=2.19 and 2.22 m.

Step 5
Benzyl N-[(S)-[(2S)-5-azido-6-hydroxy-tetrahydropyran-2-yl]-cyclopropyl-methyl]-N-benzyl -carbamate

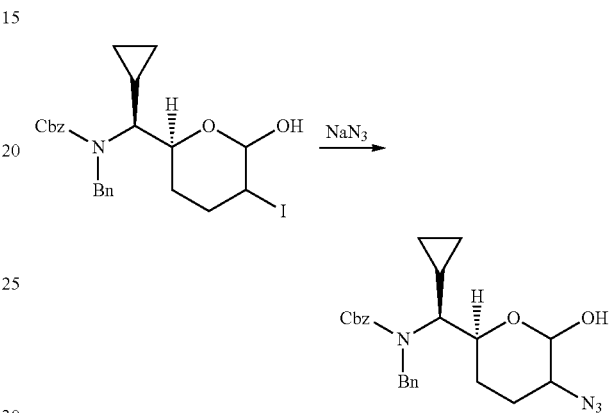

NaN₃ (0.561 g, 8.63 mmol) and K₂CO₃ (1.19 g, 8.63 mmol) was added to a solution of benzyl N-benzyl-N-[(S)-cyclopropyl-[(2S)-6-hydroxy-5-iodo-tetrahydropyran-2-yl] methyl]carbamate (1.50 g, 2.87 mmol) in dry DMF (22.0 mL) under N₂ at ambient temperature. After 4 h, the mixture was diluted with water (50.0 mL) and extracted with EtOAc (50.0 mL). The organic layer was dried over Na₂SO₄, filtered and concentrated under reduced pressure. The crude was purified by silica gel chromatography (40 g cartridge) with EtOAc and hexanes (10-30%) to produce the title compound (diastereomers) as an oil (0.80 g, 63%). LCMS m/z: ES⁺ [M+Na]⁺: 459.10; (B05) retention time=2.16 m.

Step 6
(1S,2S,3R,4S,6R)-4,6-diazido-3-(((2R,6S)-3-azido-6-((S) -(benzyl((benzyloxy)carbonyl)amino)(cyclopropyl)methyl) tetrahydro-2H-pyran-2 -yl)oxy)cyclohexane-1,2-diyl diacetate

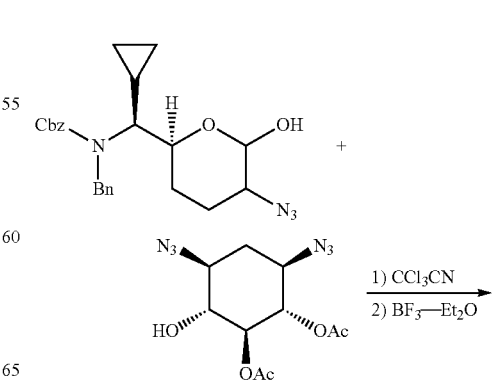

549

-continued

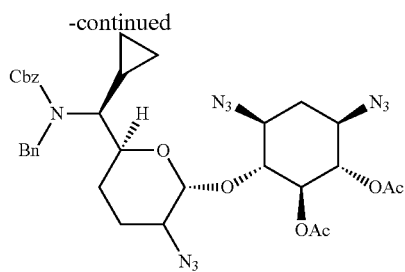

CCl₃CN (0.567 mL, 5.66 mmol) was added dropwise to a suspension of benzyl N-[(S)-[(2S)-5-azido-6-hydroxy-tetrahydropyran-2-yl]-cyclopropyl-methyl]-N-benzyl -carbamate (0.494 g, 1.13 mmol) and K₂CO₃ (0.469 g, 3.39 mmol) in dry DCM (20.0 mL) at ambient temperature under N₂. After 12 h, the solution was filtered through Celite and the filtrate was concentrated by high-vacuum. To the crude was added [(1S,2S,3R,4S,6R)-2-acetoxy-4,6-diazido-3-hydroxy-cyclohexyl]acetate (270 mg, 0.905 mmol) and ground 4 Å sieves (1.0 g) and the mixture was dissolved in dry DCM (20.0 mL). The suspension was stirred at ambient temperature for 30 min. The solution was cooled to 0° C. and BF₃·OEt₂ (0.559 mL, 4.53 mmol) was added dropwise with vigorous stirring. The solution was warmed to ambient temperature and stirred for another 2 hours. The reaction was quenched with sat. NaHCO₃ (20.0 mL). The mixture was successively extracted with DCM (3×20 mL) and the combined organic layer were dried (Na₂SO₄), filtered and concentrated under reduced pressure. The crude was purified by silica gel chromatography (40 g cartridge) with EtOAc and hexanes (0-30%) to produce the title compound as an oil (diastereomers, 0.510 mg, 79%). LCMS m/z: [M+H]⁺: 716.97; (B05) retention time=2.39 m.

Step 7
Benzyl N-[(S)-[(2S,5S,6R)-5-azido-6-[(1R,2R,3S,4R,6S)-4,6-diazido-2,3-dihydroxy -cyclohexoxy]tetrahydropyran-2-yl]-cyclopropyl-methyl]-N-benzyl-carbamate

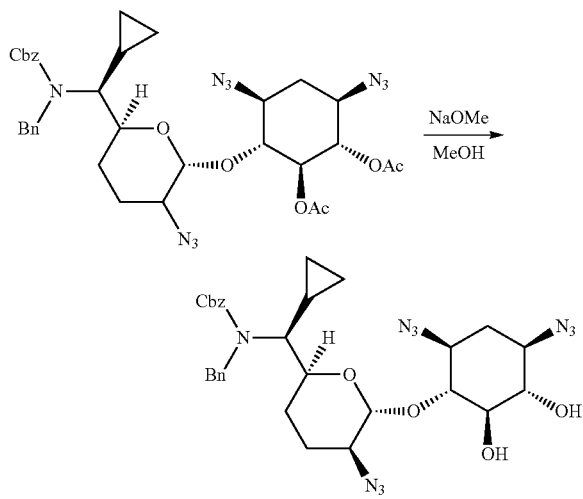

NaOMe (4.62 M, 924 µL, 4.27 mmol) was added dropwise to a solution of (1S,2S,3R,4S,6R)-4,6-diazido-3-(((2R,6S)-3-azido-6-((S) -(benzyl((benzyloxy)carbonyl)amino)(cyclopropyl)methyl)tetrahydro-2H-pyran-2-yl)oxy) cyclohexane-1,2-diyl diacetate (0.510 g, 0.712 mmol) in MeOH (30.0 mL) at room temperature. After 60 min, AcOH

550

(326 µL, 5.69 mmol) was added to the reaction. Water (20.0 mL) was added and the mixture was extracted with DCM (3×30 mL). The organic layers were combined, dried over Na₂SO₄ and then concentrated under reduced pressure to provide a mixture of two diastereomers (0.350 g, 78%) in a 7:1 ratio in favor of the trans product (see note for more details). ES⁺[M+Na]⁺: 655.06; (B05) retention time=2.23 m.

Step 8
(1S,2R,3R,4S,6R)-4,6-diamino-3-(((2R,3S,6S)-3-amino-6-((S) -amino(cyclopropyl)methyl)tetrahydro-2H-pyran-2-yl)oxy)cyclohexane-1,2-diol

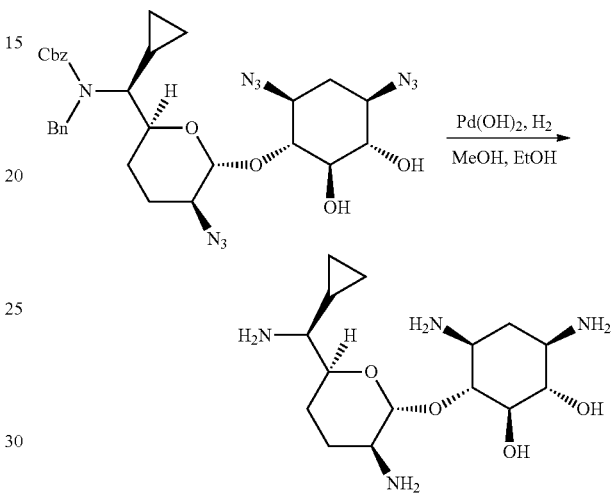

Pd(OH)₂/C (20 wt %, 300 mg, 427 µmol) was added to a solution of benzyl N-[(S)-[(2S,5S,6R)-5-azido-6-[(1R,2R,3S,4R,6S)-4,6-diazido-2,3-dihydroxy -cyclohexoxy]tetrahydropyran-2-yl]-cyclopropyl-methyl]-N-benzyl-carbamate (45.0 mg, 71.1 µmol) in MeOH (2.5 mL) and EtOH (2.5 mL). H₂ was bubbled through the suspension. After 24 h, the solution was filtered through a frit (0.22 µm diameter) and the filtrate was concentrated under reduced pressure to give the desired product as an oil which turn into solid after lyophilization (20.0 mg, 85%). ¹H NMR (500 MHz, MeOD) δ 5.34 (s, 1H), 4.24-4.19 (m, 1H), 3.40-3.35 (m, 2H), 3.15 (t, J=9.3 Hz, 1H), 3.06 (d, J=1.6 Hz, 1H), 2.92-2.84 (m, 1H), 2.79 (ddd, J=12.1, 9.9, 4.2 Hz, 1H), 2.52-2.40 (m, 2H), 2.20-2.11 (m, 1H), 2.10-2.03 (m, 1H), 1.99-1.88 (m, 1H), 1.78-1.69 (m, 1H), 1.60-1.51 (m, 1H), 1.15-1.05 (m, 1H), 0.79-0.63 (m, 2H), 0.46-0.36 (m, 2H).

Example 55

(1S,2R,3R,4S,6R)-4,6-diamino-3-[(2R,3S,6S)-3-amino-6-[(1S)-1-aminopropyl]tetrahydropyran -2-yl]oxy-cyclohexane-1,2-diol

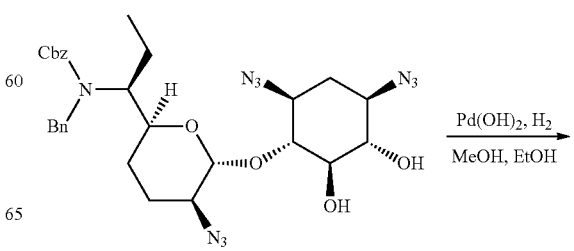

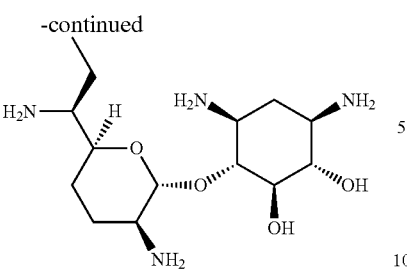

In a round bottom flask equipped with a reflux condenser were added benzyl N-[(1S)-1-[(2S,5S,6R)-5-azido-6-[(1R,2R,3S,4R,6S)-4,6-diazido-2,3-dihydroxy-cyclohexoxy]tetrahydropyran-2-yl]propyl]-N-benzyl-carbamate (made in Example 24, 38.0 mg, 0.0612 mmol) and Pd/C (10% dry on carbon, 19.5 mg, 0.0184 mmol) following by anhydrous MeOH (6.00 mL). Nitrogen was bubbled for 5 min, then ammonium format was added. The mixture was heat at 63° C. for 30 min under $N_2$, then cooled to room temperature with an ice-bath. The mixture was filtered through a fritted funnel and then concentrated under reduced pressure to give the titled product as a liquid which then lyophilized to give a solid (11.1 mg, 57%). LCMS m/z: $ES^+$ $[M+Na]^+$: 341, (A05) retention time=0.97 m. $^1$H NMR (400 MHz, $CD_3OD$) δ 5.09 (s, 1H), 4.00 (d, J=10.8 Hz, 1H), 3.35-3.20 (m, 2H), 3.15-2.97 (m, 2H), 2.93-2.58 (m, 3H), 2.19-1.97 (m, 2H), 1.86-1.58 (m, 4H), 1.56-1.36 (m, 2H), 1.06 (t, J=7.4 Hz, 3H).

Example 56

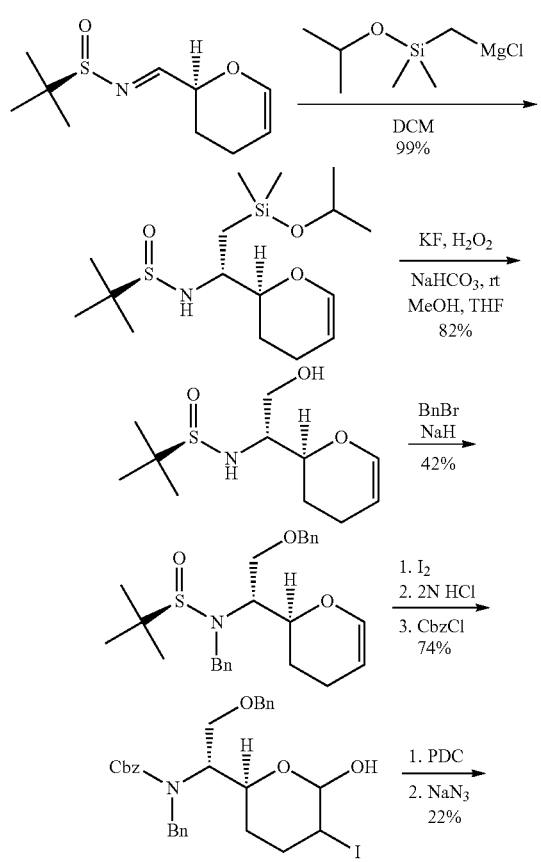

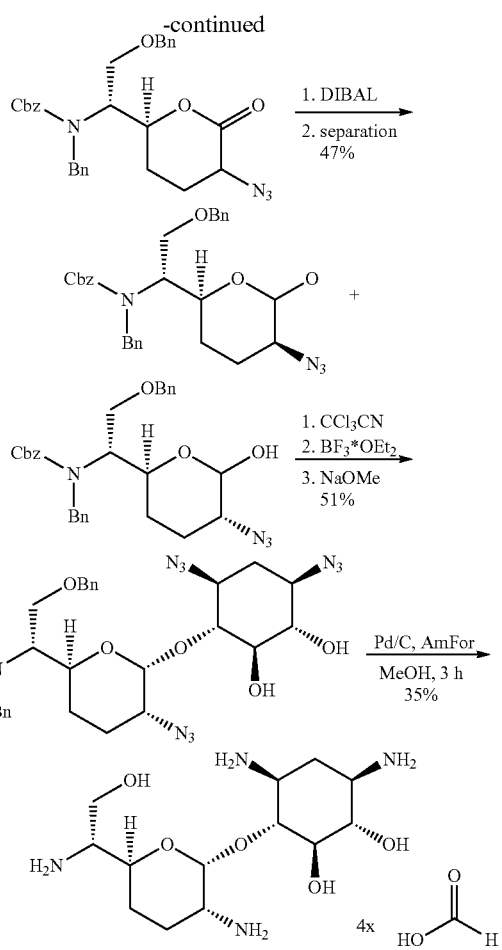

Step 1
(R)-N-[(1S)-1-[(2S)-3,4-dihydro-2H-pyran-2-yl]-2-[isopropoxy(dimethyl)silyl]ethyl]-2-methyl-propane-2-sulfinamide

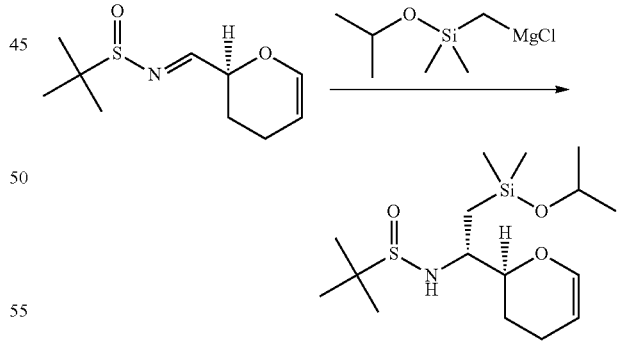

A suspension of magnesium filings (4.85 g, 199 mmol) in dry THF (125 mL) was heated at 65° C. with high agitation under an atmosphere of nitrogen. 1,2-Dibromoethane (0.52 mL, 6 mmol) was added over 1 min, followed by slow addition of chloromethyl dimethylisopropoxysilane (25 g, 150 mmol) over 15 min. The reaction was stirred at 65° C. for 90 min, then cooled to room temperature to give 1 M solution which was kept in a freezer (maximum 2 weeks).

To a solution of (NE,R)-N-[[(2S)-3,4-dihydro-2H-pyran-2-yl]methylene]-2-methyl-propane-2-sulfinamide (10 g, 46.4 mmol) in DCM (600 mL) was added dropwise chloro -[[isopropoxy (dimethyOsilyl]methyl]magnesium (1 M in THF, 93 mL, 93 mmol) at −78° C. The reaction mixture was stirred at −78° C. for 1 h, then warmed to room temperature and stirred for 3 h. The mixture was diluted with saturated NaHCO₃ (400 mL) and the layers were separated. The aqueous layer was extracted with DCM (3×300 mL). The combined organic layers were washed with brine, dried (MgSO₄), filtered and concentrated under reduced pressure to provide the title compound (11 g, 68%). ¹H NMR (400 MHz, CDCl₃) δ 6.36 (d, J=6.1 Hz, 1H), 4.69-4.63 (m, 1H), 4.04 (ddd, J=11.1, 3.5, 1.9 Hz, 1H), 3.97 (dt, J=12.1, 6.1 Hz, 1H), 3.90 (d, J=7.3 Hz, 1H), 3.61 (ddd, J=14.6, 7.3, 3.6 Hz, 1H), 2.14-2.03 (m, 1H), 2.00-1.91 (m, 1H), 1.89-1.81 (m, 1H), 1.70-1.55 (m, 1H), 1.21 (s, 9H), 1.13 (d, J=3.3 Hz, 3H), 1.12 (d, J=3.3 Hz, 3H), 0.83 (dd, J=15.0, 6.8 Hz, 1H), 0.15 (d, J=2.8 Hz, 3H), 0.13 (s, 3H). (NH was not observed) MS (ESI) [M+Na]⁺370.1.

Step 2

(R)-N-[(1R)-1-[(2S)-3,4-dihydro-2H-pyran-2-yl]-2-hydroxy-ethyl]-2-methyl-propane-2-sulfinamide

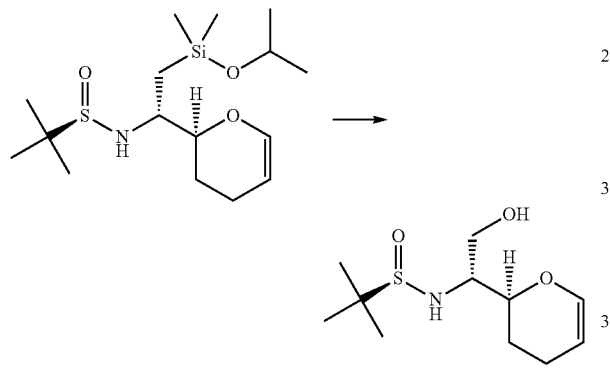

To a solution of (R)-N-[(1S)-1-[(2S)-3,4-dihydro-2H-pyran-2-yl]-2 -[isopropoxy(dimethyl)silyl]ethyl]-2-methyl-propane-2-sulfinamide (11 g, 3.16 mmol) in MeOH (600 mL) was added KF (3.11 g, 3.64 mmol) and NaHCO₃ (3.19 g, 38 mmol). H₂O₂ (35% wt in water, 5.44 mL, 63.3 mL) was added dropwise over 5 min and the reaction mixture was stirred at room temperature for 16 h. The mixture was diluted with saturated solution of Na₂S₂O₃ (400 mL) and the aqueous layer was extracted with EtOAc (3×600 mL). The combined organic layers were washed with brine (1.0 L), dried (MgSO₄), filtered and concentrated under reduced pressure to provide the title compound (7.9 g, 99%) as an oil. ¹H NMR (500 MHz, CDCl₃) δ 6.34 (d, J=6.4 Hz, 1H), 4.75-4.70 (m, 1H), 4.09 (ddd, J=10.5, 5.6, 1.7 Hz, 1H), 3.94 (d, J=7.6 Hz, 1H), 3.87-3.82 (m, 1H), 3.80-3.74 (m, 1H), 3.44-3.37 (m, 1H), 2.65 (dd, J=9.2, 4.3 Hz, 1H), 2.15-2.06 (m, 1H), 2.03-1.98 (m, 1H), 1.74-1.66 (m, 1H), 1.26 (s, 9H).

Step 3

(R)-N-benzyl-N-[(1R)-2-benzyloxy-1-[(2S)-3,4-dihydro-2H-pyran-2-yl]ethyl]-2-methyl -propane-2-sulfinamide

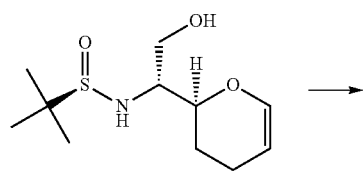

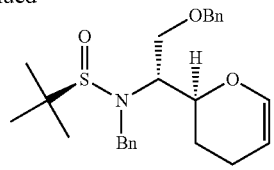

To a solution of BnBr (4.90 mL, 41.2 mmol) and (R)-N-[(1R)-1-[(2S)-3,4 -dihydro-2H-pyran-2-yl]-2-hydroxyethyl]-2-methyl-propane-2-sulfinamide (3.40 g, 13.7 mmol) in DMF (120 mL) at 0° C., was added NaH (60% oil dispersion, 1.15 g, 28.9 mmol). The reaction mixture was stirred at 0° C. for 1 h, then brine (500 mL) was added at 0° C. The aqueous layer was extracted with Et₂O (3×150 mL). The combined organic layers were dried (MgSO₄), filtered and concentrated under reduced pressure. The material was purified by silica gel (80 g, dry loading) by MPLC using a gradient of 0-50% EtOAc in hexane as eluent to provide the title compound (2.30 g, 39%) as a solid. MS (ESI) [M+Na]⁺ 450.1.

Step 4

Benzyl N-benzyl-N-[(1R)-2-benzyloxy-1-[(2S)-6-hydroxy-5-iodo-tetrahydropyran-2-yl]ethyl]carbamate

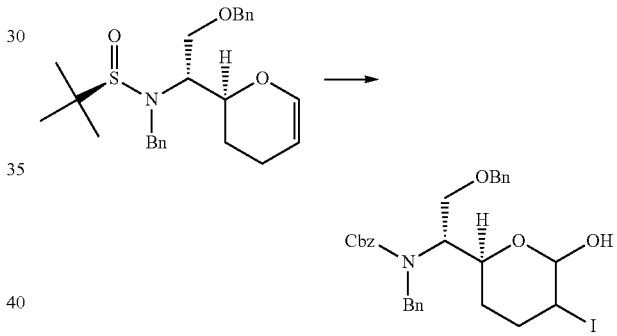

To a solution of (R)-N-benzyl-N-[(1R)-2-benzyloxy-1-[(2S)-3,4-dihydro-2H -pyran-2-yl]ethyl]-2-methyl-propane-2-sulfinamide (2.30 g, 5.38 mmol) and NaHCO₃ (1.36 g, 16.1 mmol) in ACN (100 mL) and water (100 mL) at 0° C., was added I2 (1.50 g, 5.92 mmol). The reaction mixture was stirred at 0° C. for 45 min, then a saturated solution of Na₂S₂O₃ (200 mL) was added following by EtOAc (250 mL). The layers were separated, and the aqueous layer was extracted with EtOAc (3×150 mL). The combined organic layers were washed with brine (500 mL), dried (MgSO₄), filtered and concentrated under reduced pressure. The residue was taken in dioxane (50 mL) and 2M HCl (8.07 mL, 16.1 mmol) was added dropwise. The mixture was stirred at room temperature for 30 min, then Na₂CO₃ (3.42 g, 32.3 mmol) was added. After 10 min at room temperature, CbzCl (1.54 mL, 10.7 mmol) was added dropwise. The mixture was stirred at room temperature for 2 h, then water (100 mL) was added. The aqueous layer was extracted with EtOAc (3×100 mL). The combined organic layers were washed with brine, dried (MgSO₄), filtered and concentrated under reduced pressure. The material was purified by silica gel (120 g, dry loading) by MPLC using a gradient of 0-50% EtOAc in hexane as eluent to provide the title compound (2.40 g, 74% over 3 steps) as a solid. MS (ESI) [M+H]⁺602.4.

Step 5
benzyl N-[(1R)-1-[(2S)-5-azido-6-oxo-tetrahydropyran-2-yl]-2-benzyloxy-ethyl]-N-benzyl-carbamate

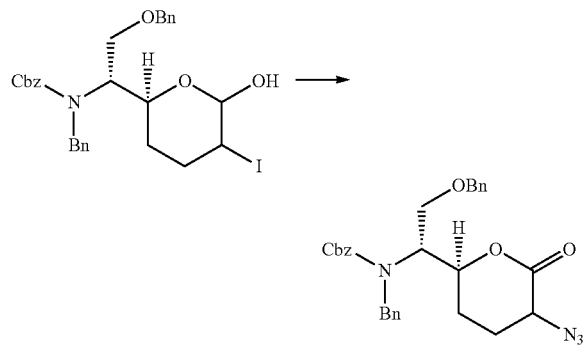

To a mixture of benzyl N-benzyl-N-[(1R)-2-benzyloxy-1-[(2S)-6-hydroxy-5-iodo-tetrahydro-pyran-2-yl]ethyl]carbamate (2.40 g, 3.99 mmol) and 4 Å molecular sieves (1.00 g) in DCM (150 mL) was added PDC (6.76 g, 18.0 mmol) at room temperature. After 18 h, the mixture was filtered on silica pad, rinsed with EtOAc and concentrated under reduced pressure. The residue was taken in DMF (25 mL) and cooled at 0° C. NaN$_3$ (285 mg, 4.39 mmol) was added and the mixture was stirred for 1 h at 0° C. The mixture was diluted with brine (250 mL) and the aqueous layer was extracted with Et$_2$O (3×150 mL). The combined organic layers were dried (MgSO$_4$), filtered and concentrated under reduced pressure. The residue was purified by silica (40 g, dry loading) by MPLC using a gradient of 0-40% EtOAc in hexane as eluent to provide the title compound (450 mg, 22% over 2 steps) as a solid. MS (ESI) [M+H]$^+$515.2.

Step 6
Benzyl N-[(1R)-1-[(2S,5R)-5-azido-6-hydroxy-tetrahydropyran-2-yl]-2-benzyloxy-ethyl]-N-benzyl-carbamate

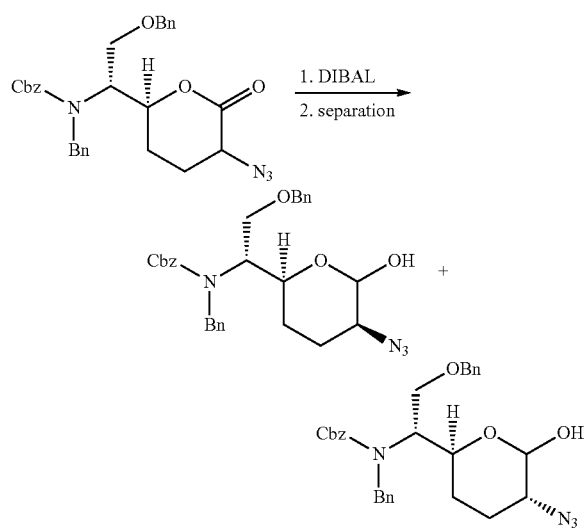

To a solution of benzyl N-[(1R)-1-[(2S)-5-azido-6-oxo-tetrahydropyran-2-yl]-2-benzyloxy-ethyl]-N-benzyl-carbamate (400 mg, 0.78 mmol) in DCM (18 mL) at −78° C., DIBAL-H (1M in toluene, 1.55 mL, 1.55 mmol) was added dropwise and the reaction mixture was stirred for 1 h. EtOH (0.5 mL) was added dropwise and the mixture was poured into a saturated solution of Rochelle's salt (300 mL). The mixture was vigorously stirred for 1 h at room temperature. The aqueous layer was extracted with DCM (2×75 mL). The combined organic layers were washed with brine, dried (MgSO$_4$) and concentrated under reduced pressure. The residue was purified by silica gel (40 g, dry loading) by MPLC using a gradient of 0-40% EtOAc in hexane as eluent to provide benzyl N-[(1R)-1-[(2S,5S)-5-azido-6-hydroxy-tetrahydropyran-2-yl]-2-benzyloxy -ethyl]-N-benzyl-carbamate (96 mg, 24%) and the desired diastereoisomer benzyl N-[(1R)-1 -[(2S,5R)-5-azido-6-hydroxy-tetrahydropyran-2-yl]-2-benzyloxy-ethyl]-N-benzyl-carbamate (188 mg, 47%) as an oil. MS (ESI) [M+H]$^+$517.3.

Step 7
Benzyl N-[(1R)-1-[(2S,5R,6R)-5-azido-6-[(1R,2R,3S,4R,6S)-4,6-diazido-2,3-dihydroxy-cyclohexoxy]tetrahydropyran-2-yl]-2-benzyloxy-ethyl]-N-benzyl-carbamate

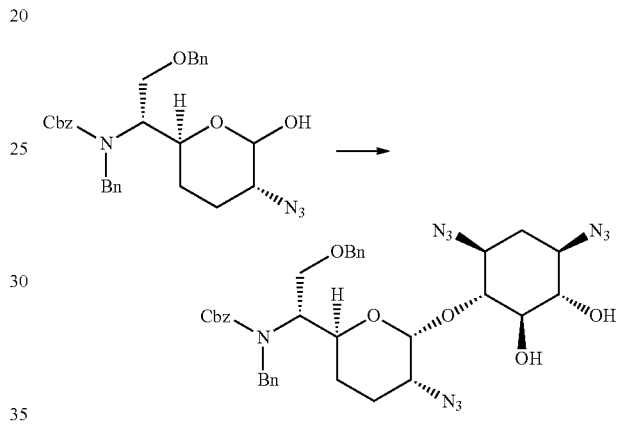

To a mixture of benzyl N-[(1R)-1-[(2S,5R)-5-azido-6-hydroxy-tetrahydropyran-2-yl]-2-benzyloxy-ethyl]-N-benzyl-carbamate (188 mg, 0.36 mmol) and K$_2$CO$_3$ (352 mg, 2.55 mmol) in dry DCM (10 mL) at room temperature was added CCl$_3$CN (0.29 mL, 2.91 mmol). The mixture was stirred at room temperature for 16 h, then filtered on celite and rinsed with DCM. The filtrate was concentrated under reduced pressure. The residue was taken in anhydrous DCM (10 mL) and [(1S,2S,3R,4S,6R)-2-acetoxy-4,6-diazido-3-hydroxy-cyclohexyl]acetate (239 mg, 0.80 mmol) was added. The mixture was cooled to −78° C., then BF$_3$·OEt$_2$ (0.14 mL, 1.13 mmol) was added dropwise. The reaction mixture was warmed to 0° C. and stirred for 1 h. The mixture was diluted with saturated NaHCO$_3$ (50 mL) and the aqueous layer was extracted with DCM (2×30 mL). The combined organic layers were washed with brine, dried (Na$_2$SO$_4$), filtered and concentrated under reduced pressure. The residue was taken in MeOH (10 mL) and NaOMe (4.62 M in MeOH, 0.55 mL, 2.55 mmol) was added. The reaction mixture was stirred at room temperature for 2 h, then concentrated under reduced pressure. The residue was diluted with DCM (20 mL) and saturated NH$_4$Cl (80 mL). The layers were separated, and the aqueous layer was extracted with DCM (2×30 mL). The combined organic layers were washed with brine, dried (Na$_2$SO$_4$), filtered and concentrated under reduced pressure. The material was purified by reverse phase chromatography (C18) using a gradient of 5-100% ACN in water (contains 0.1% formic acid) to provide the title compound (134 mg, 52% over 3 steps) as a solid. MS (ESI) [M+H]$^+$713.3.

Step 8
(1S,2R,3R,4S,6R)-4,6-diamino-3-[(2R,6S)-3-amino-6-[(1R)-1-amino-2-hydroxy -ethyl]tetrahydropyran-2-yl]oxy-cyclohexane-1,2-diol formate

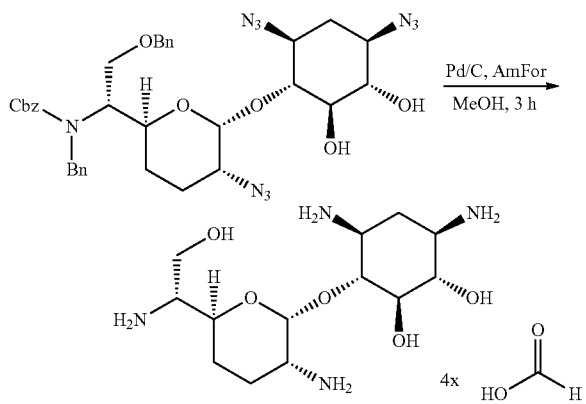

In a 2 neck flask equipped with a reflux condenser were added (1S,2R,3R,4S,6R)-4,6-diazido-3-(((2R,3R,6S)-3-azido-6-((R)-1-(benzyl(methyl)amino)-2-(benzyloxy)ethyl)tetrahydro-2H-pyran -2-yl)oxy)cyclohexane-1,2-diol (16 mg, 0.02 mmol) and Pd/C (10% dry on carbon, 7.2 mg, 0.01 mmol) followed by MeOH (5 mL). Nitrogen was bubbled for 5 min, then ammonium formate (15.6 mg, 0.25 mmol) was added. The mixture was heated at 63° C. for 3 h under $N_2$. The mixture was cooled with an ice-bath and then filtered with a filter syringe and the filtrate was concentrated under reduced pressure. The material was purified by preparative HPLC (Waters X -Bridge C18 30×150 mm; Flow rate: 40 mL/min) using a gradient of 10-25% ACN in Amfor pH 3.8 over 7 min to provide the title compound (3.90 mg, 34%) as a solid. $^1$H NMR (400 MHz, CD$_3$OD) δ 8.45 (br, 4H), 5.64 (s, 1H), 4.27-4.17 (m, 1H), 3.84-3.69 (m, 3H), 3.62-3.55 (m, 1H), 3.51-3.44 (m, 1H), 3.40-3.31 (m, 2H), 3.16-3.02 (m, 3H), 2.35-2.21 (m, 1H), 1.97-1.92 (m, 1H), 1.86-1.80 (m, 1H), 1.66-1.57 (m, 2H). MS (ESI) [M+H]$^+$ 321.4.

Example 57

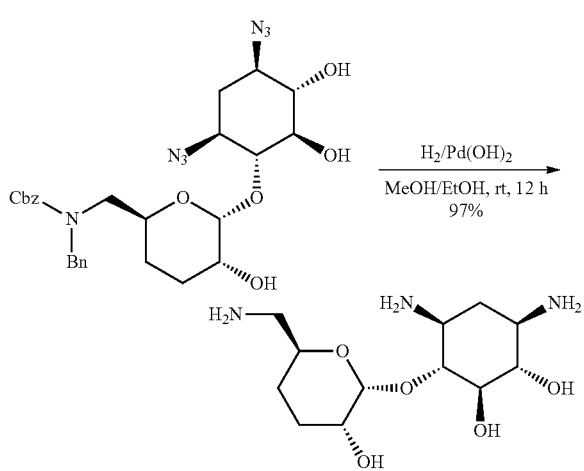

(1S,2R,3R,4S,6R)-3-[(2R,3R,6S)-6-(aminomethyl)-3-hydroxy-tetrahydropyran-2-yl]oxy-4,6-diazido-cyclohexane-1,2-diol Pd(OH)$_2$ (20 wt %, 129 mg, 0.183 mmol) was added to a solution of benzyl N -benzyl-N-[[(2S,5R,6R)-6-[(1R,2R,3S,4R,6S)-4,6-diazido-2,3-dihydroxy-cyclohexoxy]-5-hydroxy-tetrahydropyran-2-yl]methyl]carbamate (see Example 35 for synthesis, 26.0 mg, 45.8 μmol) in MeOH (2.50 mL) and EtOH (2.50 mL). H$_2$ was bubbled and the suspension was hydrogenated under hydrogen atmosphere for 12 h. The suspension was filtered through a frit (0.22 μm diameter) and the filtrate was concentrated under reduced pressure to afford the title compound (13.0 mg, 97%) as a solid. $^1$H NMR (400 MHz, MeOD) δ 5.17 (d, J=3.4 Hz, 1H), 4.07-3.97 (m, 1H), 3.72 (ddd, J=11.4, 5.1, 3.6 Hz, 1H), 3.47 (t, J=9.2 Hz, 1H), 3.28 (t, J=9.5 Hz, 1H), 3.17 (t, J=9.4 Hz, 1H), 2.90 (ddd, J=23.0, 12.6, 3.8 Hz, 2H), 2.82-2.70 (m, 2H), 2.09 (dt, J=12.7, 4.1 Hz, 1H), 1.94-1.69 (m, 4 H), 1.30 (q, J=12.5 Hz, 1H). MS (ESI) [M+H]$^+$325.2.

Example 58

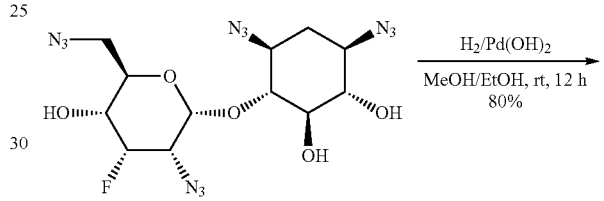

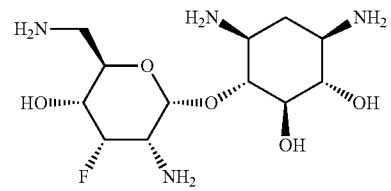

(1S,2R,3R,4S,6R)-4,6-diamino-3-[(2R,3S,4S,5R,6R)-3-amino-6-(aminomethyl)-4-fluoro-5-hydroxy-tetrahydropyran-2-yl]oxy-cyclohexane-1,2-diol Pd(OH)$_2$ (20 wt %, 105 mg, 0.149 mmol) was added to a solution of (1S,2R,3R,4S,6R)-4,6-diazido-3-(((2R,3S,4S,5R,6R)-3-azido-6-(azidomethyl)-4-fluoro-5-hydroxytetrahydro-2H-pyran-2-yl)oxy)cyclohexane-1,2-diol (see Example 42 for synthesis, 20.0 mg, 49.7 μmol) in MeOH (2.0 mL) and EtOH (2.0 mL). H$_2$ was bubbled and the suspension was hydrogenate under hydrogen atmosphere for 12 h. The mixture was filtered through a frit (0.22 μm diameter) and the filtrate was concentrated under reduced pressure to afford the title compound (12.9 mg, 80%) as a solid. $^1$H NMR (500 MHz, MeOD) δ 5.48 (d, J=4.6 Hz, 1H), 4.78 (t, J=53.0, 2.2 Hz, 1H), 4.01 (ddd, J=10.5, 5.5, 2.1 Hz, 1H), 3.56-3.44 (m, 2H), 3.31 (t, J=9.3 Hz, 1H), 3.22 (dd, J=13.2, 2.9 Hz, 1H), 3.16 (t, J=9.5 Hz, 1H), 3.05 (ddd, J=33.9, 4.6, 2.5 Hz, 1H), 2.95-2.84 (m, 2H), 2.77 (ddd, J=12.1, 9.8, 4.2 Hz, 1H), 2.07 (dt, J=12.8, 4.2 Hz, 1H), 1.32 (dd, J=24.8, 12.3 Hz, 1H).

Example 59

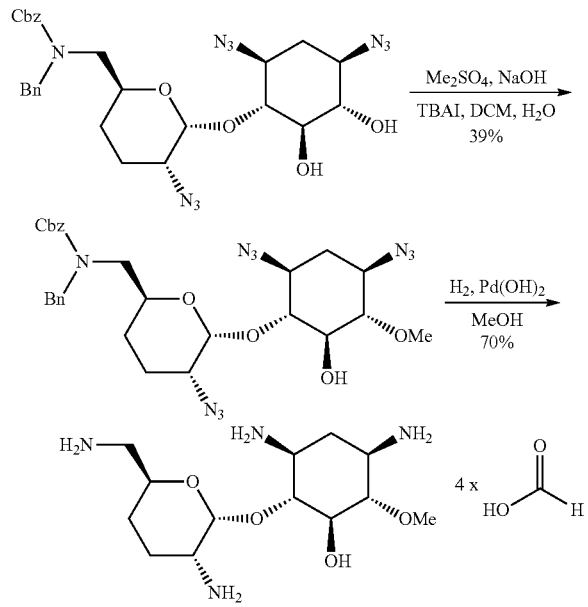

Step 1
Benzyl N-[[(5R,6R)-5-azido-6-[(1R,2R,3S,4R,6S)-4,6-diazido-2-hydroxy-3-methoxy -cyclohexoxy]tetrahydropyran-2-yl]methyl]-N-benzyl-carbamate

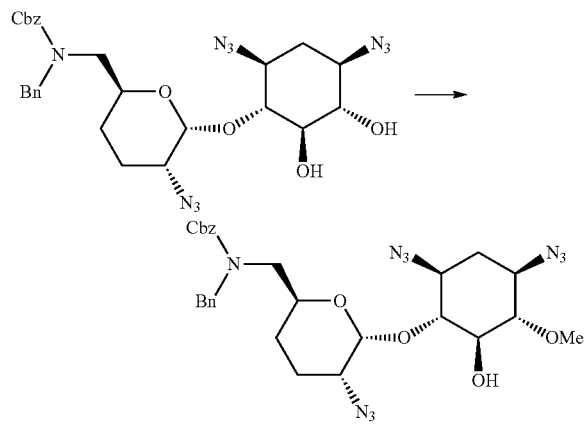

Me$_2$SO$_4$ (51 µL, 68 mmol) was added to a vigorously stirring suspension of benzyl N-[[(5R,6R)-5-azido-6-[(1R,2R,3S,4R,6S)-4,6-diazido-2,3-dihydroxy -cyclohexoxy]tetrahydropyran-2-yl]methyl]-N-benzyl-carbamate (see Example 31 for synthesis, 40 mg, 67 µmol) and TBAI (4 mg, 10 µmol) in a mixture DCM (1.0 mL) and NaOH solution (1.0 M aq., 1.0 mL, 1.0 mmol) at ambient temperature. After 2 h, concentrated NH$_4$OH (200 µL) was added and the mixture was partitioned in between water (10.0 mL) and DCM (10.0 mL). The aqueous layer was extracted with DCM (5.0 mL) and the combined organic layers were dried (Na$_2$SO$_4$), filtered and concentrated under reduced pressure. The material was purified by silica gel chromatography (12 g cartridge) using a gradient of 10-40% EtOAc in hexane as eluent and was further purified by preparative HPLC (BEH 30×150 mm C18 ACN/AmForm 70-80%) to provide the title compound (rotamers, 16 mg, 39%) as a solid. $^1$H NMR (400 MHz, CDCl$_3$) δ 7.48-7.04 (m, 10H), 5.32-5.04 (m, 3H), 4.72 (d, J=15.9 Hz, 1H), 4.47 (d, J=16.0 Hz, 1H), 4.34-4.12 (m, 1H), 3.66 (s, 3H), 3.59-3.10 (m, 8H), 2.96 (t, J=9.5 Hz, 1H), 2.19 (dt, J=13.2, 4.5 Hz, 1H), 2.06-1.92 (m, 1H), 1.92-1.81 (m, 1H), 1.73-1.51 (m, 1H), 1.47-1.28 (m, 2H). MS ESI [M+H]$^+$607.2.

Step 2
(1R,2R,3S,5R,6S)-3,5-diamino-2-[(2R,3R,6S)-3-amino-6-(aminomethyl)tetrahydropyran-2-yl]oxy-6-methoxy-cyclohexanol, formic acid

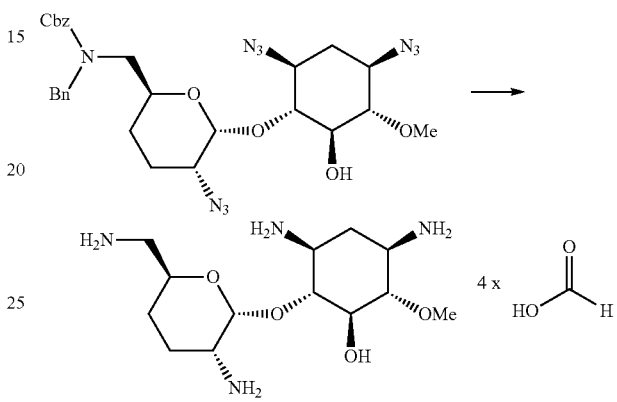

Pd(OH)$_2$ (10 wt %, 9.3 mg, 6.6 µmol) was added to a solution of benzyl N -[[(2S,5R,6R)-5-azido-6-[(1R,2R,3S,4R,6S)-4,6-diazido-2-hydroxy-3-methoxy -cyclohexoxy] tetrahydropyran-2-yl]methyl]-N-benzyl-carbamate (16 mg, 26.4 µmol) in MeOH (1.5 mL) under N$_2$ at ambient temperature. H$_2$ was bubbled through the suspension for 15 min and then the suspension was stirred for 18 h. The solution was filtered through a frit (0.22 µm diameter) and the filtrate was concentrated under reduced pressure. The material was purified by preparative HPLC (BEH 30×150 mm C18 ACN/AmForm 10-25%) to provide the title compound (9 mg, 70%). $^1$H NMR (500 MHz, D$_2$O) δ 8.53 (s, 3H), 5.79 (d, J=3.3 Hz, 1H), 4.26-4.16 (m, 1H), 3.96 (t, J=9.8 Hz, 1H), 3.82 (t, J=8.8 Hz, 1H), 3.64 (s, 3H), 3.62-3.53 (m, 1H), 3.53-3.44 (m, 1H), 3.43-3.35 (m, 2H), 3.27 (dd, J=13.5, 3.2 Hz, 1H), 3.12 (dd, J=13.6, 7.3 Hz, 1H), 2.50 (dt, J=5.5, 3.1 Hz, 1H), 2.11-1.98 (m, 2H), 1.98-1.82 (m, 2H), 1.70-1.57 (m, 1H). MS ESI [M+H]$^+$350.2

Example 60

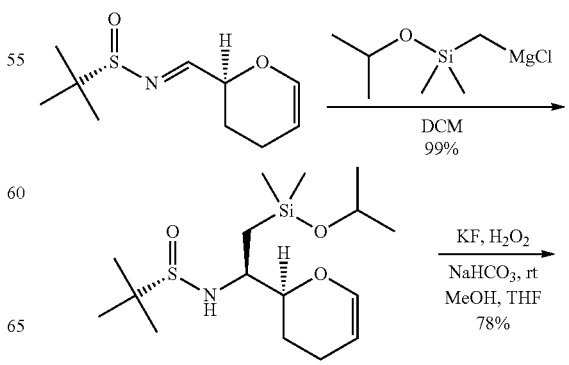

561
-continued

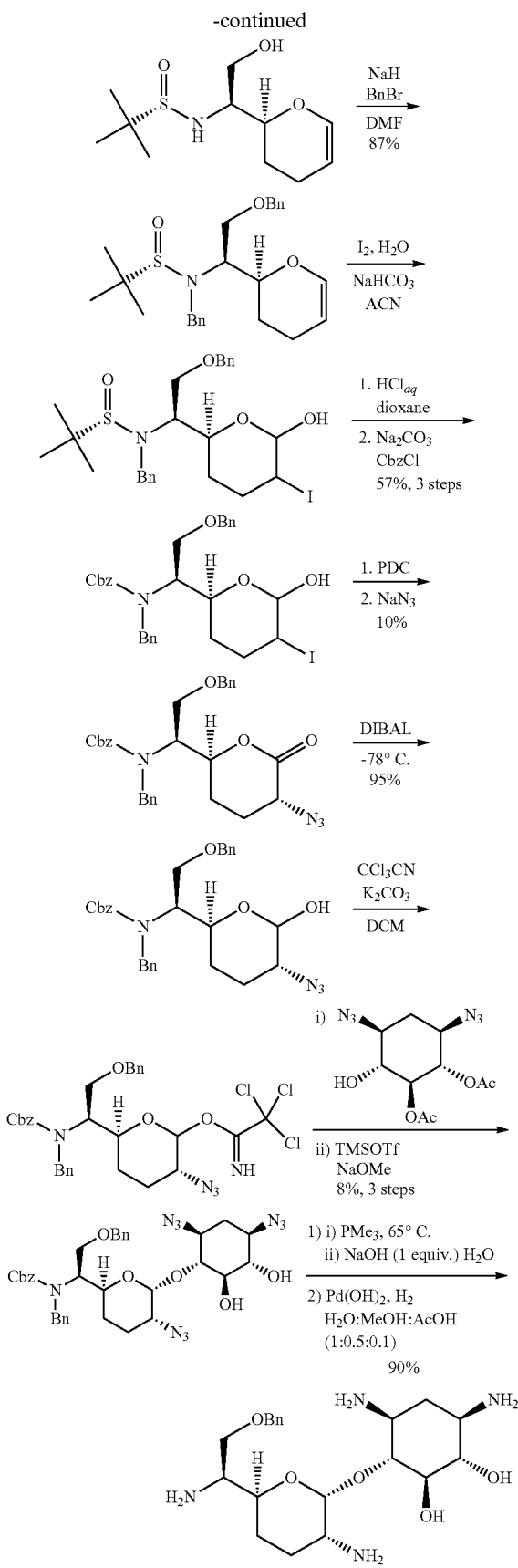

562

Step 1
(S)-N-[(1R)-1-[(2S)-3,4-dihydro-2H-pyran-2-yl]-2-[isopropoxy(dimethyl)silyl]ethyl]-2-methyl-propane-2-sulfinamide

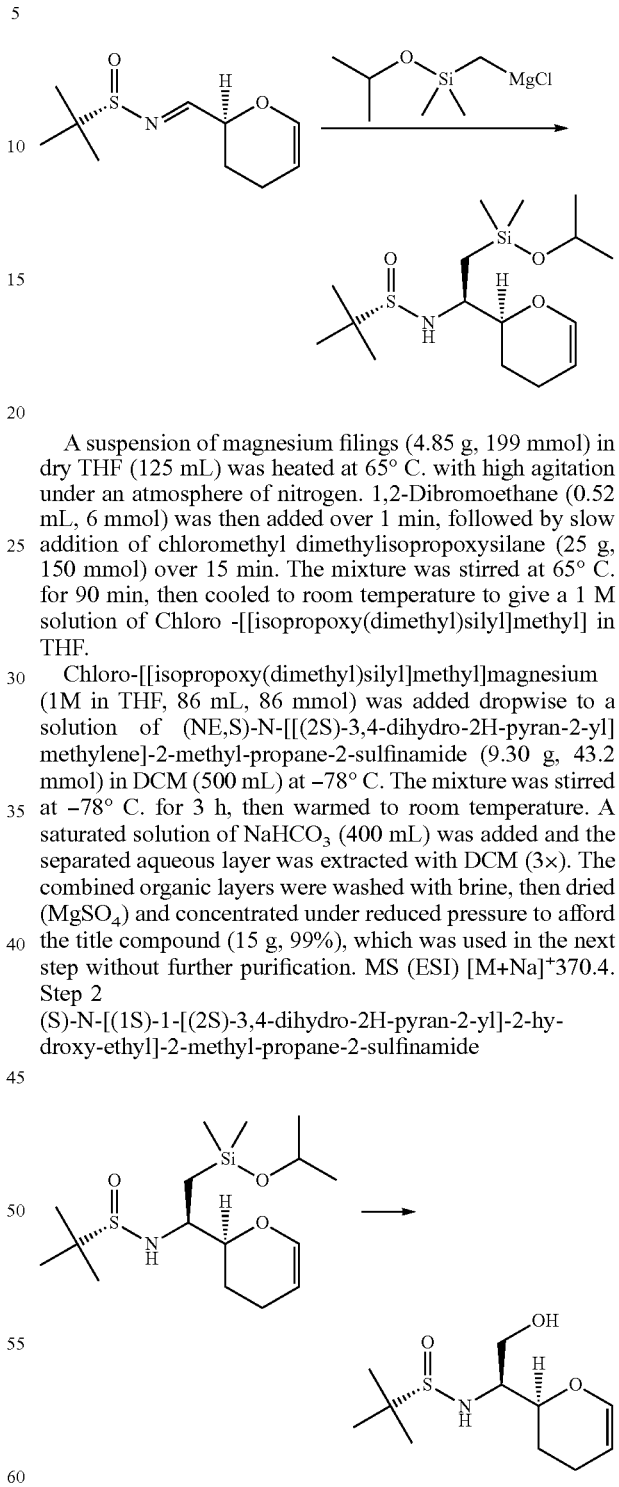

A suspension of magnesium filings (4.85 g, 199 mmol) in dry THF (125 mL) was heated at 65° C. with high agitation under an atmosphere of nitrogen. 1,2-Dibromoethane (0.52 mL, 6 mmol) was then added over 1 min, followed by slow addition of chloromethyl dimethylisopropoxysilane (25 g, 150 mmol) over 15 min. The mixture was stirred at 65° C. for 90 min, then cooled to room temperature to give a 1 M solution of Chloro -[[isopropoxy(dimethyl)silyl]methyl] in THF.

Chloro-[[isopropoxy(dimethyl)silyl]methyl]magnesium (1M in THF, 86 mL, 86 mmol) was added dropwise to a solution of (NE,S)-N-[[(2S)-3,4-dihydro-2H-pyran-2-yl] methylene]-2-methyl-propane-2-sulfinamide (9.30 g, 43.2 mmol) in DCM (500 mL) at −78° C. The mixture was stirred at −78° C. for 3 h, then warmed to room temperature. A saturated solution of NaHCO$_3$ (400 mL) was added and the separated aqueous layer was extracted with DCM (3×). The combined organic layers were washed with brine, then dried (MgSO$_4$) and concentrated under reduced pressure to afford the title compound (15 g, 99%), which was used in the next step without further purification. MS (ESI) [M+Na]$^+$370.4.

Step 2
(S)-N-[(1S)-1-[(2S)-3,4-dihydro-2H-pyran-2-yl]-2-hydroxy-ethyl]-2-methyl-propane-2-sulfinamide To a solution of (S)-N-[(1R)-1-[(2S)-3,4-dihydro-2H-pyran-2-yl]-2 -[isopropoxy(dimethyl)silyl]ethyl]-2-methyl-propane-2-sulfinamide (15.0 g, 43.2 mmol) in a mixture of THF (600 mL) and MeOH (600 mL), was added KF (2.88 g, 49.6 mmol) and NaHCO$_3$ (4.35 g, 51.8 mmol). The mixture was cooled to 5° C. and a solution of H$_2$O$_2$ (7.42 mL 30 wt % H₂O₂; 86.3 mmol) was added dropwise. The reaction mixture was warmed room temperature and was stirred for 16 h. The mixture was quenched with saturated Na₂S₂O₃ (~250 mL) and diluted with saturated NaHCO₃ (~100 mL). The aqueous layer was extracted with EtOAc (2.5 L). The organic phase was dried (MgSO₄), filtered and concentrated under reduced pressure. The crude oil was diluted with ether (1.5 L) and washed with brine (500 mL). The organic layer was dried (Na₂SO₄), filtered and concentrated under reduced pressure to afford the title compound (8.31 g, 78%). MS (ESI) [M+H]⁺248.3.

Step 3
(S)-N-benzyl-N-[(1S)-2-benzyloxy-1-[(2S)-3,4-dihydro-2H-pyran-2-yl]ethyl]-2-methyl-propane-2-sulfinamide

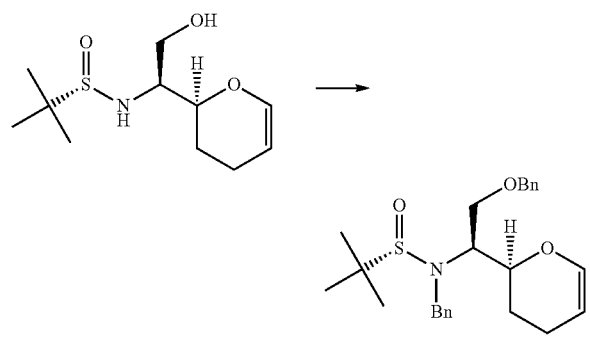

NaH (60%, 1.15 g, 28.9 mmol) was added to a mixture of BnBr (4.90 mL, 41.2 mmol) and (S)-N-[(1S)-1-[(2S)-3,4-dihydro-2H-pyran-2-yl]-2-hydroxy-ethyl]-2-methyl-propane-2-sulfinamide (3.40 g, 13.7 mmol) in DMF (100 mL) at 0° C. The reaction mixture was stirred at 0° C. for 1 h, then brine (500 mL) was added. The separated aqueous layer was extracted with EtOAc (3×150 mL). The combined organic layers were dried (Na₂SO₄), filtered and concentrated under reduced pressure. The material was purified by flash chromatography (120 g, dry loading) using a gradient of 5-45% EtOAc in hexane as eluent to provide the title compound (5.11 g, 87%). MS (ESI) [M+Na]⁺450.4.

Step 4
Benzyl N-benzyl-N-[(1S)-2-benzyloxy-1-[(2S)-6-hydroxy-5-iodo-tetrahydropyran-2-yl]ethyl]carbamate

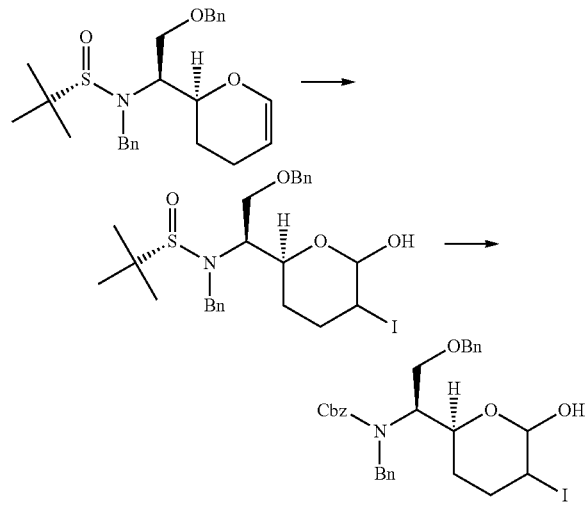

I₂ (3.34 g, 13.1 mmol) was added to a mixture of (R)-N-benzyl-N-[(1S)-2-benzyloxy-1-[(2S)-3,4-dihydro-2H-pyran-2-yl]ethyl]-2-methyl-propane-2-sulfinamide (5.11 g, 12.0 mmol) and NaHCO₃ (3.01 g, 35.9 mmol) in a mixture ACN (100 mL) and water (100 mL) at 0° C. The reaction mixture was stirred at 0° C. for 45 min, then a saturated aqueous solution of Na₂S₂O₃ (200 mL) was added. The aqueous layer was extracted with EtOAc (3×150 mL). The combined organic layer was washed with brine (500 mL), then dried (Na₂SO₄), filtered and concentrated under reduced pressure to afford (S)-N-benzyl-N-((1S)-2-(benzyloxy)-1-((2S)-6-hydroxy-5-iodotetrahydro-2H-pyran-2-yl)ethyl)-2-methylpropane-2-sulfinamide.

To the above material (S)-N-benzyl-N-((1S)-2-(benzyloxy)-1-((2S)-6-hydroxy-5-iodotetrahydro-2H-pyran-2-yl)ethyl)-2-methylpropane-2-sulfinamide was taken in dioxane (50 mL), was added aqueous solution of 1 N HCl (17.9 mL, 17.9 mmol) dropwise and the reaction mixture was stirred at room temperature for 30 min. Na₂CO₃ (7.60 g, 71.7 mmol) was then added and the mixture was stirred for 10 min. CbzCl (3.41 mL, 23.9 mmol) was added dropwise and the reaction mixture was stirred at room temperature for 2 h. The mixture was diluted with water (100 mL) and the separated aqueous layer was extracted with EtOAc (3×100 mL). The combined organic layers were washed with brine, then dried (Na₂SO₄), filtered and concentrated under reduced pressure. The material was purified by flash chromatography (120 g, dry loading) using a gradient of 0-50% EtOAc in hexane as eluent to provide the title compound (4.10 g, 57% over 3 steps). MS (ESI) [M+Na]⁺624.3.

Step 5
Benzyl N-[(1S)-1-[(2S,5R)-5-azido-6-oxo-tetrahydropyran-2-yl]-2-benzyloxy-ethyl]-N-benzyl-carbamate

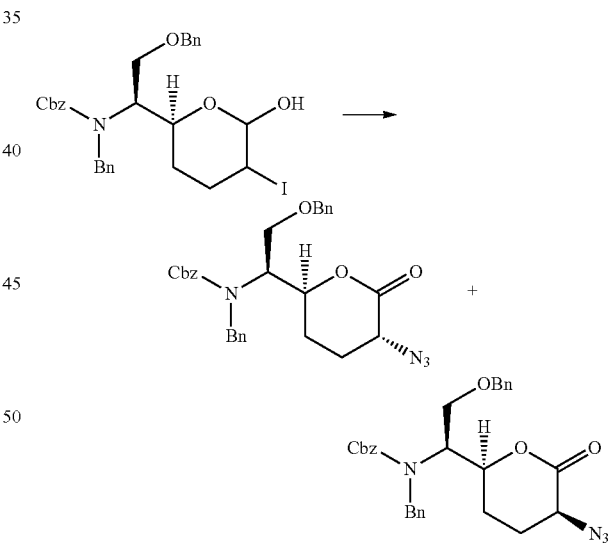

To a solution of benzyl N-benzyl-N-[(1S)-2-benzyloxy-1-[(2S)-6-hydroxy-5-iodo-tetrahydropyran-2-yl]ethyl]carbamate (4.10 g, 6.82 mmol) in DCM (200 mL), was added 4 Å molecular sieves (2.00 g), and then PDC (11.5 g, 30.7 mmol) and the suspension was stirred at room temperature for 18 h. The mixture was filtered on a silica pad, rinsed with EtOAc and concentrated under reduced pressure.

To the above material in DMF (30 mL) at 0° C., was added NaN₃ (0.49 g, 7.50 mmol) and the reaction mixture was stirred for 1 h at room temperature. The mixture was diluted with brine (250 mL) and the separated aqueous layer was extracted with Et$_2$O. The combined organic layers were dried (Na$_2$SO$_4$), filtered and concentrated under reduced pressure. The material was purified by flash chromatography (40 g, dry loading) using a gradient of 0-50% EtOAc in hexane as eluent to provide the title compound (first eluting, 350 mg, 10%) along with benzyl((S)-1-((2S,5S)-5-azido-6-oxotetrahydro-2H-pyran-2-yl)-2-(benzyloxy)ethyl)(benzyl) carbamate (second eluting, 335 mg). MS (ESI) [M+H]$^+$ 515.4.

Step 6

Benzyl N-[(1S)-1-[(2S,5R)-5-azido-6-hydroxy-tetrahydropyran-2-yl]-2-benzyloxy-ethyl]-N-benzyl-carbamate

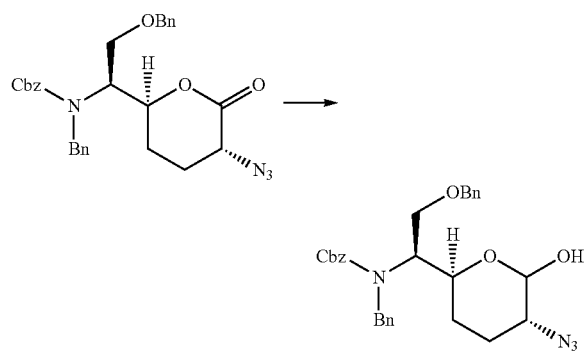

DIBAL-H (1 M in toluene, 1.36 mL, 1.36 mmol) was added dropwise to a solution of benzyl N-[(1S)-1-[(2S,5R)-5-azido-6-oxo-tetrahydropyran-2-yl]-2-benzyloxy-ethyl]-N-benzyl-carbamate (350 mg, 0.68 mmol) in DCM (20 mL) at −78° C. After 1 h at −78° C., EtOH (1 mL) was added dropwise and the mixture was poured into a saturated aqueous solution of Rochelle's salt (300 mL). The mixture was vigorously stirred for 1 h and the separated aqueous layer was extracted with DCM (2×75 mL). The combined organic layers were washed with brine, then dried (Na$_2$SO$_4$), filtered and concentrated under reduced pressure. The material was purified by flash chromatography (40 g, dry loading) using a gradient of 5-40% EtOAc in hexane to provide the title compound (334 mg, 95%) as an oil. MS (ESI) [M+Na]$^+$ 539.3.

Step 7

Benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]-2-benzyloxy-ethyl]-N-benzyl-carbamate

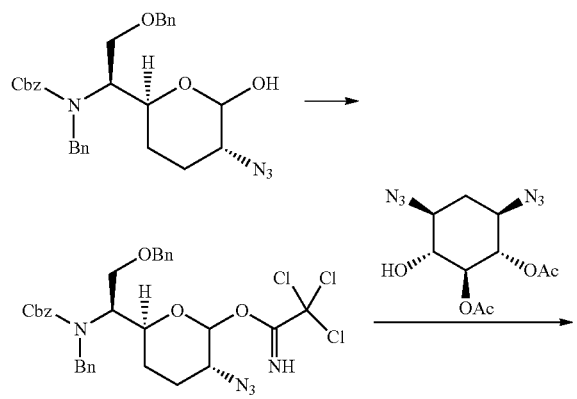

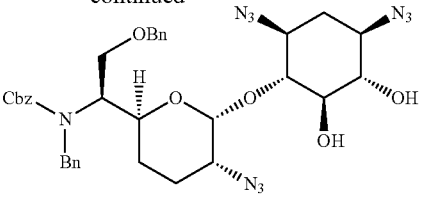

CCl$_3$CN (0.45 mL, 4.50 mmol) was added dropwise to a suspension of benzyl N-[(1S)-1-[(2S,5R)-5-azido-6-hydroxy-tetrahydropyran-2-yl]-2-benzyloxy-ethyl]-N-benzyl-carbamate (334 mg, 0.65 mmol) and K$_2$CO$_3$ (544 mg, 3.94 mmol) in dry DCM (10 mL) at room temperature. The mixture was stirred at room temperature for 18 h, then filtered on Celite and rinsed with DCM. The filtrate was concentrated under reduced pressure to afford (3R,6S)-3-azido-6-((S)-1-(benzyl((benzyloxy)carbonyl)amino)-2-(benzyloxy)ethyl)tetrahydro-2H-pyran-2-yl 2,2,2-trichloroacetimidate, which was used in the next step without further purification.

To a solution of above material in anhydrous DCM (10 mL), [(1S,2S,3R,4S,6R)-2-acetoxy-4,6-diazido-3-hydroxy-cyclohexyl]acetate (168 mg, 0.56 mmol) was added followed activated molecular sieve and the reaction mixture was stirred for 2 h. The mixture was cooled to −78° C., and then BF$_3$·Et$_2$O (0.22 mL, 1.74 mmol) was added dropwise and the reaction mixture was stirred for 1.5 h. The mixture was warmed to 0° C. and stirred for 1 h. The mixture was then diluted with saturated aqueous solution of NaHCO$_3$ (50 mL) and the separated aqueous layer was extracted with DCM (2×30 mL). The combined organic layers were washed with brine, then dried (Na$_2$SO$_4$), filtered and concentrated under reduced pressure. The material was purified by column chromatography on silica gel (40 g) using a gradient of 0-30% EtOAc in hexane as eluent to afford the bis acetate intermediate. MS (ESI) [M+Na]$^+$819.5.

To a solution of above material in MeOH (10 mL), NaOMe (4.62 M in MeOH, 0.56 mL, 2.59 mmol) was added and the reaction mixture was stirred at room temperature for 2 h. The mixture was concentrated under reduced pressure and the residue was diluted in DCM and saturated NH$_4$Cl (100 mL). The separated aqueous layer was extracted with DCM (2×30 mL). The combined organic layers were washed with brine, then dried (Na$_2$SO$_4$), filtered and concentrated under reduced pressure. The material was purified by preparative HPLC (BEH 30×150 mm C18 ACN/Am-Form 73-80%) to afford to afford the title compound (first eluting, 31 mg) along with P2 (second eluting, 70.9 mg). MS (ESI) [M+Na]$^+$735.4.

Step 8

(1S,2R,3R,4S,6R)-4,6-diamino-3-[(2R,3R,6S)-3-amino-6-[(1S)-1-amino-2-hydroxy-ethyl]tetrahydropyran-2-yl]oxy-cyclohexane-1,2-diol; acetic acid

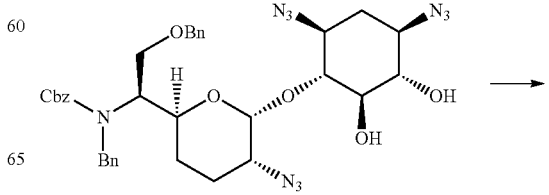

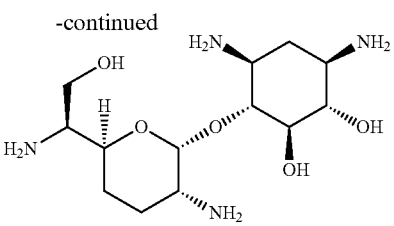

To a solution of benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]-2-benzyloxy-ethyl]-N-benzyl-carbamate (25 mg, 0.035 mmol) in tetrahydrofuran (1 mL), was added trimethyl phosphine (0.21 mL 1.0 M tetrahydrofuran solution, 0.21 mmol) at room temperature and the reaction mixture was heated to 65° C. for 30 min. The mixture was diluted 0.1 M aq. sodium hydroxide (0.42 mL, 0.042 mmol) and the mixture was stirred for 5 h. The mixture was cooled to room temperature and stirred overnight. The volatiles were concentrated under reduced pressure and the material was purified with reverse phase chromatography on C18 using 10-100% AcCN in H$_2$O (ammonium formate:Formic acid 1:1. 0.1%) to amine. MS (ESI) [M+Na]$^+$657.5.

To a solution of above material in a mixture of water: MeOH:AcOH (1:0.5:0.1, 5 mL), was added palladium(II) hydroxide (20 wt % loading on carbon, 24.6 mg, 0.018 mmol). The suspension was hydrogenated under hydrogen atmosphere for 16 h. The mixture was filtered and the filtrated was concentrated under reduced pressure and then lyophilized to afford the title compound (18.4 mg, 90%) as a salt. $^1$H (500 MHz, MeOD) δ 5.85 (d, J=3.0 Hz, 1H), 4.20-4.11 (m, 1H), 3.78 (dd, J=11.9, 4.2 Hz, 1H), 3.75-3.64 (m, 2H), 3.52 (t, J=9.1 Hz, 1H), 3.39 (t, J=9.3 Hz, 1H), 3.37-3.33 (m, 1H), 3.15 (dt, J=9.5, 8.6 Hz, 2H), 3.06 (t, J=9.2 Hz, 1H), 2.30 (d, J=12.5 Hz, 1H), 2.09-2.02 (m, 1H), 1.72 (dd, J=25.0, 12.7 Hz, 1H), 1.62-1.48 (m, 1H). 2H missing (in the 1.9 ppm peak together with acetic acid according to HSQC). MS (ESI) [M+4]$^+$321.2.

Example 61

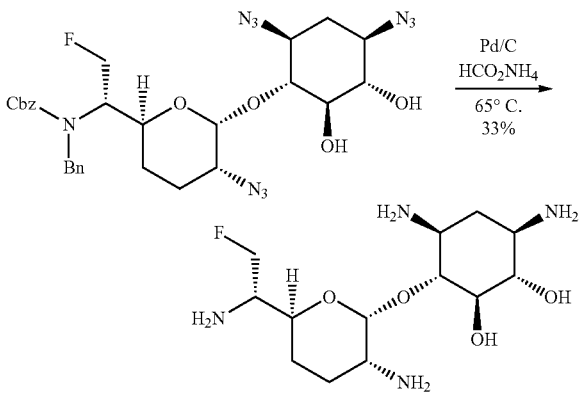

(1S,2R,3R,4S,6R)-4,6-diamino-3-[(2R,3R,6S)-3-amino-6-[(1S)-1-amino-2-fluoro-ethyl]tetrahydropyran-2-yl]oxy-cyclohexane-1,2-diol; formic acid To a mixture of benzyl N-[(1S)-1-[(2S,5R,6R)-5-azido-6-[(1R,2R,3S,4R,6S)-4,6-diazido-2,3-dihydroxy-cyclohexoxy]tetrahydropyran-2-yl]-2-fluoro-ethyl]-N-benzyl-carbamate (see Example 43 for synthesis, 10 mg, 0.016 mmol) and 10% Pd/C (5.1 mg, 0.0048 mmol) was added anhydrous MeOH (1 mL). Nitrogen was bubbled for 5 min, then ammonium formate (9.1 mg, 0.14 mmol) was added and the mixture was heated at 63° C. for 6 h. The mixture was cooled to room temperature and then filtered through a nylon filter (45 μm) and the volatiles were evaporated under reduced pressure then lyophilized (1 drop of formic acid in water) to provide the title compound (2.7 mg, 33%) as formate salt. $^1$H (500 MHz, MeOD) δ 8.21 (s, 4H), 5.85 (d, J=3.5 Hz, 1H), 4.82-4.68 (m, 2H), 4.38 (d, J=12.3 Hz, 1H), 3.93 (t, J=9.6 Hz, 1H), 3.74-3.67 (m, 1H), 3.60 (t, J=9.2 Hz, 1H), 3.46-3.39 (m, 3H), 3.20 (ddd, J=11.0, 10.0, 3.5 Hz, 1H), 2.39 (dt, J=12.4, 4.1 Hz, 1H), 2.22-2.12 (m, 1H), 2.06-1.96 (m, 1H), 1.94-1.83(m, 2H), 1.74-1.64 (m, 1H). MS (ESI) [M+H]$^+$323.2.

Example 62

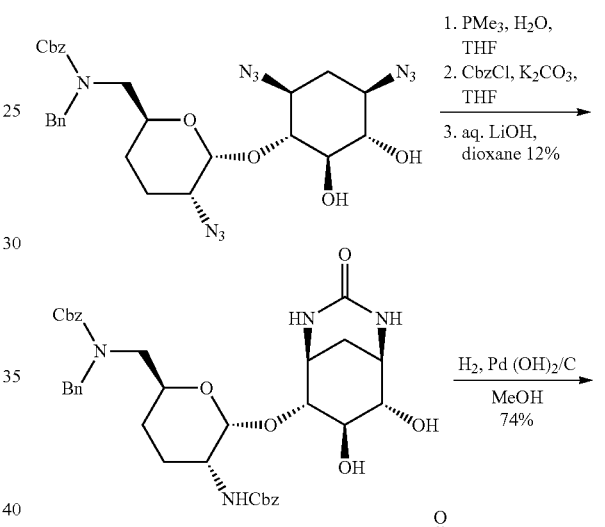

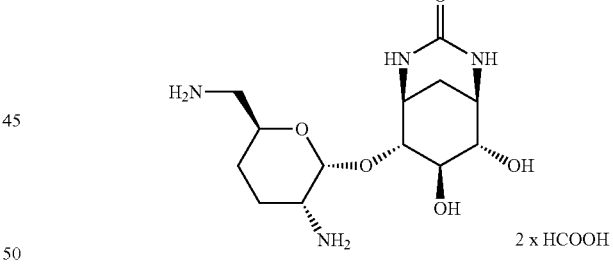

Step 1
Benzyl N-benzyl-N-[[(2S,5R,6R)-5-(benzyloxycarbonylamino)-6-[[(1R,5S,6R,7R,8S)-7,8-dihydroxy-3-oxo-2,4-diazabicyclo[3.3.1]nonan-6-yl]oxy]tetrahydropyran-2-yl]methyl]carbamate

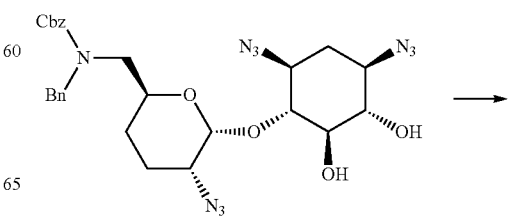

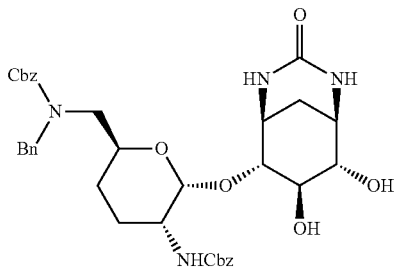

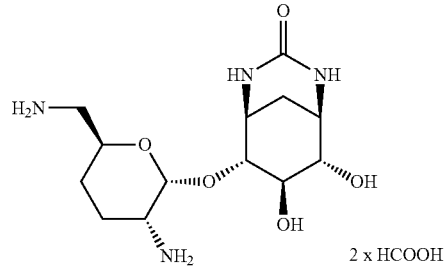

PMe₃ (1.0 M in THF, 1.14 mL, 1.14 mmol) was added to a solution of benzyl N -[[(2S,5R,6R)-5-azido-6-[(1R,2R,3S,4R,6S)-4,6-diazido-2,3-dihydroxy -cyclohexoxy]tetrahydropyran-2-yl]methyl]-N-benzyl-carbamate (see Example 31 for synthesis, 150 mg, 253 µmol) and water (150 µL, 8.33 mmol) in THF (6.0 mL) under N₂ at ambient temperature. The reaction was warmed to 40° C. under a refluxing condenser. After 18 h, the solution was cooled to room temperature and K₂CO₃ (315 mg, 2.28 mmol) was added followed by water (1.5 mL). After another 30 min, CbzCl (162 µL, 1.14 mmol) was added dropwise and the reaction mixture was stirred at for 2 h. The volatiles were evaporated under reduced pressure and the material was purified by silica gel chromatography (12 g cartridge) with using a gradient of EtOAc and hexane (30-80%) as eluent then 30% MeOH in DCM to produce benzyl N-benzyl -N-[[(2S,5R,6R)-5-(benzyloxycarbonylamino)-6-[(1R,2R,3S,4R,6S)-4,6-bis(benzyloxycarbonylamino)-2,3-dihydroxy-cyclohexoxy]tetrahydropyran-2-yl]methyl]carbamate (282 mg).

LiOH·H₂O (70 mg, 1.68 mmol) was added to a suspension of benzyl N-benzyl-N -[[(2S,5R,6R)-5-(benzyloxycarbonylamino)-6-[(1R,2R,3S,4R,6S)-4,6-bis(benzyloxycarbonylamino)-2,3-dihydroxy-cyclohexoxy]tetrahydropyran-2-yl]methyl]carbamate (220 mg, 240 µmol) in a mixture dioxane and H₂O (2.25 mL 2:1) in a microwave tube. The tube was sealed and the reaction mixture was warmed to 50° C. for 18 h. The mixture was filtered through silica gel (4.0 g) and eluted with a mixture of MeOH in DCM (80.0 mL, 4:1). To the filtrate was added HOAc (150 µL) and the mixture was concentrated under reduced pressure. The material was purified by preparative HPLC (BEH 30×150 mm C18 ACN/AmForm 40-60%) to provide the title compound (20 mg, 12% over 3 steps) as a solid. MS (ESI) [M+H]⁺675.3.

Step 2

(1R,5S,6R,7R,8S)-6-[(2R,3R,6S)-3-amino-6-(aminomethyl)tetrahydropyran-2-yl]oxy-7,8-dihydroxy-2,4-diazabicyclo[3.3.1]nonan-3-one, formic acid

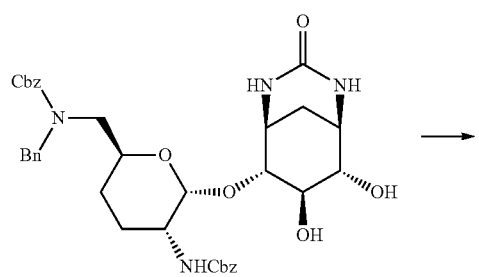

Pd(OH)₂/C (10 wt %, 25 mg, 18 µmol) was added to a solution of benzyl N -benzyl-N-[[(2S,5R,6R)-5-(benzyloxycarbonylamino)-6-[[(1R,5S,6R,7R,8S)-7,8-dihydroxy-3-oxo-2,4-diazabicyclo[3.3.1]nonan-6-yl]oxy]tetrahydropyran-2-yl]methyl]carbamate (20 mg, 30 µmol) in MeOH (1.0 mL) under N₂ at ambient temperature. H₂ was bubbled through the suspension for 15 min and the mixture was stirred under hydrogen atmosphere for 18 h. The mixture was filtered through a frit (0.45 µm diameter) and the filtrate was concentrated under reduced pressure. The material was purified by preparative HPLC (BEH 30×150 mm ACN/AmForm 10% ISO) to provide the title compound (bis-formate, 9.0 mg, 74%). ¹H (500 MHz, MeOD) δ 8.57 (s, 2H), 5.21 (s, 1H), 4.05 (t, J=9.8 Hz, 1H), 3.98-3.86 (m, 3H), 3.68 (s, 1H), 3.50 (s, 1H), 3.37 (s, 1H), 3.13 (d, J=12.7 Hz, 1H), 2.99-2.88 (m, 1H), 2.60 (d, J =13.1 Hz, 1H), 1.98-1.89 (m, 2H), 1.85 (d, J=12.5 Hz, 1H), 1.66 (d, J=13.1 Hz, 1H), 1.59-1.47 (m, 1H). MS ESI [M+H]⁺317.2.

Biological Example 1: Minimum Inhibitory Concentration Assay

Minimum inhibitory concentrations for the example compounds herein are determined by the broth microdilution method in accordance with the Clinical and Laboratory Standards Institute (CLSI) guidelines. In brief, organism suspensions are adjusted to a 0.5 McFarland standard to yield a final inoculum between 3×10⁵ and 7×10⁵ colony-forming units (CFU)/mL. Compound dilutions and inocula are made in sterile, cation adjusted Mueller-Hinton Broth (Beckton Dickinson). The inoculum is prepared by suspension of a colony from an agar plate that is prepared the previous day. Bacteria are suspended in sterile saline and added to each assay plate to obtain a final concentration of 5×10⁵ CFU/mL. An inoculum volume of 100 µL is added to wells containing 100 µL of broth with 2-fold serial dilutions of the compound. All inoculated microdilution trays are incubated in ambient air at 35° C. for 18-24 hours. Following incubation, the lowest concentration of the compound that prevents visible growth (OD 600 nm<0.05) is recorded as the MIC. The MIC is determined to be the lowest concentration of the test compound that resulted in no visible bacterial growth as compared to untreated control. Performance of the assay is monitored by the use of laboratory quality-control strains and a compound with a defined MIC spectrum (such as levofloxacin), in accordance with CLSI guidelines. Compounds are tested against multiple microbiologic panels. Panels include: 1) a multi-species primary screening panel that includes multiple defined AG-R mechanisms; 2) a panel of isogenic strains carrying different common mechanisms of AG-R that allows characterization of the SAR for AMEs, RMTs, and entry and efflux resistance mechanisms; and 3) panels of recent clinical isolates selected from Phase 3 studies and ongoing global surveillance.

Results are shown in Tables 1-3 below.
TABLE 1
Data Summary for Synthesized Aminoglycosides
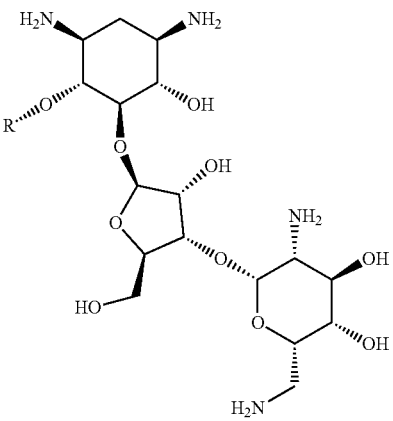
| | Geometric Mean MIC values (μg/mL) | | | | | | |
|---|---|---|---|---|---|---|---|
| | E. coli | | | P. aeruginosa | | | |
| R | ATCC 25922 | efflux parent | Δefflux[a] | ATCC 27853 | efflux parent | Δefflux[b] | translation IC$_{50}$ (nM) |
| (NH$_2$-CH$_2$-tetrahydropyran-NH$_2$) | 1.1 | 1.4 | 1.4 | 0.57 | 0.77 | 0.5 | 13 |
| (NH$_2$-CH-tetrahydropyran-NH$_2$) | 1.6 | 1 | 1 | 0.71 | 1 | 0.5 | 14 |
| (NH$_2$-CH(CH$_3$)-tetrahydropyran-NH$_2$) | 2.5 | 1 | 1 | 2 | 4 | 0.5 | 14 |
| (NH$_2$-CH(Et)-tetrahydropyran-NH$_2$) | 2 | 2 | 1 | 2 | 2 | 0.5 | 32 |

TABLE 1-continued

Data Summary for Synthesized Aminoglycosides

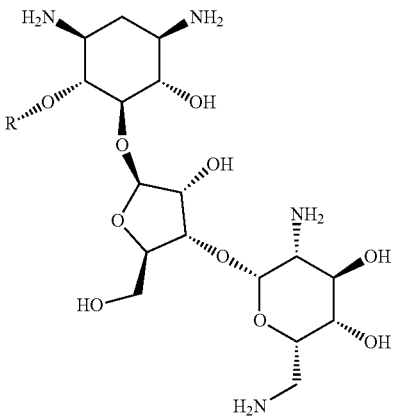

| | Geometric Mean MIC values (µg/mL) | | | | | | |
|---|---|---|---|---|---|---|---|
| | *E. coli* | | | *P. aeruginosa* | | | |
| R | ATCC 25922 | efflux parent | Δefflux[a] | ATCC 27853 | efflux parent | Δefflux[b] | translation $IC_{50}$ (nM) |
| (structure with NH$_2$, O, H, NH$_2$) | 1 | 2 | 1 | 1 | 2 | 0.5 | 26 |
| (structure with NH$_2$, HO, F, NH$_2$) | 2 | 2 | 1 | 1 | 2 | 0.5 | 10 |
| (structure with NH$_2$, HO, F, F, NH$_2$) | 4 | 4 | 2 | 4 | 8 | 1 | 63 |

[a]The tolC efflux pump has been knocked-out of this strain
[b]aph(3')-Ia likely has activity at both the 3'-hydroxy and 5"-hydroxy positions
[b]The MexAB-OprM, MexCD-OprJ, and MexEF-OprN efflux pumps have been knocked out of this strain.

TABLE 2

Data Summary for Synthesized Aminoglycosides

[Structure: aminoglycoside core with R group, showing H2N, NH2, OH substituents on cyclohexane connected via O to furanose and pyranose sugars]

| R | | E. coli | | | E. coli isogenic strains Geometric Mean MIC values (mg/L) | | | | | | |
|---|---|---|---|---|---|---|---|---|---|---|---|
| | | ATCC 25922 | efflux parent | Δefflux[a] | empty vector | aac(6')-Ib | aph(3')-II | aph(3')-Ia[b] | ant(4')-Ia | armA | nmpA |
| [tetrahydropyran with H2N-CH2 and NH2 substituents] | * | 1.1 | 0.87 | 0.87 | 0.61 | 5.7 | 0.35 | 64 | 0.5 | 0.74 | >64 |
| [tetrahydropyran with H2N-CH(Me) and NH2 substituents] | | 1.4 | 1 | 0.84 | 0.84 | 1 | 0.71 | 64 | 0.71 | 1.5 | >64 |
| [tetrahydropyran with H2N-CH(Me) and NH2 substituents, diastereomer] | | 2 | 1 | 1 | 1 | 1 | 1 | >64 | 0.5 | 1.4 | >64 |
| [tetrahydropyran with H2N-C(cyclopropyl) and NH2 substituents] | | 1 | 1 | 1 | 0.5 | 1 | 1 | >32 | — | 4 | 32 |
| [tetrahydropyran with H2N-CH(Et) and NH2 substituents] | | 2 | 1.4 | 0.71 | 1 | 1.3 | 1 | >64 | 1 | 3.2 | >64 |
| [tetrahydropyran with H2N-CH(Et) and NH2 substituents, diastereomer] | | 1.4 | 2 | 1 | 1 | 1 | 0.5 | >64 | 0.5 | 5.7 | >64 |

TABLE 2-continued
Data Summary for Synthesized Aminoglycosides
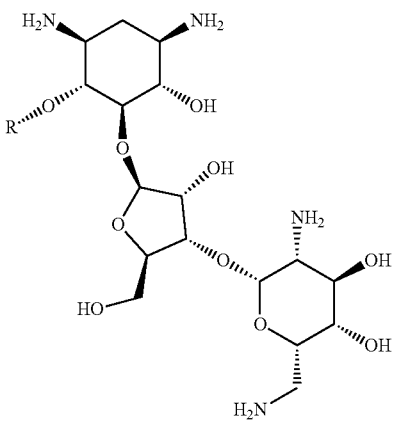
| R | | | | | | | | | | |
|---|---|---|---|---|---|---|---|---|---|---|
| 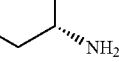 | | 64 | 32 | 32 | 32 | >64 | 32 | >64 | >64 | >64 | >64 |
|  | | 1 | 1 | 1 | 1 | 1 | — | — | — | 8 | 64 |
| 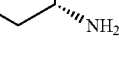 | * | 0.71 | 0.63 | 0.25 | 0.32 | 2 | 0.25 | 38 | 2 | 0.6 | >64 |
| 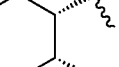 | NEO* | 1 | 0.76 | 0.79 | 0.64 | 1.6 | 18 | >64 | 2.2 | 0.75 | 80 |
|  | | 1.3 | 1.4 | 0.71 | 0.63 | 8 | 1 | >64 | 8 | 1.4 | >64 |
| 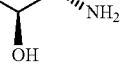 | | 2 | 1.4 | 1 | 2 | >64 | 1.4 | 64 | 64 | 2.8 | >64 |

TABLE 2-continued
Data Summary for Synthesized Aminoglycosides
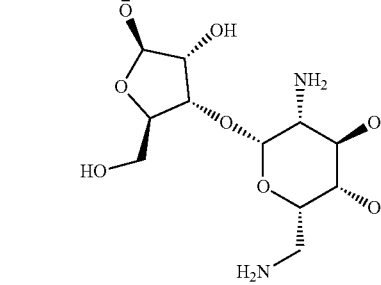
| | | | | | | | | | |
|---|---|---|---|---|---|---|---|---|---|
| 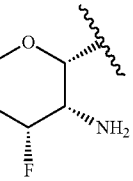 | 16 | 8 | 4 | 16 | >64 | 8 | >64 | 32 | 64 | >64 |
| 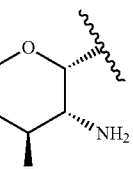 | 1 | 1 | 1 | 1 | 4 | 1 | >64 | 1 | 4 | >64 |
| 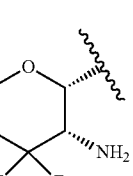 | 5 | 4 | 2 | 4 | >64 | 4 | >64 | 8 | 32 | >64 |
| 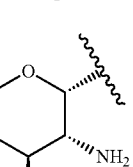 | 2 | 2 | 1 | 1.4 | 16 | 4 | >64 | 1 | 4 | 64 |
| R | *P. aeruginosa* | | | translation |
|---|---|---|---|---|
| | ATCC 27853[d] | efflux parent | Δefflux[e] | IC$_{50}$ (nM) |
| 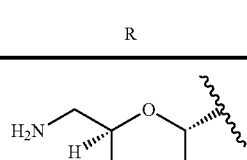 | 0.53 | 0.73 | 0.4 | 10 |
| 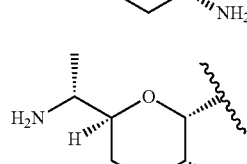 | 0.84 | 1.2 | 0.42 | 12 |

TABLE 2-continued
Data Summary for Synthesized Aminoglycosides
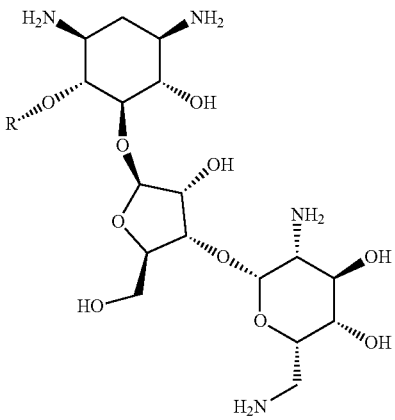
| Structure | | | | |
|---|---|---|---|---|
| (methyl, amine, THP, amine) | 2 | 4 | 0.5 | 14 |
| (cyclopropyl-amine, THP, amine) | 2 | 2 | 0.25 | 7.5 |
| (ethyl, amine, THP, amine) | 1.4 | 2 | 0.5 | 32 |
| (ethyl, amine, THP, amine) | 1 | 2 | 0.5 | 26 |
| (HOCH2, amine, THP, methyl, amine) | >64 | >64 | 16 | 1300 |
| (FCH2, amine, THP, methyl, amine) | 2 | 4 | 0.5 | 38 |

TABLE 2-continued
Data Summary for Synthesized Aminoglycosides
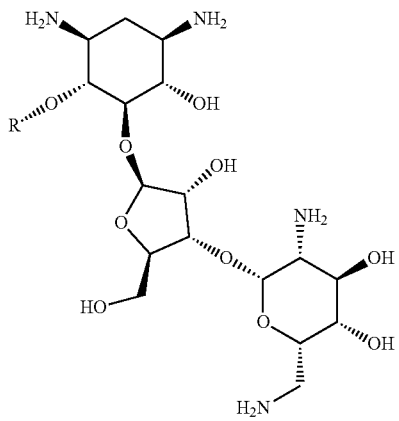
| | | | | |
|---|---|---|---|---|
| | 0.25 | 0.5 | 0.25 | 8.5 |
| | 1 | 6.8 | 2.2 | 7.3 |
| | 1 | 2 | 0.5 | 10 |
| | 2 | 4 | 0.5 | 24 |
| | 4 | 8 | 2 | 100 |
| | 1 | 2 | 0.5 | 18 |

TABLE 2-continued

Data Summary for Synthesized Aminoglycosides

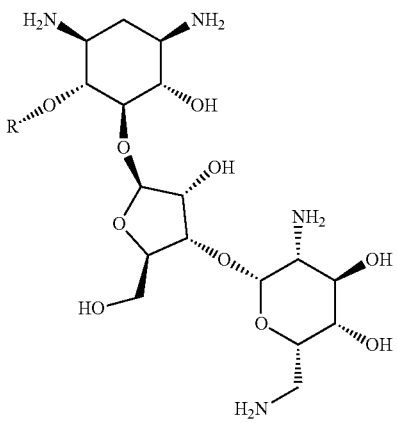

| | | | | |
|---|---|---|---|---|
| 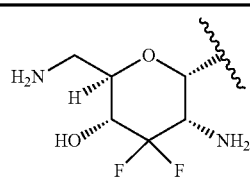 | 4 | 8 | 1 | 62 |
| 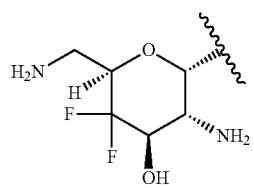 | 64 | 8 | 1 | 13 |

[a] The tolC efflux pump has been knocked-out of this strain
[b] aph(3')-Ia has activity at both the 3'-hydroxy and 5"-hydroxy positions
[c] The MexAB-OprM, MexCD-OprJ, and MexEF-OprN efflux pumps have been knocked out of this strain
[d] contains aph(3')-IIb
"—" = not measured
"*" = historical compound included for comparison purposes; NEO = neomycin

TABLE 3

Data Summary for Synthesized Aminoglycosides

| | E. coli | | | Geometric Mean MIC values (mg/L) | | | | | | |
|---|---|---|---|---|---|---|---|---|---|---|
| | | | | E. coli isogenic strains | | | | | | |
| Compound | ATCC 25922 | efflux parent | Δefflux[a] | empty vector | aac(6')-Ib | aph(3')-II | aph(3')-Ia[b] | ant(4')-Ia | armA | npmA |
| 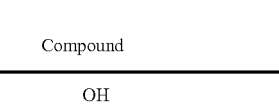 | 1 | 0.5 | 0.5 | 0.5 | 16 | 0.5 | >64 | 0.5 | 4 | >64 |

TABLE 3-continued

Data Summary for Synthesized Aminoglycosides

| Structure | ATCC 27853[d] | P. aeruginosa efflux parent | Δefflux[c] | translation IC$_{50}$ (nM) |
|---|---|---|---|---|
| [structure 1] | 1  0.5  0.5  0.5  8  0.5  16  —  0.5  >32 | | | |
| [structure 2] | 0.5 | 1 | 0.25 | 7.9 |
| [structure 3] | 1 | 1 | 0.25 | 5.7 |

[a] The tolC efflux pump has been knocked-out of this strain
[b] aph(3')-Ia has activity at both the 3'-hydroxy and 5"-hydroxy positions
[c] The MexAB-OprM, MexCD-OprJ, and MexEF-OprN efflux pumps have been knocked out of this strain
[d] contains aph(3')-IIb
"—" = not measured Biological Example 2: Translation Inhibition Assay AGs act by binding to the bacterial ribosome and interfering with translation. The impact on the AG mechanism of action of compounds disclosed herein (e.g., from Examples 1-62) are determined using a coupled transcription/translation assay that directly assesses protein synthesis inhibition in vitro. Translational inhibition for the novel AG's will be compared against existing AGs to monitor the ribosomal binding affinity consequences of each new chemical modification. The translation inhibition assay methodology was adapted from Sati, G. S.; Shcherbakov, D.; Hobbie, S.; Vasella, A.; Bottger, E.; & Crich, D. (2017). N6', N6''', and O4' modifications to neomycin affect ribosomal selectivity without compromising antibacterial activity. *ACS Infect. Dis.*, 3 (5), 368-377. Bacterial ribosomal extract and other components of the assay are provided in the *E. coli* S30 Extract System for Circular DNA by Promega. Briefly, a 30S premix containing rNTPs, tRNAs, and other required components is supplemented with amino acids and mixed with 30S ribosome extracts from *E. coli*. A 4 μL total volume of the 30S premix, amino acids, and extracts is added to each well in the reaction plate. Test aminoglycosides are dissolved in water and are serially diluted in 2-fold increments across a 12-well plate in a 1 μL volume at concentrations expected to span at least 5-fold above and below the expected IC$_{50}$ value. The reaction plate is then incubated at room temperature for 10 minutes to allow the potential binding of the ribosomal extracts and test aminoglycoside to reach equilibrium. 1 μL of template DNA (10 ng/μL), which contains the eukaryotic firefly luciferase gene, is then added to each well at a final concentration of 1.7 ng/μL for a final total reaction volume of 6 µL. The reaction plate is then incubated at 37° C. for 3 hours to allow transcription and translation of the firefly luciferase gene to progress. Following incubation, 10 µL at Luciferase Dilution Reagent (LDR) is added to each well. In a separate white assay plate, 25 µL at of Luciferase Assay Reagent (LAR) is added to each well. Then 13 µL from each well of the reaction plate is gently transferred to the white assay plate containing the LAR and mixed. Luminescence signal, which is expected to be proportional to the amount of translated firefly luciferase, is immediately measured at each test aminoglycoside concentration. To obtain the $IC_{50}$ for each test aminoglycoside, the luminescence data is plotted against the test aminoglycoside concentration and a non-linear 4-parameter fit to the data yields $IC_{50}$ values reflecting the concentration of test aminoglycoside required to inhibit the luminescence signal by 50%.

Biological Example 3: In vitro Nephrotoxicity Assay

Nephrotoxicity of the AG compounds (e.g., from Examples 1-62) will be assessed in vitro by quantitating human kidney cell (HK-2) viability and caspase production after exposure to AG. An exemplary in vitro assay is discussed in Maianti J. P.; Kanazawa H.; Dozzo P.; Matias R. D.; Feeney L. A.; Armstrong E. S.; Hildebrandt D. J.; Kane T. R.; Gliedt M. J.; Goldblum A. A.; Linsell M. S.; Aggen J. B.; Kondo J.; Hanessian S. (2014). Toxicity modulation, resistance enzyme evasion, and A-site x-ray structure of broad-spectrum antibacterial neomycin analogs. *ACS Chem. Biol.*, 9, 2067-2073.

Biological Example 4: Rat 11-Day Repeat Dose Nephrotoxicity Study

The in vivo nephrotoxicity of the AG compounds (e.g., from Examples 1-62) will be assessed in 11-day repeat dose rat toxicity studies where clinical pathology will be assessed, including hematology and clinical chemistry (creatinine levels and BUN). Upon completion of treatment, animals will be euthanized and the kidney histopathology examined.

Biological Example 5: Ototoxicity Protocol

Ototoxicity, including both vestibular and audiological effects, is a recognized class effect of aminoglycosides. The guinea pig model is one of the available non-clinical assays to study this type of toxicity. Ototoxicity studies will be conducted in the guinea pig model and compare AG compounds as disclosed herein (e.g., from Examples 1-62) with an AG comparator for loss of hearing function, and organs associated with hearing will be examined for abnormalities in gross necropsy and microscopic histopathological analysis.

Albino Hartley guinea pigs are dosed once daily with subcutaneous bolus injections to for 14 consecutive days. The dosing period is followed by a 14-day period to allow for any ototoxicity to take place. Gentamicin is administered as a positive control in this study. The ototoxicity associated with the aminoglycoside class has been found to be due to destruction of hair cells in the cochlea and vestibula. Hair cell damage appears to be selective, beginning with the outer hair cells of the lower portion of the cochlea and working inward. This process results in hearing loss primarily in the high-frequency range (as measured by auditory brainstem response (ABR)), and subsequently affects lower frequency ranges.

Groups of Albino Hartley guinea pigs are dosed with vehicle Control (saline) or compounds of the disclosure at 8, 30, and 80 mg/kg; groups of rats are dosed with gentamicin at 30 and 80 mg/kg/day. All dose groups have a subset of additional rats for TK and other analyses. Ototoxicity evaluations are performed in the Main study animals and toxicokinetic and nephrotoxicity evaluations are performed in the TK animals (e.g., body weights, serum creatinine and blood urea nitrogen (BUN), organ weight and macroscopic gross pathology). Physical examinations and otoscopic evaluations are performed on all animals pretest and on Main study animals on Day 28. Auditory brainstem response (ABR) evaluations are performed on all Main study animals pretest and on Day 28. Blood samples for clinical chemistry evaluations are collected from TK animals pretest and on Days 10 and 15. Blood samples for determination of the plasma concentrations of the test article are collected from TK animals at designated timepoints on Days 1 and 14. At study termination (Day 29), necropsy examinations included macroscopic evaluation and kidney weights (TK animals only) and histopathological evaluation of auditory system tissues (Main animals only).

ABR evaluations analyze functional hearing by noting the animal's response to an auditory stimulus. Ototoxicity is measured by a scale ranking the severity of functional hearing loss. The ABR measurements that determined the sound pressure level in which hearing is no longer detected is performed at 4, 10 and 20 kHz and is measured both pre-study and on Day 28 (14-days after dosing period). Compounds of the disclosure show an ototoxicity potential within 3-fold of that of gentamicin.

The cytocochleogram (histopathology) analysis is done to detect hair cell loss. A review of individual ABR findings compared to middle ear evaluations plus other observations related to the ear, show a correlation between hair cell loss as measured in the cytocochleogram analysis and the changes in ABR thresholds associated with hearing loss. Based on the changes in ABR and hair cell loss noted at a particular dose level, the NOAEL can be determined and compared to gentamicin.

Biological Example 6: Maximum Tolerated Dose Studies and PK

Rodents will be given a single IV injection and the effects on behavior and organs will be monitored, in particular for the non-lethal symptoms of AG-induced neuromuscular blockade. If an initial chosen dose of the test article results in symptoms, then the next dose group of three rodents will receive a 2-fold lower dose until the MTD, the highest dose that produces no observable effects on the animals, is found.

Following a single infusion, blood samples will be collected and quantified for drug levels, and estimates for PK parameters will be determined; drug levels in the kidney may be quantitated. PPB experiments will determine the fraction of AG bound to plasma protein in all relevant species.

The activity and PK/PD of novel AGs will be assessed against selected pathogens in murine in vivo efficacy and PK/PD studies, specifically a neutropenic thigh infection model and/or a neutropenic lung infection model, to assess dose-dependent cell killing and PK/PD relationships for prediction of efficacy and justification of clinical doses. Microbiology experiments will further investigate the in vitro activity against panels of AG-R strains, panels of contemporary clinical isolates, and species-specific panels that allows in-depth assessment of activity against key organisms of interest, such as *Acinetobacter* and *P. aeruginosa*.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the disclosure have been described herein for purposes of illustration, various modifications may be made without deviating from the spirit and scope of the disclosure. Accordingly, the disclosure is not limited except as by the appended claims.

What is claimed is:

1. A compound of formula (IV):

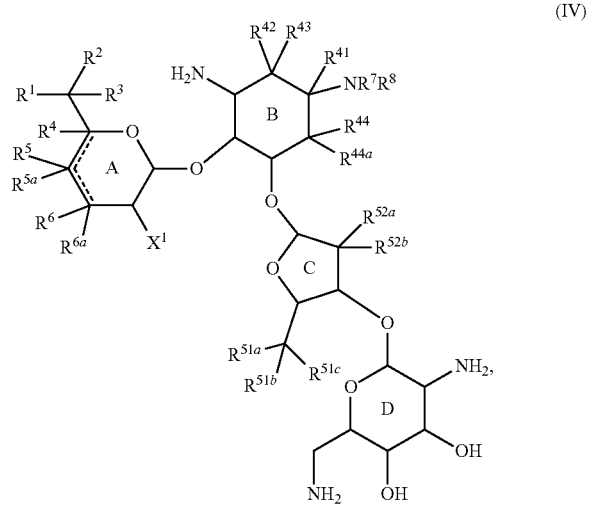

(IV)

or a pharmaceutically acceptable salt, solvate, tautomer, or stereoisomer thereof, wherein as valence and stability permit, $R^1$ is $-OR^9$ or $-NR^{10}R^{11}$, wherein $R^9$, $R^{10}$, and $R^{11}$ are independently H or $C_1$-$C_6$alkyl, wherein the $C_1$-$C_6$alkyl is unsubstituted or substituted with one or more $-OH$;

$R^2$ and $R^3$ are independently H, alkyl, cycloalkyl, or aryl, wherein the alkyl, cycloalkyl, or aryl is unsubstituted or substituted with one or more substituents independently selected from the group consisting of halogen, cyano, aryl, $-SR^{12}$, $-SO_2R^{13}$, $-OSF_2NR^{14}R^{15}$, $NR^{14}R^{15}$, and $-OR^{16}$, and wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, $-SR^{17}$, $-SO_2R^{18}$, $-NR^{19}R^{20}$, and $-OR^{21}$, and wherein each $R^{17}$, $R^{18}$, $R^{19}$, $R^{20}$, $R^{21}$ is independently H or alkyl, or $R^2$ and $R^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, $-SR^{22}$, $-SO_2R^{23}$, $-NR^{24}R^{25}$, and $-OR^{26}$, and wherein each $R^{22}$, $R^{23}$, $R^{24}$, $R^{25}$, $R^{26}$ is independently H or alkyl;

$R^4$ is H or absent;

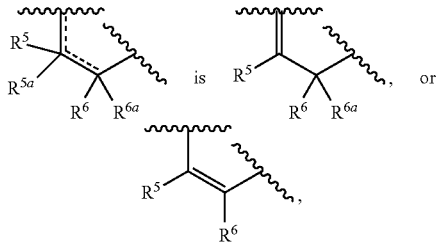

$R^5$ and $R^6$ are independently H, $-OR^{27}$, $-NR^{28}R^{29}$, halogen, or alkyl, wherein each $R^{27}$, $R^{28}$, and $R^{29}$ is independently H or $C_1$-$C_6$alkyl, wherein the alkyl or $C_1$-$C_6$alkyl is unsubstituted or substituted with one or more substituents selected from the group consisting of halogen, $-OR^{30}$, $-NR^{31}R^{32}$, $SR^{33}$, and $-SO_2R^{34}$, and wherein each $R^{30}$, $R^{31}$, $R^{32}$, $R^{33}$ and $R^{34}$ is independently H or alkyl;

$R^{5a}$ and $R^{6a}$ are, independently, absent or H, $-OR^{53}$, $-NR^{54}R^{55}$, halogen, or alkyl, wherein each $R^{53}$, $R^{54}$, and $R^{55}$ is independently H or $C_1$-$C_6$alkyl, wherein the alkyl or $C_1$-$C_6$alkyl is unsubstituted or substituted with one or more substituents selected from the group consisting of halogen, $-OR^{56}$, $-NR^{57}R^{58}$, $-SR^{59}$, and $-SO_2R^{60}$, and wherein each $R^{56}$, $R^{57}$, $R^{58}$, $R^{59}$, and $R^{60}$ is independently H or alkyl, $R^7$ is H or $C_1$-$C_3$alkyl;

$R^8$ is H, $C_1$-$C_6$alkyl, an amino protecting group, or

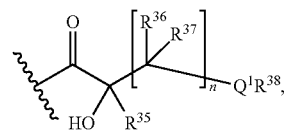

wherein $Q^1$ is NH, O, or S, n is an integer from 0 to 4, $R^{35}$ is H or $C_1$-$C_3$alkyl, each $R^{36}$ and $R^{37}$ is independently H, alkyl, halogen, or $-OH$, and $R^{38}$ is H, alkyl, or $-C(=NH)NR^{39}R^{40}$, wherein $R^{39}$ and $R^{40}$ are independently H or $C_1$-$C_3$alkyl, or $R^{35}$ and $R^{38}$, together with the atoms to which they are attached, form a heterocycloalkyl group comprising at least one N;

$R^{41}$ is H, $-CN$, $-CONH_2$ or $C_1$-$C_3$ alkyl, wherein the $C_1$-$C_3$alkyl is unsubstituted or substituted with one or more substituents selected from the group consisting of $-OH$, $-OC(O)CH_3$, $-NH_2$, $-CN$, $-CONH_2$, and halogen;

R⁴² and R⁴³ are, independently H, —OH, —OR⁴⁵, —NR⁴⁶R⁴⁷, or halogen,
  wherein each R⁴⁵, R⁴⁶, and R⁴⁷ is independently H, alkyl, —CONH₂, or —COCH₃,
  wherein the alkyl is unsubstituted or substituted with one or more substituents selected from the group consisting of —CONH₂, —OH, —NH₂, —COCH₃, aryl, substituted aryl, heteroaryl, or substituted heteroaryl;

R⁴⁴ and R⁴⁴ᵃ are, independently H, halogen, —OH, C₁-C₃alkoxy, or —OC(O)CH₃;

X¹ is H, NH₂, OH, or halogen;

R⁵¹ᵃ, R⁵¹ᵇ, and R⁵¹ᶜ are, independently, H, OH, or —OR⁵¹ᵈ,
  wherein each R⁵¹ᵈ is, independently, alkyl or —COCH₃, wherein the alkyl is unsubstituted or substituted with one or more substituents selected from the group consisting of —CONH₂, —OH, —NH₂, —COCH₃, aryl, substituted aryl, heteroaryl, or substituted heteroaryl;

R⁵²ᵃ and R⁵²ᵇ are independently H, OH, or —OR⁵²ᶜ,
  wherein each R⁵²ᶜ is, independently, alkyl or —COCH₃, wherein the alkyl is unsubstituted or substituted with one or more substituents selected from the group consisting of —CONH₂, —OH, —NH₂, —COCH₃, aryl, substituted aryl, heteroaryl, or substituted heteroaryl;
  wherein if R² and R³ are both H and R⁵ is —OR²⁷ or R⁵ᵃ is —OR⁵³, then R⁶ is not —OR²⁷,
  wherein if R² and R³ are both H and R⁵ is —OR²⁷ or R⁵ᵃ is —OR⁵³, then R⁶ᵃ is not —OR⁵³,
  wherein if R² and R³ are both H, then at least one of R⁴¹, R⁴², R⁴³, R⁴⁴ or R⁴⁴ᵃ is not H, and
  wherein if R² and R³ are both H and one of R⁴⁴ and R⁴⁴ᵃ is —OH, then at least one of R⁴¹, R⁴², or R⁴³ is not H.

2. The compound of claim 1, wherein the compound is of formula (IV-X):

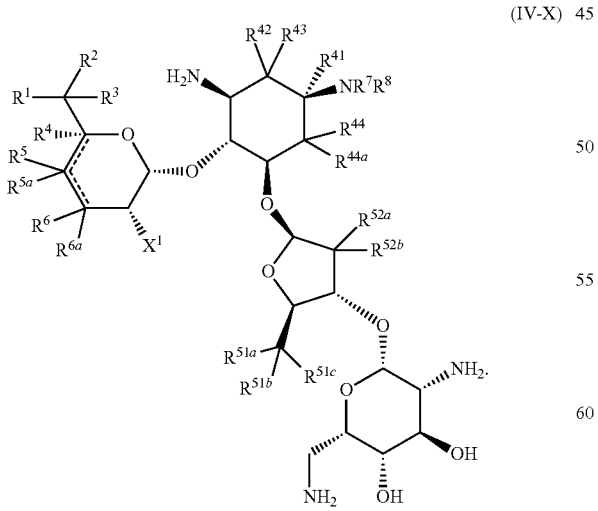

3. The compound of claim 1, wherein at least one of R² and R³ is other than H.

4. The compound of claim 1, wherein:
R⁴ is absent; and

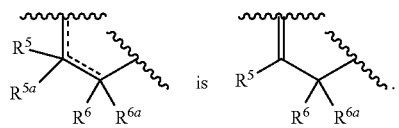

5. The compound of claim 4, wherein R⁵ is H, halogen, or —OH.

6. The compound of claim 1, wherein:
R⁴ is H; and

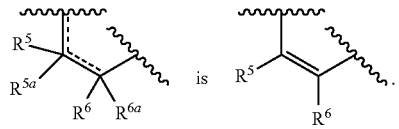

7. The compound of claim 6, wherein R⁵ is H, halogen, or —OH.

8. The compound of claim 7, wherein Ring A has the structure:

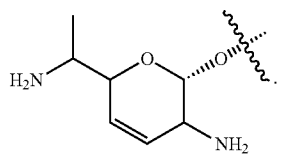

9. A compound of formula (IV):

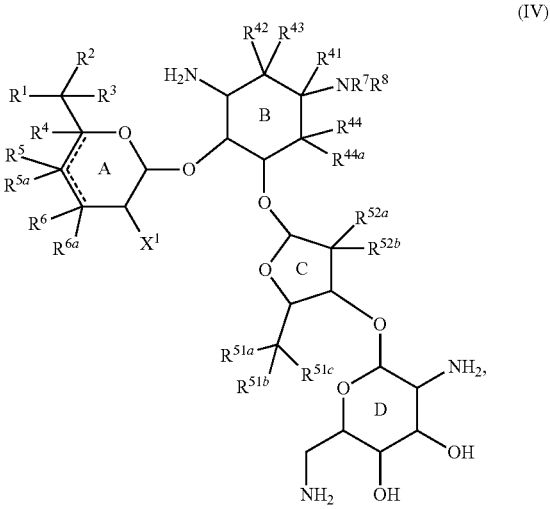

or a pharmaceutically acceptable salt, solvate, tautomer, or stereoisomer thereof, wherein as valence and stability permit,
  R¹ is —OR⁹ or —NR¹⁰R¹¹, wherein R⁹, R¹⁰, and R¹¹ are independently H or C₁-C₆alkyl, wherein the C₁-C₆alkyl is unsubstituted or substituted with one or more —OH;
  R² and R³ are independently H, alkyl, cycloalkyl, or aryl, wherein the alkyl, cycloalkyl, or aryl is unsubstituted or substituted with one or more substituents independently selected from the group consisting of halogen, cyano, aryl, —$SR^{12}$, —$SO_2R^{13}$, —$OSF_2NR^{14}R^{15}$, $NR^{14}R^{15}$, and —$OR^{16}$, and wherein each $R^{12}$, $R^{13}$, $R^{14}$, $R^{15}$, and $R^{16}$ is independently H or alkyl, or $R^1$ and $R^2$, together with the atom to which they are attached, form a heterocycloalkyl group comprising at least one heteroatom selected from the group consisting of N and O, wherein the heterocycloalkyl group is unsubstituted or substituted with one or more substituents independently selected from the group consisting of halogen, cyano, —$SR^{17}$, —$SO_2R^{18}$, —$NR^{19}R^{20}$, and —$OR^{21}$, and wherein each $R^{17}$, $R^{18}$, $R^{19}$, $R^{20}$, $R^{21}$ is independently H or alkyl, or $R^2$ and $R^3$, together with the atom to which they are attached, form a cycloalkyl group or a heterocycloalkyl group, wherein the cycloalkyl group or heterocycloalkyl group is unsubstituted or substituted with one or more substituents independently selected from the group consisting of halogen, cyano, —$SR^{22}$, —$SO_2R^{23}$, —$NR^{24}R^{25}$, and —$OR^{26}$, and wherein each $R^{22}$, $R^{23}$, $R^{24}$, $R^{25}$, $R^{26}$ is independently H or alkyl; $R^4$ is H or absent;

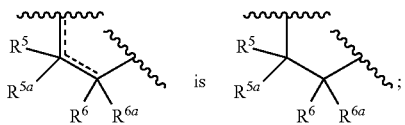

$R^5$ and $R^6$ are independently H, —$OR^{27}$, —$NR^{28}R^{29}$, halogen, or alkyl, wherein each $R^{27}$, $R^{28}$, and $R^{29}$ is independently H or $C_1$-$C_6$alkyl, wherein the alkyl or $C_1$-$C_6$alkyl is unsubstituted or substituted with one or more substituents selected from the group consisting of halogen, —$OR^{30}$, —$NR^{31}R^{32}$, $SR^{33}$, and —$SO_2R^{34}$, and wherein each $R^{30}$, $R^{31}$, $R^{32}$, $R^{33}$, and $R^{34}$ is independently H or alkyl;

$R^{5a}$ and $R^{6a}$ are, independently, absent or H, —$OR^{53}$, —$NR^{54}R^{55}$, halogen, or alkyl, wherein each $R^{53}$, $R^{54}$, and $R^{55}$ is independently H or $C_1$-$C_6$alkyl, wherein the alkyl or $C_1$-$C_6$alkyl is unsubstituted or substituted with one or more substituents selected from the group consisting of halogen, —$OR^{56}$, —$NR^{57}R^{58}$, —$SR^{59}$, and —$SO_2R^{60}$, and wherein each $R^{56}$, $R^{57}$, $R^{58}$, $R^{59}$, and $R^{60}$ is independently H or alkyl; or $R^5$ and $R^{5a}$ form an oxo group; or
$R^6$ and $R^{6a}$ form an oxo group;
with the proviso that if $R^5$ is —$OR^{27}$ or $R^{5a}$ is —$OR^{53}$, then $R^6$ is not —$OR^{27}$ and $R^{6a}$ is not —$OR^{53}$;

$R^7$ is H or $C_1$-$C_3$alkyl;
$R^8$ is H, $C_1$-$C_6$alkyl, an amino protecting group, or

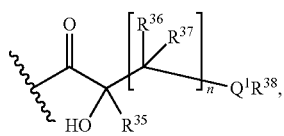

wherein $Q^1$ is NH, O, or S,
n is an integer from 0 to 4,
$R^{35}$ is H or $C_1$-$C_3$alkyl, each $R^{36}$ and $R^{37}$ is independently H, alkyl, halogen, or —OH, and $R^{38}$ is H, alkyl, or —C(=NH)$NR^{39}R^{40}$, wherein $R^{39}$ and $R^{40}$ are independently H or $C_1$-$C_3$alkyl, or $R^{35}$ and $R^{38}$, together with the atoms to which they are attached, form a heterocycloalkyl group comprising at least one N;

$R^{41}$ is H, —CN, —$CONH_2$ or $C_1$-$C_3$alkyl, wherein the $C_1$-$C_3$alkyl is unsubstituted or substituted with one or more substituents selected from the group consisting of —OH, —$OC(O)CH_3$, —$NH_2$, —CN, —$CONH_2$, and halogen;

$R^{42}$ and $R^{43}$ are, independently H, —OH, —$OR^{45}$, —$NR^{46}R^{47}$, or halogen, wherein each $R^{45}$, $R^{46}$, and $R^{47}$ is independently H, alkyl, —$CONH_2$, or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{44}$ and $R^{44a}$ are, independently H, halogen, —OH, $C_1$-$C_3$alkoxy, or —$OC(O)CH_3$;

$X^1$ is H, $NH_2$, OH, or halogen;

$R^{51a}$, $R^{51b}$, and $R^{51c}$ are, independently, H, OH, or —$OR^{51d}$, wherein each $R^{51d}$ is, independently, alkyl or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl;

$R^{52a}$ and $R^{52b}$ are independently H, OH, or —$OR^{52c}$, wherein each $R^{52c}$ is, independently, alkyl or —$COCH_3$, wherein the alkyl is unsubstituted or substituted with one or more substituents selected from the group consisting of —$CONH_2$, —OH, —$NH_2$, —$COCH_3$, aryl, substituted aryl, heteroaryl, or substituted heteroaryl; and with the proviso that:
if $R^2$ and $R^3$ are both H, then at least one of $R^{41}$, $R^{42}$, $R^{43}$, $R^{44}$, or $R^{44a}$ is not H; and
if $R^2$ and $R^3$ are both H and one of $R^{44}$ and $R^{44a}$ is —OH, then at least one of $R^{41}$, $R^{42}$, or $R^{43}$ is not H.

10. The compound of claim 9, wherein the compound is of formula (IVa-X):

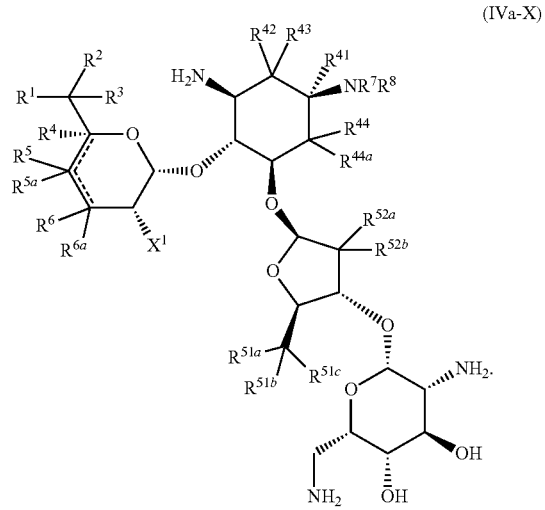

11. The compound of claim 9, wherein $R^5$ and $R^{5a}$ are independently selected from the group consisting of H, F, and OH.

12. The compound of claim 9, wherein $R^6$ and $R^{6a}$ are independently selected from the group consisting of H, F, and OH.

13. The compound of claim 9, wherein Ring A is selected from the group consisting of:

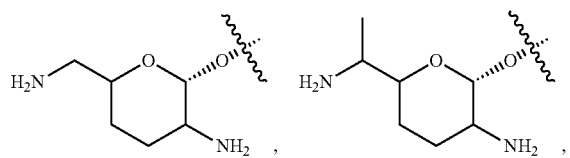

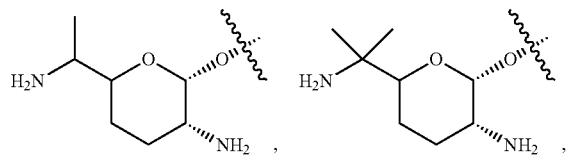

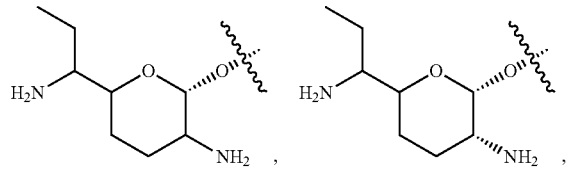

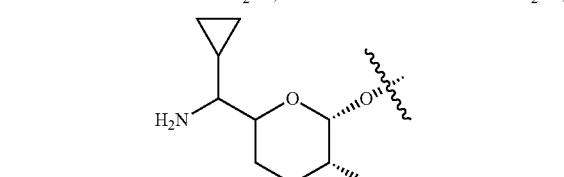

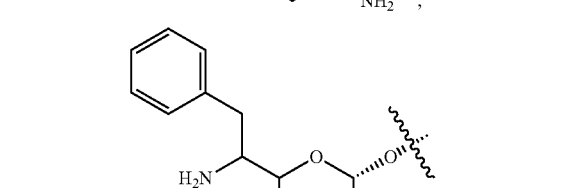

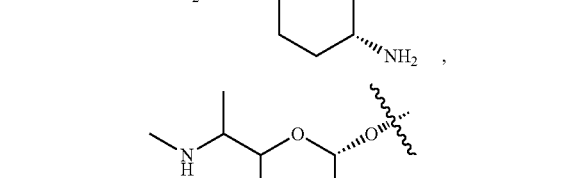

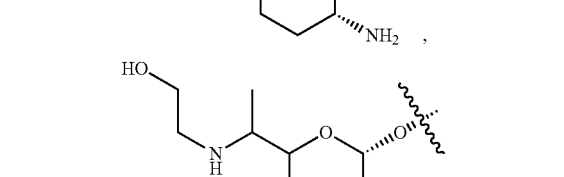

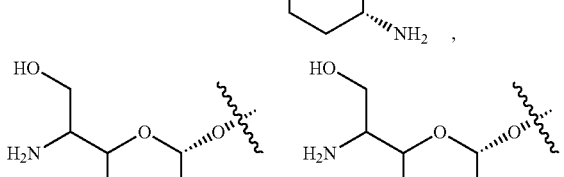

-continued

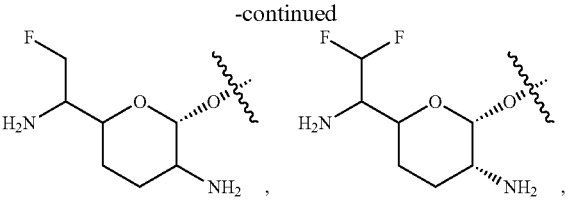

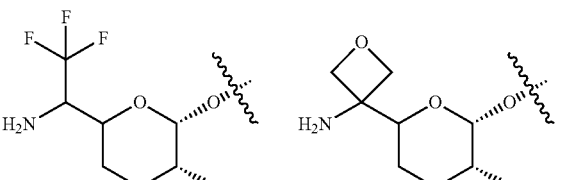

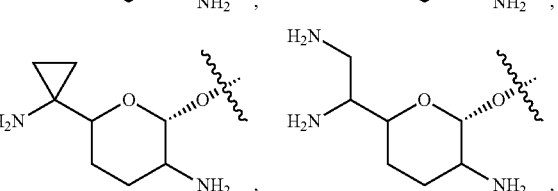

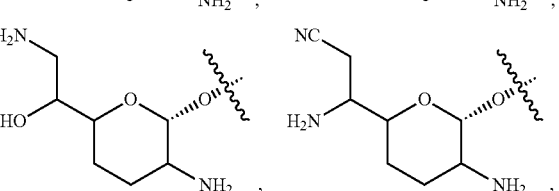

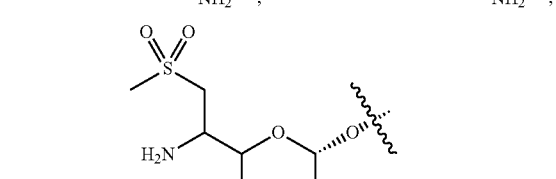

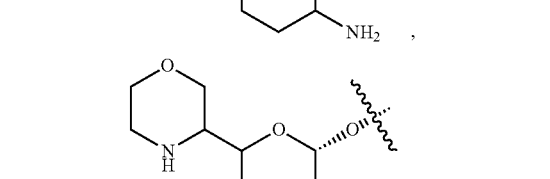

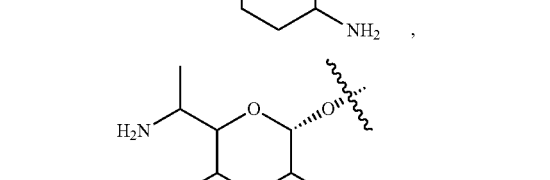

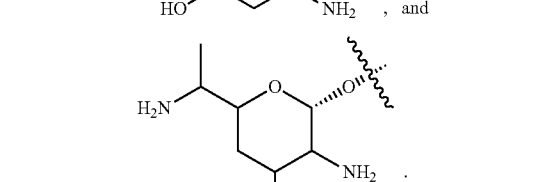

, and

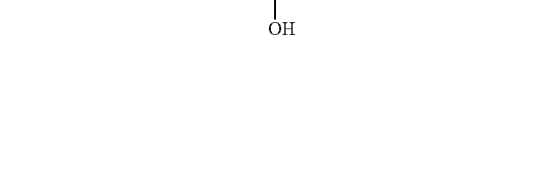

.

14. The compound of claim 9, wherein Ring A is selected from the group consisting of:

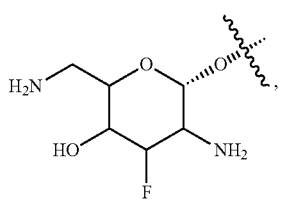
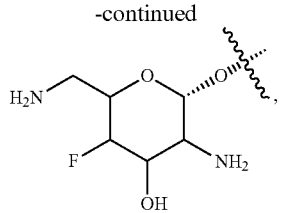
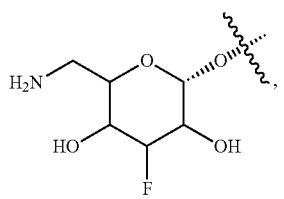
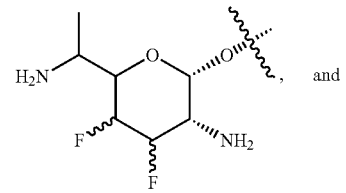, and
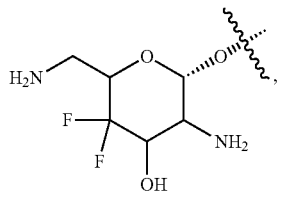
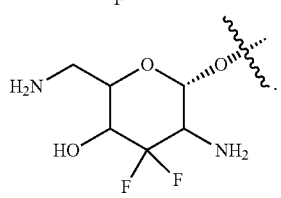
\* \* \* \* \*